US012703874B2

(12) United States Patent
Simons et al.

(10) Patent No.: US 12,703,874 B2
(45) Date of Patent: Aug. 11, 2026

(54) METHODS OF TREATING HEARING LOSS USING A SECRETED TARGET PROTEIN

(71) Applicant: Akouos, Inc., Boston, MA (US)

(72) Inventors: Emmanuel J. Simons, Brookline, MA (US); Robert Ng, Newton, MA (US); Danielle R. Lenz, Brookline, MA (US); Hao Chiang, Somerville, MA (US)

(73) Assignee: Akouos, Inc., Indianapolis, IN (US)

( * ) Notice: Subject to any disclaimer, the term of this patent is extended or adjusted under 35 U.S.C. 154(b) by 1166 days.

(21) Appl. No.: 17/628,266

(22) PCT Filed: Jul. 24, 2020

(86) PCT No.: PCT/US2020/043604

§ 371 (c)(1),
(2) Date: Jan. 19, 2022

(87) PCT Pub. No.: WO2021/021674

PCT Pub. Date: Feb. 4, 2021

(65) Prior Publication Data

US 2022/0396806 A1 Dec. 15, 2022

Related U.S. Application Data

(60) Provisional application No. 62/879,396, filed on Jul. 26, 2019.

(51) Int. Cl.
*C12N 15/86* (2006.01)
*A61K 38/00* (2006.01)
*A61P 27/16* (2006.01)
*C07K 14/475* (2006.01)

(52) U.S. Cl.
CPC .............. *C12N 15/86* (2013.01); *A61P 27/16* (2018.01); *C07K 14/475* (2013.01); *A61K 38/00* (2013.01); *C07K 2319/43* (2013.01); *C12N 2750/14143* (2013.01); *C12N 2830/42* (2013.01)

(58) Field of Classification Search
CPC .......... C12N 15/86; C12N 2750/14143; C12N 2830/42; A61P 27/16; C07K 14/475; C07K 2319/43; C07K 14/47; A61K 38/00
See application file for complete search history.

(56) References Cited

U.S. PATENT DOCUMENTS 4,797,368 A 1/1989 Carter et al.
5,122,458 A 6/1992 Post et al.
5,139,941 A 8/1992 Muzyczka et al.
5,168,062 A 12/1992 Stinski
5,478,745 A 12/1995 Samulski et al.
5,741,683 A 4/1998 Zhou et al.
6,001,650 A 12/1999 Colosi
6,057,152 A 5/2000 Samulski et al.
6,156,303 A 12/2000 Russell et al.
6,204,059 B1 3/2001 Samulski et al.
6,268,213 B1 7/2001 Samulski et al.
6,491,907 B1 12/2002 Rabinowitz et al.
6,660,514 B1 12/2003 Zolotukhin et al.
6,951,753 B2 10/2005 Shenk et al.
7,094,604 B2 8/2006 Snyder et al.
7,172,893 B2 2/2007 Rabinowitz et al.
7,201,898 B2 4/2007 Monahan et al.
7,229,823 B2 6/2007 Samulski et al.
7,282,199 B2 10/2007 Gao et al.
7,439,065 B2 10/2008 Ferrari et al.
7,588,772 B2 9/2009 Kay et al.
7,790,449 B2 9/2010 Gao et al.
9,695,220 B2 7/2017 Vandenberghe et al.
9,719,070 B2 8/2017 Vandenberghe et al.
10,119,125 B2 11/2018 Vandenberghe et al.
10,526,584 B2 1/2020 Vandenberghe et al.
11,104,885 B2 8/2021 Vandenberghe et al.
11,167,042 B2 11/2021 Stankovic et al.
11,466,258 B2 10/2022 Vandenberghe et al.
2006/0040354 A1 2/2006 O'Keefe
2006/0177819 A1 8/2006 Smith et al.
2007/0196872 A1 8/2007 Bex et al.
2009/0305344 A1 12/2009 Polo et al.
2011/0312872 A1 12/2011 Tamm et al.
2014/0179005 A1* 6/2014 Jantz .............. C12Y 105/01003
435/462
2015/0050243 A1 2/2015 Kaczmarczyk et al.
2015/0376252 A1 12/2015 Xu et al.
2016/0022769 A1 1/2016 Trese et al.
(Continued)

FOREIGN PATENT DOCUMENTS

EP 1982180 A2 10/2008
EP 2367564 A1 9/2011
(Continued)

OTHER PUBLICATIONS

Ye, X., Smallwood, P., & Nathans, J. (2010). Expression of the Norrie disease gene (Ndp) in developing and adult mouse eye, ear, and brain. Gene Expression Patterns, 11(1-2), 151-155. https://doi.org/10.1016/j.gep.2010.10.007 (Year: 2010).*
Angelidis, Charalampos E., et al. "Constitutive Expression of Heat-shock Protein 70 in Mammalian Cells Confers Thermoresistance." European Journal of Biochemistry, vol. 199, No. 1, Jul. 1991, pp. 35-39. DOI.org (Crossref), https://doi.org/10.1111/j.1432-1033.1991.tb16088.x. (Year: 1991).*
Berger, Wolfgang, et al. "Mutations in the Candidate Gene for Norrie Disease." Human Molecular Genetics, vol. 1, No. 7, 1992, pp. 461-465. DOI.org (Crossref), https://doi.org/10.1093/hmg/1.7.461. (Year: 1992).*
Boshart, M., et al. "A Very Strong Enhancer Is Located Upstream of an Immediate Early Gene of Human Cytomegalovirus." Cell, vol. 41, No. 2, Jun. 1985, pp. 521-530. DOI.org (Crossref), https://doi.org/10.1016/S0092-8674(85)80025-8. (Year: 1985).*
(Continued)

*Primary Examiner* — Jennifer Dunston
*Assistant Examiner* — Sarah E Allen
(74) *Attorney, Agent, or Firm* — Choate, Hall & Stewart LLP; Stephanie L. Schonewald; Margo R. Monroe

(57) ABSTRACT

Provided herein are compositions that include a single nucleic acid vector or two different nucleic acid vectors, and the use of these compositions to treat hearing loss in a subject.

33 Claims, 8 Drawing Sheets

Specification includes a Sequence Listing.

(56) References Cited

U.S. PATENT DOCUMENTS

2016/0076054 A1* 3/2016 Auricchio ............. C12N 15/86 435/320.1
2018/0369414 A1* 12/2018 Stankovic .............. A61P 25/02
2019/0060328 A1 2/2019 Ibanez et al.
2020/0268838 A1 8/2020 Dailey et al.
2022/0016262 A1 1/2022 Stankovic et al.
2022/0017875 A1 1/2022 Vandenberghe et al.
2022/0112278 A1 4/2022 Li et al.
2022/0288236 A1 9/2022 Burns et al.
2023/0056182 A1 2/2023 Simons et al.
2023/0287359 A1 9/2023 Vandenberghe et al.

FOREIGN PATENT DOCUMENTS

EP 2968452 A1 1/2016
EP 3386537 B1 10/2018
EP 3060575 B1 12/2018
EP 3618851 A2 3/2020
EP 3459965 B1 12/2020
EP 3744730 A1 12/2020
EP 3880826 A1 9/2021
EP 3924381 A1 12/2021
EP 3984550 A1 4/2022
EP 4007814 A1 6/2022
EP 4063510 A1 9/2022
EP 4337226 A1 3/2024
WO WO-98/10088 A1 3/1998
WO WO-2003/042397 A2 5/2003
WO WO-2005/033321 A2 4/2005
WO WO-05/073384 A3 9/2005
WO WO-06/12414 A2 2/2006
WO WO-2006/110689 A2 10/2006
WO WO-2007/092487 A2 8/2007
WO WO-2010/072684 A1 7/2010
WO WO-2014/130728 A1 8/2014
WO WO-2014/143022 A1 9/2014
WO WO-2015/054653 A2 4/2015
WO WO-2016/200906 A1 12/2016
WO WO-2016/200932 A1 12/2016
WO WO-2017/100791 A1 6/2017
WO WO-2018002938 A1 * 1/2018 ............ C12N 15/79
WO WO-2018/039375 A1 3/2018
WO WO-2018/145111 A1 8/2018
WO WO-2018/204909 A2 11/2018
WO WO-2019077001 A1 * 4/2019 ............ C12N 15/67
WO WO-2019/165292 A1 8/2019
WO WO-2020/097372 A1 5/2020
WO WO-2020/167848 A1 8/2020
WO WO-2021/021674 A1 2/2021
WO WO-2022/240778 A1 11/2022
WO WO-2024/079449 A1 4/2024

OTHER PUBLICATIONS

Damgaard, Christian Kroun, et al. "A 5' Splice Site Enhances the Recruitment of Basal Transcription Initiation Factors In Vivo." Molecular Cell, vol. 29, No. 2, Feb. 2008, pp. 271-278. DOI.org (Crossref), https://doi.org/10.1016/j.molcel.2007.11.035. (Year: 2008).*

Gray, Steven J., et al. "Optimizing Promoters for Recombinant Adeno-Associated Virus-Mediated Gene Expression in the Peripheral and Central Nervous System Using Self-Complementary Vectors." Human Gene Therapy, vol. 22, No. 9, Sep. 2011, pp. 1143-1153. (Year: 2011).*

Hernandez-Garcia, Carlos M., and John J. Finer. "Identification and Validation of Promoters and Cis-Acting Regulatory Elements." Plant Science, vol. 217-218, Mar. 2014, pp. 109-119. DOI.org (Crossref), https://doi.org/10.1016/j.plantsci.2013.12.007. (Year: 2014).*

Proudfoot, Nick J. "Ending the Message: Poly(A) Signals Then and Now." Genes & Development, vol. 25, No. 17, Sep. 2011, pp. 1770-1782. genesdev.cshlp.org, https://doi.org/10.1101/gad.17268411. (Year: 2011).*

Adachi, K. et al., Drawing a high-resolution functional map of adeno-associated virus capsid by massively parallel sequencing, Nat Commun., 5:3075 (2014).

Andersen, J. et al., Herpesvirus-Mediated Gene Delivery into the Rat Brain: Specificity and Efficiency of the Neuron-Specific Enolase Promoter, Cell Mol. Neurobiol., 13(5):503-515 (1993).

Arbuthnot, P. et al., In vitro and in vivo hepatoma cell-specific expression of a gene transferred with an adenoviral vector, Hum Gene Ther., 7(13):1503-1514 (1996).

Asokan, A. et al., The AAV Vector Toolkit: Poised at the Clinical Crossroads, Molecular Therapy, 20(4):699-708 (2012).

Baker, T. G. et al., Heat Shock Protein-Mediated Protection Against Cisplatin-Induced Hair Cell Death, JARO, 16:67-80 (2015).

Banaszynski, L. A. et al., A rapid, reversible, and tunable method to regulate protein function in living cells using synthetic small molecules, Cell, 126(5): 995-1004 (2012).

Batt, D. and Carmichael, G., Characterization of the polyomavirus late polyadenylation signal, Mol Cell Biol., 15(9):4783-4790 (1995).

Boshart, M. et al., A very strong enhancer is located upstream of an immediate early gene of human cytomegalovirus, Cell, 41(2):521-530 (1985).

Chamney, S. et al., A mutation in the Norrie disease gene (NDP) associated with familial exudative vitreoretinopathy, Eye, 25(12):1658 (2011).

Chen, C. et al., mRNA decay mediated by two distinct AU-rich elements from c-fos and granulocyte-macrophage colony-stimulating factor transcripts: different deadenylation kinetics and uncoupling from translation, Mol Cell Biol., 15(10):5777-5788 (1995).

Chen, J. et al., Expression of rat bone sialoprotein promoter in transgenic mice, J Bone Miner Res., 11(5):654-664 (1996).

Chen, Q. et al., An AU-rich element in the 3' untranslated region of the spinach chloroplast petD gene participates in sequence-specific RNA-protein complex formation, Mol Cell Biol., 15(4):2010-2018 (1995).

Cotten, M. et al., High-efficiency receptor-mediated delivery of small and large (48 kilobase gene constructs using the endosome-disruption activity of defective or chemically inactivated adenovirus particles, P.N.A.S. U.S.A., 89(13):6094-98 (1992).

Curiel, D. T., High-efficiency gene transfer employing adenovirus-polylysine-DNA complexes, Nat Immun., 13(2-3):141-64 (1994).

De Felipe, P. and Izqierdo, M., Tricistronic and tetracistronic retroviral vectors for gene transfer, Hum Gene Ther, 11(13):1921-1931 (2000).

De Felipe, P. et al., Use of the 2A sequence from foot-and-mouth disease virus in the generation of retroviral vectors for gene therapy, Gene Ther., 6(2):198-208 (1999).

De Fougerolles, A., Delivery vehicles for small interfering RNA in vivo, Hum Gene Ther., 19(2):125-132 (2008).

Di Domenico, M. et al., Towards Gene Therapy for Deafness, Journal of Cellular Physiology, 226:2494-2499 (2011).

Dmitriev, I. et al., An adenovirus vector with genetically modified fibers demonstrates expanded tropism via utilization of a coxsackievirus and adenovirus receptor-independent cell entry mechanism, J Virol., 72(12):9706-9713 (1998).

Fisher, K. et al., Transduction with recombinant adeno-associated virus for gene therapy is limited by leading-strand synthesis, J Virol., 70(1):520-532 (1996).

Furler, S. et al., Recombinant AAV vectors containing the foot and mouth disease virus 2A sequence confer efficient bicistronic gene expression in cultured cells and rat substantia nigra neurons, Gene Ther., 8(11):864-873 (2001).

Gao, G. et al., Clades of Adeno-associated viruses are widely disseminated in human tissues, J. Virol . . . 78(12): 6381-6388 (2004).

Gonnet, G. H. et al., Exhaustive Matching of the Entire Protein Sequence Database, Science, 256:1443-1445 (1992).

Gossen, M. and Bujard, H., Tight control of gene expression in mammalian cells by tetracycline-responsive promoters, Proc Natl Acad Sci USA, 89(12):5547-5551 (1992).

Gossen, M. et al., Transcriptional activation by tetracyclines in mammalian cells, Science, 268(5218):1766-1769 (1995).

(56) References Cited

OTHER PUBLICATIONS

Gyorgy, B. et al., Rescue of Hearing by Gene Delivery to Inner-Ear Hair Cells Using Exosome-Associated AAV, Molecular Therapy, 25(2):379-391 (2017).
Hansal, S. et al., Induction of antigen-specific hyporesponsiveness by transplantation of hemopoietic cells containing an MHC class I transgene regulated by a lymphocyte-specific promoter, J Immunol., 161(3):1063-1068 (1998).
Harvey, D. and Caskey, C., Inducible control of gene expression: prospects for gene therapy, Curr Opin Chem Biol., 2(4):512-518 (1998).
Heidel, J. et al., Aministration in non-human primates of escalating intravenous doses of targeted nanoparticles containing ribonucleotide reductase subunit M2 siRNA, Proc Natl Acad Sci USA, 104(14):5715-5721 (2007).
Hellen, C. and Sarnow, P., Internal ribosome entry sites in eukaryotic mRNA molecules, Genes Dev., 15(13):1593-1612 (2001).
Hu-Lieskovan, S. et al., Sequence-specific knockdown of EWS-FLI1 by targeted, nonviral delivery of small interfering RNA inhibits tumor growth in a murine model of metastatic Ewing's sarcoma, Cancer Res., 65(19):8984-8992 (2005).
Isgrig, K. et al., AAV2.7m8 is a powerful viral vector for inner ear gene therapy, Nat. Commun., 10(1):427 (2019).
Ito, T. et al., SLC26A4 mutation testing for hearing loss associated with enlargement of the vestibular aqueduct, World J. Otorhinolaryngol., 3(2):26-34 (2013).
Iwamoto, M. et al., A general chemical method to regulate protein stability in the mammalian central nervous system. Chem Biol., 17(9): 981-988 (2010).
Kanaan, N. M. et al., Rationally Engineered AAV Capsids Improve Transduction and Volumetric Spread in the CNS, Mol. Ther. Nucleic Acids, 8:184-197 (2017).
Kelleher, Z. T. and Vos, J. M., Long-term episomal gene delivery in human lymphoid cells using human and avian adenoviral-assisted transfection, Biotechniques, 17(6):1110-17 (1994).
Klump, H. et al., Retroviral vector-mediated expression of HoxB4 in hematopoietic cells using a novel coexpression strategy, Gene Ther., 8(10):811-817 (2001).
Konings, A. et al., Variations in HSP70 genes associated with noise-induced hearing loss in two independent populations, European Journal of Human Genetics, 17:329-335 (2009).
Kral, A. and O'Donoghue, G. M., Profound Deafness in Childhood, The New England Journal of Medicine, 363(15):1438-50 (2010).
Levitt, N. et al., Definition of an efficient synthetic poly(A) site, Genes Dev., 3(7):1019-1025 (1989).
Li, W. et al., Engineering and selection of shuffled AAV genomes: a new strategy for producing targeted biological nanoparticles, Mol. Ther. 16(7):1252-1260 (2008).
Liu, H. Y. et al., A novel missense mutation of NDP in a Chinese family with X-linked familial exudative vitreoretinopathy, Journal of the Chinese Medical Association, 79:633-638 (2016).
Magari, S. et al., Pharmacologic control of a humanized gene therapy system implanted into nude mice, J Clin Invest., 100(11):2865-2872 (1997).
Maier, P. et al., Retroviral vectors for gene therapy, Future Microbiol., 5(10):1507-1523 (2010).
Mattion, N. et al., Foot-and-mouth disease virus 2A protease mediates cleavage in attenuated Sabin 3 poliovirus vectors engineered for delivery of foreign antigens, J Virol., 70(11):8124-8127 (1996).
May, L. A. et al., Inner ear supporting cells protect hair cells by secreting HSP70, The Journal of Clinical Investigation, 128(8):3577-3587 (2013).
Musada, G. R. et al., Mutation spectrum of the Norrie disease pseudoglioma (NDP) gene in Indian patients with FEVR, Molecular Vision, 22:491-502 (2016).
Muzyczka, N., Use of adeno-associated virus as a general transduction vector for mammalian cells, Curr Top Microbiol Immunol, 158:97-129 (1992).
Myers, E. W. and Miller, W., Optimal Alignments in Linear Space, CABIOS, 4(1):11-17 (1988).
No, D. et al., Ecdysone-inducible gene expression in mammalian cells and transgenic mice, Proc Natl Acad Sci USA, 93(8):3346-3351 (1996).
Orkin, S. et al., Thalassemia due to a mutation in the cleavage-polyadenylation signal of the human beta-globin gene, EMBO J., 4(2):453-456 (1985).
Parzefall, T. et al., A Novel Missense NDP Mutation [p.(Cys93Arg)] with a Manifesting Carrier in an Austrian Family with Norrie Disease, Audiology Neurotology, 19(3):203-209 (2014).
Pelletier, J. et al., Cap-independent translation of poliovirus mRNA is conferred by sequence elements within the 5' noncoding region., Mol. Cell. Biol. 8(3):1103-1112 (1988).
Piccioli, P. et al., Neuroantibodies: ectopic expression of a recombinant anti-substance P antibody in the central nervous system of transgenic mice, Neuron, 15(2):373-384 (1995).
Piccioli, P. et al., Neuroantibodies: molecular cloning of a monoclonal antibody against substance P for expression in the central nervous system, Proc Natl Acad Sci USA, 88(13):5611-5615 (1991).
Poulin, K. et al., Retargeting of adenovirus vectors through genetic fusion of a single-chain or single-domain antibody to capsid protein IX, J Virol., 84(19):10074-10086 (2010).
Proudfoot, N. et al., Integrating mRNA processing with transcription, Cell, 108(4):501-512 (2002).
Rozema, D. et al., Dymanic PolyConjugates for targeted in vivo delivery of siRNA to hepatocytes, Proc Natl Acad Sci USA, 104(32):12982-12987 (2007).
Ryan, A. et al., Cellular targeting for cochlear gene therapy, Adv Otorhinolaryngol., 66:99-115 (2009).
Ryan, M. and Drew, J., Foot-and-mouth disease virus 2A oligopeptide mediated cleavage of an artificial polyprotein, EMBO J., 13(4):928-933 (1994).
Sandig, V. et al., HBV-derived promoters direct liver-specific expression of an adenovirally transduced LDL receptor gene, Gene Ther., 3(11):1002-1009 (1996).
Schek, N. et al.,Definition of the Upstream Efficiency Element of the Simian Virus 40 Late Polyadenylation Signal by Using in Vitro Analyses, Mol. Cell Biol., 12(12):5386-5393 (1992).
Sharma, A. et al., Transduction efficiency of AAV 2/6, 2/8 and 2/9 vectors for delivering genes in human corneal fibroblasts, Brain Res Bull., 81(2-3):273 (2010).
Smith, R. J. H. et al., Sensorineural hearing loss in children, The Lancet, 365:879-890 (2005).
Stein, G. et al., The osteocalcin gene: a model for multiple parameters of skeletal-specific transcriptional control, Mol Biol Rep., 24(3):185-196 (1997).
Szymanski, P. et al., Development and validation of a robust and versatile one-plasmid regulated gene expression system, Mol Ther., 15(7):1340-1347 (2007).
Thein, S. et al., The polyadenylation site mutation in the alpha-globin gene cluster, Blood, 71(2):313-319 (1988).
Tian, Y. et al., Creation of a transgenic mouse for hair-cell gene targeting by using a modified bacterial artificial chromosome containing Prestin, Dev Dyn., 231(1):199-203 (2004).
Trapani, I., et al., Effective delivery of large genes to the retina by dual AAV vectors, EMBO Mol Med., 6(2):194-211 (2014).
Wang, Y. et al., Ligand-inducible and liver-specific target gene expression in transgenic mice, Nat Biotechnol., 15(3):239-243 (1997).
Wang, Y., et al., Positive and negative regulation of gene expression in eukaryotic cells with an inducible transcriptional regulator, Gene Ther., 4(5):432-441 (1997).
Woychik, R. et al., Requirement for the 3' flanking region of the bovine growth hormone gene for accurate polyadenylylation, Proc Natl Acad Sci USA, 81(13):3944-3948 (1984).
Zhang, H. et al., Adenovirus-adeno-associated virus hybrid for large-scale recombinant adeno-associated virus production, Human Gene Therapy, 20(9):922-929 (2009).
Halpin, C. et al., Self-processing 2A-polyproteins—a system for co-ordinate expression of multiple proteins in transgenic plants, Plant J., 17(4):453-459 (1999).

(56) References Cited

OTHER PUBLICATIONS

International Search Opinion for PCT/US2020/043604 ( Methods of Treating Hearing Loss Using a Secreted Target Protein, filed Jul. 24, 2020) received by ISA/EP, 8 pages (Dec. 15, 2020).
Roesch, S. et al., Functional Testing of SLC26A4 Variants-Clinical and Molecular Analysis of a Cohort with Enlarged Vestibular Aqueduct from Austria, Int. J. Mol. Sci. 19(1):209 (2018).
Written Opinion for PCT/US2020/043604 ( Methods of Treating Hearing Loss Using a Secreted Target Protein, filed Jul. 24, 2020) received by ISA/EP, 11 pages (Dec. 15, 2020).
Zheng, J. et al., Prestin is the motor protein of cochlear outer hair cells, Nature, 405(6783):149-155 (2000).
Zinn, E. et al., In Silico Reconstruction of the Viral Evolutionary Lineage Yields a Potent Gene Therapy Vector, Cell. Rep., 12(6):1056-1068 (2015).

* cited by examiner

Anc80-NDP; 1.6E+10 vg

Anc80-NDP-UTR; 2E+10 vg

Myo7a
DAPI

200μm

100μm

METHODS OF TREATING HEARING LOSS USING A SECRETED TARGET PROTEIN

CROSS-REFERENCE TO RELATED APPLICATION

The application is a National Stage Application, filed under 35 U.S.C. § 371, of International Application No. PCT/US2020/043604 filed on Jul. 24, 2020, which claims priority to U.S. Application Ser. No. 62/879,396 filed on Jul. 26, 2019, the contents of each of which are hereby incorporated by reference in their entireties.

SEQUENCE LISTING

The instant application contains a Sequence Listing which has been submitted electronically in ASCII format and is hereby incorporated by reference in its entirety. Said ASCII copy, created on Jul. 24, 2020, is named 2013615-0076_SL.txt and is 339,816 bytes in size.

TECHNICAL FIELD

The present disclosure relates generally to the use of nucleic acids to treat hearing loss in a human subject.

BACKGROUND

Current treatments for hearing loss consist mainly of hearing amplification for mild to severe hearing loss and cochlear implants for severe to profound hearing loss; however, a long-felt need remains for agents and methods for preventing or reversing syndromic and/or non-syndromic deafness.

Hearing loss can be conductive (arising from the ear canal or middle ear), sensorineural (arising from the inner ear or auditory nerve), or mixed. Most forms of syndromic and/or non-syndromic deafness are associated with permanent hearing loss caused by damage to structures in the inner ear (sensorineural deafness), although some forms may involve changes in the middle ear (conductive hearing loss). The great majority of human sensorineural hearing loss is caused by abnormalities in the hair cells of the organ of Corti in the cochlea (poor hair cell function). The hair cells may be abnormal at birth, or may be damaged during the lifetime of an individual (e.g., as a result of noise trauma or infection).

SUMMARY

The present disclosure provides the recognition that some diseases or conditions associated with hearing loss can be treated via, e.g., replacement and/or addition of certain gene products. The present disclosure further provides that gene products involved in the development, function, and/or maintenance of inner ear cells can be useful for treatment of diseases or conditions associated with hair cell and/or supporting cell loss. The present disclosure thus provides for the administration of compositions that result in expression of gene products involved in the development, function, and/or maintenance of inner ear cells, including supporting cells and hair cells, and/or the use of such compositions in the treatment of hearing loss, or diseases or conditions associated with hearing loss. In some embodiments, a gene product can be encoded by a gene encoding a secreted target protein (e.g., an NDP gene, or a heat shock protein (HSP) gene, e.g., an HSPA1A gene) or a characteristic portion thereof. In some embodiments, a gene product can be a secreted target protein or a characteristic portion thereof.

The present disclosure further provides that adeno-associated virus (AAV) particles can be useful for administration of compositions that result in expression of gene products involved in the development, function, and/or maintenance of inner ear cells, and/or the treatment of hearing loss, or diseases or conditions associated with hearing loss. As described herein, AAV particles comprise (i) a AAV polynucleotide construct (e.g., a recombinant AAV polynucleotide construct), and (ii) a capsid comprising capsid proteins. In some embodiments, an AAV polynucleotide construct comprises a gene encoding a secreted target protein (e.g., an NDP gene or a heat shock protein (HSP) gene, e.g., an HSPA1A gene or a DNJB gene) or a characteristic portion thereof. AAV particles described herein have been engineered. Accordingly, in some embodiments, AAV particles of the present disclosure are referred to as recombinant AAV particles or rAAV particles.

Provided herein are compositions including a single AAV vector, wherein the single AAV vector comprises a nucleic acid sequence that encodes a secreted target protein. In some embodiments, when introduced into a primate cell, a nucleic acid encoding a secretion signal sequence operatively linked to the secreted target protein is generated at the locus of the secreted target protein. In some embodiments, the primate cell expresses and secretes the secreted target protein.

The present disclosure further provides compositions comprising polynucleotide constructs comprising a gene encoding a secreted target protein (e.g., an NDP gene or a heat shock protein (HSP) gene, e.g., an HSPA1A gene and a DNJB gene) or a characteristic portion thereof. In some embodiments, a construct may further include regulatory elements operably attached to a coding sequence. In certain embodiments, included regulatory elements facilitate tissue specific expression at physiologically suitable levels.

Also provided herein are methods of administering constructs and compositions described herein. In certain embodiments, administration involves surgical intervention and the delivery of AAV particles comprising therapeutic constructs. In certain embodiments, AAV particles may be delivered to the inner ear of a subject in need thereof by surgical introduction through the round window membrane. In some embodiments, efficacy of an intervention is determined through established tests, and measurements are compared to known control measurements.

In some embodiments, a single AAV vector further includes a 5' untranslated region (UTR), a 3' UTR, or both.

In some embodiments of any of the compositions described herein, a secreted target protein is norrin cysteine knot growth factor (NDP).

In some embodiments, a secreted target protein includes a sequence that is at least 80% identical (e.g., at least 82%, at least 84%, at least 86%, at least 88%, at least 90%, at least 92%, at least 94%, at least 95%, at least 96%, at least 97%, at least 98%, at least 99%, or 100%) to SEQ ID NO: 1.

In some embodiments, a secreted target protein includes a sequence that is at least 90% identical (e.g., at least 92%, at least 94%, at least 95%, at least 96%, at least 97%, at least 98%, at least 99%, or 100%) to SEQ ID NO: 1.

In some embodiments, a secreted target protein includes a sequence that is at least 99% identical to SEQ ID NO: 1.

In some embodiments of any of the compositions described herein, a nucleic acid that encodes a secreted target protein includes a sequence that is at least 80% identical (e.g., at least 82%, at least 84%, at least 86%, at least 88%, at least 90%, at least 92%, at least 94%, at least 95%, at least 96%, at least 97%, at least 98%, at least 99%, or 100%) to SEQ ID NO: 2.

In some embodiments, a nucleic acid that encodes a secreted target protein includes a sequence that is at least 90% identical (e.g., at least 92%, at least 94%, at least 95%, at least 96%, at least 97%, at least 98%, at least 99%, or 100%) to SEQ ID NO: 2.

In some embodiments, a nucleic acid that encodes a secreted target protein includes a sequence that is at least 99% identical to SEQ ID NO: 2.

In some embodiments of any of the compositions described herein, a secreted target protein is a heat shock protein. In some embodiments, a heat shock protein is a heat shock protein family A (Hsp70) member 1A (HSPA1A). In some embodiments, a heat shock protein is a heat shock protein 40 (Hsp40)/DNJ family member, e.g., Hsp40.

In some embodiments, a secreted target protein includes a sequence that is at least 80% identical (e.g., at least 82%, at least 84%, at least 86%, at least 88%, at least 90%, at least 92%, at least 94%, at least 95%, at least 96%, at least 97%, at least 98%, at least 99%, or 100%) to SEQ ID NO: 3.

In some embodiments, a secreted target protein includes a sequence that is at least 90% identical (e.g., at least 92%, at least 94%, at least 95%, at least 96%, at least 97%, at least 98%, at least 99%, or 100%) to SEQ ID NO: 3.

In some embodiments, a secreted target protein includes a sequence that is at least 99% identical to SEQ ID NO: 3.

In some embodiments of any of the compositions described herein, a nucleic acid that encodes a secreted target protein includes a sequence that is at least 80% identical (e.g., at least 82%, at least 84%, at least 86%, at least 88%, at least 90%, at least 92%, at least 94%, at least 95%, at least 96%, at least 97%, at least 98%, at least 99%, or 100%) to SEQ ID NO: 4.

In some embodiments, a nucleic acid that encodes a secreted target protein includes a sequence that is at least 90% identical (e.g., at least 92%, at least 94%, at least 95%, at least 96%, at least 97%, at least 98%, at least 99%, or 100%) to SEQ ID NO: 4.

In some embodiments, a nucleic acid that encodes a secreted target protein includes a sequence that is at least 99% identical to SEQ ID NO: 4.

In some embodiments of any of the compositions described herein, an AAV vector further includes one or both of a promoter and a Kozak sequence.

In some embodiments, an AAV vector includes a promoter that is an inducible promoter, a constitutive promoter, or a tissue-specific promoter.

In some embodiments of any of the compositions described herein, an AAV vector further includes a poly(dA) sequence.

In some embodiments of any of the compositions described herein, a secretion signal sequence includes SEQ ID NO: 5.

In some embodiments, a sequence encoding a secretion signal sequence includes SEQ ID NO: 6.

In some embodiments of any of the compositions described herein, a secretion signal sequence includes SEQ ID NO: 7.

In some embodiments, a sequence encoding the secretion signal sequence includes SEQ ID NO: 8.

In some embodiments, a single AAV vector includes a sequence that is at least 80% identical (e.g., at least 82%, at least 84%, at least 86%, at least 88%, at least 90%, at least 92%, at least 94%, at least 95%, at least 96%, at least 97%, at least 98%, at least 99%, or 100%) to SEQ ID NO: 9.

In some embodiments, a single AAV vector includes a sequence that is at least 90% identical (e.g., at least 92%, at least 94%, at least 95%, at least 96%, at least 97%, at least 98%, at least 99%, or 100%) to SEQ ID NO: 9.

In some embodiments, a single AAV vector includes a sequence that is at least 99% identical to SEQ ID NO: 9.

In some embodiments, a single AAV vector includes a sequence that is at least 80% identical (e.g., at least 82%, at least 84%, at least 86%, at least 88%, at least 90%, at least 92%, at least 94%, at least 95%, at least 96%, at least 97%, at least 98%, at least 99%, or 100%) to SEQ ID NO: 10.

In some embodiments, a single AAV vector includes a sequence that is at least 90% identical (e.g., at least 92%, at least 94%, at least 95%, at least 96%, at least 97%, at least 98%, at least 99%, or 100%) to SEQ ID NO: 10.

In some embodiments, a single AAV vector includes a sequence that is at least 99% identical to SEQ ID NO: 10.

In some embodiments of any of the compositions described herein, a composition further includes a pharmaceutically acceptable excipient.

Also provided herein are kits including a composition (e.g., any of the compositions described herein).

In some embodiments of any of the kits described herein, a composition is pre-loaded in a syringe.

Also provided herein are methods that include introducing into an inner ear of a mammal a therapeutically effective amount of a composition (e.g., any of the compositions described herein).

In some embodiments, a mammal is a human.

In some embodiments of any of the methods described herein, a mammal has been previously identified as having a defective secreted target gene.

Also provided herein are methods of increasing expression of a full-length secreted target protein in a mammalian cell that include introducing a composition (e.g., any of the compositions described herein) into the mammalian cell.

In some embodiments, a mammalian cell is a cochlear inner hair cell, a supporting cell, a ganglion cell, a clear cell, a cuboidal cell, a cartilage cell, a cell of the tegmentum vasculosum, a homogene cell, a Hensen's cell, a Deiters' cell, a pillar cell, or a border cell.

In some embodiments of any of the methods described herein, a mammalian cell is a human cell.

In some embodiments of any of the methods described herein, a mammalian cell has previously been determined to have a defective secreted target gene.

Also provided herein are methods of increasing the level of a full-length secreted target protein in an inner ear of a mammal that include: introducing into the inner ear of a mammal a therapeutically effective amount of a composition (e.g., any of the compositions described herein).

In some embodiments, a mammal has been previously identified as having a defective secreted target gene.

In some embodiments of any of the methods described herein, a mammal is a human.

Also provided herein are methods of treating syndromic and non-syndromic sensorineural hearing loss in a subject identified as having a defective secreted target gene that include: administering a therapeutically effective amount of a composition (e.g., any of the compositions described herein) into the inner ear of the subject.

In some embodiments, a subject is a human.

In some embodiments of any of the methods described herein, a subject has Norrie disease pseudoglioma.

In some embodiments of any of the methods described herein, a method further includes, prior to the administering step, determining that the subject has a defective secreted target gene.

Also provided herein are methods of treating or preventing hearing loss in a subject identified as having a defective NDP gene that include: administering a therapeutically effective amount of a composition (e.g., any of the compositions described herein) into an inner ear of the subject.

In some embodiments, a subject has been identified or diagnosed as having Norrie disease pseudoglioma.

In some embodiments of any of the methods described herein, a subject is a human.

In some embodiments of any of the methods described herein, a method further includes, (e.g., prior to the administering step) determining that the subject has a defective NDP gene.

Also provided herein are compositions including at least two different nucleic acid vectors, wherein: each of the at least two different vectors includes a coding sequence that encodes a different portion of a secreted target protein, each of the encoded portions being at least 30 amino acid residues in length, wherein the amino acid sequence of each of the encoded portions may optionally partially overlap with the amino acid sequence of a different one of the encoded portions; no single vector of the at least two different vectors encodes a full-length secreted target protein; at least one of the coding sequences includes a nucleotide sequence spanning two neighboring exons of the secreted target protein genomic DNA, and lacks an intronic sequence between the two neighboring exons; and when introduced into a mammalian cell the at least two different vectors undergo concatamerization or homologous recombination with each other, thereby forming a recombined nucleic acid that encodes a secretion signal sequence operatively linked to a full-length secreted target protein.

In some embodiments, each of at least two different vectors is a plasmid, a transposon, a cosmid, an artificial chromosome, or a viral vector.

In some embodiments, each of at least two different vectors is a human artificial chromosome (HAC), yeast artificial chromosome (YAC), bacterial artificial chromosome (BAC), or a P1-derived artificial chromosome (PAC).

In some embodiments, each of at least two different vectors is a viral vector selected from an adeno-associated virus (AAV) vector, an adenovirus vector, a lentivirus vector, or a retrovirus vector.

In some embodiments, each of at least two different vectors is an AAV vector.

In some embodiments of any of the compositions described herein, the amino acid sequence of one of the encoded portions overlaps with the amino acid sequence of a different one of the encoded portions.

In some embodiments, the amino acid sequence of each of the encoded portions partially overlaps with the amino acid sequence of a different encoded portion.

In some embodiments, the overlapping amino acid sequence is between about 30 amino acid residues to about 600 amino acid residues in length.

In some embodiments of any of the compositions described herein, vectors include two different vectors, each of which includes a different segment of an intron, wherein the intron includes the nucleotide sequence of an intron that is present in the secreted target protein genomic DNA, and wherein the two different segments overlap in sequence by at least 100 nucleotides.

In some embodiments, two different segments overlap in sequence by about 100 nucleotides to about 800 nucleotides (e.g., any of the subranges therein).

In some embodiments of any of the compositions described herein, the nucleotide sequence of each of the at least two different vectors is between about 500 nucleotides to about 10,000 nucleotides in length (e.g., any of the subranges therein).

In some embodiments of any of the compositions described herein, the nucleotide sequence of each of the at least two different vectors is between about 500 nucleotides to about 5,000 nucleotides in length (e.g., any of the subranges therein).

In some embodiments of any of the compositions described herein, the number of different vectors in the composition is two.

In some embodiments, a first of the two different vectors includes a coding sequence that encodes an N-terminal portion of the secreted target protein.

In some embodiments, an N-terminal portion of the secreted target protein is between about 30 amino acids to about 600 amino acids in length (e.g., any of the subranges therein).

In some embodiments, an N-terminal portion of the secreted target protein is between about 100 amino acids to about 500 amino acids in length (e.g., any of the subranges therein).

In some embodiments of any of the compositions described herein, a first vector further includes one or both of a promoter and a Kozak sequence.

In some embodiments of any of the compositions described herein, a first vector includes a promoter that is an inducible promoter, a constitutive promoter, or a tissue-specific promoter.

In some embodiments of any of the compositions described herein, a second of the two different vectors includes a coding sequence that encodes a C-terminal portion of the secreted target protein.

In some embodiments, a C-terminal portion of the secreted target protein is between about 30 amino acids to about 600 amino acids in length (e.g., any of the subranges therein).

In some embodiments, a C-terminal portion of the secreted target protein is between about 200 amino acids to about 500 amino acids in length (e.g., any of the subranges therein).

In some embodiments of any of the compositions described herein, a second vector further includes a poly (dA) sequence.

In some embodiments of any of the compositions described herein, a first vector, a second vector, or both vectors further includes a 5' untranslated region (UTR), a 3' UTR, or both.

In some embodiments of any of the compositions described herein, a secreted target protein is norrin cysteine knot growth factor (NDP).

In some embodiments, a secreted target protein includes a sequence that is at least 80% identical (e.g., at least 82%, at least 84%, at least 86%, at least 88%, at least 90%, at least 92%, at least 94%, at least 95%, at least 96%, at least 97%, at least 98%, at least 99%, or 100%) to SEQ ID NO: 1.

In some embodiments, a secreted target protein includes a sequence that is at least 90% identical (e.g., at least 92%, at least 94%, at least 95%, at least 96%, at least 97%, at least 98%, at least 99%, or 100%) to SEQ ID NO: 1.

In some embodiments, a secreted target protein includes a sequence that is at least 99% identical to SEQ ID NO: 1.

In some embodiments of any of the compositions described herein, a secreted target protein is a heat shock protein. In some embodiments, a heat shock protein is a heat shock protein family A (Hsp70) member 1A (HSPA1A). In some embodiments, a heat shock protein is a heat shock protein 40 (Hsp40)/DNJ family member, e.g., Hsp40.

In some embodiments, a secreted target protein includes a sequence that is at least 80% identical (e.g., at least 82%, at least 84%, at least 86%, at least 88%, at least 90%, at least 92%, at least 94%, at least 95%, at least 96%, at least 97%, at least 98%, at least 99%, or 100%) to SEQ ID NO: 3.

In some embodiments, a secreted target protein includes a sequence that is at least 90% identical (e.g., at least 92%, at least 94%, at least 95%, at least 96%, at least 97%, at least 98%, at least 99%, or 100%) to SEQ ID NO: 3.

In some embodiments, a secreted target protein includes a sequence that is at least 99% identical to SEQ ID NO: 3.

In some embodiments of any of the compositions described herein, a secretion signal sequence includes SEQ ID NO: 5.

In some embodiments of any of the compositions described herein, a secretion signal sequence includes SEQ ID NO: 7.

Also provided herein are compositions including two different nucleic acid vectors, wherein: a first nucleic acid vector of the two different nucleic acid vectors includes a promoter, a first coding sequence that encodes an N-terminal portion of an secreted target protein positioned 3' of the promoter, and a splicing donor signal sequence positioned at the 3' end of the first coding sequence; and a second nucleic acid vector of the two different nucleic acid vectors includes a splicing acceptor signal sequence, a second coding sequence that encodes a C-terminal portion of an secreted target protein positioned at the 3' end of the splicing acceptor signal sequence, and a polyadenylation sequence at the 3' end of the second coding sequence; wherein each of the encoded portions is at least 30 amino acid residues in length, wherein the amino acid sequences of the encoded portions do not overlap, wherein no single vector of the two different vectors encodes a full-length secreted target protein, and, when the coding sequences are transcribed in a mammalian cell, to produce RNA transcripts, splicing occurs between the splicing donor signal sequence on one transcript and the splicing acceptor signal sequence on the other transcript, thereby forming a recombined RNA molecule that encodes a secretion signal sequence operatively linked to a full-length secreted target protein.

In some embodiments, a coding sequence of at least one of the vectors includes a nucleotide sequence spanning two neighboring exons of secreted target genomic DNA, and lacks an intronic sequence between the two neighboring exons.

Also provided herein are compositions including: a first nucleic acid vector including a promoter, a first coding sequence that encodes an N-terminal portion of an secreted target protein positioned 3' of the promoter, a splicing donor signal sequence positioned at the 3' end of the first coding sequence, and a first detectable marker gene positioned 3' of the splicing donor signal sequence; and a second nucleic acid vector, different from the first nucleic acid vector, including a second detectable marker gene, a splicing acceptor signal sequence positioned 3' of the second detectable marker gene, a second coding sequence that encodes a C-terminal portion of an secreted target protein positioned at the 3' end of the splicing acceptor signal sequence, and a polyadenylation sequence positioned at the 3' end of the second coding sequence; wherein each of the encoded portions is at least 30 amino acid residues in length, wherein the respective amino acid sequences of the encoded portions do not overlap with each other, wherein no single vector of the two different vectors encodes a full-length secreted target protein, and, when the coding sequences are transcribed in a mammalian cell to produce RNA transcripts, splicing occurs between the splicing donor signal on one transcript and the splicing acceptor signal on the other transcript, thereby forming a recombined RNA molecule that encodes a secretion signal sequence operatively linked to a full-length secreted target protein.

In some embodiments, a coding sequence of at least one of the vectors includes a nucleotide sequence spanning two neighboring exons of secreted target genomic DNA, and lacks an intronic sequence between the two neighboring exons.

In some embodiments, a first or second detectable marker gene encodes alkaline phosphatase.

In some embodiments of any of the compositions described herein, a first and second detectable marker genes are the same.

Also provided herein are compositions including: a first nucleic acid vector including a promoter, a first coding sequence that encodes an N-terminal portion of an secreted target protein positioned 3' to the promoter, a splicing donor signal sequence positioned at the 3' end of the first coding sequence, and a F1 phage recombinogenic region positioned 3' to the splicing donor signal sequence; and a second nucleic acid vector, different from the first nucleic acid vector, including a second F1 phage recombinogenic region, a splicing acceptor signal sequence positioned 3' of the second F1 phage recombinogenic region, a second coding sequence that encodes a C-terminal portion of an secreted target protein positioned at the 3' end of the splicing acceptor signal sequence, and a polyadenylation sequence positioned at the 3' end of the second coding sequence; wherein each of the encoded portions is at least 30 amino acid residues in length, wherein the respective amino acid sequences of the encoded portions do not overlap with each other, wherein no single vector of the two different vectors encodes a full-length secreted target protein, and, when the coding sequences are transcribed in a mammalian cell to produce RNA transcripts, splicing occurs between the splicing donor signal one transcript and the splicing acceptor signal on the other transcript, thereby forming a recombined RNA molecule that encodes a secretion signal sequence operatively linked to a full-length secreted target protein.

In some embodiments, a coding sequence of at least one of the vectors includes a nucleotide sequence spanning two neighboring exons of secreted target genomic DNA, and lacks an intronic sequence between the two neighboring exons.

In some embodiments of any of the compositions described herein, a first vector, the second vector, or both vectors further includes a 5' untranslated region (UTR), a 3' UTR, or both.

In some embodiments of any of the compositions described herein, a secreted target protein is norrin cysteine knot growth factor (NDP).

In some embodiments, a secreted target protein includes a sequence that is at least 80% identical (e.g., at least 82%, at least 84%, at least 86%, at least 88%, at least 90%, at least 92%, at least 94%, at least 95%, at least 96%, at least 97%, at least 98%, at least 99%, or 100%) to SEQ ID NO: 1.

In some embodiments, a secreted target protein includes a sequence that is at least 90% identical (e.g., at least 92%, at least 94%, at least 95%, at least 96%, at least 97%, at least 98%, at least 99%, or 100%) to SEQ ID NO: 1.

In some embodiments, a secreted target protein includes a sequence that is at least 99% identical to SEQ ID NO: 1.

In some embodiments of any of the compositions described herein, a secreted target protein is a heat shock protein. In some embodiments, a heat shock protein is a heat shock protein family A (Hsp70) member 1A (HSPA1A). In some embodiments, a heat shock protein is a heat shock protein 40 (Hsp40)/DNJ family member, e.g., Hsp40.

In some embodiments, a secreted target protein includes a sequence that is at least 80% identical (e.g., at least 82%, at least 84%, at least 86%, at least 88%, at least 90%, at least 92%, at least 94%, at least 95%, at least 96%, at least 97%, at least 98%, at least 99%, or 100%) to SEQ ID NO: 3.

In some embodiments, a secreted target protein includes a sequence that is at least 90% identical (e.g., at least 92%, at least 94%, at least 95%, at least 96%, at least 97%, at least 98%, at least 99%, or 100%) to SEQ ID NO: 3.

In some embodiments, a secreted target protein includes a sequence that is at least 99% identical to SEQ ID NO: 3.

In some embodiments of any of the compositions described herein, a secretion signal sequence includes SEQ ID NO: 5.

In some embodiments of any of the compositions described herein, a secretion signal sequence includes SEQ ID NO: 7.

In some embodiments of any of the compositions described herein, a composition further includes a pharmaceutically acceptable excipient.

Also provided herein are kits including a composition (e.g., any of the compositions described herein).

In some embodiments of any of the kits described herein, a kit further includes a pre-loaded syringe including the composition.

Also provided herein are methods that include: introducing into an inner ear of a mammal a therapeutically effective amount of a composition (e.g., any of the compositions described herein).

In some embodiments, a mammal is a human.

In some embodiments of any of the methods described herein, a mammal has been previously identified as having a defective secreted target gene.

Also provided herein are methods of increasing expression of a full-length secreted target protein in a mammalian cell that include: introducing a composition (e.g., any of the compositions described herein) into the mammalian cell.

In some embodiments, a mammalian cell is a cochlear inner hair cell, a supporting cell, a ganglion cell, a clear cell, a cuboidal cell, a cartilage cell, a cell of the tegmentum vasculosum, a homogene cell, a Hensen's cell, a Deiters' cell, a pillar cell, or a border cell.

In some embodiments of any of the methods described herein, a mammalian cell is a human cell.

In some embodiments of any of the methods described herein, a mammalian cell has previously been determined to have a defective secreted target gene.

Also provided herein are methods of increasing the level of a full-length secreted target protein in an inner ear of a mammal that include: introducing into the inner ear of the mammal a therapeutically effective amount of a composition (e.g., any of the compositions described herein).

In some embodiments, a mammal has been previously identified as having a defective secreted target gene.

In some embodiments of any of the methods described herein, a mammal is a human.

Also provided herein are methods of treating syndromic and non-syndromic sensorineural hearing loss in a subject identified as having a defective secreted target gene that include: administering a therapeutically effective amount of a composition (e.g., any of the compositions described herein) into the inner ear of the subject.

In some embodiments, a subject is a human.

In some embodiments of any of the methods described herein, a subject has Norrie disease pseudoglioma.

In some embodiments of any of the methods described herein, a method further includes prior to the administering step, determining that the subject has a defective secreted target gene.

Also provided herein are methods of treating or preventing hearing loss in a subject identified as having a defective NDP gene that include: administering a therapeutically effective amount of a composition (e.g., any of the compositions described herein) into an inner ear of the subject.

In some embodiments, a subject has been identified or diagnosed as having Norrie disease pseudoglioma.

In some embodiments of any of the methods described herein, a subject is a human.

In some embodiments of any of the methods described herein, a method further includes prior to the administering step, determining that the subject has a defective NDP gene.

Also provided herein are methods of treating or preventing vision loss in a subject identified as having a defective NDP gene that include: administering a therapeutically effective amount of a composition (e.g., any of the compositions described herein) into an inner ear or central nervous system of the subject, or systemically administering a therapeutically effective amount of a composition (e.g., any of the compositions described herein) to the subject.

In some embodiments, a subject is a human.

In some embodiments of any of the methods described herein, a method further includes prior to the administering step, determining that the subject has a defective NDP gene.

Also provided herein are methods of treating or preventing vision loss in a subject identified as having a defective NDP gene that include: administering a therapeutically effective amount of a composition (e.g., any of the compositions described herein) into an inner ear or central nervous system of the subject, or systemically administering a therapeutically effective amount of a composition (e.g., any of the compositions described herein) to the subject.

In some embodiments, a subject is a human.

In some embodiments of any of the methods described herein, a method further includes prior to the administering step, determining that the subject has a defective NDP gene.

Definitions

The scope of the present disclosure is defined by the claims appended hereto and is not limited by certain embodiments described herein. Those skilled in the art, reading the present specification, will be aware of various modifications that may be equivalent to such described embodiments, or otherwise within the scope of the claims. In general, terms used herein are in accordance with their understood meaning in the art, unless clearly indicated otherwise. Explicit definitions of certain terms are provided below; meanings of these and other terms in particular instances throughout this specification will be clear to those skilled in the art from context.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

The term "a" and "an" refers to one or to more than one (i.e., at least one) of the grammatical object of the article. By way of example, "an element" encompasses one element and more than one element. Claims or descriptions that include "or" between one or more members of a group are considered satisfied if one, more than one, or all of the group members are present in, employed in, or otherwise relevant to a given product or process unless indicated to the contrary or otherwise evident from the context. In some embodiments, exactly one member of a group is present in, employed in, or otherwise relevant to a given product or process. In some embodiments, more than one, or all group members are present in, employed in, or otherwise relevant to a given product or process. It is to be understood that the present disclosure encompasses all variations, combinations, and permutations in which one or more limitations, elements, clauses, descriptive terms, etc., from one or more of the listed claims is introduced into another claim dependent on the same base claim (or, as relevant, any other claim) unless otherwise indicated or unless it would be evident to one of ordinary skill in the art that a contradiction or inconsistency would arise. Where elements are presented as lists (e.g., in Markush group or similar format), it is to be understood that each subgroup of the elements is also disclosed, and any element(s) can be removed from the group. It should be understood that, in general, where embodiments or aspects are referred to as "comprising" particular elements, features, etc., certain embodiments or aspects "consist," or "consist essentially of," such elements, features, etc. For purposes of simplicity, those embodiments have not in every case been specifically set forth in so many words herein. It should also be understood that any embodiment or aspect can be explicitly excluded from the claims, regardless of whether the specific exclusion is recited in the specification.

Throughout the specification, whenever a polynucleotide or polypeptide is represented by a sequence of letters (e.g., A, C, G, and T, which denote adenosine, cytidine, guanosine, and thymidine, respectively in the case of a polynucleotide), such polynucleotides or polypeptides are presented in 5' to 3' or N-terminus to C-terminus order, from left to right.

Administration: As used herein, the term "administration" typically refers to administration of a composition to a subject or system to achieve delivery of an agent to a subject or system. In some embodiments, an agent is, or is included in, a composition; in some embodiments, an agent is generated through metabolism of a composition or one or more components thereof. Those of ordinary skill in the art will be aware of a variety of routes that may, in appropriate circumstances, be utilized for administration to a subject, for example a human. For example, in some embodiments, administration may be systematic or local. In some embodiments, a systematic administration can be intravenous. In some embodiments, administration can be local. Local administration can involve delivery to cochlear perilymph via, e.g., injection through a round-window membrane or into scala-tympani, a scala-media injection through endolymph, perilymph and/or endolymph following canalostomy. In some embodiments, administration may involve only a single dose. In some embodiments, administration may involve application of a fixed number of doses. In some embodiments, administration may involve dosing that is intermittent (e.g., a plurality of doses separated in time) and/or periodic (e.g., individual doses separated by a common period of time) dosing. In some embodiments, administration may involve continuous dosing (e.g., perfusion) for at least a selected period of time.

Allele: As used herein, the term "allele" refers to one of two or more existing genetic variants of a specific polymorphic genomic locus.

Amelioration: As used herein, the term "amelioration" refers to prevention, reduction or palliation of a state, or improvement of a state of a subject. Amelioration may include, but does not require, complete recovery or complete prevention of a disease, disorder or condition.

Amino acid: In its broadest sense, as used herein, the term "amino acid" refers to any compound and/or substance that can be incorporated into a polypeptide chain, e.g., through formation of one or more peptide bonds. In some embodiments, an amino acid has a general structure, e.g., $H_2N$—C(H)(R)—COOH. In some embodiments, an amino acid is a naturally-occurring amino acid. In some embodiments, an amino acid is a non-natural amino acid; in some embodiments, an amino acid is a D-amino acid; in some embodiments, an amino acid is an L-amino acid. "Standard amino acid" refers to any of the twenty standard L-amino acids commonly found in naturally occurring peptides. "Nonstandard amino acid" refers to any amino acid, other than standard amino acids, regardless of whether it is prepared synthetically or obtained from a natural source. In some embodiments, an amino acid, including a carboxy-and/or amino-terminal amino acid in a polypeptide, can contain a structural modification as compared with general structure as shown above. For example, in some embodiments, an amino acid may be modified by methylation, amidation, acetylation, pegylation, glycosylation, phosphorylation, and/or substitution (e.g., of an amino group, a carboxylic acid group, one or more protons, and/or a hydroxyl group) as compared with a general structure. In some embodiments, such modification may, for example, alter circulating half-life of a polypeptide containing a modified amino acid as compared with one containing an otherwise identical unmodified amino acid. In some embodiments, such modification does not significantly alter a relevant activity of a polypeptide containing a modified amino acid, as compared with one containing an otherwise identical unmodified amino acid.

Approximately or About: As used herein, the terms "approximately" or "about" may be applied to one or more values of interest, including a value that is similar to a stated reference value. In some embodiments, the term "approximately" or "about" refers to a range of values that fall within +10% (greater than or less than) of a stated reference value unless otherwise stated or otherwise evident from context (except where such number would exceed 100% of a possible value). For example, in some embodiments, the term "approximately" or "about" may encompass a range of values that within 10%, 9%, 8%, 7%, 6%, 5%, 4%, 3%, 2%, 1%, or less of a reference value.

Associated: As used herein, the term "associated" describes two events or entities as "associated" with one another, if the presence, level and/or form of one is correlated with that of the other. For example, a particular entity (e.g., polypeptide, genetic signature, metabolite, microbe, etc.) is considered to be associated with a particular disease, disorder, or condition, if its presence, level and/or form correlates with incidence of and/or susceptibility to the disease, disorder, or condition (e.g., across a relevant population). In some embodiments, two or more entities are physically "associated" with one another if they interact, directly or indirectly, so that they are and/or remain in physical proximity with one another. In some embodiments, two or more entities that are physically associated with one another are covalently linked to one another; in some embodiments, two or more entities that are physically associated with one another are not covalently linked to one another but are non-covalently associated, for example by means of hydrogen bonds, van der Waals interaction, hydrophobic interactions, magnetism, and combinations thereof.

Biologically active: As used herein, the term "biologically active" refers to an observable biological effect or result achieved by an agent or entity of interest. For example, in some embodiments, a specific binding interaction is a biological activity. In some embodiments, modulation (e.g., induction, enhancement, or inhibition) of a biological pathway or event is a biological activity. In some embodiments, presence or extent of a biological activity is assessed through detection of a direct or indirect product produced by a biological pathway or event of interest.

Characteristic portion: As used herein, the term "characteristic portion," in the broadest sense, refers to a portion of a substance whose presence (or absence) correlates with presence (or absence) of a particular feature, attribute, or activity of the substance. In some embodiments, a characteristic portion of a substance is a portion that is found in a given substance and in related substances that share a particular feature, attribute or activity, but not in those that do not share the particular feature, attribute or activity. In some embodiments, a characteristic portion shares at least one functional characteristic with the intact substance. For example, in some embodiments, a "characteristic portion" of a protein or polypeptide is one that contains a continuous stretch of amino acids, or a collection of continuous stretches of amino acids, that together are characteristic of a protein or polypeptide. In some embodiments, each such continuous stretch generally contains at least 2, 5, 10, 15, 20, 50, or more amino acids. In general, a characteristic portion of a substance (e.g., of a protein, antibody, etc.) is one that, in addition to a sequence and/or structural identity specified above, shares at least one functional characteristic with the relevant intact substance. In some embodiments, a characteristic portion may be biologically active.

Characteristic sequence: As used herein, the term "characteristic sequence" is a sequence that is found in all members of a family of polypeptides or nucleic acids, and therefore can be used by those of ordinary skill in the art to define members of the family.

Characteristic sequence element: As used herein, the phrase "characteristic sequence element" refers to a sequence element found in a polymer (e.g., in a polypeptide or nucleic acid) that represents a characteristic portion of that polymer. In some embodiments, presence of a characteristic sequence element correlates with presence or level of a particular activity or property of a polymer. In some embodiments, presence (or absence) of a characteristic sequence element defines a particular polymer as a member (or not a member) of a particular family or group of such polymers. A characteristic sequence element typically comprises at least two monomers (e.g., amino acids or nucleotides). In some embodiments, a characteristic sequence element includes at least 2, 3, 4, 5, 6, 7, 8, 9, 10, 11, 12, 13, 14, 15, 20, 25, 30, 35, 40, 45, 50, or more monomers (e.g., contiguously linked monomers). In some embodiments, a characteristic sequence element includes at least first and second stretches of contiguous monomers spaced apart by one or more spacer regions whose length may or may not vary across polymers that share a sequence element.

Combination therapy: As used herein, the term "combination therapy" refers to those situations in which a subject is simultaneously exposed to two or more therapeutic regimens (e.g., two or more therapeutic agents). In some embodiments, two or more agents may be administered simultaneously. In some embodiments, two or more agents may be administered sequentially. In some embodiments, two or more agents may be administered in overlapping dosing regimens.

Comparable: As used herein, the term "comparable" refers to two or more agents, entities, situations, sets of conditions, subjects, populations, etc., that may not be identical to one another but that are sufficiently similar to permit comparison therebetween so that one skilled in the art will appreciate that conclusions may reasonably be drawn based on differences or similarities observed. In some embodiments, comparable sets of agents, entities, situations, sets of conditions, subjects, populations, etc. are characterized by a plurality of substantially identical features and one or a small number of varied features. Those of ordinary skill in the art will understand, in context, what degree of identity is required in any given circumstance for two or more such agents, entities, situations, sets of conditions, subjects, populations, etc. to be considered comparable. For example, those of ordinary skill in the art will appreciate that sets of agents, entities, situations, sets of conditions, subjects, populations, etc. are comparable to one another when characterized by a sufficient number and type of substantially identical features to warrant a reasonable conclusion that differences in results obtained or phenomena observed under or with different sets of circumstances, stimuli, agents, entities, situations, sets of conditions, subjects, populations, etc. are caused by or indicative of the variation in those features that are varied.

Construct: As used herein, the term "construct" refers to a composition including a polynucleotide capable of carrying at least one heterologous polynucleotide. In some embodiments, a construct can be a plasmid, a transposon, a cosmid, an artificial chromosome (e.g., a human artificial chromosome (HAC), a yeast artificial chromosome (YAC), a bacterial artificial chromosome (BAC), or a P1-derived artificial chromosome (PAC)) or a viral construct, and any Gateway® plasmids. A construct can, e.g., include sufficient cis-acting elements for expression; other elements for expression can be supplied by the host primate cell or in an in vitro expression system. A construct may include any genetic element (e.g., a plasmid, a transposon, a cosmid, an artificial chromosome, or a viral construct, etc.) that is capable of replicating when associated with proper control elements. Thus, in some embodiments, "construct" may include a cloning and/or expression construct and/or a viral construct (e.g., an adeno-associated virus (AAV) construct, an adenovirus construct, a lentivirus construct, or a retrovirus construct). As used herein, the term "vector" refers to a construct.

Conservative: As used herein, the term "conservative" refers to instances describing a conservative amino acid substitution, including a substitution of an amino acid residue by another amino acid residue having a side chain R group with similar chemical properties (e.g., charge or hydrophobicity). In general, a conservative amino acid substitution will not substantially change functional properties of interest of a protein, for example, ability of a receptor to bind to a ligand. Examples of groups of amino acids that have side chains with similar chemical properties include:

aliphatic side chains such as glycine (Gly, G), alanine (Ala, A), valine (Val, V), leucine (Leu, L), and isoleucine (Ile, I); aliphatic-hydroxyl side chains such as serine (Ser, S) and threonine (Thr, T); amide-containing side chains such as asparagine (Asn, N) and glutamine (Gln, Q); aromatic side chains such as phenylalanine (Phe, F), tyrosine (Tyr, Y), and tryptophan (Trp, W); basic side chains such as lysine (Lys, K), arginine (Arg, R), and histidine (His, H); acidic side chains such as aspartic acid (Asp, D) and glutamic acid (Glu, E); and sulfur-containing side chains such as cysteine (Cys, C) and methionine (Met, M). Conservative amino acids substitution groups include, for example, valine/leucine/isoleucine (Val/Leu/Ile, V/L/I), phenylalanine/tyrosine (Phe/Tyr, F/Y), lysine/arginine (Lys/Arg, K/R), alanine/valine (Ala/Val, A/V), glutamate/aspartate (Glu/Asp, E/D), and asparagine/glutamine (Asn/Gln, N/Q). In some embodiments, a conservative amino acid substitution can be a substitution of any native residue in a protein with alanine, as used in, for example, alanine scanning mutagenesis. In some embodiments, a conservative substitution is made that has a positive value in the PAM250 log-likelihood matrix disclosed in Gonnet, G. H. et al., 1992, Science 256:1443-1445, which is incorporated herein by reference in its entirety. In some embodiments, a substitution is a moderately conservative substitution wherein the substitution has a nonnegative value in the PAM250 log-likelihood matrix. One skilled in the art would appreciate that a change (e.g., substitution, addition, deletion, etc.) of amino acids that are not conserved between the same protein from different species is less likely to have an effect on the function of a protein and therefore, these amino acids should be selected for mutation. Amino acids that are conserved between the same protein from different species should not be changed (e.g., deleted, added, substituted, etc.), as these mutations are more likely to result in a change in function of a protein.

CONSERVATIVE AMINO ACID SUBSTITUTIONS

| For Amino Acid | Code | Replace With |
|---|---|---|
| Alanine | A | D-ala, Gly, Aib, β-Ala, Acp, L-Cys, D-Cys |
| Arginine | R | D-Arg, Lys, D-Lys, homo-Arg, D-homo-Arg, Met, Ile, D-Met, D-Ile, Orn, D-Orn |
| Asparagine | N | D-Asn, Asp, D-Asp, Glu, D-Glu, Gln, D-Gln |
| Aspartic Acid | D | D-Asp, D-Asn, Asn, Glu, D-Glu, Gln, D-Gln |
| Cysteine | C | D-Cys, S-Me-Cys, Met, D-Met, Thr, D-Thr |
| Glutamine | Q | D-Gln, Asn, D-Asn, Glu, D-Glu, Asp, D-Asp |
| Glutamic Acid | E | D-Glu, D-Asp, Asp, Asn, D-Asn, Gln, D-Gln |
| Glycine | G | Ala, D-Ala, Pro, D-Pro, Aib, β-Ala, Acp |
| Isoleucine | I | D-Ile, Val, D-Val, AdaA, AdaG, Leu, D-Leu, Met, D-Met |
| Leucine | L | D-Leu, Val, D-Val, AdaA, AdaG, Leu, D-Leu, Met, D-Met |
| Lysine | K | D-Lys, Arg, D-Arg, homo-Arg, D-homo-Arg, Met, D-Met, Ile, D-Ile, Orn, D-Orn |
| Methionine | M | D-Met, S-Me-Cys, Ile, D-Ile, Leu, D-Leu, Val, D-Val |
| Phenylalanine | F | D-Phe, Tyr, D-Thr, L-Dopa, His, D-His, Trp, D-Trp, Trans-3,4 or 5-phenylproline, AdaA, AdaG, cis-3,4 or 5-phenylproline, Bpa, D-Bpa |
| Proline | P | D-Pro, L-I-thioazolidine-4-carboxylic acid, D-or-L-1-oxazolidine-4-carboxylic acid (Kauer, U.S. Pat. No. 4,511,390) |
| Serine | S | D-Ser, Thr, D-Thr, allo-Thr, Met, D-Met, Met (O), D-Met (O), L-Cys, D-Cys |
| Threonine | T | D-Thr, Ser, D-Ser, allo-Thr, Met, D-Met, Met (O), D-Met (O), Val, D-Val |
| Tyrosine | Y | D-Tyr, Phe, D-Phe, L-Dopa, His, D-His |
| Valine | V | D-Val, Leu, D-Leu, Ile, D-Ile, Met, D-Met, AdaA, AdaG |

Control: As used herein, the term "control" refers to the art-understood meaning of a "control" being a standard against which results are compared. Typically, controls are used to augment integrity in experiments by isolating variables in order to make a conclusion about such variables. In some embodiments, a control is a reaction or assay that is performed simultaneously with a test reaction or assay to provide a comparator. For example, in one experiment, a "test" (i.e., a variable being tested) is applied. In a second experiment, a "control," the variable being tested is not applied. In some embodiments, a control is a historical control (e.g., of a test or assay performed previously, or an amount or result that is previously known). In some embodiments, a control is or comprises a printed or otherwise saved record. In some embodiments, a control is a positive control. In some embodiments, a control is a negative control.

Determining, measuring, evaluating, assessing, assaying and analyzing: As used herein, the terms "determining," "measuring," "evaluating," "assessing," "assaying," and "analyzing" may be used interchangeably to refer to any form of measurement, and include determining if an element is present or not. These terms include both quantitative and/or qualitative determinations. Assaying may be relative or absolute. For example, in some embodiments, "Assaying for the presence of" can be determining an amount of something present and/or determining whether or not it is present or absent.

Endogenous: In general, as used herein, the term "endogenous" refers to any material originating from within an organism, cell, or tissue.

Engineered: In general, as used herein, the term "engineered" refers to an aspect of having been manipulated by the hand of man. For example, a cell or organism is considered to be "engineered" if it has been manipulated so that its genetic information is altered (e.g., new genetic material not previously present has been introduced, for example by transformation, mating, somatic hybridization, transfection, transduction, or other mechanism, or previously present genetic material is altered or removed, for example by substitution or deletion mutation, or by mating protocols). As is common practice and is understood by those in the art, progeny of an engineered polynucleotide or cell are typically still referred to as "engineered" even though the actual manipulation was performed on a prior entity.

Excipient: As used herein, the term "excipient" refers to an inactive (e.g., non-therapeutic) agent that may be included in a pharmaceutical composition, for example to provide or contribute to a desired consistency or stabilizing effect. In some embodiments, suitable pharmaceutical excipients may include, for example, starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like.

Expression: As used herein, the term "expression" of a nucleic acid sequence refers to generation of any gene product (e.g., transcript, e.g., mRNA, e.g., polypeptide, etc.) from a nucleic acid sequence. In some embodiments, a gene product can be a transcript. In some embodiments, a gene product can be a polypeptide. In some embodiments, expression of a nucleic acid sequence involves one or more of the following: (1) production of an RNA template from a DNA sequence (e.g., by transcription); (2) processing of an RNA transcript (e.g., by splicing, editing, 5' cap formation, and/or 3' end formation); (3) translation of an RNA into a polypeptide or protein; and/or (4) post-translational modification of a polypeptide or protein. In some embodiments, the term "expression" refers to the transcription and/or translation of a particular nucleotide sequence encoding a protein.

Exogenous: As used herein, the term "exogenous" refers to any material introduced from or originating from outside an organism, cell, or tissue that is not produced or does not originate from the same organism, cell, or tissue in which it is being introduced.

Functional: As used herein, the term "functional" describes something that exists in a form in which it exhibits a property and/or activity by which it is characterized. For example, in some embodiments, a "functional" biological molecule is a biological molecule in a form in which it exhibits a property and/or activity by which it is characterized. In some such embodiments, a functional biological molecule is characterized relative to another biological molecule which is non-functional in that the "non-functional" version does not exhibit the same or equivalent property and/or activity as the "functional" molecule. A biological molecule may have one function, two functions (i.e., bifunctional) or many functions (i.e., multifunctional).

Gene: As used herein, the term "gene" refers to a DNA sequence in a chromosome that codes for a gene product (e.g., an RNA product, e.g., a polypeptide product). In some embodiments, a gene includes coding sequence (i.e., sequence that encodes a particular product). In some embodiments, a gene includes non-coding sequence. In some particular embodiments, a gene may include both coding (e.g., exonic) and non-coding (e.g., intronic) sequence. In some embodiments, a gene may include one or more regulatory sequences (e.g., promoters, enhancers, etc.) and/or intron sequences that, for example, may control or impact one or more aspects of gene expression (e.g., cell-type-specific expression, inducible expression, etc.). As used herein, the term "gene" generally refers to a portion of a nucleic acid that encodes a polypeptide or fragment thereof; the term may optionally encompass regulatory sequences, as will be clear from context to those of ordinary skill in the art. This definition is not intended to exclude application of the term "gene" to non-protein-coding expression units but rather to clarify that, in most cases, the term as used in this document refers to a polypeptide-coding nucleic acid. In some embodiments, a gene may encode a polypeptide, but that polypeptide may not be functional, e.g., a gene variant may encode a polypeptide that does not function in the same way, or at all, relative to the wild-type gene. In some embodiments, a gene may encode a transcript which, in some embodiments, may be toxic beyond a threshold level. In some embodiments, a gene may encode a polypeptide, but that polypeptide may not be functional and/or may be toxic beyond a threshold level.

Hearing loss: As used herein, the term "hearing loss" may be used to a partial or total inability of a living organism to hear. In some embodiments, hearing loss may be acquired. In some embodiments, hearing loss may be hereditary. In some embodiments, hearing loss may be genetic. In some embodiments, hearing loss may be as a result of disease or trauma (e.g., physical trauma, treatment with one or more agents resulting in hearing loss, etc.). In some embodiments, hearing loss may be due to one or more known genetic causes and/or syndromes. In some embodiments, hearing loss may be of unknown etiology. In some embodiments, hearing loss may or may not be mitigated by use of hearing aids or other treatments.

Heterologous: As used herein, the term "heterologous" may be used in reference to one or more regions of a particular molecule as compared to another region and/or another molecule. For example, in some embodiments, heterologous polypeptide domains, refers to the fact that polypeptide domains do not naturally occur together (e.g., in the same polypeptide). For example, in fusion proteins generated by the hand of man, a polypeptide domain from one polypeptide may be fused to a polypeptide domain from a different polypeptide. In such a fusion protein, two polypeptide domains would be considered "heterologous" with respect to each other, as they do not naturally occur together.

Identity: As used herein, the term "identity" refers to overall relatedness between polymeric molecules, e.g., between nucleic acid molecules (e.g., DNA molecules and/or RNA molecules) and/or between polypeptide molecules. In some embodiments, polymeric molecules are considered to be "substantially identical" to one another if their sequences are at least 25%, 30%, 35%, 40%, 45%, 50%, 55%, 60%, 65%, 70%, 75%, 80%, 85%, 90%, 95%, or 99% identical. Calculation of percent identity of two nucleic acid or polypeptide sequences, for example, can be performed by aligning two sequences for optimal comparison purposes (e.g., gaps can be introduced in one or both of a first and a second sequences for optimal alignment and non-identical sequences can be disregarded for comparison purposes). In some embodiments, a length of a sequence aligned for comparison purposes is at least 30%, at least 40%, at least 50%, at least 60%, at least 70%, at least 80%, at least 90%, at least 95%, or substantially 100% of length of a reference sequence; nucleotides at corresponding positions are then compared. When a position in the first sequence is occupied by the same residue (e.g., nucleotide or amino acid) as a corresponding position in the second sequence, then the two molecules (i.e., first and second) are identical at that position. Percent identity between two sequences is a function of the number of identical positions shared by the two sequences being compared, taking into account the number of gaps, and the length of each gap, which needs to be introduced for optimal alignment of the two sequences. Comparison of sequences and determination of percent identity between two sequences can be accomplished using a mathematical algorithm. For example, percent identity between two nucleotide sequences can be determined using the algorithm of Meyers and Miller (CABIOS, 1989, 4:11-17, which is herein incorporated by reference in its entirety), which has been incorporated into the ALIGN program (version 2.0). In some embodiments, nucleic acid sequence comparisons made with the ALIGN program use a PAM120 weight residue table, a gap length penalty of 12 and a gap penalty of 4.

Improve, increase, enhance, inhibit or reduce: As used herein, the terms "improve," "increase," "enhance," "inhibit," "reduce," or grammatical equivalents thereof, indicate values that are relative to a baseline or other reference measurement. In some embodiments, a value is statistically significantly difference that a baseline or other reference measurement. In some embodiments, an appropriate reference measurement may be or comprise a measurement in a particular system (e.g., in a single individual) under otherwise comparable conditions absent presence of (e.g., prior to and/or after) a particular agent or treatment, or in presence of an appropriate comparable reference agent. In some embodiments, an appropriate reference measurement may be or comprise a measurement in comparable system known or expected to respond in a particular way, in presence of the relevant agent or treatment. In some embodiments, an appropriate reference is a negative reference; in some embodiments, an appropriate reference is a positive reference.

Isolated: As used herein, the term "isolated" means altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

Nucleic acid: As used herein, the term "nucleic acid", in its broadest sense, refers to any compound and/or substance that is or can be incorporated into an oligonucleotide chain. In some embodiments, a nucleic acid is a compound and/or substance that is or can be incorporated into an oligonucleotide chain via a phosphodiester linkage. As will be clear from context, in some embodiments, "nucleic acid" refers to an individual nucleic acid residue (e.g., a nucleotide and/or nucleoside); in some embodiments, "nucleic acid" refers to an oligonucleotide chain comprising individual nucleic acid residues. In some embodiments, a "nucleic acid" is or comprises RNA; in some embodiments, a "nucleic acid" is or comprises DNA. In some embodiments, a nucleic acid is, comprises, or consists of one or more natural nucleic acid residues. In some embodiments, a nucleic acid is, comprises, or consists of one or more nucleic acid analogs. In some embodiments, a nucleic acid analog differs from a nucleic acid in that it does not utilize a phosphodiester backbone. Alternatively or additionally, in some embodiments, a nucleic acid has one or more phosphorothioate and/or 5'-N-phosphoramidite linkages rather than phosphodiester bonds. In some embodiments, a nucleic acid is, comprises, or consists of one or more natural nucleosides (e.g., adenosine, thymidine, guanosine, cytidine, uridine, deoxyadenosine, deoxythymidine, deoxy guanosine, and deoxycytidine). In some embodiments, a nucleic acid is, comprises, or consists of one or more nucleoside analogs (e.g., 2-aminoadenosine, 2-thiothymidine, inosine, pyrrolo-pyrimidine, 3-methyl adenosine, 5-methylcytidine, C-5 propynyl-cytidine, C-5 propynyl-uridine, 2-aminoadenosine, C5-bromouridine, C5-fluorouridine, C5-iodouridine, C5-propynyl-uridine, C5-propynyl-cytidine, C5-methylcytidine, 2-aminoadenosine, 7-deazaadenosine, 7-deazaguanosine, 8-oxoadenosine, 8-oxoguanosine, 0 (6)-methylguanine, 2-thiocytidine, methylated bases, intercalated bases, and combinations thereof). In some embodiments, a nucleic acid comprises one or more modified sugars (e.g., 2'-fluororibose, ribose, 2'-deoxyribose, arabinose, and hexose) as compared with those in natural nucleic acids. In some embodiments, a nucleic acid has a nucleotide sequence that encodes a functional gene product such as an RNA or protein. In some embodiments, a nucleic acid includes one or more introns. In some embodiments, nucleic acids are prepared by one or more of isolation from a natural source, enzymatic synthesis by polymerization based on a complementary template (in vivo or in vitro), reproduction in a recombinant cell or system, and chemical synthesis. In some embodiments, a nucleic acid is at least 3, 4, 5, 6, 7, 8, 9, 10, 15, 20, 25, 30, 35, 40, 45, 50, 55, 60, 65, 70, 75, 80, 85, 90, 95, 100, 1 10, 120, 130, 140, 150, 160, 170, 180, 190, 20, 225, 250, 275, 300, 325, 350, 375, 400, 425, 450, 475, 500, 600, 700, 800, 900, 1000, 1500, 2000, 2500, 3000, 3500, 4000, 4500, 5000 or more residues long. In some embodiments, a nucleic acid is partly or wholly single stranded; in some embodiments, a nucleic acid is partly or wholly double stranded. In some embodiments, a nucleic acid has a nucleotide sequence comprising at least one element that encodes, or is complementary to a sequence that encodes, a polypeptide. In some embodiments, a nucleic acid has enzymatic activity. In some embodiments, the term "nucleic acid" or "polynucleotide" refers to deoxyribonucleic acid (DNA) or ribonucleic acid (RNA), or a combination thereof, in either single- or double-stranded form. Unless specifically limited, the term encompasses nucleic acids containing known analogues of natural nucleotides that have similar binding properties as the reference nucleotides. Unless otherwise indicated, a particular nucleic acid sequence also implicitly encompasses complementary sequences as well as the sequence explicitly indicated. In some embodiments of any of the nucleic acids described herein, the nucleic acid is DNA. In some embodiments of any of the nucleic acids described herein, the nucleic acid is RNA.

Operably linked: As used herein, refers to a juxtaposition wherein the components described are in a relationship permitting them to function in their intended manner. A control element "operably linked" to a functional element is associated in such a way that expression and/or activity of the functional element is achieved under conditions compatible with the control element. In some embodiments, "operably linked" control elements are contiguous (e.g., covalently linked) with coding elements of interest; in some embodiments, control elements act in trans to or otherwise at a from the functional element of interest. In some embodiments, "operably linked" refers to functional linkage between a regulatory sequence and a heterologous nucleic acid sequence resulting in expression of the latter. For example, a first nucleic acid sequence is operably linked with a second nucleic acid sequence when the first nucleic acid sequence is placed in a functional relationship with the second nucleic acid sequence. In some embodiments, for example, a functional linkage may include transcriptional control. For instance, a promoter is operably linked to a coding sequence if the promoter affects the transcription or expression of the coding sequence. Operably linked DNA sequences can be contiguous with each other and, e.g., where necessary to join two protein coding regions, are in the same reading frame.

Pharmaceutical composition: As used herein, the term "pharmaceutical composition" refers to a composition in which an active agent is formulated together with one or more pharmaceutically acceptable carriers. In some embodiments, an active agent is present in unit dose amount appropriate for administration in a therapeutic regimen that shows a statistically significant probability of achieving a predetermined therapeutic effect when administered to a relevant population. In some embodiments, a pharmaceutical composition may be specially formulated for administration in solid or liquid form, including those adapted for, e.g., administration, for example, an injectable formulation that is, e.g., an aqueous or non-aqueous solution or suspension or a liquid drop designed to be administered into an ear canal. In some embodiments, a pharmaceutical composition may be formulated for administration via injection either in a particular organ or compartment, e.g., directly into an ear, or systemic, e.g., intravenously. In some embodiments, a formulation may be or comprise drenches (aqueous or non-aqueous solutions or suspensions), tablets, boluses, powders, granules, pastes, capsules, powders, etc. In some embodiments, an active agent may be or comprise an isolated, purified, or pure compound.

Pharmaceutically acceptable: As used herein, the term "pharmaceutically acceptable" which, for example, may be used in reference to a carrier, diluent, or excipient used to formulate a pharmaceutical composition as disclosed herein, means that a carrier, diluent, or excipient is compatible with other ingredients of a composition and not deleterious to a recipient thereof.

Pharmaceutically acceptable carrier: As used herein, the term "pharmaceutically acceptable carrier" means a pharmaceutically-acceptable material, composition or vehicle, such as a liquid or solid filler, diluent, excipient, or solvent encapsulating material, involved in carrying or transporting a subject compound from one organ, or portion of a body, to another organ, or portion of a body. Each carrier must be is "acceptable" in the sense of being compatible with other ingredients of a formulation and not injurious to a patient. Some examples of materials which can serve as pharmaceutically-acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; pH buffered solutions; polyesters, polycarbonates and/or polyanhydrides; and other non-toxic compatible substances employed in pharmaceutical formulations.

Polyadenylation: As used herein, "polyadenylation" refers to the covalent linkage of a polyadenylyl moiety, or its modified variant, to a messenger RNA molecule. In eukaryotic organisms, most messenger RNA (mRNA) molecules are polyadenylated at the 3' end. In some embodiments, a 3' poly(A) tail is a long sequence of adenine nucleotides (e.g., 50, 60, 70, 100, 200, 500, 1000, 2000, 3000, 4000, or 5000) added to the pre-mRNA through the action of an enzyme, polyadenylate polymerase. In higher eukaryotes, a poly(A) tail can be added onto transcripts that contain a specific sequence, the polyadenylation signal or "poly(A) sequence." A poly(A) tail and proteins bound to it aid in protecting mRNA from degradation by exonucleases. Polyadenylation can be affect transcription termination, export of the mRNA from the nucleus, and translation. Typically, polyadenylation occurs in the nucleus immediately after transcription of DNA into RNA, but additionally can also occur later in the cytoplasm. After transcription has been terminated, the mRNA chain can be cleaved through the action of an endonuclease complex associated with RNA polymerase. The cleavage site can be characterized by the presence of the base sequence AAUAAA near the cleavage site. After mRNA has been cleaved, adenosine residues can be added to the free 3' end at the cleavage site. As used herein, a "poly(A) sequence" is a sequence that triggers the endonuclease cleavage of an mRNA and the additional of a series of adenosines to the 3' end of the cleaved mRNA.

Polypeptide: As used herein, the term "polypeptide" refers to any polymeric chain of residues (e.g., amino acids) that are typically linked by peptide bonds. In some embodiments, a polypeptide has an amino acid sequence that occurs in nature. In some embodiments, a polypeptide has an amino acid sequence that does not occur in nature. In some embodiments, a polypeptide has an amino acid sequence that is engineered in that it is designed and/or produced through action of the hand of man. In some embodiments, a polypeptide may comprise or consist of natural amino acids, non-natural amino acids, or both. In some embodiments, a polypeptide may include one or more pendant groups or other modifications, e.g., modifying or attached to one or more amino acid side chains, at a polypeptide's N-terminus, at a polypeptide's C-terminus, or any combination thereof. In some embodiments, such pendant groups or modifications may be acetylation, amidation, lipidation, methylation, pegylation, etc., including combinations thereof. In some embodiments, polypeptides may contain L-amino acids, D-amino acids, or both and may contain any of a variety of amino acid modifications or analogs known in the art. In some embodiments, useful modifications may be or include, e.g., terminal acetylation, amidation, methylation, etc. In some embodiments, a protein may comprise natural amino acids, non-natural amino acids, synthetic amino acids, and combinations thereof. The term "peptide" is generally used to refer to a polypeptide having a length of less than about 100 amino acids, less than about 50 amino acids, less than 20 amino acids, or less than 10 amino acids. In some embodiments, a protein is antibodies, antibody fragments, biologically active portions thereof, and/or characteristic portions thereof.

Polynucleotide: As used herein, the term "polynucleotide" refers to any polymeric chain of nucleic acids. In some embodiments, a polynucleotide is or comprises RNA; in some embodiments, a polynucleotide is or comprises DNA. In some embodiments, a polynucleotide is, comprises, or consists of one or more natural nucleic acid residues. In some embodiments, a polynucleotide is, comprises, or consists of one or more nucleic acid analogs. In some embodiments, a polynucleotide analog differs from a nucleic acid in that it does not utilize a phosphodiester backbone. Alternatively or additionally, in some embodiments, a polynucleotide has one or more phosphorothioate and/or 5'-N-phosphoramidite linkages rather than phosphodiester bonds. In some embodiments, a polynucleotide is, comprises, or consists of one or more natural nucleosides (e.g., adenosine, thymidine, guanosine, cytidine, uridine, deoxyadenosine, deoxythymidine, deoxy guanosine, and deoxycytidine). In some embodiments, a polynucleotide is, comprises, or consists of one or more nucleoside analogs (e.g., 2-aminoadenosine, 2-thiothymidine, inosine, pyrrolo-pyrimidine, 3-methyl adenosine, 5-methylcytidine, C-5 propynyl-cytidine, C-5 propynyl-uridine, 2-aminoadenosine, C5-bromouridine, C5-fluorouridine, C5-iodouridine, C5-propynyl-uridine, C5-propynyl-cytidine, C5-methylcytidine, 2-aminoadenosine, 7-deazaadenosine, 7-deazaguanosine, 8-oxoadenosine, 8-oxoguanosine, 0 (6)-methylguanine, 2-thiocytidine, methylated bases, intercalated bases, and combinations thereof). In some embodiments, a polynucleotide comprises one or more modified sugars (e.g., 2'-fluororibose, ribose, 2'-deoxyribose, arabinose, and hexose) as compared with those in natural nucleic acids. In some embodiments, a polynucleotide has a nucleotide sequence that encodes a functional gene product such as an RNA or protein. In some embodiments, a polynucleotide includes one or more introns. In some embodiments, a polynucleotide is prepared by one or more of isolation from a natural source, enzymatic synthesis by polymerization based on a complementary template (in vivo or in vitro), reproduction in a recombinant cell or system, and chemical synthesis. In some embodiments, a polynucleotide is at least 3, 4, 5, 6, 7, 8, 9, 10, 15, 20, 25, 30, 35, 40, 45, 50, 55, 60, 65, 70, 75, 80, 85, 90, 95, 100, 1 10, 120, 130, 140, 150, 160, 170, 180, 190, 20, 225, 250, 275, 300, 325, 350, 375, 400, 425, 450, 475, 500, 600, 700, 800, 900, 1000, 1500, 2000, 2500, 3000, 3500, 4000, 4500, 5000 or more residues long. In some embodiments, a polynucleotide is partly or wholly single stranded;

in some embodiments, a polynucleotide is partly or wholly double stranded. In some embodiments, a polynucleotide has a nucleotide sequence comprising at least one element that encodes, or is the complement of a sequence that encodes, a polypeptide. In some embodiments, a polynucleotide has enzymatic activity. Unless otherwise specified, a "nucleotide sequence encoding an amino acid sequence" includes all nucleotide sequences that are degenerate versions of each other and thus encode the same amino acid sequence.

Modifications can be introduced into a nucleotide sequence by standard techniques known in the art, such as site-directed mutagenesis and PCR-mediated mutagenesis. Conservative amino acid substitutions are ones in which the amino acid residue is replaced with an amino acid residue having a similar side chain. Families of amino acid residues having similar side chains have been defined in the art. These families include amino acids with basic side chains (e.g., lysine, arginine, and histidine), acidic side chains (e.g., aspartic acid and glutamic acid), uncharged polar side chains (e.g., glycine, asparagine, glutamine, serine, threonine, tyrosine, cysteine, and tryptophan), nonpolar side chains (e.g., alanine, valine, leucine, isoleucine, proline, phenylalanine, and methionine), beta-branched side chains (e.g., threonine, valine, and isoleucine), and aromatic side chains (e.g., tyrosine, phenylalanine, tryptophan, and histidine).

Protein: As used herein, the term "protein" refers to a polypeptide (i.e., a string of at least two amino acids linked to one another by peptide bonds). Proteins may include moieties other than amino acids (e.g., may be glycoproteins, proteoglycans, etc.) and/or may be otherwise processed or modified. Those of ordinary skill in the art will appreciate that a "protein" can be a complete polypeptide chain as produced by a cell (with or without a signal sequence), or can be a characteristic portion thereof. Those of ordinary skill will appreciate that a protein can sometimes include more than one polypeptide chain, for example linked by one or more disulfide bonds or associated by other means.

Recombinant: As used herein, the term "recombinant" is intended to refer to polypeptides that are designed, engineered, prepared, expressed, created, manufactured, and/or or isolated by recombinant means, such as polypeptides expressed using a recombinant expression construct transfected into a host cell; polypeptides isolated from a recombinant, combinatorial human polypeptide library; polypeptides isolated from an animal (e.g., a mouse, rabbit, sheep, fish, etc.) that is transgenic for or otherwise has been manipulated to express a gene or genes, or gene components that encode and/or direct expression of the polypeptide or one or more component(s), portion(s), element(s), or domain (s) thereof; and/or polypeptides prepared, expressed, created or isolated by any other means that involves splicing or ligating selected nucleic acid sequence elements to one another, chemically synthesizing selected sequence elements, and/or otherwise generating a nucleic acid that encodes and/or directs expression of a polypeptide or one or more component(s), portion(s), element(s), or domain(s) thereof. In some embodiments, one or more of such selected sequence elements is found in nature. In some embodiments, one or more of such selected sequence elements is designed in silico. In some embodiments, one or more such selected sequence elements results from mutagenesis (e.g., in vivo or in vitro) of a known sequence element, e.g., from a natural or synthetic source such as, for example, in the germline of a source organism of interest (e.g., of a human, a mouse, etc).

Reference: As used herein, the term "reference" describes a standard or control relative to which a comparison is performed. For example, in some embodiments, an agent, animal, individual, population, sample, sequence or value of interest is compared with a reference or control agent, animal, individual, population, sample, sequence or value. In some embodiments, a reference or control is tested and/or determined substantially simultaneously with the testing or determination of interest. In some embodiments, a reference or control is a historical reference or control, optionally embodied in a tangible medium. Typically, as would be understood by those skilled in the art, a reference or control is determined or characterized under comparable conditions or circumstances to those under assessment. Those skilled in the art will appreciate when sufficient similarities are present to justify reliance on and/or comparison to a particular possible reference or control. In some embodiments, a reference is a negative control reference; in some embodiments, a reference is a positive control reference.

Regulatory Element: As used herein, the term "regulatory element" or "regulatory sequence" refers to non-coding regions of DNA that regulate, in some way, expression of one or more particular genes. In some embodiments, such genes are apposed or "in the neighborhood" of a given regulatory element. In some embodiments, such genes are located quite far from a given regulatory element. In some embodiments, a regulatory element impairs or enhances transcription of one or more genes. In some embodiments, a regulatory element may be located in cis to a gene being regulated. In some embodiments, a regulatory element may be located in trans to a gene being regulated. For example, in some embodiments, a regulatory sequence refers to a nucleic acid sequence which is regulates expression of a gene product operably linked to a regulatory sequence. In some such embodiments, this sequence may be an enhancer sequence and other regulatory elements which regulate expression of a gene product.

Sample: As used herein, the term "sample" typically refers to an aliquot of material obtained or derived from a source of interest. In some embodiments, a source of interest is a biological or environmental source. In some embodiments, a source of interest may be or comprise a cell or an organism, such as a microbe (e.g., virus), a plant, or an animal (e.g., a human). In some embodiments, a source of interest is or comprises biological tissue or fluid. In some embodiments, a biological tissue or fluid may be or comprise amniotic fluid, aqueous humor, ascites, bile, bone marrow, blood, breast milk, cerebrospinal fluid, cerumen, chyle, chime, ejaculate, endolymph, exudate, feces, gastric acid, gastric juice, lymph, mucus, pericardial fluid, perilymph, peritoneal fluid, pleural fluid, pus, rheum, saliva, sebum, semen, serum, smegma, sputum, synovial fluid, sweat, tears, urine, vaginal secretions, vitreous humour, vomit, and/or combinations or component(s) thereof. In some embodiments, a biological fluid may be or comprise an intracellular fluid, an extracellular fluid, an intravascular fluid (blood plasma), an interstitial fluid, a lymphatic fluid, and/or a transcellular fluid. In some embodiments, a biological fluid may be or comprise a plant exudate. In some embodiments, a biological tissue or sample may be obtained, for example, by aspirate, biopsy (e.g., fine needle or tissue biopsy), swab (e.g., oral, nasal, skin, or vaginal swab), scraping, surgery, washing or lavage (e.g., bronchioalveolar, ductal, nasal, ocular, oral, uterine, vaginal, or other washing or lavage). In some embodiments, a biological sample is or comprises cells obtained from an individual. In some embodiments, a sample is a "primary sample" obtained directly from a source of interest by any appropriate means. In some embodiments, as will be clear from context, the term "sample" refers to a preparation that is obtained by processing (e.g., by removing one or more components of and/or by adding one or more agents to) a primary sample. For example, filtering using a semi-permeable membrane. Such a "processed sample" may comprise, for example nucleic acids or proteins extracted from a sample or obtained by subjecting a primary sample to one or more techniques such as amplification or reverse transcription of nucleic acid, isolation and/or purification of certain components, etc.

Subject: As used herein, the term "subject" refers an organism, typically a mammal (e.g., a human, in some embodiments including prenatal human forms). In some embodiments, a subject is suffering from a relevant disease, disorder or condition. In some embodiments, a subject is susceptible to a disease, disorder, or condition. In some embodiments, a subject displays one or more symptoms or characteristics of a disease, disorder or condition. In some embodiments, a subject does not display any symptom or characteristic of a disease, disorder, or condition. In some embodiments, a subject is someone with one or more features characteristic of susceptibility to or risk of a disease, disorder, or condition. In some embodiments, a subject is a patient. In some embodiments, a subject is an individual to whom diagnosis and/or therapy is and/or has been administered. In some embodiments, the subject is a rodent (e.g., a rat or mouse), a rabbit, a sheep, a goat, a pig, a dog, a cat, a non-human primate, or a human. In some embodiments, the subject has or is at risk of hearing loss and/or vision loss. In some embodiments, the subject has been previously identified as having a mutation in a secreted target gene (e.g., a NDP gene or a HSPA1A gene). In some embodiments, the subject has been identified as having a mutation in a secreted target gene (e.g., a NDP gene or a HSPA1A gene) and has been diagnosed with hearing loss and/or vision loss. In some embodiments, the subject has been identified as having hearing loss and/or vision loss.

Substantially: As used herein, the term "substantially" refers to a qualitative condition of exhibiting total or near-total extent or degree of a characteristic or property of interest. One of ordinary skill in the art will understand that biological and chemical phenomena rarely, if ever, go to completion and/or proceed to completeness or achieve or avoid an absolute result. The term "substantially" is therefore used herein to capture a potential lack of completeness inherent in many biological and chemical phenomena.

Transfected, Transformed, or Transduced: As used herein, the term "transfected," "transformed," or "transduced" refers to a process by which exogenous nucleic acid is transferred or introduced into a cell. A "transfected," "transformed," or "transduced" mammalian cell is one that has been transfected, transformed or transduced with exogenous nucleic acid.

Transient expression: As used herein, the term "transient expression" refers to the expression of a non-integrated coding sequence for a short period of time (e.g., hours or days). The coding sequence that is transiently expressed in a cell (e.g., a mammalian cell) is lost upon multiple rounds of cell division.

Treatment: As used herein, the term "treatment" (also "treat" or "treating") refers to any administration of a therapy that partially or completely alleviates, ameliorates, eliminates, reverses, relieves, inhibits, delays onset of, reduces severity of, and/or reduces incidence of one or more symptoms, features, and/or causes of a particular disease, disorder, and/or condition. In some embodiments, such treatment may be of a subject who does not exhibit signs of the relevant disease, disorder and/or condition and/or of a subject who exhibits only early signs of the disease, disorder, and/or condition. Alternatively, or additionally, such treatment may be of a subject who exhibits one or more established signs of the relevant disease, disorder and/or condition. In some embodiments, treatment may be of a subject who has been diagnosed as suffering from the relevant disease, disorder, and/or condition. In some embodiments, treatment may be of a subject known to have one or more susceptibility factors that are statistically correlated with increased risk of development of a given disease, disorder, and/or condition.

Therapeutically effective: As used herein, a treatment is "therapeutically effective" when it results in a reduction in one or more of the number, severity, and frequency of one or more symptoms of a disease state (e.g., hearing loss or vision loss) in a subject (e.g., a human). In some embodiments, a therapeutically effective amount of a composition can result in an increase in the expression level of an active secreted target protein (e.g., an active NDP protein (e.g., a wildtype, full-length NDP protein or a variant of a NDP protein that has the desired activity) or an active HSPA1A protein (e.g., a wildtype, full-length HSPA1A protein or a variant of a HSPA1A protein that has the desired activity)) (e.g., as compared to the expression level prior to treatment with the composition). In some embodiments, a therapeutically effective amount of a composition can result in an increase in the expression level of an active secreted target protein (e.g., an active NDP protein (e.g., a wildtype, full-length NDP protein or an active variant) or an active HSPA1A protein (e.g., a wildtype, full-length HSPA1A protein or a variant of a HSPA1A protein that has the desired activity) or an active heat shock protein (e.g., a wildtype, full-length heat shock protein or a variant of a heat shock protein that has the desired activity)) in a target cell (e.g., a cochlear inner hair cell). In some embodiments, a therapeutically effective amount of a composition can result in an increase in the expression level of an active secreted target protein (e.g., an active NDP protein (e.g., a wildtype, full-length NDP protein or active variant) or an active HSPA1A protein (e.g., a wildtype, full-length HSPA1A protein or a variant of a HSPA1A protein that has the desired activity) or an active heat shock protein (e.g., a wildtype, full-length heat shock protein or a variant of a heat shock protein that has the desired activity)), and/or an increase in one or more activities of a secreted target protein (e.g., a NDP protein or a HSPA1A protein or a Hsp40 protein) in a target cell (e.g., as compared to a reference level, such as the level(s) in a subject prior to treatment, the level(s) in a subject having a mutation in a NDP gene or a HSPA1A gene, or the level(s) in a subject or a population of subjects having hearing loss and/or vision loss).

Variant: As used herein, the term "variant" refers to a version of something, e.g., a gene sequence, that is different, in some way, from another version. To determine if something is a variant, a reference version is typically chosen and a variant is different relative to that reference version. In some embodiments, a variant can have the same or a different (e.g., increased or decreased) level of activity or functionality than a wild type sequence. For example, in some embodiments, a variant can have improved functionality as compared to a wild-type sequence if it is, e.g., codon-optimized to resist degradation, e.g., by an inhibitory nucleic acid, e.g., miRNA. Such a variant is referred to herein as a gain-of-function variant. In some embodiments, a variant has a reduction or elimination in activity or functionality or a change in activity that results in a negative outcome (e.g., increased electrical activity resulting in chronic depolarization that leads to cell death). Such a variant is referred to herein as a loss-of-function variant. For example, in some embodiments, a NDP gene sequence is a wild-type sequence, which encodes a functional protein and exists in a majority of members of species with genomes containing the NDP gene. In some such embodiments, a gain-of-function variant can be a gene sequence of NDP that contains one or more nucleotide differences relative to a wild-type NDP gene sequence. In some embodiments, a gain-of-function variant is a codon-optimized sequence which encodes a transcript or polypeptide that may have improved properties (e.g., less susceptibility to degradation, e.g., less susceptibility to miRNA mediated degradation) than its corresponding wild type (e.g., non-codon optimized) version. In some embodiments, a loss-of-function variant has one or more changes that result in a transcript or polypeptide that is defective in some way (e.g., decreased function, non-functioning) relative to the wild type transcript and/or polypeptide. For example, in some embodiments, a mutation in a NDP sequence results in a non-functional or otherwise defective NDP protein. As another example, in some embodiments, a HSPA1A gene sequence is a wild-type sequence, which encodes a functional protein and exists in a majority of members of species with genomes containing the HSPA1A gene. In some such embodiments, a gain-of-function variant can be a gene sequence of HSPA1A that contains one or more nucleotide differences relative to a wild-type HSPA1A gene sequence. As another example, in some embodiments, a DNAJB1 gene sequence is a wild-type sequence, which encodes a functional protein and exists in a majority of members of species with genomes containing the DNAJB1 gene. In some such embodiments, a gain-of-function variant can be a gene sequence of DNAJB1 that contains one or more nucleotide differences relative to a wild-type DNAJB1 gene sequence. As another example, in some embodiments, a DNAJB5 gene sequence is a wild-type sequence, which encodes a functional protein and exists in a majority of members of species with genomes containing the DNAJB5 gene. In some such embodiments, a gain-of-function variant can be a gene sequence of DNAJB5 that contains one or more nucleotide differences relative to a wild-type DNAJB5 gene sequence. In some embodiments, a gain-of-function variant is a codon-optimized sequence which encodes a transcript or polypeptide that may have improved properties (e.g., less susceptibility to degradation, e.g., less susceptibility to miRNA mediated degradation) than its corresponding wild type (e.g., non-codon optimized) version. In some embodiments, a loss-of-function variant has one or more changes that result in a transcript or polypeptide that is defective in some way (e.g., decreased function, non-functioning) relative to the wild type transcript and/or polypeptide. For example, in some embodiments, a mutation in a HSPA1A sequence results in a non-functional or otherwise defective HSPA1A protein.

Unless otherwise defined, all technical and scientific terms used herein have the same meaning as commonly understood by one of ordinary skill in the art to which this disclosure belongs. Methods and materials are described herein for use in the present disclosure; other suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the disclosure will be apparent from the following detailed description and figures, and from the claims.

DETAILED DESCRIPTION OF CERTAIN EMBODIMENTS

Hearing Loss

Figures 1, 2, 3, 4, 5:
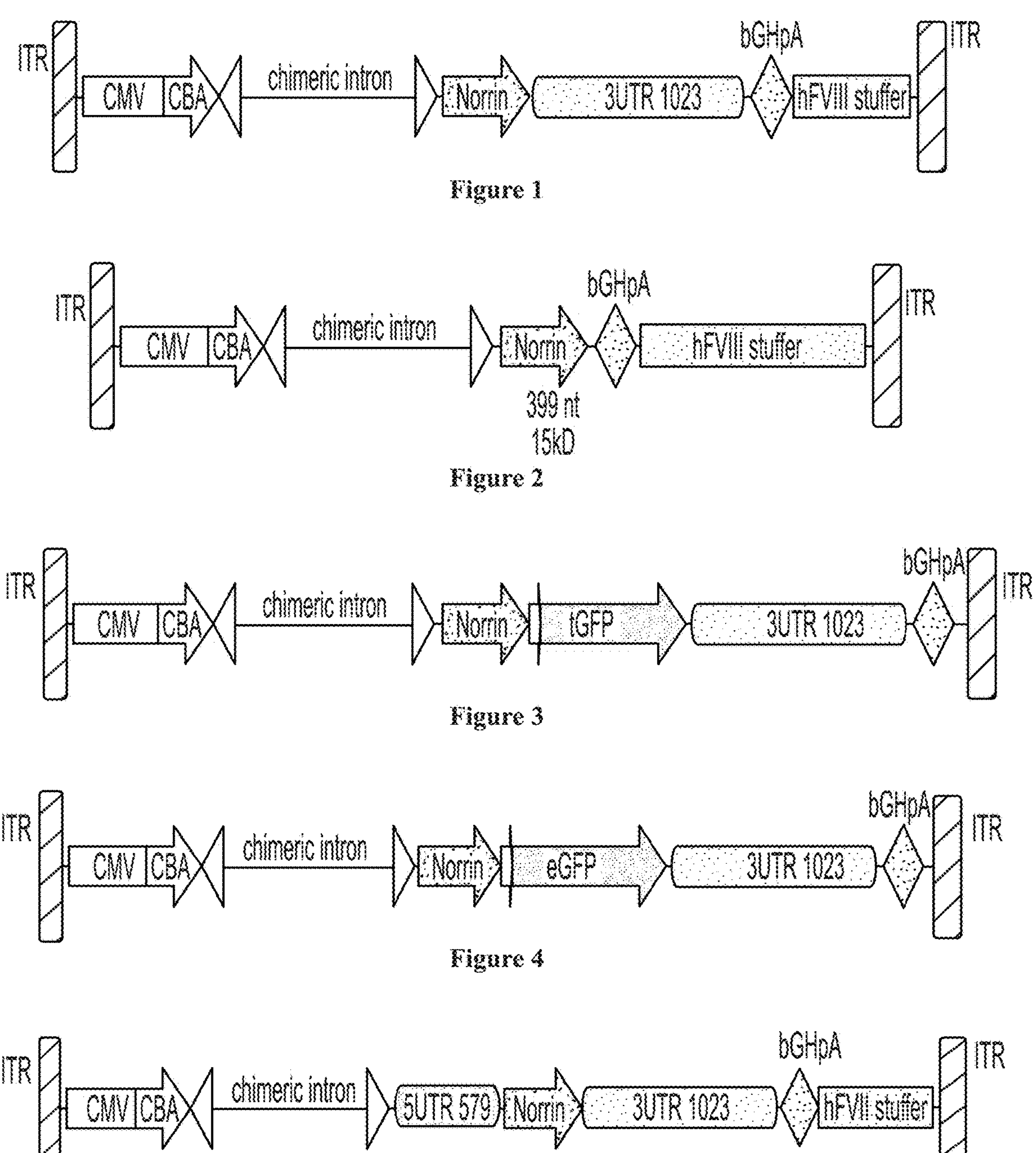
FIG. 1 is an exemplary nucleic acid vector, Construct 1 (SEQ ID NO: 9; 4185 bp) that includes an inverted terminal repeat (ITR) sequence (SEQ ID NO: 16), a CMV sequence (SEQ ID NO: 17), a CBA sequence (SEQ ID NO: 18), a chimeric intron sequence (SEQ ID NO: 19), a Norrin coding sequence (SEQ ID NO: 20), a 3' untranslated region (UTR)-1023 sequence (SEQ ID NO: 22), a bovine growth hormone (bGH) poly(A) sequence (SEQ ID NO: 23), a hFVIII stuffer sequence (SEQ ID NO: 24), and an ITR sequence (SEQ ID NO: 30).
FIG. 2 is an exemplary nucleic acid vector, Construct 2 (SEQ ID NO: 10; 3662 bp) that includes an ITR sequence (SEQ ID NO: 16), a CMV sequence (SEQ ID NO: 17), a CBA sequence (SEQ ID NO: 18), a chimeric intron sequence (SEQ ID NO: 19), a Norrin coding sequence (SEQ ID NO: 20), a bGH poly(A) sequence (SEQ ID NO: 23), a hFVIII stuffer sequence (SEQ ID NO: 25), and an ITR sequence (SEQ ID NO: 30).
FIG. 3 is an exemplary nucleic acid vector, Construct 3 (SEQ ID NO: 11, 4444 bp), that includes an ITR sequence (SEQ ID NO: 16), a CMV sequence (SEQ ID NO: 17), a CBA sequence (SEQ ID NO: 18), a chimeric intron sequence (SEQ ID NO: 19), a Norrin coding sequence (SEQ ID NO: 21), a T2A sequence (SEQ ID NO: 26), a tGFP sequence (SEQ ID NO: 27), a 3' UTR-1023 sequence (SEQ ID NO: 22), a bGH poly(A) sequence (SEQ ID NO:23), and an ITR sequence (SEQ ID NO: 30).
FIG. 4 is an exemplary nucleic acid vector, Construct 4 (SEQ ID NO: 12, 4468 bp), that includes an ITR sequence (SEQ ID NO: 16), a CMV sequence (SEQ ID NO: 17), a CBA sequence (SEQ ID NO: 18), a chimeric intron sequence (SEQ ID NO: 19), a Norrin coding sequence (SEQ ID NO: 21), a T2A sequence (SEQ ID NO: 26), an eGFP sequence (SEQ ID NO: 28), a 3' UTR-1023 sequence (SEQ ID NO: 22), a bGH poly(A) sequence (SEQ ID NO: 23), and an ITR sequence (SEQ ID NO: 30).
FIG. 5 is an exemplary nucleic acid vector, Construct 5 (SEQ ID NO: 13, 4764 bp), that includes an ITR sequence (SEQ ID NO: 16), a CMV sequence (SEQ ID NO: 17), a CBA sequence (SEQ ID NO: 18), a chimeric intron sequence (SEQ ID NO: 19), a 5'UTR-579 sequence (SEQ ID NO: 31), a Norrin coding sequence (SEQ ID NO: 20), a 3' UTR-1023 sequence (SEQ ID NO: 22), a bGH poly(A) sequence (SEQ ID NO:23), a hFVIII stuffer sequence (SEQ ID NO: 24), and an ITR sequence (SEQ ID NO: 30).

Generally, an ear can be described as including: an outer ear, middle ear, inner ear, hearing (acoustic) nerve, and auditory system (which processes sound as it travels from the ear to the brain). In addition to detecting sound, ears also help to maintain balance. Thus, in some embodiments, disorders of the inner ear can cause hearing loss, tinnitus, vertigo, imbalance, or combinations thereof.

Hearing loss can be the result of genetic factors, environmental factors, or a combination of genetic and environmental factors. About half of all people who have tinnitus—phantom noises in their auditory system (ringing, buzzing, chirping, humming, or beating)—also have an over-sensitivity to/reduced tolerance for certain sound frequency and volume ranges, known as hyperacusis (also spelled hyperacousis). A variety of non-syndromic and syndromic-related hearing losses will be known to those of skill in the art (e.g., DFNB4, and Pendred syndrome, respectively). Environmental causes of hearing impairment or loss may include, e.g., certain medications, specific infections before or after birth, and/or exposure to loud noise over an extended period. In some embodiments, hearing loss can result from noise, ototoxic agents, presbycusis, disease, infection or cancers that affect specific parts of the ear. In some embodiments, ischemic damage can cause hearing loss via pathophysiological mechanisms. In some embodiments, intrinsic abnormalities, like congenital mutations to genes that play an important role in cochlear anatomy or physiology, or genetic or anatomical changes in supporting and/or hair cells can be responsible for or contribute to hearing loss.

Hearing loss and/or deafness is one of the most common human sensory deficits, and can occur for many reasons. In some embodiments, a subject may be born with hearing loss or without hearing, while others may lose hearing slowly over time. Approximately 36 million American adults report some degree of hearing loss, and one in three people older than 60 and half of those older than 85 experience hearing loss. Approximately 1.5 in 1,000 children are born with profound hearing loss, and another two to three per 1,000 children are born with partial hearing loss (Smith et al., 2005, Lancet 365:879-890, which is incorporated in its entirety herein by reference). More than half of these cases are attributed to a genetic basis (Di Domenico, et al., 2011, J. Cell. Physiol. 226:2494-2499, which is incorporated in its entirety herein by reference).

Treatments for hearing loss currently consist of hearing amplification for mild to severe losses and cochlear implantation for severe to profound losses (Kral and O'Donoghue, 2010, N. Engl. J. Med. 363:1438-1450, which is incorporated in its entirety herein by reference). Recent research in this arena has focused on cochlear hair cell regeneration, applicable to the most common forms of hearing loss, including presbycusis, noise damage, infection, and ototoxicity. There remains a need for effective treatments, such as gene therapy, which can repair and/or mitigate a source of a hearing problem (see e.g., WO 2018/039375, WO 2019/165292, and PCT filing application US2019/060328, each of which is incorporated in its entirety herein by reference).

In some embodiments, non-syndromic hearing loss and/or deafness is not associated with other signs and symptoms. In some embodiments, syndromic hearing loss and/or deafness occurs in conjunction with abnormalities in other parts of the body. Approximately 70 percent to 80 percent of genetic hearing loss and/or deafness cases are non-syndromic; remaining cases are often caused by specific genetic syndromes. Non-syndromic deafness and/or hearing loss can have different patterns of inheritance, and can occur at any age. Types of non-syndromic deafness and/or hearing loss are generally named according to their inheritance patterns. For example, autosomal dominant forms are designated DFNA, autosomal recessive forms are DFNB, and X-linked forms are DFN. Each type is also numbered in the order in which it was first described. For example, DFNA1 was the first described autosomal dominant type of non-syndromic deafness. Between 75 percent and 80 percent of genetically causative hearing loss and/or deafness cases are inherited in an autosomal recessive pattern, which means both copies of the gene in each cell have mutations. Usually, each parent of an individual with autosomal recessive hearing loss and/or deafness is a carrier of one copy of the mutated gene, but is not affected by this form of hearing loss. Another 20 percent to 25 percent of non-syndromic hearing loss and/or deafness cases are autosomal dominant, which means one copy of the altered gene in each cell is sufficient to result in deafness and/or hearing loss. People with autosomal dominant deafness and/or hearing loss most often inherit an altered copy of the gene from a parent who is deaf and/or has hearing loss. Between 1 to 2 percent of cases of deafness and/or hearing loss show an X-linked pattern of inheritance, which means the mutated gene responsible for the condition is located on the X chromosome (one of the two sex chromosomes). Males with X-linked non-syndromic hearing loss and/or deafness tend to develop more severe hearing loss earlier in life than females who inherit a copy of the same gene mutation. A characteristic of X-linked inheritance is that fathers cannot pass X-linked traits to their sons. Mitochondrial non-syndromic deafness, which results from changes to mitochondrial DNA, occurs in less than one percent of cases in the United States. The altered mitochondrial DNA is passed from a mother to all of her sons and daughters. This type of deafness is not inherited from fathers. The causes of syndromic and non-syndromic deafness and/or hearing loss are complex. Researchers have identified more than 30 genes that, when altered, are associated with syndromic and/or non-syndromic deafness and/or hearing loss; however, some of these genes have not been fully characterized. Different mutations in the same gene can be associated with different types of deafness and/or hearing loss, and some genes are associated with both syndromic and non-syndromic deafness and/or hearing loss.

In some embodiments, deafness and/or hearing loss can be conductive (arising from the ear canal or middle ear), sensorineural (arising from the inner ear or auditory nerve), or mixed. In some embodiments, non-syndromic deafness and/or hearing loss is associated with permanent hearing loss caused by damage to structures in the inner ear (sensorineural deafness). In some embodiments, sensorineural hearing loss can be due to poor hair cell function. In some embodiments, sensorineural hearing impairments involve the eighth cranial nerve (the vestibulocochlear nerve) or the auditory portions of the brain. In some such embodiments, only the auditory centers of the brain are affected. In such a situation, cortical deafness may occur, where sounds may be heard at normal thresholds, but quality of sound perceived is so poor that speech cannot be understood. Hearing loss that results from changes in the middle ear is called conductive hearing loss. Some forms of non-syndromic deafness and/or hearing loss involve changes in both the inner ear and the middle ear, called mixed hearing loss. Hearing loss and/or deafness that is present before a child learns to speak can be classified as prelingual or congenital. Hearing loss and/or deafness that occurs after the development of speech can be classified as postlingual. Most autosomal recessive loci related to syndromic or non-syndromic hearing loss cause prelingual severe-to-profound hearing loss.

As is known to those of skill in the art, hair cells are sensory receptors for both auditory and vestibular systems of vertebrate ears. Hair cells detect movement in the environment and, in mammals, hair cells are located within the cochlea of the ear, in the organ of Corti. Mammalian ears are known to have two types of hair cells-inner hair cells and outer hair cells. Outer hair cells can amplify low level sound frequencies, either through mechanical movement of hair cell bundles or electrically-driven movement of hair cell soma. Inner hair cells transform vibrations in cochlear fluid into electrical signals that the auditory nerve transmits to the brain. In some embodiments, hair cells may be abnormal at birth, or damaged during the lifetime of an individual. In some embodiments, outer hair cells may be able to regenerate. In some embodiments, inner hair cells are not capable of regeneration after illness or injury. In some embodiments, sensorineural hearing loss is due to abnormalities in hair cells.

As is known to those of skill in the art, hair cells do not occur in isolation, and their function is supported by a wide variety of cells which can collectively be referred to as supporting cells. Supporting cells may fulfil numerous functions, and include a number of cell types, including but not limited to Hensen's cells, Deiters' cells, pillar cells, Claudius cells, inner phalangeal cells, and border cells. In some embodiments, sensorineural hearing loss is due to abnormalities in supporting cells. In some embodiments, supporting cells may be abnormal at birth, or damaged during the lifetime of an individual. In some embodiments, supporting cells may be able to regenerate. In some embodiments, certain supporting cells may not be capable of regeneration.

As described herein, mutations in an NDP gene that encodes the "norrin cysteine knot growth factor" (NDP) protein may cause hearing loss and vision loss. For example, mutations in NDP lead to Norrie disease pseudoglioma.

Provided herein are composition including a single adeno-associated virus (AAV) vector, wherein the single AAV vector that includes a nucleic acid sequence that encodes a secreted target protein; and when introduced into a primate cell, a nucleic acid encoding a full-length secreted target protein is generated at the locus of the secreted target protein, and the primate cell expresses and secretes the secreted target protein.

Also provided herein are compositions including at least two different nucleic acid vectors, wherein: each of the at least two different vectors includes a coding sequence that encodes a different portion of a secreted target protein, each of the encoded portions being at least 30 amino acid residues in length, wherein the amino acid sequence of each of the encoded portions may optionally partially overlap with the amino acid sequence of a different one of the encoded portions; no single vector of the at least two different vectors encodes a full-length secreted target protein; at least one of the coding sequences includes a nucleotide sequence spanning two neighboring exons of the secreted target protein genomic DNA, and lacks an intronic sequence between the two neighboring exons; and when introduced into a mammalian cell the at least two different vectors undergo concatamerization or homologous recombination with each other, thereby forming a recombined nucleic acid that encodes a full-length secreted target protein.

Also provided herein are compositions including two different nucleic acid vectors, wherein: a first nucleic acid vector of the two different nucleic acid vectors includes a promoter, a first coding sequence that encodes an N-terminal portion of an secreted target protein positioned 3' of the promoter, and a splicing donor signal sequence positioned at the 3' end of the first coding sequence; and a second nucleic acid vector of the two different nucleic acid vectors includes a splicing acceptor signal sequence, a second coding sequence that encodes a C-terminal portion of an secreted target protein positioned at the 3' end of the splicing acceptor signal sequence, and a polyadenylation sequence at the 3' end of the second coding sequence; wherein each of the encoded portions is at least 30 amino acid residues in length, wherein the amino acid sequences of the encoded portions do not overlap, wherein no single vector of the two different vectors encodes a full-length secreted target protein, and, when the coding sequences are transcribed in a mammalian cell, to produce RNA transcripts, splicing occurs between the splicing donor signal sequence on one transcript and the splicing acceptor signal sequence on the other transcript, thereby forming a recombined RNA molecule that encodes a full-length secreted target protein.

Also provided herein are compositions including: a first nucleic acid vector including a promoter, a first coding sequence that encodes an N-terminal portion of an secreted target protein positioned 3' of the promoter, a splicing donor signal sequence positioned at the 3' end of the first coding sequence, and a first detectable marker gene positioned 3' of the splicing donor signal sequence; and a second nucleic acid vector, different from the first nucleic acid vector, including a second detectable marker gene, a splicing acceptor signal sequence positioned 3' of the second detectable marker gene, a second coding sequence that encodes a C-terminal portion of an secreted target protein positioned at the 3' end of the splicing acceptor signal sequence, and a polyadenylation sequence positioned at the 3' end of the second coding sequence; wherein each of the encoded portions is at least 30 amino acid residues in length, wherein the respective amino acid sequences of the encoded portions do not overlap with each other, wherein no single vector of the two different vectors encodes a full-length secreted target protein, and, when the coding sequences are transcribed in a mammalian cell to produce RNA transcripts, splicing occurs between the splicing donor signal on one transcript and the splicing acceptor signal on the other transcript, thereby forming a recombined RNA molecule that encodes a full-length secreted target protein.

Also provided herein are compositions including: a first nucleic acid vector including a promoter, a first coding sequence that encodes an N-terminal portion of an secreted target protein positioned 3' to the promoter, a splicing donor signal sequence positioned at the 3' end of the first coding sequence, and a F1 phage recombinogenic region positioned 3' to the splicing donor signal sequence; and a second nucleic acid vector, different from the first nucleic acid vector, including a second F1 phage recombinogenic region, a splicing acceptor signal sequence positioned 3' of the second F1 phage recombinogenic region, a second coding sequence that encodes a C-terminal portion of an secreted target protein positioned at the 3' end of the splicing acceptor signal sequence, and a polyadenylation sequence positioned at the 3' end of the second coding sequence; wherein each of the encoded portions is at least 30 amino acid residues in length, wherein the respective amino acid sequences of the encoded portions do not overlap with each other, wherein no single vector of the two different vectors encodes a full-length secreted target protein, and, when the coding sequences are transcribed in a mammalian cell to produce RNA transcripts, splicing occurs between the splicing donor signal one transcript and the splicing acceptor signal on the other transcript, thereby forming a recombined RNA molecule that encodes a full-length secreted target protein.

Also provided herein are methods including introducing into a cochlea of a mammal a therapeutically effective amount of any of the compositions described herein.

Also provided herein are methods of increasing expression of a full-length secreted target protein in a mammalian cell that include introducing any of the compositions described herein into the mammalian cell.

Also provided herein are methods of increasing expression of a full-length secreted target protein in an inner hair cell in a cochlea of a mammal that include introducing into the cochlea a therapeutically effective amount of any of the compositions described herein.

Also provided herein are methods of treating syndromic and non-syndromic sensorineural hearing loss in a subject identified as having a defective secreted target gene that include: administering a therapeutically effective amount of any of the compositions described herein into the cochlea of the subject.

Also provided herein are methods of treating or preventing vision loss in a subject identified as having a defective NDP gene that include: administering a therapeutically effective amount of any of the compositions described herein into an inner ear or central nervous system of the subject, or systemically administering a therapeutically effective amount of any of the compositions described herein to the subject.

Also provided herein are pharmaceutical compositions and kits that include any of the compositions or AAV vectors described herein.

Additional non-limiting aspects of the compositions, kits and methods are described herein and can be used in any combination without limitation.

Secreted Target Proteins

The term "secreted target protein" refers to a protein encoded by DNA that if expressed in a cell (e.g., any of the exemplary cells described herein) can be secreted. The term "secreted target protein" also refers to a protein that includes a secretion signal. Non-limiting examples of secreted target proteins and secretion signals are described herein. In some examples, the secreted target protein is a NDP protein (e.g., any of the NDP proteins described herein). In some examples, the secreted target protein is an HSPA1A protein (e.g., any of the HPSA1A proteins described herein).

In some embodiments, the term "secreted target protein" means a protein that is expressed and secreted by a cell in a primate, and functionally contributes, at least in part, to the hearing in the primate. Non-limiting examples of secreted target proteins include NDP, HSPA1A, DNAJB1, or DNAJB5.

The term "mutation in a secreted target gene" refers to a modification in a wildtype secreted target gene that results in the production of a secreted target protein having one or more of: a deletion in one or more amino acids, one or more amino acid substitutions, and one or more amino acid insertions as compared to the wildtype secreted target protein, and/or results in a decrease in the expressed level of the encoded secreted target protein in a primate cell as compared to the expressed level of the encoded secreted target protein in a primate cell not having a mutation. In some embodiments, a mutation can result in the production of a secreted target protein having a deletion in one or more amino acids (e.g., 2, 3, 4, 5, 6, 7, 8, 9, 10, 11, 12, 13, 14, 15, 16, 17, 18, 19, or 20 amino acids). In some embodiments, the mutation can result in a frameshift in the secreted target gene.

Norrin Cystine Knot Growth Factor (NDP)

The NDP gene encodes "norrin cystine knot growth factor" (NDP). The human ND gene is located on chromosome Xp11.3. It contains 3 exons, encompassing~kilobases (kb) (NCBI Accession No. NG_009832.1). NDP encodes secreted norrin protein that plays a role in retina vascularization of Wnt signaling pathway through (FZDA) and (LRP5) coreceptor. Mutations in NDP have been associated with Norrie Disease Pseudoglioma, an X-linked recessive syndromic hearing loss that is characterized by early childhood retinopathy. About one third of individuals with Norrie disease develop progressive hearing loss, and more than half experience developmental delays in motor skills.

Various mutations in the NDP gene have been associated with hearing loss (e.g., Norrie Disease Pseudoglioma). For example, the p.His4ArgfsX21, p.Asp23GlufsX9, p.Arg38Cys, p.Ile48ValfsX55, p.His50Asp, p.Ser57*, p.Cys93Arg, p.Lys104Gln, p.Glyl13Asp, p.Arg121Gln, and p.Cys 126Arg mutation have each been associated with Norrie disease pseudoglioma. See, e.g., Musada et al., *Mol. Vis.* 22:491-502, 2016; Chamney et al., *Eye* (*Lond*) 25(12): 1658, 2011; Liu et al., *J Chin. Med. Assoc.* 79 (11): 633-638, 2016; and Parzefall et al., *Audiol. Neurootol.* 19 (3): 203-209, 2014, each of which is hereby incorporated by reference in its entirety.

As used herein, the term "active NDP protein" means a protein encoded by DNA that, if substituted for both wildtype alleles encoding full-length NDP protein in auditory hair cells, or ocular cells, of what is otherwise a wildtype mammal, and if expressed in the auditory hair cells, or ocular cells, of that mammal, results in that mammal's having a level of hearing, or vision, approximating the normal level of hearing, or vision, of a similar mammal that is entirely wildtype. Non-limiting examples of active NDP proteins are full-length NDP proteins (e.g., any of the full-length NDP proteins described herein).

For example, an active NDP protein can include a sequence of a wildtype, full-length NDP protein (e.g., a wildtype, human, full-length NDP protein) including about 1 to about amino acid substitutions (e.g., about 1 to about 22 amino acid substitutions, about 1 to about 20 amino acid substitutions, about 1 to about 18 amino acid substitutions, about 1 to about 16 amino acid substitutions, about 1 to about 15 amino acid substitutions, about 1 to about 14 amino acid substitutions, about 1 to about 12 amino acid substitutions, about 1 to about 10 amino acid substitutions, about 1 to about 8 amino acid substitutions, about 1 to about 6 amino acid substitutions, about 1 to about 5 amino acid substitutions, about 1 to about 4 amino acid substitutions, about 1 to about 2 amino acid substitutions, about 2 to about 24 amino acid substitutions, about 2 to about 22 amino acid substitutions, about 2 to about 20 amino acid substitutions, about 2 to about 18 amino acid substitutions, about 2 to about 16 amino acid substitutions, about 2 to about 15 amino acid substitutions, about 2 to about 14 amino acid substitutions, about 2 to about 12 amino acid substitutions, about 2 to about 10 amino acid substitutions, about 2 to about 8 amino acid substitutions, about 2 to about 6 amino acid substitutions, about 2 to about 5 amino acid substitutions, about 2 to about 4 amino acid substitutions, about 5 to about 24 amino acid substitutions, about 5 to about 22 amino acid substitutions, about 5 to about 20 amino acid substitutions, about 5 to about 18 amino acid substitutions, about 5 to about 16 amino acid substitutions, about 5 to about 15 amino acid substitutions, about 5 to about 14 amino acid substitutions, about 5 to about 12 amino acid substitutions, about 5 to about 10 amino acid substitutions, about 5 to about 8 amino acid substitutions, about 5 to about 6 amino acid substitutions, about 6 to about 24 amino acid substitutions, about 6 to about 22 amino acid substitutions, about 6 to about 20 amino acid substitutions, about 6 to about 18 amino acid substitutions, about 6 to about 16 amino acid substitutions, about 6 to about 15 amino acid substitutions, about 6 to about 14 amino acid substitutions, about 6 to about 12 amino acid substitutions, about 6 to about 10 amino acid substitutions, about 6 to about 8 amino acid substitutions, about 8 to about 24 amino acid substitutions, about 8 to about 22 amino acid substitutions, about 8 to about 20 amino acid substitutions, about 8 to about 18 amino acid substitutions, about 8 to about 16 amino acid substitutions, about 8 to about 15 amino acid substitutions, about 8 to about 14 amino acid substitutions, about 8 to about 12 amino acid substitutions, about 8 to about 10 amino acid substitutions, about 10 to about 24 amino acid substitutions, about 10 to about 22 amino acid substitutions, about 10 to about 20 amino acid substitutions, about 10 to about 18 amino acid substitutions, about 10 to about 16 amino acid substitutions, about 10 to about 15 amino acid substitutions, about 10 to about 14 amino acid substitutions, about 10 to about 12 amino acid substitutions, about 12 to about 24 amino acid substitutions, about 12 to about 22 amino acid substitutions, about 12 to about 20 amino acid substitutions, about 12 to about 18 amino acid substitutions, about 12 to about 16 amino acid substitutions, about 12 to about 15 amino acid substitutions, about 12 to about 14 amino acid substitutions, about 14 to about 24 amino acid substitutions, about 14 to about 22 amino acid substitutions, about 14 to about 20 amino acid substitutions, about 14 to about 18 amino acid substitutions, about 14 to about 16 amino acid substitutions, about 14 to about 15 amino acid substitutions, about 15 to about 24 amino acid substitutions, about 15 to about 22 amino acid substitutions, about 15 to about 20 amino acid substitutions, about 15 to about 18 amino acid substitutions, about 15 to about 16 amino acid substitutions, about 16 to about 24 amino acid substitutions, about 16 to about 22 amino acid substitutions, about 16 to about 20 amino acid substitutions, about 16 to about 18 amino acid substitutions, about 18 to about 24 amino acid substitutions, about 18 to about 22 amino acid substitutions, about 18 to about 20 amino acid substitutions, about 20 to about 24 amino acid substitutions, about 20 to about 22 amino acid substitutions, or about 22 to about 24 amino acid substitutions).

One skilled in the art would appreciate that amino acids that are not conserved between wildtype NDP proteins from different species can be mutated without losing activity, while those amino acids that are conserved between wildtype NDP proteins from different species should not be mutated as they are more likely (than amino acids that are not conserved between different species) to be involved in activity.

An active NDP protein can include, e.g., a sequence of a wildtype, full-length NDP protein (e.g., a wildtype, human, full-length NDP protein) that has about 1 to about 80 amino acids (e.g., about 1 to about 75 amino acids, about 1 to about 70 amino acids, about 1 to about 65 amino acids, about 1 to about 60 amino acids, about 1 to about 55 amino acids, about 1 to about 50 amino acids, about 1 to about 45 amino acids, about 1 to about 40 amino acids, about 1 to about 35 amino acids, about 1 to about 30 amino acids, about 1 to about 25 amino acids, about 1 to about 20 amino acids, about 1 to about 15 amino acids, about 1 to about 10 amino acids, about 1 to about 5 amino acids, about 5 to about 80 amino acids, about 5 to about 75 amino acids, about 5 to about 70 amino acids, about 5 to about 65 amino acids, about 5 to about 60 amino acids, about 5 to about 55 amino acids, about 5 to about 50 amino acids, about 5 to about 45 amino acids, about 5 to about 40 amino acids, about 5 to about 35 amino acids, about 5 to about 30 amino acids, about 5 to about 25 amino acids, about 5 to about 20 amino acids, about to about 15 amino acids, about 5 to about 10 amino acids, about 10 to about 80 amino acids, about 10 to about 75 amino acids, about 10 to about 70 amino acids, about 10 to about 65 amino acids, about 10 to about 60 amino acids, about 10 to about 55 amino acids, about 10 to about 50 amino acids, about 10 to about 45 amino acids, about 10 to about 40 amino acids, about 10 to about 35 amino acids, about 10 to about 30 amino acids, about 10 to about 25 amino acids, about to about 20 amino acids, about 10 to about 15 amino acids, about 15 to about 80 amino acids, about 15 to about 75 amino acids, about 15 to about 70 amino acids, about 15 to about 65 amino acids, about 15 to about 60 amino acids, about 15 to about 55 amino acids, about 15 to about 50 amino acids, about 15 to about 45 amino acids, about 15 to about 40 amino acids, about 15 to about 35 amino acids, about 15 to about 30 amino acids, about 15 to about 25 amino acids, about to about 20 amino acids, about 20 to about 80 amino acids, about 20 to about 75 amino acids, about 20 to about 70 amino acids, about 20 to about 65 amino acids, about 20 to about 60 amino acids, about 20 to about 55 amino acids, about 20 to about 50 amino acids, about 20 to about 45 amino acids, about 20 to about 40 amino acids, about 20 to about 35 amino acids, about 20 to about 30 amino acids, about 20 to about 25 amino acids, about 25 to about 80 amino acids, about 25 to about 75 amino acids, about 25 to about 70 amino acids, about 25 to about 65 amino acids, about 25 to about 60 amino acids, about 25 to about 55 amino acids, about 25 to about 50 amino acids, about 25 to about 45 amino acids, about 25 to about 40 amino acids, about 25 to about 35 amino acids, about 25 to about 30 amino acids, about 30 to about 80 amino acids, about 30 to about 75 amino acids, about 30 to about 70 amino acids, about 30 to about 65 amino acids, about 30 to about 60 amino acids, about 30 to about 55 amino acids, about 30 to about 50 amino acids, about 30 to about 45 amino acids, about 30 to about 40 amino acids, about 30 to about 35 amino acids, about 35 to about 80 amino acids, about 35 to about 75 amino acids, about 35 to about 70 amino acids, about 35 to about 65 amino acids, about 35 to about 60 amino acids, about 35 to about 55 amino acids, about 35 to about 50 amino acids, about 35 to about 45 amino acids, about 35 to about 40 amino acids, about 40 to about 80 amino acids, about 40 to about 75 amino acids, about 40 to about 70 amino acids, about 40 to about 65 amino acids, about 40 to about 60 amino acids, about 40 to about 55 amino acids, about 40 to about 50 amino acids, about 40 to about 45 amino acids, about 45 to about 80 amino acids, about 45 to about 75 amino acids, about 45 to about 70 amino acids, about 45 to about 65 amino acids, about 45 to about 60 amino acids, about 45 to about 55 amino acids, about 45 to about 50 amino acids, about 50 to about 80 amino acids, about 50 to about 75 amino acids, about 50 to about 70 amino acids, about 50 to about 65 amino acids, about 50 to about 60 amino acids, about 50 to about 55 amino acids, about 55 to about 80 amino acids, about 55 to about 75 amino acids, about 55 to about 70 amino acids, about 55 to about 65 amino acids, about 55 to about 60 amino acids, about 60 to about 80 amino acids, about 60 to about 75 amino acids, about 60 to about 70 amino acids, about 60 to about 65 amino acids, about 65 to about 80 amino acids, about 65 to about 75 amino acids, about 65 to about 70 amino acids, about 70 to about 80 amino acids, about 70 to about 75 amino acids, or about 75 to about 80 amino acids), removed from its N-terminus and/or 1 amino acid to 80 amino acids (or any of the subranges of this range described herein) removed from its C-terminus.

In some embodiments, an active NDP protein can, e.g., include the sequence of a wildtype, full-length NDP protein where 1 amino acid to 50 amino acids, 1 amino acid to 45 amino acids, 1 amino acid to 40 amino acids, 1 amino acid to 35 amino acids, 1 amino acid to 30 amino acids, 1 amino acid to 25 amino acids, 1 amino acid to 20 amino acids, 1 amino acid to 15 amino acids, 1 amino acid to 10 amino acids, 1 amino acid to 9 amino acids, 1 amino acid to 8 amino acids, 1 amino acid to 7 amino acids, 1 amino acid to 6 amino acids, 1 amino acid to 5 amino acids, 1 amino acid to 4 amino acids, 1 amino acid to 3 amino acids, about 2 amino acids to 50 amino acids, about 2 amino acids to 45 amino acids, about 2 amino acids to 40 amino acids, about 2 amino acids to 35 amino acids, about 2 amino acids to 30 amino acids, about 2 amino acids to 25 amino acids, about 2 amino acids to 20 amino acids, about 2 amino acids to 15 amino acids, about 2 amino acids to 10 amino acids, about 2 amino acids to 9 amino acids, about 2 amino acids to 8 amino acids, about 2 amino acids to 7 amino acids, about 2 amino acids to 6 amino acids, about 2 amino acids to 5 amino acids, about 2 amino acids to 4 amino acids, about 3 amino acids to 50 amino acids, about 3 amino acids to 45 amino acids, about 3 amino acids to 40 amino acids, about 3 amino acids to 35 amino acids, about 3 amino acids to 30 amino acids, about 3 amino acids to 25 amino acids, about 3 amino acids to 20 amino acids, about 3 amino acids to 15 amino acids, about 3 amino acids to 10 amino acids, about 3 amino acids to 9 amino acids, about 3 amino acids to 8 amino acids, about 3 amino acids to 7 amino acids, about 3 amino acids to 6 amino acids, about 3 amino acids to 5 amino acids, about 4 amino acids to 50 amino acids, about 4 amino acids to 45 amino acids, about 4 amino acids to 40 amino acids, about 4 amino acids to 35 amino acids, about 4 amino acids to 30 amino acids, about 4 amino acids to 25 amino acids, about 4 amino acids to 20 amino acids, about 4 amino acids to 15 amino acids, about 4 amino acids to 10 amino acids, about 4 amino acids to 9 amino acids, about 4 amino acids to 8 amino acids, about 4 amino acids to 7 amino acids, about 4 amino acids to 6 amino acids, about 5 amino acids to 50 amino acids, about 5 amino acids to 45 amino acids, about 5 amino acids to 40 amino acids, about 5 amino acids to 35 amino acids, about 5 amino acids to 30 amino acids, about 5 amino acids to 25 amino acids, about 5 amino acids to 20 amino acids, about 5 amino acids to 15 amino acids, about 5 amino acids to 10 amino acids, about 5 amino acids to 9 amino acids, about 5 amino acids to 8 amino acids, about 5 amino acids to 7 amino acids, about 6 amino acids to 50 amino acids, about 6 amino acids to 45 amino acids, about 6 amino acids to 40 amino acids, about 6 amino acids to 35 amino acids, about 6 amino acids to 30 amino acids, about 6 amino acids to 25 amino acids, about 6 amino acids to 20 amino acids, about 6 amino acids to 15 amino acids, about 6 amino acids to 10 amino acids, about 6 amino acids to 9 amino acids, about 6 amino acids to 8 amino acids, about 7 amino acids to 50 amino acids, about 7 amino acids to 45 amino acids, about 7 amino acids to 40 amino acids, about 7 amino acids to 35 amino acids, about 7 amino acids to 30 amino acids, about 7 amino acids to 25 amino acids, about 7 amino acids to 20 amino acids, about 7 amino acids to 15 amino acids, about 7 amino acids to 10 amino acids, about 7 amino acids to 9 amino acids, about 8 amino acids to 50 amino acids, about 8 amino acids to 45 amino acids, about 8 amino acids to 40 amino acids, about 8 amino acids to 35 amino acids, about 8 amino acids to 30 amino acids, about 8 amino acids to 25 amino acids, about 8 amino acids to 20 amino acids, about 8 amino acids to 15 amino acids, about 8 amino acids to 10 amino acids, about 10 amino acids to 50 amino acids, about 10 amino acids to 45 amino acids, about 10 amino acids to 40 amino acids, about 10 amino acids to 35 amino acids, about 10 amino acids to 30 amino acids, about 10 amino acids to 25 amino acids, about 10 amino acids to 20 amino acids, about 10 amino acids to 15 amino acids, about 15 amino acids to 50 amino acids, about 15 amino acids to 45 amino acids, about 15 amino acids to 40 amino acids, about 15 amino acids to 35 amino acids, about 15 amino acids to 30 amino acids, about 15 amino acids to 25 amino acids, about 15 amino acids to 20 amino acids, about 20 amino acids to 50 amino acids, about 20 amino acids to 45 amino acids, about 20 amino acids to 40 amino acids, about 20 amino acids to 35 amino acids, about 20 amino acids to 30 amino acids, about 20 amino acids to 25 amino acids, about 25 amino acids to 50 amino acids, about 25 amino acids to 45 amino acids, about 25 amino acids to 40 amino acids, about 25 amino acids to 35 amino acids, about 25 amino acids to 30 amino acids, about 30 amino acids to 50 amino acids, about 30 amino acids to 45 amino acids, about 30 amino acids to 40 amino acids, about 30 amino acids to 35 amino acids, about 35 amino acids to 50 amino acids, about 35 amino acids to 45 amino acids, about 35 amino acids to 40 amino acids, about 40 amino acids to 50 amino acids, about 40 amino acids to 45 amino acids, or about 45 amino acids to about 50 amino acids, are inserted. In some examples, the 1 amino acid to 50 amino acids (or any subrange thereof) can be inserted as a contiguous sequence into the sequence of a wildtype, full-length NDP protein. In some examples, the 1 amino acid to 50 amino acids (or any subrange thereof) are inserted in multiple, non-contiguous places in the sequence of a wildtype, full-length NDP protein. As can be appreciated in the art, the 1 amino acid to 50 amino acids can be inserted into a portion of the sequence of a wildtype, full-length NDP protein that is not well-conserved between species.

Methods of detecting mutations in a gene are well-known in the art. Non-limiting examples of such techniques include: real-time polymerase chain reaction (RT-PCR), PCR, sequencing, Southern blotting, and Northern blotting.

An exemplary human wildtype NDP protein is or includes the sequence of SEQ ID NO: 1, 33, 35, 36 or 37. Non-limiting examples of nucleic acid encoding a wildtype NDP protein are or include SEQ ID NO: 2 or SEQ ID NO: 34. As can be appreciated in the art, at least some or all of the codons in SEQ ID NO: 2 or SEQ ID NO: 34 can be codon-optimized to allow for optimal expression in a non-human mammal.

Exemplary wildtype NDP protein sequences are or include SEQ ID NO: 1, 33, 35, 36, and 37. Exemplary DNA sequences that encode an NDP protein and exemplary polypeptides encoded by an NDP gene are shown below.

NDP Polynucleotides

Among other things, the present disclosure provides polynucleotides, e.g., polynucleotides comprising an NDP gene or characteristic portion thereof, as well as compositions including such polynucleotides and methods utilizing such polynucleotides and/or compositions.

In some embodiments, a polynucleotide comprising an NDP gene or characteristic portion thereof can be DNA or RNA. In some embodiments, DNA can be genomic DNA or cDNA. In some embodiments, RNA can be an mRNA. In some embodiments, a polynucleotide comprises exons and/or introns of an NDP gene.

In some embodiments, a gene product is expressed from a polynucleotide comprising an NDP gene or characteristic portion thereof. In some embodiments, expression of such a polynucleotide can utilize one or more control elements (e.g., promoters, enhancers, splice sites, poly-adenylation sites, translation initiation sites, etc.). Thus, in some embodiments, a polynucleotide provided herein can include one or more control elements.

In some embodiments, an NDP gene is a mammalian NDP gene. In some embodiments, an NDP gene is a murine NDP gene. In some embodiments, an NDP gene is a primate NDP gene. In some embodiments, a NDP gene is a human NDP gene. An exemplary human NDP cDNA sequence is or includes the sequence of SEQ ID NO: 57. An exemplary human NDP genomic DNA sequence can be found in SEQ ID NO: 79. An exemplary human NDP cDNA sequence including untranslated regions is or includes the sequence of SEQ ID NO: 114.

```
Exemplary Human Mature NDP cDNA
                                                      (SEQ ID NO: 57)
ATGAAAACGGACAGCTCATTCATAATGGACTCGGACCCTCGACGCTGCATGAGGCACCACTATG

TGGATTCTATCAGTCACCCATTGTACAAGTGTAGCTCAAAGATGGTGCTCCTGGCCAGGTGCGA

GGGGCACTGCAGCCAGGCGTCACGCTCCGAGCCTTTGGTGTCGTTCAGCACTGTCCTCAAGCAA

CCCTTCCGTTCCTCCTGTCACTGCTGCCGGCCCCAGACTTCCAAGCTGAAGGCACTGCGGCTGC

GATGCTCAGGGGGCATGCGACTCACTGCCACCTACCGGTACATCCTCTCCTGTCACTGCGAGGA

ATGCAATTCC

Exemplary Human NDP cDNA including untranslated regions
                                                     (SEQ ID NO: 114)
AGAAGAACAAAAGCATTTGGAAGTAACAGGACCTCTTTCTAGCTCTCAGAAAAGTCTGAGAAGA

AAGGAGCCCTGCGTTCCCCTAAGCTGTGCAGCAGATACTGTGATGATGGATTGCAAGTGCAAAG

AGTAAGACAAAACTCCAGCACATAAAGGACAATGACAACCAGAAAGCTTCAGCCCGATCCTGCC

CTTTCCTTGAACGGGACTGGATCCTAGGAGGTGAAGCCATTTCCAATTTTTTGTCCTCTGCCTC

CCTCTGCTGTTCTTCTAGAGAAGTTTTTCCTTACAACAATGAGAAAACATGTACTAGCTGCATC
```

-continued

```
CTTTTCTATGCTCTCCCTGCTGGTGATAATGGGAGATACAGACAGTAAAACGGACAGCTCATTC
ATAATGGACTCGGACCCTCGACGCTGCATGAGGCACCACTATGTGGATTCTATCAGTCACCCAT
TGTACAAGTGTAGCTCAAAGATGGTGCTCCTGGCCAGGTGCGAGGGGCACTGCAGCCAGGCGTC
ACGCTCCGAGCCTTTGGTGTCGTTCAGCACTGTCCTCAAGCAACCCTTCCGTTCCTCCTGTCAC
TGCTGCCGGCCCCAGACTTCCAAGCTGAAGGCACTGCGGCTGCGATGCTCAGGGGGCATGCGAC
TCACTGCCACCTACCGGTACATCCTCTCCTGTCACTGCGAGGAATGCAATTCCTGAGGCCCGCT
GCTGTGTGTGGCTTCTGGATGGGACAACTGTAGAGGCAGTTCGACCAGCCAGGGAAAGACTGGC
AAGAAAAGAGTTAAGGCAAAAAAGGATGCAACAATTCTCCCGGGACTCTGCATATTCTAGTAAT
AAAGACTCTACATGCTTGTTGACAGAGAGAGATACTCTGGGAACTTCTTTGCAGTTCCCATCTC
CTTTCTCTGGTACAATTTCTTTTGGTTCATTTTCAGATTCAGGCATTTTCCCCCTTGGCTCTCA
ATGCTGTTTGGGTTTCCAACAATTCAGCATTAGTGGGAAAAAGTGGGCCCTCATACACAAGCGT
GTCAGGCTGTCAGTGTTTGGTGCACGCTGGGGAAGAATTTACTTTGGAAAGTAGAAAAGCCCAG
CTTTTCCTGGGACATCTTCTGTTATTGTTGATGTTTTTTTTACCTTGTCATTTTGGTCTAAGG
TTGCCATTGCTGCTAAAGGTTACCGATTTCAAAGTCCAGATACCAAGCATGTGGATATGTTTAG
CTACGTTTACTCACAGCGAGCGAACTGAGATTAAAATAACTAACAAACAGATTCTTTTATGTGA
TGCTGGAACTCTTGACAGCTATAATTATTATTCAGAAATGAGTTTTTGAAAGTAAAAGCAGCAT
AAAGAATTTGTCACAGGAAGGCTGTCTCAGATAAATTATGGTAAAATTTTGTAAGGGAGCAGAC
TTTTAAAGACTTGCACAAATACGGATCCTGCACTGAGTCTGGAAAAGGCATATATGTACTAGTG
GCATGGAGAATGCACCATACTCATGCATGCAAATTAGACAACCAAGTATGAATCTATTTGTGGG
TGTGCTATAGCTTTAGCCGTGTCACGGGCATCATTCTCTAATATCCACTTGTCCATGTGAAACA
TGTTGCCAAAATGGTGGCCTGGCTTGTCTTCTGAACGTTTGGTTCAAATGTGTTTTGGTCCTGG
AGGCTCAAATTTTGAGTTATTCCCACGTTTTGAAATAAAAAGAGTATATTCAAAA
```

A non-limiting example of a human wildtype NDP genomic DNA sequence is SEQ ID NO: 79. The exons in SEQ ID NO: 79 are: nucleotide positions 1-87 (exon 1); nucleotide positions 88-468 (exon 2) and nucleotide positions 469-1719 (exon 3).

Exemplary Human NDP Gene Sequence (NCBI Reference Sequence: NC_000023.11)

(SEQ ID NO: 79)

```
AGAAGAACAAAAGCATTTGGAAGTAACAGGACCTCTTTCTAGCTCTCAGAAAAGTCTGAGAAGA
AAGGAGCCCTGCGTTCCCCTAAGCTGTGCAGCAGATACTGTGATGATGGATTGCAAGTGCAAAG
AGTAAGACAAAACTCCAGCACATAAAGGACAATGACAACCAGAAAGCTTCAGCCCGATCCTGCC
CTTTCCTTGAACGGGACTGGATCCTAGGAGGTGAAGCCATTTCCAATTTTTTGTCCTCTGCCTC
CCTCTGCTGTTCTTCTAGAGAAGTTTTTCCTTACAACAATGAGAAAACATGTACTAGCTGCATC
CTTTTCTATGCTCTCCCTGCTGGTGATAATGGGAGATACAGACAGTAAAACGGACAGCTCATTC
ATAATGGACTCGGACCCTCGACGCTGCATGAGGCACCACTATGTGGATTCTATCAGTCACCCAT
TGTACAAGTGTAGCTCAAAGATGGTGCTCCTGGCCAGGTGCGAGGGGCACTGCAGCCAGGCGTC
ACGCTCCGAGCCTTTGGTGTCGTTCAGCACTGTCCTCAAGCAACCCTTCCGTTCCTCCTGTCAC
TGCTGCCGGCCCCAGACTTCCAAGCTGAAGGCACTGCGGCTGCGATGCTCAGGGGGCATGCGAC
TCACTGCCACCTACCGGTACATCCTCTCCTGTCACTGCGAGGAATGCAATTCCTGAGGCCCGCT
GCTGTGTGTGGCTTCTGGATGGGACAACTGTAGAGGCAGTTCGACCAGCCAGGGAAAGACTGGC
AAGAAAAGAGTTAAGGCAAAAAAGGATGCAACAATTCTCCCGGGACTCTGCATATTCTAGTAAT
```

-continued

AAAGACTCTACATGCTTGTTGACAGAGAGAGATACTCTGGGAACTTCTTTGCAGTTCCCATCTC

CTTTCTCTGGTACAATTTCTTTTGGTTCATTTTCAGATTCAGGCATTTTCCCCCTTGGCTCTCA

ATGCTGTTTGGGTTTCCAACAATTCAGCATTAGTGGGAAAAAGTGGGCCCTCATACACAAGCGT

GTCAGGCTGTCAGTGTTTGGTGCACGCTGGGGAAGAATTTACTTTGGAAAGTAGAAAAGCCCAG

CTTTTCCTGGGACATCTTCTGTTATTGTTGATGTTTTTTTTTACCTTGTCATTTTGGTCTAAGG

TTGCCATTGCTGCTAAAGGTTACCGATTTCAAAGTCCAGATACCAAGCATGTGGATATGTTTAG

CTACGTTTACTCACAGCGAGCGAACTGAGATTAAAATAACTAACAAACAGATTCTTTTATGTGA

TGCTGGAACTCTTGACAGCTATAATTATTATTCAGAAATGAGTTTTTGAAAGTAAAAGCAGCAT

AAAGAATTTGTCACAGGAAGGCTGTCTCAGATAAATTATGGTAAAATTTTGTAAGGGAGCAGAC

TTTTAAAGACTTGCACAAATACGGATCCTGCACTGAGTCTGGAAAAGGCATATATGTACTAGTG

GCATGGAGAATGCACCATACTCATGCATGCAAATTAGACAACCAAGTATGAATCTATTTGTGGG

TGTGCTATAGCTTTAGCCGTGTCACGGGCATCATTCTCTAATATCCACTTGTCCATGTGAAACA

TGTTGCCAAAATGGTGGCCTGGCTTGTCTTCTGAACGTTTGGTTCAAATGTGTTTTGGTCCTGG

AGGCTCAAATTTTGAGTTATTCCCACGTTTTGAAATAAAAAGAGTATATTCAAAA

Exemplary Mouse Mature NDP cDNA (SEQ ID NO: 81)

AAAACAGACAGTTCATTTCTGATGGAGTCTCAACGCTGCATGAGACACCATTATGTCGATTCTA

TCAGTCACCCACTGTACAAATGTAGCTCAAAGATGGTGCTCCTGGCCAGATGTGAGGGGCACTG

CAGCCAGGCATCACGCTCTGAGCCCTTGGTGTCCTTCAGCACTGTCCTCAAGCAACCTTTCCGT

TCCTCCTGTCACTGCTGCCGACCCCAGACTTCCAAGCTGAAGGCTCTGCGTCTGCGCTGCTCAG

GGGGCATGCGACTTACTGCCACTTACCGGTACATCCTCTCCTGTCACTGTGAGGAATGCAGCTC

C

Polypeptides Encoded by NDP Gene

Among other things, the present disclosure provides polypeptides encoded by an NDP gene or characteristic portion thereof. In some embodiments, an NDP gene is a mammalian NDP gene. In some embodiments, an NDP gene is a murine NDP gene. In some embodiments, an NDP gene is a primate NDP gene. In some embodiments, a NDP gene is a human NDP gene.

In some embodiments, a polypeptide comprises a NDP protein or characteristic portion thereof. In some embodiments, a NDP protein or characteristic portion thereof is mammalian NDP protein or characteristic portion thereof, e.g., primate NDP protein or characteristic portion thereof. In some embodiments, a NDP protein or characteristic portion thereof is a human NDP protein or characteristic portion thereof.

In some embodiments, a polypeptide provided herein comprises post-translational modifications. In some embodiments, a NDP protein or characteristic portion thereof provided herein comprises post-translational modifications. In some embodiments, post-translational modifications can comprise but is not limited to glycosylation (e.g., N-linked glycosylation, O-linked glycosylation), phosphorylation, acetylation, amidation, hydroxylation, methylation, ubiquitylation, sulfation, and/or a combination thereof.

An exemplary human NDP protein sequence is or includes the sequence of SEQ ID NO: 56. An exemplary human NDP protein sequence with a c-terminal flag tag is or includes the sequence of SEQ ID NO: 94. As exemplary mouse NDP protein sequence is or includes the sequence of SEQ ID NO: 80. As exemplary rhesus monkey NDP protein sequence is or includes the sequence of SEQ ID NO: 82. As exemplary rat NDP protein sequence is or includes the sequence of SEQ ID NO: 83. As exemplary chimpanzee NDP protein sequence is or includes the sequence of SEQ ID NO: 84.

Exemplary Human Mature NDP Protein (NCBI Accession No. NP_000257.1)

(SEQ ID NO: 56)

MKTDSSFIMDSDPRRCMRHHYVDSISHPLYKCSSKMVLLARCEGHCSQASRSEPLVSFSTVLKQ
PFRSSCHCCRPQTSKLKALRLRCSGGMRLTATYRYILSCHCEECNS

Exemplary Human NDP Protein Sequence with C-terminal Flag Tag (SEQ ID NO: 94)

MKTDSSFIMDSDPRRCMRHHYVDSISHPLYKCSSKMVLLARCEGHCSQASRSEPLVSFSTVLKQ
PFRSSCHCCRPQTSKLKALRLRCSGGMRLTATYRYILSCHCEECNSGSRADYKDHDGDYKDHDI
DYKDDDDK

-continued

```
Exemplary Mouse Mature NDP Protein (NCBI Accession No. NP_035013.1)
                                                        (SEQ ID NO: 80)
KTDSSFLMDSQRCMRHHYVDSISHPLYKCSSKMVLLARCEGHCSQASRSEPLVSFSTVLKQPFR
SSCHCCRPQTSKLKALRLRCSGGMRLTATYRYILSCHCEECSS

Exemplary Rhesus Monkey Mature NDP Protein (NCBI Accession No.
NP_001253901.1)
                                                        (SEQ ID NO: 82)
MRKHVLAASFSMLSLLVIMGDTDSKTDSSFIMDSDPRRCMRHHYVDSISHPLYKCSSKMVLLAR
CEGHCSQASRSEPLVSFSTVLKQPFRSSCHCCRPQTSKLKALRLRCSGGMRLTATYRYILSCHC
EECNS

Exemplary Rat Mature NDP Protein (NCBI Accession No. NP_001102284.1)
                                                        (SEQ ID NO: 83)
KTDSSFLMDSQRCMRHHYVDSISHPLYKCSSKMVLLARCEGHCSQASRSEPLVSFSTVLKQPFR
SSCHCCRPQTSKLKALRLRCSGGMRLTATYRYILSCHCEECSS

Exemplary Chimpanzee NDP Protein (NCBI Accession No. XP_016799622.1)
                                                        (SEQ ID NO: 84)
KTDSSFVMDSDPRRCMRHHYVDSISHPLYKCSSKMVLLARCEGHCSQASRSEPLVSFSTVLKQP
FRSSCHCCRPQTSKLKALRLRCSGGMRLTATYRYILSCHCEECNS
```

Heat Shock Proteins

In some embodiments of any of the compositions described herein, a secreted target protein is a heat shock protein. In some embodiments, a heat shock protein is a heat shock protein family A (Hsp70) member 1A (HSPA1A). In some embodiments, a heat shock protein is a heat shock protein 40 (Hsp40)/DNJ family member, e.g., Hsp40.

Heat Shock Protein Family a (Hsp70) Member 1A (HSPA1A)

The HSPA1A gene encodes "heat shock protein family A member 1A" (HSPA1A). The human HSPA1A gene is located on chromosome 6p21.33. It contains 1 exon, encompassing~2400 bp (NCBI Accession No. NC_000006.12). HSPA1A encodes a 70 kDa heat shock protein, which stabilizes proteins against protein aggregation and is involved in protein folding.

Hair cells are susceptible to death when exposed to therapeutic drugs (such as aminoglycoside antibiotics or cisplatin) with ototoxic side effects. The induction of heat shock proteins (such as heat shock protein 70 ("HSP70") or such as heme oxygenase-1 ("HO-1" or "HSP32")) in response to cellular stress is a highly conserved response that can significantly inhibit cell death (such as aminoglycoside-induced hair cell death) in a variety of systems. For example, adenovirus-mediated infection of inner ear supporting cells with HSP70 was shown to inhibit hair cell death (see, e.g., Lindsay May et al., *J Clin Invest.* 2013; 123 (8): 3577-3587, the contents of which is hereby incorporated by reference herein in its entirety). In addition, other heat shock proteins such as HO-1 or HSP32 have been found to offer significant protection against cisplatin-induced hair cell death (see, e.g., Tiffany Baker et al., JARO 16:67-80 (2015), the contents of which is hereby incorporated by reference herein in its entirety). As described herein, the present disclosure surprisingly found that viral transduction of an IL2ss sequence upstream of a sequence encoding an Hsp70 protein promotes a high level of secretion (see FIG. 18).

As described herein, in some embodiments, polymorphisms in Hsp70 (such as rs1043618, rs1061581 and rs2227956 in HSP70-1, HSP70-2 and HSP70-hom, respectively) may render the cochlea susceptible to hearing loss (such as a polymorphism described by Konings et al., "Variations in HSP70 genes associated with noise-induced hearing loss in two independent populations", Eur J Hum Genet. 2009 March; 17 (3): 329-33, the contents of which is hereby incorporated by reference in its entirety).

As used herein, the term "active HSPA1A protein" means a protein encoded by DNA that, if substituted for both wildtype alleles encoding full-length HSPA1A protein in auditory hair cells, or ocular cells, of what is otherwise a wildtype mammal, and if expressed in the auditory hair cells, or ocular cells, of that mammal, results in that mammal's having a level of hearing, or vision, approximating the normal level of hearing, or vision, of a similar mammal that is entirely wildtype. Non-limiting examples of active HSPA1A proteins are full-length HSPA1A proteins (e.g., any of the full-length HSPA1A proteins described herein).

For example, an active HSPA1A protein can include a sequence of a wildtype, full-length HSPA1A protein (e.g., a wildtype, human, full-length HSPA1A protein) including about 1 to about 200 amino acid substitutions (e.g., about 1 to 190 amino acid substitutions, about 1 to about 180 amino acid substitutions, about 1 to about 160 amino acid substitutions, about 1 to about 150 amino acid substitutions, about 1 to about 140 amino acid substitutions, about 1 to about 130 amino acid substitutions, about 1 to about 120 amino acid substitutions, about 1 to about 110 amino acid substitutions, about 1 to about 100 amino acid substitutions, about 1 to about 90 amino acid substitutions, about 1 to about 80 amino acid substitutions, about 1 to about 70 amino acid substitutions, about 1 to about 60 amino acid substitutions, about 1 to about 50 amino acid substitutions, about 1 to about 40 amino acid substitutions, about 1 to about 30 amino acid substitutions, about 1 to about 25 amino acid substitutions, about 1 to about 20 amino acid substitutions, about 1 to about 10 amino acid substitutions, about 1 to about 5 amino acid substitutions, about 10 to about 200 amino acid substitutions, about 10 to about 180 amino acid substitutions, about 10 to about 160 amino acid substitutions, about 10 to about 150 amino acid substitutions, about 10 to about 140 amino acid substitutions, about 10 to about 120 amino acid substitutions, about 10 to about 100 amino acid substitutions, about 10 to about 80 amino acid substitutions, about 10 to about 60 amino acid substitutions, about 10 to about 50 amino acid substitutions, about 10 to about 40 amino acid substitutions, about 10 to about 20 amino acid substitutions, about 20 to about 200 amino acid substitutions, about 20 to about 180 amino acid substitutions, about 20 to about 160 amino acid substitutions, about 20 to about 150 amino acid substitutions, about 20 to about 140 amino acid substitutions, about 20 to about 120 amino acid substitutions, about 20 to about 100 amino acid substitutions, about 20 to about 80 amino acid substitutions, about 20 to about 60 amino acid substitutions, about 20 to about 50 amino acid substitutions, about 20 to about 40 amino acid substitutions, about 40 to about 200 amino acid substitutions, about 40 to about 180 amino acid substitutions, about 40 to about 160 amino acid substitutions, about 40 to about 150 amino acid substitutions, about 40 to about 140 amino acid substitutions, about 40 to about 120 amino acid substitutions, about 40 to about 100 amino acid substitutions, about 40 to about 80 amino acid substitutions, about 40 to about 60 amino acid substitutions, about 40 to about 50 amino acid substitutions, about 50 to about 200 amino acid substitutions, about 50 to about 180 amino acid substitutions, about 50 to about 160 amino acid substitutions, about 50 to about 150 amino acid substitutions, about 50 to about 140 amino acid substitutions, about 50 to about 120 amino acid substitutions, about 50 to about 100 amino acid substitutions, about 50 to about 80 amino acid substitutions, about 50 to about 60 amino acid substitutions, about 60 to about 200 amino acid substitutions, about 60 to about 180 amino acid substitutions, about 60 to about 160 amino acid substitutions, about 60 to about 150 amino acid substitutions, about 60 to about 140 amino acid substitutions, about 60 to about 120 amino acid substitutions, about 60 to about 100 amino acid substitutions, about 60 to about 80 amino acid substitutions, about 80 to about 200 amino acid substitutions, about 80 to about 180 amino acid substitutions, about 80 to about 160 amino acid substitutions, about 80 to about 150 amino acid substitutions, about 80 to about 140 amino acid substitutions, about 80 to about 120 amino acid substitutions, about 80 to about 100 amino acid substitutions, about 100 to about 200 amino acid substitutions, about 100 to about 180 amino acid substitutions, about 100 to about 160 amino acid substitutions, about 100 to about 150 amino acid substitutions, about 100 to about 140 amino acid substitutions, about 100 to about 120 amino acid substitutions, about 120 to about 200 amino acid substitutions, about 120 to about 180 amino acid substitutions, about 120 to about 160 amino acid substitutions, about 120 to about 150 amino acid substitutions, about 120 to about 140 amino acid substitutions, about 140 to about 200 amino acid substitutions, about 140 to about 180 amino acid substitutions, about 140 to about 160 amino acid substitutions, about 140 to about 150 amino acid substitutions, about 150 to about 200 amino acid substitutions, about 150 to about 180 amino acid substitutions, about 150 to about 160 amino acid substitutions, about 160 to about 200 amino acid substitutions, about 160 to about 180 amino acid substitutions, or about 180 to about 200 amino acid substitutions).

One skilled in the art would appreciate that amino acids that are not conserved between wildtype HSPA1A proteins from different species can be mutated without losing activity, while those amino acids that are conserved between wildtype HSPA1A proteins from different species should not be mutated as they are more likely (than amino acids that are not conserved between different species) to be involved in activity.

An active HSPA1A protein can include, e.g., a sequence of a wildtype, full-length HSPA1A protein (e.g., a wildtype, human, full-length HSPA1A protein) that has about 1 to about 100 amino acids (e.g., about 1 to about 95 amino acids, about 1 to about 90 amino acids, about 1 to about 85 amino acids, about 1 to about 80 amino acids, about 1 to about 75 amino acids, about 1 to about 70 amino acids, about 1 to about 65 amino acids, about 1 to about 60 amino acids, about 1 to about 55 amino acids, about 1 to about 50 amino acids, about 1 to about 45 amino acids, about 1 to about 40 amino acids, about 1 to about 35 amino acids, about 1 to about 30 amino acids, about 1 to about 25 amino acids, about 1 to about 20 amino acids, about 1 to about 15 amino acids, about 1 to about 10 amino acids, about 1 to about 5 amino acids, about 5 to about 100 amino acids, about 5 to about 95 amino acids, about 5 to about 90 amino acids, about 5 to about 85 amino acids, about 5 to about 80 amino acids, about 5 to about 75 amino acids, about 5 to about 70 amino acids, about 5 to about 65 amino acids, about 5 to about 60 amino acids, about 5 to about 55 amino acids, about 5 to about 50 amino acids, about 5 to about 45 amino acids, about 5 to about 40 amino acids, about 5 to about 35 amino acids, about 5 to about 30 amino acids, about 5 to about 25 amino acids, about 5 to about 20 amino acids, about 5 to about 15 amino acids, about 5 to about 10 amino acids, about 10 to about 100 amino acids, about 10 to about 95 amino acids, about 10 to about 90 amino acids, about 10 to about 85 amino acids, about 10 to about 80 amino acids, about 10 to about 80 amino acids, about 10 to about 75 amino acids, about 10 to about 70 amino acids, about 10 to about 65 amino acids, about 10 to about 60 amino acids, about 10 to about 55 amino acids, about 10 to about 50 amino acids, about 10 to about 45 amino acids, about 10 to about 40 amino acids, about 10 to about 35 amino acids, about 10 to about 30 amino acids, about 10 to about 25 amino acids, about 10 to about 20 amino acids, about 10 to about 15 amino acids, about 15 to about 100 amino acids, about 15 to about 95 amino acids, about 15 to about 90 amino acids, about 15 to about 85 amino acids, about 15 to about 80 amino acids, about 15 to about 75 amino acids, about 15 to about 70 amino acids, about 15 to about 65 amino acids, about 15 to about 60 amino acids, about 15 to about 55 amino acids, about 15 to about 50 amino acids, about 15 to about 45 amino acids, about 15 to about 40 amino acids, about 15 to about 35 amino acids, about 15 to about 30 amino acids, about 15 to about 25 amino acids, about 15 to about 20 amino acids, about 20 to about 100 amino acids, about 20 to about 95 amino acids, about 20 to about 90 amino acids, about 20 to about 85 amino acids, about 20 to about 80 amino acids, about 20 to about 75 amino acids, about 20 to about 70 amino acids, about 20 to about 65 amino acids, about 20 to about 60 amino acids, about 20 to about 55 amino acids, about 20 to about 50 amino acids, about 20 to about 45 amino acids, about 20 to about 40 amino acids, about 20 to about 35 amino acids, about 20 to about 30 amino acids, about 20 to about 25 amino acids, about 25 to about 100 amino acids, about 25 to about 95 amino acids, about 25 to about 90 amino acids, about 25 to about 85 amino acids, about 25 to about 80 amino acids, about 25 to about 75 amino acids, about 25 to about 70 amino acids, about 25 to about 65 amino acids, about 25 to about 60 amino acids, about 25 to about 55 amino acids, about 25 to about 50 amino acids, about 25 to about 45 amino acids, about 25 to about 40 amino acids, about 25 to about 35 amino acids, about 25 to about 30 amino acids, about 30 to about 100 amino acids, about 30 to about 95 amino acids, about 30 to about 90 amino acids, about 30 to about 85 amino acids, about 30 to about 80 amino acids, about 30 to about 75 amino acids, about 30 to about 70 amino acids, about 30 to about 65 amino acids, about 30 to about 60 amino acids, about 30 to about 55 amino acids, about 30 to about 50 amino acids, about 30 to about 45 amino acids, about 30 to about 40 amino acids, about 30 to about 35 amino acids, about 35 to about 100 amino acids, about 35 to about 95 amino acids, about 35 to about 90 amino acids, about 35 to about 85 amino acids, about 35 to about 80 amino acids, about 35 to about 75 amino acids, about 35 to about 70 amino acids, about 35 to about 65 amino acids, about 35 to about 60 amino acids, about 35 to about 55 amino acids, about 35 to about 50 amino acids, about 35 to about 45 amino acids, about 35 to about 40 amino acids, about 40 to about 100 amino acids, about 40 to about 95 amino acids, about 40 to about 90 amino acids, about 40 to about 85 amino acids, about 40 to about 80 amino acids, about 40 to about 75 amino acids, about 40 to about 70 amino acids, about 40 to about 65 amino acids, about 40 to about 60 amino acids, about 40 to about 55 amino acids, about 40 to about 50 amino acids, about 40 to about 45 amino acids, about 45 to about 100 amino acids, about 45 to about 95 amino acids, about 45 to about 90 amino acids, about 45 to about 85 amino acids, about 45 to about 80 amino acids, about 45 to about 75 amino acids, about 45 to about 70 amino acids, about 45 to about 65 amino acids, about 45 to about 60 amino acids, about 45 to about 55 amino acids, about 45 to about 50 amino acids, about 50 to about 100 amino acids, about 50 to about 95 amino acids, about 50 to about 90 amino acids, about 50 to about 85 amino acids, about 50 to about 80 amino acids, about 50 to about 75 amino acids, about 50 to about 70 amino acids, about 50 to about 65 amino acids, about 50 to about 60 amino acids, about 50 to about 55 amino acids, about 55 to about 100 amino acids, about 55 to about 95 amino acids, about 55 to about 90 amino acids, about 55 to about 85 amino acids, about 55 to about 80 amino acids, about 55 to about 75 amino acids, about 55 to about 70 amino acids, about 55 to about 65 amino acids, about 55 to about 60 amino acids, about 60 to about 100 amino acids, about 60 to about 95 amino acids, about 60 to about 90 amino acids, about 60 to about 85 amino acids, about 60 to about 80 amino acids, about 60 to about 75 amino acids, about 60 to about 70 amino acids, about 60 to about 65 amino acids, about 65 to about 100 amino acids, about 65 to about 95 amino acids, about 65 to about 90 amino acids, about 65 to about 85 amino acids, about 65 to about 80 amino acids, about 65 to about 75 amino acids, about 65 to about 70 amino acids, about 70 to about 100 amino acids, about 70 to about 95 amino acids, about 70 to about 90 amino acids, about 70 to about 85 amino acids, about 70 to about 80 amino acids, about 70 to about 75 amino acids, about 75 to about 100 amino acids, about 75 to about 95 amino acids, about 75 to about 90 amino acids, about 75 to about 85 amino acids, about 75 to about 80 amino acids, about 80 to about 100 amino acids, about 80 to about 95 amino acids, about 80 to about 90 amino acids, about 80 to about 85 amino acids, about 85 to about 100 amino acids, about 85 to about 95 amino acids, about 85 to about 90 amino acids, about 90 to about 100 amino acids, about 90 to about 95 amino acids, or about 95 to about 100 amino acids), removed from its N-terminus and/or 1 amino acid to 80 amino acids (or any of the subranges of this range described herein) removed from its C-terminus.

In some embodiments, an active HSPA1A protein can, e.g., include the sequence of a wildtype, full-length HSPA1A protein where 1 amino acid to 50 amino acids, 1 amino acid to 45 amino acids, 1 amino acid to 40 amino acids, 1 amino acid to 35 amino acids, 1 amino acid to 30 amino acids, 1 amino acid to 25 amino acids, 1 amino acid to 20 amino acids, 1 amino acid to 15 amino acids, 1 amino acid to 10 amino acids, 1 amino acid to 9 amino acids, 1 amino acid to 8 amino acids, 1 amino acid to 7 amino acids, 1 amino acid to 6 amino acids, 1 amino acid to 5 amino acids, 1 amino acid to 4 amino acids, 1 amino acid to 3 amino acids, about 2 amino acids to 50 amino acids, about 2 amino acids to 45 amino acids, about 2 amino acids to 40 amino acids, about 2 amino acids to 35 amino acids, about 2 amino acids to 30 amino acids, about 2 amino acids to 25 amino acids, about 2 amino acids to 20 amino acids, about 2 amino acids to 15 amino acids, about 2 amino acids to 10 amino acids, about 2 amino acids to 9 amino acids, about 2 amino acids to 8 amino acids, about 2 amino acids to 7 amino acids, about 2 amino acids to 6 amino acids, about 2 amino acids to 5 amino acids, about 2 amino acids to 4 amino acids, about 3 amino acids to 50 amino acids, about 3 amino acids to 45 amino acids, about 3 amino acids to 40 amino acids, about 3 amino acids to 35 amino acids, about 3 amino acids to 30 amino acids, about 3 amino acids to 25 amino acids, about 3 amino acids to 20 amino acids, about 3 amino acids to 15 amino acids, about 3 amino acids to 10 amino acids, about 3 amino acids to 9 amino acids, about 3 amino acids to 8 amino acids, about 3 amino acids to 7 amino acids, about 3 amino acids to 6 amino acids, about 3 amino acids to 5 amino acids, about 4 amino acids to 50 amino acids, about 4 amino acids to 45 amino acids, about 4 amino acids to 40 amino acids, about 4 amino acids to 35 amino acids, about 4 amino acids to 30 amino acids, about 4 amino acids to 25 amino acids, about 4 amino acids to 20 amino acids, about 4 amino acids to 15 amino acids, about 4 amino acids to 10 amino acids, about 4 amino acids to 9 amino acids, about 4 amino acids to 8 amino acids, about 4 amino acids to 7 amino acids, about 4 amino acids to 6 amino acids, about 5 amino acids to 50 amino acids, about 5 amino acids to 45 amino acids, about 5 amino acids to 40 amino acids, about 5 amino acids to 35 amino acids, about 5 amino acids to 30 amino acids, about 5 amino acids to 25 amino acids, about 5 amino acids to 20 amino acids, about 5 amino acids to 15 amino acids, about 5 amino acids to 10 amino acids, about 5 amino acids to 9 amino acids, about 5 amino acids to 8 amino acids, about 5 amino acids to 7 amino acids, about 6 amino acids to 50 amino acids, about 6 amino acids to 45 amino acids, about 6 amino acids to 40 amino acids, about 6 amino acids to 35 amino acids, about 6 amino acids to 30 amino acids, about 6 amino acids to 25 amino acids, about 6 amino acids to 20 amino acids, about 6 amino acids to 15 amino acids, about 6 amino acids to 10 amino acids, about 6 amino acids to 9 amino acids, about 6 amino acids to 8 amino acids, about 7 amino acids to 50 amino acids, about 7 amino acids to 45 amino acids, about 7 amino acids to 40 amino acids, about 7 amino acids to 35 amino acids, about 7 amino acids to 30 amino acids, about 7 amino acids to 25 amino acids, about 7 amino acids to 20 amino acids, about 7 amino acids to 15 amino acids, about 7 amino acids to 10 amino acids, about 7 amino acids to 9 amino acids, about 8 amino acids to 50 amino acids, about 8 amino acids to 45 amino acids, about 8 amino acids to 40 amino acids, about 8 amino acids to 35 amino acids, about 8 amino acids to 30 amino acids, about 8 amino acids to 25 amino acids, about 8 amino acids to 20 amino acids, about 8 amino acids to 15 amino acids, about 8 amino acids to 10 amino acids, about 10 amino acids to 50 amino acids, about 10 amino acids to 45 amino acids, about 10 amino acids to 40 amino acids, about 10 amino acids to 35 amino acids, about 10 amino acids to 30 amino acids, about 10 amino acids to 25 amino acids, about 10 amino acids to 20 amino acids, about 10 amino acids to 15 amino acids, about 15 amino acids to 50 amino acids, about 15 amino acids to 45 amino acids, about 15 amino acids to 40 amino acids, about 15 amino acids to 35 amino acids, about 15 amino acids to 30 amino acids, about 15 amino acids to 25 amino acids, about 15 amino acids to 20 amino acids, about 20 amino acids to 50 amino acids, about 20 amino acids to 45 amino acids, about 20 amino acids to 40 amino acids, about 20 amino acids to 35 amino acids, about 20 amino acids to 30 amino acids, about 20 amino acids to 25 amino acids, about 25 amino acids to 50 amino acids, about 25 amino acids to 45 amino acids, about 25 amino acids to 40 amino acids, about 25 amino acids to 35 amino acids, about 25 amino acids to 30 amino acids, about 30 amino acids to 50 amino acids, about 30 amino acids to 45 amino acids, about 30 amino acids to 40 amino acids, about 30 amino acids to 35 amino acids, about 35 amino acids to 50 amino acids, about 35 amino acids to 45 amino acids, about 35 amino acids to 40 amino acids, about 40 amino acids to 50 amino acids, about 40 amino acids to 45 amino acids, or about 45 amino acids to about 50 amino acids, are inserted. In some examples, the 1 amino acid to 50 amino acids (or any subrange thereof) can be inserted as a contiguous sequence into the sequence of a wildtype, full-length HSPA1A protein. In some examples, the 1 amino acid to 50 amino acids (or any subrange thereof) are inserted in multiple, non-contiguous places in the sequence of a wildtype, full-length HSPA1A protein. As can be appreciated in the art, the 1 amino acid to 50 amino acids can be inserted into a portion of the sequence of a wildtype, full-length HSPA1A protein that is not well-conserved between species.

Methods of detecting mutations in a gene are well-known in the art. Non-limiting examples of such techniques include: real-time polymerase chain reaction (RT-PCR), PCR, sequencing, Southern blotting, and Northern blotting.

Exemplary wildtype HSPA1A protein sequences are or include SEQ ID NO: 85, 88,90, 91, and 92. Exemplary DNA sequences that encode a NDP protein and exemplary polypeptides encoded by an NDP gene are shown below.

HSPA1A Polynucleotides

Among other things, the present disclosure provides polynucleotides, e.g., polynucleotides comprising an HSPA1A gene or characteristic portion thereof, as well as compositions including such polynucleotides and methods utilizing such polynucleotides and/or compositions.

In some embodiments, a polynucleotide comprising an HSPA1A gene or characteristic portion thereof can be DNA or RNA. In some embodiments, DNA can be genomic DNA or cDNA. In some embodiments, RNA can be an mRNA. In some embodiments, a polynucleotide comprises exons and/or introns of an HSPA1A gene.

In some embodiments, a gene product is expressed from a polynucleotide comprising an HSPA1A gene or characteristic portion thereof. In some embodiments, expression of such a polynucleotide can utilize one or more control elements (e.g., promoters, enhancers, splice sites, polyadenylation sites, translation initiation sites, etc.). Thus, in some embodiments, a polynucleotide provided herein can include one or more control elements.

In some embodiments, an HSPA1A gene is a mammalian HSPA1A gene. In some embodiments, an HSPA1A gene is a murine HSPA1A gene. In some embodiments, an HSPA1A gene is a primate HSPA1A gene. In some embodiments, a HSPA1A gene is a human HSPA1A gene. An exemplary human HSPA1A cDNA sequence is or includes the sequence of SEQ ID NO: 86. An exemplary human HSPA1A genomic DNA sequence can be found in SEQ ID NO: 40. An exemplary human HSPA1A cDNA sequence including untranslated regions is or includes the sequence of SEQ ID NO: 115.

Exemplary Human Mature HSPA1A cDNA (SEQ ID NO: 86)

```
ATGGCCAAAGCCGCGGCGATCGGCATCGACCTGGGCACCACCTACTCCTGCGTGGGGGTGTTCC

AACACGGCAAGGTGGAGATCATCGCCAACGACCAGGGCAACCGCACCACCCCCAGCTACGTGGC

CTTCACGGACACCGAGCGGCTCATCGGGGATGCGGCCAAGAACCAGGTGGCGCTGAACCCGCAG

AACACCGTGTTTGACGCGAAGCGGCTGATCGGCCGCAAGTTCGGCGACCCGGTGGTGCAGTCGG

ACATGAAGCACTGGCCTTTCCAGGTGATCAACGACGGAGACAAGCCCAAGGTGCAGGTGAGCTA

CAAGGGGGAGACCAAGGCATTCTACCCCGAGGAGATCTCGTCCATGGTGCTGACCAAGATGAAG

GAGATCGCCGAGGCGTACCTGGGCTACCCGGTGACCAACGCGGTGATCACCGTGCCGGCCTACT

TCAACGACTCGCAGCGCCAGGCCACCAAGGATGCGGGTGTGATCGCGGGGCTCAACGTGCTGCG

GATCATCAACGAGCCCACGGCCGCCGCCATCGCCTACGGCCTGGACAGAACGGGCAAGGGGGAG

CGCAACGTGCTCATCTTTGACCTGGGCGGGGGCACCTTCGACGTGTCCATCCTGACGATCGACG

ACGGCATCTTCGAGGTGAAGGCCACGGCCGGGGACACCCACCTGGGTGGGGAGGACTTTGACAA

CAGGCTGGTGAACCACTTCGTGGAGGAGTTCAAGAGAAAACACAAGAAGGACATCAGCCAGAAC

AAGCGAGCCGTGAGGCGGCTGCGCACCGCCTGCGAGAGGGCCAAGAGGACCCTGTCGTCCAGCA

CCCAGGCCAGCCTGGAGATCGACTCCCTGTTTGAGGGCATCGACTTCTACACGTCCATCACCAG

GGCGAGGTTCGAGGAGCTGTGCTCCGACCTGTTCCGAAGCACCCTGGAGCCCGTGGAGAAGGCT

CTGCGCGACGCCAAGCTGGACAAGGCCCAGATTCACGACCTGGTCCTGGTCGGGGGCTCCACCC

GCATCCCCAAGGTGCAGAAGCTGCTGCAGGACTTCTTCAACGGGCGCGACCTGAACAAGAGCAT

CAACCCCGACGAGGCTGTGGCCTACGGGGCGGCGGTGCAGGCGGCCATCCTGATGGGGGACAAG

TCCGAGAACGTGCAGGACCTGCTGCTGCTGGACGTGGCTCCCCTGTCGCTGGGGCTGGAGACGG

CCGGAGGCGTGATGACTGCCCTGATCAAGCGCAACTCCACCATCCCCACCAAGCAGACGCAGAT

CTTCACCACCTACTCCGACAACCAACCCGGGGTGCTGATCCAGGTGTACGAGGGCGAGAGGGCC
```

-continued

ATGACGAAAGACAACAATCTGTTGGGGCGCTTCGAGCTGAGCGGCATCCCTCCGGCCCCCAGGG
GCGTGCCCCAGATCGAGGTGACCTTCGACATCGATGCCAACGGCATCCTGAACGTCACGGCCAC
GGACAAGAGCACCGGCAAGGCCAACAAGATCACCATCACCAACGACAAGGGCCGCCTGAGCAAG
GAGGAGATCGAGCGCATGGTGCAGGAGGCGGAGAAGTACAAAGCGGAGGACGAGGTGCAGCGCG
AGAGGGTGTCAGCCAAGAACGCCCTGGAGTCCTACGCCTTCAACATGAAGAGCGCCGTGGAGGA
TGAGGGGCTCAAGGGCAAGATCAGCGAGGCGGACAAGAAGAAGGTTCTGGACAAGTGTCAAGAG
GTCATCTCGTGGCTGGACGCCAACACCTTGGCCGAGAAGGACGAGTTTGAGCACAAGAGGAAGG
AGCTGGAGCAGGTGTGTAACCCCATCATCAGCGGACTGTACCAGGGTGCCGGTGGTCCCGGGCC
TGGGGGCTTCGGGGCTCAGGGTCCCAAGGGAGGGTCTGGGTCAGGCCCCACCATTGAGGAGGTG
GATTAG

Exemplary Mature HSPA1A cDNA including untranslated regions
(SEQ ID NO: 115)

AACGGCTAGCCTGAGGAGCTGCTGCGACAGTCCACTACCTTTTTCGAGAGTGACTCCCGTTGTC
CCAAGGCTTCCCAGAGCGAACCTGTGCGGCTGCAGGCACCGGCGCGTCGAGTTTCCGGCGTCCG
GAAGGACCGAGCTCTTCTCGCGGATCCAGTGTTCCGTTTCCAGCCCCCAATCTCAGAGCGGAGC
CGACAGAGAGCAGGGAACCGGCATGGCCAAAGCCGCGGCGATCGGCATCGACCTGGGCACCACC
TACTCCTGCGTGGGGGTGTTCCAACACGGCAAGGTGGAGATCATCGCCAACGACCAGGGCAACC
GCACCACCCCCAGCTACGTGGCCTTCACGGACACCGAGCGGCTCATCGGGGATGCGGCCAAGAA
CCAGGTGGCGCTGAACCCGCAGAACACCGTGTTTGACGCGAAGCGGCTGATTGGCCGCAAGTTC
GGCGACCCGGTGGTGCAGTCGGACATGAAGCACTGGCCTTTCCAGGTGATCAACGACGGAGACA
AGCCCAAGGTGCAGGTGAGCTACAAGGGGGAGACCAAGGCATTCTACCCCGAGGAGATCTCGTC
CATGGTGCTGACCAAGATGAAGGAGATCGCCGAGGCGTACCTGGGCTACCCGGTGACCAACGCG
GTGATCACCGTGCCGGCCTACTTCAACGACTCGCAGCGCCAGGCCACCAAGGATGCGGGTGTGA
TCGCGGGGCTCAACGTGCTGCGGATCATCAACGAGCCCACGGCCGCCGCCATCGCCTACGGCCT
GGACAGAACGGGCAAGGGGGAGCGCAACGTGCTCATCTTTGACCTGGGCGGGGGCACCTTCGAC
GTGTCCATCCTGACGATCGACGACGGCATCTTCGAGGTGAAGGCCACGGCCGGGGACACCCACC
TGGGTGGGGAGGACTTTGACAACAGGCTGGTGAACCACTTCGTGGAGGAGTTCAAGAGAAAACA
CAAGAAGGACATCAGCCAGAACAAGCGAGCCGTGAGGCGGCTGCGCACCGCCTGCGAGAGGGCC
AAGAGGACCCTGTCGTCCAGCACCCAGGCCAGCCTGGAGATCGACTCCCTGTTTGAGGGCATCG
ACTTCTACACGTCCATCACCAGGGCGAGGTTCGAGGAGCTGTGCTCCGACCTGTTCCGAAGCAC
CCTGGAGCCCGTGGAGAAGGCTCTGCGCGACGCCAAGCTGGACAAGGCCCAGATTCACGACCTG
GTCCTGGTCGGGGGCTCCACCCGCATCCCCAAGGTGCAGAAGCTGCTGCAGGACTTCTTCAACG
GGCGCGACCTGAACAAGAGCATCAACCCCGACGAGGCTGTGGCCTACGGGGCGGCGGTGCAGGC
GGCCATCCTGATGGGGGACAAGTCCGAGAACGTGCAGGACCTGCTGCTGCTGGACGTGGCTCCC
CTGTCGCTGGGGCTGGAGACGGCCGGAGGCGTGATGACTGCCCTGATCAAGCGCAACTCCACCA
TCCCCACCAAGCAGACGCAGATCTTCACCACCTACTCCGACAACCAACCCGGGGTGCTGATCCA
GGTGTACGAGGGCGAGAGGGCCATGACGAAAGACAACAATCTGTTGGGGCGCTTCGAGCTGAGC
GGCATCCCTCCGGCCCCCAGGGGCGTGCCCCAGATCGAGGTGACCTTCGACATCGATGCCAACG
GCATCCTGAACGTCACGGCCACGGACAAGAGCACCGGCAAGGCCAACAAGATCACCATCACCAA
CGACAAGGGCCGCCTGAGCAAGGAGGAGATCGAGCGCATGGTGCAGGAGGCGGAGAAGTACAAA
GCGGAGGACGAGGTGCAGCGCGAGAGGGTGTCAGCCAAGAACGCCCTGGAGTCCTACGCCTTCA

-continued

ACATGAAGAGCGCCGTGGAGGATGAGGGGCTCAAGGGCAAGATCAGCGAGGCGGACAAGAAGAA

GGTGCTGGACAAGTGTCAAGAGGTCATCTCGTGGCTGGACGCCAACACCTTGGCCGAGAAGGAC

GAGTTTGAGCACAAGAGGAAGGAGCTGGAGCAGGTGTGTAACCCCATCATCAGCGGACTGTACC

AGGGTGCCGGTGGTCCCGGGCCTGGGGGCTTCGGGGCTCAGGGTCCCAAGGGAGGGTCTGGGTC

AGGCCCCACCATTGAGGAGGTAGATTAGGGGCCTTTCCAAGATTGCTGTTTTTGTTTTGGAGCT

TCAAGACTTTGCATTTCCTAGTATTTCTGTTTGTCAGTTCTCAATTTCCTGTGTTTGCAATGTT

GAAATTTTTTGGTGAAGTACTGAACTTGCTTTTTTTCCGGTTTCTACATGCAGAGATGAATTTA

TACTGCCATCTTACGACTATTTCTTCTTTTTAATACACTTAACTCAGGCCATTTTTTAAGTTGG

TTACTTCAAAGTAAATAAACTTTAAAATTCAA

A non-limiting example of a human wildtype HSPA1A genomic DNA sequence is SEQ ID NO: 87.

Exemplary Human HSPA1A Gene Sequence (NCBI Reference Sequence NC 000006.12)

(SEQ ID NO: 87)

AACGGCTAGCCTGAGGAGCTGCTGCGACAGTCCACTACCTTTTTCGAGAGTGACTCCCGTTGTC

CCAAGGCTTCCCAGAGCGAACCTGTGCGGCTGCAGGCACCGGCGCGTCGAGTTTCCGGCGTCCG

GAAGGACCGAGCTCTTCTCGCGGATCCAGTGTTCCGTTTCCAGCCCCCAATCTCAGAGCGGAGC

CGACAGAGAGCAGGGAACCGGCATGGCCAAAGCCGCGGCGATCGGCATCGACCTGGGCACCACC

TACTCCTGCGTGGGGGTGTTCCAACACGGCAAGGTGGAGATCATCGCCAACGACCAGGGCAACC

GCACCACCCCCAGCTACGTGGCCTTCACGGACACCGAGCGGCTCATCGGGGATGCGGCCAAGAA

CCAGGTGGCGCTGAACCCGCAGAACACCGTGTTTGACGCGAAGCGGCTGATTGGCCGCAAGTTC

GGCGACCCGGTGGTGCAGTCGGACATGAAGCACTGGCCTTTCCAGGTGATCAACGACGGAGACA

AGCCCAAGGTGCAGGTGAGCTACAAGGGGGAGACCAAGGCATTCTACCCCGAGGAGATCTCGTC

CATGGTGCTGACCAAGATGAAGGAGATCGCCGAGGCGTACCTGGGCTACCCGGTGACCAACGCG

GTGATCACCGTGCCGGCCTACTTCAACGACTCGCAGCGCCAGGCCACCAAGGATGCGGGTGTGA

TCGCGGGGCTCAACGTGCTGCGGATCATCAACGAGCCCACGGCCGCCGCCATCGCCTACGGCCT

GGACAGAACGGGCAAGGGGGAGCGCAACGTGCTCATCTTTGACCTGGGCGGGGGCACCTTCGAC

GTGTCCATCCTGACGATCGACGACGGCATCTTCGAGGTGAAGGCCACGGCCGGGGACACCCACC

TGGGTGGGGAGGACTTTGACAACAGGCTGGTGAACCACTTCGTGGAGGAGTTCAAGAGAAAACA

CAAGAAGGACATCAGCCAGAACAAGCGAGCCGTGAGGCGGCTGCGCACCGCCTGCGAGAGGGCC

AAGAGGACCCTGTCGTCCAGCACCCAGGCCAGCCTGGAGATCGACTCCCTGTTTGAGGGCATCG

ACTTCTACACGTCCATCACCAGGGCGAGGTTCGAGGAGCTGTGCTCCGACCTGTTCCGAAGCAC

CCTGGAGCCCGTGGAGAAGGCTCTGCGCGACGCCAAGCTGGACAAGGCCCAGATTCACGACCTG

GTCCTGGTCGGGGGCTCCACCCGCATCCCCAAGGTGCAGAAGCTGCTGCAGGACTTCTTCAACG

GGCGCGACCTGAACAAGAGCATCAACCCCGACGAGGCTGTGGCCTACGGGGCGGCGGTGCAGGC

GGCCATCCTGATGGGGGACAAGTCCGAGAACGTGCAGGACCTGCTGCTGCTGGACGTGGCTCCC

CTGTCGCTGGGGCTGGAGACGGCCGGAGGCGTGATGACTGCCCTGATCAAGCGCAACTCCACCA

TCCCCACCAAGCAGACGCAGATCTTCACCACCTACTCCGACAACCAACCCGGGGTGCTGATCCA

GGTGTACGAGGGCGAGAGGGCCATGACGAAAGACAACAATCTGTTGGGGCGCTTCGAGCTGAGC

GGCATCCCTCCGGCCCCCAGGGGCGTGCCCCAGATCGAGGTGACCTTCGACATCGATGCCAACG

GCATCCTGAACGTCACGGCCACGGACAAGAGCACCGGCAAGGCCAACAAGATCACCATCACCAA

-continued

CGACAAGGGCCGCCTGAGCAAGGAGGAGATCGAGCGCATGGTGCAGGAGGCGGAGAAGTACAAA

GCGGAGGACGAGGTGCAGCGCGAGAGGGTGTCAGCCAAGAACGCCCTGGAGTCCTACGCCTTCA

ACATGAAGAGCGCCGTGGAGGATGAGGGGCTCAAGGGCAAGATCAGCGAGGCGGACAAGAAGAA

GGTGCTGGACAAGTGTCAAGAGGTCATCTCGTGGCTGGACGCCAACACCTTGGCCGAGAAGGAC

GAGTTTGAGCACAAGAGGAAGGAGCTGGAGCAGGTGTGTAACCCCATCATCAGCGGACTGTACC

AGGGTGCCGGTGGTCCCGGGCCTGGGGGCTTCGGGGCTCAGGGTCCCAAGGGAGGGTCTGGGTC

AGGCCCCACCATTGAGGAGGTAGATTAGGGGCCTTTCCAAGATTGCTGTTTTTGTTTTGGAGCT

TCAAGACTTTGCATTTCCTAGTATTTCTGTTTGTCAGTTCTCAATTTCCTGTGTTTGCAATGTT

GAAATTTTTTGGTGAAGTACTGAACTTGCTTTTTTTCCGGTTTCTACATGCAGAGATGAATTTA

TACTGCCATCTTACGACTATTTCTTCTTTTTAATACACTTAACTCAGGCCATTTTTTAAGTTGG

TTACTTCAAAGTAAATAAACTTTAAAATTCAA

Exemplary Mouse Mature HSPA1A cDNA (SEQ ID NO: 89)

ATGGCCAAGAACACGGCGATCGGCATCGACCTGGGCACCACCTACTCGTGCGTGGGCGTGTTCC

AGCACGGCAAGGTGGAGATCATCGCCAACGACCAGGGCAACCGCACGACCCCCAGCTACGTGGC

CTTCACCGACACCGAGCGCCTCATCGGAGACGCCGCCAAGAACCAGGTGGCGCTGAACCCGCAG

AACACCGTGTTCGACGCGAAGCGGCTGATCGGCCGCAAGTTCGGCGATGCGGTGGTGCAGTCCG

ACATGAAGCACTGGCCCTTCCAGGTGGTGAACGACGGCGACAAGCCCAAGGTGCAGGTGAACTA

CAAGGGCGAGAGCCGGTCGTTCTTCCCGGAGGAGATCTCGTCCATGGTGCTGACGAAGATGAAG

GAGATCGCTGAGGCGTACCTGGGCCACCCGGTGACCAACGCGGTGATCACGGTGCCCGCCTACT

TCAACGACTCTCAGCGGCAGGCCACCAAGGACGCGGGCGTGATCGCCGGTCTAAACGTGCTGCG

GATCATCAACGAGCCCACGGCGGCCGCCATCGCCTACGGGCTGGACCGGACCGGCAAGGGCGAG

CGCAACGTGCTCATCTTCGACCTGGGGGGCGGCACGTTCGACGTGTCCATCCTGACGATCGACG

ACGGCATCTTCGAGGTGAAGGCCACGGCGGGCGACACGCACCTGGGAGGGGAGGACTTCGACAA

CCGGCTGGTGAGCCACTTCGTGGAGGAGTTCAAGAGGAAGCACAAGAAGGACATCAGCCAGAAC

AAGCGCGCGGTGCGGCGGCTGCGCACTGCGTGTGAGAGGGCCAAGAGGACGCTGTCGTCCAGCA

CCCAGGCCAGCCTGGAGATCGACTCTCTGTTCGAGGGCATCGACTTCTACACATCCATCACGCG

GGCGCGGTTCGAAGAGCTGTGCTCAGACCTGTTCCGCGGCACGCTGGAGCCCGTGGAGAAGGCC

CTGCGCGACGCCAAGATGGACAAGGCGCAGATCCACGACCTGGTGCTGGTGGGCGGCTCGACGC

GCATCCCCAAGGTGCAGAAGCTGCTGCAGGACTTCTTCAACGGGCGCGACCTGAACAAGAGCAT

CAACCCGGACGAGGCGGTGGCCTACGGGGCGGCGGTGCAGGCGGCCATCCTGATGGGGGACAAG

TCGGAGAACGTGCAGGACCTGCTGCTGCTGGACGTGGCGCCGCTGTCGCTGGGCCTGGAGACTG

CGGGCGGCGTGATGACGGCGCTCATCAAGCGCAACTCCACCATCCCCACCAAGCAGACGCAGAC

CTTCACCACCTACTCGGACAACCAGCCCGGGGTGCTGATCCAGGTGTACGAGGGCGAGAGGGCC

ATGACGCGCGACAACAACCTGCTGGGGCGCTTCGAACTGAGCGGCATCCCGCCGGCGCCCAGGG

GCGTGCCACAGATCGAGGTGACCTTCGACATCGACGCCAACGGCATCCTGAACGTCACGGCCAC

CGACAAGAGCACCGGCAAGGCCAACAAGATCACCATCACCAACGACAAGGGCCGCCTGAGCAAG

GAGGAGATCGAGCGCATGGTGCAGGAGGCCGAGCGCTACAAGGCCGAGGACGAGGTGCAGCGCG

ACAGGGTGGCCGCCAAGAACGCGCTCGAATCCTATGCCTTCAACATGAAGAGCGCCGTGGAGGA

CGAGGGTCTCAAGGGCAAGCTCAGCGAGGCTGACAAGAAGAAGGTGCTGGACAAGTGCCAGGAG

GTCATCTCCTGGCTGGACTCCAACACGCTGGCCGACAAGGAGGAGTTCGTGCACAAGCGGGAGG

-continued

```
AGCTGGAGCGGGTGTGCAGCCCCATCATCAGTGGGCTGTACCAGGGTGCGGGTGCTCCTGGGGC

TGGGGGCTTCGGGGCCCAGGCGCCCAAGGGAGCCTCTGGCTCAGGACCCACCATCGAGGAGGTG

GATTAGA
```

Polypeptides Encoded by HSPA1A Gene

Among other things, the present disclosure provides polypeptides encoded by an NDP gene or characteristic portion thereof. In some embodiments, an HSPA1A gene is a mammalian HSPA1A gene. In some embodiments, an HSPA1A gene is a murine HSPA1A gene. In some embodiments, an HSPA1A gene is a primate HSPA1A gene. In some embodiments, a HSPA1A gene is a human HSPA1A gene.

In some embodiments, a polypeptide comprises a HSPA1A protein or characteristic portion thereof. In some embodiments, a HSPA1A protein or characteristic portion thereof is mammalian HSPA1A protein or characteristic portion thereof, e.g., primate HSPA1A protein or characteristic portion thereof. In some embodiments, a HSPA1A protein or characteristic portion thereof is a human HSPA1A protein or characteristic portion thereof.

In some embodiments, a polypeptide provided herein comprises post-translational modifications. In some embodiments, a HSPA1A protein or characteristic portion thereof provided herein comprises post-translational modifications. In some embodiments, post-translational modifications can comprise but is not limited to glycosylation (e.g., N-linked glycosylation, O-linked glycosylation), phosphorylation, acetylation, amidation, hydroxylation, methylation, ubiquitylation, sulfation, and/or a combination thereof.

An exemplary human HSPA1A protein sequence is or includes the sequence of SEQ ID NO: 85. An exemplary human HSPA1A protein sequence with a c-terminal flag tag is or includes the sequence of SEQ ID NO: 95. As exemplary mouse HSPA1A protein sequence is or includes the sequence of SEQ ID NO: 88. As exemplary rhesus monkey HSPA1A protein sequence is or includes the sequence of SEQ ID NO: 90. As exemplary rat HSPA1A protein sequence is or includes the sequence of SEQ ID NO: 91. As exemplary cattle HSPA1A protein sequence is or includes the sequence of SEQ ID NO: 92.

```
Exemplary Human Mature HSPA1A Protein (NCBI Accession No. NP_005336.3)
                                                          (SEQ ID NO: 85)
MAKAAAIGIDLGTTYSCVGVFQHGKVEIIANDQGNRTTPSYVAFTDTERLIGDAAKNQVALNPQ

NTVFDAKRLIGRKFGDPVVQSDMKHWPFQVINDGDKPKVQVSYKGETKAFYPEEISSMVLTKMK

EIAEAYLGYPVTNAVITVPAYFNDSQRQATKDAGVIAGLNVLRIINEPTAAAIAYGLDRTGKGE

RNVLIFDLGGGTEDVSILTIDDGIFEVKATAGDTHLGGEDFDNRLVNHFVEEFKRKHKKDISQN

KRAVRRLRTACERAKRTLSSSTQASLEIDSLFEGIDFYTSITRARFEELCSDLFRSTLEPVEKA

LRDAKLDKAQIHDLVLVGGSTRIPKVQKLLQDFFNGRDLNKSINPDEAVAYGAAVQAAILMGDK

SENVQDLLLLDVAPLSLGLETAGGVMTALIKRNSTIPTKQTQIFTTYSDNQPGVLIQVYEGERA

MTKDNNLLGRFELSGIPPAPRGVPQIEVTFDIDANGILNVTATDKSTGKANKITITNDKGRLSK

EEIERMVQEAEKYKAEDEVQRERVSAKNALESYAFNMKSAVEDEGLKGKISEADKKKVLDKCQE

VISWLDANTLAEKDEFEHKRKELEQVCNPIISGLYQGAGGPGPGGFGAQGPKGGSGSGPTIEEV

D

Exemplary Human HSPA1A Protein Sequence with C-terminal Flag Tag
                                                           (SEQ ID NO: 95)
MAKAAAIGIDLGTTYSCVGVFQHGKVEIIANDQGNRTTPSYVAFTDTERLIGDAAKNQVALNPQ

NTVFDAKRLIGRKFGDPVVQSDMKHWPFQVINDGDKPKVQVSYKGETKAFYPEEISSMVLTKMK

EIAEAYLGYPVTNAVITVPAYFNDSQRQATKDAGVIAGLNVLRIINEPTAAAIAYGLDRTGKGE

RNVLIFDLGGGTEDVSILTIDDGIFEVKATAGDTHLGGEDFDNRLVNHFVEEFKRKHKKDISQN

KRAVRRLRTACERAKRTLSSSTQASLEIDSLFEGIDFYTSITRARFEELCSDLFRSTLEPVEKA

LRDAKLDKAQIHDLVLVGGSTRIPKVQKLLQDFFNGRDLNKSINPDEAVAYGAAVQAAILMGDK

SENVQDLLLLDVAPLSLGLETAGGVMTALIKRNSTIPTKQTQIFTTYSDNQPGVLIQVYEGERA

MTKDNNLLGRFELSGIPPAPRGVPQIEVTFDIDANGILNVTATDKSTGKANKITITNDKGRLSK

EEIERMVQEAEKYKAEDEVQRERVSAKNALESYAFNMKSAVEDEGLKGKISEADKKKVLDKCQE

VISWLDANTLAEKDEFEHKRKELEQVCNPIISGLYQGAGGPGPGGFGAQGPKGGSGSGPTIEEV

DGSRADYKDHDGDYKDHDIDYKDDDDK
```

-continued

Exemplary Mouse Mature HSPA1A Protein (NCBI Accession No. NP_034609.2)

(SEQ ID NO: 88)

MAKNTAIGIDLGTTYSCVGVFQHGKVEIIANDQGNRTTPSYVAFTDTERLIGDAAKNQVALNPQ

NTVFDAKRLIGRKFGDAVVQSDMKHWPFQVVNDGDKPKVQVNYKGESRSFFPEEISSMVLTKMK

EIAEAYLGHPVTNAVITVPAYFNDSQRQATKDAGVIAGLNVLRIINEPTAAAIAYGLDRTGKGE

RNVLIFDLGGGTFDVSILTIDDGIFEVKATAGDTHLGGEDFDNRLVSHFVEEFKRKHKKDISQN

KRAVRRLRTACERAKRTLSSSTQASLEIDSLFEGIDFYTSITRARFEELCSDLFRGTLEPVEKA

LRDAKMDKAQIHDLVLVGGSTRIPKVQKLLQDFFNGRDLNKSINPDEAVAYGAAVQAAILMGDK

SENVQDLLLLDVAPLSLGLETAGGVMTALIKRNSTIPTKQTQTFTTYSDNQPGVLIQVYEGERA

MTRDNNLLGRFELSGIPPAPRGVPQIEVTFDIDANGILNVTATDKSTGKANKITITNDKGRLSK

EEIERMVQEAERYKAEDEVQRDRVAAKNALESYAFNMKSAVEDEGLKGKLSEADKKKVLDKCQE

VISWLDSNTLADKEEFVHKREELERVCSPIISGLYQGAGAPGAGGFGAQAPKGASGSGPTIEEV

D

Exemplary Rhesus Monkey Mature HSPA1A Protein (NCBI Accession No. XP_014991489.2)

(SEQ ID NO: 90)

MAKAAAIGIDLGTTYSCVGVFQHGKVEIIANDQGNRTTPSYVAFTDTERLIGDAAKNQVALNPQ

NTVFDAKRLIGRKFGDPVVQSDMKHWPFQVINDGDKPKVQVSYKGETKAFYPEEISSMVLTKMK

EIAEAYLGYPVTNAVITVPAYFNDSQRQATKDAGVIAGLNVLRIINEPTAAAIAYGLDRTGKGE

RNVLIFDLGGGTEDVSILTIDDGIFEVKATAGDTHLGGEDFDNRLVNHFVEEFKRKHKKDISQN

KRAVRRLRTACERAKRTLSSSTQASLEIDSLFEGIDFYTSITRARFEELCSDLFRSTLEPVEKA

LRDAKLDKAQIHDLVLVGGSTRIPKVQKLLQDFFNGRDLNKSINPDEAVAYGAAVQAAILMGDK

SENVQDLLLLDVAPLSLGLETAGGVMTALIKRNSTIPTKQTQIFTTYSDNQPGVLIQVYEGERA

MTKDNNLLGRFELSGIPPAPRGVPQIEVTFDIDANGILNVTATDKSTGKANKITITNDKGRLSK

EEIERMVQEAEKYKAEDEVQRERVSAKNALESYAFNMKSAVEDEGLKGKISEADKKKVLDKCQE

VISWLDANTLAEKDEFEHKRKELEQVCNPIISGLYQGAGGPGPGGFGAQGPKGGSGSGPTIEEV

D

Exemplary Rat Mature HSPA1A Protein (NCBI Accession No. NP_114177.2)

(SEQ ID NO: 91)

MAKKTAIGIDLGTTYSCVGVFQHGKVEIIANDQGNRTTPSYVAFTDTERLIGDAAKNQVALNPQ

NTVFDAKRLIGRKFGDPVVQSDMKHWPFQVVNDGDKPKVQVNYKGENRSFYPEEISSMVLTKMK

EIAEAYLGHPVTNAVITVPAYFNDSQRQATKDAGVIAGLNVLRIINEPTAAAIAYGLDRTGKGE

RNVLIFDLGGGTFDVSILTIDDGIFEVKATAGDTHLGGEDFDNRLVSHFVEEFKRKHKKDISQN

KRAVRRLRTACERAKRTLSSSTQASLEIDSLFEGIDFYTSITRARFEELCSDLFRGTLEPVEKA

LRDAKLDKAQIHDLVLVGGSTRIPKVQKLLQDFFNGRDLNKSINPDEAVAYGAAVQAAILMGDK

SENVQDLLLLDVAPLSLGLETAGGVMTALIKRNSTIPTKQTQTFTTYSDNQPGVLIQVYEGERA

MTRDNNLLGRFELSGIPPAPRGVPQIEVTFDIDANGILNVTATDKSTGKANKITITNDKGRLSK

EEIERMVQEAERYKAEDEVQRERVAAKNALESYAFNMKSAVEDEGLKGKISEADKKKVLDKCQE

VISWLDSNTLAEKEEFVHKREELERVCNPIISGLYQGAGAPGAGGFGAQAPKGGSGSGPTIEEV

D

Exemplary Cattle HSPAIA Protein (NCBI Accession No. NP_976067.3)

(SEQ ID NO: 92)

MAKNMAIGIDLGTTYSCVGVFQHGKVEIIANDQGNRTTPSYVAFTDTERLIGDAAKNQVALNPQ

NTVFDAKRLIGRKFGDPVVQSDMKHWPFRVINDGDKPKVQVSYKGETKAFYPEEISSMVLTKMK

EIAEAYLGHPVTNAVITVPAYFNDSQRQATKDAGVIAGLNVLRIINEPTAAAIAYGLDRTGKGE

-continued

```
RNVLIFDLGGGTEDVSILTIDDGIFEVKATAGDTHLGGEDFDNRLVNHFVEEFKRKHKKDISQN

KRAVRRLRTACERAKRTLSSSTQASLEIDSLFEGIDFYTSITRARFEELCSDLFRSTLEPVEKA

LRDAKLDKAQIHDLVLVGGSTRIPKVQKLLQDFFNGRDLNKSINPDEAVAYGAAVQAAILMGDK

SENVQDLLLLDVAPLSLGLETAGGVMTALIKRNSTIPTKQTQIFTTYSDNQPGVLIQVYEGERA

MTRDNNLLGRFELSGIPPAPRGVPQIEVTFDIDANGILNVTATDKSTGKANKITITNDKGRLSK

EEIERMVQEAEKYKAEDEVQRERVSAKNALESYAFNMKSAVEDEGLKGKISEADKKKVLDKCQE

VISWLDANTLAEKDEFEHKRKELEQVCNPIISRLYQGAGGPGAGGFGAQGPKGGSGSGPTIEEV

D
```

Hsp40/DNAJ Family of Proteins

A secreted protein described herein can be a heat shock protein from the Hsp40/DNAJ family. Proteins in the Hsp40/DNAJ family comprise a 70 amino-acid consensus sequence known as the J domain, which interacts with a HSP70 protein. Without being bound to any particular theory, it is believed that proteins in the Hsp40/DNAJ family play a role in regulating the adenosine triphosphatase (ATPase) activity of HSP70 heat-shock proteins (e.g., HSPA1A).

In some embodiments, a protein in the Hsp40/DNAJ family is encoded by a Type 1 (subfamily A) gene. In some embodiments, a protein in the Hsp40/DNAJ family is encoded by a Type 2 (subfamily B) gene. In some embodiments, a protein in the Hsp40/DNAJ family is encoded by a Type 3 (subfamily C) gene. In some embodiments, a protein in the Hsp40/DNAJ family is encoded by a J-like gene. In some embodiments, a protein in the Hsp40/DNAJ family is encoded by a gene listed in Table 1. Exemplary sequences for the genes can be found by reference to the Gene ID in Table 1. In some embodiments, a protein in the Hsp40/DNAJ family is listed in Table 1. Exemplary sequences for the proteins can be found by reference to the UniProt ID in Table 1.

TABLE 1

| Gene | Protein | UniProt ID | Gene ID |
|---|---|---|---|
| Type 1 (subfamily A) | | | |
| DNAJA1 | DnaJA1 | P31689 | 3301 |
| DNAJA2 | DnaJA2 | O60884 | 10294 |
| DNAJA3 | DnaJA3 | Q96EY1 | 9093 |
| DNAJA4 | DnaJA4 | Q8WW22 | 55466 |
| Type 2 (subfamily B) | | | |
| DNAJB1 | DnaJB1 | P25685 | 3337 |
| DNAJB2 | DnaJB2 | P25686 | 3300 |
| DNAJB3 | DnaJB3 | Q8WWF6 | 414061 |
| DNAJB4 | DnaJB4 | Q9UDY4 | 11080 |
| DNAJB5 | DnaJB5 | O75953 | 25822 |
| DNAJB6 | DnaJB6 | O75190 | 10049 |
| DNAJB7 | DnaJB7 | Q7Z6W7 | 150353 |
| DNAJB8 | DnaJB8 | Q8NHSO | 165721 |
| DNAJB9 | DnaJB9 | Q9UBS3 | 4189 |
| DNAJB11 | DnaJB11 | Q9UBS4 | 51726 |
| DNAJB12 | DnaJB12 | Q9NXW2 | 54788 |
| DNAJB13 | DnaJB13 | P59910 | 374407 |
| DNAJB14 | DnaJB14 | Q8TBM8 | 79982 |
| Type 3 (subfamily C) | | | |
| DNAJC1 | DnaJC1 | Q96KC8 | 64215 |
| DNAJC2 | DnaJC2 | Q99543 | 27000 |
| DNAJC3 | DnaJC3 | Q13217 | 5611 |
| DNAJC4 | DnaJC4 | Q9NNZ3 | 3338 |
| DNAJC5 | DnaJC5 | Q9H3Z4 | 80331 |
| DNAJC5B | DnaJC5B | Q9UF47 | 85479 |
| DNAJC5G | DnaJC5G | Q8N7S2 | 285126 |
| DNAJC6 | DnaJC6 | O75061 | 9829 |
| DNAJC7 | DnaJC7 | Q99615 | 7266 |
| DNAJC8 | DnaJC8 | O75937 | 22826 |
| DNAJC9 | DnaJC9 | Q8WXX5 | 23234 |
| DNAJC10 | DnaJC10 | Q8IXB1 | 54431 |
| DNAJC11 | DnaJC11 | Q9NVH1 | 55735 |
| DNAJC12 | DnaJC12 | Q9UKB3 | 56521 |
| DNAJC13 | DnaJC13 | O75165 | 23317 |
| DNAJC14 | DnaJC14 | Q6Y2X3 | 85406 |
| DNAJC15 | DnaJC15 | Q9Y5T4 | 29103 |
| DNAJC16 | DnaJC16 | Q9Y2G8 | 23341 |
| DNAJC17 | DnaJC17 | Q9NVM6 | 55192 |
| DNAJC18 | DnaJC18 | Q9H819 | 202052 |
| DNAJC19 | DnaJC19 | Q96DA6 | 131118 |
| DNAJC20 | DnaJC20 | Q8IWL3 | 150274 |
| DNAJC21 | DnaJC21 | Q5F1R6 | 134218 |
| DNAJC22 | DnaJC22 | Q8N4W6 | 79962 |
| J-like | | | |
| DNAJC23 | DnaJC23 | Q9UGP8 | 11231 |
| DNAJC24 | DnaJC24 | Q6P3W2 | 120526 |
| DNAJC25 | DnaJC25 | Q9H1X3 | 548645 |
| DNAJC26 | DnaJC26 | O14976 | 2580 |
| DNAJC27 | DnaJC27 | Q9NZQ0 | 51277 |
| DNAJC28 | DnaJC28 | Q9NX36 | 54943 |
| DNAJC29 | DnaJC29 | Q9NZJ4 | 26278 |
| DNAJC30 | DnaJC30 | Q96LL9 | 84277 |

Heat Shock Protein 40 (Hsp40) (DNA.J Homolog Subfamily B Member 1) (DNA.JB1)

In some embodiments, an Hsp40 protein is encoded by a DNAJB1 gene. The human DNAJB1 gene is located on chromosome Chr19: 14,514,770-14,529,770. It contains 7 exons (NCBI Accession No. NC_000019.10). DNAJB1 encodes a 40 kDa heat shock protein.

As used herein, the term "active DNAJB1 protein" means a protein encoded by DNA that, if substituted for both wildtype alleles encoding full-length DNAJB1 protein in auditory hair cells, or ocular cells, of what is otherwise a wildtype mammal, and if expressed in the auditory hair cells, or ocular cells, of that mammal, results in that mammal's having a level of hearing, or vision, approximating the normal level of hearing, or vision, of a similar mammal that is entirely wildtype. Non-limiting examples of active DNAJB1 proteins are full-length DNAJB1 proteins (e.g., any of the full-length DNAJB1 proteins described herein).

For example, an active DNAJB1 protein can include a sequence of a wildtype, full-length DNAJB1 protein (e.g., a wildtype, human, full-length DNAJB1 protein) including about 1 to about 200 amino acid substitutions (e.g., about 1 to 190 amino acid substitutions, about 1 to about 180 amino acid substitutions, about 1 to about 160 amino acid substitutions, about 1 to about 150 amino acid substitutions, about 1 to about 140 amino acid substitutions, about 1 to about 130 amino acid substitutions, about 1 to about 120 amino acid substitutions, about 1 to about 110 amino acid substitutions, about 1 to about 100 amino acid substitutions, about 1 to about 90 amino acid substitutions, about 1 to about 80 amino acid substitutions, about 1 to about 70 amino acid substitutions, about 1 to about 60 amino acid substitutions, about 1 to about 50 amino acid substitutions, about 1 to about 40 amino acid substitutions, about 1 to about 30 amino acid substitutions, about 1 to about 25 amino acid substitutions, about 1 to about 20 amino acid substitutions, about 1 to about 10 amino acid substitutions, about 1 to about 5 amino acid substitutions, about 10 to about 200 amino acid substitutions, about 10 to about 180 amino acid substitutions, about 10 to about 160 amino acid substitutions, about 10 to about 150 amino acid substitutions, about 10 to about 140 amino acid substitutions, about 10 to about 120 amino acid substitutions, about 10 to about 100 amino acid substitutions, about 10 to about 80 amino acid substitutions, about 10 to about 60 amino acid substitutions, about 10 to about 50 amino acid substitutions, about 10 to about 40 amino acid substitutions, about 10 to about 20 amino acid substitutions, about 20 to about 200 amino acid substitutions, about 20 to about 180 amino acid substitutions, about 20 to about 160 amino acid substitutions, about 20 to about 150 amino acid substitutions, about 20 to about 140 amino acid substitutions, about 20 to about 120 amino acid substitutions, about 20 to about 100 amino acid substitutions, about 20 to about 80 amino acid substitutions, about 20 to about 60 amino acid substitutions, about 20 to about 50 amino acid substitutions, about 20 to about 40 amino acid substitutions, about 40 to about 200 amino acid substitutions, about 40 to about 180 amino acid substitutions, about 40 to about 160 amino acid substitutions, about 40 to about 150 amino acid substitutions, about 40 to about 140 amino acid substitutions, about 40 to about 120 amino acid substitutions, about 40 to about 100 amino acid substitutions, about 40 to about 80 amino acid substitutions, about 40 to about 60 amino acid substitutions, about 40 to about 50 amino acid substitutions, about 50 to about 200 amino acid substitutions, about 50 to about 180 amino acid substitutions, about 50 to about 160 amino acid substitutions, about 50 to about 150 amino acid substitutions, about 50 to about 140 amino acid substitutions, about 50 to about 120 amino acid substitutions, about 50 to about 100 amino acid substitutions, about 50 to about 80 amino acid substitutions, about 50 to about 60 amino acid substitutions, about 60 to about 200 amino acid substitutions, about 60 to about 180 amino acid substitutions, about 60 to about 160 amino acid substitutions, about 60 to about 150 amino acid substitutions, about 60 to about 140 amino acid substitutions, about 60 to about 120 amino acid substitutions, about 60 to about 100 amino acid substitutions, about 60 to about 80 amino acid substitutions, about 80 to about 200 amino acid substitutions, about 80 to about 180 amino acid substitutions, about 80 to about 160 amino acid substitutions, about 80 to about 150 amino acid substitutions, about 80 to about 140 amino acid substitutions, about 80 to about 120 amino acid substitutions, about 80 to about 100 amino acid substitutions, about 100 to about 200 amino acid substitutions, about 100 to about 180 amino acid substitutions, about 100 to about 160 amino acid substitutions, about 100 to about 150 amino acid substitutions, about 100 to about 140 amino acid substitutions, about 100 to about 120 amino acid substitutions, about 120 to about 200 amino acid substitutions, about 120 to about 180 amino acid substitutions, about 120 to about 160 amino acid substitutions, about 120 to about 150 amino acid substitutions, about 120 to about 140 amino acid substitutions, about 140 to about 200 amino acid substitutions, about 140 to about 180 amino acid substitutions, about 140 to about 160 amino acid substitutions, about 140 to about 150 amino acid substitutions, about 150 to about 200 amino acid substitutions, about 150 to about 180 amino acid substitutions, about 150 to about 160 amino acid substitutions, about 160 to about 200 amino acid substitutions, about 160 to about 180 amino acid substitutions, or about 180 to about 200 amino acid substitutions).

One skilled in the art would appreciate that amino acids that are not conserved between wildtype DNAJB1 proteins from different species can be mutated without losing activity, while those amino acids that are conserved between wildtype DNAJB1 proteins from different species should not be mutated as they are more likely (than amino acids that are not conserved between different species) to be involved in activity.

An active DNAJB1 protein can include, e.g., a sequence of a wildtype, full-length DNAJB1 protein (e.g., a wildtype, human, full-length DNAJB1 protein) that has about 1 to about 100 amino acids (e.g., about 1 to about 95 amino acids, about 1 to about 90 amino acids, about 1 to about 85 amino acids, about 1 to about 80 amino acids, about 1 to about 75 amino acids, about 1 to about 70 amino acids, about 1 to about 65 amino acids, about 1 to about 60 amino acids, about 1 to about 55 amino acids, about 1 to about 50 amino acids, about 1 to about 45 amino acids, about 1 to about 40 amino acids, about 1 to about 35 amino acids, about 1 to about 30 amino acids, about 1 to about 25 amino acids, about 1 to about 20 amino acids, about 1 to about 15 amino acids, about 1 to about 10 amino acids, about 1 to about 5 amino acids, about 5 to about 100 amino acids, about 5 to about 95 amino acids, about 5 to about 90 amino acids, about 5 to about 85 amino acids, about 5 to about 80 amino acids, about 5 to about 75 amino acids, about 5 to about 70 amino acids, about 5 to about 65 amino acids, about 5 to about 60 amino acids, about 5 to about 55 amino acids, about 5 to about 50 amino acids, about 5 to about 45 amino acids, about 5 to about 40 amino acids, about 5 to about 35 amino acids, about 5 to about 30 amino acids, about 5 to about 25 amino acids, about 5 to about 20 amino acids, about 5 to about 15 amino acids, about 5 to about 10 amino acids, about 10 to about 100 amino acids, about 10 to about 95 amino acids, about 10 to about 90 amino acids, about 10 to about 85 amino acids, about 10 to about 80 amino acids, about 10 to about 80 amino acids, about 10 to about 75 amino acids, about 10 to about 70 amino acids, about 10 to about 65 amino acids, about 10 to about 60 amino acids, about 10 to about 55 amino acids, about 10 to about 50 amino acids, about to about 45 amino acids, about 10 to about 40 amino acids, about 10 to about 35 amino acids, about 10 to about 30 amino acids, about 10 to about 25 amino acids, about 10 to about 20 amino acids, about 10 to about 15 amino acids, about 15 to about 100 amino acids, about 15 to about 95 amino acids, about 15 to about 90 amino acids, about 15 to about 85 amino acids, about 15 to about 80 amino acids, about 15 to about 75 amino acids, about 15 to about 70 amino acids, about to about 65 amino acids, about 15 to about 60 amino acids, about 15 to about 55 amino acids, about 15 to about 50 amino acids, about 15 to about 45 amino acids, about 15 to about 40 amino acids, about 15 to about 35 amino acids, about 15 to about 30 amino acids, about 15 to about 25 amino acids, about 15 to about 20 amino acids, about 20 to about 100 amino acids, about 20 to about 95 amino acids, about 20 to about 90 amino acids, about 20 to about 85 amino acids, about to about 80 amino acids, about 20 to about 75 amino acids, about 20 to about 70 amino acids, about 20 to about 65 amino acids, about 20 to about 60 amino acids, about 20 to about 55 amino acids, about 20 to about 50 amino acids, about 20 to about 45 amino acids, about 20 to about 40 amino acids, about 20 to about 35 amino acids, about 20 to about 30 amino acids, about 20 to about 25 amino acids, about 25 to about 100 amino acids, about 25 to about 95 amino acids, about 25 to about 90 amino acids, about 25 to about 85 amino acids, about 25 to about 80 amino acids, about 25 to about 75 amino acids, about 25 to about 70 amino acids, about 25 to about 65 amino acids, about 25 to about 60 amino acids, about 25 to about 55 amino acids, about 25 to about 50 amino acids, about 25 to about 45 amino acids, about 25 to about 40 amino acids, about 25 to about 35 amino acids, about 25 to about 30 amino acids, about 30 to about 100 amino acids, about 30 to about 95 amino acids, about 30 to about 90 amino acids, about 30 to about 85 amino acids, about 30 to about 80 amino acids, about 30 to about 75 amino acids, about 30 to about 70 amino acids, about 30 to about 65 amino acids, about 30 to about 60 amino acids, about 30 to about 55 amino acids, about 30 to about 50 amino acids, about 30 to about 45 amino acids, about 30 to about 40 amino acids, about 30 to about 35 amino acids, about 35 to about 100 amino acids, about 35 to about 95 amino acids, about 35 to about 90 amino acids, about 35 to about 85 amino acids, about 35 to about 80 amino acids, about 35 to about 75 amino acids, about 35 to about 70 amino acids, about 35 to about 65 amino acids, about 35 to about 60 amino acids, about 35 to about 55 amino acids, about 35 to about 50 amino acids, about 35 to about 45 amino acids, about 35 to about 40 amino acids, about 40 to about 100 amino acids, about 40 to about 95 amino acids, about 40 to about 90 amino acids, about 40 to about 85 amino acids, about 40 to about 80 amino acids, about 40 to about 75 amino acids, about 40 to about 70 amino acids, about 40 to about 65 amino acids, about 40 to about 60 amino acids, about 40 to about 55 amino acids, about 40 to about 50 amino acids, about 40 to about 45 amino acids, about 45 to about 100 amino acids, about 45 to about 95 amino acids, about 45 to about 90 amino acids, about 45 to about 85 amino acids, about 45 to about 80 amino acids, about 45 to about 75 amino acids, about 45 to about 70 amino acids, about 45 to about 65 amino acids, about 45 to about 60 amino acids, about 45 to about 55 amino acids, about 45 to about 50 amino acids, about 50 to about 100 amino acids, about 50 to about 95 amino acids, about 50 to about 90 amino acids, about 50 to about 85 amino acids, about 50 to about 80 amino acids, about 50 to about 75 amino acids, about 50 to about 70 amino acids, about 50 to about 65 amino acids, about 50 to about 60 amino acids, about 50 to about 55 amino acids, about 55 to about 100 amino acids, about 55 to about 95 amino acids, about 55 to about 90 amino acids, about 55 to about 85 amino acids, about 55 to about 80 amino acids, about 55 to about 75 amino acids, about 55 to about 70 amino acids, about 55 to about 65 amino acids, about 55 to about 60 amino acids, about 60 to about 100 amino acids, about 60 to about 95 amino acids, about 60 to about 90 amino acids, about 60 to about 85 amino acids, about 60 to about 80 amino acids, about 60 to about 75 amino acids, about 60 to about 70 amino acids, about 60 to about 65 amino acids, about 65 to about 100 amino acids, about 65 to about 95 amino acids, about 65 to about 90 amino acids, about 65 to about 85 amino acids, about 65 to about 80 amino acids, about 65 to about 75 amino acids, about 65 to about 70 amino acids, about 70 to about 100 amino acids, about 70 to about 95 amino acids, about 70 to about 90 amino acids, about 70 to about 85 amino acids, about 70 to about 80 amino acids, about 70 to about 75 amino acids, about 75 to about 100 amino acids, about 75 to about 95 amino acids, about 75 to about 90 amino acids, about 75 to about 85 amino acids, about 75 to about 80 amino acids, about 80 to about 100 amino acids, about 80 to about 95 amino acids, about 80 to about 90 amino acids, about 80 to about 85 amino acids, about 85 to about 100 amino acids, about 85 to about 95 amino acids, about 85 to about 90 amino acids, about 90 to about 100 amino acids, about 90 to about 95 amino acids, or about 95 to about 100 amino acids), removed from its N-terminus and/or 1 amino acid to 80 amino acids (or any of the subranges of this range described herein) removed from its C-terminus.

In some embodiments, an active DNAJB1 protein can, e.g., include the sequence of a wildtype, full-length DNAJB1 protein where 1 amino acid to 50 amino acids, 1 amino acid to 45 amino acids, 1 amino acid to 40 amino acids, 1 amino acid to 35 amino acids, 1 amino acid to 30 amino acids, 1 amino acid to 25 amino acids, 1 amino acid to 20 amino acids, 1 amino acid to 15 amino acids, 1 amino acid to 10 amino acids, 1 amino acid to 9 amino acids, 1 amino acid to 8 amino acids, 1 amino acid to 7 amino acids, 1 amino acid to 6 amino acids, 1 amino acid to 5 amino acids, 1 amino acid to 4 amino acids, 1 amino acid to 3 amino acids, about 2 amino acids to 50 amino acids, about 2 amino acids to 45 amino acids, about 2 amino acids to 40 amino acids, about 2 amino acids to 35 amino acids, about 2 amino acids to 30 amino acids, about 2 amino acids to 25 amino acids, about 2 amino acids to 20 amino acids, about 2 amino acids to 15 amino acids, about 2 amino acids to 10 amino acids, about 2 amino acids to 9 amino acids, about 2 amino acids to 8 amino acids, about 2 amino acids to 7 amino acids, about 2 amino acids to 6 amino acids, about 2 amino acids to 5 amino acids, about 2 amino acids to 4 amino acids, about 3 amino acids to 50 amino acids, about 3 amino acids to 45 amino acids, about 3 amino acids to 40 amino acids, about 3 amino acids to 35 amino acids, about 3 amino acids to 30 amino acids, about 3 amino acids to 25 amino acids, about 3 amino acids to 20 amino acids, about 3 amino acids to 15 amino acids, about 3 amino acids to 10 amino acids, about 3 amino acids to 9 amino acids, about 3 amino acids to 8 amino acids, about 3 amino acids to 7 amino acids, about 3 amino acids to 6 amino acids, about 3 amino acids to 5 amino acids, about 4 amino acids to 50 amino acids, about 4 amino acids to 45 amino acids, about 4 amino acids to 40 amino acids, about 4 amino acids to 35 amino acids, about 4 amino acids to 30 amino acids, about 4 amino acids to 25 amino acids, about 4 amino acids to 20 amino acids, about 4 amino acids to 15 amino acids, about 4 amino acids to 10 amino acids, about 4 amino acids to 9 amino acids, about 4 amino acids to 8 amino acids, about 4 amino acids to 7 amino acids, about 4 amino acids to 6 amino acids, about 5 amino acids to 50 amino acids, about 5 amino acids to 45 amino acids, about 5 amino acids to 40 amino acids, about 5 amino acids to 35 amino acids, about 5 amino acids to 30 amino acids, about 5 amino acids to 25 amino acids, about 5 amino acids to 20 amino acids, about 5 amino acids to 15 amino acids, about 5 amino acids to 10 amino acids, about 5 amino acids to 9 amino acids, about 5 amino acids to 8 amino acids, about 5 amino acids to 7 amino acids, about 6 amino acids to 50 amino acids, about 6 amino acids to 45 amino acids, about 6 amino acids to 40 amino acids, about 6 amino acids to 35 amino acids, about 6 amino acids to 30 amino acids, about 6 amino acids to 25 amino acids, about 6 amino acids to 20 amino acids, about 6 amino acids to 15 amino acids, about 6 amino acids to 10 amino acids, about 6 amino acids to 9 amino acids, about 6 amino acids to 8 amino acids, about 7 amino acids to 50 amino acids, about 7 amino acids to 45 amino acids, about 7 amino acids to 40 amino acids, about 7 amino acids to 35 amino acids, about 7 amino acids to 30 amino acids, about 7 amino acids to 25 amino acids, about 7 amino acids to 20 amino acids, about 7 amino acids to 15 amino acids, about 7 amino acids to 10 amino acids, about 7 amino acids to 9 amino acids, about 8 amino acids to 50 amino acids, about 8 amino acids to 45 amino acids, about 8 amino acids to 40 amino acids, about 8 amino acids to 35 amino acids, about 8 amino acids to 30 amino acids, about 8 amino acids to 25 amino acids, about 8 amino acids to 20 amino acids, about 8 amino acids to 15 amino acids, about 8 amino acids to 10 amino acids, about 10 amino acids to 50 amino acids, about 10 amino acids to 45 amino acids, about 10 amino acids to 40 amino acids, about 10 amino acids to 35 amino acids, about 10 amino acids to 30 amino acids, about 10 amino acids to 25 amino acids, about 10 amino acids to 20 amino acids, about 10 amino acids to 15 amino acids, about 15 amino acids to 50 amino acids, about 15 amino acids to 45 amino acids, about 15 amino acids to 40 amino acids, about 15 amino acids to 35 amino acids, about 15 amino acids to 30 amino acids, about 15 amino acids to 25 amino acids, about 15 amino acids to 20 amino acids, about 20 amino acids to 50 amino acids, about 20 amino acids to 45 amino acids, about 20 amino acids to 40 amino acids, about 20 amino acids to 35 amino acids, about 20 amino acids to 30 amino acids, about 20 amino acids to 25 amino acids, about 25 amino acids to 50 amino acids, about 25 amino acids to 45 amino acids, about 25 amino acids to 40 amino acids, about 25 amino acids to 35 amino acids, about 25 amino acids to 30 amino acids, about 30 amino acids to 50 amino acids, about 30 amino acids to 45 amino acids, about 30 amino acids to 40 amino acids, about 30 amino acids to 35 amino acids, about 35 amino acids to 50 amino acids, about 35 amino acids to 45 amino acids, about 35 amino acids to 40 amino acids, about 40 amino acids to 50 amino acids, about 40 amino acids to 45 amino acids, or about 45 amino acids to about 50 amino acids, are inserted. In some examples, the 1 amino acid to 50 amino acids (or any subrange thereof) can be inserted as a contiguous sequence into the sequence of a wildtype, full-length DNAJB1 protein. In some examples, the 1 amino acid to 50 amino acids (or any subrange thereof) are inserted in multiple, non-contiguous places in the sequence of a wildtype, full-length DNAJB1 protein. As can be appreciated in the art, the 1 amino acid to 50 amino acids can be inserted into a portion of the sequence of a wildtype, full-length DNAJB1 protein that is not well-conserved between species.

Methods of detecting mutations in a gene are well-known in the art. Non-limiting examples of such techniques include: real-time polymerase chain reaction (RT-PCR), PCR, sequencing, Southern blotting, and Northern blotting.

Exemplary wildtype DNAJB1 protein sequences are or include SEQ ID NO: 38, 41 43, 44, and 45. Exemplary DNA sequences that encode a NDP protein and exemplary polypeptides encoded by an NDP gene are shown below.

DNA.JB1 Polynucleotides

Among other things, the present disclosure provides polynucleotides, e.g., polynucleotides comprising an DNAJB1 gene or characteristic portion thereof, as well as compositions including such polynucleotides and methods utilizing such polynucleotides and/or compositions.

In some embodiments, a polynucleotide comprising an DNAJB1 gene or characteristic portion thereof can be DNA or RNA. In some embodiments, DNA can be genomic DNA or cDNA. In some embodiments, RNA can be an mRNA. In some embodiments, a polynucleotide comprises exons and/or introns of an DNAJB1 gene.

In some embodiments, a gene product is expressed from a polynucleotide comprising an DNAJB1 gene or characteristic portion thereof. In some embodiments, expression of such a polynucleotide can utilize one or more control elements (e.g., promoters, enhancers, splice sites, polyadenylation sites, translation initiation sites, etc.). Thus, in some embodiments, a polynucleotide provided herein can include one or more control elements.

In some embodiments, an DNAJB1 gene is a mammalian DNAJB1 gene. In some embodiments, an DNAJB1 gene is a murine DNAJB1 gene. In some embodiments, an DNAJB1 gene is a primate DNAJB1 gene. In some embodiments, a DNAJB1 gene is a human DNAJB1 gene. An exemplary human DNAJB1 genomic sequence is or includes SEQ ID NO: 112. An exemplary human DNAJB1 cDNA sequence is or includes the sequence of SEQ ID NO: 156 or158. An exemplary human DNAJB1 cDNA sequence including untranslated regions is or includes the sequence of SEQ ID NO: 113, 157, or 159.

```
Exemplary Human DNAJB1 Genomic Sequence
                                                (SEQ ID NO: 112)
ACTTTATTCATCCTTACAAACAGGAATAATAATAGTTCTTATACAAGGTAACAGAATCTCACCA

GCACAAGAGTAAGCACTTGCTAAATTGTTATTTTGAATTTTAATAACAAATTTTATTATTTGAT

GATAGTTAGTTAAAAGTCAGCAATAATTCAGGGATAATTGGTTGAATTATTAATATTATATTAT

CACCTAGGGCGATAAGCACATCAGAAGACTTCGTTTTAAGGGAAAAAGAGACCCAAGTTAGGAG

TCAGAAGACTTGGGCTTCAAGAGTGGCTGTGGGTGGGTATAAGATTTCTCCTTGGTGACACCCA

AGGGTTGACGTAGATGACCTCTTTGATAACCAGAAAGCAAGATCAGCTTCGCTGCTCTGCGAAA

GCCAGCCGTGGAGCTGCACCTCCCTCACCGCCTAAGTCTCCCGGGAACGTCCCGGGCGAGGGAA

GGGGTCCAAAGGTCGTACACAAGAATACTGATAGCAAAGCCCCTTCCTACGCTGGTGACGGCGG

CGTGGCGCAAGATTTGTGCAAGACTCCCTCGGATTGGGAGCAAGGGTCCCGCACCTTCGTGGCT

CCCATGACAAAGTCTGCAACTCAGCCCGCTGGGGGAGCTGCAAGGAACCTGCAAGCGTCCCAGC

CCCTGCAGAGACCCCCAAGAAAAAGTACCCCCAAAACAGCCTGGGTTGCAGATTTATAAATACT
```

-continued

TCCTGCGCACATGCGCATTGGAATTTACGAGTGGCCCGGGGCGCAACGCTTGCCCACTGCGCCT

GCGCCGTCTGGCTCTTCCTTCGGGGCACAGGACCAGAAAGTGGGGTCCCGTGGTCCCGCAAAGA

AGGAAAAAGAATGGGTCAGCAGTGGCCACACGGCCCCTGTTTCTCGCTTCTTACCTCGTAATGC

TTCATGGCTCCCTCCCACGGCGGCTACTGCTCCGCGGCTGCTGCTGCCTAACTGCGCGGCACAG

CACAGGCTCCCTACAGCGCTCGCAACCGCAGCGATAGACTAAACGCGGCTCTGCGTCCGCCCCG

CCCCTCCAGGCCGCGCGCGCCCCGTCGGCCAATCAGGGCACGAGGCGCCCACGTTCGCCCCTGC

TCCTTGGGGCCGGTCCGAACCAAGACTAGGACTAGCACCAGGGGATTGACCAATCAACTTGCGA

GACCAATCGAAGGGGGCGGAACGCCTGTAGGAGGGGCTAAAGAGAAGGGGCTTGACCATCCACC

AATCCAAAGGAGGTCTCTGCCCCGCGCGTCCCTTTGCCACGCCCCCTGATGGCGTCGCTGTGGA

AACCAAGGTAAGCGACGGTTAGGCCAGACGCGGGGGCGGGGTAAGAAGTTGAGTGACAGGCAAG

GCAGCATCCACATGACAGGCGGCGCCGAAGGGGTAAATTCTGAGGTGGGCGGCCCCCGGGGTAC

ACCGGGAACAGCAGGAGAGGGCTAGGGGCTGGGGTCGCGGGCTGCGGAGTCTGGTTGGCGAGGA

GGTCACTATGGGAGGAGACTCTTGAGTGGGAGGGAAGGAAAGGCGAAACGGAGTCGCGAAAAGC

TCCCCATTTGGGAACCCCCAACCTGCAAGAACCTTGAGCCCCAGCCCCATTCTGGGGTGGCTTC

ACTGCCGTTTTTAATGAAAGCCCCGCCCCACTTTGTTTTTCTGTTTTGTTTTGTTTTTGAAACA

ATCTCGTTCTGTCCCCCAGCTGGAGTGCAGTGGCGCAATGACGGCTCACGCAACCTCCGCCTCC

CGGGTTCAAGCGATTCTCATGCCTCAGCCTCCCAAGTAGATGAGATTACAGGCACCCGCCACCA

CGCCCGACTAATTTTTGTATTTTTTTTAGTAGAGACGGGGTTTCCCCATGGTTGGCCAGGCTGG

TCTTGAACTCCTGACCTCAGGTGATCCTCCCGCCTCAGCCTCCCAAAGTGCTAGGATTACAGGC

CTGAGCCACCCCGCCCGGCCCCCCTCCACACTTTGCTCCGCCCTATGGACAGGGGAACTACATT

GGTCTCTGCCTGACGTCCAGAATCGTGTCTAGTGGCTCCAATGGGGCCACTGAGCCCTTGAAAT

GGGGCTGGTCCAGGCCGGGAACGATGGCTCACACCTGTAATCCTAGCACCTTGGGAGGCCGAGG

GGGGCAGATCACGAGGTGAGGAGTTCGAGACCAGCCTGGCAGATATGGTGAAACCTCATCGCTA

CTAAAAATACAAAAATTAGCCGGGCGTGGTGGTACACACCTGTAGTCCCAGCTAATCAGGAGGC

TGAGGCAGAAGAATTGCTTGAACCCGGGAGGCGGAGGTTGCAGTGAGCCAAGATCTCGCCACTA

CACTCCAGCCTGAGCAACAGACCGTCTCAAAAAAAAAAAAAGAAAAAAGAAAAAGAAATGGGAC

TGGTCCAAATTGAGATGTGCTGTAAATGAAAAACACATAAATTTCTGGCCAGGCACGGTGGCTC

ACACCTGTAATCCCAGCACTTCGGGAGGCCAAGACAGGCAGATCACATGAGGTCAGGAATTCAA

GACCAGCCTGGACAACGTGGTGAAACCCTGTCTCTACTAAAAATACAAAAATTAGCCAGGTGTA

ATGGTGGGCACCTGTAATCCCAGCTACTAGGGAGGCTGAGAATCGCTTGAACCCGGGAGGTGGA

GGTTGCAGTGAGCCAAGATCGCACCACTGCACTCCAGCCTGGGCGACAGAGTGAGATTCTGTCT

CAAAAAAAAAAGAAAAAAAAAGAAAAGACTTTTGACAGACAAAGGAACAGGCAGTACCTGGCAC

ACTTCTTCACCTCCTCTCCTTACTCTTGTTTCCAGATCCTGCCCCTGAGCTTTCATGAGCTGTT

GAACCATCTGGAATTCACAGGCCTGTCATGAGAGACACGATGAGAAGTCCTTAAAGGTAGATCA

CTGATTCACAGGGGAGCAGGCGGAGGCAAGGGTGAGTCAGTGCTTGGAACTCAGTCATCCAGAT

TTGGCTCTGGAAACTTCTGAAGCTGTAGCCTTTGGGGATCCCTGACTGCGAGTACAGGAAGCCA

ACGCTATGTGGTCTTCTGGAAACTCATTATCTTTTTCACTGGTGCTATCTGGGAAAAACAGATG

AAAACCTGAAGGTGTTCTGTATGTGTGCTTTCAAAAGCAAGGATCTGGCCGGACGCAGTGGCTC

AGGCCTGTAATCCCAGCACTTTGGGAGGCCGAGGCAGGAGGATCACCTGAGGTCAGGAGTTTGA

GACCAGCTTGGCCAACATGGCGAAACCATCTCTACTAAAAGTACAAAAATTATCTGGGTGTGGT

GGTGGGCACCTGTAATCACAGCTACTCAAGTAGCTGAGGCAGAAGAATCAGTTGAACCCAGGAG

-continued

GCAGAGGTTGCAGTGAGCAGAGATCACACCACTGCACTCCAGCCTGGGTGACAAGAATGAAACT

CCGTCTCAAAAAAAAAAAAAAAAAAAAAAAAAAAAAAAAAGCAGAGATATTTTTCTGGTGGGAG

TTTGAGTTTTGAGGCCTTCTGTGTCATGACAGGCCTCACTCCCTGCCCTTCTTGGGTGCTGGGG

GAGAGTATTTGCTTCCAGGCCACAAGTTAATTTTTTAGTAGAGATGGGATCTCATTATGTTGCC

CAGGCTGCTCTGGAACTCCTGGCCTCAAGTGATCCTCCCTCCTCGGCCTCCCAAAGCGCTGGGA

TTACAGGCATGAGCCATCCCACTCGGCCTGAGACCACAGTTAAAATCCTATCAGATTGAGTTAC

CTGAGGTACTTGATTGTGAGGGGCCATGGGGATAGGGTTGAAACCCTAAGACCCATCCATGTGT

TGCTCCTTCACCAGTTATGCAAATTTTCAACTTATTTAATGTGATCTGAAGAGGTGAGTCTTCC

ATCTCTGGGTTGCAGTTAGATAGGGCATGATGGTGTACAAGTAGGTGTCATTTTGAAGAGATTC

CATACATATTCCCATAAACTCAGAACGTTTTGGAAATTCCCTTTTGAGACTGCTTTTCTGAGCC

CCACACTTACTCAACAGGCACCAAATCATCCTCATGCACCTACTATGCTGCGTGTCAACCGGAA

CATACAAATAATTTCCACCCCCTCCTCACCCATAAGAAGCTGGCAGAAAGGCAAGATCCAGCCT

CCAAAGTAGAATTCCTCTTTGTTTTTGAGGGGTGTTGCAGGCTTGAGGAACCCCTTGTTTGCCC

ATCTGGCTTCCGGTAACCAGGCTGTCAGCAGAAATGAAACCCACCCTTGGAATGAAGACTGGCC

ACTTTGTTCAAGCCACTGAGGACACTGTACTGTGGCCCCCTGACAGTGCCTGTCTGTAGGGACA

GCTAGATCCTGCTGGTCCCTTCACAGTCCCAGCAGTGGCTGATTCACAATGGTGACTGGTAGAT

CTGTTGGGTCGTTGTTGAGCTGATGGTAACTAGCTCCTTTATTAAAGTAATTTCCAAGGGAGAA

ACTGCAAGAGACGGCCTAAGCTGCGGCAGCTTCCAAGGATGAGCTTTTCTGGACCTCAGGTTTG

GGGGGAACCCGAGACCATTTGAATGCCAGAGATGTGATGTGTTTGGTAATGTCGTGTCTCACAA

GCTCCTTTTGTATTTCCCATGGGCAGATCAGGTCGGATCTTGACTTTTTCCAGAACCTGGCTTG

GCTGGTTTGGGTTGTGTATGAATGAGCTGGCTCGCTGGGTGTGTGAGGGGAGGTGAAGCTGGGA

CTAGACAAGCCAGGGCTCGTTAGCAAGTTTCTGCTGTGTCAGGAATCCCAGAGAGAGGTTTCCC

AAGCCCTATCCTGTCTTGCCTGGGTTGTTTGGTTTTTCTCCTTCTTTTTTTTTTTTTCATTGAA

GTGTAATTGACATGTAGTAAAATTCACCCATTTTAGTGTAGAGCTCTGAACACATACGGTCATG

CAACCACCACTAGAATCAAGATACAGAGCATTTACACCAACCCAAAAAATTCTCCAAACTACTC

CATTTGTTGCAGGTCCCAGCCCCTGGCAAGCATTCATCTGCTTTCTGTCCTGATACTTTTGCCT

TTTCCAGAAGGTTGAGTGAAATGGAATCATGCAGCCTTTTGAGCCTGGCTTCTTTCACCCACAT

AATGCATATGAGGTTCATCTGTAATGTTGTTTTTTTGTATCCGTAGCTCATTCCTTTTTATAGC

TGAATAGTATTCCATTGTGTGGATGGATCCCATTTGTTTATCCATTCATCCATTGAAGGACAGT

TAGGGTTTAACTGCTGTTGGTAATAACTAATAAAGCCTCAGCAAACATTCGCTCATGAGACTCC

ATCTCAAAAAAAAAAACAAAAAAAGTAGATTTTACCCTGCTGGTGTTGCTATGTTGATGAAATT

GAGAGGAGCCAGGAAATGAACATTATAATAGTATCTTTTTTATTTTTATTTTTGAGATGGAGTC

TCGCTCTGTCACCCAGGCTGGAGTGCAGTGGCGCAATCTCGGCTCACTGCAACCTCCACCTTCT

GGGTTCAAGCGATTCTCCTGCATCAGCCTCCCGAATAGCTGGGTTACAGGTGTGCACCACCATG

CCCAGCTAATTTTTGTGTTTTTAGTACAGACGGAATTTCACCATGTTGGTCAGGATGGTCTCCA

TCTCTTGACCTTGTGATCCTCCCGCCTCGGCCTCCCAAAGTGCTGGGATTACAGGCATGAGCCA

CCGCACCCAGCCATGAATTTTTATATATGAACAAAGGTTTTCATTTCACATGGGTATCCCACTG

GGAGTGGGATTGTTGGCTCATATGGCTATAGCGCTTTTTGAAGGTCTTTTTTTTTTGAGAACGA

GTCTCGCTCTGTTGTCCAGGCTGGAGTGCAGTGGCACCATCTCGGCTCATTGCAACCTCCACCT

CCTAGGTTCAAGTGATTCTCCTGCCTCAGCCTCCCAAATAGCTGGGATTACAGGTGCACGCCAC

-continued

```
CATGCCTGACTAATTTTTGCATTTTTAATAGAGATGGGGTTTCACCATGTTGGCCAGGCTGGTC

TCGAACTCCTGACTTCAAGGGATCCACCTGCCTCAGCCTCCCAAAGTGCTGAGATTACAGGCAT

GAGCCACCGCACCCAGCCTTGAAGATCTTTTCCAAATTTATTTGGATTTTTATTTATTTTTGAG

ACAGGGTCTCACTGTCTCTCAGGCTAGTGTGCAGTGGCACACTCATAGCTCACTGCAGCTTGGA

ATTCCTGAGCTCAAGTGATCCTCCCACCTCAGCCTCCCAAGTAGCTGGCACGTGCCACCATGCC

CAGCTTATTTCTTTGTCATTCTTTGCAGATATGGGGTCTCACTATGTGGGCCAGGCTGATCTGG

AACTCCTGGGCTCAAGTGATCCTCCTGCCTTGGCCTCCAAAAGTGCTGGGATTACAGATGTGAG

CCACCGCACCTGGCCTGAAGGTCTTTTTTTCAACAGGTGAAGAGCTGAAGACAGGAGTAATGCA

ATTTTCTTAAAATTAAGGCTTTATGATCATCTGAGTCACATTATACACAAGCTGAGTGTCTAGT

GTAAGCACTCAGTATGCTAAACACTTCAGCATTTTACTCTCTGGGTGACCCTGGGGAAGTCACA

TGACCTCTCAGAATCTCCATCTCCCCACCTGTAAAATGGGTGTAATGATAGCCCAACCTCATAG

GGCTGTTGTGACAAGTATATGAGTTAATATTCATCGAGTACTTGGAACAGGCTTGGCCATGTCA

GTGTTAGATGTTATTATAGGCCAGACATGGTGGCTTATGCCTGTAATCCCAACACTTGGGGAGG

CCAAGGCCGGCGGATCACCTGAGCTCAGGTGTTCGAGACCAACCTGAGCAACATGGCAAAACCC

CATCTCTACCAAAACCATAATACAAAAAATTAGCCGGGCATGGTGGCAGGCACCTGTGATCCCA

ACTACTCAGGAGGCTGGGGCAGGAGGATCATTTGAACCTGGGAGGTGGAGGTTGCAGTGAGCCA

AGATTGTGCCACTGTGCTCCAGCATGGGTGACAGTGTGAGACCCCATCTCAAAAAAAAAAAAAA

ACAAAAACAAGGCCGGGTGTAGGGTTCAACCCTTGTAATCCCAGCACTTTGGGAGGCCAAGGTG

GGTGGATCATGAGATCAGGAGTTCGAGATTAGCCTGGCCAACATGGTGAAACCCAGTCTCTACT

AAAAATACAAAAATTAGCCAGGTGTGGTGGTAGGCACCTATAATCCCAGCTACTCAGGAGGCTG

AGGCAGAGAATCGCTTGAACCCAGGAGGCGGAAGTTGCAGTGAGCTGAGATCACACCACTGCAC

TCCAGCCTGGGTGACAGAGTGAGACTCCATCTCAAAAATAAAAATAAAAATGTTATTATAATGT

TCATTTCCTGTTCACTTCCTGTTCATTTCCTCTCAATTTCATCCACATAGCAACACCAGCAGCG

TAAAATCTACTCTTTTCTTTTCTTTTCTTTTCGAGACAGAGTCTGGCTCTGTTGCCCAGGCTGG

AGTACAGTGGCGTGATCTTGGCTCACTGCAACCTCCACCTCCCAGGTTCAAGCGATTCTCCTGC

CTCAGCCTCCCGAGTAGCTGGGAGTATGGGCACATGCCACCATGCCCAGCTAATTTTTGTGTTT

TTAGTAGAGACACCACGTTGGACAGGCTGGTCTCAAACTCCTGACCTCAAGTGATCCACCCGCC

TCAGCTTCCCAAAGTGCTGGGATTACAGGCATGAGCCACCGCACCCGGCCTAATCTACTCTTAT

CTCCAATTTATGGAGGACAGACCTAATGCTCCCAGAGATCAAGCAGGCTGTGGAAGATCACACA

CGTAGGAAATAAGGAAACAGTTGGTCCAGGATTTGAACTAAAGCAACTGTCCTCAGACTCACTT

GCATAGTTCCTGTATCAGTCAGGATTTTACCAAAGACACAGAGCCAGAGCCAGTAGGAGTGTGT

GTGTGTGTGTGTGTGTGTGTGTGTGTGTGTGTGTGTGTGTCTGTGTGTGTGTCTGTGTTTGT

GTGCAGAGATTTATTTCAAGGAATTGGCTTACATGCTTGTGGGGGCTGGCTAGACAACACCAAA

ATCTGCTGGGTGGGCTAGCAGGCTGGAAACTTAGGCAGGAGCTGATGCTTTTTCTGCCGGGAAA

CCTCAGTGTTTGCTTTCAGTGTTGGCTTTTTTTTTTTTTTTTTTTTCTTCGAGACAGAGTCTTG

CTCTGTCACCAGGCTGGAGTGCAGCGGCCTGATCTTGGCTCACTGCAACCTCTGCCTCCTGGGT

TCAAGTAATTCTCCTGCCTCAGCCTCCCAAAGTGCTGGGATTACAGGCGTGACCCACCACACCC

GGCCTCAGTGTTGGCTTTTTAAAGTCTCTAGACTGATTGGATGAGGCCCGCTTACATCCTCACA

TCCTTGAGGGTCATGTCCTGTTTTTAAAGTCAAGCAACTGTAGACGTGCTAACCTAACCGCATC

AACATAATAACTTCACAGCAACACCTAGATTAGTGTTTAGTTGAATAACTAGGTTCTAGAGCTT

AGCCACGCTGACACAACAAACAACTATAACAGCTTTTCCAAGTTAAGAGCCCAATATCTGCTGA
```

-continued

AGTTGACGCAGAGGCCATTTTTTCAGTAATATTCTGAAGTTCTCAGTGAGTGTTCAGGTCACAG

TACCATGTCCATTAGGAGAGAGTTACTGGGTTTGTTTGTTTGTTTAATTTCCTGGCTCCTAGAA

CTGATTAAAAAAAAAAAAATTAAAACTTCCCGAACTGGCTGGGCGTGGTGGCTCACGCCTGTAA

TCCCAGCACCTTGGGAGATCAAGGCGTGTTGATCACCTGAGGTCAGGAGTTCAAGACCAGCCTG

GCCAACATGGTGAAACCCCATCTCTACTAAAACTACAAAAATTAGCCAGGCATGGTCGCAAGCA

CCTGTAGTCCTAGCTACTTGGGAGGCTAAGGCAGGAGAATCACTTGAACCCAGGAGGCGGAGGT

TGCAGTGAGCTGAGATCGTGCCACTGCACTCCAGCCTGGGCTACAAGAGTGAAACTCCATCTCA

AAACAAACAAACAAAACTTCCTGAACATGACCCAGGCTTACTCAAGGAGGGGAGAGTTCCCAGC

TCTAACACTGACCCCAAGCACAAAGACATCCCTTCCGCAGTGTTTTTAGCAAAATGTTCCCCTC

GAGTGTGTCAAGAAACTTTTATTATTATTATTATTATTATTATTATTATTATTTTGAAACTCTC

ACTCTGTCACCCAGTCTGGAGCACAGTGGCACGATCTTGGCTCACTGCAACCTCTGCCTCTCGG

GTTGAAGCGAGTCTCATGCCTCAGCCTCCAGCGTAGCTGGGATTACAGGCACCTGCCACCGCAC

CCGACTAATTTTTGTATTTTTAGTAGAGACGGGGTTTCACCACGTTGGCCAGACTGGTCTCGAA

CTCCTGACCTCAGGTGATCCACCTGCCTCAGCCTCCCAAAGTGCTGGGATTATAGGCGTTGAGT

CACCGTGCCTGGCCTATGGCAAGAAACTTTAGAACAACCAGAAAGGCCCACCCAGAGCCATGTT

AAAGGCTTTGGAGGCTGCTGCACTTGTAATTCTAAATTAAATTTATATTATAAAATACTAGTTT

ATAAAGTCACAAGCTCTGAGTTTTTCCCCATAATGCTCCTGATAGTTATTTATATAATTTTTTT

ATGGGGAGGTTCAGGATCTCACTGTCATCCAGGCTGGAGAGCAGTGGCACAATCATAGCTGACT

GCAGCCTCAAATTCCTGGGCTCAAGCTATCCTCCTACCTTGGTCCACTGAGTAGCTGGGACTAC

AGGCTCACATCATTGCACCCGGCTAATTTTTTTTATTTTTAATTTTTTGTATAGATGGGGTCTC

ACTATGTTGCCCAGGCTGGAACTCCTGGCCTCAAAAGATCCTCCCACCTCACCTTCCCAGAATG

CTGGGATGACAGGCGTGAGCCACTGTGCCCAGCCTAGTAACTTTTTAAAAAATATCAAGTTCTC

TCTCCCCATAATTGCTTCAGGACCCCTGCTCAAGTATGGTTCTCGATGTCTAGGGAATTTCAGC

CCCATCCTCCCGGGTTGTCCAGTTCTAGTCCAGAGTTCTTGCTGATGCAGTTACCTCAGAGATC

ATTGAGTGGGCCAAGAGAACCAGATCTGCCTGCTGGATGCTCCTGATAGTTATTTATGTAACTA

TCCGCCATGATGCTCCTGATAGTTATTTATGTAACTTTTTTATGGGGAGGCTGAGGGTCTCACT

GTCACCCAGGCTGGAGTGCAGTGGCACAATCATAGCTGCCTGCAGCCTCAAATTCCTGGGCTCA

AGAGATCCTCCCGCCTCAGGAGGCAGGAGGATGGTCTTCTTCTTCAGGAGTCCCTGTCTGCCCA

GGGGCAGCTGTCACTGGAATCTTTTAGCTGCCAGGAATGAGGTGATGGCTGAAGAGCCCACCAC

TAAGAAAATGGTTAGTCACCCCTTTGACAATGCTTCCTTTGTGCCATGCCTGCTCTGAGCACTT

TGCAAATGTTGACTCATATAAACTTCAAAGCCCTCATGATGTGGGCACAACTGCTATCCTCATT

CCTCATTGTGCAGATGAGGAAGCTAAGGCCAGCAAAGGCCTAGTAACTAACCCAAGGTTACCCA

GCCGGGAAATGCTGGAGCTGGGAATGAAGCCCAGCTGTCTGGTTCCAGAGCCAGTGTTACATGG

CTCTGACCTCCCAGGCAGTTCTTCCAGGAACCTCCCCCACTTCCCTGGGCCCTTCCCAGGTGGA

ACCCCTTTCTGAGCCTCCTTTTCCCATCAGCTCTGTCCTTGACAGAGGCACCCCAGACTTTCAG

AGCCAAACGCGATCGTGTTGCCTACAATTGAGGAAACAGAGGCCTTGAAAGGTGTGTGACACAC

CTATGTCCCCCCAAATTATAAAGGTAGTTGGGGAAGAAAAAGAAGCACGTGTGTAAGAACGGGG

AATATTTATGAGGTTCTCACTGCGTTCCAGGCACTGGGGACCCAGTGCAGACAGGACCTGGCCC

CTGCCCAGGTGGCGATGTCAGACTGGGAGGGAAGACACATTGAAAGCCAAGAGACAAGATAAAT

TTCAAATTTAGCGGCAAGTGATCTTGAGAGGGCAGTAAAGGGAAGAAGGCGGGACTGGGAGGAC

-continued

CTTGGGAGATGCGCTTCCGTCCAGATCCTCACCTTGCTTTAGGAGGTGAGAACAGAGGCAGTCT

TCCGTCCCAAAATCCTTCTCCCCACGGTTGGGAGAATAGCGCTGGTGGGTTTTTTGTTCATTTT

ACTTTATTTTACTTATTTTATTTATTTATGAGACGGAGTCTCGCTCTGTTGCCGAGGCTGGAGT

GCAACGGCCGGATCTCGGCTCACTGCAACCTCCGCCTCCCCGATTCAAGCTATTCTCAGGCCTC

AATCTCCTGAGTAGCTGGGATTACAGGTTCGTGCCACCAACGCCCGGGTAATTTTTATATTTTT

AGCAGAGATGGGGTTTCACCATGTTGGCCAGGCTGGTCTCGAACTCCTGACCTCAAGTGATCCG

CCCGCCTCGGCCTCCCAAAATGCTGGGATTACAGGCGTGAGCCACCGCGCCCGGCCTGTTTGTT

AATCTTAAATAGAAACGGAGTCTCCTTATGTTGCCTAGGCTGGTCTCCAACTCCTAGGCTCAAG

AGATCCTCCTGTCTTGGCCTCAGGAAGTGATGGGATTACAGGCATGAGGCTCCGCGCCCGGCCT

GATAGGTTCTCTTATTGCCATGTTGTAGATAGAAGGGGGCCCCTGGGTTAGGCAGACACAGGTT

AGGTAGTTCGTCCGGCGTCACCGGGCGGGAGCCCACCGCAGGCCCCACGAGACAAGGGCGAGCA

GGTTCATCGCCTCCCGGGGAAAGGACTGGGTAGTCCCAGGCCCCACCCCTTCCTGGAACAGCAA

GTTCGCTGTGGGTCCCGACCTACTGACCCAGGCGGAGGGCGGGACGCAGGGTAGCTGGGGCCGC

GTAGAGAGGGAAAGAAGGTCGCGATTGGCTCGTCCCGAAAGGTGGGCGGGGCCTCCTCCGACCT

GTGCGCGCGCGCCGCGGGGAGGTGTTGCCGAGGGCGGAGCGGGAGGGGGCGTGGCCCCGCGCGG

GCGGCCGTTGACGGCGAGGCCCCGCCCCGGATGTCGCGTGTCGCTGAAAGGGCGGCGGCGATTG

GCCGGCGCCGCGGGGGCGGGCGGGGCGGAAGGTTCTGGAGGGGGCTGGCGGGCTCTGGAAGCTT

CCGCCGGACGGGTATATAGAGTCCGGGACTGGTCGGCGGCGGAGCCGGGGGACGGCGACAGCGG

GTCGGCGGGCCGCAGGAGGGGGTCATGGGTAAAGACTACTACCAGACGTTGGGCCTGGCCCGCG

GCGCGTCGGACGAGGAGATCAAGCGGGCCTACCGCCGCCAGGCGCTGCGCTACCACCCGGACAA

GAACAAGGAGCCCGGCGCCGAGGAGAAGTTCAAGGAGATCGCTGAGGCCTACGACGTGCTCAGC

GACCCGCGCAAGCGCGAGATCTTCGACCGCTACGGGGAGGAAGGTGTGTGCTCGCGGCCAGGGG

CGCGGCCCCGCCTTTTGACAGACAGGGAAACTGAGGCACGCTGGCCCCTCTCGGCGGCCCCCCG

GGAAGGACGCCCCGGGCCGTGGGGCCGAGCTGCCCCGCCCTCCGGCCTCGCGGGCCTCCGCCCT

CGGATTGGCGGCCGCGCGGTGGGAGGAGGAGCCTTGGCCCAGCCGCTCGGCCAGAAGCTTCTAG

CATGTCTGGGGCTGCCCCTCCCCGGGCGCCTCCTCCCGCGGCCCCGAGCAGCCCCGGGGTGCGG

TGCATGGGGGTGGGGGAGCCGGGGGTGACGACGGGGACGGCGCGGCGGAGCCCGCTGCGGACCC

GGGCTCACCTGGGCTCGGCCGCCGGGGTCCGCGGGGCGGCGCCTCCGGCTCAGCTGCGGGGCGA

GGGGTTGTGAATGCAGGAGCCGACCCCGTTCGTGGGCTTGGGGGCTGGGTTGGGATAATTCCCG

GGAAGTGATGACCTGGCCCCGGCAGGGCACGCAGGAGGCAGCGGCCGCCCAGGTCCGGAGAGCG

GGGCCGCCTCGGAGGGTAAGGAGAGCAGGGCTTTTTGTTCCTGTGCCCGTTGATGATTCAGGCT

GGCTTCTGGGCTTGATCTGGAGCTGACTTTTTGTGCAAGGATGGTGGCAGTGAATGCTAATGTG

TGAGGATTTAAAAACTCCCTATTTATTTTTGTTTTTTTTTTTCTTCTCTTCCTACGCACCATTA

GCCCTAAAACGTTGAGAGTAAACACTTACCGAAAGCCGACCCTGGACCATGTGTCTTTAGCCAT

CTCTTGGTGATGTTGCCAGGAGGATGGGTCAGTCCAGGAGTGGCAGGGCCTAGGTGGCACCTGG

AGGTGAACACCTAACCGCATGAGTCCTTTTCCACTGTCAGGCTACGCGGAAATACTGTTGGTAG

GGGGGCGTCTCTGCTGTTGGCAGTGAGAGGTAGAAACTTGGGGTTCTTCCTTGCTCTCCCCTGA

CAGACAAAAAAGTTCCTCCCCCATGGCTTCCAAGCTGTTTCCCCCTGTAAGGGAAGCTCGAGAG

AGAGTCTGCTGTTCAGCCATCTGACTGCTTCTAAATCTGCTTTTCAGGCCTAAAGGGGAGTGGC

CCCAGTGGCGGTAGCGGCGGTGGTGCCAATGGTACCTCTTTCAGCTACACATTCCATGGAGACC

CTCATGCCATGTTTGCTGAGTTCTTCGGTGGCAGAAATCCCTTTGACACCTTTTTTGGGCAGCG

GAACGGGGAGGAAGGCATGGACATTGATGACCCATTCTCTGGCTTCCCTATGGGCATGGGTGGC

TTCACCAACGTGAACTTTGGCCGCTCCCGCTCTGCCCAAGAGCCCGCCCGAAAGAAGCAAGATC

CCCCAGTCACCCACGACCTTCGAGTCTCCCTTGAAGAGATCTACAGCGGCTGTACCAAGAAGAT

GAAAATCTCCCACAAGCGGCTAAACCCCGACGGAAAGAGCATTCGAAACGAAGACAAAATATTG

ACCATCGAAGTGAAGAAGGGGTGGAAAGAAGGAACCAAAATCACTTTCCCCAAGGAAGGAGACC

AGACCTCCAACAACATTCGAGCTGATATCGTCTTTGTTTTAAAGGACAAGCCCCACAATATCTT

TAAGAGAGATGGCTCTGATGTCATTTATCCTGCCAGGATCAGCCTCCGGGAGGTAAGGTGCCAG

GTGGGGCGGTGTCTGTAGAGGGCGATGGCTGCTTTTTGAAGCAGTTTAGTATTTGCTGAACCAA

TGTGTTGGGGTGTGTGGTGCGTGCCAGGCTTGGGGCACAACAGTGAACAGGACTGACCAGGGCG

CTGTTGTGGAGCTTTCGTGGTGGGGACGTGTAGATTTGGGGGCCAGGTCTTAGCTGCAGAGGCC

TGATGGGTCTTATCTATGGCAGACGGCCTCTGGGCAAGAGCTGAGCCTCTTGAGCCAGCTTCCA

TCTAATGCTGTCCTTTTGCTTTTCAAGGCTCTGTGTGGCTGCACAGTGAACGTCCCCACTCTGG

ACGGCAGGACGATACCCGTCGTATTCAAAGATGTTATCAGGCCTGGCATGCGGCGAAAAGTTCC

TGGAGAAGGCCTCCCCCTCCCCAAAACACCCGAGAAACGTGGGGACCTCATTATTGAGTTTGAA

GTGATCTTCCCCGAAAGGATTCCCCAGACATCAAGAACCGTACTTGAGCAGGTTCTTCCAATAT

AGCTATCTGAGCTCCCCAAGGACTGACCAGGGACCTTTCCAGAGCTCAAGGATTTCTGGACCTT

TCTACCAGTTGTGGACCATGAGAGGGTGGGAGGGCCCAGGGAGGGCTTTCGTACTGCTGAATGT

TTTCCAGAGCATATATTACAATCTTTCAAAGTCGCACACTAGACTTCAGTGGTTTTTCGAGCTA

TAGGGCATCAGGTGGTGGGAACAGCAGGAAAAGGCATTCCAGTCTGCCCCACTGGGTCTGGCAG

CCCTCCCGGGATGGGCCCACATCCACCTCCAGTCCCTGGCCAGGGGTGAGAGGCAGACCAGCAG

ATGGACTTGATCCCTCTGTGTCTTTTTGCTTCTGGCTGGTAGATAATGTCAACCTGCAGTCTTG

ATTCCCAGACCCTGTACACTCCTCCTTTTCTGTTGTGTGATCAGTTTGTGCTTTATTCTGTATT

TGTCTCCCATGTCTTGCTCTTCTCCTGGAGAATTCTGTCTTCTCTTTGGCCATCTCAAATTGAG

AACCTAAACTATTCCTGCAGAACTGCCTGGTTGGCGTCCACAAGCAATACCTCTCGTTCCAGCA

GGACCAAGGGAGCCAGCCTCCAGTGAGTGACTCCAGCAAGTGCAGCCACCTCTCCCTTGATGGT

CTGGGAGCCTGGCCTCAGCAAGGGGCCTTCCTGACCTCTGGCTCCAGTGAAGCTGAATGTCCTC

ACTTTGTGGGTCACACTCTTTACATTTCTGTAAGGCAATCTTGGCACACGTGGGGCTTACCAGT

GGCCCAGGTAATTTTTTGTTTCATGGACTATGGACTCTTTCAAAGGGATCTGATCCTTTTGAAT

TTTGCACAGCCCTAGATACAATCCCTTTTGATAAAAGGGTCTTTGCTTCTGATTACAGGAGCAC

TGTGGAACGTCTGTAAATATGTTTTTATAATTCCATGTATAGTTGGTGTACACTCAAAACCTGT

CCCCGGCAGCCAGTGCTCTCTGTATAGGGCCATAATGGAATTCTGAAGAAATCTTGGGGAGGGA

AGGGGAGTTGGAACAAATGTCTGTTCCCTGGAGGCCAGTCCAGTGCTCAGACCTTTAGACTCAT

TGTAAGTTGCCACTGCCAACATGAGACCAAAGTGTGTGACTAGTCAATGAAGTGCGACAGCATT

AAAGACTGATGCTAAACCTCAGGGGA

Exemplary Human DNAJB1 cDNA including untranslated regions
Variant 1

(SEQ ID NO: 113)

GGAGCCGGGGGACGGCGACAGCGGGTCGGCGGGCCGCAGGAGGGGGTCATGGGTAAAGACTACT

ACCAGACGTTGGGCCTGGCCCGCGGCGCGTCGGACGAGGAGATCAAGCGGGCCTACCGCCGCCA

GGCGCTGCGCTACCACCCGGACAAGAACAAGGAGCCCGGCGCCGAGGAGAAGTTCAAGGAGATC

GCTGAGGCCTACGACGTGCTCAGCGACCCGCGCAAGCGCGAGATCTTCGACCGCTACGGGGAGG

AAGGCCTAAAGGGGAGTGGCCCCAGTGGCGGTAGCGGCGGTGGTGCCAATGGTACCTCTTTCAG

-continued

CTACACATTCCATGGAGACCCTCATGCCATGTTTGCTGAGTTCTTCGGTGGCAGAAATCCCTTT

GACACCTTTTTTGGGCAGCGGAACGGGGAGGAAGGCATGGACATTGATGACCCATTCTCTGGCT

TCCCTATGGGCATGGGTGGCTTCACCAACGTGAACTTTGGCCGCTCCCGCTCTGCCCAAGAGCC

CGCCCGAAAGAAGCAAGATCCCCCAGTCACCCACGACCTTCGAGTCTCCCTTGAAGAGATCTAC

AGCGGCTGTACCAAGAAGATGAAAATCTCCCACAAGCGGCTAAACCCCGACGGAAAGAGCATTC

GAAACGAAGACAAAATATTGACCATCGAAGTGAAGAAGGGGTGGAAAGAAGGAACCAAAATCAC

TTTCCCCAAGGAAGGAGACCAGACCTCCAACAACATTCCAGCTGATATCGTCTTTGTTTTAAAG

GACAAGCCCCACAATATCTTTAAGAGAGATGGCTCTGATGTCATTTATCCTGCCAGGATCAGCC

TCCGGGAGGCTCTGTGTGGCTGCACAGTGAACGTCCCCACTCTGGACGGCAGGACGATACCCGT

CGTATTCAAAGATGTTATCAGGCCTGGCATGCGGCGAAAAGTTCCTGGAGAAGGCCTCCCCCTC

CCCAAAACACCCGAGAAACGTGGGGACCTCATTATTGAGTTTGAAGTGATCTTCCCCGAAAGGA

TTCCCCAGACATCAAGAACCGTACTTGAGCAGGTTCTTCCAATATAGCTATCTGAGCTCCCCAA

GGACTGACCAGGGACCTTTCCAGAGCTCAAGGATTTCTGGACCTTTCTACCAGTTGTGGACCAT

GAGAGGGTGGGAGGGCCCAGGGAGGGCTTTCGTACTGCTGAATGTTTTCCAGAGCATATATTAC

AATCTTTCAAAGTCGCACACTAGACTTCAGTGGTTTTTCGAGCTATAGGGCATCAGGTGGTGGG

AACAGCAGGAAAAGGCATTCCAGTCTGCCCCACTGGGTCTGGCAGCCCTCCCGGGATGGGCCCA

CATCCACCTCCAGTCCCTGGCCAGGGGTGAGAGGCAGACCAGCAGATGGACTTGATCCCTCTGT

GTCTTTTTGCTTCTGGCTGGTAGATAATGTCAACCTGCAGTCTTGATTCCCAGACCCTGTACAC

TCCTCCTTTTCTGTTGTGTGATCAGTTTGTGCTTTATTCTGTATTTGTCTCCCATGTCTTGCTC

TTCTCCTGGAGAATTCTGTCTTCTCTTTGGCCATCTCAAATTGAGAACCTAAACTATTCCTGCA

GAACTGCCTGGTTGGCGTCCACAAGCAATACCTCTCGTTCCAGCAGGACCAAGGGAGCCAGCCT

CCAGTGAGTGACTCCAGCAAGTGCAGCCACCTCTCCCTTGATGGTCTGGGAGCCTGGCCTCAGC

AAGGGGCCTTCCTGACCTCTGGCTCCAGTGAAGCTGAATGTCCTCACTTTGTGGGTCACACTCT

TTACATTTCTGTAAGGCAATCTTGGCACACGTGGGGCTTACCAGTGGCCCAGGTAATTTTTTGT

TTCATGGACTATGGACTCTTTCAAAGGGATCTGATCCTTTTGAATTTTGCACAGCCCTAGATAC

AATCCCTTTTGATAAAAGGGTCTTTGCTTCTGATTACAGGAGCACTGTGGAACGTCTGTAAATA

TGTTTTTATAATTCCATGTATAGTTGGTGTACACTCAAAACCTGTCCCCGGCAGCCAGTGCTCT

CTGTATAGGGCCATAATGGAATTCTGAAGAAATCTTGGGGAGGGAAGGGGAGTTGGAACAAATG

TCTGTTCCCTGGAGGCCAGTCCAGTGCTCAGACCTTTAGACTCATTGTAAGTTGCCACTGCCAA

CATGAGACCAAAGTGTGTGAGTAGTCAATGAAGTGCGACAGCATTAAAGACTGATGCTAAACCT

CA

Exemplary Human DNAJB1 cDNA coding sequence Variant 1 and Variant 3

(SEQ ID NO: 156)

ATGGGTAAAGACTACTACCAGACGTTGGGCCTGGCCCGCGGCGCGTCGGACGAGGAGATCAAGC

GGGCCTACCGCCGCCAGGCGCTGCGCTACCACCCGGACAAGAACAAGGAGCCCGGCGCCGAGGA

GAAGTTCAAGGAGATCGCTGAGGCCTACGACGTGCTCAGCGACCCGCGCAAGCGCGAGATCTTC

GACCGCTACGGGGAGGAAGGCCTAAAGGGGAGTGGCCCCAGTGGCGGTAGCGGCGGTGGTGCCA

ATGGTACCTCTTTCAGCTACACATTCCATGGAGACCCTCATGCCATGTTTGCTGAGTTCTTCGG

TGGCAGAAATCCCTTTGACACCTTTTTTGGGCAGCGGAACGGGGAGGAAGGCATGGACATTGAT

GACCCATTCTCTGGCTTCCCTATGGGCATGGGTGGCTTCACCAACGTGAACTTTGGCCGCTCCC

GCTCTGCCCAAGAGCCCGCCCGAAAGAAGCAAGATCCCCCAGTCACCCACGACCTTCGAGTCTC

-continued

CCTTGAAGAGATCTACAGCGGCTGTACCAAGAAGATGAAAATCTCCCACAAGCGGCTAAACCCC

GACGGAAAGAGCATTCGAAACGAAGACAAAATATTGACCATCGAAGTGAAGAAGGGGTGGAAAG

AAGGAACCAAAATCACTTTCCCCAAGGAAGGAGACCAGACCTCCAACAACATTCCAGCTGATAT

CGTCTTTGTTTTAAAGGACAAGCCCCACAATATCTTTAAGAGAGATGGCTCTGATGTCATTTAT

CCTGCCAGGATCAGCCTCCGGGAGGCTCTGTGTGGCTGCACAGTGAACGTCCCCACTCTGGACG

GCAGGACGATACCCGTCGTATTCAAAGATGTTATCAGGCCTGGCATGCGGCGAAAAGTTCCTGG

AGAAGGCCTCCCCCTCCCCAAAACACCCGAGAAACGTGGGGACCTCATTATTGAGTTTGAAGTG

ATCTTCCCCGAAAGGATTCCCCAGACATCAAGAACCGTACTTGAGCAGGTTCTTCCAATATAG

Exemplary Human DNAJB1 cDNA including untranslated regions
Variant 2

(SEQ ID NO: 157)

GTGCATGGGGGTGGGGGAGCCGGGGGTGACGACGGGGACGGCGCGGCGGAGCCCGCTGCGGACC

CGGGCTCACCTGGGCTCGGCCGCCGGGGTCCGCGGGGCGGCGCCTCCGGCTCAGCTGCGGGGCG

AGGGGTTGTGAATGCAGGAGCCGACCCCGTTCGTGGGCTTGGGGGCTGGGTTGGGATAATTCCC

GGGAAGTGATGACCTGGCCCCGGCAGGGCACGCAGGAGGCAGCGGCCGCCCAGGTCCGGAGAGC

GGGGCCGCCTCGGAGGGCCTAAAGGGGAGTGGCCCCAGTGGCGGTAGCGGCGGTGGTGCCAATG

GTACCTCTTTCAGCTACACATTCCATGGAGACCCTCATGCCATGTTTGCTGAGTTCTTCGGTGG

CAGAAATCCCTTTGACACCTTTTTTGGGCAGCGGAACGGGGAGGAAGGCATGGACATTGATGAC

CCATTCTCTGGCTTCCCTATGGGCATGGGTGGCTTCACCAACGTGAACTTTGGCCGCTCCCGCT

CTGCCCAAGAGCCCGCCCGAAAGAAGCAAGATCCCCCAGTCACCCACGACCTTCGAGTCTCCCT

TGAAGAGATCTACAGCGGCTGTACCAAGAAGATGAAAATCTCCCACAAGCGGCTAAACCCCGAC

GGAAAGAGCATTCGAAACGAAGACAAAATATTGACCATCGAAGTGAAGAAGGGGTGGAAAGAAG

GAACCAAAATCACTTTCCCCAAGGAAGGAGACCAGACCTCCAACAACATTCGAGCTGATATCGT

CTTTGTTTTAAAGGACAAGCCCCACAATATCTTTAAGAGAGATGGCTCTGATGTCATTTATCCT

GCCAGGATCAGCCTCCGGGAGGCTCTGTGTGGCTGCACAGTGAACGTCCCCACTCTGGACGGCA

GGACGATACCCGTCGTATTCAAAGATGTTATCAGGCCTGGCATGCGGCGAAAAGTTCCTGGAGA

AGGCCTCCCCCTCCCCAAAACACCCGAGAAACGTGGGGACCTCATTATTGAGTTTGAAGTGATC

TTCCCCGAAAGGATTCCCCAGACATCAAGAACCGTACTTGAGCAGGTTCTTCCAATATAGCTAT

CTGAGCTCCCCAAGGACTGACCAGGGACCTTTCCAGAGCTCAAGGATTTCTGGACCTTTCTACC

AGTTGTGGACCATGAGAGGGTGGGAGGGCCCAGGGAGGGCTTTCGTACTGCTGAATGTTTTCCA

GAGCATATATTACAATCTTTCAAAGTCGCACACTAGACTTCAGTGGTTTTTCGAGCTATAGGGC

ATCAGGTGGTGGGAACAGCAGGAAAAGGCATTCCAGTCTGCCCCACTGGGTCTGGCAGCCCTCC

CGGGATGGGCCCACATCCACCTCCAGTCCCTGGCCAGGGGTGAGAGGCAGACCAGCAGATGGAC

TTGATCCCTCTGTGTCTTTTTGCTTCTGGCTGGTAGATAATGTCAACCTGCAGTCTTGATTCCC

AGACCCTGTACACTCCTCCTTTTCTGTTGTGTGATCAGTTTGTGCTTTATTCTGTATTTGTCTC

CCATGTCTTGCTCTTCTCCTGGAGAATTCTGTCTTCTCTTTGGCCATCTCAAATTGAGAACCTA

AACTATTCCTGCAGAACTGCCTGGTTGGCGTCCACAAGCAATACCTCTCGTTCCAGCAGGACCA

AGGGAGCCAGCCTCCAGTGAGTGACTCCAGCAAGTGCAGCCACCTCTCCCTTGATGGTCTGGGA

GCCTGGCCTCAGCAAGGGGCCTTCCTGACCTCTGGCTCCAGTGAAGCTGAATGTCCTCACTTTG

TGGGTCACACTCTTTACATTTCTGTAAGGCAATCTTGGCACACGTGGGGCTTACCAGTGGCCCA

GGTAATTTTTTGTTTCATGGACTATGGACTCTTTCAAAGGGATCTGATCCTTTTGAATTTTGCA

CAGCCCTAGATACAATCCCTTTTGATAAAAGGGTCTTTGCTTCTGATTACAGGAGCACTGTGGA

ACGTCTGTAAATATGTTTTTATAATTCCATGTATAGTTGGTGTACACTCAAAACCTGTCCCCGG

CAGCCAGTGCTCTCTGTATAGGGCCATAATGGAATTCTGAAGAAATCTTGGGGAGGGAAGGGGA

GTTGGAACAAATGTCTGTTCCCTGGAGGCCAGTCCAGTGCTCAGACCTTTAGACTCATTGTAAG

TTGCCACTGCCAACATGAGACCAAAGTGTGTGACTAGTCAATGAAGTGCGACAGCATTAAAGAC

TGATGCTAAACCTCAGGGGAAAAAAAAAAA

Exemplary Human DNAJB1 cDNA coding sequence Variant 2

(SEQ ID NO: 158)

ATGTTTGCTGAGTTCTTCGGTGGCAGAAATCCCTTTGACACCTTTTTTGGGCAGCGGAACGGGG

AGGAAGGCATGGACATTGATGACCCATTCTCTGGCTTCCCTATGGGCATGGGTGGCTTCACCAA

CGTGAACTTTGGCCGCTCCCGCTCTGCCCAAGAGCCCGCCCGAAAGAAGCAAGATCCCCCAGTC

ACCCACGACCTTCGAGTCTCCCTTGAAGAGATCTACAGCGGCTGTACCAAGAAGATGAAAATCT

CCCACAAGCGGCTAAACCCCGACGGAAAGAGCATTCGAAACGAAGACAAAATATTGACCATCGA

AGTGAAGAAGGGGTGGAAAGAAGGAACCAAAATCACTTTCCCCAAGGAAGGAGACCAGACCTCC

AACAACATTCCAGCTGATATCGTCTTTGTTTTAAAGGACAAGCCCCACAATATCTTTAAGAGAG

ATGGCTCTGATGTCATTTATCCTGCCAGGATCAGCCTCCGGGAGGCTCTGTGTGGCTGCACAGT

GAACGTCCCCACTCTGGACGGCAGGACGATACCCGTCGTATTCAAAGATGTTATCAGGCCTGGC

ATGCGGCGAAAAGTTCCTGGAGAAGGCCTCCCCCTCCCCAAAACACCCGAGAAACGTGGGGACC

TCATTATTGAGTTTGAAGTGATCTTCCCCGAAAGGATTCCCCAGACATCAAGAACCGTACTTGA

GCAGGTTCTTCCAATATAG

Exemplary Human DNAJB1 cDNA including untranslated regions Variant 3

(SEQ ID NO: 159)

GTGGAAACCAAGGTAAGCGACGGTTAGGCCAGACGCGGGGGCGGGGTAAGAAGTTGAGTGACAG

GCAAGGCAGCATCCACATGACAGGCGGCGCCGAAGGGGTAAATTCTGAGATCCTGCCCCTGAGC

TTTCATGAGCTGTTGAACCATCTGGAATTCACAGGCCTGTCATGAGAGACACGATGAGAAGTCC

TTAAAGGCCTAAAGGGGAGTGGCCCCAGTGGCGGTAGCGGCGGTGGTGCCAATGGTACCTCTTT

CAGCTACACATTCCATGGAGACCCTCATGCCATGTTTGCTGAGTTCTTCGGTGGCAGAAATCCC

TTTGACACCTTTTTTGGGCAGCGGAACGGGGAGGAAGGCATGGACATTGATGACCCATTCTCTG

GCTTCCCTATGGGCATGGGTGGCTTCACCAACGTGAACTTTGGCCGCTCCCGCTCTGCCCAAGA

GCCCGCCCGAAAGAAGCAAGATCCCCCAGTCACCCACGACCTTCGAGTCTCCCTTGAAGAGATC

TACAGCGGCTGTACCAAGAAGATGAAAATCTCCCACAAGCGGCTAAACCCCGACGGAAAGAGCA

TTCGAAACGAAGACAAAATATTGACCATCGAAGTGAAGAAGGGGTGGAAAGAAGGAACCAAAAT

CACTTTCCCCAAGGAAGGAGACCAGACCTCCAACAACATTCCAGCTGATATCGTCTTTGTTTTA

AAGGACAAGCCCCACAATATCTTTAAGAGAGATGGCTCTGATGTCATTTATCCTGCCAGGATCA

GCCTCCGGGAGGCTCTGTGTGGCTGCACAGTGAACGTCCCCACTCTGGACGGCAGGACGATACC

CGTCGTATTCAAAGATGTTATCAGGCCTGGCATGCGGCGAAAAGTTCCTGGAGAAGGCCTCCCC

CTCCCCAAAACACCCGAGAAACGTGGGGACCTCATTATTGAGTTTGAAGTGATCTTCCCCGAAA

GGATTCCCCAGACATCAAGAACCGTACTTGAGCAGGTTCTTCCAATATAGCTATCTGAGCTCCC

CAAGGACTGACCAGGGACCTTTCCAGAGCTCAAGGATTTCTGGACCTTTCTACCAGTTGTGGAC

CATGAGAGGGTGGGAGGGCCCAGGGAGGGCTTTCGTACTGCTGAATGTTTTCCAGAGCATATAT

TACAATCTTTCAAAGTCGCACACTAGACTTCAGTGGTTTTTCGAGCTATAGGGCATCAGGTGGT

GGGAACAGCAGGAAAAGGCATTCCAGTCTGCCCCACTGGGTCTGGCAGCCCTCCCGGGATGGGC

CCACATCCACCTCCAGTCCCTGGCCAGGGGTGAGAGGCAGACCAGCAGATGGACTTGATCCCTC

-continued

```
TGTGTCTTTTTGCTTCTGGCTGGTAGATAATGTCAACCTGCAGTCTTGATTCCCAGACCCTGTA

CACTCCTCCTTTTCTGTTGTGTGATCAGTTTGTGCTTTATTCTGTATTTGTCTCCCATGTCTTG

CTCTTCTCCTGGAGAATTCTGTCTTCTCTTTGGCCATCTCAAATTGAGAACCTAAACTATTCCT

GCAGAACTGCCTGGTTGGCGTCCACAAGCAATACCTCTCGTTCCAGCAGGACCAAGGGAGCCAG

CCTCCAGTGAGTGACTCCAGCAAGTGCAGCCACCTCTCCCTTGATGGTCTGGGAGCCTGGCCTC

AGCAAGGGGCCTTCCTGACCTCTGGCTCCAGTGAAGCTGAATGTCCTCACTTTGTGGGTCACAC

TCTTTACATTTCTGTAAGGCAATCTTGGCACACGTGGGGCTTACCAGTGGCCCAGGTAATTTTT

TGTTTCATGGACTATGGACTCTTTCAAAGGGATCTGATCCTTTTGAATTTTGCACAGCCCTAGA

TACAATCCCTTTTGATAAAAGGGTCTTTGCTTCTGATTACAGGAGCACTGTGGAACGTCTGTAA

ATATGTTTTTATAATTCCATGTATAGTTGGTGTACACTCAAAACCTGTCCCCGGCAGCCAGTGC

TCTCTGTATAGGGCCATAATGGAATTCTGAAGAAATCTTGGGGAGGGAAGGGGAGTTGGAACAA

ATGTCTGTTCCCTGGAGGCCAGTCCAGTGCTCAGACCTTTAGACTCATTGTAAGTTGCCACTGC

CAACATGAGACCAAAGTGTGTGACTAGTCAATGAAGTGCGACAGCATTAAAGACTGATGCTAAA

CCTCAGGGGA
```

Polypeptides Encoded by DNAJB1 Gene

Exemplary Human Mature DNAJB1 Protein Isoform 1 and Isoform 3

(SEQ ID NO: 160)

```
MGKDYYQTLGLARGASDEEIKRAYRRQALRYHPDKNKEPGAEEKFKEIAEAYDVLSDPRKREIF

DRYGEEGLKGSGPSGGSGGGANGTSFSYTFHGDPHAMFAEFFGGRNPFDTFFGQRNGEEGMDID

DPFSGFPMGMGGFTNVNFGRSRSAQEPARKKQDPPVTHDLRVSLEEIYSGCTKKMKISHKRLNP

DGKSIRNEDKILTIEVKKGWKEGTKITFPKEGDQTSNNIPADIVFVLKDKPHNIFKRDGSDVIY

PARISLREALCGCTVNVPTLDGRTIPVVFKDVIRPGMRRKVPGEGLPLPKTPEKRGDLIIEFEV

IFPERIPQTSRTVLEQVLPI
```

Exemplary Human Mature DNAJB1 Protein Isoform 2

(SEQ ID NO: 161)

```
MFAEFFGGRNPFDTFFGQRNGEEGMDIDDPFSGFPMGMGGFTNVNFGRSRSAQEPARKKQDPPV

THDLRVSLEEIYSGCTKKMKISHKRLNPDGKSIRNEDKILTIEVKKGWKEGTKITFPKEGDQTS

NNIPADIVFVLKDKPHNIFKRDGSDVIYPARISLREALCGCTVNVPTLDGRTIPVVFKDVIRPG

MRRKVPGEGLPLPKTPEKRGDLIIEFEVIFPERIPQTSRTVLEQVLPI
```

Heat Shock Protein 40 (Hsp40) (DNA.J Homolog Subfamily B Member 5) (DNA.JB5)

In some embodiments, an Hsp40 protein is encoded by a DNAJB5 gene. The human DNAJB5 gene is located on chromosome Chr19: 14,514,770-14,529,770. It contains 7 exons (NCBI Accession No. NC_000019.10). DNAJB5 encodes a 40 kDa heat shock protein.

As used herein, the term “active DNAJB5 protein” means a protein encoded by DNA that, if substituted for both wildtype alleles encoding full-length DNAJB5 protein in auditory hair cells, or ocular cells, of what is otherwise a wildtype mammal, and if expressed in the auditory hair cells, or ocular cells, of that mammal, results in that mammal’s having a level of hearing, or vision, approximating the normal level of hearing, or vision, of a similar mammal that is entirely wildtype. Non-limiting examples of active DNAJB5 proteins are full-length DNAJB5 proteins (e.g., any of the full-length DNAJB5 proteins described herein).

For example, an active DNAJB5 protein can include a sequence of a wildtype, full-length DNAJB5 protein (e.g., a wildtype, human, full-length DNAJB5 protein) including about 1 to about 200 amino acid substitutions (e.g., about 1 to 190 amino acid substitutions, about 1 to about 180 amino acid substitutions, about 1 to about 160 amino acid substitutions, about 1 to about 150 amino acid substitutions, about 1 to about 140 amino acid substitutions, about 1 to about 130 amino acid substitutions, about 1 to about 120 amino acid substitutions, about 1 to about 110 amino acid substitutions, about 1 to about 100 amino acid substitutions, about 1 to about 90 amino acid substitutions, about 1 to about 80 amino acid substitutions, about 1 to about 70 amino acid substitutions, about 1 to about 60 amino acid substitutions, about 1 to about 50 amino acid substitutions, about 1 to about 40 amino acid substitutions, about 1 to about 30 amino acid substitutions, about 1 to about 25 amino acid substitutions, about 1 to about 20 amino acid substitutions, about 1 to about 10 amino acid substitutions, about 1 to about 5 amino acid substitutions, about 10 to about 200 amino acid substitutions, about 10 to about 180 amino acid substitutions, about 10 to about 160 amino acid substitutions, about 10 to about 150 amino acid substitutions, about 10 to about 140 amino acid substitutions, about 10 to about 120 amino acid substitutions, about 10 to about 100 amino acid substitutions, about 10 to about 80 amino acid substitutions, about 10 to about 60 amino acid substitutions, about 10 to about 50 amino acid substitutions, about 10 to about 40 amino acid substitutions, about 10 to about 20 amino acid substitutions, about 20 to about 200 amino acid substitutions, about 20 to about 180 amino acid substitutions, about 20 to about 160 amino acid substitutions, about 20 to about 150 amino acid substitutions, about 20 to about 140 amino acid substitutions, about 20 to about 120 amino acid substitutions, about 20 to about 100 amino acid substitutions, about 20 to about 80 amino acid substitutions, about 20 to about 60 amino acid substitutions, about 20 to about 50 amino acid substitutions, about 20 to about 40 amino acid substitutions, about 40 to about 200 amino acid substitutions, about 40 to about 180 amino acid substitutions, about 40 to about 160 amino acid substitutions, about 40 to about 150 amino acid substitutions, about 40 to about 140 amino acid substitutions, about 40 to about 120 amino acid substitutions, about 40 to about 100 amino acid substitutions, about 40 to about 80 amino acid substitutions, about 40 to about 60 amino acid substitutions, about 40 to about 50 amino acid substitutions, about 50 to about 200 amino acid substitutions, about 50 to about 180 amino acid substitutions, about 50 to about 160 amino acid substitutions, about 50 to about 150 amino acid substitutions, about 50 to about 140 amino acid substitutions, about 50 to about 120 amino acid substitutions, about 50 to about 100 amino acid substitutions, about 50 to about 80 amino acid substitutions, about 50 to about 60 amino acid substitutions, about 60 to about 200 amino acid substitutions, about 60 to about 180 amino acid substitutions, about 60 to about 160 amino acid substitutions, about 60 to about 150 amino acid substitutions, about 60 to about 140 amino acid substitutions, about 60 to about 120 amino acid substitutions, about 60 to about 100 amino acid substitutions, about 60 to about 80 amino acid substitutions, about 80 to about 200 amino acid substitutions, about 80 to about 180 amino acid substitutions, about 80 to about 160 amino acid substitutions, about 80 to about 150 amino acid substitutions, about 80 to about 140 amino acid substitutions, about 80 to about 120 amino acid substitutions, about 80 to about 100 amino acid substitutions, about 100 to about 200 amino acid substitutions, about 100 to about 180 amino acid substitutions, about 100 to about 160 amino acid substitutions, about 100 to about 150 amino acid substitutions, about 100 to about 140 amino acid substitutions, about 100 to about 120 amino acid substitutions, about 120 to about 200 amino acid substitutions, about 120 to about 180 amino acid substitutions, about 120 to about 160 amino acid substitutions, about 120 to about 150 amino acid substitutions, about 120 to about 140 amino acid substitutions, about 140 to about 200 amino acid substitutions, about 140 to about 180 amino acid substitutions, about 140 to about 160 amino acid substitutions, about 140 to about 150 amino acid substitutions, about 150 to about 200 amino acid substitutions, about 150 to about 180 amino acid substitutions, about 150 to about 160 amino acid substitutions, about 160 to about 200 amino acid substitutions, about 160 to about 180 amino acid substitutions, or about 180 to about 200 amino acid substitutions).

One skilled in the art would appreciate that amino acids that are not conserved between wildtype DNAJB5 proteins from different species can be mutated without losing activity, while those amino acids that are conserved between wildtype DNAJB5 proteins from different species should not be mutated as they are more likely (than amino acids that are not conserved between different species) to be involved in activity.

An active DNAJB5 protein can include, e.g., a sequence of a wildtype, full-length DNAJB5 protein (e.g., a wildtype, human, full-length DNAJB5 protein) that has about 1 to about 100 amino acids (e.g., about 1 to about 95 amino acids, about 1 to about 90 amino acids, about 1 to about 85 amino acids, about 1 to about 80 amino acids, about 1 to about 75 amino acids, about 1 to about 70 amino acids, about 1 to about 65 amino acids, about 1 to about 60 amino acids, about 1 to about 55 amino acids, about 1 to about 50 amino acids, about 1 to about 45 amino acids, about 1 to about 40 amino acids, about 1 to about 35 amino acids, about 1 to about 30 amino acids, about 1 to about 25 amino acids, about 1 to about 20 amino acids, about 1 to about 15 amino acids, about 1 to about 10 amino acids, about 1 to about 5 amino acids, about to about 100 amino acids, about 5 to about 95 amino acids, about 5 to about 90 amino acids, about 5 to about 85 amino acids, about 5 to about 80 amino acids, about 5 to about 75 amino acids, about 5 to about 70 amino acids, about 5 to about 65 amino acids, about 5 to about 60 amino acids, about 5 to about 55 amino acids, about 5 to about 50 amino acids, about 5 to about 45 amino acids, about 5 to about 40 amino acids, about 5 to about 35 amino acids, about 5 to about 30 amino acids, about 5 to about 25 amino acids, about 5 to about 20 amino acids, about 5 to about 15 amino acids, about 5 to about 10 amino acids, about 10 to about 100 amino acids, about 10 to about 95 amino acids, about 10 to about 90 amino acids, about 10 to about 85 amino acids, about 10 to about 80 amino acids, about 10 to about 80 amino acids, about 10 to about 75 amino acids, about 10 to about 70 amino acids, about 10 to about 65 amino acids, about 10 to about 60 amino acids, about 10 to about 55 amino acids, about 10 to about 50 amino acids, about to about 45 amino acids, about 10 to about 40 amino acids, about 10 to about 35 amino acids, about 10 to about 30 amino acids, about 10 to about 25 amino acids, about 10 to about 20 amino acids, about 10 to about 15 amino acids, about 15 to about 100 amino acids, about 15 to about 95 amino acids, about 15 to about 90 amino acids, about 15 to about 85 amino acids, about 15 to about 80 amino acids, about 15 to about 75 amino acids, about 15 to about 70 amino acids, about to about 65 amino acids, about 15 to about 60 amino acids, about 15 to about 55 amino acids, about 15 to about 50 amino acids, about 15 to about 45 amino acids, about 15 to about 40 amino acids, about 15 to about 35 amino acids, about 15 to about 30 amino acids, about 15 to about 25 amino acids, about 15 to about 20 amino acids, about 20 to about 100 amino acids, about 20 to about 95 amino acids, about 20 to about 90 amino acids, about 20 to about 85 amino acids, about to about 80 amino acids, about 20 to about 75 amino acids, about 20 to about 70 amino acids, about 20 to about 65 amino acids, about 20 to about 60 amino acids, about 20 to about 55 amino acids, about 20 to about 50 amino acids, about 20 to about 45 amino acids, about 20 to about 40 amino acids, about 20 to about 35 amino acids, about 20 to about 30 amino acids, about 20 to about 25 amino acids, about 25 to about 100 amino acids, about 25 to about 95 amino acids, about 25 to about 90 amino acids, about 25 to about 85 amino acids, about 25 to about 80 amino acids, about 25 to about 75 amino acids, about 25 to about 70 amino acids, about 25 to about 65 amino acids, about 25 to about 60 amino acids, about 25 to about 55 amino acids, about 25 to about 50 amino acids, about 25 to about 45 amino acids, about 25 to about 40 amino acids, about 25 to about 35 amino acids, about 25 to about 30 amino acids, about 30 to about 100 amino acids, about 30 to about 95 amino acids, about 30 to about 90 amino acids, about 30 to about 85 amino acids, about 30 to about 80 amino acids, about 30 to about 75 amino acids, about 30 to about 70 amino acids, about 30 to about 65 amino acids, about 30 to about 60 amino acids, about 30 to about 55 amino acids, about 30 to about 50 amino acids, about 30 to about 45 amino acids, about 30 to about 40 amino acids, about 30 to about 35 amino acids, about 35 to about 100 amino acids, about 35 to about 95 amino acids, about 35 to about 90 amino acids, about 35 to about 85 amino acids, about 35 to about 80 amino acids, about 35 to about 75 amino acids, about 35 to about 70 amino acids, about 35 to about 65 amino acids, about 35 to about 60 amino acids, about 35 to about 55 amino acids, about 35 to about 50 amino acids, about 35 to about 45 amino acids, about 35 to about 40 amino acids, about 40 to about 100 amino acids, about 40 to about 95 amino acids, about 40 to about 90 amino acids, about 40 to about 85 amino acids, about 40 to about 80 amino acids, about 40 to about 75 amino acids, about 40 to about 70 amino acids, about 40 to about 65 amino acids, about 40 to about 60 amino acids, about 40 to about 55 amino acids, about 40 to about 50 amino acids, about 40 to about 45 amino acids, about 45 to about 100 amino acids, about 45 to about 95 amino acids, about 45 to about 90 amino acids, about 45 to about 85 amino acids, about 45 to about 80 amino acids, about 45 to about 75 amino acids, about 45 to about 70 amino acids, about 45 to about 65 amino acids, about 45 to about 60 amino acids, about 45 to about 55 amino acids, about 45 to about 50 amino acids, about 50 to about 100 amino acids, about 50 to about 95 amino acids, about 50 to about 90 amino acids, about 50 to about 85 amino acids, about 50 to about 80 amino acids, about 50 to about 75 amino acids, about 50 to about 70 amino acids, about 50 to about 65 amino acids, about 50 to about 60 amino acids, about 50 to about 55 amino acids, about 55 to about 100 amino acids, about 55 to about 95 amino acids, about 55 to about 90 amino acids, about 55 to about 85 amino acids, about 55 to about 80 amino acids, about 55 to about 75 amino acids, about 55 to about 70 amino acids, about 55 to about 65 amino acids, about 55 to about 60 amino acids, about 60 to about 100 amino acids, about 60 to about 95 amino acids, about 60 to about 90 amino acids, about 60 to about 85 amino acids, about 60 to about 80 amino acids, about 60 to about 75 amino acids, about 60 to about 70 amino acids, about 60 to about 65 amino acids, about 65 to about 100 amino acids, about 65 to about 95 amino acids, about 65 to about 90 amino acids, about 65 to about 85 amino acids, about 65 to about 80 amino acids, about 65 to about 75 amino acids, about 65 to about 70 amino acids, about 70 to about 100 amino acids, about 70 to about 95 amino acids, about 70 to about 90 amino acids, about 70 to about 85 amino acids, about 70 to about 80 amino acids, about 70 to about 75 amino acids, about 75 to about 100 amino acids, about 75 to about 95 amino acids, about 75 to about 90 amino acids, about 75 to about 85 amino acids, about 75 to about 80 amino acids, about 80 to about 100 amino acids, about 80 to about 95 amino acids, about 80 to about 90 amino acids, about 80 to about 85 amino acids, about 85 to about 100 amino acids, about 85 to about 95 amino acids, about 85 to about 90 amino acids, about 90 to about 100 amino acids, about 90 to about 95 amino acids, or about 95 to about 100 amino acids), removed from its N-terminus and/or 1 amino acid to 80 amino acids (or any of the subranges of this range described herein) removed from its C-terminus.

In some embodiments, an active DNAJB5 protein can, e.g., include the sequence of a wildtype, full-length DNAJB5 protein where 1 amino acid to 50 amino acids, 1 amino acid to 45 amino acids, 1 amino acid to 40 amino acids, 1 amino acid to 35 amino acids, 1 amino acid to 30 amino acids, 1 amino acid to 25 amino acids, 1 amino acid to 20 amino acids, 1 amino acid to 15 amino acids, 1 amino acid to 10 amino acids, 1 amino acid to 9 amino acids, 1 amino acid to 8 amino acids, 1 amino acid to 7 amino acids, 1 amino acid to 6 amino acids, 1 amino acid to 5 amino acids, 1 amino acid to 4 amino acids, 1 amino acid to 3 amino acids, about 2 amino acids to 50 amino acids, about 2 amino acids to 45 amino acids, about 2 amino acids to 40 amino acids, about 2 amino acids to 35 amino acids, about 2 amino acids to 30 amino acids, about 2 amino acids to 25 amino acids, about 2 amino acids to 20 amino acids, about 2 amino acids to 15 amino acids, about 2 amino acids to 10 amino acids, about 2 amino acids to 9 amino acids, about 2 amino acids to 8 amino acids, about 2 amino acids to 7 amino acids, about 2 amino acids to 6 amino acids, about 2 amino acids to 5 amino acids, about 2 amino acids to 4 amino acids, about 3 amino acids to 50 amino acids, about 3 amino acids to 45 amino acids, about 3 amino acids to 40 amino acids, about 3 amino acids to 35 amino acids, about 3 amino acids to 30 amino acids, about 3 amino acids to 25 amino acids, about 3 amino acids to 20 amino acids, about 3 amino acids to 15 amino acids, about 3 amino acids to 10 amino acids, about 3 amino acids to 9 amino acids, about 3 amino acids to 8 amino acids, about 3 amino acids to 7 amino acids, about 3 amino acids to 6 amino acids, about 3 amino acids to 5 amino acids, about 4 amino acids to 50 amino acids, about 4 amino acids to 45 amino acids, about 4 amino acids to 40 amino acids, about 4 amino acids to 35 amino acids, about 4 amino acids to 30 amino acids, about 4 amino acids to 25 amino acids, about 4 amino acids to 20 amino acids, about 4 amino acids to 15 amino acids, about 4 amino acids to 10 amino acids, about 4 amino acids to 9 amino acids, about 4 amino acids to 8 amino acids, about 4 amino acids to 7 amino acids, about 4 amino acids to 6 amino acids, about 5 amino acids to 50 amino acids, about 5 amino acids to 45 amino acids, about 5 amino acids to 40 amino acids, about 5 amino acids to 35 amino acids, about 5 amino acids to 30 amino acids, about 5 amino acids to 25 amino acids, about 5 amino acids to 20 amino acids, about 5 amino acids to 15 amino acids, about 5 amino acids to 10 amino acids, about 5 amino acids to 9 amino acids, about 5 amino acids to 8 amino acids, about 5 amino acids to 7 amino acids, about 6 amino acids to 50 amino acids, about 6 amino acids to 45 amino acids, about 6 amino acids to 40 amino acids, about 6 amino acids to 35 amino acids, about 6 amino acids to 30 amino acids, about 6 amino acids to 25 amino acids, about 6 amino acids to 20 amino acids, about 6 amino acids to 15 amino acids, about 6 amino acids to 10 amino acids, about 6 amino acids to 9 amino acids, about 6 amino acids to 8 amino acids, about 7 amino acids to 50 amino acids, about 7 amino acids to 45 amino acids, about 7 amino acids to 40 amino acids, about 7 amino acids to 35 amino acids, about 7 amino acids to 30 amino acids, about 7 amino acids to 25 amino acids, about 7 amino acids to 20 amino acids, about 7 amino acids to 15 amino acids, about 7 amino acids to 10 amino acids, about 7 amino acids to 9 amino acids, about 8 amino acids to 50 amino acids, about 8 amino acids to 45 amino acids, about 8 amino acids to 40 amino acids, about 8 amino acids to 35 amino acids, about 8 amino acids to 30 amino acids, about 8 amino acids to 25 amino acids, about 8 amino acids to 20 amino acids, about 8 amino acids to 15 amino acids, about 8 amino acids to 10 amino acids, about 10 amino acids to 50 amino acids, about 10 amino acids to 45 amino acids, about 10 amino acids to 40 amino acids, about 10 amino acids to 35 amino acids, about 10 amino acids to 30 amino acids, about 10 amino acids to 25 amino acids, about 10 amino acids to 20 amino acids, about 10 amino acids to 15 amino acids, about 15 amino acids to 50 amino acids, about 15 amino acids to 45 amino acids, about 15 amino acids to 40 amino acids, about 15 amino acids to 35 amino acids, about 15 amino acids to 30 amino acids, about 15 amino acids to 25 amino acids, about 15 amino acids to 20 amino acids, about 20 amino acids to 50 amino acids, about 20 amino acids to 45 amino acids, about 20 amino acids to 40 amino acids, about 20 amino acids to 35 amino acids, about 20 amino acids to 30 amino acids, about 20 amino acids to 25 amino acids, about 25 amino acids to 50 amino acids, about 25 amino acids to 45 amino acids, about 25 amino acids to 40 amino acids, about 25 amino acids to 35 amino acids, about 25 amino acids to 30 amino acids, about 30 amino acids to 50 amino acids, about 30 amino acids to 45 amino acids, about 30 amino acids to 40 amino acids, about 30 amino acids to 35 amino acids, about 35 amino acids to 50 amino acids, about 35 amino acids to 45 amino acids, about 35 amino acids to 40 amino acids, about 40 amino acids to 50 amino acids, about 40 amino acids to 45 amino acids, or about 45 amino acids to about 50 amino acids, are inserted. In some examples, the 1 amino acid to 50 amino acids (or any subrange thereof) can be inserted as a contiguous sequence into the sequence of a wildtype, full-length DNAJB5 protein. In some examples, the 1 amino acid to 50 amino acids (or any subrange thereof) are inserted in multiple, non-contiguous places in the sequence of a wildtype, full-length DNAJB5 protein. As can be appreciated in the art, the 1 amino acid to 50 amino acids can be inserted into a portion of the sequence of a wildtype, full-length DNAJB5 protein that is not well-conserved between species.

Methods of detecting mutations in a gene are well-known in the art. Non-limiting examples of such techniques include: real-time polymerase chain reaction (RT-PCR), PCR, sequencing, Southern blotting, and Northern blotting.

Exemplary wildtype DNAJB5 protein sequences are or include SEQ ID NO: 38, 41 43, 44, and 45. Exemplary DNA sequences that encode a NDP protein and exemplary polypeptides encoded by an NDP gene are shown below.

DNA.JB5 Polynucleotides

Among other things, the present disclosure provides polynucleotides, e.g., polynucleotides comprising an DnaJ homolog subfamily B member 5 (DNAJB5) gene or characteristic portion thereof, as well as compositions including such polynucleotides and methods utilizing such polynucleotides and/or compositions.

In some embodiments, a polynucleotide comprising an DNAJB5 gene or characteristic portion thereof can be DNA or RNA. In some embodiments, DNA can be genomic DNA or cDNA. In some embodiments, RNA can be an mRNA. In some embodiments, a polynucleotide comprises exons and/or introns of an DNAJB5 gene.

In some embodiments, a gene product is expressed from a polynucleotide comprising an DNAJB5 gene or characteristic portion thereof. In some embodiments, expression of such a polynucleotide can utilize one or more control elements (e.g., promoters, enhancers, splice sites, polyadenylation sites, translation initiation sites, etc.). Thus, in some embodiments, a polynucleotide provided herein can include one or more control elements.

In some embodiments, an DNAJB5 gene is a mammalian DNAJB5 gene. In some embodiments, an DNAJB5 gene is a murine DNAJB5 gene. In some embodiments, an DNAJB5 gene is a primate DNAJB5 gene. In some embodiments, a DNAJB5 gene is a human DNAJB5 gene. An exemplary human DNAJB5 cDNA sequence is or includes the sequence of SEQ ID NO: 165 or 168 or 171. An exemplary human DNAJB5 genomic DNA sequence can be found in SEQ ID NO: 162. An exemplary human DNAJB5 cDNA sequence including untranslated regions is or includes the sequence of SEQ ID NO: 163, 164, 166, 167, 169, or 170.

```
Exemplary Human DNAJB5 Genomic Sequence
                                                  (SEQ ID NO: 162)
CTGAGCTGAGTGACAGGAAGACGGTTCAATGGGCGGCGCGGAGGCGGAGCCGTGGGGGCGGGCT

CCCGGTCCCGCTATCGGCGGCCGGCGGGCAGGCGACTCCTGTCCCGGGTGGAGGCGGCGGAGCC

GGAGCCGGGGGAGGGGGCAGCGGCTGTCTCACGGACCACGGCGGCGCCCGCAGCTCCTCACCGG

TGAGGGCGCCAAGCCAGGACTCGGGGGTCCCGGGAGCGGGGCGTCGTGAAGCCAGGGCTCCTGG

TGTTGGGGGGTTGGGACACTGAGGGCCCGTAGGCTCTGCTGCCTTGGGGATGCGGGGCCCCGGG

GTCTGCAGGGTGCTCGGAGTCCTAGACCAGGGCTTGGCTGTCACAGGGGGCAGCCAGCGTCTGA

GTCGGGGAGGGGAGGGGAGGGGAGGGTCGAGTCGGACCGGACCAGATTGGGTTCTGTGGGGCGG

AGGCATCTGTGAGCAGACCAGCCAGCCAGCGCGGGTGACATCACCGACCACCCTCCCCCGCCCG

AGCCCCCTCCCCTCCTCTCCTCGCCGCGCCTTTTGTCCCGGCCGAGCTCCGCTCTGCCCCGCCC

ATCTGCGAGGGAGGAGACTCCCGTCAGTGACTTCATTGAGTAGGTTCTTGGGGATTGGGGTCGG

GTCCTCCCCAGTGAGAGGCGACAGGAGCTCACTGCCTCTCGGGCCCTCACAATCACACCTGTCA

CAGGTATACACGCTGCCACTCACAAACACACGCTTGCACTCCCAGCCTCACTGACACGCTGCCA

TACAGCCGCTCACAGCCAGCCAGACACTGCTGCACCTGAGAGCAGGTGGCCGCGGGTCTTCTCC

CTTCACTCTCCACATTTGGGGATCAGGTCCGGCACCTGCTGCGCCAGACAGGCCTTGCTGGGCA

CGCGCCTCTGAGAGTCCAAGGAGGTGGCTTCCAGAGCTGCAGCACTTCAGGCCGGCTCCGGTGG

AGCGATCAGAGGTGAGGGGCTTGGCTGGGCATGTTTAAGCGCACAGTGCTCTCCTGCCCACCCC
```

-continued

CAGCAGCACCCCCACTGCAGGCCCGAGGAGCTTTCCGGAGCTTCCCACACTCCTGGGGAGAAGA

CTTCTTAGCCAGCTTGATGTTTAAAATTCAGCTGGAGCCCTTAAAACTTCGAGCGTGGACGCTG

AATGGGTTTGTAAAGTTTCGGTAAGTCCCTCCGGAGAAGGGCACTCACACCCATACCCAGTCAA

ACCCTCCACGCGGCCATCCCCTCCATTGCCTTCCTGCTTCCTCCAACTCATCCTCATCCCCTCT

GTGAGATACAGGAACCCCCCTCCGGCCTCACGGAGATATTTGAATGAATTGCACCCCTTATCAT

TCCTTTTCTCAAACCCTTCAGGTATCCATTTTCCACAGACATTTCCTCCATTATTTCAACTCTC

CACATTCCTCCCTTTCAACCCATCATTAACCCATTTTCCACCTCAGCCATTTCCATCTGTCACT

CATCCCCCTCCATCAGTACCTCATTTTCTGTATCAGCCATCTCCCCTCCCTGTACCTCAACAGT

CCCCCTCGCCATTTTCTCCCCATTTTTCCTTCCTGCCTCTACCTTAACATCCTCCTCATTCTTC

TCCATCAAAGGCAGTGCCATGCCATGGGGCTCCTTTGTCATTCCAACACGTGGCCTGTGGGTAG

GGGGGAAGGGAAGGAGGGAGGAAAGCAGAAAGAGAAAAAGGAGGCAGATCCTGAAAGAGCTTGC

CCTGTGTCTGCGGAGGCAAGAGATGTATGGGCCTAGAGCAGCTAGCAGGTGGGTACCAGGGAGG

AAGCTGGCCGGGTGTGGAGGTAATGCAGGGACACCAAAAGGAGGTGGGTGGTTGGTGAGCCGTT

CCACTGGCCCTCTGCCTGGAAGCTGCTCTCGTTCTCTAGGGGCACCCTCTTGGTGTGCTAGGGT

TCTTTCCCAGTCCCAGGGGAAAGAAGGTGTGGGTTGAGGCAGAAATGGCAGACCACCCCCCCCC

GCTCCCTCTCAGACGGCTTTTGCTGCCATTTCCGAAAACGGTTGCCCCCCCCCCCAACGAGGTG

CTCTTTCTTCTCTGCCTCTCCCAACCCCACCCCCCACCCCATCTCCCCCACAGACGTGACATGC

TGGTGGGGGGCAATGGGGGAGTACCCGCCTTTGTGGAGCCTTTTCTTCGTCAGAGAAAGGTGAC

TCCCAGAACCATGAGTCAACCCAGCCACCTGCAGCAGGGCCTGTGGGGGCAGCAGTGAGGGCCA

TTGTCCCTGCCCACCTAGGGCCTTGGGCGCCTCCCCCTTACCCGGTTACAGGCCTCACTCCTGG

AAGGACACCCTGTACACCTCCCTGCTGTGAAGCAGTCAGAGGCAGAAAGGCAGGTCTCAGCTGT

GGCTGCCAGCCTAGGACATTGCTAGAAAGACTCTGGTTCTCCTGGCTTTGGCAGGGGTTGGCCA

AGTCTCAGAAGGGCTGAGAATGGCTTCTGGCCATCCCCCAGAGAGCTCTAGCTACAGGAAAGTC

CCCCTTCCCCTGATATCCACCACAGACACACCGATAGAGGGAGACTGGAATGGAAGAATTCGGG

TTGTACGTTTCTCTTATAACAAATGCTCCTGCACCCACCTTAAAAGGGACTCAGAGGAATATGG

GTCTGATGATGGGCCGGATCCTAAACCACAGGGTGGACTGGGGGCGTAGGGTGAGGCTAGGAGA

GGTATTAAGGAAATGGTGGTTGGTTAGTGCCCAATTGTCTCCTAACAGCTGGGGTTGAAAAAGT

CCTGTCCCCAGGATGCTTTTGTTCACTCACACTGGTGCTTAGGCGGCACAGCCCTCACAGTTTT

GTGTGTAGACGCTGGCAAATGAGTAAAGGGAACTGTTGCCCTGGTTGGGGGAAGGATAGTGTCG

CCCCCCCTGCTAATGAGGGAGTTGGAAACAGCAGTTTCCAAAGGCTGTGAGTCACCCTGTGATC

TGAGTCACACGTGAGGCTTAGCATCGTCAGAGGGGTGGGGGCGGGGAGGCCTGGGGTCTCCGAT

GGCAGACAGGACTCCAGACACCCATTCCCTGACTCAGTCTGGCTGGCCAGGACAGCTGGCGGAA

GACCCAGGCCTGTTCCCGGTCCTGGGCCACTGCCCCAGCTGCCCTCAGCCTGGGCACCATGCCT

GAGGCGTGGCGTAGGAGACCACGATGCTCAGGTGACCTCACCCGTTACACTGACCTTCGCCAGC

TCCTGTGTGTGGGTCGCTCAGTCCATGGTGCCACCTCGCTCAGCAGGGCCTCTCAGGGGTCCTC

AGTCTGGCCCAAGGACCAGGGCCTCAGCCTAGCCCCAAGAGTGGGCCACAACCTTCAGCTTCCT

GCTGGGAAAACCCAGGAGGTGAGGACGGAATCACAGAATTCTAGAATGTCAGAGCCAGAAGAGA

TCATCTAGTCCAAACCTTTCATTTTACAGATGGGGGGACGCAGGCCCACAGAACAGGCATGACC

TGCTGAAGGTTACCCAGGGAGTCATTTAGGGATTGCAAGATCATCAGGAACAGGGCTGGGGCAG

AAGAGAAGGCATCAAGTCTTGGCCCTGGGTTTCTTTCAGAAACAAGGAGACCAGTGCTGGTCCA

-continued

GTGGCTGTGATGGGAAAAGATTATTACAAGATTCTTGGGATCCCATCGGGGGCCAACGAGGATG

AGATCAAGAAAGCCTACCGGAAGATGGCCTTGAAGTACCACCCAGACAAGAATAAAGAACCCAA

CGCTGAGGAGAAGTTTAAGGAGATTGCAGAGGCCTATGATGTGCTAAGTGACCCCAAGAAACGG

GGCCTGTATGACCAGTATGGGGAGGAAGGTAAGAGGGCAGCACTCCAGCCCAATCCCGGACCCC

TCCGCTTGGTAGGGGTCCCAGGTGCACCAGTTTGTGTAGCGGGGAACTGGAGGCTGTGGAGGGG

GTGAGGGCAGCAAGGGTTTCCAGCACTGTCACCCAGAGAAGAGAGAAGCCCACCCACTACCCAG

CTCAGCTCACCCTAGTTCTCCCCGCCTCTCTCTGCCCCCTCCCTCCTCGGGTTCAGGCCTTAGA

GAGGTCTGAAGCAAGAGCCAGAGGCCTTCCCCGCCCTTCTTTCCTTCCCAGCCTTATTAGTCCT

GCCTGAAGTCTCCGCTGCTTCATTGGCTGATGAGGAAGGTTGGGGAGAGGGAGTGTGTGGCTCT

CTGAGGACAGAGCATTTACATTCATCAGCATAAAAGTCTGGCCCTTAAGCAGCCTGGGAATTAA

CTACCAGAGCTCTGAGCAGAAATGGTTTTCCCCTTCTCTCCCCCGGCCCTGCCTGCTTCTGGCC

AGCAGAACAGAGGTGGAGCTTTGCCTCCCAGAGGAAGTGGCAGGGATCCAAGGGTGGACGGGGA

ACTGCTGCTGGCATCTTCCCCCTTCCCTGGGGTAGCTGGTGGCCATGGGGTGGGAGGCAGGAAA

GGCCCAAATAAAGCCTCTGAGAGGGAGGCCCCTCCCAGCACATCCCACGGCCATGATGTAGCTG

CTAATTCTGGGCCTGCCCCTCAGGGCTGCCTGCCACCCGCCAGCCACAGGCACCTGTCAGGCTA

TATTAAGAGACATTGTCACGCTGAGGACTCTCCTTCCTGGGAAGAACTGTCCTTCCTCCCCAAC

AGAATCCACCTTTCTTTCACATTCTCCTCCTCTTCACCCTCCCCTTTCTATCCTCAAAACTAAA

TGGGCTAATCATATGTAGATAAGAAGGTTATTTTCTTCCCCTCCTCCTGGCCTTGTGTTCCATG

CCCCTCTGTGAACCCTCATCCTCCCAACTCCCTTTTCCTATTCTCCATGCTGCCGGTTCCTTCC

ATTCTTCCTGCCTACCTCCTAGACGTGCCAACTCCCAGATTCACCAGATACCGGCTGGAACCCC

CAGTATTCTTTCAGCTAAGACATTTTTCTCTCTGGCATGGAGGGATGGGAGGGATAGGAGTGGA

AAAGAGGGAAGCAGTGCAGACACCATGCCACCATGTGACCTGTCTTGGAATTGCACCCATTCCT

CCATTCAGCCTCACCTTTGTTTAGAAAGAAGGCAGGAGCTGGGAGAGCTCCCTTGAGATACTTC

ACCCCTTCTGCCTAAGTGAAGGGGTCCAGACACCAGGTTCTGATGCAGAACCCCATCCCAGGAA

GGCCCCTGAGGATGCGGCATGGCCTTAAGGGGACCTCCATGGCCTGGGGAGGGAGAAGCAGCTT

AGAAATGTTGGTTATATTTCTGTCCACCCTGCCCAATCCCCAGCAGCCATTTATTATAGAGCAG

TTATACACACAGACTCTGTGTGCAGCTCCAGCTAGGGACAAGTTGCTCCCAGCTTGAAAAGGGG

GTGGTAGTGGAAGAATAGAAATCCCTATAGAGAGAATTACCCCTTCCCATCATCATGAGTCGAG

CCTCCCTCCCTCTCTCACTGAGCTCTGCCAGGCTGCTTGAACTCGCTTGATAATCAGCCCCTCG

ATAGAAGGAAAGGAGAGATCCTAGGTCTTGGGGGAGGGGTGAAGAGGCAGCTGCCACAAGTCCC

TGAACCGTCTGCCACTTGGCCTCTCTAGTGAAACTCAAATCTGCCCTTGTGGTCCCAGGAAATA

AGAGGCTAATTTAGGCTCAGATCTCCATGATCAGTTGAAATTCTAGATAAATGGCCTCAAAGAG

AAGGGTCTCTTTCCTAGCCTGGACCCCACCCATAGTCTCTGTATTCCGGAGCAGTTCTCAGTGT

GAACCGTCTCCCCACATCCCCCACTACTGCCAGCACCCCCTCCTGTGCATGAAGGCTGCCTCCA

GGAATCTGAGCCCCTTAGACAGGACCTGACAGAGAGAGCAGCTAAGGTCACCACTGCCATGTGC

CAGCCCATTCATGCATTTTGGTTGCTCAACATTAGGTGTGGGGTATGGCGTTTGCTGTTGTATA

ACTCCAGGGAGCTCCATTCCCATTGTAGTCTATGTCTGTACAATGTGTGAATGACACTCCCTAA

AGTTGTGTAACACCGAGCAGAGTGTGGGAACAAAGCATTTAAAAACTTTTTCTAGAAAAATAGC

TCTTCATCTCCAAGCTAATGAGCTTTCCCACTTTTTAAGGCTTCCTGATTTCCCGTTTGAGCAG

GGGCCAGGGAAAGAGGAAACACTGCTAGAAGCAGAGTGAAAGTGGTCTTCCTCCCGGGTTGGAT

CCCTAGCCTATTTGCGACTGTTCACTTACCAGCCCCCTCTGTGGTCACATCCTGTCTGATGGCC

-continued

CCTTGTCCTATATGTCTTTGGAGATAAGCAAAGATTTGGGAACCAAGTATCACTTGTAATGTGA

CACCAGGCTAGTCATTCAAGGCTTTTTGAGACATCTTTGGACCATGAGTATGTGGAAAAGATTA

CAGGACTGGAAGTCACATCCTCTAAGTCCTCTAGTCCTGGCTTTTCCACCTATTGGGTAAGCAA

GCCTCTTTGAATCTCAAGTTGTGCATCGTTATTAAATATATAATTAGGAATGGAAGATAATCTT

GCCAGAAGCCTTTCTTACTCTATTAGCCTGGCCCTCTCTGTGGGATTTAAAGGTTGCTTCTTTC

TTTAAGCCTGTGAACTGGGAGCTAGAGGGCAGGGGGAAGACACTGGGATTGGGGCCAGAATAAG

CCACACTGCCCCTAACTTCTCCTCCCCTCTAGGCCTGAAGACCGGCGGTGGCACATCAGGTGGC

TCCAGTGGCTCCTTTCACTACACCTTTCATGGGGACCCCCATGCCACCTTTGCCTCCTTCTTTG

GTGGCTCCAACCCCTTCGATATCTTCTTTGCCAGCAGCCGCTCCACTCGGCCCTTCAGTGGCTT

TGACCCAGATGACATGGATGTGGATGAAGATGAGGACCCATTTGGCGCTTTCGGCCGTTTTGGC

TTCAATGGGCTGAGTAGGGGTCCAAGGCGAGCCCCAGAACCACTGTACCCTCGGCGCAAGGTGC

AGGACCCCCCAGTGGTGCACGAGCTGCGGGTGTCCCTGGAGGAGATCTACCATGGCTCCACCAA

GCGCATGAAGATCACAAGGCGTCGCCTCAACCCTGATGGGCGAACTGTGCGCACCGAGGACAAG

ATCCTGCACATAGTCATCAAGCGTGGCTGGAAGGAAGGCACCAAGATCACCTTCCCCAAAGAAG

GCGACGCCACACCTGACAACATCCCTGCTGACATCGTCTTTGTGCTCAAAGACAAGCCCCATGC

ACACTTCCGCCGAGATGGCACCAACGTGCTCTACAGTGCCCTGATCAGCCTCAAGGAGGTGGGG

CCTAGTCAGGCTGTGTGTGTGTGCTGGGGAGATGGTGGGGACATTCCCTCTCTTCCCGCCAGCT

GGCACATTCTTTCCCCACCTCAGTCTATTTCCTTCCTTCCCACTCACCTTACCCCACCTTTTCC

TCACTTTCTGCTTCGTCTTTCCCAGGCGCTGTGTGGCTGCACTGTGAACATTCCCACTATCGAC

GGCCGAGTGATCCCTTTGCCCTGCAATGATGTCATCAAGCCAGGCACCGTGAAGAGACTCCGTG

GGGAGGGCCTTCCCTTCCCCAAAGTGCCAACTCAGCGAGGAGACCTCATTGTTGAGTTCAAAGT

TCGCTTCCCAGACAGATTAACACCACAGACAAGACAGATCCTTAAGCAGCACCTACCCTGTTCC

TAGGCTCTGCCCCAGCCAGTCCAGAGCCTACCACAGCAATACCCCCAACACTCACTCCACTCAA

TGTGCACCCAGCTTGATGTCCACTGGACACTGGCAACTTTTTCTAAAATGCAAAAAAAAGCCAC

TGGTTTTCAGGAAAATGTTCCTGTCCCTGACCCCTTTTAGAGCTGGGCTGCCTGGGGGGAGTGG

GAGGGAGGTGGGGAGAGCTAGCCCAGGCCAGGGGTCAATGTTCATGTCACTAGCTTTCAATCCA

GTTTCCACTGCAGTGGCTGGAGAGTGACCTGAGTGCTACTTGAAGATATGTAGAGATTCCTTAT

CCATGCCTGTACATAGCATGTCCTCCTCCCCTCAGCTTTGCTAATACCAGTCCCCTCCCTTCCC

TTTGGCTTCCTGCTGTTGGGGGTGGAAAAGACTAGAAAGGACATTGCTTTCTCAGCCCCACCCC

CAGGTCCACAGTGTCCAAGGTAATGGCACACATATTCATGCACAAGAAGCACTCACCTAGAGCT

GTCTGTGCCTCTCTGGGAGAAAGGAGAGAGGATAAGAAGGGAAAGTTCACAACCTGTGAACAGG

GACTTGAGCACGAGACACTTTTCATCTGGAGCAGGGGGGTGAGCTCCTCAGCAGCCTCCGTAAC

AGCTGCCCTGCCTACACCTGCAGAGCTGGAGGTTCTGTCCTCCCTGCTGCTCTCAGGAGTGTTC

AAGGGTGGAGGGCAGGGAATGGGGCCTGAGGTATTAAGGCTAAGAGGTGGGGGACAGGGCCCAT

CTACCAGCCTTCATCAGGAAGGGAAAGGGCTTTGGGGTCAGGTGGCAGCTATTCCCCACCAAGA

GATTCAGGGTCACAGGTTTTTCCCCACACCTCTGAACTCAGGGCCTAGCCACCCCCAAACTTCC

AAATCCCACTTTTGTGATATGTGAAGCTACTCATTTCTTACCCTTGGAGGCTGTGTGGGGAATT

TCCAGCCCTTTTATGCCTGTGTGATCCCACCCCACCCCCATAGTTGTATAAAGGTCATAGTGAA

-continued

GAAGCTGGGGGAAGACTGCTTCAGCCAGATCCTGGGGTGGGGTCTTTAGGTTTTCTCACTTTGA

CAACCCCCGAATGTTTTTATAGTAGTTTTTTTGTATTTTTTTGTAATGACAGTATTATGTAAAA

AATAAAGTATTTTAAAAATATGGCA

Exemplary Human DNAJB5 cDNA including untranslated regions
Variant 1

(SEQ ID NO: 163)

AGTGAGAGGCGACAGGAGCTCACTGCCTCTCGGGCCCTCACAATCACACCTGTCACAGGTATAC

ACGCTGCCACTCACAAACACACGCTTGCACTCCCAGCCTCACTGACACGCTGCCATACAGCCGC

TCACAGCCAGCCAGACACTGCTGCACCTGAGAGCAGGTGGCCGCGGGTCTTCTCCCTTCACTCT

CCACATTTGGGGATCAGGTCCGGCACCTGCTGCGCCAGACAGGCCTTGCTGGGCACGCGCCTCT

GAGAGTCCAAGGAGGTGGCTTCCAGAGCTGCAGCACTTCAGGCCGGCTCCGGTGGAGCGATCAG

AGGTGAGGGGCTTGGCTGGGCATGTTTAAGCGCACAGTGCTCTCCTGCCCACCCCCAGCAGCAC

CCCCACTGCAGGCCCGAGGAGCTTTCCGGAGCTTCCCACACTCCTGGGGAGAAGACTTCTTAGC

CAGCTTGATGTTTAAAATTCAGCTGGAGCCCTTAAAACTTCGAGCGTGGACGCTGAATGGGTTT

GTAAAGTTTCGAAACAAGGAGACCAGTGCTGGTCCAGTGGCTGTGATGGGAAAAGATTATTACA

AGATTCTTGGGATCCCATCGGGGGCCAACGAGGATGAGATCAAGAAAGCCTACCGGAAGATGGC

CTTGAAGTACCACCCAGACAAGAATAAAGAACCCAACGCTGAGGAGAAGTTTAAGGAGATTGCA

GAGGCCTATGATGTGCTAAGTGACCCCAAGAAACGGGGCCTGTATGACCAGTATGGGGAGGAAG

GCCTGAAGACCGGCGGTGGCACATCAGGTGGCTCCAGTGGCTCCTTTCACTACACCTTTCATGG

GGACCCCCATGCCACCTTTGCCTCCTTCTTTGGTGGCTCCAACCCCTTCGATATCTTCTTTGCC

AGCAGCCGCTCCACTCGGCCCTTCAGTGGCTTTGACCCAGATGACATGGATGTGGATGAAGATG

AGGACCCATTTGGCGCTTTCGGCCGTTTTGGCTTCAATGGGCTGAGTAGGGGTCCAAGGCGAGC

CCCAGAACCACTGTACCCTCGGCGCAAGGTGCAGGACCCCCCAGTGGTGCACGAGCTGCGGGTG

TCCCTGGAGGAGATCTACCATGGCTCCACCAAGCGCATGAAGATCACAAGGCGTCGCCTCAACC

CTGATGGGCGAACTGTGCGCACCGAGGACAAGATCCTGCACATAGTCATCAAGCGTGGCTGGAA

GGAAGGCACCAAGATCACCTTCCCCAAAGAAGGCGACGCCACACCTGACAACATCCCTGCTGAC

ATCGTCTTTGTGCTCAAAGACAAGCCCCATGCACACTTCCGCCGAGATGGCACCAACGTGCTCT

ACAGTGCCCTGATCAGCCTCAAGGAGGCGCTGTGTGGCTGCACTGTGAACATTCCCACTATCGA

CGGCCGAGTGATCCCTTTGCCCTGCAATGATGTCATCAAGCCAGGCACCGTGAAGAGACTCCGT

GGGGAGGGCCTTCCCTTCCCCAAAGTGCCAACTCAGCGAGGAGACCTCATTGTTGAGTTCAAAG

TTCGCTTCCCAGACAGATTAACACCACAGACAAGACAGATCCTTAAGCAGCACCTACCCTGTTC

CTAGGCTCTGCCCCAGCCAGTCCAGAGCCTACCACAGCAATACCCCCAACACTCACTCCACTCA

ATGTGCACCCAGCTTGATGTCCACTGGACACTGGCAACTTTTTCTAAAATGCAAAAAAAAGCCA

CTGGTTTTCAGGAAAATGTTCCTGTCCCTGACCCCTTTTAGAGCTGGGCTGCCTGGGGGGAGTG

GGAGGGAGGTGGGGAGAGCTAGCCCAGGCCAGGGGTCAATGTTCATGTCACTAGCTTTCAATCC

AGTTTCCACTGCAGTGGCTGGAGAGTGACCTGAGTGCTACTTGAAGATATGTAGAGATTCCTTA

TCCATGCCTGTACATAGCATGTCCTCCTCCCCTCAGCTTTGCTAATACCAGTCCCCTCCCTTCC

CTTTGGCTTCCTGCTGTTGGGGGTGGAAAAGACTAGAAAGGACATTGCTTTCTCAGCCCCACCC

CCAGGTCCACAGTGTCCAAGGTAATGGCACACATATTCATGCACAAGAAGCACTCACCTAGAGC

TGTCTGTGCCTCTCTGGGAGAAAGGAGAGAGGATAAGAAGGGAAAGTTCACAACCTGTGAACAG

GGACTTGAGCACGAGACACTTTTCATCTGGAGCAGGGGGGTGAGCTCCTCAGCAGCCTCCGTAA

CAGCTGCCCTGCCTACACCTGCAGAGCTGGAGGTTCTGTCCTCCCTGCTGCTCTCAGGAGTGTT

-continued

CAAGGGTGGAGGGCAGGGAATGGGGCCTGAGGTATTAAGGCTAAGAGGTGGGGGACAGGGCCCA

TCTACCAGCCTTCATCAGGAAGGGAAAGGGCTTTGGGGTCAGGTGGCAGCTATTCCCCACCAAG

AGATTCAGGGTCACAGGTTTTTCCCCACACCTCTGAACTCAGGGCCTAGCCACCCCCAAACTTC

CAAATCCCACTTTTGTGATATGTGAAGCTACTCATTTCTTACCCTTGGAGGCTGTGTGGGGAAT

TTCCAGCCCTTTTATGCCTGTGTGATCCCACCCCACCCCCATAGTTGTATAAAGGTCATAGTGA

AGAAGCTGGGGGAAGACTGCTTCAGCCAGATCCTGGGGTGGGGTCTTTAGGTTTTCTCACTTTG

ACAACCCCCGAATGTTTTTATAGTAGTTTTTTTGTATTTTTTTGTAATGACAGTATTATGTAAA

AAATAAAGTATTTTAAAAATATGGCATCTGAGCAGGAGCAACAAACCTGGGATGGGGGTGGCTG

AGGAGGGCCACTGTCATCCTCCCTCCCGGGCTCTGGTCACCTTTGAGAAGCCCAAGCAGGCCCT

CAGTATAAGCTGAAGCTGACCTCTGCCTTCCTCGAAGCCTCCTGGGATTTCTAAAACTTATACT

TCAAACACAGCACAGACAGAAAGTACCACTCAGCTATTAGAAGAAACATCTATTTGGGAAGGAA

AAATATCCCTGCTCATGAGAGACAGAGACCATTGTCTTCAGATGTGCTAGCATGAAAACAGATT

TTCTCTTCTTGTCTAAATTTTCTCTGAGTCAGACAAATTTTCCTTCTAGGAGAAAATTTTTTTC

TAGGAGGGGGTGGAGAACTTTTTTTTTTTTTTTTTTTTTTTGACACGGAGTCTTGCTCTGTCGC

CCAGGCTGGAGTGCAGTGATGCGATCTTGGTTCACTGCAGCCTCT

Exemplary Human DNAJB5 cDNA including untranslated regions Variant 4

(SEQ ID NO: 164)

GTCCCGGGTGGAGGCGGCGGAGCCGGAGCCGGGGGAGGGGGCAGCGGCTGTCTCACGGACCACG

GCGGCGCCCGCAGCTCCTCACCGGTCCGGCACCTGCTGCGCCAGACAGGCCTTGCTGGGCACGC

GCCTCTGAGAGTCCAAGGAGGTGGCTTCCAGAGCTGCAGCACTTCAGGCCGGCTCCGGTGGAGC

GATCAGAGGTGAGGGGCTTGGCTGGGCATGTTTAAGCGCACAGTGCTCTCCTGCCCACCCCCAG

CAGCACCCCCACTGCAGGCCCGAGGAGCTTTCCGGAGCTTCCCACACTCCTGGGGAGAAGACTT

CTTAGCCAGCTTGATGTTTAAAATTCAGCTGGAGCCCTTAAAACTTCGAGCGTGGACGCTGAAT

GGGTTTGTAAAGTTTCGAAACAAGGAGACCAGTGCTGGTCCAGTGGCTGTGATGGGAAAAGATT

ATTACAAGATTCTTGGGATCCCATCGGGGGCCAACGAGGATGAGATCAAGAAAGCCTACCGGAA

GATGGCCTTGAAGTACCACCCAGACAAGAATAAAGAACCCAACGCTGAGGAGAAGTTTAAGGAG

ATTGCAGAGGCCTATGATGTGCTAAGTGACCCCAAGAAACGGGGCCTGTATGACCAGTATGGGG

AGGAAGGCCTGAAGACCGGCGGTGGCACATCAGGTGGCTCCAGTGGCTCCTTTCACTACACCTT

TCATGGGGACCCCCATGCCACCTTTGCCTCCTTCTTTGGTGGCTCCAACCCCTTCGATATCTTC

TTTGCCAGCAGCCGCTCCACTCGGCCCTTCAGTGGCTTTGACCCAGATGACATGGATGTGGATG

AAGATGAGGACCCATTTGGCGCTTTCGGCCGTTTTGGCTTCAATGGGCTGAGTAGGGGTCCAAG

GCGAGCCCCAGAACCACTGTACCCTCGGCGCAAGGTGCAGGACCCCCCAGTGGTGCACGAGCTG

CGGGTGTCCCTGGAGGAGATCTACCATGGCTCCACCAAGCGCATGAAGATCACAAGGCGTCGCC

TCAACCCTGATGGGCGAACTGTGCGCACCGAGGACAAGATCCTGCACATAGTCATCAAGCGTGG

CTGGAAGGAAGGCACCAAGATCACCTTCCCCAAAGAAGGCGACGCCACACCTGACAACATCCCT

GCTGACATCGTCTTTGTGCTCAAAGACAAGCCCCATGCACACTTCCGCCGAGATGGCACCAACG

TGCTCTACAGTGCCCTGATCAGCCTCAAGGAGGCGCTGTGTGGCTGCACTGTGAACATTCCCAC

TATCGACGGCCGAGTGATCCCTTTGCCCTGCAATGATGTCATCAAGCCAGGCACCGTGAAGAGA

CTCCGTGGGGAGGGCCTTCCCTTCCCCAAAGTGCCAACTCAGCGAGGAGACCTCATTGTTGAGT

TCAAAGTTCGCTTCCCAGACAGATTAACACCACAGACAAGACAGATCCTTAAGCAGCACCTACC

CTGTTCCTAGGCTCTGCCCCAGCCAGTCCAGAGCCTACCACAGCAATACCCCCAACACTCACTC

-continued

CACTCAATGTGCACCCAGCTTGATGTCCACTGGACACTGGCAACTTTTTCTAAAATGCAAAAAA

AAGCCACTGGTTTTCAGGAAAATGTTCCTGTCCCTGACCCCTTTTAGAGCTGGGCTGCCTGGGG

GGAGTGGGAGGGAGGTGGGGAGAGCTAGCCCAGGCCAGGGGTCAATGTTCATGTCACTAGCTTT

CAATCCAGTTTCCACTGCAGTGGCTGGAGAGTGACCTGAGTGCTACTTGAAGATATGTAGAGAT

TCCTTATCCATGCCTGTACATAGCATGTCCTCCTCCCCTCAGCTTTGCTAATACCAGTCCCCTC

CCTTCCCTTTGGCTTCCTGCTGTTGGGGGTGGAAAAGACTAGAAAGGACATTGCTTTCTCAGCC

CCACCCCCAGGTCCACAGTGTCCAAGGTAATGGCACACATATTCATGCACAAGAAGCACTCACC

TAGAGCTGTCTGTGCCTCTCTGGGAGAAAGGAGAGAGGATAAGAAGGGAAAGTTCACAACCTGT

GAACAGGGACTTGAGCACGAGACACTTTTCATCTGGAGCAGGGGGGTGAGCTCCTCAGCAGCCT

CCGTAACAGCTGCCCTGCCTACACCTGCAGAGCTGGAGGTTCTGTCCTCCCTGCTGCTCTCAGG

AGTGTTCAAGGGTGGAGGGCAGGGAATGGGGCCTGAGGTATTAAGGCTAAGAGGTGGGGGACAG

GGCCCATCTACCAGCCTTCATCAGGAAGGGAAAGGGCTTTGGGGTCAGGTGGCAGCTATTCCCC

ACCAAGAGATTCAGGGTCACAGGTTTTTCCCCACACCTCTGAACTCAGGGCCTAGCCACCCCCA

AACTTCCAAATCCCACTTTTGTGATATGTGAAGCTACTCATTTCTTACCCTTGGAGGCTGTGTG

GGGAATTTCCAGCCCTTTTATGCCTGTGTGATCCCACCCCACCCCCATAGTTGTATAAAGGTCA

TAGTGAAGAAGCTGGGGGAAGACTGCTTCAGCCAGATCCTGGGGTGGGGTCTTTAGGTTTTCTC

ACTTTGACAACCCCCGAATGTTTTTATAGTAGTTTTTTTGTATTTTTTTGTAATGACAGTATTA

TGTAAAAAATAAAGTATTTTAAAAATATGGCATCTGAGCAGGAGCAACAAACCTGGGATGGGGG

TGGCTGAGGAGGGCCACTGTCATCCTCCCTCCCGGGCTCTGGTCACCTTTGAGAAGCCCAAGCA

GGCCCTCAGTATAAGCTGAAGCTGACCTCTGCCTTCCTCGAAGCCTCCTGGGATTTCTAAAACT

TATACTTCAAACACAGCACAGACAGAAAGTACCACTCAGCTATTAGAAGAAACATCTATTTGGG

AAGGAAAAATATCCCTGCTCATGAGAGACAGAGACCATTGTCTTCAGATGTGCTAGCATGAAAA

CAGATTTTCTCTTCTTGTCTAAATTTTCTCTGAGTCAGACAAATTTTCCTTCTAGGAGAAAATT

TTTTTCTAGGAGGGGGTGGAGAACTTTTTTTTTTTTTTTTTTTTTTTGACACGGAGTCTTGCTC

TGTCGCCCAGGCTGGAGTGCAGTGATGCGATCTTGGTTCACTGCAGCCTCT

Exemplary Human DNAJB5 cDNA coding sequence Variant 1 and Variant 4

(SEQ ID NO: 165)

ATGTTTAAGCGCACAGTGCTCTCCTGCCCACCCCCAGCAGCACCCCCACTGCAGGCCCGAGGAG

CTTTCCGGAGCTTCCCACACTCCTGGGGAGAAGACTTCTTAGCCAGCTTGATGTTTAAAATTCA

GCTGGAGCCCTTAAAACTTCGAGCGTGGACGCTGAATGGGTTTGTAAAGTTTCGAAACAAGGAG

ACCAGTGCTGGTCCAGTGGCTGTGATGGGAAAAGATTATTACAAGATTCTTGGGATCCCATCGG

GGGCCAACGAGGATGAGATCAAGAAAGCCTACCGGAAGATGGCCTTGAAGTACCACCCAGACAA

GAATAAAGAACCCAACGCTGAGGAGAAGTTTAAGGAGATTGCAGAGGCCTATGATGTGCTAAGT

GACCCCAAGAAACGGGGCCTGTATGACCAGTATGGGGAGGAAGGCCTGAAGACCGGCGGTGGCA

CATCAGGTGGCTCCAGTGGCTCCTTTCACTACACCTTTCATGGGGACCCCCATGCCACCTTTGC

CTCCTTCTTTGGTGGCTCCAACCCCTTCGATATCTTCTTTGCCAGCAGCCGCTCCACTCGGCCC

TTCAGTGGCTTTGACCCAGATGACATGGATGTGGATGAAGATGAGGACCCATTTGGCGCTTTCG

GCCGTTTTGGCTTCAATGGGCTGAGTAGGGGGTCCAAGGCGAGCCCCAGAACCACTGTACCCTCG

GCGCAAGGTGCAGGACCCCCCAGTGGTGCACGAGCTGCGGGTGTCCCTGGAGGAGATCTACCAT

GGCTCCACCAAGCGCATGAAGATCACAAGGCGTCGCCTCAACCCTGATGGGCGAACTGTGCGCA

CCGAGGACAAGATCCTGCACATAGTCATCAAGCGTGGCTGGAAGGAAGGCACCAAGATCACCTT

-continued

CCCCAAAGAAGGCGACGCCACACCTGACAACATCCCTGCTGACATCGTCTTTGTGCTCAAAGAC

AAGCCCCATGCACACTTCCGCCGAGATGGCACCAACGTGCTCTACAGTGCCCTGATCAGCCTCA

AGGAGGCGCTGTGTGGCTGCACTGTGAACATTCCCACTATCGACGGCCGAGTGATCCCTTTGCC

CTGCAATGATGTCATCAAGCCAGGCACCGTGAAGAGACTCCGTGGGGAGGGCCTTCCCTTCCCC

AAAGTGCCAACTGAGCGAGGAGACCTCATTGTTGAGTTCAAAGTTCGCTTCCCAGACAGATTAA

CACCACAGACAAGACAGATCCTTAAGCAGCACCTACCCTGTTCCTAG

Exemplary Human DNAJB5 cDNA including untranslated regions
Variant 2

(SEQ ID NO: 166)

GTCCCGGGTGGAGGCGGCGGAGCCGGAGCCGGGGGAGGGGGCAGCGGCTGTCTCACGGACCACG

GCGGCGCCCGCAGCTCCTCACCGCAGCACCCCCACTGCAGGCCCGAGGAGCTTTCCGGAGCTTC

CCACACTCCTGGGGAGAAGACTTCTTAGCCAGCTTGATGTTTAAAATTCAGCTGGAGCCCTTAA

AACTTCGAGCGTGGACGCTGAATGGGTTTGTAAAGTTTCGAAACAAGGAGACCAGTGCTGGTCC

AGTGGCTGTGATGGGAAAAGATTATTACAAGATTCTTGGGATCCCATCGGGGGCCAACGAGGAT

GAGATCAAGAAAGCCTACCGGAAGATGGCCTTGAAGTACCACCCAGACAAGAATAAAGAACCCA

ACGCTGAGGAGAAGTTTAAGGAGATTGCAGAGGCCTATGATGTGCTAAGTGACCCCAAGAAACG

GGGCCTGTATGACCAGTATGGGGAGGAAGGCCTGAAGACCGGCGGTGGCACATCAGGTGGCTCC

AGTGGCTCCTTTCACTACACCTTTCATGGGGACCCCCATGCCACCTTTGCCTCCTTCTTTGGTG

GCTCCAACCCCTTCGATATCTTCTTTGCCAGCAGCCGCTCCACTCGGCCCTTCAGTGGCTTTGA

CCCAGATGACATGGATGTGGATGAAGATGAGGACCCATTTGGCGCTTTCGGCCGTTTTGGCTTC

AATGGGCTGAGTAGGGGTCCAAGGCGAGCCCCAGAACCACTGTACCCTCGGCGCAAGGTGCAGG

ACCCCCCAGTGGTGCACGAGCTGCGGGTGTCCCTGGAGGAGATCTACCATGGCTCCACCAAGCG

CATGAAGATCACAAGGCGTCGCCTCAACCCTGATGGGCGAACTGTGCGCACCGAGGACAAGATC

CTGCACATAGTCATCAAGCGTGGCTGGAAGGAAGGCACCAAGATCACCTTCCCCAAAGAAGGCG

ACGCCACACCTGACAACATCCCTGCTGACATCGTCTTTGTGCTCAAAGACAAGCCCCATGCACA

CTTCCGCCGAGATGGCACCAACGTGCTCTACAGTGCCCTGATCAGCCTCAAGGAGGCGCTGTGT

GGCTGCACTGTGAACATTCCCACTATCGACGGCCGAGTGATCCCTTTGCCCTGCAATGATGTCA

TCAAGCCAGGCACCGTGAAGAGACTCCGTGGGGAGGGCCTTCCCTTCCCCAAAGTGCCAACTCA

GCGAGGAGACCTCATTGTTGAGTTCAAAGTTCGCTTCCCAGACAGATTAACACCACAGACAAGA

CAGATCCTTAAGCAGCACCTACCCTGTTCCTAGGCTCTGCCCCAGCCAGTCCAGAGCCTACCAC

AGCAATACCCCCAACACTCACTCCACTCAATGTGCACCCAGCTTGATGTCCACTGGACACTGGC

AACTTTTTCTAAAATGCAAAAAAAAGCCACTGGTTTTCAGGAAAATGTTCCTGTCCCTGACCCC

TTTTAGAGCTGGGCTGCCTGGGGGGAGTGGGAGGGAGGTGGGGAGAGCTAGCCCAGGCCAGGGG

TCAATGTTCATGTCACTAGCTTTCAATCCAGTTTCCACTGCAGTGGCTGGAGAGTGACCTGAGT

GCTACTTGAAGATATGTAGAGATTCCTTATCCATGCCTGTACATAGCATGTCCTCCTCCCCTCA

GCTTTGCTAATACCAGTCCCCTCCCTTCCCTTTGGCTTCCTGCTGTTGGGGGTGGAAAAGACTA

GAAAGGACATTGCTTTCTCAGCCCCACCCCCAGGTCCACAGTGTCCAAGGTAATGGCACACATA

TTCATGCACAAGAAGCACTCACCTAGAGCTGTCTGTGCCTCTCTGGGAGAAAGGAGAGAGGATA

AGAAGGGAAAGTTCACAACCTGTGAACAGGGACTTGAGCACGAGACACTTTTCATCTGGAGCAG

GGGGGTGAGCTCCTCAGCAGCCTCCGTAACAGCTGCCCTGCCTACACCTGCAGAGCTGGAGGTT

CTGTCCTCCCTGCTGCTCTCAGGAGTGTTCAAGGGTGGAGGGCAGGGAATGGGGCCTGAGGTAT

TAAGGCTAAGAGGTGGGGGACAGGGCCCATCTACCAGCCTTCATCAGGAAGGGAAAGGGCTTTG

-continued

GGGTCAGGTGGCAGCTATTCCCCACCAAGAGATTCAGGGTCACAGGTTTTTCCCCACACCTCTG

AACTCAGGGCCTAGCCACCCCCAAACTTCCAAATCCCACTTTTGTGATATGTGAAGCTACTCAT

TTCTTACCCTTGGAGGCTGTGTGGGGAATTTCCAGCCCTTTTATGCCTGTGTGATCCCACCCCA

CCCCCATAGTTGTATAAAGGTCATAGTGAAGAAGCTGGGGGAAGACTGCTTCAGCCAGATCCTG

GGGTGGGGTCTTTAGGTTTTCTCACTTTGACAACCCCCGAATGTTTTTATAGTAGTTTTTTTGT

ATTTTTTTGTAATGAGAGTATTATGTAAAAAATAAAGTATTTTAAAAATA

Exemplary Human DNAJB5 cDNA including untranslated regions Variant 6

(SEQ ID NO: 167)

GTCCCGGGTGGAGGCGGCGGAGCCGGAGCCGGGGGAGGGGGCAGCGGCTGTCTCACGGACCACG

GCGGCGCCCGCAGCTCCTCACCGCACCCCCACTGCAGGCCCGAGGAGCTTTCCGGAGCTTCCCA

CACTCCTGGGGAGAAGACTTCTTAGCCAGCTTGATGTTTAAAATTCAGCTGGAGCCCTTAAAAC

TTCGAGCGTGGACGCTGAATGGGTTTGTAAAGTTTCGAAACAAGGAGACCAGTGCTGGTCCAGT

GGCTGTGATGGGAAAAGATTATTACAAGATTCTTGGGATCCCATCGGGGGCCAACGAGGATGAG

ATCAAGAAAGCCTACCGGAAGATGGCCTTGAAGTACCACCCAGACAAGAATAAAGAACCCAACG

CTGAGGAGAAGTTTAAGGAGATTGCAGAGGCCTATGATGTGCTAAGTGACCCCAAGAAACGGGG

CCTGTATGACCAGTATGGGGAGGAAGGCCTGAAGACCGGCGGTGGCACATCAGGTGGCTCCAGT

GGCTCCTTTCACTACACCTTTCATGGGGACCCCCATGCCACCTTTGCCTCCTTCTTTGGTGGCT

CCAACCCCTTCGATATCTTCTTTGCCAGCAGCCGCTCCACTCGGCCCTTCAGTGGCTTTGACCC

AGATGACATGGATGTGGATGAAGATGAGGACCCATTTGGCGCTTTCGGCCGTTTTGGCTTCAAT

GGGCTGAGTAGGGGTCCAAGGCGAGCCCCAGAACCACTGTACCCTCGGCGCAAGGTGCAGGACC

CCCCAGTGGTGCACGAGCTGCGGGTGTCCCTGGAGGAGATCTACCATGGCTCCACCAAGCGCAT

GAAGATCACAAGGCGTCGCCTCAACCCTGATGGGCGAACTGTGCGCACCGAGGACAAGATCCTG

CACATAGTCATCAAGCGTGGCTGGAAGGAAGGCACCAAGATCACCTTCCCCAAAGAAGGCGACG

CCACACCTGACAACATCCCTGCTGACATCGTCTTTGTGCTCAAAGACAAGCCCCATGCACACTT

CCGCCGAGATGGCACCAACGTGCTCTACAGTGCCCTGATCAGCCTCAAGGAGGCGCTGTGTGGC

TGCACTGTGAACATTCCCACTATCGACGGCCGAGTGATCCCTTTGCCCTGCAATGATGTCATCA

AGCCAGGCACCGTGAAGAGACTCCGTGGGGAGGGCCTTCCCTTCCCCAAAGTGCCAACTCAGCG

AGGAGACCTCATTGTTGAGTTCAAAGTTCGCTTCCCAGACAGATTAACACCACAGACAAGACAG

ATCCTTAAGCAGCACCTACCCTGTTCCTAGGCTCTGCCCCAGCCAGTCCAGAGCCTACCACAGC

AATACCCCCAACACTCACTCCACTCAATGTGCACCCAGCTTGATGTCCACTGGACACTGGCAAC

TTTTTCTAAAATGCAAAAAAAAGCCACTGGTTTTCAGGAAAATGTTCCTGTCCCTGACCCCTTT

TAGAGCTGGGCTGCCTGGGGGGAGTGGGAGGGAGGTGGGGAGAGCTAGCCCAGGCCAGGGGTCA

ATGTTCATGTCACTAGCTTTCAATCCAGTTTCCACTGCAGTGGCTGGAGAGTGACCTGAGTGCT

ACTTGAAGATATGTAGAGATTCCTTATCCATGCCTGTACATAGCATGTCCTCCTCCCCTCAGCT

TTGCTAATACCAGTCCCCTCCCTTCCCTTTGGCTTCCTGCTGTTGGGGGTGGAAAAGACTAGAA

AGGACATTGCTTTCTCAGCCCCACCCCCAGGTCCACAGTGTCCAAGGTAATGGCACACATATTC

ATGCACAAGAAGCACTCACCTAGAGCTGTCTGTGCCTCTCTGGGAGAAAGGAGAGAGGATAAGA

AGGGAAAGTTCACAACCTGTGAACAGGGACTTGAGCACGAGACACTTTTCATCTGGAGCAGGGG

GGTGAGCTCCTCAGCAGCCTCCGTAACAGCTGCCCTGCCTACACCTGCAGAGCTGGAGGTTCTG

TCCTCCCTGCTGCTCTCAGGAGTGTTCAAGGGTGGAGGGCAGGGAATGGGGCCTGAGGTATTAA

GGCTAAGAGGTGGGGGACAGGGCCCATCTACCAGCCTTCATCAGGAAGGGAAAGGGCTTTGGGG

-continued

TCAGGTGGCAGCTATTCCCCACCAAGAGATTCAGGGTCACAGGTTTTTCCCCACACCTCTGAAC

TCAGGGCCTAGCCACCCCCAAACTTCCAAATCCCACTTTTGTGATATGTGAAGCTACTCATTTC

TTACCCTTGGAGGCTGTGTGGGGAATTTCCAGCCCTTTTATGCCTGTGTGATCCCACCCCACCC

CCATAGTTGTATAAAGGTCATAGTGAAGAAGCTGGGGGAAGACTGCTTCAGCCAGATCCTGGGG

TGGGGTCTTTAGGTTTTCTCACTTTGACAACCCCCGAATGTTTTTATAGTAGTTTTTTTGTATT

TTTTTGTAATGAGAGTATTATGTAAAAAATAAAGTATTTTAAAAATA

Exemplary Human DNAJB5 cDNA coding sequence Variant 2 and Variant 6

(SEQ ID NO: 168)

ATGTTTAAAATTCAGCTGGAGCCCTTAAAACTTCGAGCGTGGACGCTGAATGGGTTTGTAAAGT

TTCGAAACAAGGAGACCAGTGCTGGTCCAGTGGCTGTGATGGGAAAAGATTATTACAAGATTCT

TGGGATCCCATCGGGGGCCAACGAGGATGAGATCAAGAAAGCCTACCGGAAGATGGCCTTGAAG

TACCACCCAGACAAGAATAAAGAACCCAACGCTGAGGAGAAGTTTAAGGAGATTGCAGAGGCCT

ATGATGTGCTAAGTGACCCCAAGAAACGGGGCCTGTATGACCAGTATGGGGAGGAAGGCCTGAA

GACCGGCGGTGGCACATCAGGTGGCTCCAGTGGCTCCTTTCACTACACCTTTCATGGGGACCCC

CATGCCACCTTTGCCTCCTTCTTTGGTGGCTCCAACCCCTTCGATATCTTCTTTGCCAGCAGCC

GCTCCACTCGGCCCTTCAGTGGCTTTGACCCAGATGACATGGATGTGGATGAAGATGAGGACCC

ATTTGGCGCTTTCGGCCGTTTTGGCTTCAATGGGCTGAGTAGGGGTCCAAGGCGAGCCCCAGAA

CCACTGTACCCTCGGCGCAAGGTGCAGGACCCCCCAGTGGTGCACGAGCTGCGGGTGTCCCTGG

AGGAGATCTACCATGGCTCCACCAAGCGCATGAAGATCACAAGGCGTCGCCTCAACCCTGATGG

GCGAACTGTGCGCACCGAGGACAAGATCCTGCACATAGTCATCAAGCGTGGCTGGAAGGAAGGC

ACCAAGATCACCTTCCCCAAAGAAGGCGACGCCACACCTGACAACATCCCTGCTGACATCGTCT

TTGTGCTCAAAGACAAGCCCCATGCACACTTCCGCCGAGATGGCACCAACGTGCTCTACAGTGC

CCTGATCAGCCTCAAGGAGGCGCTGTGTGGCTGCACTGTGAACATTCCCACTATCGACGGCCGA

GTGATCCCTTTGCCCTGCAATGATGTCATCAAGCCAGGCACCGTGAAGAGACTCCGTGGGGAGG

GCCTTCCCTTCCCCAAAGTGCCAACTCAGCGAGGAGACCTCATTGTTGAGTTCAAAGTTCGCTT

CCCAGACAGATTAACACCACAGACAAGACAGATCCTTAAGCAGCACCTACCCTGTTCCTAG

Exemplary Human DNAJB5 cDNA including untranslated regions Variant 3

(SEQ ID NO: 169)

GTCCCGGGTGGAGGCGGCGGAGCCGGAGCCGGGGGAGGGGGCAGCGGCTGTCTCACGGACCACG

GCGGCGCCCGCAGCTCCTCACCGAAACAAGGAGACCAGTGCTGGTCCAGTGGCTGTGATGGGAA

AAGATTATTACAAGATTCTTGGGATCCCATCGGGGGCCAACGAGGATGAGATCAAGAAAGCCTA

CCGGAAGATGGCCTTGAAGTACCACCCAGACAAGAATAAAGAACCCAACGCTGAGGAGAAGTTT

AAGGAGATTGCAGAGGCCTATGATGTGCTAAGTGACCCCAAGAAACGGGGCCTGTATGACCAGT

ATGGGGAGGAAGGCCTGAAGACCGGCGGTGGCACATCAGGTGGCTCCAGTGGCTCCTTTCACTA

CACCTTTCATGGGGACCCCCATGCCACCTTTGCCTCCTTCTTTGGTGGCTCCAACCCCTTCGAT

ATCTTCTTTGCCAGCAGCCGCTCCACTCGGCCCTTCAGTGGCTTTGACCCAGATGACATGGATG

TGGATGAAGATGAGGACCCATTTGGCGCTTTCGGCCGTTTTGGCTTCAATGGGCTGAGTAGGGG

TCCAAGGCGAGCCCCAGAACCACTGTACCCTCGGCGCAAGGTGCAGGACCCCCCAGTGGTGCAC

GAGCTGCGGGTGTCCCTGGAGGAGATCTACCATGGCTCCACCAAGCGCATGAAGATCACAAGGC

GTCGCCTCAACCCTGATGGGCGAACTGTGCGCACCGAGGACAAGATCCTGCACATAGTCATCAA

GCGTGGCTGGAAGGAAGGCACCAAGATCACCTTCCCCAAAGAAGGCGACGCCACACCTGACAAC

ATCCCTGCTGACATCGTCTTTGTGCTCAAAGACAAGCCCCATGCACACTTCCGCCGAGATGGCA

CCAACGTGCTCTACAGTGCCCTGATCAGCCTCAAGGAGGCGCTGTGTGGCTGCACTGTGAACAT

TCCCACTATCGACGGCCGAGTGATCCCTTTGCCCTGCAATGATGTCATCAAGCCAGGCACCGTG

AAGAGACTCCGTGGGGAGGGCCTTCCCTTCCCCAAAGTGCCAACTCAGCGAGGAGACCTCATTG

TTGAGTTCAAAGTTCGCTTCCCAGACAGATTAACACCACAGACAAGACAGATCCTTAAGCAGCA

CCTACCCTGTTCCTAGGCTCTGCCCCAGCCAGTCCAGAGCCTACCACAGCAATACCCCCAACAC

TCACTCCACTCAATGTGCACCCAGCTTGATGTCCACTGGACACTGGCAACTTTTTCTAAAATGC

AAAAAAAAGCCACTGGTTTTCAGGAAAATGTTCCTGTCCCTGACCCCTTTTAGAGCTGGGCTGC

CTGGGGGGAGTGGGAGGGAGGTGGGGAGAGCTAGCCCAGGCCAGGGGTCAATGTTCATGTCACT

AGCTTTCAATCCAGTTTCCACTGCAGTGGCTGGAGAGTGACCTGAGTGCTACTTGAAGATATGT

AGAGATTCCTTATCCATGCCTGTACATAGCATGTCCTCCTCCCCTCAGCTTTGCTAATACCAGT

CCCCTCCCTTCCCTTTGGCTTCCTGCTGTTGGGGGTGGAAAAGACTAGAAAGGACATTGCTTTC

TCAGCCCCACCCCCAGGTCCACAGTGTCCAAGGTAATGGCACACATATTCATGCACAAGAAGCA

CTCACCTAGAGCTGTCTGTGCCTCTCTGGGAGAAAGGAGAGAGGATAAGAAGGGAAAGTTCACA

ACCTGTGAACAGGGACTTGAGCACGAGACACTTTTCATCTGGAGCAGGGGGGTGAGCTCCTCAG

CAGCCTCCGTAACAGCTGCCCTGCCTACACCTGCAGAGCTGGAGGTTCTGTCCTCCCTGCTGCT

CTCAGGAGTGTTCAAGGGTGGAGGGCAGGGAATGGGGCCTGAGGTATTAAGGCTAAGAGGTGGG

GGACAGGGCCCATCTACCAGCCTTCATCAGGAAGGGAAAGGGCTTTGGGGTCAGGTGGCAGCTA

TTCCCCACCAAGAGATTCAGGGTCACAGGTTTTTCCCCACACCTCTGAACTCAGGGCCTAGCCA

CCCCCAAACTTCCAAATCCCACTTTTGTGATATGTGAAGCTACTCATTTCTTACCCTTGGAGGC

TGTGTGGGGAATTTCCAGCCCTTTTATGCCTGTGTGATCCCACCCCACCCCCATAGTTGTATAA

AGGTCATAGTGAAGAAGCTGGGGGAAGACTGCTTCAGCCAGATCCTGGGGTGGGGTCTTTAGGT

TTTCTCACTTTGACAACCCCCGAATGTTTTTATAGTAGTTTTTTTGTATTTTTTTGTAATGACA

GTATTATGTAAAAAATAAAGTATTTTAAAAATATGGCATCTGAGCAGGAGCAACAAACCTGGGA

TGGGGGTGGCTGAGGAGGGCCACTGTCATCCTCCCTCCCGGGCTCTGGTCACCTTTGAGAAGCC

CAAGCAGGCCCTCAGTATAAGCTGAAGCTGACCTCTGCCTTCCTCGAAGCCTCCTGGGATTTCT

AAAACTTATACTTCAAACACAGCACAGACAGAAAGTACCACTCAGCTATTAGAAGAAACATCTA

TTTGGGAAGGAAAAATATCCCTGCTCATGAGAGACAGAGACCATTGTCTTCAGATGTGCTAGCA

TGAAAACAGATTTTCTCTTCTTGTCTAAATTTTCTCTGAGTCAGACAAATTTTCCTTCTAGGAG

AAAATTTTTTTCTAGGAGGGGGTGGAGAACTTTTTTTTTTTTTTTTTTTTTTTGACACGGAGTC

TTGCTCTGTCGCCCAGGCTGGAGTGCAGTGATGCGATCTTGGTTCACTGCAGCCTCT

Exemplary Human DNAJB5 cDNA including untranslated regions
Variant 5

(SEQ ID NO: 170)

GTCCCGGGTGGAGGCGGCGGAGCCGGAGCCGGGGGAGGGGGCAGCGGCTGTCTCACGGACCACG

GCGGCGCCCGCAGCTCCTCACCGGTCCGGCACCTGCTGCGCCAGACAGGCCTTGCTGGGCACGC

GCCTCTGAGAGTCCAAGGAGGTGGCTTCCAGAGCTGCAGCACTTCAGGCCGGCTCCGGTGGAGC

GATCAGAGAAACAAGGAGACCAGTGCTGGTCCAGTGGCTGTGATGGGAAAAGATTATTACAAGA

TTCTTGGGATCCCATCGGGGGCCAACGAGGATGAGATCAAGAAAGCCTACCGGAAGATGGCCTT

GAAGTACCACCCAGACAAGAATAAAGAACCCAACGCTGAGGAGAAGTTTAAGGAGATTGCAGAG

GCCTATGATGTGCTAAGTGACCCCAAGAAACGGGGCCTGTATGACCAGTATGGGGAGGAAGGCC

TGAAGACCGGCGGTGGCACATCAGGTGGCTCCAGTGGCTCCTTTCACTACACCTTTCATGGGGA

CCCCCATGCCACCTTTGCCTCCTTCTTTGGTGGCTCCAACCCCTTCGATATCTTCTTTGCCAGC

-continued

AGCCGCTCCACTCGGCCCTTCAGTGGCTTTGACCCAGATGACATGGATGTGGATGAAGATGAGG

ACCCATTTGGCGCTTTCGGCCGTTTTGGCTTCAATGGGCTGAGTAGGGGTCCAAGGCGAGCCCC

AGAACCACTGTACCCTCGGCGCAAGGTGCAGGACCCCCCAGTGGTGCACGAGCTGCGGGTGTCC

CTGGAGGAGATCTACCATGGCTCCACCAAGCGCATGAAGATCACAAGGCGTCGCCTCAACCCTG

ATGGGCGAACTGTGCGCACCGAGGACAAGATCCTGCACATAGTCATCAAGCGTGGCTGGAAGGA

AGGCACCAAGATCACCTTCCCCAAAGAAGGCGACGCCACACCTGACAACATCCCTGCTGACATC

GTCTTTGTGCTCAAAGACAAGCCCCATGCACACTTCCGCCGAGATGGCACCAACGTGCTCTACA

GTGCCCTGATCAGCCTCAAGGAGGCGCTGTGTGGCTGCACTGTGAACATTCCCACTATCGACGG

CCGAGTGATCCCTTTGCCCTGCAATGATGTCATCAAGCCAGGCACCGTGAAGAGACTCCGTGGG

GAGGGCCTTCCCTTCCCCAAAGTGCCAACTCAGCGAGGAGACCTCATTGTTGAGTTCAAAGTTC

GCTTCCCAGACAGATTAACACCACAGACAAGACAGATCCTTAAGCAGCACCTACCCTGTTCCTA

GGCTCTGCCCCAGCCAGTCCAGAGCCTACCACAGCAATACCCCCAACACTCACTCCACTCAATG

TGCACCCAGCTTGATGTCCACTGGACACTGGCAACTTTTTCTAAAATGCAAAAAAAAGCCACTG

GTTTTCAGGAAAATGTTCCTGTCCCTGACCCCTTTTAGAGCTGGGCTGCCTGGGGGGAGTGGGA

GGGAGGTGGGGAGAGCTAGCCCAGGCCAGGGGTCAATGTTCATGTCACTAGCTTTCAATCCAGT

TTCCACTGCAGTGGCTGGAGAGTGACCTGAGTGCTACTTGAAGATATGTAGAGATTCCTTATCC

ATGCCTGTACATAGCATGTCCTCCTCCCCTCAGCTTTGCTAATACCAGTCCCCTCCCTTCCCTT

TGGCTTCCTGCTGTTGGGGGTGGAAAAGACTAGAAAGGACATTGCTTTCTCAGCCCCACCCCCA

GGTCCACAGTGTCCAAGGTAATGGCACACATATTCATGCACAAGAAGCACTCACCTAGAGCTGT

CTGTGCCTCTCTGGGAGAAAGGAGAGAGGATAAGAAGGGAAAGTTCACAACCTGTGAACAGGGA

CTTGAGCACGAGACACTTTTCATCTGGAGCAGGGGGGTGAGCTCCTCAGCAGCCTCCGTAACAG

CTGCCCTGCCTACACCTGCAGAGCTGGAGGTTCTGTCCTCCCTGCTGCTCTCAGGAGTGTTCAA

GGGTGGAGGGCAGGGAATGGGGCCTGAGGTATTAAGGCTAAGAGGTGGGGGACAGGGCCCATCT

ACCAGCCTTCATCAGGAAGGGAAAGGGCTTTGGGGTCAGGTGGCAGCTATTCCCCACCAAGAGA

TTCAGGGTCACAGGTTTTTCCCCACACCTCTGAACTCAGGGCCTAGCCACCCCCAAACTTCCAA

ATCCCACTTTTGTGATATGTGAAGCTACTCATTTCTTACCCTTGGAGGCTGTGTGGGGAATTTC

CAGCCCTTTTATGCCTGTGTGATCCCACCCCACCCCCATAGTTGTATAAAGGTCATAGTGAAGA

AGCTGGGGGAAGACTGCTTCAGCCAGATCCTGGGGTGGGGTCTTTAGGTTTTCTCACTTTGACA

ACCCCCGAATGTTTTTATAGTAGTTTTTTTGTATTTTTTTGTAATGACAGTATTATGTAAAAAA

TAAAGTATTTTAAAAATATGGCATCTGAGCAGGAGCAACAAACCTGGGATGGGGGTGGCTGAGG

AGGGCCACTGTCATCCTCCCTCCCGGGCTCTGGTCACCTTTGAGAAGCCCAAGCAGGCCCTCAG

TATAAGCTGAAGCTGACCTCTGCCTTCCTCGAAGCCTCCTGGGATTTCTAAAACTTATACTTCA

AACACAGCACAGACAGAAAGTACCACTCAGCTATTAGAAGAAACATCTATTTGGGAAGGAAAAA

TATCCCTGCTCATGAGAGACAGAGACCATTGTCTTCAGATGTGCTAGCATGAAAACAGATTTTC

TCTTCTTGTCTAAATTTTCTCTGAGTCAGACAAATTTTCCTTCTAGGAGAAAATTTTTTTCTAG

GAGGGGGTGGAGAACTTTTTTTTTTTTTTTTTTTTTTGACACGGAGTCTTGCTCTGTCGCCCA

GGCTGGAGTGCAGTGATGCGATCTTGGTTCACTGCAGCCTCT

-continued

Exemplary Human DNAJB5 cDNA coding sequence Variant 3 and Variant 5

(SEQ ID NO: 171)

ATGGGAAAAGATTATTACAAGATTCTTGGGATCCCATCGGGGGCCAACGAGGATGAGATCAAGA

AAGCCTACCGGAAGATGGCCTTGAAGTACCACCCAGACAAGAATAAAGAACCCAACGCTGAGGA

GAAGTTTAAGGAGATTGCAGAGGCCTATGATGTGCTAAGTGACCCCAAGAAACGGGGCCTGTAT

GACCAGTATGGGGAGGAAGGCCTGAAGACCGGCGGTGGCACATCAGGTGGCTCCAGTGGCTCCT

TTCACTACACCTTTCATGGGGACCCCCATGCCACCTTTGCCTCCTTCTTTGGTGGCTCCAACCC

CTTCGATATCTTCTTTGCCAGCAGCCGCTCCACTCGGCCCTTCAGTGGCTTTGACCCAGATGAC

ATGGATGTGGATGAAGATGAGGACCCATTTGGCGCTTTCGGCCGTTTTGGCTTCAATGGGCTGA

GTAGGGGTCCAAGGCGAGCCCCAGAACCACTGTACCCTCGGCGCAAGGTGCAGGACCCCCCAGT

GGTGCACGAGCTGCGGGTGTCCCTGGAGGAGATCTACCATGGCTCCACCAAGCGCATGAAGATC

ACAAGGCGTCGCCTCAACCCTGATGGGCGAACTGTGCGCACCGAGGACAAGATCCTGCACATAG

TCATCAAGCGTGGCTGGAAGGAAGGCACCAAGATCACCTTCCCCAAAGAAGGCGACGCCACACC

TGACAACATCCCTGCTGACATCGTCTTTGTGCTCAAAGACAAGCCCCATGCACACTTCCGCCGA

GATGGCACCAACGTGCTCTACAGTGCCCTGATCAGCCTCAAGGAGGCGCTGTGTGGCTGCACTG

TGAACATTCCCACTATCGACGGCCGAGTGATCCCTTTGCCCTGCAATGATGTCATCAAGCCAGG

CACCGTGAAGAGACTCCGTGGGGAGGGCCTTCCCTTCCCCAAAGTGCCAACTCAGCGAGGAGAC

CTCATTGTTGAGTTCAAAGTTCGCTTCCCAGACAGATTAACACCACAGACAAGACAGATCCTTA

AGCAGCACCTACCCTGTTCCTAG

Polypeptides Encoded by DNAJB5 Gene

---

Exemplary Human Mature DNAJB5 Protein Isoform 1 (encoded by Variant 1 and Variant 4)

(SEQ ID NO: 172)

MFKRTVLSCPPPAAPPLQARGAFRSFPHSWGEDFLASLMFKIQLEPLKLRAWTLNGFVKFRNKE

TSAGPVAVMGKDYYKILGIPSGANEDEIKKAYRKMALKYHPDKNKEPNAEEKFKEIAEAYDVLS

DPKKRGLYDQYGEEGLKTGGGTSGGSSGSFHYTFHGDPHATFASFFGGSNPFDIFFASSRSTRP

FSGFDPDDMDVDEDEDPFGAFGRFGFNGLSRGPRRAPEPLYPRRKVQDPPVVHELRVSLEEIYH

GSTKRMKITRRRLNPDGRTVRTEDKILHIVIKRGWKEGTKITFPKEGDATPDNIPADIVFVLKD

KPHAHFRRDGTNVLYSALISLKEALCGCTVNIPTIDGRVIPLPCNDVIKPGTVKRLRGEGLPFP

KVPTQRGDLIVEFKVRFPDRLTPQTRQILKQHLPCS

Exemplary Human Mature DNAJB5 Protein Isoform 2 (encoded by Variant 2 and Variant 6)

(SEQ ID NO: 173)

MFKIQLEPLKLRAWTLNGFVKFRNKETSAGPVAVMGKDYYKILGIPSGANEDEIKKAYRKMALK

YHPDKNKEPNAEEKFKEIAEAYDVLSDPKKRGLYDQYGEEGLKTGGGTSGGSSGSFHYTFHGDP

HATFASFFGGSNPFDIFFASSRSTRPFSGFDPDDMDVDEDEDPFGAFGRFGFNGLSRGPRRAPE

PLYPRRKVQDPPVVHELRVSLEEIYHGSTKRMKITRRRLNPDGRTVRTEDKILHIVIKRGWKEG

TKITFPKEGDATPDNIPADIVFVLKDKPHAHFRRDGTNVLYSALISLKEALCGCTVNIPTIDGR

VIPLPCNDVIKPGTVKRLRGEGLPFPKVPTQRGDLIVEFKVRFPDRLTPQTRQILKQHLPCS

Exemplary Human Mature DNAJB5 Protein Isoform 3 (encoded by Variant 3 and Variant 5)

(SEQ ID NO: 174)

MGKDYYKILGIPSGANEDEIKKAYRKMALKYHPDKNKEPNAEEKFKEIAEAYDVLSDPKKRGLY

DQYGEEGLKTGGGTSGGSSGSFHYTFHGDPHATFASFFGGSNPFDIFFASSRSTRPFSGFDPDD

-continued

```
MDVDEDEDPFGAFGRFGFNGLSRGPRRAPEPLYPRRKVQDPPVVHELRVSLEEIYHGSTKRMKI

TRRRLNPDGRTVRTEDKILHIVIKRGWKEGTKITFPKEGDATPDNIPADIVFVLKDKPHAHFRR

DGTNVLYSALISLKEALCGCTVNIPTIDGRVIPLPCNDVIKPGTVKRLRGEGLPFPKVPTQRGD

LIVEFKVRFPDRLTPQTRQILKQHLPCS
```

Constructs

Among other things, the present disclosure provides that some polynucleotides as described herein are polynucleotide constructs. Polynucleotide constructs according to the present disclosure include all those known in the art, including cosmids, plasmids (e.g., naked or contained in liposomes) and viral constructs (e.g., lentiviral, retroviral, adenoviral, and adeno-associated viral constructs) that incorporate a polynucleotide comprising an NDP gene or characteristic portion thereof. In addition, polynucleotide constructs according to the present disclosure include all those known in the art, including cosmids, plasmids (e.g., naked or contained in liposomes) and viral constructs (e.g., lentiviral, retroviral, adenoviral, and adeno-associated viral constructs) that incorporate a polynucleotide comprising an HSPA1A gene or characteristic portion thereof. Moreover, polynucleotide constructs according to the present disclosure include all those known in the art, including cosmids, plasmids (e.g., naked or contained in liposomes) and viral constructs (e.g., lentiviral, retroviral, adenoviral, and adeno-associated viral constructs) that incorporate a polynucleotide comprising a gene encoding a secreted target protein (e.g., a NDP gene (e.g., any of the exemplary NDP genes described herein), a HSPA1A gene (e.g., any of the exemplary HSPA1A genes described herein)) gene or characteristic portion thereof.

Those of skill in the art will be capable of selecting suitable constructs, as well as cells, for making any of the polynucleotides described herein. In some embodiments, a construct is a plasmid (i.e., a circular DNA molecule that can autonomously replicate inside a cell). In some embodiments, a construct can be a cosmid (e.g., pWE or sCos series).

In some embodiments, a construct is a viral construct. In some embodiments, a viral construct is a lentivirus, retrovirus, adenovirus, or adeno-associated virus construct. In some embodiments, a construct is an adeno-associated virus (AAV) construct (see, e.g., Asokan et al., Mol. Ther. 20:699-7080, 2012, which is incorporated in its entirety herein by reference). In some embodiments, a viral construct is an adenovirus construct. In some embodiments, a viral construct may also be based on or derived from an alphavirus. Alphaviruses include Sindbis(and VEEV) virus, Aura virus, Babanki virus, Barmah Forest virus, Bebaru virus, Cabassou virus, Chikungunya virus, Eastern equine encephalitis virus, Everglades virus, Fort Morgan virus, Getah virus, Highlands J virus, Kyzylagach virus, Mayaro virus, Me Tri virus, Middelburg virus, Mosso das Pedras virus, Mucambo virus, Ndumu virus, O'nyong-nyong virus, Pixuna virus, Rio Negro virus, Ross River virus, Salmon pancreas disease virus, Semliki Forest virus, Southern elephant seal virus, Tonate virus, Trocara virus, Una virus, Venezuelan equine encephalitis virus, Western equine encephalitis virus, and Whataroa virus. Generally, the genome of such viruses encode nonstructural (e.g., replicon) and structural proteins (e.g., capsid and envelope) that can be translated in the cytoplasm of the host cell. Ross River virus, Sindbis virus, Semliki Forest virus (SFV), and Venezuelan equine encephalitis virus (VEEV) have all been used to develop viral constructs for coding sequence delivery. Pseudotyped viruses may be formed by combining alphaviral envelope glycoproteins and retroviral capsids. Examples of alphaviral constructs can be found in U.S. Publication Nos. 20150050243, 20090305344, and 20060177819; constructs and methods of their making are incorporated herein by reference to each of the publications in its entirety.

Constructs provided herein can be of different sizes. In some embodiments, a construct is a plasmid and can include a total length of up to about 1 kb, up to about 2 kb, up to about 3 kb, up to about 4 kb, up to about 5 kb, up to about 6 kb, up to about 7 kb, up to about 8 kb, up to about 9 kb, up to about 10 kb, up to about 11 kb, up to about 12 kb, up to about 13 kb, up to about 14 kb, or up to about 15 kb. In some embodiments, a construct is a plasmid and can have a total length in a range of about 1 kb to about 2 kb, about 1 kb to about 3 kb, about 1 kb to about 4 kb, about 1 kb to about 5 kb, about 1 kb to about 6 kb, about 1 kb to about 7 kb, about 1 kb to about 8 kb, about 1 kb to about 9 kb, about 1 kb to about 10 kb, about 1 kb to about 11 kb, about 1 kb to about 12 kb, about 1 kb to about 13 kb, about 1 kb to about 14 kb, or about 1 kb to about 15 kb.

In some embodiments, a construct is a viral construct and can have a total number of nucleotides of up to 10 kb. In some embodiments, a viral construct can have a total number of nucleotides in the range of about 1 kb to about 2 kb, 1 kb to about 3 kb, about 1 kb to about 4 kb, about 1 kb to about 5 kb, about 1 kb to about 6 kb, about 1 kb to about 7 kb, about 1 kb to about 8 kb, about 1 kb to about 9 kb, about 1 kb to about 10 kb, about 2 kb to about 3 kb, about 2 kb to about 4 kb, about 2 kb to about 5 kb, about 2 kb to about 6 kb, about 2 kb to about 7 kb, about 2 kb to about 8 kb, about 2 kb to about 9 kb, about 2 kb to about 10 kb, about 3 kb to about 4 kb, about 3 kb to about 5 kb, about 3 kb to about 6 kb, about 3 kb to about 7 kb, about 3 kb to about 8 kb, about 3 kb to about 9 kb, about 3 kb to about 10 kb, about 4 kb to about 5 kb, about 4 kb to about 6 kb, about 4 kb to about 7 kb, about 4 kb to about 8 kb, about 4 kb to about 9 kb, about 4 kb to about 10 kb, about 5 kb to about 6 kb, about 5 kb to about 7 kb, about 5 kb to about 8 kb, about 5 kb to about 9 kb, about 5 kb to about 10 kb, about 6 kb to about 7 kb, about 6 kb to about 8 kb, about 6 kb to about 9 kb, about 6 kb to about 10 kb, about 7 kb to about 8 kb, about 7 kb to about 9 kb, about 7 kb to about 10 kb, about 8 kb to about 9 kb, about 8 kb to about 10 kb, or about 9 kb to about 10 kb.

In some embodiments, a construct is a lentivirus construct and can have a total number of nucleotides of up to 8 kb. In some examples, a lentivirus construct can have a total number of nucleotides of about 1 kb to about 2 kb, about 1 kb to about 3 kb, about 1 kb to about 4 kb, about 1 kb to about 5 kb, about 1 kb to about 6 kb, about 1 kb to about 7 kb, about 1 kb to about 8 kb, about 2 kb to about 3 kb, about 2 kb to about 4 kb, about 2 kb to about 5 kb, about 2 kb to about 6 kb, about 2 kb to about 7 kb, about 2 kb to about 8 kb, about 3 kb to about 4 kb, about 3 kb to about 5 kb, about 3 kb to about 6 kb, about 3 kb to about 7 kb, about 3 kb to about 8 kb, about 4 kb to about 5 kb, about 4 kb to about 6 kb, about 4 kb to about 7 kb, about 4 kb to about 8 kb, about 5 kb to about 6 kb, about 5 kb to about 7 kb, about 5 kb to about 8 kb, about 6 kb to about 8 kb, about 6 kb to about 7 kb, or about 7 kb to about 8 kb In some embodiments, a construct is an adenovirus construct and can have a total number of nucleotides of up to 8 kb. In some embodiments, an adenovirus construct can have a total number of nucleotides in the range of about 1 kb to about 2 kb, about 1 kb to about 3 kb, about 1 kb to about 4 kb, about 1 kb to about 5 kb, about 1 kb to about 6 kb, about 1 kb to about 7 kb, about 1 kb to about 8 kb, about 2 kb to about 3 kb, about 2 kb to about 4 kb, about 2 kb to about 5 kb, about 2 kb to about 6 kb, about 2 kb to about 7 kb, about 2 kb to about 8 kb, about 3 kb to about 4 kb, about 3 kb to about 5 kb, about 3 kb to about 6 kb, about 3 kb to about 7 kb, about 3 kb to about 8 kb, about 4 kb to about 5 kb, about 4 kb to about 6 kb, about 4 kb to about 7 kb, about 4 kb to about 8 kb, about 5 kb to about 6 kb, about 5 kb to about 7 kb, about 5 kb to about 8 kb, about 6 kb to about 7 kb, about 6 kb to about 8 kb, or about 7 kb to about 8 kb.

Any of the constructs described herein can further include a control sequence, e.g., a control sequence selected from the group of a transcription initiation sequence, a transcription termination sequence, a promoter sequence, an enhancer sequence, an RNA splicing sequence, a polyadenylation (poly(A)) sequence, a Kozak consensus sequence, and/or additional untranslated regions which may house pre- or post-transcriptional regulatory and/or control elements. In some embodiments, a promoter can be a native promoter, a constitutive promoter, an inducible promoter, and/or a tissue-specific promoter. Non-limiting examples of control sequences are described herein.

AAV Particles

Among other things, the present disclosure provides AAV particles that comprise a construct encoding an NDP gene or characteristic portion thereof described herein, and a capsid described herein. In addition, the present disclosure provides AAV particles that comprise a construct encoding an HSPA1A gene or characteristic portion thereof described herein, and a capsid described herein. In addition, the present disclosure provides AAV particles that comprise a construct encoding a gene encoding a secreted target protein (e.g., a NDP gene (e.g., any of the exemplary NDP genes described herein), a HSPA1A gene (e.g., any of the exemplary HSPA1A genes described herein)) gene or characteristic portion thereof described herein, and a capsid described herein.

In some embodiments, AAV particles can be described as having a serotype, which is a description of the construct strain and the capsid strain. For example, in some embodiments an AAV particle may be described as AAV2, wherein the particle has an AAV2 capsid and a construct that comprises characteristic AAV2 Inverted Terminal Repeats (ITRs). In some embodiments, an AAV particle may be described as AAV1, In some embodiments, an AAV particle may be described as AAV2, In some embodiments, an AAV particle may be described as AAV3. In some embodiments, an AAV particle may be described as AAV4. In some embodiments, an AAV particle may be described as AAV5. In some embodiments, an AAV particle may be described as AAV6. In some embodiments, an AAV particle may be described as AAV7. In some embodiments, an AAV particle may be described as AAV8. In some embodiments, an AAV particle may be described as AAV9. In some embodiments, an AAV particle may be AAV-rh8. In some embodiments, an AAV particle may comprise an AAV-rh10 capsid. In some embodiments, an AAV particle may comprise an AAV-rh39 capsid. In some embodiments, an AAV particle may comprise an AAV-rh43 capsid. In some embodiments, an AAV particle may comprise an AAV Anc80 capsid. In some embodiments, an AAV particle may be described as a pseudotype, wherein the capsid and construct are derived from different AAV strains as described herein, for example, AAV2/9 would refer to an AAV particle that comprises a construct utilizing the AAV2 ITRs and an AAV9 capsid. In some embodiments, an AAV particle may be described as other AAV variants and serotypes as described herein.

AAV Construct

The present disclosure provides polynucleotide constructs that comprise a gene encoding a secreted target protein (e.g., a NDP gene (e.g., any of the exemplary NDP genes described herein), a HSPA1A gene (e.g., any of the exemplary HSPA1A genes described herein)) gene or characteristic portion thereof. For example, the present disclosure provides polynucleotide constructs that comprise an NDP gene or characteristic portion thereof. In some embodiments described herein, a polynucleotide comprising an NDP gene or characteristic portion thereof can be included in an AAV particle. As another example, the present disclosure also provides polynucleotide constructs that comprise an HSPA1A gene or characteristic portion thereof. In some embodiments described herein, a polynucleotide comprising an HSPA1A gene or characteristic portion thereof can be included in an AAV particle.

In some embodiments, a polynucleotide construct comprises one or more components derived from or modified from a naturally occurring AAV genomic construct. In some embodiments, a sequence derived from an AAV construct is an AAV1 construct, an AAV2 construct, an AAV3 construct, an AAV4 construct, an AAV5 construct, an AAV6 construct, an AAV7 construct, an AAV8 construct, an AAV9 construct, an AAV2.7m8 construct, an AAV8BP2 construct, an AAV293 construct, or AAV Anc80 construct. Additional exemplary AAV constructs that can be used herein are known in the art. See, e.g., Kanaan et al., Mol. Ther. Nucleic Acids 8:184-197, 2017; Li et al., Mol. Ther. 16 (7): 1252-1260, 2008; Adachi et al., Nat. Commun. 5:3075, 2014; Isgrig et al., Nat. Commun. 10 (1): 427, 2019; and Gao et al., J. Virol. 78 (12): 6381-6388, 2004; each of which is incorporated in its entirety herein by reference.

In some embodiments, provided constructs comprise coding sequence, e.g., an gene encoding a secreted target protein (e.g., an NDP gene, e.g., an HSPA1A gene) or a characteristic portion thereof, one or more regulatory and/or control sequences, and optionally 5' and 3' AAV derived inverted terminal repeats (ITRs). In some embodiments wherein a 5' and 3' AAV derived ITR is utilized, the polynucleotide construct may be referred to as an AAV construct. In some embodiments, provided AAV constructs are packaged into an AAV capsid to form an AAV particle.

In some embodiments, AAV derived sequences (which are comprised in a polynucleotide construct) typically include the cis-acting 5' and 3' ITR sequences (see, e.g., B. J. Carter, in "Handbook of Parvoviruses," ed., P. Tijsser, CRC Press, pp. 155 168, 1990, which is incorporated herein by reference in its entirety). Typical AAV2-derived ITR sequences are about 145 nucleotides in length. In some embodiments, at least 80% of a typical ITR sequence (e.g., at least 85%, at least 90%, or at least 95%) is incorporated into a construct provided herein. The ability to modify these ITR sequences is within the skill of the art. (See, e.g., texts such as Sambrook et al., "Molecular Cloning. A Laboratory Manual", 2d ed., Cold Spring Harbor Laboratory, New York, 1989; and K. Fisher et al., J Virol. 70:520 532, 1996, each of which is incorporated in its entirety by reference). In some embodiments, any of the coding sequences and/or constructs described herein are flanked by 5' and 3' AAV ITR sequences. The AAV ITR sequences may be obtained from any known AAV, including presently identified AAV types.

In some embodiments, polynucleotide constructs described in accordance with this disclosure and in a pattern known to the art (see, e.g., Asokan et al., Mol. Ther. 20:699-7080, 2012, which is incorporated herein by reference in its entirety) are typically comprised of, a coding sequence or a portion thereof, at least one and/or control sequence, and optionally 5' and 3' AAV inverted terminal repeats (ITRs). In some embodiments, provided constructs can be packaged into a capsid to create an AAV particle. An AAV particle may be delivered to a selected target cell. In some embodiments, provided constructs comprise an additional optional coding sequence that is a nucleic acid sequence (e.g., inhibitory nucleic acid sequence), heterologous to the construct sequences, which encodes a polypeptide, protein, functional RNA molecule (e.g., miRNA, miRNA inhibitor) or other gene product, of interest. In some embodiments, a nucleic acid coding sequence is operatively linked to and/or control components in a manner that permits coding sequence transcription, translation, and/or expression in a cell of a target tissue.

Figures 19A, 19B, 19C:
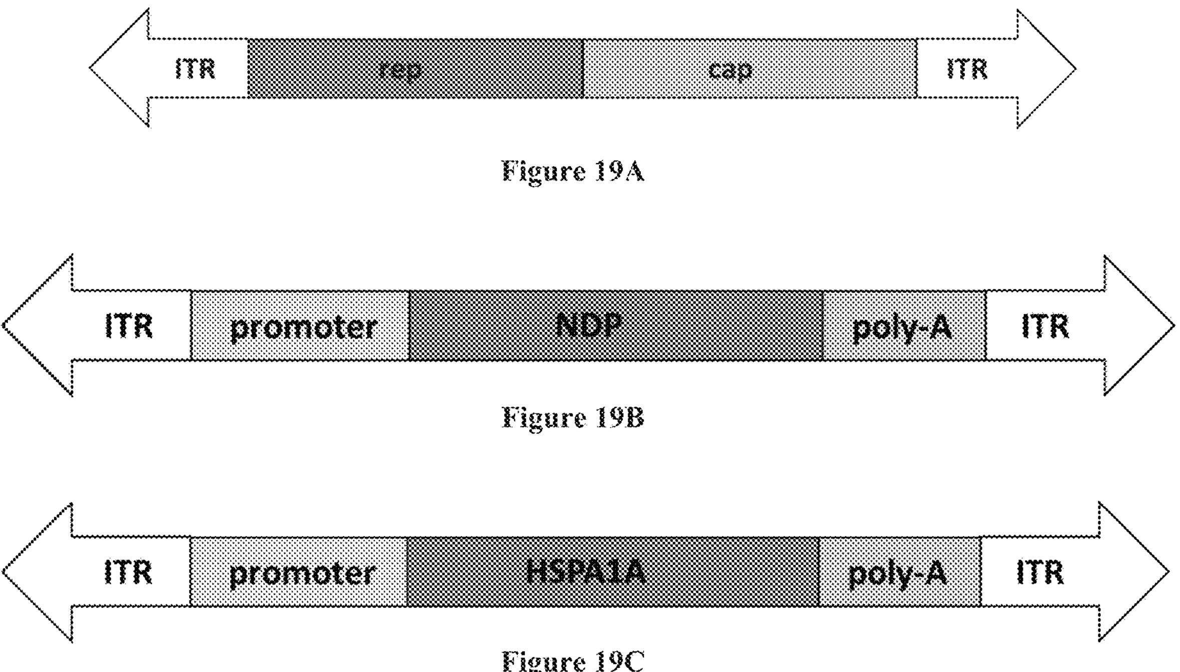
FIG. 19A depicts a simplified wild-type AAV genome.
FIG. 19B depicts a simplified AAV construct capable of expressing an NDP gene.
FIG. 19C depicts a simplified AAV construct capable of expressing an HSPA1A gene.

As shown in FIG. 19A, an unmodified AAV endogenous genome includes two open reading frames, "cap" and "rep," which are flanked by ITRs. As shown in FIG. 19B, exemplary AAV constructs similarly include ITRs flanking a coding region, e.g., a coding sequence (e.g., a secreted target protein gene, e.g., an NDP gene). As shown in FIG. 19C, exemplary AAV constructs similarly include ITRs flanking a coding region, e.g., a coding sequence (e.g., a secreted target protein gene, e.g., an HSPA1A gene). In some embodiments, an AAV construct also comprises conventional control elements that are operably linked to the coding sequence in a manner that permits its transcription, translation and/or expression in a cell transfected with the plasmid construct or infected with the virus produced by the disclosure. In some embodiments, an AAV construct optionally comprises a promoter (shown in FIG. 19B), an enhancer, an untranslated region (e.g., a 5' UTR, 3' UTR), a Kozak sequence, an internal ribosomal entry site (IRES), splicing sites (e.g., an acceptor site, a donor site), a polyadenylation site (shown FIG. 19B), or any combination thereof. Such additional elements are described further herein.

In some embodiments, an AAV construct is a recombinant AAV construct or "rAAV" construct. In some embodiments, an AAV construct can include at least 500 bp, at least 1 kb, at least 1.5 kb, at least 2 kb, at least 2.5 kb, at least 3 kb, at least 3.5 kb, at least 4 kb, or at least 4.5 kb. In some embodiments, an AAV construct can include at most 7.5 kb, at most 7 kb, at most 6.5 kb, at most 6 kb, at most 5.5 kb, at most 5 kb, at most 4.5 kb, at most 4 kb, at most 3.5 kb, at most 3 kb, or at most 2.5 kb. In some embodiments, an AAV construct can include about 1 kb to about 2 kb, about 1 kb to about 3 kb, about 1 kb to about 4 kb, about 1 kb to about 5 kb, about 2 kb to about 3 kb, about 2 kb to about 4 kb, about 2 kb to about 5 kb, about 3 kb to about 4 kb, about 3 kb to about 5 kb, or about 4 kb to about 5 kb. AAV constructs are typically composed of, at a minimum, a transgene or a portion thereof and a regulatory sequence, and optionally 5' and 3' AAV inverted terminal repeats (ITRs). Such an AAV construct is packaged into a capsid and delivered to a selected target cell (e.g., a cochlear hair cell).

Any of the constructs described herein can further include regulatory and/or control sequences, e.g., a control sequence selected from the group of a transcription initiation sequence, a transcription termination sequence, a promoter sequence, an enhancer sequence, an RNA splicing sequence, a polyadenylation (poly(A)) sequence, a Kozak consensus sequence, and/or any combination thereof. In some embodiments, a promoter can be a native promoter, a constitutive promoter, an inducible promoter, and/or a tissue-specific promoter. Non-limiting examples of control sequences are described herein.

The AAV sequences of the vector typically comprise the cis-acting 5' and 3' ITR sequences (See, e.g., B. J. Carter, in "Handbook of Parvoviruses", ed., P. Tijsser, CRC Press, pp. 155 168, 1990, the contents of which is hereby incorporated by reference herein in its entirety). Typical AAV ITR sequences are about 145 nucleotides in length. In some embodiments, at least 75% of a typical ITR sequence (e.g., at least 80%, at least 85%, at least 90%, or at least 95%) is incorporated into the AAV vector. The ability to modify these ITR sequences is within the skill of the art. (See, e.g., texts such as Sambrook et al., "Molecular Cloning. A Laboratory Manual", 2d ed., Cold Spring Harbor Laboratory, New York, 1989; and K. Fisher et al., J Virol. 70:520 532, 1996, each of which is incorporated in its entirety herein by reference). In some embodiments, any of the coding sequences described herein is flanked by 5' and 3' AAV ITR sequences in the AAV vectors. The AAV ITR sequences may be obtained from any known AAV, including presently identified AAV types.

AAV vectors as described herein may include any of the regulatory elements described herein (e.g., one or more of a promoter, a polyadenylation (poly(A)) signal sequence, and an IRES).

In some embodiments, the AAV vector is selected from the group consisting of: an AAV1 vector, an AAV2 vector, an AAV3 vector, an AAV4 vector, an AAV5 vector, an AAV6 vector, an AAV7 vector, an AAV8 vector, an AAV9 vector, an AAV2.7m8 vector, an AAV8BP2 vector, and an AAV293 vector. Additional exemplary AAV vectors that can be used herein are known in the art. See, e.g., Kanaan et al., *Mol. Ther. Nucleic Acids* 8:184-197, 2017; Li et al., *Mol. Ther.* 16 (7): 1252-1260; Adachi et al., *Nat. Commun.* 5:3075, 2014; Isgrig et al., *Nat. Commun.* 10 (1): 427, 2019; and Gao et al., *J. Virol.* 78 (12): 6381-6388, each of which is incorporated in its entirety herein by reference.

In some embodiments, an AAV vector provided herein includes or consists of a sequence that is at least 80% identical (e.g., at least 82%, at least 84%, at least 85%, at least 86%, at least 88%, at least 90%, at least 92%, at least 94%, at least 95%, at least 96%, at least 98%, at least 99%, or 100% identical) to SEQ ID NO: 9, 10, 11, 12, or 13.

In some embodiments, the vector(s) is an adenovirus vector (see, e.g., Dmitriev et al. (1998) *J. Virol.* 72:9706-9713; and Poulin et al., *J. Virol* 8:10074-10086, 2010, each of which is incorporated in its entirety herein by reference). In some embodiments, the vector(s) is a retrovirus (see, e.g., Maier et al. (2010) *Future Microbiol* 5:1507-23, the contents of which is incorporated in its entirety herein).

The vectors provided herein can be of different sizes. The choice of vector that is used in any of the compositions, kits, and methods described herein may depend on the size of the vector.

In some embodiments, the vector(s) can have a total number of nucleotides of up to 10 kb. In some embodiments, the viral vector(s) can have a total number of nucleotides in the range of about 1 kb to about 2 kb, 1 kb to about 3 kb, about 1 kb to about 4 kb, about 1 kb to about 5 kb, about 1 kb to about 6 kb, about 1 kb to about 7 kb, about 1 kb to about 8 kb, about 1 kb to about 9 kb, about 1 kb to about 10 kb, about 2 kb to about 3 kb, about 2 kb to about 4 kb, about 2 kb to about 5 kb, about 2 kb to about 6 kb, about 2 kb to about 7 kb, about 2 kb to about 8 kb, about 2 kb to about 9 kb, about 2 kb to about 10 kb, about 3 kb to about 4 kb, about 3 kb to about 5 kb, about 3 kb to about 6 kb, about 3 kb to about 7 kb, about 3 kb to about 8 kb, about 3 kb to about 9 kb, about 3 kb to about 10 kb, about 4 kb to about 5 kb, about 4 kb to about 6 kb, about 4 kb to about 7 kb, about 4 kb to about 8 kb, about 4 kb to about 9 kb, about 4 kb to about 10 kb, about 5 kb to about 6 kb, about 5 kb to about 7 kb, about 5 kb to about 8 kb, about 5 kb to about 9 kb, about 5 kb to about 10 kb, about 6 kb to about 7 kb, about 6 kb to about 8 kb, about 6 kb to about 9 kb, about 6 kb to about 10 kb, about 7 kb to about 8 kb, about 7 kb to about 9 kb, about 7 kb to about 10 kb, about 8 kb to about 9 kb, about 8 kb to about 10 kb, or about 9 kb to about 10 kb.

In some embodiments, the vector(s) is a lentivirus and can have a total number of nucleotides of up to 8 kb. In some examples, the lentivirus(es) can have a total number of nucleotides of about 1 kb to about 2 kb, about 1 kb to about 3 kb, about 1 kb to about 4 kb, about 1 kb to about 5 kb, about 1 kb to about 6 kb, about 1 kb to about 7 kb, about 1 kb to about 8 kb, about 2 kb to about 3 kb, about 2 kb to about 4 kb, about 2 kb to about 5 kb, about 2 kb to about 6 kb, about 2 kb to about 7 kb, about 2 kb to about 8 kb, about 3 kb to about 4 kb, about 3 kb to about 5 kb, about 3 kb to about 6 kb, about 3 kb to about 7 kb, about 3 kb to about 8 kb, about 4 kb to about 5 kb, about 4 kb to about 6 kb, about 4 kb to about 7 kb, about 4 kb to about 8 kb, about 5 kb to about 6 kb, about 5 kb to about 7 kb, about 5 kb to about 8 kb, about 6 kb to about 8 kb, about 6 kb to about 7 kb, or about 7 kb to about 8 kb.

In some embodiments, the vector(s) is an adenovirus and can have a total number of nucleotides of up to 8 kb. In some embodiments, the adenovirus(es) can have a total number of nucleotides in the range of about 1 kb to about 2 kb, about 1 kb to about 3 kb, about 1 kb to about 4 kb, about 1 kb to about 5 kb, about 1 kb to about 6 kb, about 1 kb to about 7 kb, about 1 kb to about 8 kb, about 2 kb to about 3 kb, about 2 kb to about 4 kb, about 2 kb to about 5 kb, about 2 kb to about 6 kb, about 2 kb to about 7 kb, about 2 kb to about 8 kb, about 3 kb to about 4 kb, about 3 kb to about 5 kb, about 3 kb to about 6 kb, about 3 kb to about 7 kb, about 3 kb to about 8 kb, about 4 kb to about 5 kb, about 4 kb to about 6 kb, about 4 kb to about 7 kb, about 4 kb to about 8 kb, about 5 kb to about 6 kb, about 5 kb to about 7 kb, about 5 kb to about 8 kb, about 6 kb to about 7 kb, about 6 kb to about 8 kb, or about 7 kb to about 8 kb.

In some embodiments, the vector(s) is an adeno-associated virus (AAV vector) and can include a total number of nucleotides of up to 5 kb. In some embodiments, the AAV vector(s) can include a total number of nucleotides in the range of about 1 kb to about 2 kb, about 1 kb to about 3 kb, about 1 kb to about 4 kb, about 1 kb to about 5 kb, about 2 kb to about 3 kb, about 2 kb to about 4 kb, about 2 kb to about 5 kb, about 3 kb to about 4 kb, about 3 kb to about 5 kb, or about 4 kb to about 5 kb.

Provided herein are exemplary vectors that can be used in any of the compositions and methods described herein. See, e.g., FIGS. 1-5, 11-13.

A variety of different methods known in the art can be used to introduce any of vectors disclosed herein into a mammalian cell (e.g., an inner ear cell, a cochlear inner hair cell). Non-limiting examples of methods for introducing nucleic acid into a mammalian cell include: lipofection, transfection (e.g., calcium phosphate transfection, transfection using highly branched organic compounds, transfection using cationic polymers, dendrimer-based transfection, optical transfection, particle-based transfection (e.g., nanoparticle transfection), or transfection using liposomes (e.g., cationic liposomes)), microinjection, electroporation, cell squeezing, sonoporation, protoplast fusion, impalefection, hydrodynamic delivery, gene gun, magnetofection, viral transfection, and nucleofection.

Any of the vectors described herein can further include a control sequence, e.g., a control sequence selected from the group of a transcription initiation sequence, a transcription termination sequence, a promoter sequence, an enhancer sequence, an RNA splicing sequence, a polyadenylation (polyA) signal, and a Kozak consensus sequence. Non-limiting examples of these control sequences are described herein. In some embodiments, a promoter can be a native promoter, a constitutive promoter, an inducible promoter, and/or a tissue-specific promoter.

```
Exemplary Construct 1
                                                    (SEQ ID NO: 9)
CCTGCAGGCAGCTGCGCGCTCGCTCGCTCACTGAGGCCGCCCGGGCGTCGGGCGACCTTTGGTC

GCCCGGCCTCAGTGAGCGAGCGAGCGCGCAGAGAGGGAGTGGCCAACTCCATCACTAGGGGTTC

CTGCGGCCGCACGCGTGACATTGATTATTGACTAGTTATTAATAGTAATCAATTACGGGGTCAT

TAGTTCATAGCCCATATATGGAGTTCCGCGTTACATAACTTACGGTAAATGGCCCGCCTGGCTG

ACCGCCCAACGACCCCCGCCCATTGACGTCAATAATGACGTATGTTCCCATAGTAACGCCAATA

GGGACTTTCCATTGACGTCAATGGGTGGACTATTTACGGTAAACTGCCCACTTGGCAGTACATC

AAGTGTATCATATGCCAAGTACGCCCCCTATTGACGTCAATGACGGTAAATGGCCCGCCTGGCA

TTATGCCCAGTACATGACCTTATGGGACTTTCCTACTTGGCAGTACATCTACGTATTAGTCATC

GCTATTACCATGGGTCGAGGTGAGCCCCACGTTCTGCTTCACTCTCCCCATCTCCCCCCCCTCC

CCACCCCCAATTTTGTATTTATTTATTTTTTAATTATTTTGTGCAGCGATGGGGGCGGGGGGGG

GGGGGGCGCGCGCCAGGCGGGGCGGGGCGGGGCGAGGGGCGGGGCGGGGCGAGGCGGAGAGGTG

CGGCGGCAGCCAATCAGAGCGGCGCGCTCCGAAAGTTTCCTTTTATGGCGAGGCGGCGGCGGCG

GCGGCCCTATAAAAAGCGAAGCGCGCGGCGGGCGGGAGTCGCTGCGTTGCCTTCGCCCCGTGCC
```

-continued

CCGCTCCGCGCCGCCTCGCGCCGCCCGCCCCGGCTCTGACTGACCGCGTTACTCCCACAGGTGA

GCGGGCGGGACGGCCCTTCTCCTCCGGGCTGTAATTAGCGCTTGGTTTAATGACGGCTCGTTTC

TTTTCTGTGGCTGCGTGAAAGCCTTAAAGGGCTCCGGGAGGGCCCTTTGTGCGGGGGGGAGCGG

CTCGGGGGGTGCGTGCGTGTGTGTGTGCGTGGGGAGCGCCGCGTGCGGCCCGCGCTGCCCGGCG

GCTGTGAGCGCTGCGGGCGCGGCGCGGGGCTTTGTGCGCTCCGCGTGTGCGCGAGGGGAGCGCG

GCCGGGGGCGGTGCCCCGCGGTGCGGGGGGGCTGCGAGGGGAACAAAGGCTGCGTGCGGGGTGT

GTGCGTGGGGGGGTGAGCAGGGGGTGTGGGCGCGGCGGTCGGGCTGTAACCCCCCCCTGCACCC

CCCTCCCCGAGTTGCTGAGCACGGCCCGGCTTCGGGTGCGGGGCTCCGTGCGGGGCGTGGCGCG

GGGCTCGCCGTGCCGGGCGGGGGGTGGCGGCAGGTGGGGGTGCCGGGCGGGGCGGGGCCGCCTC

GGGCCGGGGAGGGCTCGGGGGAGGGGCGCGGCGGCCCCCGGAGCGCCGGCGGCTGTCGAGGCGC

GGCGAGCCGCAGCCATTGCCTTTTATGGTAATCGTGCGAGAGGGCGCAGGGACTTCCTTTGTCC

CAAATCTGTGCGGAGCCGAAATCTGGGAGGCGCCGCCGCACCCCCTCTAGCGGGCGCGGGGCGA

AGCGGTGCGGCGCCGGCAGGAAGGAAATGGGCGGGGAGGGCCTTCGTGCGTCGCCGCGCCGCCG

TCCCCTTCTCCCTCTCCAGCCTCGGGGCTGTCCGCGGGGGGACGGCTGCCTTCGGGGGGGACGG

GGCAGGGCGGGGTTCGGCTTCTGGCGTGTGACCGGCGGCTCTAGAGCCTCTGCTAACCATGTTC

ATGCCTTCTTCTTTTTCCTACAGCTCCTGGGCAACGTGCTGGTTATTGTGACCGGTGCCACCAT

GAGAAAACATGTACTAGCTGCATCCTTTTCTATGCTCTCCCTGCTGGTGATAATGGGAGATACA

GACAGTAAAACGGACAGCTCATTCATAATGGACTCGGACCCTCGACGCTGCATGAGGCACCACT

ATGTGGATTCTATCAGTCACCCATTGTACAAGTGTAGCTCAAAGATGGTGCTCCTGGCCAGGTG

CGAGGGGCACTGCAGCCAGGCGTCACGCTCCGAGCCTTTGGTGTCGTTCAGCACTGTCCTCAAG

CAACCCTTCCGTTCCTCCTGTCACTGCTGCCGGCCCCAGACTTCCAAGCTGAAGGCACTGCGGC

TGCGATGCTCAGGGGGCATGCGACTCACTGCCACCTACCGATACATCCTCTCCTGTCACTGCGA

GGAATGCAATTCCTAAGGCCCGCTGCTGTGTGTGGCTTCTGGATGGGACAACTGTAGAGGCAGT

TCGACCAGCCAGGGAAAGACTGGCAAGAAAAGAGTTAAGGCAAAAAAGGATGCAACAATTCTCC

GGGGACTCTGCATATTCTAGTAATAAAGACTCTACATGCTTGTTGACAGAGAGAGATACTCTGG

GAACTTCTTTGCAGTTCCCATCTCCTTTCTCTGGTACAATTTCTTTTGGTTCATTTTCAGATTC

AGGCATTTTCCCCCTTGGCTCTCAATGCTGTTTGGGTTTCCAACAATTCAGCATTAGTGGGAAA

AAGTGGGCCCTCATACACAAGCGTGTCAGGCTGTCAGTGTTTGGTGCACGCTGGGGAAGAATTT

ACTTTGGAAAGTAGAAAAGCCCAGCTTTTCCTGGGACATCTTCTGTTATTGTTGATGTTTTTTT

TTACCTTGTCATTTTGGTCTAAGGTTGCCATTGCTGCTAAAGGTTACCGATTTCAAAGTCCAGA

TACCAAGCATGTGGATATGTTTAGCTACGTTTACTCACAGCCAGCGAACTGACATTAAAATAAC

TAACAAACAGATTCTTTTATGTGATGCTGGAACTCTTGACAGCTATAATTATTATTCAGAAATG

ACTTTTTGAAAGTAAAAGCAGCATAAAGAATTTGTCACAGGAAGGCTGTCTCAGATAAATTATG

GTAAAATTTTGTAAGGGAGCAGACTTTTAAAGACTTGCACAAATACGGATCCTGCACTGACTCT

GGAAAAGGCATATATGTACTAGTGGCATGGAGAATGCACCATACTCATGCATGCAAATTAGACA

ACCAAGTATGAATCTATTTGTGGGTGTGCTATAGCTTTAGCCGTGTCACGGGCATCATTCTCTA

ATATCCACTTGTCCATGTGAAACATGTTGCCAAAATGGTGGCCTGGCTTGTCTTCTGAACGTTT

GGTTCAAATGTGTTTTGGTCCTGGAGGCTCAAATTTTGAGTTATTCCCACGTTTTGAAATAAAA

AGAGTATATTCAAAAGAGCTCCTGTGCCTTCTAGTTGCCAGCCATCTGTTGTTTGCCCCTCCCC

CGTGCCTTCCTTGACCCTGGAAGGTGCCACTCCCACTGTCCTTTCCTAATAAAATGAGGAAATT

GCATCGCATTGTCTGAGTAGGTGTCATTCTATTCTGGGGGGTGGGGTGGGGCAGGACAGCAAGG

-continued

GGGAGGATTGGGAAGACAATAGCAGGCATGCTGGGGATGCGGTGGGCTCTATGGCAATTCAGAC

TCCCACTAGAAGAAACAGAACTTGAAAAAAGGATAATTGTGGTGAACACCTCAACCCAGTGGTC

CAAAAACTGAAAAACTTTGACCCCGAGCACCCTCACACAGATAGACTACTGAAAGAAGGAGAAA

GGGGCACTTACTCAGTCTCCCTTATCAGATTGCCTTACGAGGAGTACTAGACTCCCTCAAGCAA

ATAGATCTCACTTACCACTTGCAAAGGTATACTACTTTCACTCTATTAGACCTATATATCTGAC

CAGGGTCCTATTCCAAGACAACTCTTCTACTCTTCCAGCAGACTCTTATAGAAAGAAAGATTCT

GGGGTCCAAGAAAGCAGTACTTTCTTACAAGGAGCCAAAAAAAATAACCTTTCTTTAGCACTTC

TAACCTTGGAGTGAACTGGTGATCAAAGAGAGGTTGGCTCCCTGGGGACAAGTGCCACAAATTC

AGTCAACTACAAGAAAGTTGAGAACACTGTTCTCCCGAAACCAAGCTTGAATTCAGCTGACGTG

CCTCGGACCGCTAGGAACCCCTAGTGATGGAGTTGGCCACTCCCTCTCTGCGCGCTCGCTCGCT

CACTGAGGCCGGGCGACCAAAGGTCGCCCGACGCCCGGGCTTTGCCCGGGCGGCCTCAGTGAGC

GAGCGAGCGCGCAGCTGCCTGCAGG

Exemplary Construct 2

(SEQ ID NO: 10)

CCTGCAGGCAGCTGCGCGCTCGCTCGCTCACTGAGGCCGCCCGGGCGTCGGGCGACCTTTGGTC

GCCCGGCCTCAGTGAGCGAGCGAGCGCGCAGAGAGGGAGTGGCCAACTCCATCACTAGGGGTTC

CTGCGGCCGCACGCGTGACATTGATTATTGACTAGTTATTAATAGTAATCAATTACGGGGTCAT

TAGTTCATAGCCCATATATGGAGTTCCGCGTTACATAACTTACGGTAAATGGCCCGCCTGGCTG

ACCGCCCAACGACCCCCGCCCATTGACGTCAATAATGACGTATGTTCCCATAGTAACGCCAATA

GGGACTTTCCATTGACGTCAATGGGTGGACTATTTACGGTAAACTGCCCACTTGGCAGTACATC

AAGTGTATCATATGCCAAGTACGCCCCCTATTGACGTCAATGACGGTAAATGGCCCGCCTGGCA

TTATGCCCAGTACATGACCTTATGGGACTTTCCTACTTGGCAGTACATCTACGTATTAGTCATC

GCTATTACCATGGGTCGAGGTGAGCCCCACGTTCTGCTTCACTCTCCCCATCTCCCCCCCCTCC

CCACCCCCAATTTTGTATTTATTTATTTTTTAATTATTTTGTGCAGCGATGGGGGCGGGGGGGG

GGGGGGCGCGCGCCAGGCGGGGCGGGGCGGGGCGAGGGGCGGGGCGGGGCGAGGCGGAGAGGTG

CGGCGGCAGCCAATCAGAGCGGCGCGCTCCGAAAGTTTCCTTTTATGGCGAGGCGGCGGCGGCG

GCGGCCCTATAAAAAGCGAAGCGCGCGGCGGGCGGGAGTCGCTGCGTTGCCTTCGCCCCGTGCC

CCGCTCCGCGCCGCCTCGCGCCGCCCGCCCCGGCTCTGACTGACCGCGTTACTCCCACAGGTGA

GCGGGCGGGACGGCCCTTCTCCTCCGGGCTGTAATTAGCGCTTGGTTTAATGACGGCTCGTTTC

TTTTCTGTGGCTGCGTGAAAGCCTTAAAGGGCTCCGGGAGGGCCCTTTGTGCGGGGGGGAGCGG

CTCGGGGGGTGCGTGCGTGTGTGTGTGCGTGGGGAGCGCCGCGTGCGGCCCGCGCTGCCCGGCG

GCTGTGAGCGCTGCGGGCGCGGCGCGGGGCTTTGTGCGCTCCGCGTGTGCGCGAGGGGAGCGCG

GCCGGGGGCGGTGCCCCGCGGTGCGGGGGGGCTGCGAGGGGAACAAAGGCTGCGTGCGGGGTGT

GTGCGTGGGGGGGTGAGCAGGGGGTGTGGGCGCGGCGGTCGGGCTGTAACCCCCCCCTGCACCC

CCCTCCCCGAGTTGCTGAGCACGGCCCGGCTTCGGGTGCGGGGCTCCGTGCGGGGCGTGGCGCG

GGGCTCGCCGTGCCGGGCGGGGGGTGGCGGCAGGTGGGGGTGCCGGGCGGGGCGGGGCCGCCTC

GGGCCGGGGAGGGCTCGGGGGAGGGGCGCGGCGGCCCCCGGAGCGCCGGCGGCTGTCGAGGCGC

GGCGAGCCGCAGCCATTGCCTTTTATGGTAATCGTGCGAGAGGGCGCAGGGACTTCCTTTGTCC

CAAATCTGTGCGGAGCCGAAATCTGGGAGGCGCCGCCGCACCCCCTCTAGCGGGCGCGGGGCGA

AGCGGTGCGGCGCCGGCAGGAAGGAAATGGGCGGGGAGGGCCTTCGTGCGTCGCCGCGCCGCCG

TCCCCTTCTCCCTCTCCAGCCTCGGGGCTGTCCGCGGGGGGACGGCTGCCTTCGGGGGGGACGG

-continued

GGCAGGGCGGGGTTCGGCTTCTGGCGTGTGACCGGCGGCTCTAGAGCCTCTGCTAACCATGTTC

ATGCCTTCTTCTTTTTCCTACAGCTCCTGGGCAACGTGCTGGTTATTGTGACCGGTGCCACCAT

GAGAAAACATGTACTAGCTGCATCCTTTTCTATGCTCTCCCTGCTGGTGATAATGGGAGATACA

GACAGTAAAACGGACAGCTCATTCATAATGGACTCGGACCCTCGACGCTGCATGAGGCACCACT

ATGTGGATTCTATCAGTCACCCATTGTACAAGTGTAGCTCAAAGATGGTGCTCCTGGCCAGGTG

CGAGGGGCACTGCAGCCAGGCGTCACGCTCCGAGCCTTTGGTGTCGTTCAGCACTGTCCTCAAG

CAACCCTTCCGTTCCTCCTGTCACTGCTGCCGGCCCCAGACTTCCAAGCTGAAGGCACTGCGGC

TGCGATGCTCAGGGGGCATGCGACTCACTGCCACCTACCGATACATCCTCTCCTGTCACTGCGA

GGAATGCAATTCCTAAGAGCTCCTGTGCCTTCTAGTTGCCAGCCATCTGTTGTTTGCCCCTCCC

CCGTGCCTTCCTTGACCCTGGAAGGTGCCACTCCCACTGTCCTTTCCTAATAAAATGAGGAAAT

TGCATCGCATTGTCTGAGTAGGTGTCATTCTATTCTGGGGGGTGGGGTGGGGCAGGACAGCAAG

GGGGAGGATTGGGAAGACAATAGCAGGCATGCTGGGGATGCGGTGGGCTCTATGGGTTGACTAA

AGATTGAACCTTATTCAAAGTTAGACTCTCTTTGTTAAAGACAAACAAAACTTCCAATAATTGA

GCAACTAATAGAAAGACTCAACTTGTGAGCGAGTACTTATTAATTGAGAATAGTGAGTGAGTCT

GGCAAAATATATTAGAAAGTGACACTGAGTTTAAAAAAGTGACACCTTTGATTCTGAACAGTGA

ACTTTGAGACTGAAAAACTACAGCTTTGAGGCTAAATACTTGATCAAATAAAACTAGTTAGTCA

AAAAACTGAGTGAAAGTCCAACAGAAAAAAGAGGGCCCACTTCCACCAGTGACACAAAATCCAG

ATTGATCGTTCTTTAAGTGACTATTCTTGCCAGAATCAGCAAGGTGGATACAAAGGACTCTGAG

AAAGAACTCTCTGAACTCTGGGCAAGGCCCCAGTCCAAAGCAATTAGTATCCTTAGGACCAGAA

AAATCTGTGGAAGGTCAGAATTTCTTGTCTGAGAAAAACAAAGCAATTCAGACTCCCACTAGAA

GAAACAGAACTTGAAAAAAGGATAATTGTGGTGAACACCTCAACCCAGTGGTCCAAAAACTGAA

AAACTTTGACCCCGAGCACCCTCACACAGATAGACTACTGAAAGAAGGAGAAAGGGGCACTTAC

TCAGTCTCCCTTATCAGATTGCCTTACGAGGAGTAGTAGACTCCCTCAAGCAAATAGATCTCAC

TTACCACTTGCAAAGGTATACTACTTTCACTCTATTAGACCTATATATCTGACCAGGGTCCTAT

TCCAAGACAACTCTTCTAGTCTTCCAGCAGACTCTTATAGAAAGAAAGATTCTGGGGTCCAAGA

AAGCAGTACTTTCTTACAAGGAGCCAAAAAAAATAACCTTTCTTTAGCACTTCTAACCTTGGAG

TGAACTGGTGATCAAAGAGAGGTTGGCTCCCTGGGGACAAGTGCCACAAATTCAGTCAACTACA

AGAAAGTTGAGAACACTGTTCTCCCGAAACCAAGCTTGAATTCAGCTGACGTGCCTCGGACCGC

TAGGAACCCCTAGTGATGGAGTTGGCCACTCCCTCTCTGCGCGCTCGCTCGCTCACTGAGGCCG

GGCGACCAAAGGTCGCCCGACGCCCGGGCTTTGCCCGGGCGGCCTCAGTGAGCGAGCGAGCGCG

CAGCTGCCTGCAGG

Exemplary Construct 3

(SEQ ID NO: 11)

CCTGCAGGCAGCTGCGCGCTCGCTCGCTCACTGAGGCCGCCCGGGCGTCGGGCGACCTTTGGTC

GCCCGGCCTCAGTGAGCGAGCGAGCGCGCAGAGAGGGAGTGGCCAACTCCATCACTAGGGGTTC

CTGCGGCCGCACGCGTGACATTGATTATTGACTAGTTATTAATAGTAATCAATTACGGGGTCAT

TAGTTCATAGCCCATATATGGAGTTCCGCGTTACATAACTTACGGTAAATGGCCCGCCTGGCTG

ACCGCCCAACGACCCCCGCCCATTGACGTCAATAATGACGTATGTTCCCATAGTAACGCCAATA

GGGACTTTCCATTGACGTCAATGGGTGGACTATTTACGGTAAACTGCCCACTTGGCAGTACATC

AAGTGTATCATATGCCAAGTACGCCCCCTATTGACGTCAATGACGGTAAATGGCCCGCCTGGCA

TTATGCCCAGTACATGACCTTATGGGACTTTCCTACTTGGCAGTACATCTACGTATTAGTCATC

GCTATTACCATGGGTCGAGGTGAGCCCCACGTTCTGCTTCACTCTCCCCATCTCCCCCCCCTCC

-continued

CCACCCCCAATTTTGTATTTATTTATTTTTTAATTATTTTGTGCAGCGATGGGGGCGGGGGGG

GGGGGGCGCGCGCCAGGCGGGGCGGGGCGGGGCGAGGGGCGGGGCGGGGCGAGGCGGAGAGGTG

CGGCGGCAGCCAATCAGAGCGGCGCGCTCCGAAAGTTTCCTTTTATGGCGAGGCGGCGGCGGCG

GCGGCCCTATAAAAAGCGAAGCGCGCGGCGGGCGGGAGTCGCTGCGTTGCCTTCGCCCCGTGCC

CCGCTCCGCGCCGCCTCGCGCCGCCCGCCCCGGCTCTGACTGACCGCGTTACTCCCACAGGTGA

GCGGGCGGGACGGCCCTTCTCCTCCGGGCTGTAATTAGCGCTTGGTTTAATGACGGCTCGTTTC

TTTTCTGTGGCTGCGTGAAAGCCTTAAAGGGCTCCGGGAGGGCCCTTTGTGCGGGGGGGAGCGG

CTCGGGGGGTGCGTGCGTGTGTGTGTGCGTGGGGAGCGCCGCGTGCGGCCCGCGCTGCCCGGCG

GCTGTGAGCGCTGCGGGCGCGGCGCGGGGCTTTGTGCGCTCCGCGTGTGCGCGAGGGGAGCGCG

GCCGGGGGCGGTGCCCCGCGGTGCGGGGGGGCTGCGAGGGGAACAAAGGCTGCGTGCGGGGTGT

GTGCGTGGGGGGGTGAGCAGGGGGTGTGGGCGCGGCGGTCGGGCTGTAACCCCCCCCTGCACCC

CCCTCCCCGAGTTGCTGAGCACGGCCCGGCTTCGGGTGCGGGGCTCCGTGCGGGGCGTGGCGCG

GGGCTCGCCGTGCCGGGCGGGGGGTGGCGGCAGGTGGGGGTGCCGGGCGGGGCGGGGCCGCCTC

GGGCCGGGGAGGGCTCGGGGGAGGGGCGCGGCGGCCCCCGGAGCGCCGGCGGCTGTCGAGGCGC

GGCGAGCCGCAGCCATTGCCTTTTATGGTAATCGTGCGAGAGGGCGCAGGGACTTCCTTTGTCC

CAAATCTGTGCGGAGCCGAAATCTGGGAGGCGCCGCCGCACCCCCTCTAGCGGGCGCGGGGCGA

AGCGGTGCGGCGCCGGCAGGAAGGAAATGGGCGGGGAGGGCCTTCGTGCGTCGCCGCGCCGCCG

TCCCCTTCTCCCTCTCCAGCCTCGGGGCTGTCCGCGGGGGGACGGCTGCCTTCGGGGGGGACGG

GGCAGGGCGGGGTTCGGCTTCTGGCGTGTGACCGGCGGCTCTAGAGCCTCTGCTAACCATGTTC

ATGCCTTCTTCTTTTTCCTACAGCTCCTGGGCAACGTGCTGGTTATTGTGACCGGTGCCACCAT

GAGAAAACATGTACTAGCTGCATCCTTTTCTATGCTCTCCCTGCTGGTGATAATGGGAGATACA

GACAGTAAAACGGACAGCTCATTCATAATGGACTCGGACCCTCGACGCTGCATGAGGCACCACT

ATGTGGATTCTATCAGTCACCCATTGTACAAGTGTAGCTCAAAGATGGTGCTCCTGGCCAGGTG

CGAGGGGCACTGCAGCCAGGCGTCACGCTCCGAGCCTTTGGTGTCGTTCAGCACTGTCCTCAAG

CAACCCTTCCGTTCCTCCTGTCACTGCTGCCGGCCCCAGACTTCCAAGCTGAAGGCACTGCGGC

TGCGATGCTCAGGGGGCATGCGACTCACTGCCACCTACCGATACATCCTCTCCTGTCACTGCGA

GGAATGCAATTCCGGCTCCGGAGAGGGCAGAGGAAGTCTGCTAACATGCGGTGACGTCGAGGAG

AATCCTGGCCCAATGGAGAGCGACGAGAGCGGCCTGCCCGCCATGGAGATCGAGTGCCGCATCA

CCGGCACCCTGAACGGCGTGGAGTTCGAGCTGGTGGGCGGCGGAGAGGGCACCCCCGAGCAGGG

CCGCATGACCAACAAGATGAAGAGCACCAAAGGCGCCCTGACCTTCAGCCCCTACCTGCTGAGC

CACGTGATGGGCTACGGCTTCTACCACTTCGGCACCTACCCCAGCGGCTACGAGAACCCCTTCC

TGCACGCCATCAACAACGGCGGCTACACCAACACCCGCATCGAGAAGTACGAGGACGGCGGCGT

GCTGCACGTGAGCTTCAGCTACCGCTACGAGGCCGGCCGCGTGATCGGCGACTTCAAGGTGATG

GGCACCGGCTTCCCCGAGGACAGCGTGATCTTCACCGACAAGATCATCCGCAGCAACGCCACCG

TGGAGCACCTGCACCCCATGGGCGATAACGATCTGGATGGCAGCTTCACCCGCACCTTCAGCCT

GCGCGACGGCGGCTACTACAGCTCCGTGGTGGACAGCCACATGCACTTCAAGAGCGCCATCCAC

CCCAGCATCCTGCAGAACGGGGGCCCCATGTTCGCCTTCCGCCGCGTGGAGGAGGATCACAGCA

ACACCGAGCTGGGCATCGTGGAGTACCAGCACGCCTTCAAGACCCCGGATGCAGATGCCGGTGA

AGAATAAGGCCCGCTGCTGTGTGTGGCTTCTGGATGGGACAACTGTAGAGGCAGTTCGACCAGC

CAGGGAAAGACTGGCAAGAAAAGAGTTAAGGCAAAAAAGGATGCAACAATTCTCCCGGGACTCT

-continued

GCATATTCTAGTAATAAAGACTCTACATGCTTGTTGACAGAGAGAGATACTCTGGGAACTTCTT

TGCAGTTCCCATCTCCTTTCTCTGGTACAATTTCTTTTGGTTCATTTTCAGATTCAGGCATTTT

CCCCCTTGGCTCTCAATGCTGTTTGGGTTTCCAACAATTCAGCATTAGTGGGAAAAAGTGGGCC

CTCATACACAAGCGTGTCAGGCTGTCAGTGTTTGGTGCACGCTGGGGAAGAATTTACTTTGGAA

AGTAGAAAAGCCCAGCTTTTCCTGGGACATCTTCTGTTATTGTTGATGTTTTTTTTTACCTTGT

CATTTTGGTCTAAGGTTGCCATTGCTGCTAAAGGTTACCGATTTCAAAGTCCAGATACCAAGCA

TGTGGATATGTTTAGCTACGTTTACTCACAGCCAGCGAACTGACATTAAAATAACTAACAAACA

GATTCTTTTATGTGATGCTGGAACTCTTGACAGCTATAATTATTATTCAGAAATGACTTTTTGA

AAGTAAAAGCAGCATAAAGAATTTGTCACAGGAAGGCTGTCTCAGATAAATTATGGTAAAATTT

TGTAAGGGAGCAGACTTTTAAAGACTTGCACAAATACGGATCCTGCACTGACTCTGGAAAAGGC

ATATATGTACTAGTGGCATGGAGAATGCACCATACTCATGCATGCAAATTAGACAACCAAGTAT

GAATCTATTTGTGGGTGTGCTATAGCTTTAGCCGTGTCACGGGCATCATTCTCTAATATCCACT

TGTCCATGTGAAACATGTTGCCAAAATGGTGGCCTGGCTTGTCTTCTGAACGTTTGGTTCAAAT

GTGTTTTGGTCCTGGAGGCTCAAATTTTGAGTTATTCCCACGTTTTGAAATAAAAAGAGTATAT

TCAAAAGAGCTCCTGTGCCTTCTAGTTGCCAGCCATCTGTTGTTTGCCCCTCCCCCGTGCCTTC

CTTGACCCTGGAAGGTGCCACTCCCACTGTCCTTTCCTAATAAAATGAGGAAATTGCATCGCAT

TGTCTGAGTAGGTGTCATTCTATTCTGGGGGGTGGGGTGGGGCAGGACAGCAAGGGGGAGGATT

GGGAAGACAATAGCAGGCATGCTGGGGATGCGGTGGGCTCTATGGAAGCTTGAATTCAGCTGAC

GTGCCTCGGACCGCTAGGAACCCCTAGTGATGGAGTTGGCCACTCCCTCTCTGCGCGCTCGCTC

GCTCACTGAGGCCGGGCGACCAAAGGTCGCCCGACGCCCGGGCTTTGCCCGGGCGGCCTCAGTG

AGCGAGCGAGCGCGCAGCTGCCTGCAGG

Exemplary Construct 4

(SEQ ID NO: 12)

CCTGCAGGCAGCTGCGCGCTCGCTCGCTCACTGAGGCCGCCCGGGCGTCGGGCGACCTTTGGTC

GCCCGGCCTCAGTGAGCGAGCGAGCGCGCAGAGAGGGAGTGGCCAACTCCATCACTAGGGGTTC

CTGCGGCCGCACGCGTGACATTGATTATTGACTAGTTATTAATAGTAATCAATTACGGGGTCAT

TAGTTCATAGCCCATATATGGAGTTCCGCGTTACATAACTTACGGTAAATGGCCCGCCTGGCTG

ACCGCCCAACGACCCCCGCCCATTGACGTCAATAATGACGTATGTTCCCATAGTAACGCCAATA

GGGACTTTCCATTGACGTCAATGGGTGGACTATTTACGGTAAACTGCCCACTTGGCAGTACATC

AAGTGTATCATATGCCAAGTACGCCCCCTATTGACGTCAATGACGGTAAATGGCCCGCCTGGCA

TTATGCCCAGTACATGACCTTATGGGACTTTCCTACTTGGCAGTACATCTACGTATTAGTCATC

GCTATTACCATGGGTCGAGGTGAGCCCCACGTTCTGCTTCACTCTCCCCATCTCCCCCCCCTCC

CCACCCCCAATTTTGTATTTATTTATTTTTTAATTATTTTGTGCAGCGATGGGGGCGGGGGGGG

GGGGGGCGCGCGCCAGGCGGGGCGGGGCGGGGCGAGGGGCGGGGCGGGGCGAGGCGGAGAGGTG

CGGCGGCAGCCAATCAGAGCGGCGCGCTCCGAAAGTTTCCTTTTATGGCGAGGCGGCGGCGGCG

GCGGCCCTATAAAAAGCGAAGCGCGCGGCGGGCGGGAGTCGCTGCGTTGCCTTCGCCCCGTGCC

CCGCTCCGCGCCGCCTCGCGCCGCCCGCCCCGGCTCTGACTGACCGCGTTACTCCCACAGGTGA

GCGGGCGGGACGGCCCTTCTCCTCCGGGCTGTAATTAGCGCTTGGTTTAATGACGGCTCGTTTC

TTTTCTGTGGCTGCGTGAAAGCCTTAAAGGGCTCCGGGAGGGCCCTTTGTGCGGGGGGGAGCGG

CTCGGGGGGTGCGTGCGTGTGTGTGTGCGTGGGGAGCGCCGCGTGCGGCCCGCGCTGCCCGGCG

GCTGTGAGCGCTGCGGGCGCGGCGCGGGGCTTTGTGCGCTCCGCGTGTGCGCGAGGGGAGCGCG

GCCGGGGGCGGTGCCCCGCGGTGCGGGGGGGCTGCGAGGGGAACAAAGGCTGCGTGCGGGGTGT

-continued

GTGCGTGGGGGGGTGAGCAGGGGGTGTGGGCGCGGCGGTCGGGCTGTAACCCCCCCCTGCACCC

CCCTCCCCGAGTTGCTGAGCACGGCCCGGCTTCGGGTGCGGGGCTCCGTGCGGGGCGTGGCGCG

GGGCTCGCCGTGCCGGGCGGGGGGTGGCGGCAGGTGGGGGTGCCGGGCGGGGCGGGGCCGCCTC

GGGCCGGGGAGGGCTCGGGGGAGGGGCGCGGCGGCCCCCGGAGCGCCGGCGGCTGTCGAGGCGC

GGCGAGCCGCAGCCATTGCCTTTTATGGTAATCGTGCGAGAGGGCGCAGGGACTTCCTTTGTCC

CAAATCTGTGCGGAGCCGAAATCTGGGAGGCGCCGCCGCACCCCCTCTAGCGGGCGCGGGGCGA

AGCGGTGCGGCGCCGGCAGGAAGGAAATGGGCGGGGAGGGCCTTCGTGCGTCGCCGCGCCGCCG

TCCCCTTCTCCCTCTCCAGCCTCGGGGCTGTCCGCGGGGGGACGGCTGCCTTCGGGGGGGACGG

GGCAGGGCGGGGTTCGGCTTCTGGCGTGTGACCGGCGGCTCTAGAGCCTCTGCTAACCATGTTC

ATGCCTTCTTCTTTTTCCTACAGCTCCTGGGCAACGTGCTGGTTATTGTGACCGGTGCCACCAT

GAGAAAACATGTACTAGCTGCATCCTTTTCTATGCTCTCCCTGCTGGTGATAATGGGAGATACA

GACAGTAAAACGGACAGCTCATTCATAATGGACTCGGACCCTCGACGCTGCATGAGGCACCACT

ATGTGGATTCTATCAGTCACCCATTGTACAAGTGTAGCTCAAAGATGGTGCTCCTGGCCAGGTG

CGAGGGGCACTGCAGCCAGGCGTCACGCTCCGAGCCTTTGGTGTCGTTCAGCACTGTCCTCAAG

CAACCCTTCCGTTCCTCCTGTCACTGCTGCCGGCCCCAGACTTCCAAGCTGAAGGCACTGCGGC

TGCGATGCTCAGGGGGCATGCGACTCACTGCCACCTACCGATACATCCTCTCCTGTCACTGCGA

GGAATGCAATTCCGGCTCCGGAGAGGGCAGAGGAAGTCTGCTAACATGCGGTGACGTCGAGGAG

AATCCTGGCCCAATGGTGAGCAAGGGCGAGGAGCTGTTCACCGGGGTGGTGCCCATCCTGGTCG

AGCTGGACGGCGACGTAAACGGCCACAAGTTCAGCGTGTCCGGCGAGGGCGAGGGCGATGCCAC

CTACGGCAAGCTGACCCTGAAGTTCATCTGCACCACCGGCAAGCTGCCCGTGCCCTGGCCCACC

CTCGTGACCACCCTGACCTACGGCGTGCAGTGCTTCAGCCGCTACCCCGACCACATGAAGCAGC

ACGACTTCTTCAAGTCCGCCATGCCCGAAGGCTACGTCCAGGAGCGCACCATCTTCTTCAAGGA

CGACGGCAACTACAAGACCCGCGCCGAGGTGAAGTTCGAGGGCGACACCCTGGTGAACCGCATC

GAGCTGAAGGGCATCGACTTCAAGGAGGACGGCAACATCCTGGGGCACAAGCTGGAGTACAACT

ACAACAGCCACAACGTCTATATCATGGCCGACAAGCAGAAGAACGGCATCAAGGTGAACTTCAA

GATCCGCCACAACATCGAGGACGGCAGCGTGCAGCTCGCCGACCACTACCAGCAGAACACCCCC

ATCGGCGACGGCCCCGTGCTGCTGCCCGACAACCACTACCTGAGCACCCAGTCCGCCCTGAGCA

AAGACCCCAACGAGAAGCGCGATCACATGGTCCTGCTGGAGTTCGTGACCGCCGCCGGGATCAC

TCTCGGCATGGACGAGCTGTACAAGTAATAAGGCCCGCTGCTGTGTGTGGCTTCTGGATGGGAC

AACTGTAGAGGCAGTTCGACCAGCCAGGGAAAGACTGGCAAGAAAAGAGTTAAGGCAAAAAAGG

ATGCAACAATTCTCCCGGGACTCTGCATATTCTAGTAATAAAGACTCTACATGCTTGTTGACAG

AGAGAGATACTCTGGGAACTTCTTTGCAGTTCCCATCTCCTTTCTCTGGTACAATTTCTTTTGG

TTCATTTTCAGATTCAGGCATTTTCCCCCTTGGCTCTCAATGCTGTTTGGGTTTCCAACAATTC

AGCATTAGTGGGAAAAAGTGGGCCCTCATACACAAGCGTGTCAGGCTGTCAGTGTTTGGTGCAC

GCTGGGGAAGAATTTACTTTGGAAAGTAGAAAAGCCCAGCTTTTCCTGGGACATCTTCTGTTAT

TGTTGATGTTTTTTTTACCTTGTCATTTTGGTCTAAGGTTGCCATTGCTGCTAAAGGTTACCG

ATTTCAAAGTCCAGATACCAAGCATGTGGATATGTTTAGCTACGTTTACTCACAGCCAGCGAAC

TGACATTAAAATAACTAACAAACAGATTCTTTTATGTGATGCTGGAACTCTTGACAGCTATAAT

TATTATTCAGAAATGAGTTTTTGAAAGTAAAAGCAGCATAAAGAATTTGTCACAGGAAGGCTGT

CTCAGATAAATTATGGTAAAATTTTGTAAGGGAGCAGACTTTTAAAGACTTGCACAAATACGGA

-continued

TCCTGCACTGACTCTGGAAAAGGCATATATGTACTAGTGGCATGGAGAATGCACCATACTCATG

CATGCAAATTAGACAACCAAGTATGAATCTATTTGTGGGTGTGCTATAGCTTTAGCCGTGTCAC

GGGCATCATTCTCTAATATCCACTTGTCCATGTGAAACATGTTGCCAAAATGGTGGCCTGGCTT

GTCTTCTGAACGTTTGGTTCAAATGTGTTTTGGTCCTGGAGGCTCAAATTTTGAGTTATTCCCA

CGTTTTGAAATAAAAAGAGTATATTCAAAAGAGCTCCTGTGCCTTCTAGTTGCCAGCCATCTGT

TGTTTGCCCCTCCCCCGTGCCTTCCTTGACCCTGGAAGGTGCCACTCCCACTGTCCTTTCCTAA

TAAAATGAGGAAATTGCATCGCATTGTCTGAGTAGGTGTCATTCTATTCTGGGGGGTGGGGTGG

GGCAGGACAGCAAGGGGGAGGATTGGGAAGACAATAGCAGGCATGCTGGGGATGCGGTGGGCTC

TATGGAAGCTTGAATTCAGCTGACGTGCCTCGGACCGCTAGGAACCCCTAGTGATGGAGTTGGC

CACTCCCTCTCTGCGCGCTCGCTCGCTCACTGAGGCCGGGCGACCAAAGGTCGCCCGACGCCCG

GGCTTTGCCCGGGCGGCCTCAGTGAGCGAGCGAGCGCGCAGCTGCCTGCAGG

Exemplary Construct 5

(SEQ ID NO: 13)

CCTGCAGGCAGCTGCGCGCTCGCTCGCTCACTGAGGCCGCCCGGGCGTCGGGCGACCTTTGGTC

GCCCGGCCTCAGTGAGCGAGCGAGCGCGCAGAGAGGGAGTGGCCAACTCCATCACTAGGGGTTC

CTGCGGCCGCACGCGTGACATTGATTATTGACTAGTTATTAATAGTAATCAATTACGGGGTCAT

TAGTTCATAGCCCATATATGGAGTTCCGCGTTACATAACTTACGGTAAATGGCCCGCCTGGCTG

ACCGCCCAACGACCCCCGCCCATTGACGTCAATAATGACGTATGTTCCCATAGTAACGCCAATA

GGGACTTTCCATTGACGTCAATGGGTGGACTATTTACGGTAAACTGCCCACTTGGCAGTACATC

AAGTGTATCATATGCCAAGTACGCCCCCTATTGACGTCAATGACGGTAAATGGCCCGCCTGGCA

TTATGCCCAGTACATGACCTTATGGGACTTTCCTACTTGGCAGTACATCTACGTATTAGTCATC

GCTATTACCATGGGTCGAGGTGAGCCCCACGTTCTGCTTCACTCTCCCCATCTCCCCCCCCTCC

CCACCCCCAATTTTGTATTTATTTATTTTTTAATTATTTTGTGCAGCGATGGGGGCGGGGGGGG

GGGGGGCGCGCGCCAGGCGGGGCGGGGCGGGGCGAGGGGCGGGGCGGGGCGAGGCGGAGAGGTG

CGGCGGCAGCCAATCAGAGCGGCGCGCTCCGAAAGTTTCCTTTTATGGCGAGGCGGCGGCGGCG

GCGGCCCTATAAAAAGCGAAGCGCGCGGCGGGCGGGAGTCGCTGCGTTGCCTTCGCCCCGTGCC

CCGCTCCGCGCCGCCTCGCGCCGCCCGCCCCGGCTCTGACTGACCGCGTTACTCCCACAGGTGA

GCGGGCGGGACGGCCCTTCTCCTCCGGGCTGTAATTAGCGCTTGGTTTAATGACGGCTCGTTTC

TTTTCTGTGGCTGCGTGAAAGCCTTAAAGGGCTCCGGGAGGGCCCTTTGTGCGGGGGGGAGCGG

CTCGGGGGGTGCGTGCGTGTGTGTGTGCGTGGGGAGCGCCGCGTGCGGCCCGCGCTGCCCGGCG

GCTGTGAGCGCTGCGGGCGCGGCGCGGGGCTTTGTGCGCTCCGCGTGTGCGCGAGGGGAGCGCG

GCCGGGGGCGGTGCCCCGCGGTGCGGGGGGGCTGCGAGGGGAACAAAGGCTGCGTGCGGGGTGT

GTGCGTGGGGGGGTGAGCAGGGGGTGTGGGCGCGGCGGTCGGGCTGTAACCCCCCCCTGCACCC

CCCTCCCCGAGTTGCTGAGCACGGCCCGGCTTCGGGTGCGGGGCTCCGTGCGGGGCGTGGCGCG

GGGCTCGCCGTGCCGGGCGGGGGGTGGCGGCAGGTGGGGGTGCCGGGCGGGGCGGGGCCGCCTC

GGGCCGGGGAGGGCTCGGGGGAGGGGCGCGGCGGCCCCCGGAGCGCCGGCGGCTGTCGAGGCGC

GGCGAGCCGCAGCCATTGCCTTTTATGGTAATCGTGCGAGAGGGCGCAGGGACTTCCTTTGTCC

CAAATCTGTGCGGAGCCGAAATCTGGGAGGCGCCGCCGCACCCCCTCTAGCGGGCGCGGGGCGA

AGCGGTGCGGCGCCGGCAGGAAGGAAATGGGCGGGGAGGGCCTTCGTGCGTCGCCGCGCCGCCG

TCCCCTTCTCCCTCTCCAGCCTCGGGGCTGTCCGCGGGGGGACGGCTGCCTTCGGGGGGGACGG

GGCAGGGCGGGGTTCGGCTTCTGGCGTGTGACCGGCGGCTCTAGAGCCTCTGCTAACCATGTTC

ATGCCTTCTTCTTTTTCCTACAGCTCCTGGGCAACGTGCTGGTTATTGTGACCGGTAAGATGCT

-continued

CCGTGGAAGGGAGCCGAGCGGTGGGCAGAGGCTGAGTCCCCGATAACGAGCGCCTCACATTTCC

GTGGCATTCCCATTTGCTAGTGCGCTGCTGCGGCCGCACGCCTGATTGATATATGACTGCAATG

GCACTTTTCCATTTGACATTCTCTCTCTCTCTCCCTCTCTCTCTCCCTCTCTCTCCCT

CTCTCTCTCTCCCTGTGTCGCTTAAACAACAGTCCTAACTTTTGTGTGTTGCAAATATAAAAGG

CAAGCCATGTGACAGAGGGACAGAAGAACAAAAGCATTTGGAAGTAACAGGACCTCTTTCTAGC

TCTCAGAAAAGTCTGAGAAGAAAGGAGCCCTGCGTTCCCCTAAGCTGTGCAGCAGATACTGTGA

TGATGGATTGCAAGTGCAAAGAGTAAGACAAAACTCCAGCACATAAAGGACAATGACAACCAGA

AAGCTTCAGCCCGATCCTGCCCTTTCCTTGAACGGGACTGGATCCTAGGAGGTGAAGCCATTTC

CAATTTTTTGTCCTCTGCCTCCCTCTGCTGTTCTTCTAGAGAAGTTTTTCCTTACAACAGCCAC

CATGAGAAAACATGTACTAGCTGCATCCTTTTCTATGCTCTCCCTGCTGGTGATAATGGGAGAT

ACAGACAGTAAAACGGACAGCTCATTCATAATGGACTCGGACCCTCGACGCTGCATGAGGCACC

ACTATGTGGATTCTATCAGTCACCCATTGTACAAGTGTAGCTCAAAGATGGTGCTCCTGGCCAG

GTGCGAGGGGCACTGCAGCCAGGCGTCACGCTCCGAGCCTTTGGTGTCGTTCAGCACTGTCCTC

AAGCAACCCTTCCGTTCCTCCTGTCACTGCTGCCGGCCCCAGACTTCCAAGCTGAAGGCACTGC

GGCTGCGATGCTCAGGGGGCATGCGACTCACTGCCACCTACCGATACATCCTCTCCTGTCACTG

CGAGGAATGCAATTCCTAAGGCCCGCTGCTGTGTGTGGCTTCTGGATGGGACAACTGTAGAGGC

AGTTCGACCAGCCAGGGAAAGACTGGCAAGAAAAGAGTTAAGGCAAAAAAGGATGCAACAATTC

TCCCGGGACTCTGCATATTCTAGTAATAAAGACTCTAGATGCTTGTTGACAGAGAGAGATACTC

TGGGAACTTCTTTGCAGTTCCCATCTCCTTTCTCTGGTACAATTTCTTTTGGTTCATTTTCAGA

TTCAGGCATTTTCCCCCTTGGCTCTCAATGCTGTTTGGGTTTCCAACAATTCAGCATTAGTGGG

AAAAAGTGGGCCCTCATACACAAGCGTGTCAGGCTGTCAGTGTTTGGTGCACGCTGGGGAAGAA

TTTACTTTGGAAAGTAGAAAAGCCCAGCTTTTCCTGGGACATCTTCTGTTATTGTTGATGTTTT

TTTTTACCTTGTCATTTTGGTCTAAGGTTGCCATTGCTGCTAAAGGTTACCGATTTCAAAGTCC

AGATACCAAGCATGTGGATATGTTTAGCTACGTTTACTCACAGCCAGCGAACTGACATTAAAAT

AACTAACAAACAGATTCTTTTATGTGATGCTGGAACTCTTGACAGCTATAATTATTATTCAGAA

ATGACTTTTTGAAAGTAAAAGCAGCATAAAGAATTTGTCACAGGAAGGCTGTCTCAGATAAATT

ATGGTAAAATTTTGTAAGGGAGCAGACTTTTAAAGACTTGCACAAATACGGATCCTGCACTGAC

TCTGGAAAAGGCATATATGTACTAGTGGCATGGAGAATGCACCATACTCATGCATGCAAATTAG

ACAACCAAGTATGAATCTATTTGTGGGTGTGCTATAGCTTTAGCCGTGTCACGGGCATCATTCT

CTAATATCCACTTGTCCATGTGAAACATGTTGCCAAAATGGTGGCCTGGCTTGTCTTCTGAACG

TTTGGTTCAAATGTGTTTTGGTCCTGGAGGCTCAAATTTTGAGTTATTCCCACGTTTTGAAATA

AAAAGAGTATATTCAAAAGAGCTCCTGTGCCTTCTAGTTGCCAGCCATCTGTTGTTTGCCCCTC

CCCCGTGCCTTCCTTGACCCTGGAAGGTGCCACTCCCACTGTCCTTTCCTAATAAAATGAGGAA

ATTGCATCGCATTGTCTGAGTAGGTGTCATTCTATTCTGGGGGGTGGGGTGGGGCAGGACAGCA

AGGGGGAGGATTGGGAAGACAATAGCAGGCATGCTGGGGATGCGGTGGGCTCTATGGCAATTCA

GACTCCCACTAGAAGAAACAGAACTTGAAAAAAGGATAATTGTGGTGAACACCTCAACCCAGTG

GTCCAAAAACTGAAAAACTTTGACCCCGAGCACCCTCACACAGATAGACTACTGAAAGAAGGAG

AAAGGGGCACTTACTCAGTCTCCCTTATCAGATTGCCTTACGAGGAGTACTAGACTCCCTCAAG

CAAATAGATCTCACTTACCACTTGCAAAGGTATACTACTTTCACTCTATTAGACCTATATATCT

GAGGAGGGTCCTATTCCAAGACAACTCTTCTACTCTTCGAGCAGACTCTTATAGAAAGAAAGAT

-continued

TCTGGGGTCCAAGAAAGCAGTACTTTCTTACAAGGAGCCAAAAAAAATAACCTTTCTTTAGCAC

TTCTAACCTTGGAGTGAACTGGTGATCAAAGAGAGGTTGGCTCCCTGGGGACAAGTGCCACAAA

TTCAGTCAACTACAAGAAAGTTGAGAACACTGTTCTCCCGAAACCAAGCTTGAATTCAGCTGAC

GTGCCTCGGACCGCTAGGAACCCCTAGTGATGGAGTTGGCCACTCCCTCTCTGCGCGCTCGCTC

GCTCACTGAGGCCGGGCGACCAAAGGTCGCCCGACGCCCGGGCTTTGCCCGGGCGGCCTCAGTG

AGCGAGCGAGCGCGCAGCTGCCTGCAGG

Exemplary Construct 6

(SEQ ID NO: 96)

CTGCGCGCTCGCTCGCTCACTGAGGCCGCCCGGGCGTCGGGCGACCTTTGGTCGCCCGGCCTCA

GTGAGCGAGCGAGCGCGCAGAGAGGGAGTGGCCAACTCCATCACTAGGGGTTCCTGCGGCCGCA

CGCGTGACATTGATTATTGACTAGTTATTAATAGTAATCAATTACGGGGTCATTAGTTCATAGC

CCATATATGGAGTTCCGCGTTACATAACTTACGGTAAATGGCCCGCCTGGCTGACCGCCCAACG

ACCCCCGCCCATTGACGTCAATAATGACGTATGTTCCCATAGTAACGCCAATAGGGACTTTCCA

TTGACGTCAATGGGTGGACTATTTACGGTAAACTGCCCACTTGGCAGTACATCAAGTGTATCAT

ATGCCAAGTACGCCCCCTATTGACGTCAATGACGGTAAATGGCCCGCCTGGCATTATGCCCAGT

ACATGACCTTATGGGACTTTCCTACTTGGCAGTACATCTACGTATTAGTCATCGCTATTACCAT

GGGTCGAGGTGAGCCCCACGTTCTGCTTCACTCTCCCCATCTCCCCCCCCTCCCCACCCCCAAT

TTTGTATTTATTTATTTTTTAATTATTTTGTGCAGCGATGGGGGCGGGGGGGGGGGGGGCGCGC

GCCAGGCGGGGCGGGGCGGGGCGAGGGGCGGGGCGGGGCGAGGCGGAGAGGTGCGGCGGCAGCC

AATCAGAGCGGCGCGCTCCGAAAGTTTCCTTTTATGGCGAGGCGGCGGCGGCGGCGGCCCTATA

AAAAGCGAAGCGCGCGGCGGGCGGGAGTCGCTGCGTTGCCTTCGCCCCGTGCCCCGCTCCGCGC

CGCCTCGCGCCGCCCGCCCCGGCTCTGACTGACCGCGTTACTCCCACAGGTGAGCGGGCGGGAC

GGCCCTTCTCCTCCGGGCTGTAATTAGCGCTTGGTTTAATGACGGCTCGTTTCTTTTCTGTGGC

TGCGTGAAAGCCTTAAAGGGCTCCGGGAGGGCCCTTTGTGCGGGGGGGAGCGGCTCGGGGGGTG

CGTGCGTGTGTGTGTGCGTGGGGAGCGCCGCGTGCGGCCCGCGCTGCCCGGCGGCTGTGAGCGC

TGCGGGCGCGGCGCGGGGCTTTGTGCGCTCCGCGTGTGCGCGAGGGGAGCGCGGCCGGGGGCGG

TGCCCCGCGGTGCGGGGGGGCTGCGAGGGGAACAAAGGCTGCGTGCGGGGTGTGTGCGTGGGGG

GGTGAGCAGGGGGTGTGGGCGCGGCGGTCGGGCTGTAACCCCCCCCTGCACCCCCCTCCCCGAG

TTGCTGAGCACGGCCCGGCTTCGGGTGCGGGGCTCCGTGCGGGGCGTGGCGCGGGGCTCGCCGT

GCCGGGCGGGGGGTGGCGGCAGGTGGGGGTGCCGGGCGGGGCGGGGCCGCCTCGGGCCGGGGAG

GGCTCGGGGGAGGGGCGCGGCGGCCCCCGGAGCGCCGGCGGCTGTCGAGGCGCGGCGAGCCGCA

GCCATTGCCTTTTATGGTAATCGTGCGAGAGGGCGCAGGGACTTCCTTTGTCCCAAATCTGTGC

GGAGCCGAAATCTGGGAGGCGCCGCCGCACCCCCTCTAGCGGGCGCGGGGCGAAGCGGTGCGGC

GCCGGCAGGAAGGAAATGGGCGGGGAGGGCCTTCGTGCGTCGCCGCGCCGCCGTCCCCTTCTCC

CTCTCCAGCCTCGGGGCTGTCCGCGGGGGGACGGCTGCCTTCGGGGGGGACGGGGCAGGGCGGG

GTTCGGCTTCTGGCGTGTGACCGGCGGCTCTAGAGCCTCTGCTAACCATGTTCATGCCTTCTTC

TTTTTCCTACAGCTCCTGGGCAACGTGCTGGTTATTGTGACCGGTGCCACCATGTACCGGATGC

AGCTGCTGAGCTGTATCGCCCTGTCTCTGGCCCTGGTCACCAATTCTGCCAAAGCCGCGGCGAT

CGGCATCGACCTGGGCACCACCTACTCCTGCGTGGGGGTGTTCCAACACGGCAAGGTGGAGATC

ATCGCCAACGACCAGGGCAACCGCACCACCCCCAGCTACGTGGCCTTCACGGACACCGAGCGGC

TCATCGGGGATGCGGCCAAGAACCAGGTGGCGCTGAACCCGCAGAACACCGTGTTTGACGCGAA

GCGGCTGATCGGCCGCAAGTTCGGCGACCCGGTGGTGCAGTCGGACATGAAGCACTGGCCTTTC

-continued

```
CAGGTGATCAACGACGGAGACAAGCCCAAGGTGCAGGTGAGCTACAAGGGGGAGACCAAGGCAT
TCTACCCCGAGGAGATCTCGTCCATGGTGCTGACCAAGATGAAGGAGATCGCCGAGGCGTACCT
GGGCTACCCGGTGACCAACGCGGTGATCACCGTGCCGGCCTACTTCAACGACTCGCAGCGCCAG
GCCACCAAGGATGCGGGTGTGATCGCGGGGCTCAACGTGCTGCGGATCATCAACGAGCCCACGG
CCGCCGCCATCGCCTACGGCCTGGACAGAACGGGCAAGGGGGAGCGCAACGTGCTCATCTTTGA
CCTGGGCGGGGGCACCTTCGACGTGTCCATCCTGACGATCGACGACGGCATCTTCGAGGTGAAG
GCCACGGCCGGGGACACCCACCTGGGTGGGGAGGACTTTGACAACAGGCTGGTGAACCACTTCG
TGGAGGAGTTCAAGAGAAAACACAAGAAGGACATCAGCCAGAACAAGCGAGCCGTGAGGCGGCT
GCGCACCGCCTGCGAGAGGGCCAAGAGGACCCTGTCGTCCAGCACCCAGGCCAGCCTGGAGATC
GACTCCCTGTTTGAGGGCATCGACTTCTACACGTCCATCACCAGGGCGAGGTTCGAGGAGCTGT
GCTCCGACCTGTTCCGAAGCACCCTGGAGCCCGTGGAGAAGGCTCTGCGCGACGCCAAGCTGGA
CAAGGCCCAGATTCACGACCTGGTCCTGGTCGGGGGCTCCACCCGCATCCCCAAGGTGCAGAAG
CTGCTGCAGGACTTCTTCAACGGGCGCGACCTGAACAAGAGCATCAACCCCGACGAGGCTGTGG
CCTACGGGGCGGCGGTGCAGGCGGCCATCCTGATGGGGGACAAGTCCGAGAACGTGCAGGACCT
GCTGCTGCTGGACGTGGCTCCCCTGTCGCTGGGGCTGGAGACGGCCGGAGGCGTGATGACTGCC
CTGATCAAGCGCAACTCCACCATCCCCACCAAGCAGACGCAGATCTTCACCACCTACTCCGAGA
ACCAACCCGGGGTGCTGATCCAGGTGTACGAGGGCGAGAGGGCCATGACGAAAGACAACAATCT
GTTGGGGCGCTTCGAGCTGAGCGGCATCCCTCCGGCCCCCAGGGGCGTGCCCCAGATCGAGGTG
ACCTTCGACATCGATGCCAACGGCATCCTGAACGTCACGGCCACGGACAAGAGCACCGGCAAGG
CCAACAAGATCACCATCACCAACGACAAGGGCCGCCTGAGCAAGGAGGAGATCGAGCGCATGGT
GCAGGAGGCGGAGAAGTACAAAGCGGAGGACGAGGTGCAGCGCGAGAGGGTGTCAGCCAAGAAC
GCCCTGGAGTCCTACGCCTTCAACATGAAGAGCGCCGTGGAGGATGAGGGGCTCAAGGGCAAGA
TCAGCGAGGCGGACAAGAAGAAGGTTCTGGACAAGTGTCAAGAGGTCATCTCGTGGCTGGACGC
CAACACCTTGGCCGAGAAGGACGAGTTTGAGCACAAGAGGAAGGAGCTGGAGCAGGTGTGTAAC
CCCATCATCAGCGGACTGTACCAGGGTGCCGGTGGTCCCGGGCCTGGGGGCTTCGGGGCTCAGG
GTCCCAAGGGAGGGTCTGGGTCAGGCCCCACCATTGAGGAGGTGGATTAAGAGCTCGCTGATCA
GCCTCGACTGTGCCTTCTAGTTGCCAGCCATCTGTTGTTTGCCCCTCCCCCGTGCCTTCCTTGA
CCCTGGAAGGTGCCACTCCCACTGTCCTTTCCTAATAAAATGAGGAAATTGCATCGCATTGTCT
GAGTAGGTGTCATTCTATTCTGGGGGGTGGGGTGGGGCAGGACAGCAAGGGGGAGGATTGGGAA
GACAATAGCAGGCATGCTGGGGATGCGGTGGGCTCTATGGAAGCTTGAATTCAGCTGACGTGCC
TCGGACCGCTAGGAACCCCTAGTGATGGAGTTGGCCACTCCCTCTCTGCGCGCTCGCTCGCTCA
CTGAGGCCGGGCGACCAAAGGTCGCCCGACGCCCGGGCTTTGCCCGGGCGGCCTCAGTGAGCGA
GCGAGCGCGCAG
```

| Components (5' to 3' order) | Size (nt) | Origins and Notes | Position (in construct) | SEQ ID NO |
|---|---|---|---|---|
| 5'ITR | 119 | AAV ITR (AF043303.1) | 1-119 | 116 |
| Cloning site | 14 | N/A (/NotI/MluI) | 120-133 | 117 |
| CMV enhancer | 381 | NCBI K03104.1 (140 . . . 520) | 134-514 | 118 |
| CBA promoter | 279 | NCBI X00182.1 (268 . . . 543) | 515-791 | 119 |

-continued

| Components (5' to 3' order) | Size (nt) | Origins and Notes | Position (in construct) | SEQ ID NO |
|---|---|---|---|---|
| Chimeric intron | 1013 | NCBI X00182.1 (544 . . . 1503) NCBI V00882.1 (1250 . . . 1317); XbaI cloning site | 792-1804 | 120 |
| Cloning site | 39 | N/A; AgeI | 1805-1843 | 121 |
| IL2ss | 60 | NCBI AAB86861.1 | 1844-1903 | 122 |
| Hsp70 | 1920 | NCBI NM_005345 | 1904-3823 | 123 |

-continued

| Components (5' to 3' order) | Size (nt) | Origins and Notes | Position (in construct) | SEQ ID NO |
|---|---|---|---|---|
| Cloning site | 24 | Stop codon/SacI | 3824-3847 | 124 |
| BGHpA | 225 | NCBI M57764.1 (2326 . . . 2550); termination site | 3848-4072 | 125 |
| Cloning site | 34 | N/A; HindIII/EcoRI/PvuII/RsrII | 4073-4106 | 126 |
| 3'ITR | 130 | AAV ITR (AF043303.1) | 4107-4236 | 127 |

Exemplary Construct 7

(SEQ ID NO: 97)

```
CTGCGCGCTCGCTCGCTCACTGAGGCCGCCCGGGCGTCGGGCGACCTTTGGTCGCCCGGCCTCA

GTGAGCGAGCGAGCGCGCAGAGAGGGAGTGGCCAACTCCATCACTAGGGGTTCCTGCGGCCGCA

CGCGTGACATTGATTATTGACTAGTTATTAATAGTAATCAATTACGGGGTCATTAGTTCATAGC

CCATATATGGAGTTCCGCGTTACATAACTTACGGTAAATGGCCCGCCTGGCTGACCGCCCAACG

ACCCCCGCCCATTGACGTCAATAATGACGTATGTTCCCATAGTAACGCCAATAGGGACTTTCCA

TTGACGTCAATGGGTGGACTATTTACGGTAAACTGCCCACTTGGCAGTACATCAAGTGTATCAT

ATGCCAAGTACGCCCCCTATTGACGTCAATGACGGTAAATGGCCCGCCTGGCATTATGCCCAGT

ACATGACCTTATGGGACTTTCCTACTTGGCAGTACATCTACGTATTAGTCATCGCTATTACCAT

GGGTCGAGGTGAGCCCCACGTTCTGCTTCACTCTCCCCATCTCCCCCCCCTCCCCACCCCCAAT

TTTGTATTTATTTATTTTTTAATTATTTTGTGCAGCGATGGGGGCGGGGGGGGGGGGGGCGCGC

GCCAGGCGGGGCGGGGCGGGGCGAGGGGCGGGGCGGGGCGAGGCGGAGAGGTGCGGCGGCAGCC

AATCAGAGCGGCGCGCTCCGAAAGTTTCCTTTTATGGCGAGGCGGCGGCGGCGGCGGCCCTATA

AAAAGCGAAGCGCGCGGCGGGCGGGAGTCGCTGCGTTGCCTTCGCCCCGTGCCCCGCTCCGCGC

CGCCTCGCGCCGCCCGCCCCGGCTCTGACTGACCGCGTTACTCCCACAGGTGAGCGGGCGGGAC

GGCCCTTCTCCTCCGGGCTGTAATTAGCGCTTGGTTTAATGACGGCTCGTTTCTTTTCTGTGGC

TGCGTGAAAGCCTTAAAGGGCTCCGGGAGGGCCCTTTGTGCGGGGGGGAGCGGCTCGGGGGGTG

CGTGCGTGTGTGTGTGCGTGGGGAGCGCCGCGTGCGGCCCGCGCTGCCCGGCGGCTGTGAGCGC

TGCGGGCGCGGCGCGGGGCTTTGTGCGCTCCGCGTGTGCGCGAGGGGAGCGCGGCCGGGGGCGG

TGCCCCGCGGTGCGGGGGGGCTGCGAGGGGAACAAAGGCTGCGTGCGGGGTGTGTGCGTGGGGG

GGTGAGCAGGGGGTGTGGGCGCGGCGGTCGGGCTGTAACCCCCCCCTGCACCCCCCTCCCCGAG

TTGCTGAGCACGGCCCGGCTTCGGGTGCGGGGCTCCGTGCGGGGCGTGGCGCGGGGCTCGCCGT

GCCGGGCGGGGGGTGGCGGCAGGTGGGGGTGCCGGGCGGGGCGGGGCCGCCTCGGGCCGGGGAG

GGCTCGGGGGAGGGGCGCGGCGGCCCCCGGAGCGCCGGCGGCTGTCGAGGCGCGGCGAGCCGCA

GCCATTGCCTTTTATGGTAATCGTGCGAGAGGGCGCAGGGACTTCCTTTGTCCCAAATCTGTGC

GGAGCCGAAATCTGGGAGGCGCCGCCGCACCCCCTCTAGCGGGCGCGGGGCGAAGCGGTGCGGC

GCCGGCAGGAAGGAAATGGGCGGGGAGGGCCTTCGTGCGTCGCCGCGCCGCCGTCCCCTTCTCC

CTCTCCAGCCTCGGGGCTGTCCGCGGGGGGACGGCTGCCTTCGGGGGGGACGGGGCAGGGCGGG

GTTCGGCTTCTGGCGTGTGACCGGCGGCTCTAGAGCCTCTGCTAACCATGTTCATGCCTTCTTC

TTTTTCCTACAGCTCCTGGGCAACGTGCTGGTTATTGTGACCGGTGCCACCATGGCCAAAGCCG

CGGCGATCGGCATCGACCTGGGCACCACCTACTCCTGCGTGGGGGTGTTCCAACACGGCAAGGT

GGAGATCATCGCCAACGACCAGGGCAACCGCACCACCCCCAGCTACGTGGCCTTCACGGACACC

GAGCGGCTCATCGGGGATGCGGCCAAGAACCAGGTGGCGCTGAACCCGCAGAACACCGTGTTTG

ACGCGAAGCGGCTGATCGGCCGCAAGTTCGGCGACCCGGTGGTGCAGTCGGACATGAAGCACTG

GCCTTTCCAGGTGATCAACGACGGAGACAAGCCCAAGGTGCAGGTGAGCTACAAGGGGGAGACC
```

-continued

```
AAGGCATTCTACCCCGAGGAGATCTCGTCCATGGTGCTGACCAAGATGAAGGAGATCGCCGAGG

CGTACCTGGGCTACCCGGTGACCAACGCGGTGATCACCGTGCCGGCCTACTTCAACGACTCGCA

GCGCCAGGCCACCAAGGATGCGGGTGTGATCGCGGGGCTCAACGTGCTGCGGATCATCAACGAG

CCCACGGCCGCCGCCATCGCCTACGGCCTGGACAGAACGGGCAAGGGGGAGCGCAACGTGCTCA

TCTTTGACCTGGGCGGGGGCACCTTCGACGTGTCCATCCTGACGATCGACGACGGCATCTTCGA

GGTGAAGGCCACGGCCGGGGACACCCACCTGGGTGGGGAGGACTTTGACAACAGGCTGGTGAAC

CACTTCGTGGAGGAGTTCAAGAGAAAACACAAGAAGGACATCAGCCAGAACAAGCGAGCCGTGA

GGCGGCTGCGCACCGCCTGCGAGAGGGCCAAGAGGACCCTGTCGTCCAGCACCCAGGCCAGCCT

GGAGATCGACTCCCTGTTTGAGGGCATCGACTTCTACACGTCCATCACCAGGGCGAGGTTCGAG

GAGCTGTGCTCCGACCTGTTCCGAAGCACCCTGGAGCCCGTGGAGAAGGCTCTGCGCGACGCCA

AGCTGGACAAGGCCCAGATTCACGACCTGGTCCTGGTCGGGGGCTCCACCCGCATCCCCAAGGT

GCAGAAGCTGCTGCAGGACTTCTTCAACGGGCGCGACCTGAACAAGAGCATCAACCCCGACGAG

GCTGTGGCCTACGGGGCGGCGGTGCAGGCGGCCATCCTGATGGGGGACAAGTCCGAGAACGTGC

AGGACCTGCTGCTGCTGGACGTGGCTCCCCTGTCGCTGGGGCTGGAGACGGCCGGAGGCGTGAT

GACTGCCCTGATCAAGCGCAACTCCACCATCCCCACCAAGCAGACGCAGATCTTCACCACCTAC

TCCGACAACCAACCCGGGGTGCTGATCCAGGTGTACGAGGGCGAGAGGGCCATGACGAAAGACA

ACAATCTGTTGGGGCGCTTCGAGCTGAGCGGCATCCCTCCGGCCCCCAGGGGCGTGCCCCAGAT

CGAGGTGACCTTCGACATCGATGCCAACGGCATCCTGAACGTCACGGCCACGGACAAGAGCACC

GGCAAGGCCAACAAGATCACCATCACCAACGACAAGGGCCGCCTGAGCAAGGAGGAGATCGAGC

GCATGGTGCAGGAGGCGGAGAAGTACAAAGCGGAGGACGAGGTGCAGCGCGAGAGGGTGTCAGC

CAAGAACGCCCTGGAGTCCTACGCCTTCAACATGAAGAGCGCCGTGGAGGATGAGGGGCTCAAG

GGCAAGATCAGCGAGGCGGACAAGAAGAAGGTTCTGGACAAGTGTCAAGAGGTCATCTCGTGGC

TGGACGCCAACACCTTGGCCGAGAAGGACGAGTTTGAGCACAAGAGGAAGGAGCTGGAGCAGGT

GTGTAACCCCATCATCAGCGGACTGTACCAGGGTGCCGGTGGTCCCGGGCCTGGGGGCTTCGGG

GCTCAGGGTCCCAAGGGAGGGTCTGGGTCAGGCCCCACCATTGAGGAGGTGGATTAAGAGCTCG

CTGATCAGCCTCGACTGTGCCTTCTAGTTGCCAGCCATCTGTTGTTTGCCCCTCCCCCGTGCCT

TCCTTGACCCTGGAAGGTGCCACTCCCACTGTCCTTTCCTAATAAAATGAGGAAATTGCATCGC

ATTGTCTGAGTAGGTGTCATTCTATTCTGGGGGGTGGGGTGGGGCAGGACAGCAAGGGGGAGGA

TTGGGAAGACAATAGCAGGCATGCTGGGGATGCGGTGGGCTCTATGGAAGCTTGAATTCAGCTG

ACGTGCCTCGGACCGCTAGGAACCCCTAGTGATGGAGTTGGCCACTCCCTCTCTGCGCGCTCGC

TCGCTCACTGAGGCCGGGCGACCAAAGGTCGCCCGACGCCCGGGCTTTGCCCGGGCGGCCTCAG

TGAGCGAGCGAGCGCGCAG
```

| Components (5' to 3' order) | Size (nt) | Origins and Notes | Position (in construct) | SEQ ID NO |
|---|---|---|---|---|
| 5'ITR | 119 | AAV ITR (AF043303.1) | 1-119 | 128 |
| Cloning site | 14 | N/A (/NotI/MluI) | 120-133 | 129 |
| CMV enhancer | 381 | NCBI K03104.1 (140 . . . 520) | 134-514 | 130 |
| CBA promoter | 279 | NCBI X00182.1 (268 . . . 543) | 515-791 | 131 |
| Chimeric intron | 1013 | NCBI X00182.1 (544 . . . 1503) NCBI V00882.1 (1250 . . . 1317); XbaI cloning site | 792-1804 | 132 |

-continued

| Components (5' to 3' order) | Size (nt) | Origins and Notes | Position (in construct) | SEQ ID NO |
|---|---|---|---|---|
| Cloning site | 39 | N/A; AgeI | 1805-1843 | 133 |
| Hsp70 | 1923 | NCBI NM_005345 | 1844-3766 | 134 |
| Cloning site | 24 | Stop codon/SacI | 3767-3790 | 135 |
| BGHpA | 225 | NCBI M57764.1 (2326 . . . 2550); termination site | 3791-4015 | 136 |
| Cloning site | 34 | N/A; HindIII/EcoRI/PvuII/RsrII | 4016-4049 | 137 |
| 3'ITR | 130 | AAV2AAV ITR (AF043303.1) | 4050-4179 | 138 |

Exemplary Construct 8

(SEQ ID NO: 98)

CTGCGCGCTCGCTCGCTCACTGAGGCCGCCCGGGCGTCGGGCGACCTTTGGTCGCCCGGCCTCA

GTGAGCGAGCGAGCGCGCAGAGAGGGAGTGGCCAACTCCATCACTAGGGGTTCCTGCGGCCGCA

CGCGTGACATTGATTATTGACTAGTTATTAATAGTAATCAATTACGGGGTCATTAGTTCATAGC

CCATATATGGAGTTCCGCGTTACATAACTTACGGTAAATGGCCCGCCTGGCTGACCGCCCAACG

ACCCCCGCCCATTGACGTCAATAATGACGTATGTTCCCATAGTAACGCCAATAGGGACTTTCCA

TTGACGTCAATGGGTGGACTATTTACGGTAAACTGCCCACTTGGCAGTACATCAAGTGTATCAT

ATGCCAAGTACGCCCCCTATTGACGTCAATGACGGTAAATGGCCCGCCTGGCATTATGCCCAGT

ACATGACCTTATGGGACTTTCCTACTTGGCAGTACATCTACGTATTAGTCATCGCTATTACCAT

GGGTCGAGGTGAGCCCCACGTTCTGCTTCACTCTCCCCATCTCCCCCCCCTCCCCACCCCCAAT

TTTGTATTTATTTATTTTTTAATTATTTTGTGCAGCGATGGGGGCGGGGGGGGGGGGGGCGCGC

GCCAGGCGGGGCGGGGCGGGGCGAGGGGCGGGGCGGGGCGAGGCGGAGAGGTGCGGCGGCAGCC

AATCAGAGCGGCGCGCTCCGAAAGTTTCCTTTTATGGCGAGGCGGCGGCGGCGGCGGCCCTATA

AAAAGCGAAGCGCGCGGCGGGCGGGAGTCGCTGCGTTGCCTTCGCCCCGTGCCCCGCTCCGCGC

CGCCTCGCGCCGCCCGCCCCGGCTCTGACTGACCGCGTTACTCCCACAGGTGAGCGGGCGGGAC

GGCCCTTCTCCTCCGGGCTGTAATTAGCGCTTGGTTTAATGACGGCTCGTTTCTTTTCTGTGGC

TGCGTGAAAGCCTTAAAGGGCTCCGGGAGGGCCCTTTGTGCGGGGGGGAGCGGCTCGGGGGGTG

CGTGCGTGTGTGTGTGCGTGGGGAGCGCCGCGTGCGGCCCGCGCTGCCCGGCGGCTGTGAGCGC

TGCGGGCGCGGCGCGGGGCTTTGTGCGCTCCGCGTGTGCGCGAGGGGAGCGCGGCCGGGGGCGG

TGCCCCGCGGTGCGGGGGGGCTGCGAGGGGAACAAAGGCTGCGTGCGGGGTGTGTGCGTGGGGG

GGTGAGCAGGGGGTGTGGGCGCGGCGGTCGGGCTGTAACCCCCCCCTGCACCCCCCTCCCCGAG

TTGCTGAGCACGGCCCGGCTTCGGGTGCGGGGCTCCGTGCGGGGCGTGGCGCGGGGCTCGCCGT

GCCGGGCGGGGGGTGGCGGCAGGTGGGGGTGCCGGGCGGGGCGGGGCCGCCTCGGGCCGGGGAG

GGCTCGGGGGAGGGGCGCGGCGGCCCCCGGAGCGCCGGCGGCTGTCGAGGCGCGGCGAGCCGCA

GCCATTGCCTTTTATGGTAATCGTGCGAGAGGGCGCAGGGACTTCCTTTGTCCCAAATCTGTGC

GGAGCCGAAATCTGGGAGGCGCCGCCGCACCCCCTCTAGCGGGCGCGGGGCGAAGCGGTGCGGC

GCCGGCAGGAAGGAAATGGGCGGGGAGGGCCTTCGTGCGTCGCCGCGCCGCCGTCCCCTTCTCC

CTCTCCAGCCTCGGGGCTGTCCGCGGGGGGACGGCTGCCTTCGGGGGGGACGGGGCAGGGCGGG

GTTCGGCTTCTGGCGTGTGACCGGCGGCTCTAGAGCCTCTGCTAACCATGTTCATGCCTTCTTC

TTTTTCCTACAGCTCCTGGGCAACGTGCTGGTTATTGTGACCGGTGCCACCATGGCCAAAGCCG

CGGCGATCGGCATCGACCTGGGCACCACCTACTCCTGCGTGGGGGTGTTCCAACACGGCAAGGT

GGAGATCATCGCCAACGACCAGGGCAACCGCACCACCCCCAGCTACGTGGCCTTCACGGACACC

GAGCGGCTCATCGGGGATGCGGCCAAGAACCAGGTGGCGCTGAACCCGCAGAACACCGTGTTTG

ACGCGAAGCGGCTGATCGGCCGCAAGTTCGGCGACCCGGTGGTGCAGTCGGACATGAAGCACTG

GCCTTTCCAGGTGATCAACGACGGAGACAAGCCCAAGGTGCAGGTGAGCTACAAGGGGGAGACC

AAGGCATTCTACCCCGAGGAGATCTCGTCCATGGTGCTGACCAAGATGAAGGAGATCGCCGAGG

CGTACCTGGGCTACCCGGTGACCAACGCGGTGATCACCGTGCCGGCCTACTTCAACGACTCGCA

GCGCCAGGCCACCAAGGATGCGGGTGTGATCGCGGGGCTCAACGTGCTGCGGATCATCAACGAG

CCCACGGCCGCCGCCATCGCCTACGGCCTGGACAGAACGGGCAAGGGGGAGCGCAACGTGCTCA

TCTTTGACCTGGGCGGGGGCACCTTCGACGTGTCCATCCTGACGATCGACGACGGCATCTTCGA

GGTGAAGGCCACGGCCGGGGACACCCACCTGGGTGGGGAGGACTTTGACAACAGGCTGGTGAAC

-continued

CACTTCGTGGAGGAGTTCAAGAGAAAACACAAGAAGGACATCAGCCAGAACAAGCGAGCCGTGA

GGCGGCTGCGCACCGCCTGCGAGAGGGCCAAGAGGACCCTGTCGTCCAGCACCCAGGCCAGCCT

GGAGATCGACTCCCTGTTTGAGGGCATCGACTTCTACACGTCCATCACCAGGGCGAGGTTCGAG

GAGCTGTGCTCCGACCTGTTCCGAAGCACCCTGGAGCCCGTGGAGAAGGCTCTGCGCGACGCCA

AGCTGGACAAGGCCCAGATTCACGACCTGGTCCTGGTCGGGGGCTCCACCCGCATCCCCAAGGT

GCAGAAGCTGCTGCAGGACTTCTTCAACGGGCGCGACCTGAACAAGAGCATCAACCCCGACGAG

GCTGTGGCCTACGGGGCGGCGGTGCAGGCGGCCATCCTGATGGGGGACAAGTCCGAGAACGTGC

AGGACCTGCTGCTGCTGGACGTGGCTCCCCTGTCGCTGGGGCTGGAGACGGCCGGAGGCGTGAT

GACTGCCCTGATCAAGCGCAACTCCACCATCCCCACCAAGCAGACGCAGATCTTCACCACCTAC

TCCGACAACCAACCCGGGGTGCTGATCCAGGTGTACGAGGGCGAGAGGGCCATGACGAAAGACA

ACAATCTGTTGGGGCGCTTCGAGCTGAGCGGCATCCCTCCGGCCCCCAGGGGCGTGCCCCAGAT

CGAGGTGACCTTCGACATCGATGCCAACGGCATCCTGAACGTCACGGCCACGGACAAGAGCACC

GGCAAGGCCAACAAGATCACCATCACCAACGACAAGGGCCGCCTGAGCAAGGAGGAGATCGAGC

GCATGGTGCAGGAGGCGGAGAAGTACAAAGCGGAGGACGAGGTGCAGCGCGAGAGGGTGTCAGC

CAAGAACGCCCTGGAGTCCTACGCCTTCAACATGAAGAGCGCCGTGGAGGATGAGGGGCTCAAG

GGCAAGATCAGCGAGGCGGACAAGAAGAAGGTTCTGGACAAGTGTCAAGAGGTCATCTCGTGGC

TGGACGCCAACACCTTGGCCGAGAAGGACGAGTTTGAGCACAAGAGGAAGGAGCTGGAGCAGGT

GTGTAACCCCATCATCAGCGGACTGTACCAGGGTGCCGGTGGTCCCGGGCCTGGGGGCTTCGGG

GCTCAGGGTCCCAAGGGAGGGTCTGGGTCAGGCCCCACCATTGAGGAGGTGGATGGATCCCGGG

CTGAGTACAAAGACCATGACGGTGATTATAAAGATCATGACATCGACTACAAGGATGACGATGA

CAAGGGCTCCGGAGAGGGCAGAGGAAGTCTGCTAACATGCGGTGACGTCGAGGAGAATCCTGGC

CCAATGGAGAGCGACGAGAGCGGCCTGCCCGCCATGGAGATCGAGTGCCGCATCACCGGCACCC

TGAACGGCGTGGAGTTCGAGCTGGTGGGCGGCGGAGAGGGCACCCCCGAGCAGGGCCGCATGAC

CAACAAGATGAAGAGCACCAAAGGCGCCCTGACCTTCAGCCCCTACCTGCTGAGCCACGTGATG

GGCTACGGCTTCTACCACTTCGGCACCTACCCCAGCGGCTACGAGAACCCCTTCCTGCACGCCA

TCAACAACGGCGGCTACACCAACACCCGCATCGAGAAGTACGAGGACGGCGGCGTGCTGCACGT

GAGCTTCAGCTACCGCTACGAGGCCGGCCGCGTGATCGGCGACTTCAAGGTGATGGGCACCGGC

TTCCCCGAGGACAGCGTGATCTTCACCGACAAGATCATCCGCAGCAACGCCACCGTGGAGCACC

TGCACCCCATGGGCGATAACGATCTGGATGGCAGCTTCACCCGCACCTTCAGCCTGCGCGACGG

CGGCTACTACAGCTCCGTGGTGGACAGCCACATGCACTTCAAGAGCGCCATCCACCCCAGCATC

CTGCAGAACGGGGGCCCCATGTTCGCCTTCCGCCGCGTGGAGGAGGATCACAGCAACACCGAGC

TGGGCATCGTGGAGTACCAGCACGCCTTCAAGACCCCGGATGCAGATGCCGGTGAAGAATAAGA

GCTCGCTGATCAGCCTCGACTGTGCCTTCTAGTTGCCAGCCATCTGTTGTTTGCCCCTCCCCCG

TGCCTTCCTTGACCCTGGAAGGTGCCACTCCCACTGTCCTTTCCTAATAAAATGAGGAAATTGC

ATCGCATTGTCTGAGTAGGTGTCATTCTATTCTGGGGGGTGGGGTGGGGCAGGACAGCAAGGGG

GAGGATTGGGAAGACAATAGCAGGCATGCTGGGGATGCGGTGGGCTCTATGGAAGCTTGAATTC

AGCTGACGTGCCTCGGACCGCTAGGAACCCCTAGTGATGGAGTTGGCCACTCCCTCTCTGCGCG

CTCGCTCGCTCACTGAGGCCGGGCGACCAAAGGTCGCCCGACGCCCGGGCTTTGCCCGGGCGGC

CTCAGTGAGCGAGCGAGCGCGCAG

| Components (5' to 3' order) | Size (nt) | Origins and Notes | Position (in construct) | SEQ ID NO |
|---|---|---|---|---|
| 5'ITR | 119 | AAV2 ITR (AF043303.1) | 1-119 | 139 |
| Cloning site | 14 | N/A (/NotI/MluI) | 120-133 | 140 |
| CMV enhancer | 381 | NCBI K03104.1 (140 . . . 520) | 134-514 | 141 |
| CBA promoter | 279 | NCBI X00182.1 (268 . . . 543) | 515-791 | 142 |
| Chimeric intron | 1013 | NCBI X00182.1 (544 . . . 1503) NCBI V00882.1 (1250 . . . 1317); XbaI cloning site | 792-1804 | 143 |
| Cloning site | 39 | N/A; AgeI | 1805-1843 | 144 |
| Hsp70 | 1923 | NCBI NM_005345 | 1844-3766 | 145 |
| Linker | 12 | BamHI/GSRA | 3767-3778 | 146 |
| 3xFLAG | 66 | NCBI AVE26326.1 | 3779-3844 | 147 |
| Linker | 9 | GSG linker | 3845-3853 | 148 |
| T2A | 54 | NCBI YP_009665206.1 | 3854-3907 | 149 |
| tGFP | 696 | NCBI ADD23343.1 | 3908-4603 | 150 |
| Cloning site | 24 | Stop codon/SacI | 3767-3790 | 151 |
| BGHpA | 225 | NCBI M57764.1 (2326 . . .2550); termination site | 3791-4015 | 152 |
| Cloning site | 34 | N/A; HindIII/EcoRI/PvuII/RsrII | 4016-4049 | 153 |
| 3'ITR | 130 | AAV2 ITR (AF043303.1) | 4050-4179 | 154 |

Exemplary Construct Components

Inverted Terminal Repeat Sequences (ITRs)

AAV derived sequences of a construct typically comprises the cis-acting 5' and 3' ITRs (see, e.g., B. J. Carter, in "Handbook of Parvoviruses", ed., P. Tijsser, CRC Press, pp. 155 168 (1990), which is incorporated in its entirety herein by reference). Generally, ITRs are able to form a hairpin. The ability to form a hairpin can contribute to an ITRs ability to self-prime, allowing primase-independent synthesis of a second DNA strand. ITRs can also aid in efficient encapsidation of an AAV construct in an AAV particle.

An rAAV particle (e.g., an AAV2/Anc80 particle) of the present disclosure can comprise a rAAV construct comprising a coding sequence (e.g., a gene encoding a secreted target protein or any characteristic portion thereof, e.g., an NDP gene or any characteristic portion thereof, e.g., an HSPA1A gene or any characteristic portion thereof) and associated elements flanked by a 5' and a 3' AAV ITR sequences. In some embodiments, an ITR is or comprises about 145 nucleic acids. In some embodiments, all or substantially all of a sequence encoding an ITR is used. An AAV ITR sequence may be obtained from any known AAV, including presently identified mammalian AAV types. In some embodiments an ITR is an AAV2 ITR.

An example of a construct molecule employed in the present disclosure is a "cis-acting" construct containing a transgene, in which the selected transgene sequence and associated regulatory elements are flanked by 5' or "left" and 3' or "right" AAV ITR sequences. 5' and left designations refer to a position of an ITR sequence relative to an entire construct, read left to right, in a sense direction. For example, in some embodiments, a 5' or left ITR is an ITR that is closest to a promoter (as opposed to a polyadenylation sequence) for a given construct, when a construct is depicted in a sense orientation, linearly. Concurrently, 3' and right designations refer to a position of an ITR sequence relative to an entire construct, read left to right, in a sense direction. For example, in some embodiments, a 3' or right ITR is an ITR that is closest to a polyadenylation sequence (as opposed to a promoter sequence) for a given construct, when a construct is depicted in a sense orientation, linearly. ITRs as provided herein are depicted in 5' to 3' order in accordance with a sense strand. Accordingly, one of skill in the art will appreciate that a 5' or "left" orientation ITR can also be depicted as a 3' or "right" ITR when converting from sense to antisense direction. Further, it is well within the ability of one of skill in the art to transform a given sense ITR sequence (e.g., a 5'/left AAV ITR) into an antisense sequence (e.g., 3'/right ITR sequence). One of ordinary skill in the art would understand how to modify a given ITR sequence for use as either a 5'/left or 3'/right ITR, or an antisense version thereof.

For example, an ITR (e.g., a 5' ITR) can have a sequence according to SEQ ID NO: 60, 62, 116, 128, or 139. In some embodiments, an ITR (e.g., a 3' ITR) can have a sequence according to SEQ ID NO: 61, 63, 127, 138, or 152. In some embodiments, an ITR includes one or more modifications, e.g., truncations, deletions, substitutions or insertions, as is known in the art. In some embodiments, an ITR comprises fewer than 145 nucleotides, e.g., 127, 130, 134 or 141 nucleotides. For example, in some embodiments, an ITR comprises 110, 111, 112, 113, 114, 115, 116, 117, 118, 119, 120, 121, 122, 123,124, 125, 126, 127, 128, 129, 130, 131, 132, 133, 134, 135, 136, 137, 138, 139, 140, 141, 142, 143 144, or 145 nucleotides. In some embodiments, an ITR (e.g., a 5' ITR) can have a sequence according to SEQ ID NO: 62. In some embodiments, an ITR (e.g., a 3' ITR) can have a sequence according to SEQ ID NO: 63.

A non-limiting example of a 5' AAV ITR sequence is SEQ ID NO: 60. A non-limiting example of a 3' AAV ITR sequence is SEQ ID NO: 61. In some embodiments, rAAV constructs of the present disclosure comprise a 5' AAV ITR and/or a 3' AAV ITR. In some embodiments, a 5' AAV ITR sequence is SEQ ID NO: 62. In some embodiments, a 3' AAV ITR sequence is SEQ ID NO: 63. In some embodiments, the 5' and a 3' AAV ITRs (e.g., SEQ ID NOs: 60 and 61, or 62 and 63) flank a portion of a coding sequence, e.g., all or a portion of an NDP gene or HSPA1A gene (e.g., SEQ ID NO: 57 or 86). The ability to modify these ITR sequences is within the skill of the art. (See, e.g., texts such as Sambrook et al. "Molecular Cloning. A Laboratory Manual", 2d ed., Cold Spring Harbor Laboratory, New York (1989); and K. Fisher et al., J Virol., 70:520 532 (1996), each of which is incorporated in its entirety herein by reference). In some embodiments, a 5' ITR sequence is at least 85%, 90%, 95%, 98% or 99% identical to a 5' ITR sequence represented by SEQ ID NO: 60 or 62. In some embodiments, a 3' ITR sequence is at least 85%, 90%, 95%, 98% or 99% identical to a 3' ITR sequence represented by SEQ ID NO: 61 or 63.

```
Exemplary 5' AAV ITR
                                          (SEQ ID NO: 60)
TTGGCCACTCCCTCTCTGCGCGCTCGCTCGCTCACTGAGGCCGCCCGGG
CAAAGCCCGGGCGTCGGGCGACCTTTGGTCGCCCGGCCTCAGTGAGCGA
GCGAGCGCGCAGAGAGGGAGTGGCCAACTCCATCACTAGGGGTTCCT

Exemplary 3' AAV ITR
                                          (SEQ ID NO: 61)
AGGAACCCCTAGTGATGGAGTTGGCCACTCCCTCTCTGCGCGCTCGCTC
GCTCACTGAGGCCGGGCGACCAAAGGTCGCCCGACGCCCGGGCTTTGCC
CGGGCGGCCTCAGTGAGCGAGCGAGCGCGCAGAGAGGGAGTGGCCAA

Exemplary 5' AAV ITR
                                          (SEQ ID NO: 62)
CTGCGCGCTCGCTCGCTCACTGAGGCCGCCCGGGCGTCGGGCGACCTTT
GGTCGCCCGGCCTCAGTGAGCGAGCGAGCGCGCAGAGAGGGAGTGGCCA
ACTCCATCACTAGGGGTTCCT

Exemplary 3' AAV ITR
                                          (SEQ ID NO: 63)
AGGAACCCCTAGTGATGGAGTTGGCCACTCCCTCTCTGCGCGCTCGCTC
GCTCACTGAGGCCGGGCGACCAAAGGTCGCCCGACGCCCGGGCTTTGCC
CGGGCGGCCTCAGTGAGCGAGCGAGCGCGCAG
```

Promoters

The term "promoter" means a DNA sequence recognized by enzymes/proteins in a mammalian cell required to initiate the transcription of a specific gene (e.g., a secreted target gene (e.g., a NDP gene (e.g., any of the exemplary NDP genes described herein), a HSPA1A gene (e.g., any of the exemplary HSPA1A genes described herein)). A promoter typically refers to, e.g., a nucleotide sequence to which an RNA polymerase and/or any associated factor binds and at which transcription is initiated. Non-limiting examples of promoters are described herein. Additional examples of promoters are known in the art.

In some embodiments, a vector encoding an N-terminal portion of secreted target protein (e.g., a NDP protein (e.g., any of the exemplary NDP proteins described herein), a HSPA1A protein (e.g., any of the exemplary HSPA1A proteins described herein) can include a promoter and/or an enhancer. The vector encoding the N-terminal portion of the secreted target protein (e.g., a NDP protein (e.g., any of the exemplary NDP proteins described herein), a HSPA1A protein (e.g., any of the exemplary HSPA1A proteins described herein) can include any of the promoters and/or enhancers described herein or known in the art.

In some embodiments, the promoter is an inducible promoter, a constitutive promoter, a mammalian cell promoter, a viral promoter, a chimeric promoter, an engineered promoter, a tissue-specific promoter, or any other type of promoter known in the art. In some embodiments, the promoter is a RNA polymerase II promoter, such as a mammalian RNA polymerase II promoter. In some embodiments, the promoter is a RNA polymerase III promoter, including, but not limited to, a H1 promoter, a human U6 promoter, a mouse U6 promoter, or a swine U6 promoter. The promoter will generally be one that is able to promote transcription in an inner hair cell In some examples, the promoter is a cochlea-specific promoter or a cochlea-oriented promoter.

A variety of promoters are known in the art that can be used herein. Non-limiting examples of promoters that can be used herein include: human EF1a, human cytomegalovirus (CMV) (U.S. Pat. No. 5,168,062), human ubiquitin C (UBC), mouse phosphoglycerate kinase 1, polyoma adenovirus, simian virus 40 (SV40), β-globin, β-actin, α-fetoprotein, γ-globin, β-interferon, γ-glutamyl transferase, mouse mammary tumor virus (MMTV), Rous sarcoma virus, rat insulin, glyceraldehyde-3-phosphate dehydrogenase, metallothionein II (MT II), amylase, cathepsin, MI muscarinic receptor, retroviral LTR (e.g. human T-cell leukemia virus HTLV), AAV ITR, interleukin-2, collagenase, platelet-derived growth factor, adenovirus 5 E2, stromelysin, murine MX gene, glucose regulated proteins (GRP78 and GRP94), α-2-macroglobulin, vimentin, MHC class I gene H-2κ b, HSP70, proliferin, tumor necrosis factor, thyroid stimulating hormone a gene, immunoglobulin light chain, T-cell receptor, HLA DQa and DQB, interleukin-2 receptor, MHC class II, MHC class II HLA-DRα, muscle creatine kinase, prealbumin (transthyretin), elastase I, albumin gene, c-fos, c-HA-ras, neural cell adhesion molecule (NCAM), $H_2B$ (TH2B) histone, rat growth hormone, human serum amyloid (SAA), troponin I (TN I), duchenne muscular dystrophy, human immunodeficiency virus, and Gibbon Ape Leukemia Virus (GALV) promoters. Additional examples of promoters are known in the art. See, e.g., Lodish, Molecular Cell Biology, Freeman and Company, New York 2007. In some embodiments, the promoter is the CMV immediate early promoter. In some embodiments, the promoter is a CAG promoter or a CAG/CBA promoter. In some embodiments, the promoter is a CBA promoter, e.g., a CBA promoter comprising or consisting of SEQ ID NO: 18.

The term "constitutive" promoter refers to a nucleotide sequence that, when operably linked with a nucleic acid encoding a protein (e.g., a secreted target protein (e.g., a NDP protein (e.g., any of the exemplary NDP proteins described herein), a HSPA1A protein (e.g., any of the exemplary HSPA1A proteins described herein)), causes RNA to be transcribed from the nucleic acid in a mammalian cell under most or all physiological conditions.

Examples of constitutive promoters include, without limitation, the retroviral Rous sarcoma virus (RSV) LTR promoter, the cytomegalovirus (CMV) promoter (see, e.g., Boshart et al, Cell 41:521-530, 1985), the SV40 promoter, the dihydrofolate reductase promoter, the beta-actin promoter, the phosphoglycerol kinase (PGK) promoter, and the EF1-alpha promoter (Invitrogen).

Inducible promoters allow regulation of gene expression and can be regulated by exogenously supplied compounds, environmental factors such as temperature, or the presence of a specific physiological state, e.g., acute phase, a particular differentiation state of the cell, or in replicating cells only. Inducible promoters and inducible systems are available from a variety of commercial sources, including, without limitation, Invitrogen, Clontech, and Ariad. Additional examples of inducible promoters are known in the art.

Examples of inducible promoters regulated by exogenously supplied compounds include the zinc-inducible sheep metallothionine (MT) promoter, the dexamethasone (Dex)-inducible mouse mammary tumor virus (MMTV) promoter, the T7 polymerase promoter system (WO 98/10088); the ecdysone insect promoter (No et al, *Proc. Natl. Acad. Sci. U.S.A.* 93:3346-3351, 1996), the tetracycline-repressible system (Gossen et al, *Proc. Natl. Acad. Sci. U.S.A.* 89:5547-5551, 1992), the tetracycline-inducible system (Gossen et al, *Science* 268:1766-1769, 1995, see also Harvey et al, *Curr. Opin. Chem. Biol.* 2:512-518, 1998), the RU486-inducible system (Wang et al, *Nat. Biotech.* 15:239-243, 1997) and Wang et al, *Gene Ther.* 4:432-441, 1997), and the rapamycin-inducible system (Magari et al. *J. Clin. Invest.* 100:2865-2872, 1997), each of which is incorporated by reference in their entireties herein.

The term "tissue-specific" promoter refers to a promoter that is active only in certain specific cell types and/or tissues (e.g., transcription of a specific gene occurs only within cells expressing transcription regulatory proteins that bind to the tissue-specific promoter).

In some embodiments, the regulatory sequences impart tissue-specific gene expression capabilities. In some cases, the tissue-specific regulatory sequences bind tissue-specific transcription factors that induce transcription in a tissue-specific manner.

Exemplary tissue-specific promoters include but are not limited to the following: a liver-specific thyroxin binding globulin (TBG) promoter, an insulin promoter, a glucagon promoter, a somatostatin promoter, a pancreatic polypeptide (PPY) promoter, a synapsin-1 (Syn) promoter, a creatine kinase (MCK) promoter, a mammalian desmin (DES) promoter, an alpha-myosin heavy chain (a-MHC) promoter, and a cardiac Troponin T (cTnT) promoter. Additional exemplary promoters include Beta-actin promoter, hepatitis B virus core promoter (Sandig et al., *Gene Ther.* 3:1002-1009, 1996), alpha-fetoprotein (AFP) promoter (Arbuthnot et al., *Hum. Gene Ther.* 7:1503-1514, 1996), bone osteocalcin promoter (Stein et al., *Mol. Biol. Rep.* 24:185-196, 1997); bone sialoprotein promoter (Chen et al., *J. Bone Miner. Res.* 11:654-664, 1996), CD2 promoter (Hansal et al., *J. Immu-*

*nol.* 161:1063-1068, 1998); immunoglobulin heavy chain promoter; T cell receptor alpha-chain promoter, neuronal such as neuron-specific enolase (NSE) promoter (Andersen et al., *Cell. Mol. Neurobiol.* 13:503-515, 1993), neurofilament light-chain gene promoter (Piccioli et al., *Proc. Natl. Acad. Sci. U.S.A.* 88:5611-5615, 1991), and the neuron-specific vgf gene promoter (Piccioli et al., *Neuron* 15:373-384, 1995), each of which is incorporated by reference in their entireties herein.

In some embodiments, the tissue-specific promoter is a cochlea-specific promoter. In some embodiments, the tissue-specific promoter is a cochlear hair cell-specific promoter. Non-limiting examples of cochlear hair cell-specific promoters include but are not limited to: a ATOH1 promoter, a POU4F3 promoter, a LHX3 promoter, a MYO7A promoter, a MY06 promoter, a α9ACHR promoter, and a α10ACHR promoter. In some embodiments, the promoter is an cochlear hair cell-specific promoter such as a PRESTIN promoter or an ONCOMOD promoter. See, e.g., Zheng et al., *Nature* 405:149-155, 2000; Tian et al. *Dev. Dyn.* 231:199-203, 2004; and Ryan et al., *Adv. Otorhinolaryngol.* 66:99-115, 2009, each of which is incorporated by reference in their entireties herein.

In some embodiments, a tissue-specific promoter is an ear cell specific promoter. In some embodiments, a tissue-specific promoter is an inner ear cell specific promoter. Non-limiting examples of inner ear non-sensory cell-specific promoters include but are not limited to: GJB2, GJB6, SLC26A4, *TECTA*, DFNA5, COCH, NDP, SYN1, GFAP, PLP, TAK1, or SOX21. In some embodiments, a cochlear non-sensory cell specific promoter may be an inner ear supporting cell specific promoter. Non-limiting examples of inner ear supporting cell specific promoters include but are not limited to: SOX2, FGFR3, PROX1, GLAST1, LGR5, HES1, HES5, NOTCH1, JAG1, CDKNIA, CDKNIB, SOX10, P75, CD44, HEY2, LFNG, or S100b.

In some embodiments, provided AAV constructs comprise a promoter sequence selected from a CAG, a CBA, a CMV, or a CB7 promoter. In some embodiments of any of the therapeutic compositions described herein, the first or sole AAV construct further includes at least one promoter sequence selected from Cochlea and/or inner ear specific promoters.

```
Exemplary CBA promoter
                                                        (SEQ ID NO: 64)
GTCGAGGTGAGCCCCACGTTCTGCTTCACTCTCCCCATCTCCCCCCCCTCCCCACCCCCAATTT

TGTATTTATTTATTTTTTAATTATTTTGTGCAGCGATGGGGGCGGGGGGGGGGGGGGGGCGCGC

GCCAGGCGGGGCGGGGCGGGGCGAGGGGCGGGGCGGGGCGAGGCGGAGAGGTGCGGCGGCAGCC

AATCAGAGCGGCGCGCTCCGAAAGTTTCCTTTTATGGCGAGGCGGCGGCGGCGGCGGCCCTATA

AAAAGCGAAGCGCGCGGCGGGCG

Exemplary CBA promoter
                                                        (SEQ ID NO: 65)
GTCGAGGTGAGCCCCACGTTCTGCTTCACTCTCCCCATCTCCCCCCCCTCCCCACCCCCAATTT

TGTATTTATTTATTTTTTAATTATTTTGTGCAGCGATGGGGGCGGGGGGGGGGGGGGGGCGCGC

CAGGCGGGGCGGGGCGGGGCGAGGGGCGGGGCGGGGCGAGGCGGAGAGGTGCGGCGGCAGCCAA

TCAGAGCGGCGCGCTCCGAAAGTTTCCTTTTATGGCGAGGCGGCGGCGGCGGCGGCCCTATAAA

AAGCGAAGCGCGCGGCGGGCG

Exemplary CMV/CBA enhancer/promoter
                                                        (SEQ ID NO: 66)
GACATTGATTATTGACTAGTTATTAATAGTAATCAATTACGGGGTCATTAGTTCATAGCCCATA

TATGGAGTTCCGCGTTACATAACTTACGGTAAATGGCCCGCCTGGCTGACCGCCCAACGACCCC

CGCCCATTGACGTCAATAATGACGTATGTTCCCATAGTAACGCCAATAGGGACTTTCCATTGAC

GTCAATGGGTGGACTATTTACGGTAAACTGCCCACTTGGCAGTACATCAAGTGTATCATATGCC

AAGTACGCCCCCTATTGACGTCAATGACGGTAAATGGCCCGCCTGGCATTATGCCCAGTACATG

ACCTTATGGGACTTTCCTACTTGGCAGTACATCTACGTATTAGTCATCGCTATTACCATGGGTC

GAGGTGAGCCCCACGTTCTGCTTCACTCTCCCCATCTCCCCCCCCTCCCCACCCCCAATTTTGT

ATTTATTTATTTTTTAATTATTTTGTGCAGCGATGGGGGCGGGGGGGGGGGGGGGGCGCGCGCC

AGGCGGGGCGGGGCGGGGCGAGGGGCGGGGCGGGGCGAGGCGGAGAGGTGCGGCGGCAGCCAAT

CAGAGCGGCGCGCTCCGAAAGTTTCCTTTTATGGCGAGGCGGCGGCGGCGGCGGCCCTATAAAA

AGCGAAGCGCGCGGCGGGCG
```

-continued

Exemplary CMV/CBA enhancer/promoter (SEQ ID NO: 67)

GACATTGATTATTGACTAGTTATTAATAGTAATCAATTACGGGGTCATTAGTTCATAGCCCATA

TATGGAGTTCCGCGTTACATAACTTACGGTAAATGGCCCGCCTGGCTGACCGCCCAACGACCCC

CGCCCATTGACGTCAATAATGACGTATGTTCCCATAGTAACGCCAATAGGGACTTTCCATTGAC

GTCAATGGGTGGACTATTTACGGTAAACTGCCCACTTGGCAGTACATCAAGTGTATCATATGCC

AAGTACGCCCCCTATTGACGTCAATGACGGTAAATGGCCCGCCTGGCATTATGCCCAGTACATG

ACCTTATGGGACTTTCCTACTTGGCAGTACATCTACGTATTAGTCATCGCTATTACCATGGGTC

GAGGTGAGCCCCACGTTCTGCTTCACTCTCCCCATCTCCCCCCCCTCCCCACCCCCAATTTTGT

ATTTATTTATTTTTTAATTATTTTGTGCAGCGATGGGGGCGGGGGGGGGGGGGGCGCGCGCCAG

GCGGGGCGGGGCGGGGCGAGGGGCGGGGCGGGGCGAGGCGGAGAGGTGCGGCGGCAGCCAATCA

GAGCGGCGCGCTCCGAAAGTTTCCTTTTATGGCGAGGCGGCGGCGGCGGCGGCCCTATAAAAAG

CGAAGCGCGCGGCGGGCG

Exemplary CAG enhancer/promoter (SEQ ID NO: 101)

GACATTGATTATTGACTAGTTATTAATAGTAATCAATTACGGGGTCATTAGTTCATAGCCCATA

TATGGAGTTCCGCGTTACATAACTTACGGTAAATGGCCCGCCTGGCTGACCGCCCAACGACCCC

CGCCCATTGACGTCAATAATGACGTATGTTCCCATAGTAACGCCAATAGGGACTTTCCATTGAC

GTCAATGGGTGGACTATTTACGGTAAACTGCCCACTTGGCAGTACATCAAGTGTATCATATGCC

AAGTACGCCCCCTATTGACGTCAATGACGGTAAATGGCCCGCCTGGCATTATGCCCAGTACATG

ACCTTATGGGACTTTCCTACTTGGCAGTACATCTACGTATTAGTCATCGCTATTACCATGGGTC

GAGGTGAGCCCCACGTTCTGCTTCACTCTCCCCATCTCCCCCCCCTCCCCACCCCCAATTTTGT

ATTTATTTATTTTTTAATTATTTTGTGCAGCGATGGGGGCGGGGGGGGGGGGGGGGCGCGCGCC

AGGCGGGGCGGGGCGGGGCGAGGGGCGGGGCGGGGCGAGGCGGAGAGGTGCGGCGGCAGCCAAT

CAGAGCGGCGCGCTCCGAAAGTTTCCTTTTATGGCGAGGCGGCGGCGGCGGCGGCCCTATAAAA

AGCGAAGCGCGCGGCGGGCGGGAGTCGCTGCGTTGCCTTCGCCCCGTGCCCCGCTCCGCGCCGC

CTCGCGCCGCCCGCCCCGGCTCTGACTGACCGCGTTACTCCCACAGGTGAGCGGGCGGGACGGC

CCTTCTCCTCCGGGCTGTAATTAGCGCTTGGTTTAATGACGGCTCGTTTCTTTTCTGTGGCTGC

GTGAAAGCCTTAAAGGGCTCCGGGAGGGCCCTTTGTGCGGGGGGGAGCGGCTCGGGGGGTGCGT

GCGTGTGTGTGTGCGTGGGGAGCGCCGCGTGCGGCCCGCGCTGCCCGGCGGCTGTGAGCGCTGC

GGGCGCGGCGCGGGGCTTTGTGCGCTCCGCGTGTGCGCGAGGGGAGCGCGGCCGGGGGCGGTGC

CCCGCGGTGCGGGGGGGCTGCGAGGGGAACAAAGGCTGCGTGCGGGGTGTGTGCGTGGGGGGGT

GAGCAGGGGGTGTGGGCGCGGCGGTCGGGCTGTAACCCCCCCCTGCACCCCCCTCCCCGAGTTG

CTGAGCACGGCCCGGCTTCGGGTGCGGGGCTCCGTGCGGGGCGTGGCGCGGGGCTCGCCGTGCC

GGGCGGGGGGTGGCGGCAGGTGGGGGTGCCGGGCGGGGCGGGGCCGCCTCGGGCCGGGGAGGGC

TCGGGGGAGGGGCGCGGCGGCCCCCGGAGCGCCGGCGGCTGTCGAGGCGCGGCGAGCCGCAGCC

ATTGCCTTTTATGGTAATCGTGCGAGAGGGCGCAGGGACTTCCTTTGTCCCAAATCTGTGCGGA

GCCGAAATCTGGGAGGCGCCGCCGCACCCCCTCTAGCGGGCGCGGGGCGAAGCGGTGCGGCGCC

GGCAGGAAGGAAATGGGCGGGGAGGGCCTTCGTGCGTCGCCGCGCCGCCGTCCCCTTCTCCCTC

TCCAGCCTCGGGGCTGTCCGCGGGGGGACGGCTGCCTTCGGGGGGGACGGGGCAGGGCGGGGTT

CGGCTTCTGGCGTGTGACCGGCGGCTCTAGAGCCTCTGCTAACCATGTTCATGCCTTCTTCTTT

TTCCTAGAG

-continued

Exemplary CAG enhancer/promoter (SEQ ID NO: 102)

GACATTGATTATTGAGTAGTTATTAATAGTAATCAATTACGGGGTCATTAGTTCATAGCCCATA

TATGGAGTTCCGCGTTACATAACTTACGGTAAATGGCCCGCCTGGCTGACCGCCCAACGACCCC

CGCCCATTGAGGTCAATAATGAGGTATGTTCCCATAGTAACGCCAATAGGGAGTTTCCATTGAG

GTCAATGGGTGGACTATTTACGGTAAACTGCCCACTTGGCAGTACATCAAGTGTATCATATGCC

AAGTACGCCCCCTATTGACGTCAATGACGGTAAATGGCCCGCCTGGCATTATGCCCAGTACATG

ACCTTATGGGACTTTCCTACTTGGCAGTACATCTACGTATTAGTCATCGCTATTACCATGGGTC

GAGGTGAGCCCCACGTTCTGCTTCACTCTCCCCATCTCCCCCCCCTCCCCACCCCCAATTTTGT

ATTTATTTATTTTTTAATTATTTTGTGCAGCGATGGGGGCGGGGGGGGGGGGGGCGCGCGCCAG

GCGGGGCGGGGCGGGGCGAGGGGCGGGGCGGGGCGAGGCGGAGAGGTGCGGCGGCAGCCAATCA

GAGCGGCGCGCTCCGAAAGTTTCCTTTTATGGCGAGGCGGCGGCGGCGGCGGCCCTATAAAAAG

CGAAGCGCGCGGCGGGCGGGAGTCGCTGCGTTGCCTTCGCCCCGTGCCCCGCTCCGCGCCGCCT

CGCGCCGCCCGCCCCGGCTCTGACTGACCGCGTTACTCCCACAGGTGAGCGGGCGGGACGGCCC

TTCTCCTCCGGGCTGTAATTAGCGCTTGGTTTAATGACGGCTCGTTTCTTTTCTGTGGCTGCGT

GAAAGCCTTAAAGGGCTCCGGGAGGGCCCTTTGTGCGGGGGGGAGCGGCTCGGGGGGTGCGTGC

GTGTGTGTGTGCGTGGGGAGCGCCGCGTGCGGCCCGCGCTGCCCGGCGGCTGTGAGCGCTGCGG

GCGCGGCGCGGGGCTTTGTGCGCTCCGCGTGTGCGCGAGGGGAGCGCGGCCGGGGGCGGTGCCC

CGCGGTGCGGGGGGGCTGCGAGGGGAACAAAGGCTGCGTGCGGGGTGTGTGCGTGGGGGGGTGA

GCAGGGGGTGTGGGCGCGGCGGTCGGGCTGTAACCCCCCCCTGCACCCCCCTCCCCGAGTTGCT

GAGCACGGCCCGGCTTCGGGTGCGGGGCTCCGTGCGGGGCGTGGCGCGGGGCTCGCCGTGCCGG

GCGGGGGGTGGCGGCAGGTGGGGGTGCCGGGCGGGGCGGGGCCGCCTCGGGCCGGGGAGGGCTC

GGGGGAGGGGCGCGGCGGCCCCCGGAGCGCCGGCGGCTGTCGAGGCGCGGCGAGCCGCAGCCAT

TGCCTTTTATGGTAATCGTGCGAGAGGGCGCAGGGACTTCCTTTGTCCCAAATCTGTGCGGAGC

CGAAATCTGGGAGGCGCCGCCGCACCCCCTCTAGCGGGCGCGGGGCGAAGCGGTGCGGCGCCGG

CAGGAAGGAAATGGGCGGGGAGGGCCTTCGTGCGTCGCCGCGCCGCCGTCCCCTTCTCCCTCTC

CAGCCTCGGGGCTGTCCGCGGGGGGACGGCTGCCTTCGGGGGGGACGGGGCAGGGCGGGGTTCG

GCTTCTGGCGTGTGACCGGCGGCTCTAGAGCCTCTGCTAACCATGTTCATGCCTTCTTCTTTTT

CCTACAG

In certain embodiments, a promoter is an endogenous human ATOH1 enhancer-promoter as set forth in SEQ ID NO: 68. In some embodiments, an enhancer-promoter sequence is at least 85%, 90%, 95%, 98% or 99% identical to enhancer-promoter sequence represented by SEQ ID NO: 18.

Exemplary Human ATOH1 enhancer-promoter (SEQ ID NO: 68)

CTATGGAGTTTGCATAACAAACGTTTGGCAGCTCGCTCTCTTACACTCCATTAACAAGCTGTAA

CATATAGCTGCAGGTTGCTATAATCTCATTAATATTTTGGAAACTTGAATATTGAGTATTTCTG

AGTGCTCATTCCCCATATGCCAGCCACTTCTGCCATGCTGACTGGTTCCTTTCTCTCCATTATT

AGCAATTAGCTTCTTACCTTCCAAAGTCAGATCCAAGGTATCCAAGATACTAGCAAAGGAATCA

ACTATGTGTGCAAGTTAAGCATGCTTAATATCACCCAAACAAACAAAGAGGCAGCATTTCTTAA

AGTAATGAAGATAGATAAATCGGGTTAGTCCTTTGCGACACTGCTGGTGCTTTCTAGAGTTTTA

TATATTTTAAGCAGCTTGCTTTATATTCTGTCTTTGCCTCCCACCCCACCAGCACTTTTATTTG

TGGAGGGTTTTGGCTCGCCACACTTTGGGAAACTTATTTGATTTCACGGAGAGCTGAAGGAAGA

-continued

TCATTTTTGGCAACAGACAAGTTTAAACACGATTTCTATGGGACATTGCTAACTGGGGCCCCTA

AGGAGAAAGGGGAAACTGAGCGGAGAATGGGTTAAATCCTTGGAAGCAGGGGAGAGGCAGGGGA

GGAGAGAAGTCGGAGGAGTATAAAGAAAAGGACAGGAACCAAGAAGCGTGGGGGTGGTTTGCCG

TAATGTGAGTGTTTCTTAATTAGAGAACGGTTGACAATAGAGGGTCTGGCAGAGGCTCCTGGCC

GCGGTGCGGAGCGTCTGGAGCGGAGCACGCGCTGTCAGCTGGTGAGCGCACTCTCCTTTCAGGC

AGCTCCCCGGGGAGCTGTGCGGCCACATTTAACACCATCATCACCCCTCCCCGGCCTCCTCAAC

CTCGGCCTCCTCCTCGTCGACAGCCTTCCTTGGCCCCCACCAGCAGAGCTCACAGTAGCGAGCG

TCTCTCGCCGTCTCCCGCACTCGGCCGGGGCCTCTCTCCTCCCCCAGCTGCGCAGCGGGAGCCG

CCACTGCCCACTGCACCTCCCAGCAACCAGCCCAGCACGCAAAGAAGCTGCGCAAAGTTAAAGC

CAAGCAATGCCAAGGGGAGGGGAAGCTGGAGGCGGGCTTTGAGTGGCTTCTGGGCGCCTGGCGG

GTCCAGAATCGCCCAGAGCCGCCCGCGGTCGTGCACATCTGACCCGAGTCAGCTTGGGCACCAG

CCGAGAGCCGGCTCCGCACCGCTCCCGCACCCCAGCCGCCGGGGTGGTGACACACACCGGAGTC

GAATTACAGGCCTGCAATTAACATATGAATCTGAGGAATTTAAAAGAAGGAAAAAAAAAAAAAA

ACCTGAGCAGGCTTGGGAGTCCTCTGCACACAAGAACTTTTCTCGGGGTGTAAAAACTCTTTGA

TTGGCTGCTCGCACGCGCCTGCCCGCGCCCTCCATTGGCTGAGAAGACACGCGACCGGCGCGAG

GAGGGGGTTGGGAGAGGAGCGGGGGGAGACTGAGTGGCGCGTGCCGCTTTTTAAAGGGGCGCAG

CGCCTTCAGCAACCGGAGAAGCATAGTTGCACGCGACCTGGTGTGTGATCTCCGAGTGGGTGGG

GGAGGGTCGAGGAGGGAAAAAAAAATAAGACGTTGCAGAAGAGACCCGGAAAGGGCCTTTTTTT

TGGTTGAGCTGGTGTCCCAGTGCTGCCTCCGATCCTGAGCCTCCGAGCCTTTGCAGTGCAA

In certain embodiments, a promoter is an endogenous human SLC26A4 immediate promoter as set forth in SEQ ID NO: 103 or 93. In certain embodiments, a promoter is an endogenous human SLC26A4 enhancer-promoter as set forth in SEQ ID NO: 47, 48 or 50. In some embodiments, an enhancer-promoter sequence is at least 85%, 90%, 95%, 98% or 99% identical to a promoter or enhancer-promoter sequence represented by SEQ ID NO: 103, 93, 47, 48, or 50. In certain embodiments, a promoter is a human SLC26A4 endogenous enhancer-promoter sequence comprised within SEQ ID NO: 47, 48, or 50.

Exemplary Human SLC26A4 immediate promoter (SEQ ID NO: 103)

CTGCCTTCTGAGAGCGCTATAAAGGCAGCGGAAGGGTAGTCCGCGGGGCATTCCGGGCGG

Exemplary Human SLC26A4 immediate promoter (SEQ ID NO: 93)

CTCTAGGCGGGCTCTGCTCTTCTTTAAGGAGTCCCACAGGGCCTGGCCCGCCCCTGACCT

Exemplary Human SLC26A4 enhancer-promoter (SEQ ID NO: 47)

TAAAGAGTTGTGAGTTGTGTAGGTGAGTTGCCATGGAGCTACAAATATGAGTTGATATTCTGAA

ATCCTAGACAGCCATCTCCAAGGTTAAGAAAAATCCTTATGCACTCACTTGCAAAGATATCCAC

AGCATGCTCTTAATGGAGAAAAACAAAGCCTTAGATCAAATATGTAAAGTAATTTTTAGTTTTT

TGAAAAGGTATGTTTGGGCTATAGATAAATCTGTTCAAAAAACATGAGAGAAGATAATAATGGT

TGAAAGGAGACACAGTGCTTGCCCTCAAGAAGTTTTTGTCTAGTGAGGGAGAGAGAACTTGTAT

GTAAATAAAATTGTGTTACTAAGGTAGATAGTGAGAAGTAACTTAAGAGAGGATCAGATAAGGT

ATTAAGAGAATACAGAAAAGGGTCTGGATTAATTCTGAACAGCATCAAAGAATGTTCTTGCAAG

AGATAGTGTTTTCACCAGATCTTGAAGGTATGGATGAGGGTATACAGAGTGAGTATATTCAGAT

TCTACTTTAAAACAAATACTTTCCTCTGTTGTAGTGGAGTTGAGCTATACATCCAACAATAATG

AAAAAATACACGCATATATACATATATGGAGAGAGATACATATTTTAGTAGATGTAGCAATTGA

TTAATAAATGTACAGTTTAAGTCGCATGCAAAACCTTGGAGTGATAGCAAACTTCATTGTAGGA

-continued

TGTTTAGCAGCATCTCTGGTCTCTACTCACTAGATCCCAATAGCATCTCCCTAGGTGTGACAAC

CAAAAATGTCTCCAGGCATTGACCTCTGGAGGCAAAAAAAGCCCTTTATTAAGAACCAGTGGTA

TAGATAAGTAAAACATACACAAGAGATTCCTCCCCTCTTCTCTGTATGTGAATAAAAATTGCAA

AGTTCATGACCTGGATTTTCCTTTTAGGTTTCTTCTTTAGTGGTTCTTAACTTCATTGGGTGAA

GTAAGCCTTTGAAGATCTGTTGAAAGCTGTTGACTCATTCACTTCTCAGGAAAACGCACATGCT

GACTACCATTTCAGAGAATTTGCATCAGGGTTCTCTGGGGAGGAGTTCTGAGTTCTGTTTCCAG

GAGCTCGTAGAATTGTCATGGTCTGCATATGCAAGGCAGGTGGATTACGGAAGGTTGATGTACA

GAGGTCTGTATTTTGGAGCCTCTTCTGTATTTACTTCAGAACACTAACAATCAGGCGAGAATGT

TCTGGTTTATCAAACCCTTCCTTCTGCCTTTCATCTTAACCATGCATTAGTTTTAACAAAGTTC

ATCCCAACAGAAGACAAAACACTGATGAGGTAGGATAGCTCCAGCTCCTCCTCCCTCTCTTCTA

GTCTTGATTTCCATGTAGTCCAGTTTATTCCTTCCCTGATTGTCCAGGAGAATGAGAAAAAGAA

AAAACAGAGTCTAGTGGGTAAGAAAGGGCCACCTGGACGGCTTGATTTGGATTGTGAAATAAAA

CACACACACATGCACACGTAGAATAAGTGGCTAAAATCTGAGTAAATCGTGAACTCTCTGTATC

CTCCACCCATTGAATACTCCTAAAAGACTTTCTAGAAATTCAAGGACTTATTAATATAGAAACC

TGGCCATTGTTCCTCTTCTCCTCCCCATGTGGTATGAGAGCACCTGTGGCAGGCTCCCAGAGAC

CACGGACCTCTTCCTCTAGGCGGGCTCTGCTCTTCTTTAAGGAGTCCCACAGGGCCTGGCCCGC

CCCTGACCTCGCAACCCTTGAGATTAGTAACGGGATGAGTGAGGATCCGGGTGGCCCCTGCGTG

GCAGCCAGTAAGAGTCTCAGCCTTCCCGGTTCGGGAAAGGGGAAGAATGCAGGAGGGGTAGGAT

TTCTTTCCTGATAGGATCGGTTGGGAAAGACCGCAGCCTGTGTGTGTCTTTCCCTTCGACCAAG

GTGTCTGTTGCTCCGTAAATAAAACGTCCCACTGCCTTCTGAGAGCGCTATAAAGGCAGCGGAA

GGGTAGTCCGCGGGGC

Exemplary Human SLC26A4 enhancer-promoter (SEQ ID NO: 48)

GGCTGCTCGGAAAACAGGACGAGGGGAGAGACTTGCTCAATAAGCTGAAAGTTCTGCCCCCGAG

AGGGCTGCGACAGCTGCTGGAATGTGCCTGCAGCGTCCGCCTCTTGGGGACCCGCGGAGCGCGC

CCTGACGGTTCCACGCCTGGCCCGGGGGTCTGCACCTCTCCTCCAGTGCGCACCTGGAGCTGCG

TCCCGGGTCAGGTGCGGGGAGGGAGGGAATCTCAGTGTCCCCTTCCAGCCTTGCAAGCGCCTTT

GGCCCCTGCCCCAGCCCCTCGGTTTGGGGGAGATTTCAGAACGCGGACAGCGCCCTGGCTGCGG

GCCATAGGGGACTGGGTGGAACTCGGGAAGCCCCCAGAGCAGGGGCTTACTCGCTTCAAGTTTG

GGGAACCCCGGGCAGCGGGTGCAGGCCACGAGACCCGAAGGTTCTCAGGTGCCCCCCTGCAGGC

TGGCCGTGCGCGCCGTGGGGCGCTTGTCGCGAGCGCCGAGGGCTGCAGGACGCGGACCAGACTC

GCGGTGCAGGGGGGCCTGGCTGCAGCTAACAGGTGATCCCGTTCTTTCTGTTCCTCGCTCTTCC

CCTCCGATCGTCCTCGCTTACCGCGTGTCCTCCCTCCTCGCTGTCCTCTGGCTCGCAGGTCATG

GCAGCGCCAGGCGGCAGGTCGGAGCCGCCGCAGCTCCCCGAGTACAGCTGCAGCTACATGGTGT

CGCGGCCGGTCTACAGCGAGCTCGCTTTCCAGCAACAGCACGAGCGGCGCCTGCAGGAGCGCAA

GACGCTGCGGGAGAGCCTGGCCAAGTGCTGCAGGTAGCGGCCGCGCGGGCCTGCGTAGAGAGAA

GCGGAGCGGGGCGTCCACGCCTTGGGGAGGGAAGGGCGTCCCCAGCGGGCGAGAGTGGGGTGCG

GGCGGCGGAGCCCCTGGGCGCCAGCTGCTTCTCCCAGAGGCCCGACTTTCGGTCTCCGGTCCTC

CACGCCGCCCTTCTGGTGGGAGGGTGGCTCCATCAGTCTCGGGCCCGAAATGAACTTACCTGGG

AAACTCGCCTTTGGGGAGAGTGGGTTCTAGGAGCCCCGTCTCTCTTTTTCCTCTCTGAAGGAAA

CTTGGAGTGCCTCTTGGGGTACAGTGGGTCCCTGTTGCCTTCTTGGGAGCTTGTTTAAATGAAA

TGAATAGGGAAACCCAGCTCTTGACCAGGAGGAGTCCTTGAAACACTCAAGCTAAGTAGGCGGG

-continued

CTACCATTCAGTTAGAGACCAGGATGCAAGCTAGAACCCAGGGGAGCGCGGGGTGTGCCAAGTA

CTTCATCAGCAGGCTGTGGGACCCCTGGGGAAAGCCACCCTCAGTCTCTAAACCCAAACATGCC

GTAACTAGATGTCACAAACATAAAGAAATTAGAGTTTCTAAAACCTTTCATTATAG

Exemplary Human SLC26A4 enhancer-promoter (SEQ ID NO: 50)

CGGAAGGTTGATGTACAGAGGTCTGTATTTTGGAGCCTCTTCTGTATTTACTTCAGAACACTAA

CAATCAGGCGAGAATGTTCTGGTTTATCAAACCCTTCCTTCTGCCTTTCATCTTAACCATGCAT

TAGTTTTAACAAAGTTCATCCCAACAGAAGACAAAACACTGATGAGGTAGGATAGCTCCAGCTC

CTCCTCCCTCTCTTCTAGTCTTGATTTCCATGTAGTCCAGTTTATTCCTTCCCTGATTGTCCAG

GAGAATGAGAAAAAGAAAAAACAGAGTCTAGTGGGTAAGAAAGGGCCACCTGGACGGCTTGATT

TGGATTGTGAAATAAAACACACACACATGCACACGTAGAATAAGTGGCTAAAATCTGAGTAAAT

CGTGAACTCTCTGTATCCTCCACCCATTGAATACTCCTAAAAGACTTTCTAGAAATTCAAGGAC

TTATTAATATAGAAACCTGGCCATTGTTCCTCTTCTCCTCCCCATGTGGTATGAGAGCACCTGT

GGCAGGCTCCCAGAGACCACGGACCTCTTCCTCTAGGCGGGCTCTGCTCTTCTTTAAGGAGTCC

CACAGGGCCTGGCCCGCCCCTGACCTCGCAACCCTTGAGATTAGTAACGGGATGAGTGAGGATC

CGGGTGGCCCCTGCGTGGCAGCCAGTAAGAGTCTCAGCCTTCCCGGTTCGGGAAAGGGGAAGAA

TGCAGGAGGGGTAGGATTTCTTTCCTGATAGGATCGGTTGGGAAAGACCGCAGCCTGTGTGTGT

CTTTCCCTTCGACCAAGGTGTCTGTTGCTCCGTAAATAAAACGTCCCACTGCCTTCTGAGAGCG

CTATAAAGGCAGCGGAAGGGTAGTCCGCGGGGCATTCCGGGCGGGGCGCGAGCAGAGACAGGTG

AGTT

In certain embodiments, a promoter is a human LGR5 enhancer-promoter as set forth in SEQ ID NO: 51. In some embodiments, an enhancer-promoter sequence is at least 85%, 90%, 95%, 98% or 99% identical to enhancer-promoter sequence represented by SEQ ID NO: 51. In some embodiments, a promoter is a human LGR5 endogenous enhancer-promoter sequence comprised within SEQ ID NO: 51.

Exemplary Human LGR5 enhancer-promoter (SEQ ID NO: 51)

AGGGCTATTTGTACCTCAACGAGGGCTTCTCTCCAAGAAAGCCCTGAATC

CTTTTCCTCCTTTTTCCTGCAGATTCACTATAGGACACTTTTTGAAGCAA

GAGCATGCATTTTCCCCCTGGCGCTCTGCAGCGGTTCTCAGAGCCCAGTG

TCACTCACATAGGTGGGACTGCTCTCAGTTCAGAGAGCGCTGGGACACTT

AAGATGAAAAGTCCCTGGAAGTTAGCAAACAGCCATCTGTCACTCTGGCA

TCGATTTAGTAAAAGTGAGTTCTAGGGTATTCTAAACGAGTTTTAAAAAA

CAAATGAGTGAGTTCGAGTTCCTCACCCCGCAAGAGATAGGAAGGCAGCA

GTGGAGTGCTCGCTCAGGAGCTGTATTTGTTTAGCGATTAGCCTAGAGCT

TTGATTTTAGGGCAAAAGCGAGCCAGACAGTGCGGCAGACGTAAGGATCA

AAAAGGCCACCTATCATTCGCCGGGGACGCCTGCCTCCTTACCCTGATAA

CGTAACTATTTCTCTGCATAGGATTTTAGTTTTTGTGTTTTTGTTTTGTT

TTATTCTGTTTAATCACTTCAAGTATCTCATCCATTATTTGAAGCGGGCT

CGGAGGAAACGTGCCGCATCCTCCAGTCCTTGTGCGTCTGTTTAGGTCTC

TCCGAAGCAGGTCCCTCTCGACTCTTAGATCTGGGTCTCCAGCACGCATG

-continued

AAGGGGTAAGGGTGGGGGGGTCCCCTATTCCGGCGCGCGGCGTTGAGCAC

TGAATCTTCCAGGCGGAGGCTCAGTGGGAGCGCCGAGAACTCGCCAGTAC

CGCGCGCTGCCTGCTGCCTGCTGCCTCCCAGCCCAGGACTTGGGAAAGGA

GGGAGGGGACAAGTGGAGGGAAAGTGGGGCCGGGCGGGGGGTGCCTGGGA

AGCCAGGCTGCGCTGACGTCACTGGGCGCGCAATTCGGGCTGGAGCGCTT

TAAAAAACGAGCGTGCAAGCAGAGATGCTGCTCCACACCGCTCAGGCCGC

GAGCAGCAGCAAGGCGCACCGCCACTGTCGCCGCTGCAGCCAGGGCTGCT

CCGAAGGCCGGCGTGGCGGCAACCGGCACCTCTGTCCCCGCCGCGCTTCT

CCTCGCCGCCCACGCCGTGGGGTCAGGAACGCGGCGTCTGGCGCTGCAGA

CGCCCGCTGAGTTGCAGAAGCCCACGGAGCGGCGCCCGGCGCGCCACGGC

CCGTAGCAGTCCGGTGCTGCTCTCCGCCCGCGTCCGGCTCGTGGCCCCCT

ACTTCGGGCACCGACCGGT

In certain embodiments, a promoter is a human SYN1 enhancer-promoter as set forth in SEQ ID NO: 52. In some embodiments, an enhancer-promoter sequence is at least 85%, 90%, 95%, 98% or 99% identical to enhancer-promoter sequence represented by SEQ ID NO: 52. In some embodiments, a promoter is a human SYN1 endogenous enhancer-promoter sequence comprised within SEQ ID NO: 52.

Exemplary Human SYN1 enhancer-promoter (SEQ ID NO: 52)

TGCGTATGAGTGCAAGTGGGTTTTAGGACCAGGATGAGGCGGGGTGGGGG

TGCCTACCTGACGACCGACCCCGACCCACTGGACAAGCACCCAACCCCCA

TTCCCCAAATTGCGCATCCCCTATCAGAGAGGGGGAGGGGAAACAGGATG

CGGCGAGGCGCGTGCGCACTGCCAGCTTCAGCACCGCGGACAGTGCCTTC

GCCCCCGCCTGGCGGCGCGCGCCACCGCCGCCTCAGCACTGAAGGCGCGC

TGACGTCACTCGCCGGTCCCCCGCAAACTCCCCTTCCCGGCCACCTTGGT

CGCGTCCGCGCCGCCGCCGGCCCAGCCGGACCGCACCACGCGAGGCGCGA

GATAGGGGGGCACGGGCGCGACCATCTGCGCTGCGGCGCCGGCGACTCAG

CGCTGCCTCAGTCTGCGGTGGGCAGCGGAGGAGTCGTGTCGTGCCTGAGA

GCGCAGTCGAGAA

In certain embodiments, a promoter is a human GFAP enhancer-promoter as set forth in SEQ ID NO: 53. In some embodiments, an enhancer-promoter sequence is at least 85%, 90%, 95%, 98% or 99% identical to enhancer-promoter sequence represented by SEQ ID NO: 53. In some embodiments, a promoter is a human GFAP endogenous enhancer-promoter sequence comprised within SEQ ID NO: 53.

Exemplary Human GFAP enhancer-promoter (SEQ ID NO: 53)

CCCACCTCCCTCTCTGTGCTGGGACTCACAGAGGGAGACCTCAGGAGGCA

GTCTGTCCATCACATGTCCAAATGCAGAGCATACCCTGGGCTGGGCGCAG

TGGCGCACAACTGTAATTCCAGCACTTTGGGAGGCTGATGTGGAAGGATC

ACTTGAGCCCAGAAGTTCTAGACCAGCCTGGGCAACATGGCAAGACCCTA

TCTCTACAAAAAAAGTTAAAAAATCAGCCACGTGTGGTGAGACACACCTG

TAGTCCCAGCTATTCAGGAGGCTGAGGTGAGGGGATCACTTAAGGCTGGG

AGGTTGAGGCTGCAGTGAGTCGTGGTTGCGCCACTGCACTCCAGCCTGGG

CAACAGTGAGACCCTGTCTCAAAAGACAAAAAAAAAAAAAAAAAAAAAAA

GAACATATCCTGGTGTGGAGTAGGGGACGCTGCTCTGACAGAGGCTCGGG

GGCCTGAGCTGGCTCTGTGAGCTGGGGAGGAGGCAGACAGCCAGGCCTTG

TCTGCAAGCAGACCTGGCAGCATTGGGCTGGCCGCCCCCCAGGGCCTCCT

CTTCATGCCCAGTGAATGACTCACCTTGGCACAGACACAATGTTCGGGGT

GGGCACAGTGCCTGCTTCCCGCCGCACCCCAGCCCCCCTCAAATGCCTTC

CGAGAAGCCCATTGAGCAGGGGGCTTGCATTGCACCCCAGCCTGACAGCC

TGGCATCTTGGGATAAAAGCAGCACAGCCCCCTAGGGGCTGCCCTTGCTG

TGTGGCGCCACCGGCGGTGGAGAACAAGGCTCTATTCAGCCTGTGCCCAG

GAAAGGGGATCAGGGGATGCCCAGGCATGGACAGTGGGTGGCAGGGGGGG

AGAGGAGGGCTGTCTGCTTCCCAGAAGTCCAAGGACACAAATGGGTGAGG

GGACTGGGCAGGGTTCTGACCCTGTGGGACCAGAGTGGAGGGCGTAGATG

GACCTGAAGTCTCCAGGGACAACAGGGCCCAGGTCTCAGGCTCCTAGTTG

GGCCCAGTGGCTCCAGCGTTTCCAAACCCATCCATCCCCAGAGGTTCTTC

CCATCTCTCCAGGCTGATGTGTGGGAACTCGAGGAAATAAATCTCCAGTG

GGAGACGGAGGGGTGGCCAGGGAAACGGGGCGCTGCAGGAATAAAGACGA

-continued

GCCAGCACAGCCAGCTCATGTGTAACGGCTTTGTGGAGCTGTCAAGGCCT

GGTCTCTGGGAGAGAGGCACAGGGAGGCCAGACAAGGAAGGGGTGACCTG

GAGGGACAGATCCAGGGGCTAAAGTCCTGATAAGGCAAGAGAGTGCCGGC

CCCCTCTTGCCCTATCAGGACCTCCACTGCCACATAGAGGCCATGATTGA

CCCTTAGACAAAGGGCTGGTGTCCAATCCCAGCCCCCAGCCCCAGAACTC

CAGGGAATGAATGGGCAGAGAGCAGGAATGTGGGACATCTGTGTTCAAGG

GAAGGACTCCAGGAGTCTGCTGGGAATGAGGCCTAGTAGGAAATGAGGTG

GCCCTTGAGGGTACAGAACAGGTTCATTCTTCGCCAAATTCCCAGCACCT

TGCAGGCACTTACAGCTGAGTGAGATAATGCCTGGGTTATGAAATCAAAA

AGTTGGAAAGCAGGTCAGAGGTCATCTGGTACAGCCCTTCCTTCCCTTTT

TTTTTTTTTTTTTTGTGAGACAAGGTCTCTCTCTGTTGCCCAGGCTGGAG

TGGCGCAAACACAGCTCACTGCAGCCTCAACCTACTGGGCTCAAGCAATC

CTCCAGCCTCAGCCTCCCAAAGTGCTGGGATTACAAGCATGAGCCACCCC

ACTCAGCCCTTTCCTTCCTTTTTAATTGATGCATAATAATTGTAAGTATT

CATCATGGTCCAACCAACCCTTTCTTGACCCACCTTCCTAGAGAGAGGGT

CCTCTTGCTTCAGCGGTCAGGGCCCCAGACCCATGGTCTGGCTCCAGGTA

CCACCTGCCTCATGCAGGAGTTGGCGTGCCCAGGAAGCTCTGCCTCTGGG

CACAGTGACCTCAGTGGGGTGAGGGGAGCTCTCCCCATAGCTGGGCTGCG

GCCCAACCCCACCCCCTCAGGCTATGCCAGGGGGTGTTGCCAGGGGCACC

CGGGCATCGCCAGTCTAGCCCACTCCTTCATAAAGCCCTCGCATCCCAGG

AGCGAGCAGAGCCAGAGCAGGTTGGAGAGGAGACGCATCACCTCCGCTGC

TCGC

Exemplary NDP_promoter_NG_009832.1

(SEQ ID NO: 99)

AGCTGCAGGTATTTAACCCACACACATAGTTACCTTTGTCACTTTTCTAC

TAGTTGTTGTGTAATGGGTTAGCTTTATCTATTAGTTTCTCCTTCATATA

GCTCAAGGAGTCAAGGAATACACGTTCTCATTGTTTCTAAATCAGACCTA

AAGTTTTATTCTAAATGATGCAGATGAAGGGGCTTATTAAAGTGCCATTG

TGAATTTAATCATGTATATGCTGCTAAAAATCATTTAATGGATGAACAAC

CCGGAAAAAAAGAACTCTCACCACCCACACACATCGTGATAAAATAGGGC

AGCGTTTTGCACTTGCTTTAACAGCATCGCCTGAGAAAAAAATTTCTGGT

TCCCATCTTTCCCCTCTCTTACTTAAAATTTCAACTTCATCACAGTCAGC

TGCCGAATCGTTCAACAGAATGCCACACTGCCTTTGTATTTCCAAAACTA

TACGTCTCTATTGCGGACGGCACATCTTTATGGCAGCCACATGCTTGAAA

AAGAATTAAATTCAGAATATTCATTTGGCCTCTTATTAGTTCCATAATAC

CATTAAAAAAGAAAGAAAGAAAGAAACTTCCTCGCCCTTGTTCTGCTACG

CTGTTCCCATCGTAAGATGCTCCGTGGAAGGGAGCCGAGCGGTGGGCAGA

GGCTGAGTCCCCGATAACGAGCGCCTCACATTTCCGTGGCATTCCCATTT

GCTAGTGCGCTGCTGCGGCCGCACGCCTGATTGATATATGACTGCAATGG

CACTTTTCCATTTGACATTCTCTCTCTCTCTCTCCCTCTCTCTCTCTCCC

TCTCTCTCTCCCTCTCTCTCTCTCCCTGTGTCGCTTAAACAACAGTCCTA

-continued

ACTTTTGTGTGTTGCAAATATAAAAGGCAAGCCATGTGACAGAGGGACAG

AAGAACAAAAGCATTTGGAAGTAACAGGACCTCTTTCTAGCTCTCAGAAA

AGTCTGAGAAGAAAGGAGCCCTGCGTTCCCCTAAGGTAAGCAGGAAAACA

AGCG

Enhancers

In some instances, a vector can include an enhancer sequence. The term "enhancer" refers to a nucleotide sequence that can increase the level of transcription of a nucleic acid encoding a protein of interest (e.g., a secreted target protein (e.g., a NDP protein (e.g., any of the exemplary NDP proteins described herein), a HSPA1A protein (e.g., any of the exemplary HSPA1A proteins described herein))). Enhancer sequences (50-1500 basepairs in length) generally increase the level of transcription by providing additional binding sites for transcription-associated proteins (e.g., transcription factors). In some embodiments, an enhancer sequence is found within an intronic sequence. Unlike promoter sequences, enhancer sequences can act at much larger distance away from the transcription start site (e.g., as compared to a promoter). Non-limiting examples of enhancers include a RSV enhancer, a CMV enhancer, and a SV40 enhancer. In some embodiments, the CMV enhancer sequence comprises or consists of SEQ ID NO: 17. In some embodiments, a construct comprises a CMV enhancer exemplified by SEQ ID NO: 69. In some embodiments, an enhancer sequence is at least 85%, 90%, 95%, 98% or 99% identical to the enhancer sequence represented by SEQ ID NO: 69. In some embodiments, an SV-40 derived enhancer is the SV-40 T intron sequence, which is exemplified by SEQ ID NO: 70. In some embodiments, a an enhancer sequence is at least 85%, 90%, 95%, 98% or 99% identical to the enhancer sequence represented by SEQ ID NO: 70.

Exemplary CMV enhancer
(SEQ ID NO: 69)
GACATTGATTATTGACTAGTTATTAATAGTAATCAATTACGGGGTCATTA

GTTCATAGCCCATATATGGAGTTCCGCGTTACATAACTTACGGTAAATGG

CCCGCCTGGCTGACCGCCCAACGACCCCCGCCCATTGACGTCAATAATGA

CGTATGTTCCCATAGTAACGCCAATAGGGACTTTCCATTGACGTCAATGG

GTGGACTATTTACGGTAAACTGCCCACTTGGCAGTACATCAAGTGTATCA

TATGCCAAGTACGCCCCCTATTGACGTCAATGACGGTAAATGGCCCGCCT

GGCATTATGCCCAGTACATGACCTTATGGGACTTTCCTACTTGGCAGTAC

ATCTACGTATTAGTCATCGCTATTACCATGG

Exemplary SV-40 synthetic intron
(SEQ ID NO: 70)
GGAGTCGCTGCGTTGCCTTCGCCCCGTGCCCCGCTCCGCGCCGCCTCGCG

CCGCCCGCCCCGGCTCTGACTGACCGCGTTACTCCCACAGGTGAGCGGGC

GGGACGGCCCTTCTCCTCCGGGCTGTAATTAGCGCTTGGTTTAATGACGG

CTCGTTTCTTTTCTGTGGCTGCGTGAAAGCCTTAAAGGGCTCCGGGAGGG

CCCTTTGTGCGGGGGGGAGCGGCTCGGGGGGTGCGTGCGTGTGTGTGTGC

GTGGGGAGCGCCGCGTGCGGCCCGCGCTGCCCGGCGGCTGTGAGCGCTGC

GGGCGCGGCGCGGGGCTTTGTGCGCTCCGCGTGTGCGCGAGGGGAGCGCG

GCCGGGGGCGGTGCCCCGCGGTGCGGGGGGGCTGCGAGGGGAACAAAGGC

-continued

TGCGTGCGGGGTGTGTGCGTGGGGGGGTGAGCAGGGGGTGTGGGCGCGGC

GGTCGGGCTGTAACCCCCCCCTGCACCCCCCTCCCCGAGTTGCTGAGCAC

GGCCCGGCTTCGGGTGCGGGGCTCCGTGCGGGGCGTGGCGCGGGGCTCGC

CGTGCCGGGCGGGGGGTGGCGGCAGGTGGGGGTGCCGGGCGGGGCGGGGC

CGCCTCGGGCCGGGGAGGGCTCGGGGGAGGGGCGCGGCGGCCCCCGGAGC

GCCGGCGGCTGTCGAGGCGCGGCGAGCCGCAGCCATTGCCTTTTATGGTA

ATCGTGCGAGAGGGCGCAGGGACTTCCTTTGTCCCAAATCTGTGCGGAGC

CGAAATCTGGGAGGCGCCGCCGCACCCCCTCTAGCGGGCGCGGGGCGAAG

CGGTGCGGCGCCGGCAGGAAGGAAATGGGCGGGGAGGGCCTTCGTGCGTC

GCCGCGCCGCCGTCCCCTTCTCCCTCTCCAGCCTCGGGGCTGTCCGCGGG

GGGACGGCTGCCTTCGGGGGGGACGGGGCAGGGCGGGGTTCGGCTTCTGG

CGTGTGACCGGCGGCTCTAGAGCCTCTGCTAACCATGTTCATGCCTTCTT

CTTTTTCCTACAG

Splice Sites

In some embodiments, any of the constructs provided herein can include splice donor and/or splice acceptor sequences, which are functional during RNA processing occurring during transcription. In some embodiments, splice sites are involved in trans-splicing.

Exemplary splice donor intron
(SEQ ID NO: 155)
GTAAGTATCAAGGTTACAAGACAGGTTTAAGGAGACCAATAGAAACTGGG

CTTGTCGAGACAGAGAAGACTCTTGCGTTTCT

Exemplary splice acceptor intron
(SEQ ID NO: 104)
GATAGGCACCTATTGGTCTTACTGACATCCACTTTGCCTTTCTCTCCACA

G

Polyadenylation Sequences

In some embodiments, any of the vectors provided herein can include a polyadenylation (poly(A)) signal sequence. Most nascent eukaryotic mRNAs possess a poly(A) tail at their 3' end which is added during a complex process that includes cleavage of the primary transcript and a coupled polyadenylation reaction driven by the poly(A) sisignal sequence (see, e.g., Proudfoot et al., Cell 108:501-512, 2002). The poly(A) tail confers mRNA stability and transferability (Molecular Biology of the Cell, Third Edition by B. Alberts et al., Garland Publishing, 1994). In some embodiments, the poly(A) sisignal sequence is positioned 3' to the nucleic acid sequence encoding the C-terminus of the secreted target protein (e.g., a NDP protein (e.g., any of the exemplary NDP proteins described herein), a HSPA1A protein (e.g., any of the exemplary HSPA1A proteins described herein)).

As used herein, "polyadenylation" refers to the covalent linkage of a polyadenylyl moiety, or its modified variant, to a messenger RNA molecule. In eukaryotic organisms, most messenger RNA (mRNA) molecules are polyadenylated at the 3' end. The 3' poly(A) tail is a long sequence of adenine nucleotides (e.g., 50, 60, 70, 100, 200, 500, 1000, 2000, 3000, 4000, or 5000 (SEQ ID NO: 100)) added to the pre-mRNA through the action of an enzyme, polyadenylate polymerase. In higher eukaryotes, the poly(A) tail is added onto transcripts that contain a specific sequence, the polyadenylation (or poly(A)) signal. The poly(A) tail and the protein bound to it aid in protecting mRNA from degradation by exonucleases. Polyadenylation is also important for transcription termination, export of the mRNA from the nucleus, and translation. Polyadenylation occurs in the nucleus immediately after transcription of DNA into RNA, but also can occur later in the cytoplasm. After transcription has been terminated, the mRNA chain is cleaved through the action of an endonuclease complex associated with RNA polymerase. The cleavage site is usually characterized by the presence of the base sequence AAUAAA near the cleavage site. After the mRNA has been cleaved, adenosine residues are added to the free 3' end at the cleavage site.

As used herein, a "poly(A) signal sequence" or "polyadenylation signal sequence" is a sequence that triggers the endonuclease cleavage of an mRNA and the addition of a series of adenosines to the 3' end of the cleaved mRNA.

There are several poly(A) signal sequences that can be used, including those derived from bovine growth hormone (bgh) (Woychik et al., *Proc. Natl. Acad. Sci. U.S.A.* 81 (13): 3944-3948, 1984; U.S. Pat. No. 5,122,458, each of which is incorporated herein by reference in its entirety), mouse-β-globin, mouse-a-globin (Orkin et al., *EMBO J.* 4 (2): 453-456, 1985; Thein et al., *Blood* 71 (2): 313-319, 1988, each of which is incorporated herein by reference in its entirety), human collagen, polyoma virus (Batt et al., *Mol. Cell Biol.* 15 (9): 4783-4790, 1995, which is incorporated herein by reference in its entirety), the Herpes simplex virus thymidine kinase gene (HSV TK), IgG heavy-chain gene polyadenylation signal (US 2006/0040354, which is incorporated herein by reference in its entirety), human growth hormone (hGH) (Szymanski et al., *Mol. Therapy* 15 (7): 1340-1347, 2007, which is incorporated herein by reference in its entirety), the group consisting of SV40 poly(A) site, such as the SV40 late and early poly(A) site (Schek et al., *Mol. Cell Biol.* 12 (12): 5386-5393, 1992, which is incorporated herein by reference in its entirety).

The poly(A) signal sequence can be AATAAA. The AATAAA sequence may be substituted with other hexanucleotide sequences with homology to AATAAA and that are capable of signaling polyadenylation, including ATTAAA, AGTAAA, CATAAA, TATAAA, GATAAA, ACTAAA, AATATA, AAGAAA, AATAAT, AAAAAA, AATGAA, AATCAA, AACAAA, AATCAA, AATAAC, AATAGA, AATTAA, or AATAAG (see, e.g., WO 06/12414, which is incorporated herein by reference in its entirety).

In some embodiments, the poly(A) signal sequence can be a synthetic polyadenylation site (see, e.g., the pCl-neo expression vector of Promega that is based on Levitt el al, *Genes Dev.* 3 (7): 1019-1025, 1989, which is incorporated herein by reference in its entirety). In some embodiments, the poly(A) signal sequence is the polyadenylation signal of bovine growth hormone (SEQ ID NO: 23). In some embodiments, the poly(A) signal sequence is the polyadenylation signal of soluble neuropilin-1 (sNRP) (AAATAAAATACGAAATG (SEQ ID NO: 46)) (see, e.g., WO 05/073384, which is incorporated herein by reference in its entirety). In some embodiments, a poly(A) signal sequence comprises or consists of the SV40 poly(A) site. In some embodiments, a poly(A) signal comprises or consists of SEQ ID NO: 72. In some embodiments, a poly(A) signal sequence comprises or consists of bGHpA. In some embodiments, a poly(A) signal comprises or consists of SEQ ID NO: 71. Additional examples of poly(A) signal sequences are known in the art. In some embodiments, a poly(A) sequence is at least 85%, 90%, 95%, 98% or 99% identical to the poly(A) sequence represented by SEQ ID NO: 71 or 72.

```
Exemplary bGH poly(A) signal sequence
                                        (SEQ ID NO: 71)
CTGTGCCTTCTAGTTGCCAGCCATCTGTTGTTTGCCCCTCCCCCGTGCCT

TCCTTGACCCTGGAAGGTGCCACTCCCACTGTCCTTTCCTAATAAAATGA

GGAAATTGCATCGCATTGTCTGAGTAGGTGTCATTCTATTCTGGGGGGTG

GGGTGGGGCAGGACAGCAAGGGGGAGGATTGGGAAGACAATAGCAGGCAT

GCTGGGGATGCGGTGGGCTCTATGG

Exemplary SV40 poly(A) signal sequence
                                        (SEQ ID NO: 72)
AACTTGTTTATTGCAGCTTATAATGGTTACAAATAAAGCAATAGCATCAC

AAATTTCACAAATAAAGCATTTTTTTCACTGCATTCTAGTTGTGGTTTGT

CCAAACTCATCAATGTATCTTA
```

Internal Ribosome Entry Sites (IRES)

In some embodiments, a vector encoding the C-terminal portion of the secreted target protein (e.g., a NDP protein (e.g., any of the exemplary NDP proteins described herein), a HSPA1A protein (e.g., any of the exemplary HSPA1A proteins described herein)) can include a polynucleotide internal ribosome entry site (IRES). An IRES sequence is used to produce more than one polypeptide from a single gene transcript. An IRES forms a complex secondary structure that allows translation initiation to occur from any position with an mRNA immediately downstream from where the IRES is located (see, e.g., Pelletier and Sonenberg, *Mol. Cell. Biol.* 8(3): 1103-1112, 1988, which is incorporated herein in its entirety by reference).

There are several IRES sequences known to those in skilled in the art, including those from, e.g., foot and mouth disease virus (FMDV), encephalomyocarditis virus (EMCV), human rhinovirus (HRV), cricket paralysis virus, human immunodeficiency virus (HIV), hepatitis A virus (HAV), hepatitis C virus (HCV), and poliovirus (PV). See e.g., Alberts, Molecular Biology of the Cell, Garland Science, 2002; and Hellen et al., *Genes Dev.* 15(13): 1593-612, 2001, each of which is incorporated herein in their entireties by reference.

In some embodiments, the IRES sequence that is incorporated into the vector that encodes the C-terminal portion of a secreted target protein (e.g., a NDP protein (e.g., any of the exemplary NDP proteins described herein), a HSPA1A protein (e.g., any of the exemplary HSPA1A proteins described herein)) is the foot and mouth disease virus (FMDV) 2A sequence. The Foot and Mouth Disease Virus 2A sequence is a small peptide (approximately 18 amino acids in length) that has been shown to mediate the cleavage of polyproteins (Ryan, M D et al., *EMBO* 4:928-933, 1994; Mattion et al., *J. Virology* 70:8124-8127, 1996; Furler et al., *Gene Therapy* 8:864-873, 2001; and Halpin et al., *Plant Journal* 4:453-459, 1999, each of which is incorporated in its entirety herein by reference). The cleavage activity of the 2A sequence has previously been demonstrated in artificial systems including plasmids and gene therapy vectors (AAV and retroviruses) (Ryan et al., EMBO 4:928-933, 1994; Mattion et al., *J. Virology* 70:8124-8127, 1996; Furler et al., *Gene Therapy* 8:864-873, 2001; and Halpin et al., *Plant Journal* 4:453-459, 1999; de Felipe et al., *Gene Therapy* 6:198-208, 1999; de Felipe et al., *Human Gene Therapy*

11:1921-1931, 2000; and Klump et al., *Gene Therapy* 8:811-817, 2001, each of which is incorporated in its entirety herein by reference).

An IRES can be utilized in an AAV construct. In some embodiments, a construct encoding the C-terminal portion of the secreted target protein (e.g., a NDP protein (e.g., any of the exemplary NDP proteins described herein), a HSPA1A protein (e.g., any of the exemplary HSPA1A proteins described herein)) can include a polynucleotide internal ribosome entry site (IRES). In some embodiments, an IRES can be part of a composition comprising more than one construct. In some embodiments, an IRES is used to produce more than one polypeptide from a single gene transcript.

Reporter Sequences or Elements

In some embodiments, constructs provided herein can optionally include a sequence encoding a reporter polypeptide and/or protein ("a reporter sequence"). Non-limiting examples of reporter sequences include DNA sequences encoding: a beta-lactamase, a beta-galactosidase (LacZ), an alkaline phosphatase, a thymidine kinase, a green fluorescent protein (GFP), a red fluorescent protein, an mCherry fluorescent protein, a yellow fluorescent protein, a chloramphenicol acetyltransferase (CAT), and a luciferase. Additional examples of reporter sequences are known in the art. When associated with regulatory elements which drive their expression, the reporter sequence can provide signals detectable by conventional means, including enzymatic, radiographic, colorimetric, fluorescence, or other spectrographic assays; fluorescent activating cell sorting (FACS) assays; immunological assays (e.g., enzyme linked immunosorbent assay (ELISA), radioimmunoassay (RIA), and immunohistochemistry).

In some embodiments, the reporter sequence is tGFP (SEQ ID NO: 27). In some embodiments, the reporter sequence is eGFP (SEQ ID NO: 28 or SEQ ID NO: 29). In some embodiments, the reporter sequence is the LacZ gene, and the presence of a vector carrying the LacZ gene in a mammalian cell (e.g., a cochlear hair cell, an ocular cell, such as a retinal cell) is detected by assays for beta-galactosidase activity. When the reporter is a fluorescent protein (e.g., green fluorescent protein) or luciferase, the presence of a vector carrying the fluorescent protein or luciferase in a mammalian cell (e.g., a cochlear hair cell, an ocular cell, such as a retinal cell) may be measured by fluorescent techniques (e.g., fluorescent microscopy or FACS) or light production in a luminometer (e.g., a spectrophotometer or an IVIS imaging instrument). In some embodiments, the reporter sequence can be used to verify the tissue-specific targeting capabilities and tissue-specific promoter regulatory activity of any of the vectors described herein.

In some embodiments, a reporter sequence is the LacZ gene, and the presence of a construct carrying the LacZ gene in a mammalian cell (e.g., a cochlear hair cell) is detected by assays for beta-galactosidase activity. When the reporter is a fluorescent protein (e.g., green fluorescent protein) or luciferase, the presence of a construct carrying the fluorescent protein or luciferase in a mammalian cell (e.g., a cochlear hair cell) may be measured by fluorescent techniques (e.g., fluorescent microscopy or FACS) or light production in a luminometer (e.g., a spectrophotometer or an IVIS imaging instrument). In some embodiments, a reporter sequence can be used to verify the tissue-specific targeting capabilities and tissue-specific promoter regulatory and/or control activity of any of the constructs described herein.

In some embodiments, a reporter sequence is a FLAG tag (e.g., a 3xFLAG tag), and the presence of a construct carrying the FLAG tag in a mammalian cell (e.g., an inner ear cell, e.g., a cochlear hair or supporting cell) is detected by protein binding or detection assays (e.g., Western blots, immunohistochemistry, radioimmunoassay (RIA), mass spectrometry). An exemplary 3xFLAG tag sequence is provided as SEQ ID NO: 105.

```
Exemplary 3xFLAG tag sequence
                                          (SEQ ID NO: 105)
GGATCCCGGGCTGACTACAAAGACCATGACGGTGATTATAAAGATCATGA

CATCGACTACAAGGATGACGATGACAAG
```

Flanking Untranslated Regions, 5' UTRs and 3' UTRs

In some embodiments, any of the vectors described herein (e.g., any of the at least two different vectors) can include an untranslated region, such as a 5'UTR or a 3' UTR.

Untranslated regions (UTRs) of a gene are transcribed but not translated. A 5' UTR starts at the transcription start site and continues to the start codon but does not include the start codon. A 3' UTR starts immediately following the stop codon and continues until the transcriptional termination signal. There is a growing body of evidence about the regulatory roles played by the UTRs in terms of stability of the nucleic acid molecule and translation. The regulatory and/or control features of a UTR can be incorporated into any of the vectors, constructs, compositions, kits, or methods as described herein to otherwise modulate the expression of a secreted target protein (e.g., a NDP protein, a HSPA1A protein).

Natural 5' UTRs include a sequence that plays a role in translation initiation. They harbor signatures like Kozak sequences, which are commonly known to be involved in the process by which the ribosome initiates translation of many genes. Kozak sequences have the consensus sequence CCR(A/G)CCAUGG, where R is a purine (A or G) three bases upstream of the start codon (AUG), and the start codon is followed by another "G". The 5'UTRs have also been known to form secondary structures that are involved in elongation factor binding.

In some embodiments, a 5'UTR is included in any of the vectors described herein. Non-limiting examples of 5'UTRs, including those from the following genes: albumin, serum amyloid A, Apolipoprotein A/B/E, transferrin, alpha fetoprotein, erythropoietin, and Factor VIII, can be used to enhance expression of a nucleic acid molecule, such as an mRNA.

In some embodiments, a 5'UTR from an mRNA that is transcribed by a cell in the cochlea or retina can be included in any of the vectors, compositions, kits, and methods described herein. In some embodiments, a 5' UTR is derived from the endogenous SLC26A4 gene loci and may include all or part of the endogenous sequence exemplified by SEQ ID NO: 21. In some embodiments, a 5' UTR sequence is at least 85%, 90%, 95%, 98% or 99% identical to the 5' UTR sequence represented by SEQ ID NO: 21.

3' UTRs are found immediately 3' to the stop codon of the gene of interest. In some embodiments, a 3' UTR from an mRNA that is transcribed by a cell in the cochlea can be included in any of the constructs, compositions, kits, and methods described herein. In some embodiments, a 3' UTR is derived from the endogenous SLC26A4 gene loci and may include all or part of the endogenous sequence exemplified by SEQ ID NO: 22. In some embodiments, a 3' UTR sequence is at least 85%, 90%, 95%, 98% or 99% identical to the 3' UTR sequence represented by SEQ ID NO: 22.

3'UTRs are known to have stretches of adenosines and uridines (in the RNA form) or thymidines (in the DNA form) embedded in them. These AU-rich signatures are particularly prevalent in genes with high rates of turnover. Based on their sequence features and functional properties, the AU-rich elements (AREs) can be separated into three classes (Chen et al., *Mol. Cell. Biol.* 15:5777-5788, 1995; Chen et al., *Mol. Cell. Biol.* 15:2010-2018, 1995, each of which is incorporated herein by reference in its entirety): Class I AREs contain several dispersed copies of an AUUUA motif within U-rich regions. For example, c-Myc and MyoD mRNAs contain class I AREs. Class II AREs possess two or more overlapping UUAUUUA (U/A) (U/A) nonamers. GM-CSF and TNF-alpha mRNAs are examples that contain class II AREs. Class III AREs are less well defined. These U-rich regions do not contain an AUUUA motif. Two well-studied examples of this class are c-Jun and myogenin mRNAs.

Most proteins that bind to the AREs are known to destabilize the messenger, whereas members of the ELAV family, most notably HuR, have been documented to increase the stability of mRNA. HuR binds to AREs of all the three classes. Engineering the HuR specific binding sites into the 3'UTR of nucleic acid molecules will lead to HuR binding and thus, stabilization of the message in vivo.

An exemplary human wildtype 5'UTR is or includes the sequence of SEQ ID NO: 14 or 30. An exemplary human wildtype 3'UTR is or includes the sequence of SEQ ID NO: 15 or 22.

In some embodiments of any of the compositions described herein, a 5' untranslated region (UTR), a 3'UTR, or both are included in a vector (e.g., any of the vectors described herein). For example, any of the 5'UTRs described herein can be operatively linked to the start codon in any of the coding sequences described herein. For example, any of the 3'UTRs can be operably linked to the 3'-terminal codon (last codon) in any of the coding sequences described herein.

In some embodiments of any of the compositions described herein, the 5'UTR includes at least 10 contiguous (e.g., at least 15 contiguous, at least 20 contiguous, at least 25 contiguous, at least 30 contiguous, at least 35 contiguous, at least 40 contiguous, at least 45 contiguous, at least 50 contiguous, at least 55 contiguous, at least 60 contiguous, at least 65 contiguous, at least 70 contiguous, at least 75 contiguous, at least 80 contiguous, at least 85 contiguous, at least 90 contiguous, at least 95 contiguous, at least 100 contiguous, at least 105 contiguous, at least 110 contiguous, at least 115 contiguous, at least 120 contiguous, at least 125 contiguous, at least 130 contiguous, at least 135 contiguous, at least 140 contiguous, at least 145 contiguous, at least 150 contiguous, at least 155 contiguous, at least 160 contiguous, at least 165 contiguous, at least 170 contiguous, at least 175 contiguous, at least 180 contiguous, at least 185 contiguous, at least 190 contiguous, at least 195 contiguous, at least 200 contiguous, at least 205 contiguous, at least 210 contiguous, at least 215 contiguous, at least 220 contiguous, at least 225 contiguous, at least 230 contiguous, at least 235 contiguous, at least 240 contiguous, at least 245 contiguous, at least 250 contiguous, at least 255 contiguous, at least 260 contiguous, at 265 contiguous, at least 270 contiguous, at least 275 contiguous, at least 280 contiguous, at least 285 contiguous, at least 290 contiguous, at least 295 contiguous, at least 300 contiguous, at least 305 contiguous, at least 310 contiguous, at least 315 contiguous, at least 320 contiguous, at least 325 contiguous, at least 330 contiguous, at least 335 contiguous, at least 340 contiguous, at least 345 contiguous, at least 350 contiguous, at least 355 contiguous, at least 360 contiguous, at least 365 contiguous, at least 370 contiguous, at least 375 contiguous, at least 380 contiguous, at least 385 contiguous, at least 390 contiguous, at least 395 contiguous, at least 400 contiguous, at least 405 contiguous, at least 410 contiguous, at least 415 contiguous, at least 420 contiguous, at least 425 contiguous, at least 430 contiguous, at least 435 contiguous, at least 440 contiguous, at least 445 contiguous, at least 450 contiguous, at least 455 contiguous, at least 460 contiguous, at least 465 contiguous, at least 470 contiguous, at least 475 contiguous, at least 480 contiguous, at least 485 contiguous, at least 490 contiguous, at least 495 contiguous, at least 500 contiguous, at least 505 contiguous, at least 510 contiguous, at least 515 contiguous, at least 520 contiguous, at least 525 contiguous, at least 530 contiguous, at least 535 contiguous, at least 540 contiguous, at least 545 contiguous, or at least 550 contiguous) nucleotides from anywhere within SEQ ID NO: 14 or SEQ ID NO: 31.

For example, a 5'UTR can include or consist of one or more of: nucleotide positions 1 to 550, nucleotide positions 1 to 500, nucleotide positions 1 to 450, nucleotide positions 1 to 400, nucleotide positions 1 to 350, nucleotide positions 1 to 300, nucleotide positions 1 to 250, nucleotide positions 1 to 200, nucleotide positions 1 to 150, nucleotide positions 1 to 100, nucleotide positions 1 to 50, nucleotide positions 50 to 550, nucleotide positions 50 to 500, nucleotide positions 50 to 450, nucleotide positions 50 to 400, nucleotide positions 50 to 350, nucleotide positions 50 to 300, nucleotide positions 50 to 250, nucleotide positions 50 to 200, nucleotide positions 50 to 150, nucleotide positions 50 to 100, nucleotide positions 100 to 550, nucleotide positions 100 to 500, nucleotide positions 100 to 450, nucleotide positions 100 to 400, nucleotide positions 100 to 350, nucleotide positions 100 to 300, nucleotide positions 100 to 250, nucleotide positions 100 to 200, nucleotide positions 100 to 150, nucleotide positions 150 to 550, nucleotide positions 150 to 500, nucleotide positions 150 to 450, nucleotide positions 150 to 400, nucleotide positions 150 to 350, nucleotide positions 150 to 300, nucleotide positions 150 to 250, nucleotide positions 150 to 200, nucleotide positions 200 to 550, nucleotide positions 200 to 500, nucleotide positions 200 to 450, nucleotide positions 200 to 400, nucleotide positions 200 to 350, nucleotide positions 200 to 300, nucleotide positions 200 to 250, nucleotide positions 250 to 550, nucleotide positions 250 to 500, nucleotide positions 250 to 450, nucleotide positions 250 to 400, nucleotide positions 250 to 350, nucleotide positions 250 to 300, nucleotide positions 300 to 550, nucleotide positions 300 to 500, nucleotide positions 300 to 450, nucleotide positions 300 to 400, nucleotide positions 300 to 350, nucleotide positions 350 to 550, nucleotide positions 350 to 500, nucleotide positions 350 to 450, nucleotide positions 350 to 400, nucleotide positions 400 to 550, nucleotide positions 400 to 500, nucleotide positions 400 to 450, nucleotide positions 450 to 500, or nucleotide positions 500 to 550, of SEQ ID NO: 14 or SEQ ID NO: 31.

In some embodiments of any of the compositions described herein, the 5'UTR includes a sequence that is at least 70% (e.g., at least 72%, at least 74%, at least 75%, at least 76%, at least 78%, at least 80%, at least 82%, at least 84%, at least 85%, at least 86%, at least 88%, at least 90%, at least 92%, at least 94%, at least 95%, at least 96%, at least 97%, at least 98%, at least 99%, or 100%) identical to SEQ ID NO: 14 or SEQ ID NO: 31.

Exemplary 5' UTR Sequence (SEQ ID NO: 14)

```
AAGATGCTCCGTGGAAGGGAGCCGAGCGGTGGGCAGAGGCTGAGTCCCCG

ATAACGAGCGCCTCACATTTCCGTGGCATTCCCATTTGCTAGTGCGCTGC

TGCGGCCGCACGCCTGATTGATATATGACTGCAATGGCACTTTTCCATTT

GACATTCTCTCTCTCTCTCCCTCTCTCTCTCCCTCTCTCTCCCT

CTCTCTCTCCCTGTGTCGCTTAAACAACAGTCCTAACTTTTGTGTGTT

GCAAATATAAAAGGCAAGCCATGTGACAGAGGGACAGAAGAACAAAAGCA

TTTGGAAGTAACAGGACCTCTTTCTAGCTCTCAGAAAAGTCTGAGAAGAA

AGGAGCCCTGCGTTCCCCTAAGCTGTGCAGCAGATAGTGTGATGATGGAT

TGCAAGTGCAAAGAGTAAGACAAAACTCCAGCACATAAAGGACAATGACA

ACCAGAAAGCTTCAGCCCGATCCTGCCCTTTCCTTGAACGGGACTGGATC

CTAGGAGGTGAAGCCATTTCCAATTTTTTGTCCTCTGCCTCCCTCTGCTG

TTCTTCTAGAGAAGTTTTTCCTTACAACA
```

Exemplary 5' UTR Sequence (SEQ ID NO: 31)

```
AAGATGCTCCGTGGAAGGGAGCCGAGCGGTGGGCAGAGGCTGAGTCCCCG

ATAACGAGCGCCTCACATTTCCGTGGCATTCCCATTTGCTAGTGCGCTGC

TGCGGCCGCACGCCTGATTGATATATGACTGCAATGGCACTTTTCCATTT

GACATTCTCTCTCTCTCTCCCTCTCTCTCTCCCTCTCTCTCCCT

CTCTCTCTCCCTGTGTCGCTTAAACAACAGTCCTAACTTTTGTGTGTT

GCAAATATAAAAGGCAAGCCATGTGACAGAGGGACAGAAGAACAAAAGCA

TTTGGAAGTAACAGGACCTCTTTCTAGCTCTCAGAAAAGTCTGAGAAGAA

AGGAGCCCTGCGTTCCCCTAAGCTGTGCAGCAGATAGTGTGATGATGGAT

TGCAAGTGCAAAGAGTAAGACAAAACTCCAGCACATAAAGGACAATGACA

ACCAGAAAGCTTCAGCCCGATCCTGCCCTTTCCTTGAACGGGACTGGATC

CTAGGAGGTGAAGCCATTTCCAATTTTTTGTCCTCTGCCTCCCTCTGCTG

TTCTTCTAGAGAAGTTTTTCCTTACAACA
```

In some embodiments of any of the compositions described herein, the 3'UTR includes at least 10 contiguous (e.g., at least 15 contiguous, at least 20 contiguous, at least 25 contiguous, at least 30 contiguous, at least 35 contiguous, at least 40 contiguous, at least 45 contiguous, at least 50 contiguous, at least 55 contiguous, at least 60 contiguous, at least 65 contiguous, at least 70 contiguous, at least 75 contiguous, at least 80 contiguous, at least 85 contiguous, at least 90 contiguous, at least 95 contiguous, at least 100 contiguous, at least 105 contiguous, at least 110 contiguous, at least 115 contiguous, at least 120 contiguous, at least 125 contiguous, at least 130 contiguous, at least 135 contiguous, at least 140 contiguous, at least 145 contiguous, at least 150 contiguous, at least 155 contiguous, at least 160 contiguous, at least 165 contiguous, at least 170 contiguous, at least 175 contiguous, at least 180 contiguous, at least 185 contiguous, at least 190 contiguous, at least 195 contiguous, at least 200 contiguous, at least 205 contiguous, at least 210 contiguous, at least 215 contiguous, at least 220 contiguous, at least 225 contiguous, at least 230 contiguous, at least 235 contiguous, at least 240 contiguous, at least 245 contiguous, at least 250 contiguous, at least 255 contiguous, at least 260 contiguous, at 265 contiguous, at least 270 contiguous, at least 275 contiguous, at least 280 contiguous, at least 285 contiguous, at least 290 contiguous, at least 295 contiguous, at least 300 contiguous, at least 305 contiguous, at least 310 contiguous, at least 315 contiguous, at least 320 contiguous, at least 325 contiguous, at least 330 contiguous, at least 335 contiguous, at least 340 contiguous, at least 345 contiguous, at least 350 contiguous, at least 355 contiguous, at least 360 contiguous, at least 365 contiguous, at least 370 contiguous, at least 375 contiguous, at least 380 contiguous, at least 385 contiguous, at least 390 contiguous, at least 395 contiguous, at least 400, at least 405 contiguous, at least 410 contiguous, at least 415 contiguous, at least 420 contiguous, at least 425 contiguous, at least 430 contiguous, at least 435 contiguous, at least 440 contiguous, at least 445 contiguous, at least 450 contiguous, contiguous, 455 contiguous, at least 460 contiguous, at least 465 contiguous, at least 470 contiguous, at least 475 contiguous, at least 480 contiguous, at least 485 contiguous, at least 490 contiguous, at least 495 contiguous, at least 500 contiguous, at least 505 contiguous, at least 510 contiguous, at least 515 contiguous, at least 520 contiguous, at least 525 contiguous, at least 530 contiguous, at least 535 contiguous, at least 540 contiguous, at least 545 contiguous, at least 550 contiguous, at least 555 contiguous, at least 560 contiguous, at least 565 contiguous, at least 570 contiguous, at least 575 contiguous, at least 580 contiguous, at least 585 contiguous, at least 590 contiguous, at least 595 contiguous, at least 600 contiguous, at least 605 contiguous, at least 610 contiguous, at least 615 contiguous, at least 620 contiguous, at least 625 contiguous, at least 630 contiguous, at least 635 contiguous, at least 640 contiguous, at least 645 contiguous, at least 650 contiguous, at least 655 contiguous, at least 660 contiguous, at least 665 contiguous, at least 670 contiguous, at least 675 contiguous, at least 680 contiguous, at least 685 contiguous, at least 690 contiguous, at least 695 contiguous, at least 700 contiguous, at least 705 contiguous, at least 710 contiguous, at least 715 contiguous, at least 720 contiguous, at least 725 contiguous, at least 730 contiguous, at least 735 contiguous, at least 740 contiguous, at least 745 contiguous, at least 750 contiguous, at least 755 contiguous, at least 760 contiguous, at least 765 contiguous, at least 770 contiguous, at least 775 contiguous, at least 780 contiguous, at least 785 contiguous, at least 790 contiguous, at least 795 contiguous, at least 800 contiguous, at least 805 contiguous, at least 810 contiguous, at least 815 contiguous, at least 820 contiguous, at least 825 contiguous, at least 830 contiguous, at least 835 contiguous, at least 840 contiguous, at least 845 contiguous, at least 850 contiguous, at least 855 contiguous, at least 860 contiguous, at least 865 contiguous, at least 870 contiguous, at least 875 contiguous, at least 880 contiguous, at least 885 contiguous, at least 890 contiguous, at least 895 contiguous, at least 900 contiguous, at least 905 contiguous, at least 910 contiguous, at least 915 contiguous, at least 920 contiguous, at least 925 contiguous, at least 930 contiguous, at least 935 contiguous, at least 940 contiguous, at least 945 contiguous, at least 950 contiguous, at least 955 contiguous, at least 960 contiguous, at least 965 contiguous, at least 970 contiguous, at least 975 contiguous, at least 980 contiguous, at least 985 contiguous, at least 990 contiguous, at least 995 contiguous, at least 1000 contiguous, at least 1005 contiguous, or at least 1010 contiguous) nucleotides from anywhere within SEQ ID NO: 15 or SEQ ID NO: 22.

For example, a 3'UTR can include or consist of one or more of: nucleotide positions 1 to 1000, nucleotide positions 1 to 950, nucleotide positions 1 to 900, nucleotide positions 1 to 850, nucleotide positions 1 to 800, nucleotide positions 1 to 750, nucleotide positions 1 to 700, nucleotide positions 1 to 650, nucleotide positions 1 to 600, nucleotide positions 1 to 550, nucleotide positions 1 to 500, nucleotide positions 1 to 450, nucleotide positions 1 to 400, nucleotide positions 1 to 350, nucleotide positions 1 to 300, nucleotide positions 1 to 250, nucleotide positions 1 to 200, nucleotide positions 1 to 150, nucleotide positions 1 to 100, nucleotide positions 1 to 50, nucleotide positions 50 to 1000, nucleotide positions 50 to 950, nucleotide positions 50 to 900, nucleotide positions 50 to 850, nucleotide positions 50 to 800, nucleotide positions 50 to 750, nucleotide positions 50 to 700, nucleotide positions 50 to 650, nucleotide positions 50 to 600, nucleotide positions 50 to 550, nucleotide positions 50 to 500, nucleotide positions 50 to 450, nucleotide positions 50 to 400, nucleotide positions 50 to 350, nucleotide positions 50 to 300, nucleotide positions 50 to 250, nucleotide positions 50 to 200, nucleotide positions 50 to 150, nucleotide positions 50 to 100, nucleotide positions 100 to 1000, nucleotide positions 100 to 950, nucleotide positions 100 to 900, nucleotide positions 100 to 850, nucleotide positions 100 to 800, nucleotide positions 100 to 750, nucleotide positions 100 to 700, nucleotide positions 100 to 650, nucleotide positions 100 to 600, nucleotide positions 100 to 550, nucleotide positions 100 to 500, nucleotide positions 100 to 450, nucleotide positions 100 to 400, nucleotide positions 100 to 350, nucleotide positions 100 to 300, nucleotide positions 100 to 250, nucleotide positions 100 to 200, nucleotide positions 100 to 150, nucleotide positions 150 to 1000, nucleotide positions 150 to 950, nucleotide positions 150 to 900, nucleotide positions 150 to 850, nucleotide positions 150 to 800, nucleotide positions 150 to 750, nucleotide positions 150 to 700, nucleotide positions 150 to 650, nucleotide positions 150 to 600, nucleotide positions 150 to 550, nucleotide positions 150 to 500, nucleotide positions 150 to 450, nucleotide positions 150 to 400, nucleotide positions 150 to 350, nucleotide positions 150 to 300, nucleotide positions 150 to 250, nucleotide positions 150 to 200, nucleotide positions 200 to 1000, nucleotide positions 200 to 950, nucleotide positions 200 to 900, nucleotide positions 200 to 850, nucleotide positions 200 to 800, nucleotide positions 200 to 750, nucleotide positions 200 to 700, nucleotide positions 200 to 650, nucleotide positions 200 to 600, nucleotide positions 200 to 550, nucleotide positions 200 to 500, nucleotide positions 200 to 450, nucleotide positions 200 to 400, nucleotide positions 200 to 350, nucleotide positions 200 to 300, nucleotide positions 200 to 250, nucleotide positions 250 to 1000, nucleotide positions 250 to 950, nucleotide positions 250 to 900, nucleotide positions 250 to 850, nucleotide positions 250 to 800, nucleotide positions 250 to 750, nucleotide positions 250 to 700, nucleotide positions 250 to 650, nucleotide positions 250 to 600, nucleotide positions 250 to 550, nucleotide positions 250 to 500, nucleotide positions 250 to 450, nucleotide positions 250 to 400, nucleotide positions 250 to 350, nucleotide positions 250 to 300, nucleotide positions 300 to 1000, nucleotide positions 300 to 950, nucleotide positions 300 to 900, nucleotide positions 300 to 850, nucleotide positions 300 to 800, nucleotide positions 300 to 750, nucleotide positions 300 to 700, nucleotide positions 300 to 650, nucleotide positions 300 to 600, nucleotide positions 300 to 550, nucleotide positions 300 to 500, nucleotide positions 300 to 450, nucleotide positions 300 to 400, nucleotide positions 300 to 350, nucleotide positions 350 to 1000, nucleotide positions 350 to 950, nucleotide positions 350 to 900, nucleotide positions 350 to 850, nucleotide positions 350 to 800, nucleotide positions 350 to 750, nucleotide positions 350 to 700, nucleotide positions 350 to 650, nucleotide positions 350 to 600, nucleotide positions 350 to 550, nucleotide positions 350 to 500, nucleotide positions 350 to 450, nucleotide positions 350 to 400, nucleotide positions 400 to 1000, nucleotide positions 400 to 950, nucleotide positions 400 to 900, nucleotide positions 400 to 850, nucleotide positions 400 to 800, nucleotide positions 400 to 750, nucleotide positions 400 to 700, nucleotide positions 400 to 650, nucleotide positions 400 to 600, nucleotide positions 400 to 550, nucleotide positions 400 to 500, nucleotide positions 400 to 450, nucleotide positions 450 to 1000, nucleotide positions 450 to 950, nucleotide positions 450 to 900, nucleotide positions 450 to 850, nucleotide positions 450 to 800, nucleotide positions 450 to 750, nucleotide positions 450 to 700, nucleotide positions 450 to 650, nucleotide positions 450 to 600, nucleotide positions 450 to 550, nucleotide positions 450 to 500, nucleotide positions 500 to 1000, nucleotide positions 500 to 950, nucleotide positions 500 to 900, nucleotide positions 500 to 850, nucleotide positions 500 to 800, nucleotide positions 500 to 750, nucleotide positions 500 to 700, nucleotide positions 500 to 650, nucleotide positions 500 to 600, nucleotide positions 500 to 550, nucleotide positions 550 to 1000, nucleotide positions 550 to 950, nucleotide positions 550 to 900, nucleotide positions 550 to 850, nucleotide positions 550 to 800, nucleotide positions 550 to 750, nucleotide positions 550 to 700, nucleotide positions 550 to 650, nucleotide positions 550 to 600, nucleotide positions 600 to 1000, nucleotide positions 600 to 950, nucleotide positions 600 to 900, nucleotide positions 600 to 850, nucleotide positions 600 to 800, nucleotide positions 600 to 750, nucleotide positions 600 to 700, nucleotide positions 600 to 650, nucleotide positions 650 to 1000, nucleotide positions 650 to 950, nucleotide positions 650 to 900, nucleotide positions 650 to 850, nucleotide positions 650 to 800, nucleotide positions 650 to 750, nucleotide positions 650 to 700, nucleotide positions 700 to 1000, nucleotide positions 700 to 950, nucleotide positions 700 to 900, nucleotide positions 700 to 850, nucleotide positions 700 to 800, nucleotide positions 700 to 750, nucleotide positions 750 to 1000, nucleotide positions 750 to 950, nucleotide positions 750 to 900, nucleotide positions 750 to 850, nucleotide positions 750 to 800, nucleotide positions 800 to 1000, nucleotide positions 800 to 950, nucleotide positions 800 to 900, nucleotide positions 800 to 850, nucleotide positions 850 to 1000, nucleotide positions 850 to 950, nucleotide positions 850 to 900, nucleotide positions 900 to 1000, nucleotide positions 900 to 950, or nucleotide positions 950 to 1000, of SEQ ID NO: 15 or SEQ ID NO: 22.

In some embodiments of any of the compositions described herein, the 3'UTR includes a sequence that is at least 70% (e.g., at least 72%, at least 74%, at least 75%, at least 76%, at least 78%, at least 80%, at least 82%, at least 84%, at least 85%, at least 86%, at least 88%, at least 90%, at least 92%, at least 94%, at least 95%, at least 96%, at least 97%, at least 98%, at least 99%, or 100%) identical to SEQ ID NO: 15 or SEQ ID NO: 22.

```
Exemplary 3'UTR Sequence, 3'UTR-1023
                                          (SEQ ID NO: 15)
GGCCCGCTGCTGTGTGTGGCTTCTGGATGGGACAACTGTAGAGGCAGTTC

GACCAGCCAGGGAAAGACTGGCAAGAAAAGAGTTAAGGCAAAAAAGGATG

CAACAATTCTCCCGGGACTCTGCATATTCTAGTAATAAAGACTCTACATG

CTTGTTGACAGAGAGAGATACTCTGGGAACTTCTTTGCAGTTCCCATCTC

CTTTCTCTGGTACAATTTCTTTTGGTTCATTTTCAGATTCAGGCATTTTC
```

-continued

```
CCCCTTGGCTCTCAATGCTGTTTGGGTTTCCAACAATTCAGCATTAGTGG

GAAAAAGTGGGCCCTCATACACAAGCGTGTCAGGCTGTCAGTGTTTGGTG

CACGCTGGGGAAGAATTTACTTTGGAAAGTAGAAAAGCCCAGCTTTTCCT

GGGACATCTTCTGTTATTGTTGATGTTTTTTTTACCTTGTCATTTTGGT

CTAAGGTTGCCATTGCTGCTAAAGGTTACCGATTTCAAAGTCCAGATACC

AAGCATGTGGATATGTTTAGCTACGTTTACTCACAGCCAGCGAACTGACA

TTAAAATAACTAACAAACAGATTCTTTTATGTGATGCTGGAACTCTTGAC

AGCTATAATTATTATTCAGAAATGACTTTTTGAAAGTAAAAGCAGCATAA

AGAATTTGTCACAGGAAGGCTGTCTCAGATAAATTATGGTAAAATTTTGT

AAGGGAGCAGACTTTTAAAGACTTGCACAAATACGGATCCTGCACTGAGT

CTGGAAAAGGCATATATGTAGTAGTGGCATGGAGAATGCACCATACTCAT

GCATGCAAATTAGACAACCAAGTATGAATCTATTTGTGGGTGTGCTATAG

CTTTAGCCGTGTCACGGGCATCATTCTCTAATATCCACTTGTCCATGTGA

AACATGTTGCCAAAATGGTGGCCTGGCTTGTCTTCTGAACGTTTGGTTCA

AATGTGTTTTGGTCCTGGAGGCTCAAATTTTGAGTTATTCCCACGTTTTG

AAATAAAAAGAGTATATTCAAAA
```

Exemplary 3'UTR Sequence (SEQ ID NO: 22)

```
TGCCCGCTGCTGTGTGTGGCTTCTGGATGGGACAACTGTAGAGGCAGTTC

GACCAGCCAGGGAAAGACTGGCAAGAAAAGAGTTAAGGCAAAAAAGGATG

CAACAATTCTCCCGGGACTCTGCATATTCTAGTAATAAAGACTCTACATG

CTTGTTGACAGAGAGAGATACTCTGGGAACTTCTTTGCAGTTCCCATCTC

CTTTCTCTGGTACAATTTCTTTTGGTTCATTTTCAGATTCAGGCATTTTC

CCCCTTGGCTCTCAATGCTGTTTGGGTTTCCAACAATTCAGCATTAGTGG

GAAAAAGTGGGCCCTCATACACAAGCGTGTCAGGCTGTCAGTGTTTGGTG

CACGCTGGGGAAGAATTTACTTTGGAAAGTAGAAAAGCCCAGCTTTTCCT

GGGACATCTTCTGTTATTGTTGATGTTTTTTTTACCTTGTCATTTTGGT

CTAAGGTTGCCATTGCTGCTAAAGGTTACCGATTTCAAAGTCCAGATACC

AAGCATGTGGATATGTTTAGCTACGTTTACTCACAGCCAGCGAACTGACA

TTAAAATAACTAACAAACAGATTCTTTTATGTGATGCTGGAACTCTTGAC

AGCTATAATTATTATTCAGAAATGACTTTTTGAAAGTAAAAGCAGCATAA

AGAATTTGTCACAGGAAGGCTGTCTCAGATAAATTATGGTAAAATTTTGT

AAGGGAGCAGACTTTTAAAGACTTGCACAAATACGGATCCTGCACTGACT

CTGGAAAAGGCATATATGTACTAGTGGCATGGAGAATGCACCATACTCAT

GCATGCAAATTAGACAACCAAGTATGAATCTATTTGTGGGTGTGCTATAG

CTTTAGCCGTGTCACGGGCATCATTCTCTAATATCCACTTGTCCATGTGA

AACATGTTGCCAAAATGGTGGCCTGGCTTGTCTTCTGAACGTTTGGTTCA

AATGTGTTTTGGTCCTGGAGGCTCAAATTTTGAGTTATTCCCACGTTTTG

AAATAAAAAGAGTATATTCAAAA
```

In some embodiments, the introduction, removal, or modification of 3'UTR AREs can be used to modulate the stability of an mRNA encoding a secreted target protein (e.g., a NDP protein, a HSPA1A protein). In other embodiments, AREs can be removed or mutated to increase the intracellular stability and thus increase translation and production of a secreted target protein (e.g., a NDP protein, a HSPA1A protein).

In other embodiments, non-ARE sequences may be incorporated into the 5' or 3' UTRs. In some embodiments, introns or portions of intron sequences may be incorporated into the flanking regions of the polynucleotides in any of the vectors, compositions, kits, and methods provided herein. Incorporation of intronic sequences may increase protein production as well as mRNA levels.

In some embodiments of any of the vectors described herein, the vector includes a chimeric intron sequence (SEQ ID NO: 19).

Exemplary Chimeric Intron cDNA Sequence (SEQ ID NO: 19)

```
GGAGTCGCTGCGTTGCCTTCGCCCCGTGCCCCGCTCCGCGCCGCCTCGCG

CCGCCCGCCCCGGCTCTGACTGACCGCGTTACTCCCACAGGTGAGCGGGC

GGGACGGCCCTTCTCCTCCGGGCTGTAATTAGCGCTTGGTTTAATGACGG

CTCGTTTCTTTTCTGTGGCTGCGTGAAAGCCTTAAAGGGCTCCGGGAGGG

CCCTTTGTGCGGGGGGGAGCGGCTCGGGGGGTGCGTGCGTGTGTGTGTGC

GTGGGGAGCGCCGCGTGCGGCCCGCGCTGCCCGGCGGCTGTGAGCGCTGC

GGGCGCGGCGCGGGGCTTTGTGCGCTCCGCGTGTGCGCGAGGGGAGCGCG

GCCGGGGGCGGTGCCCCGCGGTGCGGGGGGGCTGCGAGGGGAACAAAGGC

TGCGTGCGGGGTGTGTGCGTGGGGGGGTGAGCAGGGGGTGTGGGCGCGGC

GGTCGGGCTGTAACCCCCCCCTGCACCCCCCTCCCCGAGTTGCTGAGCAC

GGCCCGGCTTCGGGTGCGGGGCTCCGTGCGGGGCGTGGCGCGGGGCTCGC

CGTGCCGGGCGGGGGGTGGCGGCAGGTGGGGGTGCCGGGCGGGGCGGGGC

CGCCTCGGGCCGGGGAGGGCTCGGGGGAGGGGCGCGGCGGCCCCCGGAGC

GCCGGCGGCTGTCGAGGCGCGGCGAGCCGCAGCCATTGCCTTTTATGGTA

ATCGTGCGAGAGGGCGCAGGGACTTCCTTTGTCCCAAATCTGTGCGGAGC

CGAAATCTGGGAGGCGCCGCCGCACCCCCTCTAGCGGGCGCGGGGCGAAG

CGGTGCGGCGCCGGCAGGAAGGAAATGGGCGGGGAGGGCCTTCGTGCGTC

GCCGCGCCGCCGTCCCCTTCTCCCTCTCCAGCCTCGGGGCTGTCCGCGGG

GGGACGGCTGCCTTCGGGGGGGACGGGGCAGGGCGGGGTTCGGCTTCTGG

CGTGTGACCGGCGGCTCTAGAGCCTCTGCTAACCATGTTCATGCCTTCTT

CTTTTTCCTACAGCTCCTGGGCAACGTGCTGGTTATTGTG
```

Additional Sequences

In some embodiments, constructs of the present disclosure may comprise a T2A element or sequence. In some embodiments, constructs of the present disclosure may include one or more cloning sites. In some such embodiments, cloning sites may not be fully removed prior to manufacturing for administration to a subject. In some embodiments, cloning sites may have functional roles including as linker sequences, or as portions of a Kozak site. As will be appreciated by those skilled in the art, cloning sites may vary significantly in primary sequence while retaining their desired function. In some embodiments, constructs may contain any combination of cloning sites, exemplary cloning sites are represented by SEQ ID NO:73-77, 106, 75 and 107, respectively, in order of appearance.

Exemplary cloning site A (SEQ ID NO: 73)

TTGTCGACGCGGCCGCACGCGT

Exemplary cloning site B (SEQ ID NO: 74)

CTCCTGGGCAACGTGCTGGTTATTGTGACCGGTCGCTAGCCACC

Exemplary cloning site C (SEQ ID NO: 75)

TAAGAGCTCGCTGATCAGCCTCGA

Exemplary cloning site D (SEQ ID NO: 76)

AAGCTTGAATTCAGCTGACGTGCCTCGGACCGTCCTAGG

Exemplary cloning site E (SEQ ID NO: 77)

GCGGCCGCACGCGT

Exemplary cloning site F (SEQ ID NO: 106)

CTCCTGGGCAACGTGCTGGTTATTGTGACCGGTGCCACC

Exemplary cloning site G (SEQ ID NO: 75)

TAAGAGCTCGCTGATCAGCCTCGA

Exemplary cloning site H (SEQ ID NO: 107)

AAGCTTGAATTCAGCTGACGTGCCTCGGACCGCT

Destabilization Domains

In some embodiments, any of the constructs provided herein can optionally include a sequence encoding a destabilizing domain ("a destabilizing sequence") for temporal control of protein expression. Non-limiting examples of destabilizing sequences include sequences encoding a FK506 sequence, a dihydrofolate reductase (DHFR) sequence, or other exemplary destabilizing sequences.

In the absence of a stabilizing ligand, a protein sequence operatively linked to a destabilizing sequence is degraded by ubiquitination. In contrast, in the presence of a stabilizing ligand, protein degradation is inhibited, thereby allowing the protein sequence operatively linked to the destabilizing sequence to be actively expressed. As a positive control for stabilization of protein expression, protein expression can be detected by conventional means, including enzymatic, radiographic, colorimetric, fluorescence, or other spectrographic assays; fluorescent activating cell sorting (FACS) assays; immunological assays (e.g., enzyme linked immunosorbent assay (ELISA), radioimmunoassay (RIA), and immunohistochemistry).

Additional examples of destabilizing sequences are known in the art. In some embodiments, the destabilizing sequence is a FK506-and rapamycin-binding protein (FKBP12) sequence, and the stabilizing ligand is Shield-1 (Shld1) (Banaszynski et al. (2012) Cell 126 (5): 995-1004, which is incorporated in its entirety herein by reference). In some embodiments, a destabilizing sequence is a DHFR sequence, and a stabilizing ligand is trimethoprim (TMP) (Iwamoto et al. (2010) Chem Biol 17:981-988, which is incorporated in its entirety herein by reference).

In some embodiments, a destabilizing sequence is a FKBP12 sequence, and a presence of an AAV construct carrying the FKBP12 gene in a subject cell (e.g., a supporting cochlear outer hair cell) is detected by western blotting. In some embodiments, a destabilizing sequence can be used to verify the temporally-specific activity of any of the AAV constructs described herein.

Exemplary DHFR destabilizing amino acid sequence (SEQ ID NO: 108)

MISLIAALAVDYVIGMENAMPWNLPADLAWFKRNTLNKPVIMGR

HTWESIGRPLPGRKNIILSSQPSTDDRVTWVKSVDEAIAACGDV

PEIMVIGGGRVIEQFLPKAQKLYLTHIDAEVEGDTHFPDYEPDD

WESVFSEFHDADAQNSHSYCFEILERR

Exemplary DHFR destabilizing nucleotide sequence (SEQ ID NO: 109)

GGTACCATCAGTCTGATTGCGGCGTTAGCGGTAGATTACGTTAT

CGGCATGGAAAACGCCATGCCGTGGAACCTGCCTGCCGATCTCG

CCTGGTTTAAACGCAACACCTTAAATAAACCCGTGATTATGGGC

CGCCATACCTGGGAATCAATCGGTCGTCCGTTGCCAGGACGCAA

AAATATTATCCTCAGCAGTCAACCGAGTACGGACGATCGCGTAA

CGTGGGTGAAGTCGGTGGATGAAGCCATCGCGGCGTGTGGTGAC

GTACCAGAAATCATGGTGATTGGCGGCGGTCGCGTTATTGAACA

GTTCTTGCCAAAAGCGCAAAAACTGTATCTGACGCATATCGACG

CAGAAGTGGAAGGCGACACCCATTTCCCGGATTACGAGCCGGAT

GACTGGGAATCGGTATTCAGCGAATTCCACGATGCTGATGCGCA

GAACTCTCACAGCTATTGCTTTGAGATTCTGGAGCGGCGATAA

Exemplary destabilizing domain (SEQ ID NO: 110)

ATCAGTCTGATTGCGGCGTTAGCGGTAGATTACGTTATCGGCAT

GGAAAACGCCATGCCGTGGAACCTGCCTGCCGATCTCGCCTGGT

TTAAACGCAACACCTTAAATAAACCCGTGATTATGGGCCGCCAT

ACCTGGGAATCAATCGGTCGTCCGTTGCCAGGACGCAAAAATAT

TATCCTCAGCAGTCAACCGAGTACGGACGATCGCGTAACGTGGG

TGAAGTCGGTGGATGAAGCCATCGCGGCGTGTGGTGACGTACCA

GAAATCATGGTGATTGGCGGCGGTCGCGTTATTGAACAGTTCTT

GCCAAAAGCGCAAAAACTGTATCTGACGCATATCGACGCAGAAG

TGGAAGGCGACACCCATTTCCCGGATTACGAGCCGGATGACTGG

GAATCGGTATTCAGCGAATTCCACGATGCTGATGCGCAGAACTC

TCACAGCTATTGCTTTGAGATTCTGGAGCGGCGA

Exemplary FKBP12 destabilizing peptide amino acid sequence (SEQ ID NO: 111)

MGVEKQVIRPGNGPKPAPGQTVTVHCTGFGKDGDLSQKFWSTKD

EGQKPFSFQIGKGAVIKGWDEGVIGMQIGEVARLRCSSDYAYGA

GGFPAWGIQPNSVLDFEIEVLSVQ

AAV Capsids

The present disclosure provides one or more polynucleotide constructs packaged into an AAV capsid. In some embodiments, an AAV capsid is from or derived from an AAV capsid of an AAV2, 3, 4, 5, 6, 7, 8, 9, 10, rh8, rh10, rh39, rh43 or Anc80 serotype, or one or more hybrids thereof. In some embodiments, an AAV capsid is from an AAV ancestral serotype. In some embodiments, an AAV capsid is an ancestral (Anc) AAV capsid. An Anc capsid is created from a construct sequence that is constructed using evolutionary probabilities and evolutionary modeling to determine a probable ancestral sequence. Thus, an Anc capsid/construct sequence is not known to have existed in nature. For example, in some embodiments, an AAV capsid is an Anc80 capsid (e.g., an Anc80L65 capsid). In some embodiments, an AAV capsid is created using a template nucleotide coding sequence comprising SEQ ID NO: 58. In some embodiments, the capsid comprises a polypeptide represented by SEQ ID NO: 59. In some embodiments, the capsid comprises a polypeptide with at least 85%, 90%, 95%, 98% or 99% sequence identity to the polypeptide represented by SEQ ID NO: 59.

As provided herein, any combination of AAV capsids and AAV constructs (e.g., comprising AAV ITRs) may be used in recombinant AAV (rAAV) particles of the present disclosure. For example, wild type or variant AAV2 ITRs and Anc80 capsid, wild type or variant AAV2 ITRs and AAV6 capsid, etc. In some embodiments of the present disclosure, an AAV particle is wholly comprised of AAV2 components (e.g., capsid and ITRs are AAV2 serotype). In some embodiments, an AAV particle is an AAV2/6, AAV2/8 or AAV2/9 particle (e.g., an AAV6, AAV8 or AAV9 capsid with an AAV construct having AAV2 ITRs). In some embodiments of the present disclosure, an AAV particle is an AAV2/Anc80 particle that comprises an Anc80 capsid (e.g., comprising a polypeptide of SEQ ID NO: 58) that encapsulates an AAV construct with AAV2 ITRs (e.g., SEQ ID NOs: 60 and 61) flanking a portion of a coding sequence, for example, a gene encoding a secreted target protein (e.g., an NDP gene, e.g., an HSPA1A gene) or characteristic portion thereof (e.g., SEQ ID NO: 1, 33, 3, 33, or 85). Other AAV particles are known in the art and are described in, e.g., Sharma et al., Brain Res Bull. 2010 Feb. 15; 81 (2-3): 273, which is incorporated in its entirety herein by reference. In some embodiments, a capsid sequence is at least 85%, 90%, 95%, 98% or 99% identical to a capsid nucleotide or amino acid sequence represented by SEQ ID NO: 8 or 9, respectively.

```
Exemplary AAV Anc80 Capsid DNA Sequence
                                    (SEQ ID NO: 58)
ATGGCTGCCGATGGTTATCTTCCAGATTGGCTCGAGGACAACCT

CTCTGAGGGCATTCGCGAGTGGTGGGACTTGAAACCTGGAGCCC

CGAAACCCAAAGCCAACCAGCAAAAGCAGGACGACGGCCGGGGT

CTGGTGCTTCCTGGCTACAAGTACCTCGGACCCTTCAACGGACT

CGACAAGGGGGAGCCCGTCAACGCGGCGGACGCAGCGGCCCTCG

AGCACGACAAGGCCTACGACCAGCAGCTCAAAGCGGGTGACAAT

CCGTACCTGCGGTATAACCACGCCGACGCCGAGTTTCAGGAGCG

TCTGCAAGAAGATACGTCTTTTGGGGGCAACCTCGGGCGAGCAG

TCTTCCAGGCCAAGAAGCGGGTTCTCGAACCTCTCGGTCTGGTT

GAGGAAGGCGCTAAGACGGCTCCTGGAAAGAAGAGACCGGTAGA

GCAATCACCCCAGGAACCAGACTCCTCTTCGGGCATCGGCAAGA

AAGGCCAGCAGCCCGCGAAGAAGAGACTCAACTTTGGGCAGACA

GGCGACTCAGAGTCAGTGCCCGACCCTCAACCACTCGGAGAACC

CCCCGCAGCCCCCTCTGGTGTGGGATCTAATACAATGGCAGCAG

GCGGTGGCGCTCCAATGGCAGACAATAACGAAGGCGCCGACGGA

GTGGGTAACGCCTCAGGAAATTGGCATTGCGATTCCACATGGCT

GGGCGACAGAGTCATCACCACCAGCACCCGAACCTGGGCCCTCC
```

-continued

```
CCACCTACAACAACCACCTCTACAAGCAAATCTCCAGCCAATCG

GGAGCAAGCACCAACGACAACACCTACTTCGGCTACAGCACCCC

CTGGGGGTATTTTGACTTTAACAGATTCCACTGCCACTTCTCAC

CACGTGACTGGCAGCGACTCATCAACAACAACTGGGGATTCCGG

CCCAAGAGACTCAACTTCAAGCTCTTCAACATCCAGGTCAAGGA

GGTCACGACGAATGATGGCACCACGACCATCGCCAATAACCTTA

CCAGCACGGTTCAGGTCTTTACGGACTCGGAATACCAGCTCCCG

TACGTCCTCGGCTCTGCGCACCAGGGCTGCCTGCCTCCGTTCCC

GGCGGACGTCTTCATGATTCCTCAGTACGGGTACCTGACTCTGA

ACAATGGCAGTCAGGCCGTGGGCCGTTCCTCCTTCTACTGCCTG

GAGTACTTTCCTTCTCAAATGCTGAGAACGGGCAACAACTTTGA

GTTCAGCTACACGTTTGAGGACGTGCCTTTTCACAGCAGCTACG

CGCACAGCCAAAGCCTGGACCGGCTGATGAACCCCCTCATCGAC

CAGTACCTGTACTACCTGTCTCGGACTCAGACCACGAGTGGTAC

CGCAGGAAATCGGACGTTGCAATTTTCTCAGGCCGGGCCTAGTA

GCATGGCGAATCAGGCCAAAAACTGGCTACCCGGGCCCTGCTAC

CGGCAGCAACGCGTCTCCAAGACAGCGAATCAAAATAACAACAG

CAACTTTGCCTGGACCGGTGCCACCAAGTATCATCTGAATGGCA

GAGACTCTCTGGTAAATCCCGGTCCCGCTATGGCAACCCACAAG

GACGACGAAGACAAATTTTTTCCGATGAGCGGAGTCTTAATATT

TGGGAAACAGGGAGCTGGAAATAGCAACGTGGACCTTGACAACG

TTATGATAACGAGTGAGGAAGAAATTAAAACCACCAACCGAGTG

GCCACAGAACAGTACGGCACGGTGGCCACTAACCTGCAATCGTC

AAACACCGCTCCTGCTACAGGGACCGTCAACAGTCAAGGAGCCT

TACCTGGCATGGTCTGGCAGAACCGGGACGTGTACCTGCAGGGT

CCTATCTGGGCCAAGATTCCTCACACGGACGGACACTTTCATCC

CTCGCCGCTGATGGGAGGCTTTGGACTGAAACACCCGCCTCCTC

AGATCCTGATTAAGAATACACCTGTTCCCGCGAATCCTCCAACT

ACCTTCAGTCCAGCTAAGTTTGCGTCGTTCATCACGCAGTACAG

CACCGGACAGGTCAGCGTGGAAATTGAATGGGAGCTGCAGAAAG

AAAACAGCAAACGCTGGAACCCAGAGATTCAATACACTTCCAAC

TACAACAAATCTACAAATGTGGACTTTGCTGTTGACACAAATGG

CGTTTATTCTGAGCCTCGCCCCATCGGCACCCGTTACCTCACCC

GTAATCTG

Exemplary AAV Anc80 Capsid Amino Acid
Sequence
                                    (SEQ ID NO: 59)
MAADGYLPDWLEDNLSEGIREWWDLKPGAPKPKANQQKQDDGRG

LVLPGYKYLGPFNGLDKGEPVNAADAAALEHDKAYDQQLKAGDN

PYLRYNHADAEFQERLQEDTSFGGNLGRAVFQAKKRVLEPLGLV

EEGAKTAPGKKRPVEQSPQEPDSSSGIGKKGQQPAKKRLNFGQT

GDSESVPDPQPLGEPPAAPSGVGSNTMAAGGGAPMADNNEGADG
```

-continued

```
VGNASGNWHCDSTWLGDRVITTSTRTWALPTYNNHLYKQISSQS
GASTNDNTYFGYSTPWGYFDFNRFHCHFSPRDWQRLINNNWGFR
PKRLNFKLFNIQVKEVTTNDGTTTIANNLTSTVQVFTDSEYQLP
YVLGSAHQGCLPPFPADVFMIPQYGYLTLNNGSQAVGRSSFYCL
EYFPSQMLRTGNNFEFSYTFEDVPFHSSYAHSQSLDRLMNPLID
QYLYYLSRTQTTSGTAGNRTLQFSQAGPSSMANQAKNWLPGPCY
RQQRVSKTANQNNNSNFAWTGATKYHLNGRDSLVNPGPAMATHK
DDEDKFFPMSGVLIFGKQGAGNSNVDLDNVMITSEEEIKTTNPV
ATEQYGTVATNLQSSNTAPATGTVNSQGALPGMVWQNRDVYLQG
PIWAKIPHTDGHFHPSPLMGGFGLKHPPPQILIKNTPVPANPPT
TFSPAKFASFITQYSTGQVSVEIEWELQKENSKRWNPEIQYTSN
YNKSTNVDFAVDTNGVYSEPRPIGTRYLTRNL*
```

Compositions

Among other things, the present disclosure provides compositions. In some embodiments, a composition comprises a construct as described herein. In some embodiments, a composition comprises one or more constructs as described herein. In some embodiments, a composition comprises a plurality of constructs as described herein. In some embodiments, when more than one construct is included in the composition, the constructs are each different.

In some embodiments, a composition comprises an AAV particle as described herein. In some embodiments, a composition comprises one or more AAV particles as described herein. In some embodiments, a composition comprises a plurality of AAV particles. In come embodiments, when more than one AAV particle is included in the composition, the AAV particles are each different.

In some embodiments, a composition comprises secreted target protein. In some embodiments, a composition comprises a cell.

In some embodiments, a composition is or comprises a pharmaceutical composition.

Single AAV Construct Compositions

In some embodiments, the present disclosure provides compositions or systems comprising AAV particles comprised of a single construct. In some such embodiments, a single construct may deliver a polynucleotide that encodes a functional (e.g., wild type or otherwise functional, e.g., codon optimized) copy of a gene encoding a secreted target protein (e.g., an NDP gene, e.g., an HSPA1A) or characteristic portion thereof. In some embodiments, a construct is or comprises an rAAV construct. In some embodiments described herein, a single rAAV construct is capable of expressing a full-length secreted target protein (e.g., NDP, e.g., HSPA1A) messenger RNA or a characteristic protein thereof in a target cell (e.g., an inner ear cell). In some embodiments, a single construct (e.g., any of the constructs described herein) can include a sequence encoding a functional secreted target protein (e.g., any construct that generates functional secreted target protein). In some embodiments, a single construct (e.g., any of the constructs described herein) can include a sequence encoding a functional secreted target protein (e.g., any construct that generates functional secreted target protein) and optionally additional polypeptide sequences (e.g., regulatory sequences, and/or reporter sequences).

In some embodiments, a single construct composition or system may comprise any or all of the exemplary construct components described herein. In some embodiments, an exemplary single construct is represented by SEQ ID NO: 9. In some embodiments, an exemplary single construct is represented by SEQ ID NO: 10. In some embodiments, an exemplary single construct is represented by SEQ ID NO: 11. In some embodiments, an exemplary single construct is represented by SEQ ID NO: 12. In some embodiments, an exemplary single construct is represented by SEQ ID NO: 13. In some embodiments, an exemplary single construct is represented by SEQ ID NO: 96. In some embodiments, an exemplary single construct is represented by SEQ ID NO: 97. In some embodiments, an exemplary single construct is represented by SEQ ID NO: 98. In some embodiments, an exemplary single construct is at least 85%, 90%, 95%, 98% or 99% identical to the sequence represented by SEQ ID NO: 9, 10, 11, 13, 96, 97, or 98. One skilled in the art would recognize that constructs may undergo additional modifications including codon-optimization, introduction of novel but functionally equivalent (e.g., silent mutations), addition of reporter sequences, and/or other routine modification.

In some embodiments, an exemplary construct comprises: a 5' ITR exemplified by SEQ ID NO: 129, optionally a cloning site exemplified by SEQ ID NO: 129, a CMV enhancer exemplified by SEQ ID NO: 130, a CBA promoter exemplified by SEQ ID NO: 131, a chimeric intron exemplified by SEQ ID NO: 132, optionally a cloning site exemplified by SEQ ID NO: 133, an NDP coding region exemplified by SEQ ID NO: 1 or an HSPA1A coding region exemplified by SEQ ID NO: 134 (optionally, wherein a IL2ss coding region precedes the HSPA1A codon region exemplified by SEQ ID NO: 122), optionally a cloning site exemplified by SEQ ID NO: 135, a poly(A) site exemplified by SEQ ID NO: 136, optionally a cloning site exemplified by SEQ ID NO: 137, and a 3' ITR exemplified by SEQ ID NO: 138.

In some embodiments, an exemplary construct comprises: a 5' ITR exemplified by SEQ ID NO: 139, optionally a cloning site exemplified by SEQ ID NO: 140, a CMV enhancer exemplified by SEQ ID NO: 141, a CBA promoter exemplified by SEQ ID NO: 142, a chimeric intron exemplified by SEQ ID NO: 143, optionally a cloning site exemplified by SEQ ID NO: 144, an NDP coding region exemplified by SEQ ID NO: 1 or an HSPA1A coding region as exemplified by SEQ ID NO: 145, optionally a reporter sequence exemplified by SEQ ID NO: 148, optionally a cloning site exemplified by SEQ ID NO: 149, a poly(A) site exemplified by SEQ ID NO: 150, optionally a cloning site exemplified by SEQ ID NO: 151, and a 3' ITR exemplified by SEQ ID NO: 152.

Multiple AAV Construct Compositions

The present disclosure recognizes that some coding sequences encoding a protein (e.g., secreted target protein) may be delivered by dividing the coding sequence into multiple portions, which are each included in a different construct. In some embodiments, provided herein are compositions or systems comprising at least two different constructs (e.g., two, three, four, five, or six). In some embodiments, each of the at least two different constructs includes a coding sequence that encodes a different portion of a coding region (e.g., encoding a target protein, e.g., an inner ear target protein, e.g., a secreted target protein), each of the encoded portions being at least 10 amino acids (e.g., at least about 10 amino acids, at least about 20 amino acids, at least about 30 amino acids, at least about 60 amino acids, at least about 70 amino acids, at least about 80 amino acids, at least about 90 amino acids, at least about 100 amino acids, at least about 110 amino acids, at least about 120 amino acids, at least about 130 amino acids, at least about 140 amino acids, at least about 150 amino acids, at least about 160 amino acids, at least about 170 amino acids, at least about 180 amino acids, at least about 190 amino acids, at least about 200 amino acids, at least about 210 amino acids, at least about 220 amino acids, at least about 230 amino acids, at least about 240 amino acids, at least about 250 amino acids, at least about 260 amino acids, at least about 270 amino acids, at least about 280 amino acids, at least about 290 amino acids, at least about 300 amino acids, at least about 310 amino acids, at least about 320 amino acids, at least about 330 amino acids, at least about 340 amino acids, at least about 350 amino acids, at least about 360 amino acids, at least about 370 amino acids, at least about 380 amino acids, at least about 390 amino acids, at least about 400 amino acids, at least about 410 amino acids, at least about 420 amino acids, at least about 430 amino acids, at least about 440 amino acids, at least about 450 amino acids, at least about 460 amino acids, at least about 470 amino acids, at least about 480 amino acids, at least about 490 amino acids, at least about 500 amino acids, at least about 510 amino acids, at least about 520 amino acids, at least about 530 amino acids, at least about 540 amino acids, at least about 550 amino acids, at least about 560 amino acids, at least about 570 amino acids, at least about 580 amino acids, at least about 590 amino acids, at least about 600 amino acids, at least about 610 amino acids, at least about 620 amino acids, at least about 630 amino acids, at least about 640 amino acids, at least about 650 amino acids, at least about 660 amino acids, at least about 670 amino acids, at least about 680 amino acids, at least about 690 amino acids, at least about 700 amino acids, at least about 710 amino acids, at least about 720 amino acids, at least about 730 amino acids, at least about 740 amino acids, at least about 750 amino acids, at least about 760 amino acids, at least about 770 amino acids, at least about 780 amino acids, at least about 790 amino acids, at least about 800 amino acids, at least about 810 amino acids, or at least about 820 amino acids) where the amino acid sequence of each of the encoded portions may optionally partially overlap with the amino acid sequence of a different one of the encoded portions; no single construct of the at least two different constructs encodes the active target protein; and, when introduced into a subject cell (e.g., an animal cell, e.g., a primate cell, e.g., a human cell), the at least two different constructs undergo homologous recombination with each other, where the recombined nucleic acid encodes an active target protein (e.g., a gene product encoded by an gene encoding a secreted target protein or a characteristic portion thereof). In some embodiments, one of the nucleic acid constructs can include a coding sequence that encodes a portion of a target protein (e.g., an inner ear target protein, e.g., a secreted target protein), where the encoded portion is at most about 820 amino acids (e.g., at most about 10 amino acids, at most about 20 amino acids, at most about 30 amino acids, at most about 60 amino acids, at most about 70 amino acids, at most about 80 amino acids, at most about 90 amino acids, at most about 100 amino acids, at most about 110 amino acids, at most about 120 amino acids, at most about 130 amino acids, at most about 140 amino acids, at most about 150 amino acids, at most about 160 amino acids, at most about 170 amino acids, at most about 180 amino acids, at most about 190 amino acids, at most about 200 amino acids, at most about 210 amino acids, at most about 220 amino acids, at most about 230 amino acids, at most about 240 amino acids, at most about 250 amino acids, at most about 260 amino acids, at most about 270 amino acids, at most about 280 amino acids, at most about 290 amino acids, at most about 300 amino acids, at most about 310 amino acids, at most about 320 amino acids, at most about 330 amino acids, at most about 340 amino acids, at most about 350 amino acids, at most about 360 amino acids, at most about 370 amino acids, at most about 380 amino acids, at most about 390 amino acids, at most about 400 amino acids, at most about 410 amino acids, at most about 420 amino acids, at most about 430 amino acids, at most about 440 amino acids, at most about 450 amino acids, at most about 460 amino acids, at most about 470 amino acids, at most about 480 amino acids, at most about 490 amino acids, at most about 500 amino acids, at most about 510 amino acids, at most about 520 amino acids, at most about 530 amino acids, at most about 540 amino acids, at most about 550 amino acids, at most about 560 amino acids, at most about 570 amino acids, at most about 580 amino acids, at most about 590 amino acids, at most about 600 amino acids, at most about 610 amino acids, at most about 620 amino acids, at most about 630 amino acids, at most about 640 amino acids, at most about 650 amino acids, at most about 660 amino acids, at most about 670 amino acids, at most about 680 amino acids, at most about 690 amino acids, at most about 700 amino acids, at most about 710 amino acids, at most about 720 amino acids, at most about 730 amino acids, at most about 740 amino acids, at most about 750 amino acids, at most about 760 amino acids, at most about 770 amino acids, at most about 780 amino acids, at most about 790 amino acids, at most about 800 amino acids, at most about 810 amino acids, or at most about 820 amino acids).

In some embodiments, at least one of the constructs includes a nucleotide sequence spanning two neighboring exons of target genomic DNA (e.g., an inner ear target genomic DNA, e.g., NDP genomic DNA, e.g., HSPA1A genomic DNA), and lacks the intronic sequence that naturally occurs between the two neighboring exons.

In some embodiments, an amino acid sequence of an encoded portion of each of the constructs does not overlap, even in part, with an amino acid sequence of a different one of the encoded portions. In some embodiments, an amino acid sequence of an encoded portion of a construct partially overlaps with an amino acid sequence of an encoded portion of a different construct. In some embodiments, an amino acid sequence of an encoded portion of each construct partially overlaps with an amino acid sequence of an encoded portion of at least one different construct. In some embodiments, an overlapping amino acid sequence is between about 10 amino acid residues to about 820 amino acids, or any of the subranges of this range (e.g., about 10 amino acids, about 20 amino acids, about 30 amino acids, about 60 amino acids, about 70 amino acids, about 80 amino acids, about 90 amino acids, about 100 amino acids, about 110 amino acids, about 120 amino acids, about 130 amino acids, about 140 amino acids, about 150 amino acids, about 160 amino acids, about 170 amino acids, about 180 amino acids, about 190 amino acids, about 200 amino acids, about 210 amino acids, about 220 amino acids, about 230 amino acids, about 240 amino acids, about 250 amino acids, about 260 amino acids, about 270 amino acids, about 280 amino acids, about 290 amino acids, about 300 amino acids, about 310 amino acids, about 320 amino acids, about 330 amino acids, about 340 amino acids, about 350 amino acids, about 360 amino acids, about 370 amino acids, about 380 amino acids, about 390 amino acids, about 400 amino acids, about 410 amino acids, about 420 amino acids, about 430 amino acids, about 440 amino acids, about 450 amino acids, about 460 amino acids, about 470 amino acids, about 480 amino acids, about 490 amino acids, about 500 amino acids, about 510 amino acids, about 520 amino acids, about 530 amino acids, about 540 amino acids, about 550 amino acids, about 560 amino acids, about 570 amino acids, about 580 amino acids, about 590 amino acids, about 600 amino acids, about 610 amino acids, about 620 amino acids, about 630 amino acids, about 640 amino acids, about 650 amino acids, about 660 amino acids, about 670 amino acids, about 680 amino acids, about 690 amino acids, about 700 amino acids, about 710 amino acids, about 720 amino acids, about 730 amino acids, about 740 amino acids, about 750 amino acids, about 760 amino acids, about 770 amino acids, about 780 amino acids, about 790 amino acids, about 800 amino acids, about 810 amino acids, or about 820 amino acids in length).

In some examples, a desired gene product (e.g., a therapeutic gene product) is encoded by at least two different constructs. In some embodiments, each of at least two different constructs includes a different segment of an intron, where the intron includes a nucleotide sequence of an intron that is present in a target genomic DNA (e.g., an inner ear cell target genomic DNA (e.g., NDP genomic DNA, e.g., HSPA1A genomic DNA) (e.g., any of the exemplary introns in SEQ ID NO: 3 described herein). In some embodiments, different intron segments overlap. In some embodiments, different intron segments overlap in sequence by at most about 12,000 nucleotides (e.g., at most about 100 nucleotides, at most about 200 nucleotides, at most about 300 nucleotides, at most about 600 nucleotides, at most about 700 nucleotides, at most about 800 nucleotides, at most about 900 nucleotides, at most about 1,000 nucleotides, at most about 1,100 nucleotides, at most about 1,200 nucleotides, at most about 1,300 nucleotides, at most about 1,400 nucleotides, at most about 1,500 nucleotides, at most about 1,600 nucleotides, at most about 1,700 nucleotides, at most about 1,800 nucleotides, at most about 1,900 nucleotides, at most about 2,000 nucleotides, at most about 2,100 nucleotides, at most about 2,200 nucleotides, at most about 2,300 nucleotides, at most about 2,400 nucleotides, at most about 2,500 nucleotides, at most about 2,600 nucleotides, at most about 2,700 nucleotides, at most about 2,800 nucleotides, at most about 2,900 nucleotides, at most about 3,000 nucleotides, at most about 3,100 nucleotides, at most about 3,200 nucleotides, at most about 3,300 nucleotides, at most about 3,400 nucleotides, at most about 3,500 nucleotides, at most about 3,600 nucleotides, at most about 3,700 nucleotides, at most about 3,800 nucleotides, at most about 3,900 nucleotides, at most about 4,000 nucleotides, at most about 4,100 nucleotides, at most about 4,200 nucleotides, at most about 4,300 nucleotides, at most about 4,400 nucleotides, at most about 4,500 nucleotides, at most about 4,600 nucleotides, at most about 4,700 nucleotides, at most about 4,800 nucleotides, at most about 4,900 nucleotides, at most about 5,000 nucleotides, at most about 5,100 nucleotides, at most about 5,200 nucleotides, at most about 5,300 nucleotides, at most about 5,400 nucleotides, at most about 5,500 nucleotides, at most about 5,600 nucleotides, at most about 5,700 nucleotides, at most about 5,800 nucleotides, at most about 5,900 nucleotides, at most about 6,000 nucleotides, at most about 6,100 nucleotides, at most about 6,200 nucleotides, at most about 6,300 nucleotides, at most about 6,400 nucleotides, at most about 6,500 nucleotides, at most about 6,600 nucleotides, at most about 6,700 nucleotides, at most about 6,800 nucleotides, at most about 6,900 nucleotides, at most about 7,000 nucleotides, at most about 7,100 nucleotides, at most about 7,200 nucleotides, at most about 7,300 nucleotides, at most about 7,400 nucleotides, at most about 7,500 nucleotides, at most about 7,600 nucleotides, at most about 7,700 nucleotides, at most about 7,800 nucleotides, at most about 7,900 nucleotides, at most about 8,000 nucleotides, at most about 8,100 nucleotides, at most about 8,200 nucleotides, at most about 8,300 nucleotides, at most about 8,400 nucleotides, at most about 8,500 nucleotides, at most about 8,600 nucleotides, at most about 8,700 nucleotides, at most about 8,800 nucleotides, at most about 8,900 nucleotides, at most about 9,000 nucleotides, at most about 9,100 nucleotides, at most about 9,200 nucleotides, at most about 9,300 nucleotides, at most about 9,400 nucleotides, at most about 9,500 nucleotides, at most about 9,600 nucleotides, at most about 9,700 nucleotides, at most about 9,800 nucleotides, at most about 9,900 nucleotides, at most about 10,000 nucleotides, at most about 10,100 nucleotides, at most about 10,200 nucleotides, at most about 10,300 nucleotides, at most about 10,400 nucleotides, at most about 10,500 nucleotides, at most about 10,600 nucleotides, at most about 10,700 nucleotides, at most about 10,800 nucleotides, at most about 10,900 nucleotides, at most about 11,000 nucleotides, at most about 11,100 nucleotides, at most about 11,200 nucleotides, at most about 11,300 nucleotides, at most about 11,400 nucleotides, at most about 11,500 nucleotides, at most about 11,600 nucleotides, at most about 11,700 nucleotides, at most about 11,800 nucleotides, at most about 11,900 nucleotides, or at most about 12,000 nucleotides) in length. In some embodiments, the overlapping nucleotide sequence in any two of the different constructs can include part or all of one or more exons of a target gene (e.g., an inner ear cell target gene (e.g., a secreted target protein (e.g., NDP, e.g., HSPA1A) gene) (e.g., any one or more of the exemplary exons in SEQ ID NO: 3 described herein).

In some embodiments, a composition or system is or comprises two, three, four, or five different constructs. In compositions where the number of different constructs in the composition is two, the first of the two different constructs can include a coding sequence that encodes an N-terminal portion of a protein (e.g., secreted target protein), which may be referred to as a lead portion, a first construct, or a 5' portion (e.g., an N-terminal portion of an inner ear cell protein, e.g., an N-terminal portion of a secreted target protein). In some examples, an N-terminal portion of the target gene is at least about 10 amino acids (e.g., at least about 10 amino acids, at least about 20 amino acids, at least about 30 amino acids, at least about 60 amino acids, at least about 70 amino acids, at least about 80 amino acids, at least about 90 amino acids, at least about 100 amino acids, at least about 110 amino acids, at least about 120 amino acids, at least about 130 amino acids, at least about 140 amino acids, at least about 150 amino acids, at least about 160 amino acids, at least about 170 amino acids, at least about 180 amino acids, at least about 190 amino acids, at least about 200 amino acids, at least about 210 amino acids, at least about 220 amino acids, at least about 230 amino acids, at least about 240 amino acids, at least about 250 amino acids, at least about 260 amino acids, at least about 270 amino acids, at least about 280 amino acids, at least about 290 amino acids, at least about 300 amino acids, at least about 310 amino acids, at least about 320 amino acids, at least about 330 amino acids, at least about 340 amino acids, at least about 350 amino acids, at least about 360 amino acids, at least about 370 amino acids, at least about 380 amino acids, at least about 390 amino acids, at least about 400 amino acids, at least about 410 amino acids, at least about 420 amino acids, at least about 430 amino acids, at least about 440 amino acids, at least about 450 amino acids, at least about 460 amino acids, at least about 470 amino acids, at least about 480 amino acids, at least about 490 amino acids, at least about 500 amino acids, at least about 510 amino acids, at least about 520 amino acids, at least about 530 amino acids, at least about 540 amino acids, at least about 550 amino acids, at least about 560 amino acids, at least about 570 amino acids, at least about 580 amino acids, at least about 590 amino acids, at least about 600 amino acids, at least about 610 amino acids, at least about 620 amino acids, at least about 630 amino acids, at least about 640 amino acids, at least about 650 amino acids, at least about 660 amino acids, at least about 670 amino acids, at least about 680 amino acids, at least about 690 amino acids, at least about 700 amino acids, at least about 710 amino acids, at least about 720 amino acids, at least about 730 amino acids, at least about 740 amino acids, at least about 750 amino acids, at least about 760 amino acids, at least about 770 amino acids, at least about 780 amino acids, at least about 790 amino acids, at least about 800 amino acids, at least about 810 amino acids, or at least about 820 amino acids) in length. In some examples, a first construct includes one or both of a promoter (e.g., any of the promoters described herein or known in the art) and a Kozak sequence (e.g., any of the exemplary Kozak sequences described herein or known in the art). In some examples, a first construct includes a promoter that is an inducible promoter, a constitutive promoter, or a tissue-specific promoter. In some examples, a second of the two different constructs includes a coding sequence that encodes a C-terminal portion of the protein, which may be referred to as a terminal portion, a second construct, or a 3' portion (e.g., a C-terminal portion of an inner ear cell target protein, e.g., a C-terminal portion of a secreted target protein). In some examples, a C-terminal portion of the target protein is at least about 10 amino acids (e.g., at least about 10 amino acids, at least about 20 amino acids, at least about 30 amino acids, at least about 60 amino acids, at least about 70 amino acids, at least about 80 amino acids, at least about 90 amino acids, at least about 100 amino acids, at least about 110 amino acids, at least about 120 amino acids, at least about 130 amino acids, at least about 140 amino acids, at least about 150 amino acids, at least about 160 amino acids, at least about 170 amino acids, at least about 180 amino acids, at least about 190 amino acids, at least about 200 amino acids, at least about 210 amino acids, at least about 220 amino acids, at least about 230 amino acids, at least about 240 amino acids, at least about 250 amino acids, at least about 260 amino acids, at least about 270 amino acids, at least about 280 amino acids, at least about 290 amino acids, at least about 300 amino acids, at least about 310 amino acids, at least about 320 amino acids, at least about 330 amino acids, at least about 340 amino acids, at least about 350 amino acids, at least about 360 amino acids, at least about 370 amino acids, at least about 380 amino acids, at least about 390 amino acids, at least about 400 amino acids, at least about 410 amino acids, at least about 420 amino acids, at least about 430 amino acids, at least about 440 amino acids, at least about 450 amino acids, at least about 460 amino acids, at least about 470 amino acids, at least about 480 amino acids, at least about 490 amino acids, at least about 500 amino acids, at least about 510 amino acids, at least about 520 amino acids, at least about 530 amino acids, at least about 540 amino acids, at least about 550 amino acids, at least about 560 amino acids, at least about 570 amino acids, at least about 580 amino acids, at least about 590 amino acids, at least about 600 amino acids, at least about 610 amino acids, at least about 620 amino acids, at least about 630 amino acids, at least about 640 amino acids, at least about 650 amino acids, at least about 660 amino acids, at least about 670 amino acids, at least about 680 amino acids, at least about 690 amino acids, at least about 700 amino acids, at least about 710 amino acids, at least about 720 amino acids, at least about 730 amino acids, at least about 740 amino acids, at least about 750 amino acids, at least about 760 amino acids, at least about 770 amino acids, at least about 780 amino acids, at least about 790 amino acids, at least about 800 amino acids, at least about 810 amino acids, or at least about 820 amino acids) in length. In some examples, a second construct further includes a poly(A) sequence.

In some examples where the number of different constructs in the composition is two, an N-terminal portion encoded by one of the two constructs can include a portion including amino acid position 1 to about amino acid position 820, or any subrange of this range (e.g., amino acid 1 to at least about amino acid 10, amino acid 1 to at least about amino acid 20, amino acid 1 to at least about amino acid 30, amino acid 1 to at least about amino acid 60, amino acid 1 to at least about amino acid 70, amino acid 1 to at least about amino acid 80, amino acid 1 to at least about amino acid 90, amino acid 1 to at least about amino acid 100, amino acid 1 to at least about amino acid 110, amino acid 1 to at least about amino acid 120, amino acid 1 to at least about amino acid 130, amino acid 1 to at least about amino acid 140, amino acid 1 to at least about amino acid 150, amino acid 1 to at least about amino acid 160, amino acid 1 to at least about amino acid 170, amino acid 1 to at least about amino acid 180, amino acid 1 to at least about amino acid 190, amino acid 1 to at least about amino acid 200, amino acid 1 to at least about amino acid 210, amino acid 1 to at least about amino acid 220, amino acid 1 to at least about amino acid 230, amino acid 1 to at least about amino acid 240, amino acid 1 to at least about amino acid 250, amino acid 1 to at least about amino acid 260, amino acid 1 to at least about amino acid 270, amino acid 1 to at least about amino acid 280, amino acid 1 to at least about amino acid 290, amino acid 1 to at least about amino acid 300, amino acid 1 to at least about amino acid 310, amino acid 1 to at least about amino acid 320, amino acid 1 to at least about amino acid 330, amino acid 1 to at least about amino acid 340, amino acid 1 to at least about amino acid 350, amino acid 1 to at least about amino acid 360, amino acid 1 to at least about amino acid 370, amino acid 1 to at least about amino acid 380, amino acid 1 to at least about amino acid 390, amino acid 1 to at least about amino acid 400, amino acid 1 to at least about amino acid 410, amino acid 1 to at least about amino acid 420, amino acid 1 to at least about amino acid 430, amino acid 1 to at least about amino acid 440, amino acid 1 to at least about amino acid 450, amino acid 1 to at least about amino acid 460, amino acid 1 to at least about amino acid 470, amino acid 1 to at least about amino acid 480, amino acid 1 to at least about amino acid 490, amino acid 1 to at least about amino acid 500, amino acid 1 to at least about amino acid 510, amino acid 1 to at least about amino acid 520, amino acid 1 to at least about amino acid 530, amino acid 1 to at least about amino acid 540, amino acid 1 to at least about amino acid 550, amino acid 1 to at least about amino acid 560, amino acid 1 to at least about amino acid 570, amino acid 1 to at least about amino acid 580, amino acid 1 to at least about amino acid 590, amino acid 1 to at least about amino acid 600, amino acid 1 to at least about amino acid 610, amino acid 1 to at least about amino acid 620, amino acid 1 to at least about amino acid 630, amino acid 1 to at least about amino acid 640, amino acid 1 to at least about amino acid 650, amino acid 1 to at least about amino acid 660, amino acid 1 to at least about amino acid 670, amino acid 1 to at least about amino acid 680, amino acid 1 to at least about amino acid 690, amino acid 1 to at least about amino acid 700, amino acid 1 to at least about amino acid 710, amino acid 1 to at least about amino acid 720, amino acid 1 to at least about amino acid 730, amino acid 1 to at least about amino acid 740, amino acid 1 to at least about amino acid 750, amino acid 1 to at least about amino acid 760, amino acid 1 to at least about amino acid 770, amino acid 1 to at least about amino acid 780, amino acid 1 to at least about amino acid 790, amino acid 1 to at least about amino acid 800, amino acid 1 to at least about amino acid 810, or amino acid 1 to at least about amino acid 820) of an inner ear cell target protein (e.g., SEQ ID NO: 6 or 7). In some examples where the number of different constructs in the composition is two, an N-terminal portion of the precursor inner ear cell target protein can include a portion including at most amino acid position 1 to amino acid position 820 or any subrange of this range (e.g., amino acid 1 to at most about amino acid 10, amino acid 1 to at most about amino acid 20, amino acid 1 to at most about amino acid 30, amino acid 1 to at most about amino acid 60, amino acid 1 to at most about amino acid 70, amino acid 1 to at most about amino acid 80, amino acid 1 to at most about amino acid 90, amino acid 1 to at most about amino acid 100, amino acid 1 to at most about amino acid 110, amino acid 1 to at most about amino acid 120, amino acid 1 to at most about amino acid 130, amino acid 1 to at most about amino acid 140, amino acid 1 to at most about amino acid 150, amino acid 1 to at most about amino acid 160, amino acid 1 to at most about amino acid 170, amino acid 1 to at most about amino acid 180, amino acid 1 to at most about amino acid 190, amino acid 1 to at most about amino acid 200, amino acid 1 to at most about amino acid 210, amino acid 1 to at most about amino acid 220, amino acid 1 to at most about amino acid 230, amino acid 1 to at most about amino acid 240, amino acid 1 to at most about amino acid 250, amino acid 1 to at most about amino acid 260, amino acid 1 to at most about amino acid 270, amino acid 1 to at most about amino acid 280, amino acid 1 to at most about amino acid 290, amino acid 1 to at most about amino acid 300, amino acid 1 to at most about amino acid 310, amino acid 1 to at most about amino acid 320, amino acid 1 to at most about amino acid 330, amino acid 1 to at most about amino acid 340, amino acid 1 to at most about amino acid 350, amino acid 1 to at most about amino acid 360, amino acid 1 to at most about amino acid 370, amino acid 1 to at most about amino acid 380, amino acid 1 to at most about amino acid 390, amino acid 1 to at most about amino acid 400, amino acid 1 to at most about amino acid 410, amino acid 1 to at most about amino acid 420, amino acid 1 to at most about amino acid 430, amino acid 1 to at most about amino acid 440, amino acid 1 to at most about amino acid 450, amino acid 1 to at most about amino acid 460, amino acid 1 to at most about amino acid 470, amino acid 1 to at most about amino acid 480, amino acid 1 to at most about amino acid 490, amino acid 1 to at most about amino acid 500, amino acid 1 to at most about amino acid 510, amino acid 1 to at most about amino acid 520, amino acid 1 to at most about amino acid 530, amino acid 1 to at most about amino acid 540, amino acid 1 to at most about amino acid 550, amino acid 1 to at most about amino acid 560, amino acid 1 to at most about amino acid 570, amino acid 1 to at most about amino acid 580, amino acid 1 to at most about amino acid 590, amino acid 1 to at most about amino acid 600, amino acid 1 to at most about amino acid 610, amino acid 1 to at most about amino acid 620, amino acid 1 to at most about amino acid 630, amino acid 1 to at most about amino acid 640, amino acid 1 to at most about amino acid 650, amino acid 1 to at most about amino acid 660, amino acid 1 to at most about amino acid 670, amino acid 1 to at most about amino acid 680, amino acid 1 to at most about amino acid 690, amino acid 1 to at most about amino acid 700, amino acid 1 to at most about amino acid 710, amino acid 1 to at most about amino acid 720, amino acid 1 to at most about amino acid 730, amino acid 1 to at most about amino acid 740, amino acid 1 to at most about amino acid 750, amino acid 1 to at most about amino acid 760, amino acid 1 to at most about amino acid 770, amino acid 1 to at most about amino acid 780, amino acid 1 to at most about amino acid 790, amino acid 1 to at most about amino acid 800, amino acid 1 to at most about amino acid 810, or amino acid 1 to at most about amino acid 820) of an inner ear cell target protein (e.g., SEQ ID NO: 6 or 7)

In some examples where the number of different constructs in the composition is two, a C-terminal portion encoded by one of the two constructs can include a portion including the final amino acid (e.g., about amino acid position 820) to about amino acid position 1, or any subrange of this range (e.g., amino acid 820 to at least about amino acid 10, amino acid 820 to at least about amino acid 20, amino acid 820 to at least about amino acid 30, amino acid 820 to at least about amino acid 60, amino acid 820 to at least about amino acid 70, amino acid 820 to at least about amino acid 80, amino acid 820 to at least about amino acid 90, amino acid 820 to at least about amino acid 100, amino acid 820 to at least about amino acid 110, amino acid 820 to at least about amino acid 120, amino acid 820 to at least about amino acid 130, amino acid 820 to at least about amino acid 140, amino acid 820 to at least about amino acid 150, amino acid 820 to at least about amino acid 160, amino acid 820 to at least about amino acid 170, amino acid 820 to at least about amino acid 180, amino acid 820 to at least about amino acid 190, amino acid 820 to at least about amino acid 200, amino acid 820 to at least about amino acid 210, amino acid 820 to at least about amino acid 220, amino acid 820 to at least about amino acid 230, amino acid 820 to at least about amino acid 240, amino acid 820 to at least about amino acid 250, amino acid 820 to at least about amino acid 260, amino acid 820 to at least about amino acid 270, amino acid 820 to at least about amino acid 280, amino acid 820 to at least about amino acid 290, amino acid 820 to at least about amino acid 300, amino acid 820 to at least about amino acid 310, amino acid 820 to at least about amino acid 320, amino acid 820 to at least about amino acid 330, amino acid 820 to at least about amino acid 340, amino acid 820 to at least about amino acid 350, amino acid 820 to at least about amino acid 360, amino acid 820 to at least about amino acid 370, amino acid 820 to at least about amino acid 380, amino acid 820 to at least about amino acid 390, amino acid 820 to at least about amino acid 400, amino acid 820 to at least about amino acid 410, amino acid 820 to at least about amino acid 420, amino acid 820 to at least about amino acid 430, amino acid 820 to at least about amino acid 440, amino acid 820 to at least about amino acid 450, amino acid 820 to at least about amino acid 460, amino acid 820 to at least about amino acid 470, amino acid 820 to at least about amino acid 480, amino acid 820 to at least about amino acid 490, amino acid 820 to at least about amino acid 500, amino acid 820 to at least about amino acid 510, amino acid 820 to at least about amino acid 520, amino acid 820 to at least about amino acid 530, amino acid 820 to at least about amino acid 540, amino acid 820 to at least about amino acid 550, amino acid 820 to at least about amino acid 560, amino acid 820 to at least about amino acid 570, amino acid 820 to at least about amino acid 580, amino acid 820 to at least about amino acid 590, amino acid 820 to at least about amino acid 600, amino acid 820 to at least about amino acid 610, amino acid 820 to at least about amino acid 620, amino acid 820 to at least about amino acid 630, amino acid 820 to at least about amino acid 640, amino acid 820 to at least about amino acid 650, amino acid 820 to at least about amino acid 660, amino acid 820 to at least about amino acid 670, amino acid 820 to at least about amino acid 680, amino acid 820 to at least about amino acid 690, amino acid 820 to at least about amino acid 700, amino acid 820 to at least about amino acid 710, amino acid 820 to at least about amino acid 720, amino acid 820 to at least about amino acid 730, amino acid 820 to at least about amino acid 740, amino acid 820 to at least about amino acid 750, amino acid 820 to at least about amino acid 760, amino acid 820 to at least about amino acid 770, amino acid 820 to at least about amino acid 780, amino acid 820 to at least about amino acid 790, amino acid 820 to at least about amino acid 800, amino acid 820 to at least about amino acid 810, or amino acid 820 to at least about amino acid 820) of an inner ear cell target protein (e.g., SEQ ID NO: 6 or 7). In some examples where the number of different constructs in the composition is two, a C-terminal portion of the precursor inner ear cell target protein can include a portion including the final amino acid (e.g., about amino acid position 820) to at most about amino acid position 1, or any subrange of this range (e.g., amino acid 820 to at most about amino acid 10, amino acid 820 to at most about amino acid 20, amino acid 820 to at most about amino acid 30, amino acid 820 to at most about amino acid 60, amino acid 820 to at most about amino acid 70, amino acid 820 to at most about amino acid 80, amino acid 820 to at most about amino acid 90, amino acid 820 to at most about amino acid 100, amino acid 820 to at most about amino acid 110, amino acid 820 to at most about amino acid 120, amino acid 820 to at most about amino acid 130, amino acid 820 to at most about amino acid 140, amino acid 820 to at most about amino acid 150, amino acid 820 to at most about amino acid 160, amino acid 820 to at most about amino acid 170, amino acid 820 to at most about amino acid 180, amino acid 820 to at most about amino acid 190, amino acid 820 to at most about amino acid 200, amino acid 820 to at most about amino acid 210, amino acid 820 to at most about amino acid 220, amino acid 820 to at most about amino acid 230, amino acid 820 to at most about amino acid 240, amino acid 820 to at most about amino acid 250, amino acid 820 to at most about amino acid 260, amino acid 820 to at most about amino acid 270, amino acid 820 to at most about amino acid 280, amino acid 820 to at most about amino acid 290, amino acid 820 to at most about amino acid 300, amino acid 820 to at most about amino acid 310, amino acid 820 to at most about amino acid 320, amino acid 820 to at most about amino acid 330, amino acid 820 to at most about amino acid 340, amino acid 820 to at most about amino acid 350, amino acid 820 to at most about amino acid 360, amino acid 820 to at most about amino acid 370, amino acid 820 to at most about amino acid 380, amino acid 820 to at most about amino acid 390, amino acid 820 to at most about amino acid 400, amino acid 820 to at most about amino acid 410, amino acid 820 to at most about amino acid 420, amino acid 820 to at most about amino acid 430, amino acid 820 to at most about amino acid 440, amino acid 820 to at most about amino acid 450, amino acid 820 to at most about amino acid 460, amino acid 820 to at most about amino acid 470, amino acid 820 to at most about amino acid 480, amino acid 820 to at most about amino acid 490, amino acid 820 to at most about amino acid 500, amino acid 820 to at most about amino acid 510, amino acid 820 to at most about amino acid 520, amino acid 820 to at most about amino acid 530, amino acid 820 to at most about amino acid 540, amino acid 820 to at most about amino acid 550, amino acid 820 to at most about amino acid 560, amino acid 820 to at most about amino acid 570, amino acid 820 to at most about amino acid 580, amino acid 820 to at most about amino acid 590, amino acid 820 to at most about amino acid 600, amino acid 820 to at most about amino acid 610, amino acid 820 to at most about amino acid 620, amino acid 820 to at most about amino acid 630, amino acid 820 to at most about amino acid 640, amino acid 820 to at most about amino acid 650, amino acid 820 to at most about amino acid 660, amino acid 820 to at most about amino acid 670, amino acid 820 to at most about amino acid 680, amino acid 820 to at most about amino acid 690, amino acid 820 to at most about amino acid 700, amino acid 820 to at most about amino acid 710, amino acid 820 to at most about amino acid 720, amino acid 820 to at most about amino acid 730, amino acid 820 to at most about amino acid 740, amino acid 820 to at most about amino acid 750, amino acid 820 to at most about amino acid 760, amino acid 820 to at most about amino acid 770, amino acid 820 to at most about amino acid 780, amino acid 820 to at most about amino acid 790, amino acid 820 to at most about amino acid 800, amino acid 820 to at most about amino acid 810, or amino acid 820 to at most about amino acid 820, or any length sequence there between of an inner ear cell target protein (e.g., SEQ ID NO: 6 or 7).

In some embodiments, splice sites are involved in trans-splicing. In some embodiments, a splice donor site (Trapani et al. EMBO Mol. Med. 6 (2): 194-211, 2014, which is incorporated in its entirety herein by reference) follows the coding sequence in the N-terminal construct. In the C-terminal construct, a splice acceptor site may be subcloned just before the coding sequence for NDP or HSPA1A or other secreted target protein. In some embodiments, within the coding sequence, a silent mutation can be introduced, generating an additional site for restriction digestion.

In some embodiments, any of the constructs provided herein can be included in a composition suitable for administration to an animal for the amelioration of symptoms associated with syndromic and/or non-syndromic hearing loss.

Pharmaceutical Compositions

Among other things, the present disclosure provides pharmaceutical compositions. In some embodiments compositions provided herein are suitable for administration to an animal for the amelioration of symptoms associated with syndromic and/or non-syndromic hearing loss.

In some embodiments, pharmaceutical compositions of the present disclosure may comprise, e.g., a polynucleotide, e.g., one or more constructs, as described herein. In some embodiments, a pharmaceutical composition may comprise one or more AAV particles, e.g., one or more rAAV construct encapsidated by one or more AAV serotype capsids, as described herein.

In some embodiments, a pharmaceutical composition comprises one or more pharmaceutically or physiologically acceptable carriers, diluents or excipients. As used herein, the term "pharmaceutically acceptable carrier" includes solvents, dispersion media, coatings, antibacterial agents, antifungal agents, and the like that are compatible with pharmaceutical administration. Supplementary active compounds can also be incorporated into any of the compositions described herein. Such compositions may include one or more buffers, such as neutral-buffered saline, phosphate-buffered saline, and the like; one or more carbohydrates, such as glucose, mannose, sucrose, and dextran; mannitol; one or more proteins, polypeptides, or amino acids, such as glycine; one or more antioxidants; one or more chelating agents, such as EDTA or glutathione; and/or one or more preservatives. In some embodiments, formulations are in a dosage forms, such as injectable solutions, injectable gels, drug-release capsules, and the like.

In some embodiments, compositions of the present disclosure are formulated for intravenous administration. In some embodiments compositions of the present disclosure are formulated for intra-cochlear administration. In some embodiments, a therapeutic composition is formulated to comprise a lipid nanoparticle, a polymeric nanoparticle, a mini-circle DNA and/or a CELiD DNA.

In some embodiments, a therapeutic composition is formulated to comprise a synthetic perilymph solution. For example, in some embodiments, a synthetic perilymph solution includes 20-200 mM NaCl; 1-5 mM KCl; 0.1-10 mM $CaCl_2$; 1-10 mM glucose; and 2-50 mM HEPES, with a pH between about 6 and about 9. In some embodiments, a therapeutic composition is formulated to comprise a physiologically suitable solution. For example, in some embodiments, a physiologically suitable solution comprises commercially available 1xPBS with pluronic acid F68, prepared to a final concentration of: 8.10 mM Sodium Phosphate Dibasic, 1.5 mM Monopotassium Phosphate, 2.7 mM Potassium Chloride, 172 mM Sodium Chloride, and 0.001% Pluronic Acid F68). In some embodiments, alternative pluronic acids are utilized. In some embodiments, alternative ion concentrations are utilized.

In some embodiments, any of the pharmaceutical compositions described herein may further comprise one or more agents that promote the entry of a nucleic acid or any of the constructs described herein into a mammalian cell (e.g., a liposome or cationic lipid). In some embodiments, any of the constructs described herein can be formulated using natural and/or synthetic polymers. Non-limiting examples of polymers that may be included in any of the compositions described herein can include, but are not limited to, DYNAMIC POLYCONJUGATE® (Arrowhead Research Corp., Pasadena, Calif.), formulations from Mirus Bio (Madison, Wis.) and Roche Madison (Madison, Wis.), PhaseRX polymer formulations such as, without limitation, SMARTT POLYMER TECHNOLOGY® (PhaseRX, Seattle, Wash.), DMRI/DOPE, poloxamer, VAXFECTIN® adjuvant from Vical (San Diego, Calif.), chitosan, cyclodextrin from Calando Pharmaceuticals (Pasadena, Calif.), dendrimers and poly(lactic-co-glycolic acid) (PLGA) polymers, RONDEL™ (RNAi/Oligonucleotide Nanoparticle Delivery) polymers (Arrowhead Research Corporation, Pasadena, Calif.), and pH responsive co-block polymers, such as, but not limited to, those produced by PhaseRX (Seattle, Wash.). Many of these polymers have demonstrated efficacy in delivering oligonucleotides in vivo into a mammalian cell (see, e.g., deFougerolles, Human Gene Ther. 19:125-132, 2008; Rozema et al., Proc. Natl. Acad. Sci. U.S.A. 104: 12982-12887, 2007; Rozema et al., Proc. Natl. Acad. Sci. U.S.A. 104:12982-12887, 2007; Hu-Lieskovan et al., Cancer Res. 65:8984-8982, 2005; Heidel et al., Proc. Natl. Acad. Sci. U.S.A. 104:5715-5721, 2007, each of which is incorporated in its entirety herein by reference).

In some embodiments, a composition includes a pharmaceutically acceptable carrier (e.g., phosphate buffered saline, saline, or bacteriostatic water). Upon formulation, solutions will be administered in a manner compatible with a dosage formulation and in such amount as is therapeutically effective. Formulations are easily administered in a variety of dosage forms such as injectable solutions, injectable gels, drug-release capsules, and the like.

In some embodiments, a composition provided herein can be, e.g., formulated to be compatible with their intended route of administration. A non-limiting example of an intended route of administration is local administration (e.g., intra-cochlear administration).

In some embodiments, a provided composition comprises one nucleic acid construct. In some embodiments, a provided composition comprises two or more different constructs. In some embodiments, a composition that include a single nucleic acid construct comprising a coding sequence that encodes a secreted target protein and/or a functional characteristic portion thereof. In some embodiments, compositions comprise a single nucleic acid construct comprising a coding sequence that encodes a secreted target protein and/or a functional characteristic portion thereof, which, when introduced into a mammalian cell, that coding sequence is integrated into the genome of the mammalian cell. In some embodiments, a composition comprising at least two different constructs, e.g., constructs comprise coding sequences that encode a different portion of a secreted target protein, the constructs can be combined to generate a sequence encoding an active secreted target protein (e.g., a full-length secreted target protein) in a mammalian cell, and thereby treat associated syndromic or non-syndromic sensorineural hearing loss in a subject in need thereof.

In some embodiments, a single dose of any of the compositions described herein can include a total sum amount of the at least two different vectors of at least 1 ng, at least 2 ng, at least 4 ng, about 6 ng, about 8 ng, at least 10 ng, at least 20 ng, at least 30 ng, at least 40 ng, at least 50 ng, at least 60 ng, at least 70 ng, at least 80 ng, at least 90 ng, at least 100 ng, at least 200 ng, at least 300 ng, at least 400 ng, at least 500 ng, at least 1 μg, at least 2 μg, at least 4 μg, at least 6 μg, at least 8 μg, at least 10 μg, at least 12 μg, at least 14 μg, at least 16 μg, at least 18 μg, at least 20 μg, at least 22 μg, at least 24 μg, at least 26 μg, at least 28 μg, at least 30 μg at least 32 μg, at least 34 μg, at least 36 μg, at least 38 μg, at least 40 μg, at least 42 μg, at least 44 μg, at least 46 μg, at least 48 μg, at least 50 μg, at least 52 μg, at least 54 μg, at least 56 μg, at least 58 ug, at least 60 μg, at least 62 μg, at least 64 μg, at least 66 μg, at least 68 μg, at least 70 μg, at least 72 μg, at least 74 μg, at least 76 μg, at least 78 μg, at least 80 μg, at least 82 μg, at least 84 ug, at least 86 μg, at least 88 μg, at least 90 μg, at least 92 μg, at least 94 μg, at least 96 μg, at least 98 μg, at least 100 μg, at least 102 μg, at least 104 μg, at least 106 μg, at least 108 μg, at least 110 μg, at least 112 μg, at least 114 μg, at least 116 μg, at least 118 μg, at least 120 μg, at least 122 μg, at least 124 μg, at least 126 μg, at least 128 μg, at least 130 μg at least 132 μg, at least 134 μg, at least 136 μg, at least 138 μg, at least 140 μg, at least 142 μg, at least 144 μg, at least 146 μg, at least 148 μg, at least 150 μg, at least 152 μg, at least 154 μg, at least 156 μg, at least 158 μg, at least 160 μg, at least 162 μg, at least 164 μg, at least 166 μg, at least 168 μg, at least 170 μg, at least 172 μg, at least 174 μg, at least 176 μg, at least 178 μg, at least 180 μg, at least 182 μg, at least 184 μg, at least 186 μg, at least 188 μg, at least 190 μg, at least 192 μg, at least 194 μg, at least 196 μg, at least 198 μg, or at least 200 μg, e.g., in a buffered solution.

The compositions provided herein can be, e.g., formulated to be compatible with their intended route of administration. A non-limiting example of an intended route of administration is local administration (e.g., intra-cochlear administration).

In some embodiments, the therapeutic compositions are formulated to include a lipid nanoparticle. In some embodiments, the therapeutic compositions are formulated to include a polymeric nanoparticle. In some embodiments, the therapeutic compositions are formulated to comprise a mini-circle DNA. In some embodiments, the therapeutic compositions are formulated to comprise a CELiD DNA. In some embodiments, the therapeutic compositions are formulated to comprise a synthetic perilymph solution. An exemplary synthetic perilymph solution includes 20-200 mM NaCl; 1-5 mM KCl; 0.1-10 mM $CaCl_2$); 1-10 mM glucose; 2-50 mM HEPES, having a pH of between about 6 and about 9.

Also provided are kits including any of the compositions described herein. In some embodiments, a kit can include a solid composition (e.g., a lyophilized composition including the at least two different vectors described herein) and a liquid for solubilizing the lyophilized composition. In some embodiments, a kit can include a pre-loaded syringe including any of the compositions described herein.

In some embodiments, the kit includes a vial comprising any of the compositions described herein (e.g., formulated as an aqueous composition, e.g., an aqueous pharmaceutical composition).

In some embodiments, the kits can include instructions for performing any of the methods described herein.

Also provided are kits including any of the compositions described herein. In some embodiments, a kit can include a solid composition (e.g., a lyophilized composition including the at least two different constructs described herein) and a liquid for solubilizing the lyophilized composition. In some embodiments, a kit can include a pre-loaded syringe including any of the compositions described herein.

Genetically Modified Cells

The present disclosure also provides a cell (e.g., an animal cell, e.g., a mammalian cell, e.g., a primate cell, e.g., a human cell) that includes any of the nucleic acids, constructs or compositions described herein. In some embodiments, an animal cell is a human cell (e.g., a human supporting cell or a human hair cell). In other embodiments, an animal cell is a non-human mammal (e.g., Simian cell, Felidae cell, Canidae cell etc.). A person skilled in the art will appreciate that the nucleic acids and constructs described herein can be introduced into any animal cell (e.g., the supporting or hair cells of any animal suitable for veterinary intervention). Non-limiting examples of constructs and methods for introducing constructs into animal cells are described herein.

In some embodiments, an animal cell can be any cell of the inner ear, including hair and/or supporting cells. Non-limiting examples such cells include: Hensen's cells, Deiters' cells, cells of the endolymphatic sac and duct, transitional cells in the saccule, utricle, and ampulla, inner and outer hair cells, spiral ligament cells, spiral ganglion cells, spiral prominence cells, external saccule cells, marginal cells, intermediate cells, basal cells, inner pillar cells, outer pillar cells, Claudius cells, inner border cells, inner phalangeal cells, or cells of the stria vascularis.

In some embodiments, an animal cell is a specialized cell of the cochlea. In some embodiments, an animal cell is a hair cell. In some embodiments, an animal cell is a cochlear inner hair cell or a cochlear outer hair cell. In some embodiments, an animal cell is a cochlear inner hair cell. In some embodiments, an animal cell is a cochlear outer hair cell.

In some embodiments, an animal cell is in vitro. In some embodiments, an animal cell is of a cell type which is endogenously present in an animal, e.g., in a primate and/or human. In some embodiments, an animal cell is an autologous cell obtained from an animal and cultured ex vivo.

Also provided herein is a cell (e.g., a mammalian cell) that includes any of the nucleic acids, vectors (e.g., at least two different vectors described herein), or compositions described herein. Skilled practitioners will appreciate that the nucleic acids and vectors described herein can be introduced into any mammalian cell. Non-limiting examples of vectors and methods for introducing vectors into mammalian cells are described herein.

In some embodiments, the cell is a human cell, a mouse cell, a porcine cell, a rabbit cell, a dog cell, a cat cell, a rat cell, or a non-human primate cell. In some embodiments, the cell is a specialized cell of the cochlea. In some embodiments, the cell is a cochlear hair cell, such as a cochlear inner hair cell, a cochlear out hair cell, a supporting cell, a ganglion cell, a clear cell, a cuboidal cell, a cartilage cell, a cell of the tegmentum vasculosum, a homogene cell, a Hensen's cell, a Deiters' cell, a pillar cell, or a border cell. In some embodiments, the cell is an ocular cell (e.g. a retinal cell, a retinal ganglion cell, an amacrine cell, a hortizontal cell, a bipolar cell, a photoreceptor cell).

In some embodiments, the mammalian cell is in vitro. In some embodiments, the mammalian cell is present in a mammal. In some embodiments, the mammalian cell is an autologous cell obtained from a subject and cultured ex vivo.

Methods

Among other things, the present disclosure provides methods. In some embodiments, a method comprises introducing a composition as described herein into the inner ear (e.g., a cochlea) of a subject. For example, provided herein are methods that in some embodiments include administering to an inner ear (e.g., cochlea) of a subject (e.g., an animal, e.g., a mammal, e.g., a primate, e.g., a human) a therapeutically effective amount of any composition described herein. In some embodiments of any of these methods, the subject has been previously identified as having a defective inner ear cell target gene (e.g., a supporting and/or hearing cell target gene having a mutation that results in a decrease in the expression and/or activity of a supporting and/or hearing cell target protein encoded by the gene). Some embodiments of any of these methods further include, prior to the introducing or administering step, determining that the subject has a defective inner ear cell target gene. Some embodiments of any of these methods can further include detecting a mutation in an inner ear cell target gene in a subject. Some embodiments of any of the methods can further include identifying or diagnosing a subject as having non-syndromic or syndromic sensorineural hearing loss.

In some embodiments, provided herein are methods of correcting an inner ear cell target gene defect (e.g., a defect in a secreted target protein gene) in an inner ear of a subject, e.g., an animal, e.g., a mammal, e.g., a primate, e.g., a human. In some embodiments, methods include administering to the inner ear of a subject a therapeutically effective amount of any of the compositions described herein, where the administering repairs and or ameliorates the inner ear cell target gene defect in any cell subset of the inner ear of a subject. In some embodiments, the inner ear target cell may be a sensory cell, e.g., a hair cell, and/or a non-sensory cell, e.g., a supporting cell, and/or all or any subset of inner ear cells.

Also provided herein are methods that include introducing into an inner ear of a mammal a therapeutically effective amount of any of the compositions described herein.

Also provided herein are methods of increasing expression of a full-length secreted target protein in any subset of inner ear cells (e.g., mammalian cells, e.g., animal cells, e.g., primate cells, e.g., human cells) that include introducing any of the compositions described herein into the cell.

Also provided herein are methods of increasing the expression level of a full-length secreted target protein in any subset of inner ear cells of a subject (e.g., an animal, e.g., a mammal, e.g., a primate, e.g., a human) that include introducing into the inner ear of the mammal a therapeutically effective amount of any of the compositions described herein. Also provided herein are methods of increasing the expression level of a full-length secreted target protein in any subset of an inner ear cells of a subject (e.g., an animal, e.g., a mammal, e.g., a primate, e.g., a human) that include administering to the inner ear of the subject a therapeutically effective amount of any of the compositions described herein, where the administering results in an increase in the expression level of the inner ear cell target protein (e.g., a secreted target protein) in any cell subset of the inner ear of a subject. In some embodiments, the inner ear target cell may be a sensory cell, e.g., a hair cell, and/or a non-sensory cell, e.g., a supporting cell, and/or all or any subset of inner ear cells.

Also provided herein are methods of treating syndromic and non-syndromic sensorineural hearing loss in a subject identified as having a defective secreted target gene that include: administering a therapeutically effective amount of any of the composition described herein into the inner ear of the subject.

Also provided herein are methods of treating or preventing hearing loss, e.g., non-syndromic sensorineural hearing loss or syndromic sensorineural hearing loss in a subject (e.g., an animal, e.g., a mammal, e.g., a primate, e.g., a human) identified as having a defective NDP gene or defective HSPA1A gene that include: administering a therapeutically effective amount of any of the compositions described herein into an inner ear of the subject.

Also provided herein are methods of treating or preventing vision loss in a subject (e.g., an animal, e.g., a mammal, e.g., a primate, e.g., a human) identified as having a defective NDP gene or defective HSPA1A gene that include: administering a therapeutically effective amount of any of the compositions described herein into an inner ear or central nervous system of the subject, or systemically administering a therapeutically effective amount of any of these compositions described herein to the subject.

In some embodiments of any of the methods described herein, the subject (e.g., animal, e.g., mammal, e.g., primate, e.g., human) has been previously identified as having a defective secreted target gene (e.g., a defective NDP gene or a defective HSPA1A gene) (e.g., a NDP gene having a mutation that results in a decrease in the expression and/or activity of a NDP protein encoded by the gene, or a HSPA1A gene having a mutation that results in a decrease in the expression and/or activity of a HSPA1A protein encoded by the gene). Some embodiments of any of these methods further include, prior to the introducing or administering step, determining that the subject has a defective secreted target gene (e.g., a defective NDP gene or a defective HSPA1A gene). Some embodiments of any of these methods can further include detecting a mutation in a secreted target gene (e.g., a NDP gene or a HSPA1A gene) in a subject. Some embodiments of any of the methods can further include identifying or diagnosing a subject as having hearing loss and/or vision loss.

In some embodiments of any of these methods, two or more doses of any of the compositions described herein are introduced or administered into the cochlea of the mammal or subject. Some embodiments of any of these methods can include introducing or administering a first dose of the composition into the cochlea of the mammal or subject, assessing hearing function of the mammal or subject following the introducing or the administering of the first dose, and administering an additional dose of the composition into the cochlea of the mammal or subject found not to have a hearing function within a normal range (e.g., as determined using any test for hearing known in the art).

In some embodiments of any of the methods described herein, the composition can be formulated for intra-cochlear administration. In some embodiments of any of the methods described herein, the compositions described herein can be administered via intra-cochlear administration or local administration. In some embodiments of any of the methods described herein, the compositions are administered through the use of a medical device (e.g., any of the exemplary medical devices described herein).

Also provided herein are methods of restoring synapses and/or preserving spiral ganglion nerves in a subject identified or diagnosed as having an inner ear disorder that include: administering to the inner ear of the subject a therapeutically effective amount of any of the compositions described herein.

Also provided herein are methods of reducing the size of, and/or restoring the vestibular aqueduct to an appropriate size. Also provided herein are methods of restoring endolymphatic pH to an appropriate and/or acceptable level in a subject identified or diagnosed as having an inner ear disorder that include: administering to the inner ear of the subject a therapeutically effective amount of any of the compositions described herein.

Also provided herein are methods that include administering to an inner ear of a subject a therapeutically effective amount of any of the compositions described herein.

Also provided herein are surgical methods for treatment of hearing loss (e.g., non-syndromic sensorineural hearing loss or syndromic sensorineural hearing loss). In some embodiments, the methods include the steps of: introducing into a cochlea of a subject a first incision at a first incision point; and administering intra-cochlearly a therapeutically effective amount of any of the compositions provided herein. In some embodiments, the composition is administered to the subject at the first incision point. In some embodiments, the composition is administered to the subject into or through the first incision.

In some embodiments of any of the methods described herein, any composition described herein is administered to the subject into or through the cochlea oval window membrane. In some embodiments of any of the methods described herein, any of the compositions described herein is administered to the subject into or through the cochlea round window membrane. In some embodiments of any of the methods described herein, the composition is administered using a medical device capable of creating a plurality of incisions in the round window membrane. In some embodiments, the medical device includes a plurality of micro-needles. In some embodiments, the medical device includes a plurality of micro-needles including a generally circular first aspect, where each micro-needle has a diameter of at least about 10 microns. In some embodiments, the medical device includes a base and/or a reservoir capable of holding the composition. In some embodiments, the medical device includes a plurality of hollow micro-needles individually including a lumen capable of transferring the composition. In some embodiments, the medical device includes a means for generating at least a partial vacuum.

In some embodiments, technologies of the present disclosure are used to treat subjects with or at risk of hearing loss. For example, in some embodiments, a subject has an autosomal recessive hearing loss attributed to at least one pathogenic variant of NDP or HSPA1A. It will be understood by those in the art that many different mutations in NDP or HSPA1A can result in a pathogenic variant. In some such embodiments, a pathogenic variant causes or is at risk of causing hearing loss.

In some embodiments, intra-cochlear administration can be performed using any of the methods described herein or known in the art. For example, a composition can be administered or introduced into the cochlea using the following surgical technique: first using visualization with a 0 degree, 2.5-mm rigid endoscope, the external auditory canal is cleared and a round knife is used to sharply delineate an approximately 5-mm tympanomeatal flap. The tympanomeatal flap is then elevated and the middle ear is entered posteriorly. The chorda tympani nerve is identified and divided, and a currette is used to remove the scutal bone, exposing the round window membrane. To enhance apical distribution of the administered or introduced composition, a surgical laser may be used to make a small 2-mm fenestration in the oval window to allow for perilymph displacement during trans-round window membrane infusion of the composition. The microinfusion device is then primed and brought into the surgical field. The device is maneuvered to the round window, and the tip is seated within the bony round window overhang to allow for penetration of the membrane by the microneedle(s). The footpedal is engaged to allow for a measured, steady infusion of the composition. The device is then withdrawn and the round window and stapes foot plate are sealed with a gelfoam patch.

In some embodiments of any of these methods, two or more doses of any of the compositions described herein are introduced or administered into the eye of the mammal or subject. Some embodiments of any of these methods can include introducing or administering a first dose of the composition into the eye (e.g., intraocular space) of the mammal or subject, assessing hearing function of the mammal or subject following the introducing or the administering of the first dose, and administering an additional dose of the composition into the eye of the mammal or subject found not to have a vision within a normal range (e.g., as determined using any test for vision known in the art).

In some embodiments of any of the methods described herein, the composition can be formulated for intra-ocular administration. In some embodiments of any of the methods described herein, the compositions described herein can be administered via intra-ocular administration or local administration. In some embodiments of any of the methods described herein, the composition if formulated for systemic administration.

In some embodiments, intra-ocular administration can be performed using any of the methods described herein or known in the art.

In some embodiments of any of the methods described herein, the subject or mammal is a rodent, a non-human primate, or a human. In some embodiments of any of the methods described herein, the subject or mammal is an adult, a teenager, a juvenile, a child, a toddler, an infant, or a newborn. In some embodiments of any of the methods described herein, the subject or mammal is 1-5, 1-10, 1-20, 1-30, 1-40, 1-50, 1-60, 1-70, 1-80, 1-90, 1-100, 1-110, 2-5, 2-10, 10-20, 20-30, 30-40, 40-50, 50-60, 60-70, 70-80, 80-90, 90-100, 100-110, 10-30, 10-40, 10-50, 10-60, 10-70, 10-80, 10-90, 10-100, 10-110, 20-40, 20-50, 20-60, 20-70, 20-80, 20-90, 20-100, 20-110, 30-50, 30-60, 30-70, 30-80, 30-90, 30-100, 40-60, 40-70, 40-80, 40-90, 40-100, 50-70, 50-80, 50-90, 50-100, 60-80, 60-90, 60-100, 70-90, 70-100, 70-110, 80-100, 80-110, or 90-110 years of age. In some embodiments of any of the methods described herein, the subject or mammal is 1, 2, 3, 4, 5, 6, 7, 8, 9, 10, or 11 months of age.

In some embodiments of any of the methods described herein, the subject or mammal has or is at risk of developing hearing loss and/or vision loss (e.g., Norrie Disease Pseudoglioma). In some embodiments of any of the methods described herein, the subject or mammal has been previously identified as having a mutation in a secreted target gene (e.g., a NDP gene or a HSPA1A gene). In some embodiments of any of the methods described herein, the subject or mammal has any of the mutations in a secreted target gene (e.g., a NDP gene or a HSPA1A gene) that are described herein or are known in the art to be associated with hearing loss and/or vision loss.

In some embodiments of any of the methods described herein, the subject or mammal has been identified as being a carrier of a mutation in a secreted target gene (e.g., a NDP gene or a HSPA1A gene) (e.g., via genetic testing). In some embodiments of any of the methods described herein, the subject or human has been identified as having a mutation in a secreted target gene (e.g., a NDP gene or a HSPA1A gene) and has been diagnosed with hearing loss and/or vision loss (e.g., Norrie Disease Pseudoglioma).

In some embodiments, successful treatment of hearing loss (e.g., Usher syndrome type III) can be determined in a subject using any of the conventional functional hearing tests known in the art. Non-limiting examples of functional hearing tests are various types of audiometric assays (e.g., pure-tone testing, speech testing, test of the middle ear, auditory brainstem response, and otoacoustic emissions).

In some embodiments, successful treatment of vision loss can be determined in a subject using any of the conventional functional vision tests known in the art. Non-limiting examples of functional retinal and vision tests are acuity testing, intraocular pressure (IOP) testing, and an electroretinogram (ERG).

Also provided herein are methods of increasing expression of an active secreted target protein (e.g., a full-length secreted target protein (e.g., a full-length NDP protein (e.g., any of the exemplary full-length NDP proteins described herein) or a full-length HSPA1A protein (e.g., any of the exemplary full-length HPSA1A proteins described herein)) in a mammalian cell that include introducing any of the compositions described herein into the mammalian cell. In some embodiments of these methods, the mammalian cell is a cochlear hair cell (e.g., an inner hair cell, an outer hair cell) or an ocular cell (e.g., a retinal cell). In some embodiments of these methods, the mammalian cell is a human cell (e.g., a human cochlear hair cell). In some embodiments of these methods, the mammalian cell is in vitro. In some embodiments of these methods, the mammalian cell is in a mammal. In some embodiments of these methods, the mammalian cell is originally obtained from a mammal and is cultured ex vivo. In some embodiments, the mammalian cell has previously been determined to have a defective secreted target gene (e.g., a defective NDP gene or a defective HSPA1A gene). Methods for introducing any of the compositions described herein into a mammalian cell are known in the art (e.g., via lipofection or through the use of a viral vector, e.g., any of the viral vectors described herein).

An increase in expression of an active secreted target protein (e.g., a full-length secreted target protein (e.g., a full-length NDP protein or a full-length HSPA1A protein)) as described herein is, e.g., as compared to a control or to the level of expression of an active secreted target protein (e.g., a full-length secreted target protein (e.g., a full-length NDP protein or a full-length HSPA1A protein)) prior to the introduction of the vector(s).

Methods of detecting expression and/or activity of a secreted target protein (e.g., a NDP protein or a HSPA1A protein) are known in the art. In some embodiments, the level of expression of a secreted target protein (e.g., a NDP protein or a HSPA1A protein) can be detected directly (e.g., detecting NDP protein or detecting NDP mRNA, or detecting HSPA1A protein or detecting HSPA1A mRNA). Non-limiting examples of techniques that can be used to detect expression and/or activity of a secreted target protein directly include: real-time PCR, Western blotting, immunoprecipitation, immunohistochemistry, ELISA or immunofluorescence. In some embodiments, expression of a secreted target protein (e.g., a NDP protein or a HSPA1A protein) can be detected indirectly (e.g., through functional hearing tests, functional retinal and vision tests).

Administration

Provided herein are therapeutic delivery systems for treating hearing loss and/or vision loss (e.g., Norrie Disease Pseudoglioma). In one aspect, the therapeutic delivery systems include i) a medical device capable of creating one or a plurality of incisions in a round window membrane of an inner ear of a human subject in need thereof, and ii) an effective dose of a composition (e.g., any of the compositions described herein). In some embodiments, the medical device includes a plurality of micro-needles.

Also provided herein are surgical methods for treatment of hearing loss (e.g., Norrie Disease Pseudoglioma). In some embodiments, the methods include the steps of: introducing into a cochlea of a human subject a first incision at a first incision point; and administering intra-cochlearly a therapeutically effective amount of any of the compositions provided herein. In some embodiments, the composition is administered to the subject at the first incision point. In some embodiments, the composition is administered to the subject into or through the first incision.

In some embodiments of any of the methods described herein, any of the compositions described herein is administered to the subject into or through the cochlea oval window membrane. In some embodiments of any of the methods described herein, any of the compositions described herein is administered to the subject into or through the cochlea round window membrane. In some embodiments of any of the methods described herein, the composition is administered using a medical device capable of creating a plurality of incisions in the round window membrane. In some embodiments, the medical device includes a plurality of micro-needles. In some embodiments, the medical device includes a plurality of micro-needles including a generally circular first aspect, where each micro-needle has a diameter of at least about 10 microns. In some embodiments, the medical device includes a base and/or a reservoir capable of holding the composition. In some embodiments, the medical device includes a plurality of hollow micro-needles individually including a lumen capable of transferring the composition. In some embodiments, the medical device includes a means for generating at least a partial vacuum.

Also provided herein are surgical methods for treatment of vision loss (e.g., Norrie Disease Pseudoglioma). In some embodiments, the methods include the steps of: administering intra-ocularly a therapeutically effective amount of any of the compositions provided herein.

Evaluating Hearing Loss and Recovery

In some embodiments, hearing function is determined using auditory brainstem response measurements (ABR). In some embodiments, hearing is tested by measuring distortion product optoacoustic emissions (DPOAEs). In some such embodiments, measurements are taken from one or both ears of a subject. In some such embodiments, recordings are compared to prior recordings for the same subject and/or known thresholds on such response measurements used to define, e.g., hearing loss versus acceptable hearing ranges to be defined as normal hearing. In some embodiments, a subject has ABR and/or DPOAE measurements recorded prior to receiving any treatment. In some embodiments, a subject treated with one or more technologies described herein will have improvements on ABR and/or DPOAE measurements after treatment as compared to before treatment. In some embodiments, ABR and/or DPOAE measurements are taken after treatment is administered and at regular follow-up intervals post-treatment.

In some embodiments, hearing function is determined using speech pattern recognition or is determined by a speech therapist. In some embodiments, hearing function is determined by pure tone testing. In some embodiments, hearing function is determined by bone conduction testing. In some embodiments, hearing function is determined by acoustic reflex testing. In some embodiments hearing function is determined by tympanometry. In some embodiments, hearing function is determined by any combination of hearing analysis known in the art. In some such embodiments, measurements are taken holistically, and/or from one or both ears of a subject. In some such embodiments, recordings and/or professional analysis are compared to prior recordings and/or analysis for the same subject and/or known thresholds on such response measurements used to define, e.g., hearing loss versus acceptable hearing ranges to be defined as normal hearing. In some embodiments, a subject has speech pattern recognition, pure tone testing, bone conduction testing, acoustic reflex testing and/or tympanometry measurements and/or analysis conducted prior to receiving any treatment. In some embodiments a subject treated with one or more technologies described herein will have improvements on speech pattern recognition, pure tone testing, bone conduction testing, acoustic reflex testing and/or tympanometry measurements after treatment as compared to before treatment. In some embodiments, speech pattern recognition, pure tone testing, bone conduction testing, acoustic reflex testing and/or tympanometry measurements are taken after treatment is administered and at regular follow-up intervals post-treatment.

Methods of Characterizing

The term "mutation in a secreted target protein (or NDP or HSPA1A) gene" refers to a modification in a known consensus functional secreted target protein (or NDP or HSPA1A) gene that results in the production of a secreted target protein (or NDP protein or HSPA1A protein) having one or more of: a deletion in one or more amino acids, one or more amino acid substitutions, and one or more amino acid insertions as compared to the consensus functional secreted target protein, and/or results in a decrease in the expressed level of the encoded secreted target protein in a mammalian cell as compared to the expressed level of the encoded secreted target protein in a mammalian cell not having a mutation. In some embodiments, a mutation can result in the production of a secreted target protein having a deletion in one or more amino acids (e.g., 2, 3, 4, 5, 6, 7, 8, 9, 10, 11, 12, 13, 14, 15 16, 17, 18, 19, 20, or more amino acids). In some embodiments, the mutation can result in a frameshift in the NDP gene. The term "frameshift" is known in the art to encompass any mutation in a coding sequence that results in a shift in the reading frame of the coding sequence. In some embodiments, a frameshift can result in a nonfunctional protein. In some embodiments, a point mutation can be a nonsense mutation (i.e., result in a premature stop codon in an exon of the gene). A nonsense mutation can result in the production of a truncated protein (as compared to a corresponding consensus functional protein) that may or may not be functional. In some embodiments, the mutation can result in the loss (or a decrease in the level) of expression of NDP mRNA or secreted target protein or both the mRNA and protein. In some embodiments, the mutation can result in the production of an altered secreted target protein having a loss or decrease in one or more biological activities (functions) as compared to a consensus functional secreted target protein.

In some embodiments, the mutation is an insertion of one or more nucleotides into a secreted target protein (or NDP or HSPA1A) gene. In some embodiments, the mutation is in a regulatory and/or control sequence of the secreted target gene, i.e., a portion of the gene that is not coding sequence. In some embodiments, a mutation in a regulatory and/or control sequence may be in a promoter or enhancer region and prevent or reduce the proper transcription of the NDP gene or HSPA1A gene. In some embodiments, a mutation is in a known heterologous gene known to interact with a secreted target protein, or the NDP gene or the HSPA1A.

Methods of genotyping and/or detecting expression or activity of secreted target protein (or NDP or HSPA1A) mRNA and/or secreted target protein are known in the art (see e.g., Ito et al., World J Otorhinolaryngol. 2013 May 28; 3 (2): 26-34, and Roesch et al., Int J Mol Sci. 2018 January; 19 (1): 209, each of which is incorporated in its entirety herein by reference). In some embodiments, level of expression of secreted target protein (or NDP or HSPA1A) mRNA or secreted target protein may be detected directly (e.g., detecting secreted target protein, e.g., detecting secreted target protein (or NDP or HSPA1A) mRNA etc.). Non-limiting examples of techniques that can be used to detect expression and/or activity of secreted target protein (or NDP or HSPA1A) directly include, e.g., real-time PCR, quantitative real-time PCR, Western blotting, immunoprecipitation, immunohistochemistry, mass spectrometry, or immunofluorescence. In some embodiments, expression of secreted target protein (or NDP or HSPA1A) can be detected indirectly (e.g., through functional hearing tests, ABRs, DPOAEs, etc.).

In some embodiments, tissue samples (e.g., comprising one or more inner ear cells, e.g., comprising one or more hair cells and/or one or more supporting cells) may be evaluated via morphological analysis to determine morphology of hair cells and/or support cells before and after administration of any agents (e.g., compositions, e.g., compositions comprising constructs, and/or particles, etc.) as described herein. In some such embodiments, standard immunohistochemical or histological analyses may be performed. In some embodiments, if cells are used in vitro or ex vivo, additional immunocytochemical or immunohistochemical analyses may be performed. In some embodiments, one or more assays of one or more proteins or transcripts (e.g., western blot, ELISA, polymerase chain reactions) may be performed on one or more samples from a subject or in vitro cell populations.

Production Methods

AAV systems are generally well known in the art (see, e.g., Kelleher and Vos, Biotechniques, 17 (6): 1110-17 (1994); Cotten et al., P.N.A.S. U.S.A., 89 (13): 6094-98 (1992); Curiel, Nat Immun, 13 (2-3): 141-64 (1994); Muzyczka, Curr Top Microbiol Immunol, 158:97-129 (1992); and Asokan A, et al., Mol. Ther., 20 (4): 699-708 (2012), each of which is incorporated in its entirety herein by reference). Methods for generating and using AAV constructs are described, for example, in U.S. Pat. Nos. 5,139,941, 4,797,368 and PCT filing application US2019/060328, each of which is incorporated in its entirety herein by reference.

Methods for obtaining viral constructs are known in the art. For example, to produce AAV constructs, the methods typically involve culturing a host cell which contains a nucleic acid sequence encoding an AAV capsid protein or fragment thereof; a functional rep gene; a recombinant AAV construct composed of AAV inverted terminal repeats (ITRs) and a coding sequence; and/or sufficient helper functions to permit packaging of the recombinant AAV construct into the AAV capsid proteins.

In some embodiments, components to be cultured in a host cell to package an AAV construct in an AAV capsid may be provided to the host cell in trans. Alternatively, any one or more components (e.g., recombinant AAV construct, rep sequences, cap sequences, and/or helper functions) may be provided by a stable host cell that has been engineered to contain one or more such components using methods known to those of skill in the art. In some embodiments, such a stable host cell contains such component(s) under the control of an inducible promoter. In some embodiments, such component(s) may be under the control of a constitutive promoter. In some embodiments, a selected stable host cell may contain selected component(s) under the control of a constitutive promoter and other selected component(s) under the control of one or more inducible promoters. For example, a stable host cell may be generated that is derived from HEK293 cells (which contain E1 helper functions under the control of a constitutive promoter), but that contain the rep and/or cap proteins under the control of inducible promoters. Other stable host cells may be generated by one of skill in the art using routine methods.

Recombinant AAV construct, rep sequences, cap sequences, and helper functions required for producing an AAV of the disclosure may be delivered to a packaging host cell using any appropriate genetic element (e.g., construct). A selected genetic element may be delivered by any suitable method known in the art, e.g., to those with skill in nucleic acid manipulation and include genetic engineering, recombinant engineering, and synthetic techniques (see, e.g., Sambrook et al, Molecular Cloning: A Laboratory Manual, Cold Spring Harbor Press, Cold Spring Harbor, N.Y., which is incorporated in its entirety herein by reference). Similarly, methods of generating AAV particles are well known and any suitable method can be used with the present disclosure (see, e.g., K. Fisher et al, J. Virol., 70:520-532 (1993) and U.S. Pat. No. 5,478,745, which are incorporated in their entirety herein by reference).

In some embodiments, recombinant AAVs may be produced using a triple transfection method (e.g., as described in U.S. Pat. No. 6,001,650, which is incorporated in its entirety herein by reference). In some embodiments, recombinant AAVs are produced by transfecting a host cell with a recombinant AAV construct (comprising a coding sequence) to be packaged into AAV particles, an AAV helper function construct, and an accessory function construct. An AAV helper function construct encodes "AAV helper function" sequences (i.e., rep and cap), which function in trans for productive AAV replication and encapsidation. In some embodiments, the AAV helper function construct supports efficient AAV construct production without generating any detectable wild type AAV particles (i.e., AAV particles containing functional rep and cap genes). Non-limiting examples of constructs suitable for use with the present disclosure include pHLP19 (see, e.g., U.S. Pat. No. 6,001,650, which is incorporated in its entirety herein by reference) and pRep6cap6 construct (see, e.g., U.S. Pat. No. 6,156,303, which is incorporated in its entirety herein by reference). An accessory function construct encodes nucleotide sequences for non-AAV derived viral and/or cellular functions upon which AAV is dependent for replication (i.e., "accessory functions"). Accessory functions may include those functions required for AAV replication, including, without limitation, those moieties involved in activation of AAV gene transcription, stage specific AAV mRNA splicing, AAV DNA replication, synthesis of cap expression products, and AAV capsid assembly. Viral-based accessory functions can be derived from any known helper viruses such as adenovirus, herpesvirus (other than herpes simplex virus type-1), and vaccinia virus.

Additional methods for generating and isolating AAV viral constructs suitable for delivery to a subject are described in, e.g., U.S. Pat. Nos. 7,790,449; 7,282,199; WO 2003/042397; WO 2005/033321, WO 2006/110689; and U.S. Pat. No. 7,588,772, each of which is incorporated in its entirety herein by reference. In one system, a producer cell line is transiently transfected with a construct that encodes a coding sequence flanked by ITRs and a construct(s) that encodes rep and cap. In another system, a packaging cell line that stably supplies rep and cap is transiently transfected with a construct encoding a coding sequence flanked by ITRs. In each of these systems, AAV particles are produced in response to infection with helper adenovirus or herpesvirus, and AAVs are separated from contaminating virus. Other systems do not require infection with helper virus to recover the AAV—the helper functions (i.e., adenovirus E1, E2a, VA, and E4 or herpesvirus UL5, UL8, UL52, and UL29, and herpesvirus polymerase) are also supplied, in trans, by the system. In such systems, helper functions can be supplied by transient transfection of the cells with constructs that encode the helper functions, or the cells can be engineered to stably contain genes encoding the helper functions, the expression of which can be controlled at the transcriptional or posttranscriptional level.

In some embodiments, viral construct titers post-purification are determined. In some embodiments, titers are determined using quantitative PCR. In certain embodiments, a TaqMan® probe specific to a construct is utilized to determine construct levels. In certain embodiments, the TaqMan® probe is represented by SEQ ID NO: 49, while forward and reverse amplifying primers are exemplified by SEQ ID NO: 54 and 55 respectively.

```
Exemplary TaqMan probe for quantification of
constructs
                                        (SEQ ID NO: 49)
/56-FAM/TAATTCCAA/ZEN/CCAGCAGAGTCAGGGC/3IABkFQ/

Exemplary forward qPCR primer for
quantification of constructs
                                        (SEQ ID NO: 54)
GATACAGCTAGAGTCCTGATTGC

Exemplary reverse qPCR primer for
quantification of constructs
                                        (SEQ ID NO: 55)
GATCTGCCAAGTACCTCACTATG
```

As described herein, in some embodiments, a viral construct of the present disclosure is an adeno-associated virus (AAV) construct. Several AAV serotypes have been characterized, including AAV1, AAV2, AAV3 (e.g., AAV3B), AAV4, AAV5, AAV6, AAV7, AAV8, AAV9, AAV10, AAV11, and AAV Anc80, as well as variants thereof. In some embodiments, an AAV particle is an AAV2/6, AAV2/8, AAV2/9, or AAV2/Anc80 particle (e.g., with AAV6, AAV8, AAV9 or Anc80 capsid and construct with AAV2 ITR). Other AAV particles and constructs are described in, e.g., Sharma et al., Brain Res Bull. 2010 Feb. 15; 81 (2-3): 273, which is incorporated in its entirety herein by reference. Generally, any AAV particle may be used to deliver a coding sequence described herein. However, the serotypes have different tropisms, e.g., they preferentially infect different tissues. In some embodiments, an AAV construct is a self-complementary AAV construct.

The present disclosure provides, among other things, methods of making AAV-based constructs. In some embodiments, such methods include use of host cells. In some embodiments, a host cell is a mammalian cell. A host cell may be used as a recipient of an AAV helper construct, an AAV minigene plasmid, an accessory function construct, and/or other transfer DNA associated with the production of recombinant AAVs. The term includes the progeny of an original cell that has been transfected. Thus, a "host cell" as used herein may refer to a cell that has been transfected with an exogenous DNA sequence. It is understood that the progeny of a single parental cell may not necessarily be completely identical in morphology or in genomic or total DNA complement as the original parent, due to natural, accidental, or deliberate mutation.

Additional methods for generating and isolating AAV particles suitable for delivery to a subject are described in, e.g., U.S. Pat. Nos. 7,790,449; 7,282,199; WO 2003/042397; WO 2005/033321, WO 2006/110689; and U.S. Pat. No. 7,588,772, each of which is incorporated in its entirety herein by reference. In one system, a producer cell line is transiently transfected with a construct that encodes a coding sequence flanked by ITRs and a construct(s) that encodes rep and cap. In another system, a packaging cell line that stably supplies rep and cap is transiently transfected with a construct encoding a coding sequence flanked by ITRs. In each of these systems, AAV particles are produced in response to infection with helper adenovirus or herpesvirus, and AAV particles are separated from contaminating virus. Other systems do not require infection with helper virus to recover the AAV particles—the helper functions (i.e., adenovirus E1, E2a, VA, and E4 or herpesvirus UL5, UL8, UL52, and UL29, and herpesvirus polymerase) are also supplied, in trans, by the system. In such systems, helper functions can be supplied by transient transfection of the cells with constructs that encode the helper functions, or the cells can be engineered to stably contain genes encoding the helper functions, the expression of which can be controlled at the transcriptional or posttranscriptional level.

In yet another system, a coding sequence flanked by ITRs and rep/cap genes are introduced into insect host cells by infection with baculovirus-based constructs. Such production systems are known in the art (see generally, e.g., Zhang et al., 2009, Human Gene Therapy 20:922-929, which is incorporated in its entirety herein by reference). Methods of making and using these and other AAV production systems are also described in U.S. Pat. Nos. 5,139,941; 5,741,683; 6,057,152; 6,204,059; 6,268,213; 6,491,907; 6,660,514; 6,951,753; 7,094,604; 7,172,893; 7,201,898; 7,229,823; and 7,439,065, each of which is incorporated in its entirety herein by reference.

EXAMPLES

The disclosure is further described in detail by reference to the following experimental examples. These examples are provided for purposes of illustration only, and are not intended to be limiting unless otherwise specified. Thus, the disclosure should in no way be construed as being limited to the following examples, but rather should be construed to encompass any and all variations that become evident as a result of the teaching provided herein.

It is believed that one or ordinary skill in the art can, using the preceding description and following Examples, as well as what is known in the art, to make and utilize technologies of the present disclosure.

Example 1. NDP Expression in HEK293FT Cells

HEK293FT cells were transfected with exemplary NDP vectors using jetprime reagent and were seeded overnight at 7E4 cells/well in a 24-well format (FIGS. 1-3). 72 hours post-transfection supernatant was collected and NDP protein expression was determined by Western blot. Thirty microliters of each supernatant sample was loaded into a well of a 4-12% Bis-Tris protein gel. As shown FIG. 6, all three tested vectors secreted high levels of NDP. Therefore, the vectors described herein can be used to secrete full-length NDP.

Example 2. NDP Expression in P2 Cochlear Mouse Explants

Figures 6, 7:
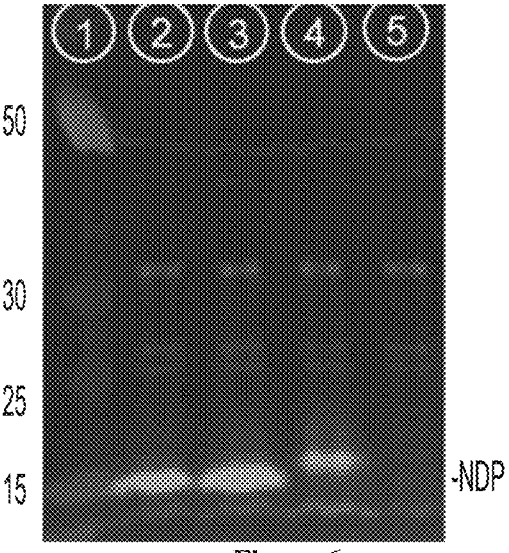
FIG. 6 is an exemplary image of a Western blot showing harvested supernatant of HEK293FT cells transfected with plasmid 1, plasmid 2 or plasmid 3, and blotted with NDP antibody. Lane 1-prestained Page Ruler; Lane 2-Construct 1; Lane 3-Construct 2; Lane 4-Construct 3; Lane 5-untransfected control supernatant.
FIG. 7 is an exemplary fluorescent image showing Myo7a staining following ex vivo cochlea transduction with Anc80.NDP.UTR (Construct 1) or Anc80.NDP (Construct 2).
Figure 8:
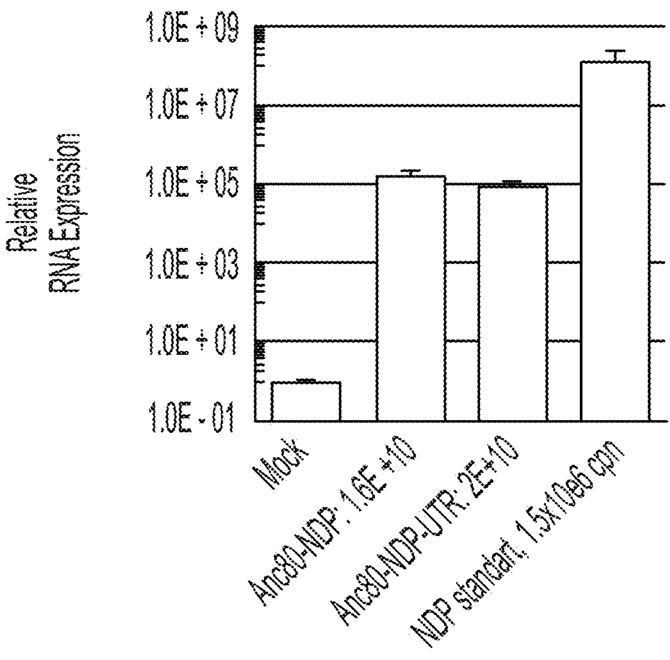
FIG. 8 is a bar graph showing relative NDP RNA expression levels (relative to mouse GAPDH (mGADPH)) in mouse explants transduced with Anc80.NDP.UTR (Construct 1) or Anc80.NDP (Construct 2).
Figure 9:
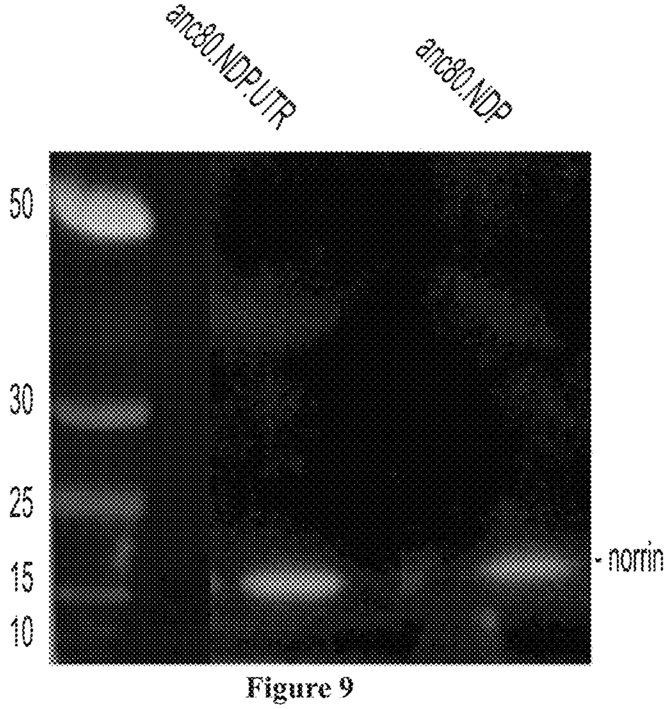
FIG. 9 is an exemplary image of a Western blot showing secreted norrin (or NDP protein) detected in the supernatant of cochlea explant cultures transduced with Anc80.NDP.UTR (Construct 1) or Anc80.NDP (Construct 2).

P2 cochlear explants from WT mice were infected 16 hours after plating and were harvested for RNA and immunofluorescence 72 hours after infection. As shown in FIG. 7, NDP was efficiently expressed in cochlear explants. As shown in FIG. 7, outer hair cells (OHC) and inner hair cells (IHC) of P2 cochlear explants express Myo7a when transduced with either AAV.Anc80-NDP (MOI 1.6E+10 VG/cochlea; FIG. 1) or AAV.Anc80-NDP-UTR (MOI 2E+10 VG/cochlea; FIG. 2). Transfection with either vector did not disrupt the structural integrity of OHCs or IHCs of the cochlea. Thus, FIG. 7 shows lack of toxicity of NDP constructs with viable and organized outer hair cells (OHC), inner hair cells (IHC) and stereociliary bundles. Cochlear explants infected with AAV.Anc80-NDP or AAV.Anc80-NDP-UTR expressed Myo7a in both the OHC and IHC. Ex vivo cochlea transduction of Anc80.NDP did not result in acute hair cell (Myo7) loss. Using RTqPCR, high expression of NDP mRNA (relative to mGADPH) were detected at the same level for both Anc80.NDP and Anc80.NDP.3'UTR (FIG. 8). Secreted norrin protein was also detected in the supernatant of cochlea explant culture (FIG. 9).

Example 3. Promoter Selection

Figure 10:
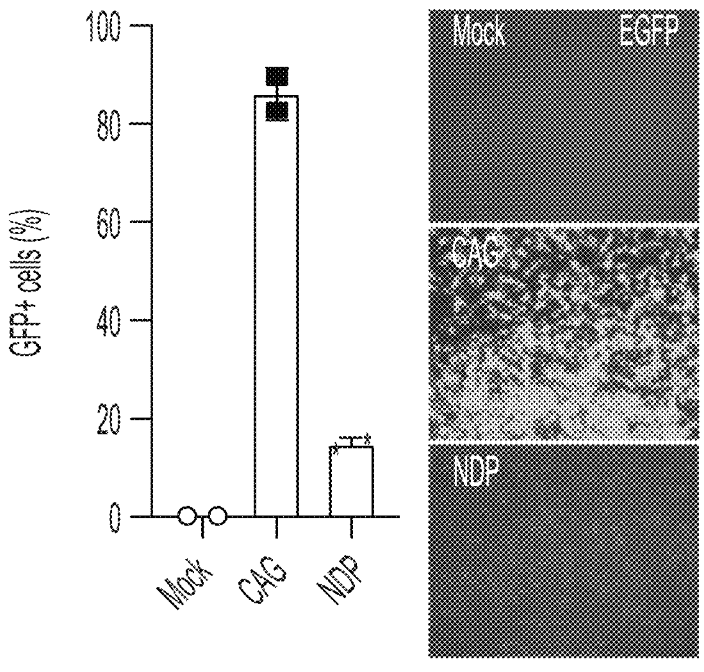
FIG. 10 shows an exemplary image of EGFP protein expression in HEK cells using constructs described herein (mock, CAG-EGFP, NDP-EGFP).
Figure 11:
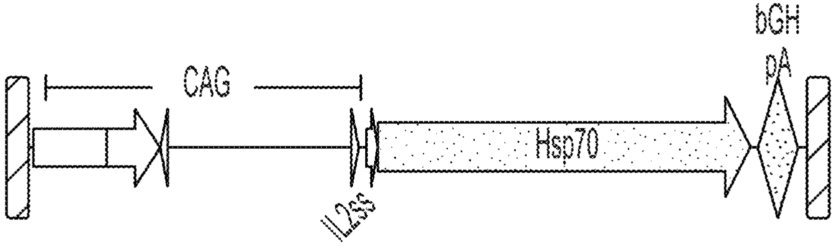
FIG. 11 is an exemplary nucleic acid vector, Construct 6 (SEQ ID NO: 96, 4236 bp), that includes a 5'ITR sequence (SEQ ID NO: 116), a CMV enhancer sequence (SEQ ID NO: 118), a CBA promoter sequence (SEQ ID NO: 119), a chimeric intron sequence (SEQ ID NO: 120), a IL2 stuffer sequence (SEQ ID NO: 122), a Hsp70 coding sequence (SEQ ID NO: 123), a bGH poly(A) sequence (SEQ ID NO: 125), and an ITR sequence (SEQ ID NO: 127).
Figure 12:
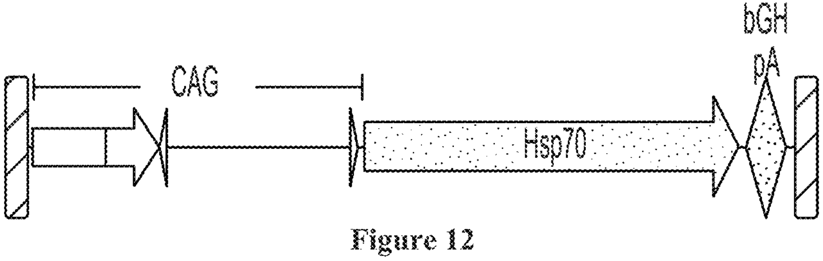
FIG. 12 is an exemplary nucleic acid vector, Construct 7 (SEQ ID NO: 97, 4179 bp), that includes a 5'ITR sequence (SEQ ID NO: 128), a CMV enhancer sequence (SEQ ID NO: 130), a CBA promoter sequence (SEQ ID NO: 131), a chimeric intron sequence (SEQ ID NO: 132), a Hsp70 coding sequence (SEQ ID NO: 134), a bGH poly(A) sequence (SEQ ID NO: 136), and an ITR sequence (SEQ ID NO: 138).
Figure 13:
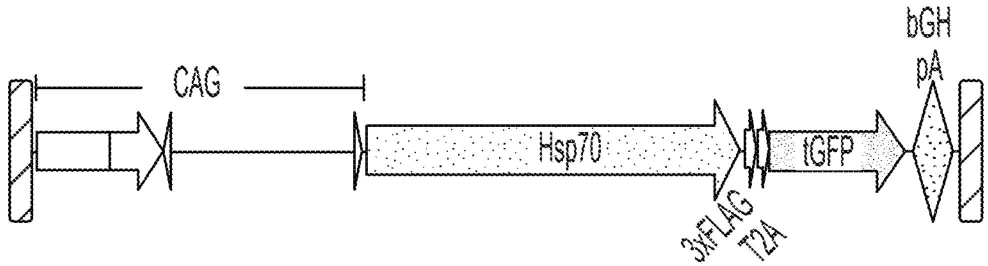
FIG. 13 is an exemplary nucleic acid vector, Construct 8 (SEQ ID NO: 98, 4179 bp), that includes a 5'ITR sequence (SEQ ID NO: 139), a CMV enhancer sequence (SEQ ID NO: 141), a CBA promoter sequence (SEQ ID NO: 142), a chimeric intron sequence (SEQ ID NO: 143), a Hsp70 coding sequence (SEQ ID NO: 145), a 3xFLAG sequence (SEQ ID NO: 147), a T2A sequence (SEQ ID NO: 149), a tGFP sequence (SEQ ID NO: 150), a bGH poly(A) sequence (SEQ ID NO:152), and an ITR sequence (SEQ ID NO: 154).

The present example further confirms use of constructs as described herein in methods treating hearing loss using a secreted target protein in accordance with the present disclosure. HEK293FT cells were transfected with 800 ng plasmid DNA (mock, CAG-EGFP, NDP-EGFP) using jetprime reagent and were seeded overnight at 1.5E5 cells/well in a 24-well format (FIG. 10). 72 hours post-transfection supernatant was collected and EGFP protein expression was determined by EGFP flow cytometry. As shown FIG. 10, CAG-EGFP resulted in over 80% GFP+ cells and NDP-EGFP resulted in less than 20% GFP+ cells.

Example 4. HSP70 Expression in HEK293FT Cells

Figure 14:
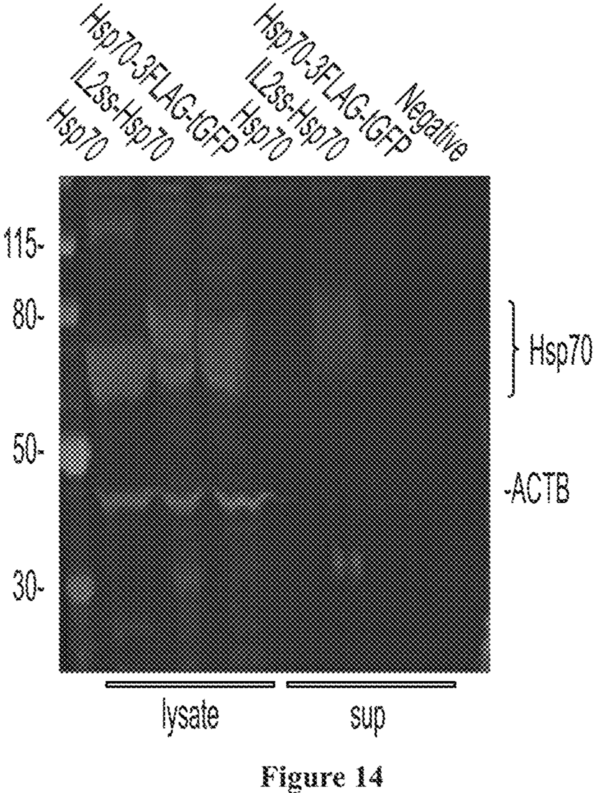
FIG. 14 is an exemplary image of a Western blot showing secreted HSP70 protein detected in the lysate or supernatant of cochlea explant cultures transduced with CAG-Hsp70 (Construct 7), CAG-IL2ss-HSP70 (Construct 6), or CAG-Hsp70-3xFlag-tGFP (Construct 8).

The present example further confirms use of constructs as described herein in methods treating hearing loss using a secreted target protein in accordance with the present disclosure. HEK293FT cells were transfected with exemplary HSP70 vectors using jetprime reagent and were seeded overnight at 1.4E5 cells/well in a 24-well format (FIGS. 11-13). 72 hours post-transfection supernatant (~450 μL) and cell (100 μL RIPA) was collected and HSP70 protein expression was determined by Western blot. Thirty microliters of each supernatant sample was loaded into a well of a 4-12% Bis-Tris protein gel and immunoblotted with polyclonal HSP70 and ACTB antibodies. As shown FIG. 14, all three tested vectors secreted high levels of HSP70. Therefore, the vectors described herein can be used to secrete full-length HSP70.

Example 5. HSP70 Expression in P2 Cochlear Mouse Explants

Figure 15:
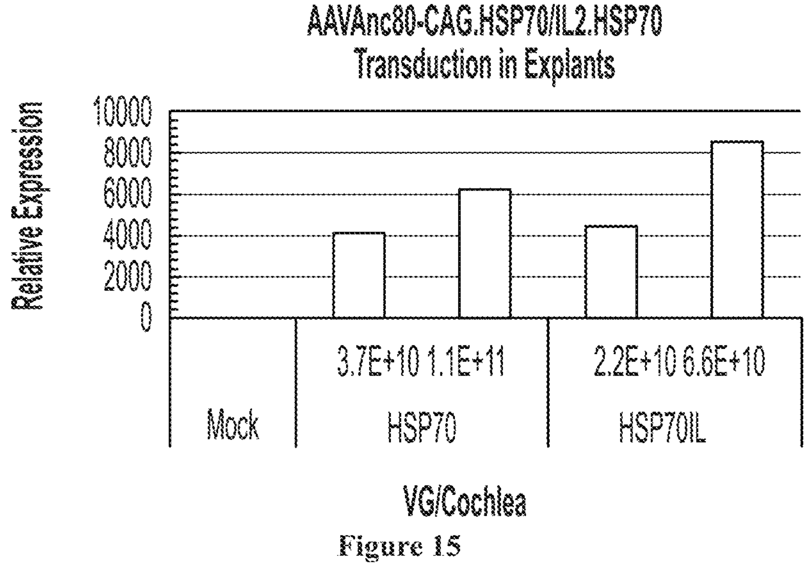
FIG. 15 depicts a bar graph showing relative Hsp70 RNA expression levels (relative to mouse mGADPH) in mouse explants transduced with Anc80-CAG.HSP70 (Construct 7) (3.7E+10 vg/cochlea and 1.1E+11 vg/cochlea) or Anc80-CAG.IL2ss.HSP70 (Construct 6) (2.2E+10 vg/cochlea and 6.6E+10 vg/cochlea).
Figure 16:
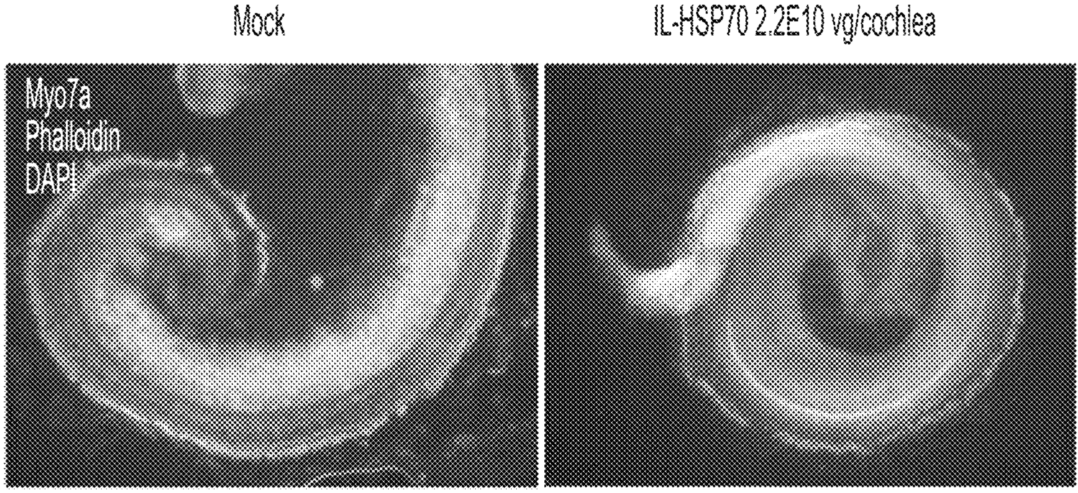
FIG. 16 are exemplary fluorescent images showing Myo7a staining following ex vivo cochlea tolerability of Anc80-CAG.IL2ss.HSP70 (left image: mock solution (control); right imageAnc80-CAG.IL2ss.HSP70 (Construct 6) (2.2E+10 vg/cochlea)).

P2 cochlear explants from WT mice were infected 16 hours after plating and were harvested for RNA and immunofluorescence 72 hours after infection. As shown in FIG. 16, Myo7a staining confirms ex vivo cochlea tolerability of AAV.Anc80-IL.HSP70 (or AAV.Anc80-ILss.HSP70). As shown in FIG. 16, outer hair cells (OHC) and inner hair cells (IHC) of P2 cochlear explants express Myo7a when transduced with either AAV.Anc80-IL.HSP70 (MOI 2.2E+10 VG/cochlea or 6.6E+10; FIGS. 15 and 16) or AAV.Anc80-CAG.HSP70 (MOI 3.7E+10 VG/cochlea or 1.1E+11 VG/cochlea; FIG. 15). Transfection with either vector did not disrupt the structural integrity of OHCs or IHCs of the cochlea (see FIG. 16). FIG. 15 confirms that Hsp70 expression in cochlea of transduced P2 cochlear mouse explants. Thus, FIG. 16 confirms lack of toxicity of HSP70 constructs with viable and organized outer hair cells (OHC), inner hair cells (IHC) and stereociliary bundles. Cochlear explants infected with AAV.Anc80-CAG.HSP70 or AAV.Anc80-IL2.HSP70 expressed Myo7a in both the OHC and IHC. Ex vivo cochlea transduction of AAV.Anc80-CAG.HSP70 or AAV.Anc80-IL2.HSP70 did not result in acute hair cell (Myo7) loss. Using RTqPCR, high expression of HSP70 mRNA (relative to mGADPH) were detected at similar levels for both Anc80.CAG.HSP70 and Anc80.IL2.HSP70 (FIG. 15).

Figure 17:
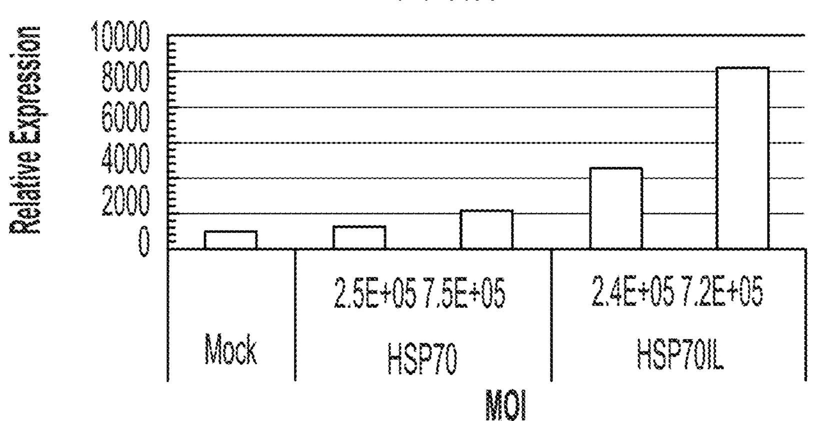
FIG. 17 depicts a bar graph showing relative Hsp70 RNA expression levels (relative to human Actin) in HEK cells transduced with Anc80-CAG.HSP70 (Construct 7) (2.5E+5 MOI and 7.5E+5 MOI) or Anc80-CAG.IL2ss.HSP70 (Construct 6) (2.4E+5 MOI and 7.2E+5 MOI).
Figure 18:
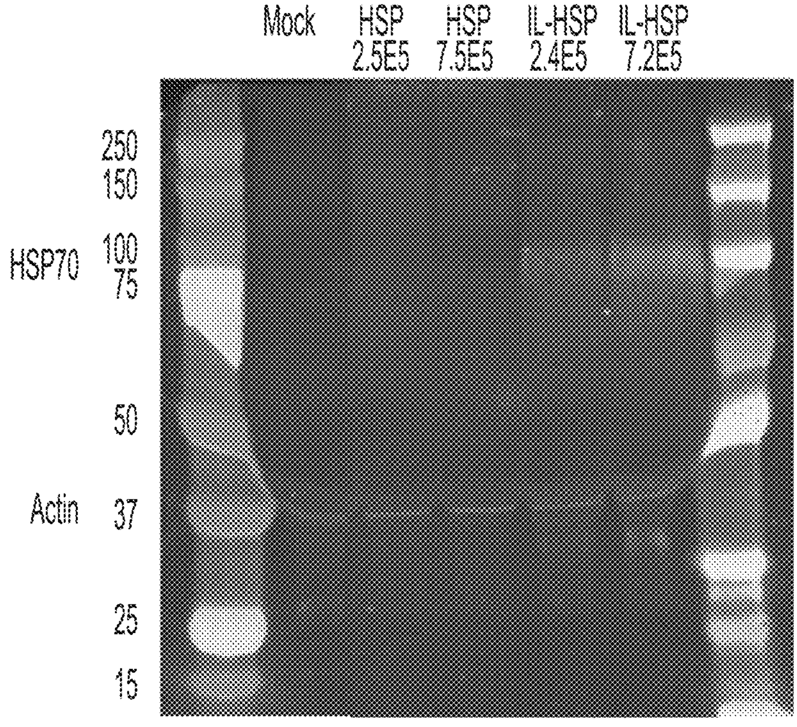
FIG. 18 is an exemplary image of a Western blot showing secreted HSP70 protein detected in supernatant (media) of HEK cells transduced with CAG-Hsp70 (Construct 7) (2.5E+5 MOI and 7.5E+5 MOI) and CAG-IL2ss-HSP70 (Construct 6) (2.4E+5 MOI and 7.2E+5 MOI).

Secreted HSP70 protein was also detected in the supernatant of cochlea explant culture (FIGS. 18-19). FIG. 17 shows that HEK293FT transduction of AAV.Anc80-IL2.HSP70 (MOI 2.4E+5 and 7.2E+5) performed better than HEK293FT transduction of AAV.Anc80-CAG.HSP70 (MOI 2.5E+5 and 7.5E+5). FIG. 18 shows a Western Blot of HSP70 protein expressed by the exemplary vectors provided herein (Actin protein expression was used as a control).

EMBODIMENTS

Embodiment 1. A composition comprising a single adeno-associated virus (AAV) vector, wherein the single AAV vector comprises a nucleic acid sequence that encodes a secreted target protein; and when introduced into a mammalian cell, a nucleic acid encoding a secretion signal sequence operatively linked to the secreted target protein is generated at the locus of the secreted target protein, and the mammalian cell expresses and secretes the secreted target protein.

Embodiment 2. The composition of embodiment 1, wherein the single AAV vector further comprises a 5' untranslated region (UTR), a 3' UTR, or both.

Embodiment 3. The composition of embodiment 1 or 2, wherein the secreted target protein is norrin cysteine knot growth factor (NDP).

Embodiment 4. The composition of embodiment 3, wherein the secreted target protein comprises a sequence that is at least 80% identical to SEQ ID NO: 1.

Embodiment 5. The composition of embodiment 4, wherein the secreted target protein comprises a sequence that is at least 90% identical to SEQ ID NO: 1.

Embodiment 6. The composition of embodiment 5, wherein the secreted target protein comprises a sequence that is at least 99% identical to SEQ ID NO: 1.

Embodiment 7. The composition of any one of embodiments 3-6, wherein the nucleic acid that encodes the secreted target protein comprises a sequence that is at least 80% identical to SEQ ID NO: 2.

Embodiment 8. The composition of embodiment 7, wherein the nucleic acid that encodes the secreted target protein comprises a sequence that is at least 90% identical to SEQ ID NO: 2.

Embodiment 9. The composition of embodiment 8, wherein the nucleic acid that encodes the secreted target protein comprises a sequence that is at least 99% identical to SEQ ID NO: 2.

Embodiment The composition of embodiment 1 or 2, wherein the secreted target protein is heat shock protein, optionally a heat shock protein family A (Hsp70) member 1A (HSPA1A) or heat shock protein family 40 (Hsp40)/DnaJ member.

Embodiment 11. The composition of embodiment 10, wherein the secreted target protein comprises a sequence that is at least 80% identical to SEQ ID NO: 3.

Embodiment 12. The composition of embodiment 11, wherein the secreted target protein comprises a sequence that is at least 90% identical to SEQ ID NO: 3.

Embodiment 13. The composition of embodiment 12, wherein the secreted target protein comprises a sequence that is at least 99% identical to SEQ ID NO: 3.

Embodiment 14. The composition of any one of embodiments 10-13, wherein the nucleic acid that encodes the secreted target protein comprises a sequence that is at least 80% identical to SEQ ID NO: 4.

Embodiment 15. The composition of embodiment 14, wherein the nucleic acid that encodes the secreted target protein comprises a sequence that is at least 90% identical to SEQ ID NO: 4.

Embodiment 16. The composition of embodiment 15, wherein the nucleic acid that encodes the secreted target protein comprises a sequence that is at least 99% identical to SEQ ID NO: 4.

Embodiment 17. The composition of any one of embodiments 1-16, wherein the AAV vector further comprises one or both of a promoter and a Kozak sequence.

Embodiment 18. The composition of embodiment 17, wherein the AAV vector comprises a promoter that is an inducible promoter, a constitutive promoter, or a tissue-specific promoter.

Embodiment 19. The composition of any one of embodiments 1-18, wherein the AAV vector further comprises a poly(dA) sequence.

Embodiment 20. The composition of any one of embodiments 1-19, wherein the secretion signal sequence comprises SEQ ID NO: 5.

Embodiment 21. The composition of embodiment 20, wherein the sequence encoding the secretion signal sequence comprises SEQ ID NO: 6.

Embodiment 22. The composition of any one of embodiments 1-19, wherein the secretion signal sequence comprises SEQ ID NO: 7.

Embodiment 23. The composition of embodiment 22, wherein the sequence encoding the secretion signal sequence comprises SEQ ID NO: 8.

Embodiment 24. The composition of embodiment 1, wherein the single AAV vector comprises a sequence that is at least 80% identical to SEQ ID NO: 9.

Embodiment 25. The composition of embodiment 24, wherein the single AAV vector comprises a sequence that is at least 90% identical to SEQ ID NO: 9.

Embodiment 26. The composition of embodiment 25, wherein the single AAV vector comprises a sequence that is at least 99% identical to SEQ ID NO: 9.

Embodiment 27. The composition of embodiment 1, wherein the single AAV vector comprises a sequence that is at least 80% identical to SEQ ID NO: 10.

Embodiment 28. The composition of embodiment 27, wherein the single AAV vector comprises a sequence that is at least 90% identical to SEQ ID NO: 10.

Embodiment 29. The composition of embodiment 28, wherein the single AAV vector comprises a sequence that is at least 99% identical to SEQ ID NO: 10.

Embodiment 30. The composition of any one of embodiments 1-29, further comprising a pharmaceutically acceptable excipient.

Embodiment 31. A kit comprising a composition of any one of embodiments 1-30.

Embodiment 32. The kit of embodiment 31, wherein the composition is pre-loaded in a syringe.

Embodiment 33. A method comprising introducing into an inner ear of a mammal a therapeutically effective amount of the composition of any one of embodiments 1-30.

Embodiment 34. The method of embodiment 33, wherein the mammal is a human [0532] or a primate.

Embodiment 35. The method of embodiment 33 or 34, wherein the mammal has been previously identified as having a defective secreted target gene.

Embodiment 36. A method of increasing expression of a full-length secreted target protein in a mammalian cell, the method comprising introducing the composition of any one of embodiments 1-30 into the mammalian cell.

Embodiment 37. The method of embodiment 36, wherein the mammalian cell is a cochlear inner hair cell, a supporting cell, a ganglion cell, a clear cell, a cuboidal cell, a cartilage cell, a cell of the tegmentum vasculosum, a homogene cell, a Hensen's cell, a Deiters' cell, a pillar cell, or a border cell.

Embodiment 38. The method of embodiment 36 or 37, wherein the mammalian cell is a human cell or a primate cell.

Embodiment 39. The method of any one of embodiments 36-38, wherein the mammalian cell has previously been determined to have a defective secreted target gene.

Embodiment 40. A method of increasing the level of a full-length secreted target protein in an inner ear of a mammal, the method comprising introducing into the inner ear of the mammal a therapeutically effective amount of the composition of any one of embodiments 1-30.

Embodiment 41. The method of embodiment 40, wherein the mammal has been previously identified as having a defective secreted target gene.

Embodiment 42. The method of embodiment 40 or 41, wherein the mammal is a human or a primate.

Embodiment 43. A method of treating syndromic and non-syndromic sensorineural hearing loss in a subject identified as having a defective secreted target gene, the method comprising: administering a therapeutically effective amount of a composition of any one of embodiments 1-30 into the inner ear of the subject.

Embodiment 44. The method of embodiment 43, wherein the subject is a human or a primate.

Embodiment 45. The method of embodiment 43 or 44, wherein the subject has Norrie disease pseudoglioma or the subject has been identified or diagnosed as having a Hsp70 polymorphism (such as rs1043618, rs1061581 and rs2227956 in HSP70-1, HSP70-2 and HSP70-hom, respectively) that makes the cochlea susceptible to hearing loss (such as a polymorphism as described by Konings et al., "Variations in HSP70 genes associated with noise-induced hearing loss in two independent populations", Eur J Hum Genet. 2009 March; 17 (3): 329-33, the contents of which is hereby incorporated by reference in its entirety).

Embodiment 46. The method of any one of embodiments 43-45, further comprising, prior to the administering step, determining that the subject has a defective secreted target gene.

Embodiment 47. A method of treating or preventing hearing loss in a subject identified as having a defective NDP gene or a defective HSPA1A gene, the method comprising: administering a therapeutically effective amount of a composition of any one of embodiments 1-30 into an inner ear of the subject.

Embodiment 48. The method of embodiment 47, wherein the subject has been identified or diagnosed as having Norrie disease pseudoglioma or the subject has been identified or diagnosed as having a Hsp70 polymorphism (such as rs1043618, rs1061581 and rs2227956 in HSP70-1, HSP70-2 and HSP70-hom, respectively) that makes the cochlea susceptible to hearing loss (such as a polymorphism as described by Konings et al., "Variations in HSP70 genes associated with noise-induced hearing loss in two independent populations", Eur J Hum Genet. 2009 March; 17 (3): 329-33, the contents of which is hereby incorporated by reference in its entirety).

Embodiment 49. The method of embodiment 47 or 48, wherein the subject is a human or a primate.

Embodiment 50. The method of any one of embodiments 47-49, further comprising prior to the administering step, determining that the subject has a defective NDP gene or a defective HSPA1A gene.

Embodiment 51. A composition comprising at least two different nucleic acid vectors, wherein: each of the at least two different vectors comprises a coding sequence that encodes a different portion of a secreted target protein, each of the encoded portions being at least 30 amino acid residues in length, wherein the amino acid sequence of each of the encoded portions may optionally partially overlap with the amino acid sequence of a different one of the encoded portions; no single vector of the at least two different vectors encodes a full-length secreted target protein; at least one of the coding sequences comprises a nucleotide sequence spanning two neighboring exons of the secreted target protein genomic DNA, and lacks an intronic sequence between the two neighboring exons; and when introduced into a mammalian cell the at least two different vectors undergo concatamerization or homologous recombination with each other, thereby forming a recombined nucleic acid that encodes a secretion signal sequence operatively linked to a full-length secreted target protein.

Embodiment 52. The composition of embodiment 51, wherein each of the at least two different vectors is a plasmid, a transposon, a cosmid, an artificial chromosome, or a viral vector.

Embodiment 53. The composition of embodiment 51, wherein each of the at least two different vectors is a human artificial chromosome (HAC), yeast artificial chromosome (YAC), bacterial artificial chromosome (BAC), or a P1-derived artificial chromosome (PAC).

Embodiment 54. The composition of embodiment 51, wherein each of the at least two different vectors is a viral vector selected from an adeno-associated virus (AAV) vector, an adenovirus vector, a lentivirus vector, or a retrovirus vector.

Embodiment 55. The composition of embodiment 51, wherein each of the at least two different vectors is an AAV vector.

Embodiment 56. The composition of any one of embodiments 51-55, wherein the amino acid sequence of one of the encoded portions overlaps with the amino acid sequence of a different one of the encoded portions.

Embodiment 57. The composition of embodiment 56, wherein the amino acid sequence of each of the encoded portions partially overlaps with the amino acid sequence of a different encoded portion.

Embodiment 58. The composition of embodiment 57, wherein the overlapping amino acid sequence is between about 30 amino acid residues to about 600 amino acid residues in length.

Embodiment 59. The composition of any one of embodiments 51-55, wherein the vectors include two different vectors, each of which comprises a different segment of an intron, wherein the intron comprises the nucleotide sequence of an intron that is present in the secreted target protein genomic DNA, and wherein the two different segments overlap in sequence by at least 100 nucleotides.

Embodiment 60. The composition of embodiment 59, wherein the two different segments overlap in sequence by about 100 nucleotides to about 800 nucleotides.

Embodiment 61. The composition of any one of embodiments 51-60, wherein the nucleotide sequence of each of the at least two different vectors is between about 500 nucleotides to about 10,000 nucleotides in length.

Embodiment 62. The composition of embodiment 61, wherein the nucleotide sequence of each of the at least two different vectors is between about 500 nucleotides to about 5,000 nucleotides in length.

Embodiment 63. The composition of any one of embodiments 51-62, wherein the number of different vectors in the composition is two.

Embodiment 64. The composition of embodiment 63, wherein a first of the two different vectors comprises a coding sequence that encodes an N-terminal portion of the secreted target protein.

Embodiment 65. The composition of embodiment 64, wherein the N-terminal portion of the secreted target protein is between about 30 amino acids to about 600 amino acids in length.

Embodiment 66. The composition of embodiment 65, wherein the N-terminal portion of the secreted target protein is between about 100 amino acids to about 500 amino acids in length.

Embodiment 67. The composition of any one of embodiments 64-66, wherein the first vector further comprises one or both of a promoter and a Kozak sequence.

Embodiment 68. The composition of embodiment 67, wherein the first vector comprises a promoter that is an inducible promoter, a constitutive promoter, or a tissue-specific promoter.

Embodiment 69. The composition of any one of embodiments 64-68, wherein the second of the two different vectors comprises a coding sequence that encodes a C-terminal portion of the secreted target protein.

Embodiment 70. The composition of embodiment 69, wherein the C-terminal portion of the secreted target protein is between about 30 amino acids to about 600 amino acids in length.

Embodiment 71. The composition of embodiment 70, wherein the C-terminal portion of the secreted target protein is between about 200 amino acids to about 500 amino acids in length.

Embodiment 72. The composition of any one of embodiments 69-71, wherein the second vector further comprises a poly(dA) sequence.

Embodiment 73. The composition of any one of embodiments 63-72, wherein the first vector, the second vector, or both vectors further comprises a 5' untranslated region (UTR), a 3' UTR, or both.

Embodiment 74. The composition of any one of embodiments 51-73, wherein the secreted target protein is norrin cysteine knot growth factor (NDP).

Embodiment 75. The composition of embodiment 74, wherein the secreted target protein comprises a sequence that is at least 80% identical to SEQ ID NO: 1.

Embodiment 76. The composition of embodiment 75, wherein the secreted target protein comprises a sequence that is at least 90% identical to SEQ ID NO: 1.

Embodiment 77. The composition of embodiment 76, wherein the secreted target protein comprises a sequence that is at least 99% identical to SEQ ID NO: 1.

Embodiment 78. The composition of any one of embodiments 51-73, wherein the secreted target protein is heat shock protein family A (Hsp70) member 1A (HSPA1A), a heat shock protein family 40 (Hsp40) DnaJ homolog subfamily B member 1, or a heat shock protein family 40 (Hsp40)/DnaJ member.

Embodiment 79. The composition of embodiment 78, wherein the secreted target protein comprises a sequence that is at least 80% identical to SEQ ID NO: 3.

Embodiment 80. The composition of embodiment 79, wherein the secreted target protein comprises a sequence that is at least 90% identical to SEQ ID NO: 3.

Embodiment 81. The composition of embodiment 80, wherein the secreted target protein comprises a sequence that is at least 99% identical to SEQ ID NO: 3.

Embodiment 82. The composition of any one of embodiments 51-81, wherein the secretion signal sequence comprises SEQ ID NO: 5.

Embodiment 83. The composition of any one of embodiments 51-81, wherein the secretion signal sequence comprises SEQ ID NO: 7.

Embodiment 84. A composition comprising two different nucleic acid vectors, wherein: a first nucleic acid vector of the two different nucleic acid vectors comprises a promoter, a first coding sequence that encodes an N-terminal portion of an secreted target protein positioned 3' of the promoter, and a splicing donor signal sequence positioned at the 3' end of the first coding sequence; and a second nucleic acid vector of the two different nucleic acid vectors comprises a splicing acceptor signal sequence, a second coding sequence that encodes a C-terminal portion of an secreted target protein positioned at the 3' end of the splicing acceptor signal sequence, and a polyadenylation sequence at the 3' end of the second coding sequence; wherein each of the encoded portions is at least 30 amino acid residues in length, wherein the amino acid sequences of the encoded portions do not overlap, wherein no single vector of the two different vectors encodes a full-length secreted target protein, and, when the coding sequences are transcribed in a mammalian cell, to produce RNA transcripts, splicing occurs between the splicing donor signal sequence on one transcript and the splicing acceptor signal sequence on the other transcript, thereby forming a recombined RNA molecule that encodes a secretion signal sequence operatively linked to a full-length secreted target protein.

Embodiment 85. The composition of embodiment 84, wherein the coding sequence of at least one of the vectors comprises a nucleotide sequence spanning two neighboring exons of secreted target genomic DNA, and lacks an intronic sequence between the two neighboring exons.

Embodiment 86. A composition comprising: a first nucleic acid vector comprising a promoter, a first coding sequence that encodes an N-terminal portion of an secreted target protein positioned 3' of the promoter, a splicing donor signal sequence positioned at the 3' end of the first coding sequence, and a first detectable marker gene positioned 3' of the splicing donor signal sequence; and a second nucleic acid vector, different from the first nucleic acid vector, comprising a second detectable marker gene, a splicing acceptor signal sequence positioned 3' of the second detectable marker gene, a second coding sequence that encodes a C-terminal portion of an secreted target protein positioned at the 3' end of the splicing acceptor signal sequence, and a polyadenylation sequence positioned at the 3' end of the second coding sequence; wherein each of the encoded portions is at least 30 amino acid residues in length, wherein the respective amino acid sequences of the encoded portions do not overlap with each other, wherein no single vector of the two different vectors encodes a full-length secreted target protein, and, when the coding sequences are transcribed in a mammalian cell to produce RNA transcripts, splicing occurs between the splicing donor signal on one transcript and the splicing acceptor signal on the other transcript, thereby forming a recombined RNA molecule that encodes a secretion signal sequence operatively linked to a full-length secreted target protein.

Embodiment 87. The composition of embodiment 86, wherein the coding sequence of at least one of the vectors comprises a nucleotide sequence spanning two neighboring exons of secreted target genomic DNA, and lacks an intronic sequence between the two neighboring exons.

Embodiment 88. The composition of embodiment 87, wherein the first or second detectable marker gene encodes alkaline phosphatase.

Embodiment 89. The composition of embodiment 87 or 88, wherein the first and second detectable marker genes are the same.

Embodiment 90. A composition comprising: a first nucleic acid vector comprising a promoter, a first coding sequence that encodes an N-terminal portion of an secreted target protein positioned 3' to the promoter, a splicing donor signal sequence positioned at the 3' end of the first coding sequence, and a F1 phage recombinogenic region positioned 3' to the splicing donor signal sequence; and a second nucleic acid vector, different from the first nucleic acid vector, comprising a second F1 phage recombinogenic region, a splicing acceptor signal sequence positioned 3' of the second F1 phage recombinogenic region, a second coding sequence that encodes a C-terminal portion of an secreted target protein positioned at the 3' end of the splicing acceptor signal sequence, and a polyadenylation sequence positioned at the 3' end of the second coding sequence; wherein each of the encoded portions is at least 30 amino acid residues in length, wherein the respective amino acid sequences of the encoded portions do not overlap with each other, wherein no single vector of the two different vectors encodes a full-length secreted target protein, and, when the coding sequences are transcribed in a mammalian cell to produce RNA transcripts, splicing occurs between the splicing donor signal one transcript and the splicing acceptor signal on the other transcript, thereby forming a recombined RNA molecule that encodes a secretion signal sequence operatively linked to a full-length secreted target protein.

Embodiment 91. The composition of embodiment 90, wherein the coding sequence of at least one of the vectors comprises a nucleotide sequence spanning two neighboring exons of secreted target genomic DNA, and lacks an intronic sequence between the two neighboring exons.

Embodiment 92. The composition of any one of embodiments 84-91, wherein the first vector, the second vector, or both vectors further comprises a 5' untranslated region (UTR), a 3' UTR, or both.

Embodiment 93. The composition of any one of embodiments 84-92, wherein the secreted target protein is norrin cysteine knot growth factor (NDP).

Embodiment 94. The composition of embodiment 93, wherein the secreted target protein comprises a sequence that is at least 80% identical to SEQ ID NO: 1.

Embodiment 95. The composition of embodiment 94, wherein the secreted target protein comprises a sequence that is at least 90% identical to SEQ ID NO: 1.

Embodiment 96. The composition of embodiment 95, wherein the secreted target protein comprises a sequence that is at least 99% identical to SEQ ID NO: 1.

Embodiment 97. The composition of any one of embodiments 84-92, wherein the secreted target protein is heat shock protein family A (Hsp70) member 1A (HSPA1A), a heat shock protein family 40 (Hsp40)/DnaJ member.

Embodiment 98. The composition of embodiment 97, wherein the secreted target protein comprises a sequence that is at least 80% identical to SEQ ID NO: 3.

Embodiment 99. The composition of embodiment 98, wherein the secreted target protein comprises a sequence that is at least 90% identical to SEQ ID NO: 3.

Embodiment 100. The composition of embodiment 99, wherein the secreted target protein comprises a sequence that is at least 99% identical to SEQ ID NO: 3.

Embodiment 101. The composition of any one of embodiments 84-100, wherein the secretion signal sequence comprises SEQ ID NO: 5.

Embodiment 102. The composition of any one of embodiments 84-100, wherein the secretion signal sequence comprises SEQ ID NO: 7.

Embodiment 103. The composition of any one of embodiments 51-102, further comprising a pharmaceutically acceptable excipient.

Embodiment 104. A kit comprising a composition of any one of embodiments 51-103.

Embodiment 105. A kit of embodiment 104, further comprising a pre-loaded syringe comprising the composition.

Embodiment 106. A method comprising introducing into an inner ear of a mammal a therapeutically effective amount of the composition of any one of embodiments 51-103.

Embodiment 107. The method of embodiment 106, wherein the mammal is a human or a primate.

Embodiment 108. The method of embodiment 106 or 107, wherein the mammal has been previously identified as having a defective secreted target gene.

Embodiment 109. A method of increasing expression of a full-length secreted target protein in a mammalian cell, the method comprising introducing the composition of any one of embodiments 51-103 into the mammalian cell.

Embodiment 110. The method of embodiment 109, wherein the mammalian cell is a cochlear inner hair cell, a supporting cell, a ganglion cell, a clear cell, a cuboidal cell, a cartilage cell, a cell of the tegmentum vasculosum, a homogene cell, a Hensen's cell, a Deiters' cell, a pillar cell, or a border cell.

Embodiment 111. The method of embodiment 109 or 110, wherein the mammalian cell is a human cell or a primate cell.

Embodiment 112. The method of any one of embodiments 109-111, wherein the mammalian cell has previously been determined to have a defective secreted target gene.

Embodiment 113. A method of increasing the level of a full-length secreted target protein in an inner ear of a mammal, the method comprising introducing into the inner ear of the mammal a therapeutically effective amount of the composition of any one of embodiments 51-103.

Embodiment 114. The method of embodiment 113, wherein the mammal has been previously identified as having a defective secreted target gene.

Embodiment 115. The method of embodiment 113 or 114, wherein the mammal is a human or a primate.

Embodiment 116. A method of treating syndromic and non-syndromic sensorineural hearing loss in a subject identified as having a defective secreted target gene, the method comprising:

administering a therapeutically effective amount of a composition of any one of embodiments 51-103 into the inner ear of the subject.

Embodiment 117. The method of embodiment 116, wherein the subject is a human or a primate.

Embodiment 118. The method of embodiment 116 or 117, wherein the subject has Norrie disease pseudoglioma or the subject has been identified or diagnosed as having a Hsp70 polymorphism (such as rs1043618, rs1061581 and rs2227956 in HSP70-1, HSP70-2 and HSP70 -hom, respectively) that makes the cochlea susceptible to hearing loss (such as a polymorphism as described by Konings et al., "Variations in HSP70 genes associated with noise-induced hearing loss in two independent populations", Eur J Hum Genet. 2009 March; 17 (3): 329-33, the contents of which is hereby incorporated by reference in its entirety).

Embodiment 119. The method of any one of embodiments 116-118, further comprising, prior to the administering step, determining that the subject has a defective secreted target gene.

Embodiment 120. A method of treating or preventing hearing loss in a subject identified as having a defective NDP gene or a defective HSPA1A gene, the method comprising: administering a therapeutically effective amount of a composition of any one of embodiments 51-103 into an inner ear of the subject.

Embodiment 121. The method of embodiment 120, wherein the subject has been identified or diagnosed as having Norrie disease pseudoglioma or the subject has been identified or diagnosed as having a Hsp70 polymorphism (such as rs1043618, rs1061581 and rs2227956 in HSP70-1, HSP70-2 and HSP70-hom, respectively) that makes the cochlea susceptible to hearing loss (such as a polymorphism as described by Konings et al., "Variations in HSP70 genes associated with noise-induced hearing loss in two independent populations", Eur J Hum Genet. 2009 March; 17 (3): 329-33, the contents of which is hereby incorporated by reference in its entirety).

Embodiment 122. The method of embodiment 120 or 121, wherein the subject is a human or a primate.

Embodiment 123. The method of any one of embodiments 120-122, further comprising prior to the administering step, determining that the subject has a defective NDP gene or a defective HSPA1A gene.

Embodiment 124. A method of treating or preventing vision loss in a subject identified as having a defective NDP gene or a defective HSPA1A gene, the method comprising: administering a therapeutically effective amount of a composition of any one of embodiments 1-30 into an inner ear or central nervous system of the subject, or systemically administering a therapeutically effective amount of a composition of any one of embodiments 1-30 to the subject.

Embodiment 125. The method of embodiment 124, wherein the subject is a human or a primate.

Embodiment 126. The method of embodiment 124 or 125, further comprising prior to the administering step, determining that the subject has a defective NDP gene or a defective HSPA1A gene.

Embodiment 127. A method of treating or preventing vision loss in a subject identified as having a defective NDP gene or a defective HSPA1A gene, the method comprising: administering a therapeutically effective amount of a composition of any one of embodiments 51-103 into an inner ear or central nervous system of the subject, or systemically administering a therapeutically effective amount of a composition of any one of embodiments 51-103 to the subject.

Embodiment 128. The method of embodiment 127, wherein the subject is a human.

Embodiment 129. The method of embodiment 127 or 128, further comprising prior to the administering step, determining that the subject has a defective NDP gene or a defective HSPA1A gene.

OTHER EMBODIMENTS

It is to be understood that while the present disclosure has been described in conjunction with the detailed description thereof, the foregoing description is intended to illustrate and not limit the scope of the present disclosure, which is defined by the scope of the appended claims. Other aspects, advantages, and modifications are within the scope of the following claims.

All publications, patent applications, patents, and other references mentioned herein are incorporated by reference in their entirety. In case of conflict, the present specification, including definitions, will control. Section headings and any descriptions of materials, methods, and examples are illustrative only and not intended to be limiting.

```
Exemplary Sequences
mature NDP protein
                                                     SEQ ID NO: 1
KTDSSFIMDSDPRRCMRHHYVDSISHPLYKCSSKMVLLARCEGHCSQASRSEPLVSFSTVLKQP

FRSSCHCCRPQTSKLKALRLRCSGGMRLTATYRYILSCHCEECNS

mature NDP cDNA
                                                     SEQ ID NO: 2
AAAACGGACAGCTCATTCATAATGGACTCGGACCCTCGACGCTGCATGAGGCACCACTATGTGG

ATTCTATCAGTCACCCATTGTACAAGTGTAGCTCAAAGATGGTGCTCCTGGCCAGGTGCGAGGG

GCACTGCAGCCAGGCGTCACGCTCCGAGCCTTTGGTGTCGTTCAGCACTGTCCTCAAGCAACCC

TTCCGTTCCTCCTGTCACTGCTGCCGGCCCCAGACTTCCAAGCTGAAGGCACTGCGGCTGCGAT

GCTCAGGGGGCATGCGACTCACTGCCACCTACCGATACATCCTCTCCTGTCACTGCGAGGAATG

CAATTCCTAA

mature HSPA1A protein
                                                     SEQ ID NO: 3
MAKAAAIGIDLGTTYSCVGVFQHGKVEIIANDQGNRTTPSYVAFTDTERLIGDAAKNQVALNPQ

NTVFDAKRLIGRKFGDPVVQSDMKHWPFQVINDGDKPKVQVSYKGETKAFYPEEISSMVLTKMK

EIAEAYLGYPVTNAVITVPAYFNDSQRQATKDAGVIAGLNVLRIINEPTAAAIAYGLDRTGKGE

RNVLIFDLGGGTFDVSILTIDDGIFEVKATAGDTHLGGEDFDNRLVNHFVEEFKRKHKKDISQN
```

-continued

KRAVRRLRTACERAKRTLSSSTQASLEIDSLFEGIDFYTSITRARFEELCSDLFRSTLEPVEKA

LRDAKLDKAQIHDLVLVGGSTRIPKVQKLLQDFFNGRDLNKSINPDEAVAYGAAVQAAILMGDK

SENVQDLLLLDVAPLSLGLETAGGVMTALIKRNSTI

PTKQTQIFTTYSDNQPGVLIQVYEGERAMTKDNNLLGRFELSGIPPAPRGVPQIEVTFDIDANG

ILNVTATDKSTGKANKITITNDKGRLSKEEIERMVQEAEKYKAEDEVQRERVSAKNALESYAFN

MKSAVEDEGLKGKISEADKKKVLDKCQEVISWLDANTLAEKDEFEHKRKELEQVCNPIISGLYQ

GAGGPGPGGFGAQGPKGGSGSGPTIEEVD mature HSPA1A cDNA

SEQ ID NO: 4

ATGGCCAAAGCCGCGGCGATCGGCATCGACCTGGGCACCACCTACTCCTGCGTGGGGGTGTTCC

AACACGGCAAGGTGGAGATCATCGCCAACGACCAGGGCAACCGCACCACCCCCAGCTACGTGGC

CTTCACGGACACCGAGCGGCTCATCGGGGATGCGGCCAAGAACCAGGTGGCGCTGAACCCGCAG

AACACCGTGTTTGACGCGAAGCGGCTGATCGGCCGCAAGTTCGGCGACCCGGTGGTGCAGTCGG

ACATGAAGCACTGGCCTTTCCAGGTGATCAACGACGGAGACAAGCCCAAGGTGCAGGTGAGCTA

CAAGGGGGAGACCAAGGCATTCTACCCCGAGGAGATCTCGTCCATGGTGCTGACCAAGATGAAG

GAGATCGCCGAGGCGTACCTGGGCTACCCGGTGACCAACGCGGTGATCACCGTGCCGGCCTACT

TCAACGACTCGCAGCGCCAGGCCACCAAGGATGCGGGTGTGATCGCGGGGCTCAACGTGCTGCG

GATCATCAACGAGCCCACGGCCGCCGCCATCGCCTACGGCCTGGACAGAACGGGCAAGGGGGAG

CGCAACGTGCTCATCTTTGACCTGGGCGGGGGCACCTTCGACGTGTCCATCCTGACGATCGACG

ACGGCATCTTCGAGGTGAAGGCCACGGCCGGGGACACCCACCTGGGTGGGGAGGACTTTGACAA

CAGGCTGGTGAACCACTTCGTGGAGGAGTTCAAGAGAAAACACAAGAAGGACATCAGCCAGAAC

AAGCGAGCCGTGAGGCGGCTGCGCACCGCCTGCGAGAGGGCCAAGAGGACCCTGTCGTCCAGCA

CCCAGGCCAGCCTGGAGATCGACTCCCTGTTTGAGGGCATCGACTTCTACACGTCCATCACCAG

GGCGAGGTTCGAGGAGCTGTGCTCCGACCTGTTCCGAAGCACCCTGGAGCCCGTGGAGAAGGCT

CTGCGCGACGCCAAGCTGGACAAGGCCCAGATTCACGACCTGGTCCTGGTCGGGGGCTCCACCC

GCATCCCCAAGGTGCAGAAGCTGCTGCAGGACTTCTTCAACGGGCGCGACCTGAACAAGAGCAT

CAACCCCGACGAGGCTGTGGCCTACGGGGCGGCGGTGCAGGCGGCCATCCTGATGGGGGACAAG

TCCGAGAACGTGCAGGACCTGCTGCTGCTGGACGTGGCTCCCCTGTCGCTGGGGCTGGAGACGG

CCGGAGGCGTGATGACTGCCCTGATCAAGCGCAACTCCACCATCCCCACCAAGCAGACGCAGAT

CTTCACCACCTACTCCGACAACCAACCCGGGGTGCTGATCCAGGTGTACGAGGGCGAGAGGGCC

ATGACGAAAGACAACAATCTGTTGGGGCGCTTCGAGCTGAGCGGCATCCCTCCGGCCCCCAGGG

GCGTGCCCCAGATCGAGGTGACCTTCGACATCGATGCCAACGGCATCCTGAACGTCACGGCCAC

GGACAAGAGCACCGGCAAGGCCAACAAGATCACCATCACCAACGACAAGGGCCGCCTGAGCAAG

GAGGAGATCGAGCGCATGGTGCAGGAGGCGGAGAAGTACAAAGCGGAGGACGAGGTGCAGCGCG

AGAGGGTGTCAGCCAAGAACGCCCTGGAGTCCTACGCCTTCAACATGAAGAGCGCCGTGGAGGA

TGAGGGGCTCAAGGGCAAGATCAGCGAGGCGGACAAGAAGAAGGTTCTGGACAAGTGTCAAGAG

GTCATCTCGTGGCTGGACGCCAACACCTTGGCCGAGAAGGACGAGTTTGAGCACAAGAGGAAGG

AGCTGGAGCAGGTGTGTAACCCCATCATCAGCGGACTGTACCAGGGTGCCGGTGGTCCCGGGCC

TGGGGGCTTCGGGGCTCAGGGTCCCAAGGGAGGGTCTGGGTCAGGCCCCACCATTGAGGAGGTG

GATTAG

-continued

NDP secretion signal protein

SEQ ID NO: 5

MRKHVLAASFSMLSLLVIMGDTDS

NDP secretion signal cDNA

SEQ ID NO: 6

AGAAAACATGTACTAGCTGCATCCTTTTCTATGCTCTCCCTGCTGGTGATAATGGGAGATACAG

ACAGT

Human Norrin secretion signal protein

SEQ ID NO: 7

MRKHVLAASFSMLSLLVIMGDTDS

Human Norrin secretion signal cDNA

SEQ ID NO: 8

ATGAGAAAACATGTACTAGCTGCATCCTTTTCTATGCTCTCCCTGCTGGTGATAATGGGAGATA

CAGACAGT

NDP Construct 1

SEQ ID NO: 9

CCTGCAGGCAGCTGCGCGCTCGCTCGCTCACTGAGGCCGCCCGGGCGTCGGGCGACCTTTGGTC

GCCCGGCCTCAGTGAGCGAGCGAGCGCGCAGAGAGGGAGTGGCCAACTCCATCACTAGGGGTTC

CTGCGGCCGCACGCGTGACATTGATTATTGACTAGTTATTAATAGTAATCAATTACGGGGTCAT

TAGTTCATAGCCCATATATGGAGTTCCGCGTTACATAACTTACGGTAAATGGCCCGCCTGGCTG

ACCGCCCAACGACCCCCGCCCATTGACGTCAATAATGACGTATGTTCCCATAGTAACGCCAATA

GGGACTTTCCATTGACGTCAATGGGTGGACTATTTACGGTAAACTGCCCACTTGGCAGTACATC

AAGTGTATCATATGCCAAGTACGCCCCCTATTGACGTCAATGACGGTAAATGGCCCGCCTGGCA

TTATGCCCAGTACATGACCTTATGGGACTTTCCTACTTGGCAGTACATCTACGTATTAGTCATC

GCTATTACCATGGGTCGAGGTGAGCCCCACGTTCTGCTTCACTCTCCCCATCTCCCCCCCCTCC

CCACCCCCAATTTTGTATTTATTTATTTTTTAATTATTTTGTGCAGCGATGGGGGCGGGGGGGG

GGGGGGCGCGCGCCAGGCGGGGCGGGGCGGGGCGAGGGGCGGGGCGGGGCGAGGCGGAGAGGTG

CGGCGGCAGCCAATCAGAGCGGCGCGCTCCGAAAGTTTCCTTTTATGGCGAGGCGGCGGCGGCG

GCGGCCCTATAAAAAGCGAAGCGCGCGGCGGGCGGGAGTCGCTGCGTTGCCTTCGCCCCGTGCC

CCGCTCCGCGCCGCCTCGCGCCGCCCGCCCCGGCTCTGACTGACCGCGTTACTCCCACAGGTGA

GCGGGCGGGACGGCCCTTCTCCTCCGGGCTGTAATTAGCGCTTGGTTTAATGACGGCTCGTTTC

TTTTCTGTGGCTGCGTGAAAGCCTTAAAGGGCTCCGGGAGGGCCCTTTGTGCGGGGGGGAGCGG

CTCGGGGGGTGCGTGCGTGTGTGTGTGCGTGGGGAGCGCCGCGTGCGGCCCGCGCTGCCCGGCG

GCTGTGAGCGCTGCGGGCGCGGCGCGGGGCTTTGTGCGCTCCGCGTGTGCGCGAGGGGAGCGCG

GCCGGGGGCGGTGCCCCGCGGTGCGGGGGGGCTGCGAGGGGAACAAAGGCTGCGTGCGGGGTGT

GTGCGTGGGGGGGTGAGCAGGGGGTGTGGGCGCGGCGGTCGGGCTGTAACCCCCCCCTGCACCC

CCCTCCCCGAGTTGCTGAGCACGGCCCGGCTTCGGGTGCGGGGCTCCGTGCGGGGCGTGGCGCG

GGGCTCGCCGTGCCGGGCGGGGGGTGGCGGCAGGTGGGGGTGCCGGGCGGGGCGGGGCCGCCTC

GGGCCGGGGAGGGCTCGGGGGAGGGGCGCGGCGGCCCCCGGAGCGCCGGCGGCTGTCGAGGCGC

GGCGAGCCGCAGCCATTGCCTTTTATGGTAATCGTGCGAGAGGGCGCAGGGACTTCCTTTGTCC

CAAATCTGTGCGGAGCCGAAATCTGGGAGGCGCCGCCGCACCCCCTCTAGCGGGCGCGGGGCGA

AGCGGTGCGGCGCCGGCAGGAAGGAAATGGGCGGGGAGGGCCTTCGTGCGTCGCCGCGCCGCCG

TCCCCTTCTCCCTCTCCAGCCTCGGGGCTGTCCGCGGGGGGACGGCTGCCTTCGGGGGGGACGG

GGCAGGGCGGGGTTCGGCTTCTGGCGTGTGACCGGCGGCTCTAGAGCCTCTGCTAACCATGTTC

ATGCCTTCTTCTTTTTCCTACAGCTCCTGGGCAACGTGCTGGTTATTGTGACCGGTGCCACCAT

GAGAAAACATGTACTAGCTGCATCCTTTTCTATGCTCTCCCTGCTGGTGATAATGGGAGATACA

-continued

GACAGTAAAACGGACAGCTCATTCATAATGGACTCGGACCCTCGACGCTGCATGAGGCACCACT
ATGTGGATTCTATCAGTCACCCATTGTACAAGTGTAGCTCAAAGATGGTGCTCCTGGCCAGGTG
CGAGGGGCACTGCAGCCAGGCGTCACGCTCCGAGCCTTTGGTGTCGTTCAGCACTGTCCTCAAG
CAACCCTTCCGTTCCTCCTGTCACTGCTGCCGGCCCCAGACTTCCAAGCTGAAGGCACTGCGGC
TGCGATGCTCAGGGGGCATGCGACTCACTGCCACCTACCGATACATCCTCTCCTGTCACTGCGA
GGAATGCAATTCCTAAGGCCCGCTGCTGTGTGTGGCTTCTGGATGGGACAACTGTAGAGGCAGT
TCGACCAGCCAGGGAAAGACTGGCAAGAAAAGAGTTAAGGCAAAAAAGGATGCAACAATTCTCC
GGGGACTCTGCATATTCTAGTAATAAAGACTCTACATGCTTGTTGACAGAGAGAGATACTCTGG
GAACTTCTTTGCAGTTCCCATCTCCTTTCTCTGGTACAATTTCTTTTGGTTCATTTTCAGATTC
AGGCATTTTCCCCCTTGGCTCTCAATGCTGTTTGGGTTTCCAACAATTCAGCATTAGTGGGAAA
AAGTGGGCCCTCATACACAAGCGTGTCAGGCTGTCAGTGTTTGGTGCACGCTGGGGAAGAATTT
ACTTTGGAAAGTAGAAAAGCCCAGCTTTTCCTGGGACATCTTCTGTTATTGTTGATGTTTTTTT
TTACCTTGTCATTTTGGTCTAAGGTTGCCATTGCTGCTAAAGGTTACCGATTTCAAAGTCCAGA
TACCAAGCATGTGGATATGTTTAGCTACGTTTACTCACAGCCAGCGAACTGACATTAAAATAAC
TAACAAACAGATTCTTTTATGTGATGCTGGAACTCTTGACAGCTATAATTATTATTCAGAAATG
ACTTTTTGAAAGTAAAAGCAGCATAAAGAATTTGTCACAGGAAGGCTGTCTCAGATAAATTATG
GTAAAATTTTGTAAGGGAGCAGACTTTTAAAGACTTGCACAAATACGGATCCTGCACTGACTCT
GGAAAAGGCATATATGTACTAGTGGCATGGAGAATGCACCATACTCATGCATGCAAATTAGACA
ACCAAGTATGAATCTATTTGTGGGTGTGCTATAGCTTTAGCCGTGTCACGGGCATCATTCTCTA
ATATCCACTTGTCCATGTGAAACATGTTGCCAAAATGGTGGCCTGGCTTGTCTTCTGAACGTTT
GGTTCAAATGTGTTTTGGTCCTGGAGGCTCAAATTTTGAGTTATTCCCACGTTTTGAAATAAAA
AGAGTATATTCAAAAGAGCTCCTGTGCCTTCTAGTTGCCAGCCATCTGTTGTTTGCCCCTCCCC
CGTGCCTTCCTTGACCCTGGAAGGTGCCACTCCCACTGTCCTTTCCTAATAAAATGAGGAAATT
GCATCGCATTGTCTGAGTAGGTGTCATTCTATTCTGGGGGGTGGGGTGGGGCAGGACAGCAAGG
GGGAGGATTGGGAAGACAATAGCAGGCATGCTGGGGATGCGGTGGGCTCTATGGCAATTCAGAC
TCCCACTAGAAGAAACAGAACTTGAAAAAAGGATAATTGTGGTGAACACCTCAACCCAGTGGTC
CAAAAACTGAAAAACTTTGACCCCGAGCACCCTCACACAGATAGACTACTGAAAGAAGGAGAAA
GGGGCACTTACTCAGTCTCCCTTATCAGATTGCCTTACGAGGAGTACTAGACTCCCTCAAGCAA
ATAGATCTCACTTACCACTTGCAAAGGTATACTACTTTCACTCTATTAGACCTATATATCTGAC
CAGGGTCCTATTCCAAGACAACTCTTCTACTCTTCCAGCAGACTCTTATAGAAAGAAAGATTCT
GGGGTCCAAGAAAGCAGTACTTTCTTACAAGGAGCCAAAAAAAATAACCTTTCTTTAGCACTTC
TAACCTTGGAGTGAACTGGTGATCAAAGAGAGGTTGGCTCCCTGGGGACAAGTGCCACAAATTC
AGTCAACTACAAGAAAGTTGAGAACACTGTTCTCCCGAAACCAAGCTTGAATTCAGCTGACGTG
CCTCGGACCGCTAGGAACCCCTAGTGATGGAGTTGGCCACTCCCTCTCTGCGCGCTCGCTCGCT
CACTGAGGCCGGGCGACCAAAGGTCGCCCGACGCCCGGGCTTTGCCCGGGCGGCCTCAGTGAGC
GAGCGAGCGCGCAGCTGCCTGCAGG

NDP Construct 2

SEQ ID NO: 10

CCTGCAGGCAGCTGCGCGCTCGCTCGCTCACTGAGGCCGCCCGGGCGTCGGGCGACCTTTGGTC
GCCCGGCCTCAGTGAGCGAGCGAGCGCGCAGAGAGGGAGTGGCCAACTCCATCACTAGGGGTTC
CTGCGGCCGCACGCGTGACATTGATTATTGACTAGTTATTAATAGTAATCAATTACGGGGTCAT

-continued

TAGTTCATAGCCCATATATGGAGTTCCGCGTTACATAACTTACGGTAAATGGCCCGCCTGGCTG

ACCGCCCAACGACCCCCGCCCATTGACGTCAATAATGACGTATGTTCCCATAGTAACGCCAATA

GGGACTTTCCATTGACGTCAATGGGTGGACTATTTACGGTAAACTGCCCACTTGGCAGTACATC

AAGTGTATCATATGCCAAGTACGCCCCCTATTGACGTCAATGACGGTAAATGGCCCGCCTGGCA

TTATGCCCAGTACATGACCTTATGGGACTTTCCTACTTGGCAGTACATCTACGTATTAGTCATC

GCTATTACCATGGGTCGAGGTGAGCCCCACGTTCTGCTTCACTCTCCCCATCTCCCCCCCCTCC

CCACCCCCAATTTTGTATTTATTTATTTTTTAATTATTTTGTGCAGCGATGGGGGCGGGGGGGG

GGGGGGCGCGCGCCAGGCGGGGCGGGGCGGGGCGAGGGGCGGGGCGGGGCGAGGCGGAGAGGTG

CGGCGGCAGCCAATCAGAGCGGCGCGCTCCGAAAGTTTCCTTTTATGGCGAGGCGGCGGCGGCG

GCGGCCCTATAAAAAGCGAAGCGCGCGGCGGGCGGGAGTCGCTGCGTTGCCTTCGCCCCGTGCC

CCGCTCCGCGCCGCCTCGCGCCGCCCGCCCCGGCTCTGACTGACCGCGTTACTCCCACAGGTGA

GCGGGCGGGACGGCCCTTCTCCTCCGGGCTGTAATTAGCGCTTGGTTTAATGACGGCTCGTTTC

TTTTCTGTGGCTGCGTGAAAGCCTTAAAGGGCTCCGGGAGGGCCCTTTGTGCGGGGGGGAGCGG

CTCGGGGGGTGCGTGCGTGTGTGTGTGCGTGGGGAGCGCCGCGTGCGGCCCGCGCTGCCCGGCG

GCTGTGAGCGCTGCGGGCGCGGCGCGGGGCTTTGTGCGCTCCGCGTGTGCGCGAGGGGAGCGCG

GCCGGGGGCGGTGCCCCGCGGTGCGGGGGGGCTGCGAGGGGAACAAAGGCTGCGTGCGGGGTGT

GTGCGTGGGGGGGTGAGCAGGGGGTGTGGGCGCGGCGGTCGGGCTGTAACCCCCCCCTGCACCC

CCCTCCCCGAGTTGCTGAGCACGGCCCGGCTTCGGGTGCGGGGCTCCGTGCGGGGCGTGGCGCG

GGGCTCGCCGTGCCGGGCGGGGGGTGGCGGCAGGTGGGGGTGCCGGGCGGGGCGGGGCCGCCTC

GGGCCGGGGAGGGCTCGGGGGAGGGGCGCGGCGGCCCCCGGAGCGCCGGCGGCTGTCGAGGCGC

GGCGAGCCGCAGCCATTGCCTTTTATGGTAATCGTGCGAGAGGGCGCAGGGACTTCCTTTGTCC

CAAATCTGTGCGGAGCCGAAATCTGGGAGGCGCCGCCGCACCCCCTCTAGCGGGCGCGGGGCGA

AGCGGTGCGGCGCCGGCAGGAAGGAAATGGGCGGGGAGGGCCTTCGTGCGTCGCCGCGCCGCCG

TCCCCTTCTCCCTCTCCAGCCTCGGGGCTGTCCGCGGGGGGACGGCTGCCTTCGGGGGGGACGG

GGCAGGGCGGGGTTCGGCTTCTGGCGTGTGACCGGCGGCTCTAGAGCCTCTGCTAACCATGTTC

ATGCCTTCTTCTTTTTCCTACAGCTCCTGGGCAACGTGCTGGTTATTGTGACCGGTGCCACCAT

GAGAAAACATGTACTAGCTGCATCCTTTTCTATGCTCTCCCTGCTGGTGATAATGGGAGATACA

GACAGTAAAACGGACAGCTCATTCATAATGGACTCGGACCCTCGACGCTGCATGAGGCACCACT

ATGTGGATTCTATCAGTCACCCATTGTACAAGTGTAGCTCAAAGATGGTGCTCCTGGCCAGGTG

CGAGGGGCACTGCAGCCAGGCGTCACGCTCCGAGCCTTTGGTGTCGTTCAGCACTGTCCTCAAG

CAACCCTTCCGTTCCTCCTGTCACTGCTGCCGGCCCCAGACTTCCAAGCTGAAGGCACTGCGGC

TGCGATGCTCAGGGGGCATGCGACTCACTGCCACCTACCGATACATCCTCTCCTGTCACTGCGA

GGAATGCAATTCCTAAGAGCTCCTGTGCCTTCTAGTTGCCAGCCATCTGTTGTTTGCCCCTCCC

CCGTGCCTTCCTTGACCCTGGAAGGTGCCACTCCCACTGTCCTTTCCTAATAAAATGAGGAAAT

TGCATCGCATTGTCTGAGTAGGTGTCATTCTATTCTGGGGGGTGGGGTGGGGCAGGACAGCAAG

GGGGAGGATTGGGAAGACAATAGCAGGCATGCTGGGGATGCGGTGGGCTCTATGGGTTGACTAA

AGATTGAACCTTATTCAAAGTTAGACTCTCTTTGTTAAAGACAAACAAAACTTCCAATAATTCA

GCAACTAATAGAAAGACTCAACTTGTGAGCCACTACTTATTAATTGAGAATAGTCACTGAGTCT

GGCAAAATATATTAGAAAGTGAGACTGAGTTTAAAAAAGTGAGACCTTTGATTCTGAACAGTGA

ACTTTGAGACTGAAAAACTACAGCTTTGAGGCTAAATACTTGATCAAATAAAACTAGTTAGTGA

AAAAACTGAGTGAAAGTCCAACAGAAAAAAGAGGGCCCACTTCCACGAGTGAGACAAAATCCAG

-continued

ATTGATCGTTCTTTAAGTGACTATTCTTGCCAGAATCAGCAAGGTGGATACAAAGGACTCTGAG

AAAGAACTCTCTGAACTCTGGGCAAGGCCCCAGTCCAAAGCAATTAGTATCCTTAGGACCAGAA

AAATCTGTGGAAGGTCAGAATTTCTTGTCTGAGAAAAACAAAGCAATTCAGACTCCCACTAGAA

GAAACAGAACTTGAAAAAAGGATAATTGTGGTGAACACCTCAACCCAGTGGTCCAAAAACTGAA

AAACTTTGACCCCGAGCACCCTCACACAGATAGACTACTGAAAGAAGGAGAAAGGGGCACTTAC

TCAGTCTCCCTTATCAGATTGCCTTACGAGGAGTAGTAGACTCCCTCAAGCAAATAGATCTCAC

TTACCACTTGCAAAGGTATACTACTTTCACTCTATTAGACCTATATATCTGACCAGGGTCCTAT

TCCAAGACAACTCTTCTAGTCTTCCAGCAGACTCTTATAGAAAGAAAGATTCTGGGGTCCAAGA

AAGCAGTACTTTCTTACAAGGAGCCAAAAAAAATAACCTTTCTTTAGCACTTCTAACCTTGGAG

TGAACTGGTGATCAAAGAGAGGTTGGCTCCCTGGGGACAAGTGCCACAAATTCAGTCAACTACA

AGAAAGTTGAGAACACTGTTCTCCCGAAACCAAGCTTGAATTCAGCTGACGTGCCTCGGACCGC

TAGGAACCCCTAGTGATGGAGTTGGCCACTCCCTCTCTGCGCGCTCGCTCGCTCACTGAGGCCG

GGCGACCAAAGGTCGCCCGACGCCCGGGCTTTGCCCGGGCGGCCTCAGTGAGCGAGCGAGCGCG

CAGCTGCCTGCAGG

NDP Construct 3

SEQ ID NO: 11

CCTGCAGGCAGCTGCGCGCTCGCTCGCTCACTGAGGCCGCCCGGGCGTCGGGCGACCTTTGGTC

GCCCGGCCTCAGTGAGCGAGCGAGCGCGCAGAGAGGGAGTGGCCAACTCCATCACTAGGGGTTC

CTGCGGCCGCACGCGTGACATTGATTATTGACTAGTTATTAATAGTAATCAATTACGGGGTCAT

TAGTTCATAGCCCATATATGGAGTTCCGCGTTACATAACTTACGGTAAATGGCCCGCCTGGCTG

ACCGCCCAACGACCCCCGCCCATTGACGTCAATAATGACGTATGTTCCCATAGTAACGCCAATA

GGGACTTTCCATTGACGTCAATGGGTGGACTATTTACGGTAAACTGCCCACTTGGCAGTACATC

AAGTGTATCATATGCCAAGTACGCCCCCTATTGACGTCAATGACGGTAAATGGCCCGCCTGGCA

TTATGCCCAGTACATGACCTTATGGGACTTTCCTACTTGGCAGTACATCTACGTATTAGTCATC

GCTATTACCATGGGTCGAGGTGAGCCCCACGTTCTGCTTCACTCTCCCCATCTCCCCCCCCTCC

CCACCCCCAATTTTGTATTTATTTATTTTTTAATTATTTTGTGCAGCGATGGGGGCGGGGGGGG

GGGGGGCGCGCGCCAGGCGGGGCGGGGCGGGGCGAGGGGCGGGGCGGGGCGAGGCGGAGAGGTG

CGGCGGCAGCCAATCAGAGCGGCGCGCTCCGAAAGTTTCCTTTTATGGCGAGGCGGCGGCGGCG

GCGGCCCTATAAAAAGCGAAGCGCGCGGCGGGCGGGAGTCGCTGCGTTGCCTTCGCCCCGTGCC

CCGCTCCGCGCCGCCTCGCGCCGCCCGCCCCGGCTCTGACTGACCGCGTTACTCCCACAGGTGA

GCGGGCGGGACGGCCCTTCTCCTCCGGGCTGTAATTAGCGCTTGGTTTAATGACGGCTCGTTTC

TTTTCTGTGGCTGCGTGAAAGCCTTAAAGGGCTCCGGGAGGGCCCTTTGTGCGGGGGGGAGCGG

CTCGGGGGGTGCGTGCGTGTGTGTGTGCGTGGGGAGCGCCGCGTGCGGCCCGCGCTGCCCGGCG

GCTGTGAGCGCTGCGGGCGCGGCGCGGGGCTTTGTGCGCTCCGCGTGTGCGCGAGGGGAGCGCG

GCCGGGGGCGGTGCCCCGCGGTGCGGGGGGGCTGCGAGGGGAACAAAGGCTGCGTGCGGGGTGT

GTGCGTGGGGGGGTGAGCAGGGGGTGTGGGCGCGGCGGTCGGGCTGTAACCCCCCCCTGCACCC

CCCTCCCCGAGTTGCTGAGCACGGCCCGGCTTCGGGTGCGGGGCTCCGTGCGGGGCGTGGCGCG

GGGCTCGCCGTGCCGGGCGGGGGGTGGCGGCAGGTGGGGGTGCCGGGCGGGGCGGGGCCGCCTC

GGGCCGGGGAGGGCTCGGGGGAGGGGCGCGGCGGCCCCCGGAGCGCCGGCGGCTGTCGAGGCGC

GGCGAGCCGCAGCCATTGCCTTTTATGGTAATCGTGCGAGAGGGCGCAGGGACTTCCTTTGTCC

CAAATCTGTGCGGAGCCGAAATCTGGGAGGCGCCGCCGCACCCCCTCTAGCGGGCGCGGGGCGA

-continued
AGCGGTGCGGCGCCGGCAGGAAGGAAATGGGCGGGGAGGGCCTTCGTGCGTCGCCGCGCCGCCG

TCCCCTTCTCCCTCTCCAGCCTCGGGGCTGTCCGCGGGGGGACGGCTGCCTTCGGGGGGGACGG

GGCAGGGCGGGGTTCGGCTTCTGGCGTGTGACCGGCGGCTCTAGAGCCTCTGCTAACCATGTTC

ATGCCTTCTTCTTTTTCCTACAGCTCCTGGGCAACGTGCTGGTTATTGTGACCGGTGCCACCAT

GAGAAAACATGTACTAGCTGCATCCTTTTCTATGCTCTCCCTGCTGGTGATAATGGGAGATACA

GACAGTAAAACGGACAGCTCATTCATAATGGACTCGGACCCTCGACGCTGCATGAGGCACCACT

ATGTGGATTCTATCAGTCACCCATTGTACAAGTGTAGCTCAAAGATGGTGCTCCTGGCCAGGTG

CGAGGGGCACTGCAGCCAGGCGTCACGCTCCGAGCCTTTGGTGTCGTTCAGCACTGTCCTCAAG

CAACCCTTCCGTTCCTCCTGTCACTGCTGCCGGCCCCAGACTTCCAAGCTGAAGGCACTGCGGC

TGCGATGCTCAGGGGGCATGCGACTCACTGCCACCTACCGATACATCCTCTCCTGTCACTGCGA

GGAATGCAATTCCGGCTCCGGAGAGGGCAGAGGAAGTCTGCTAACATGCGGTGACGTCGAGGAG

AATCCTGGCCCAATGGAGAGCGACGAGAGCGGCCTGCCCGCCATGGAGATCGAGTGCCGCATCA

CCGGCACCCTGAACGGCGTGGAGTTCGAGCTGGTGGGCGGCGGAGAGGGCACCCCCGAGCAGGG

CCGCATGACCAACAAGATGAAGAGCACCAAAGGCGCCCTGACCTTCAGCCCCTACCTGCTGAGC

CACGTGATGGGCTACGGCTTCTACCACTTCGGCACCTACCCCAGCGGCTACGAGAACCCCTTCC

TGCACGCCATCAACAACGGCGGCTACACCAACACCCGCATCGAGAAGTACGAGGACGGCGGCGT

GCTGCACGTGAGCTTCAGCTACCGCTACGAGGCCGGCCGCGTGATCGGCGACTTCAAGGTGATG

GGCACCGGCTTCCCCGAGGACAGCGTGATCTTCACCGACAAGATCATCCGCAGCAACGCCACCG

TGGAGCACCTGCACCCCATGGGCGATAACGATCTGGATGGCAGCTTCACCCGCACCTTCAGCCT

GCGCGACGGCGGCTACTACAGCTCCGTGGTGGACAGCCACATGCACTTCAAGAGCGCCATCCAC

CCCAGCATCCTGCAGAACGGGGGCCCCATGTTCGCCTTCCGCCGCGTGGAGGAGGATCACAGCA

ACACCGAGCTGGGCATCGTGGAGTACCAGCACGCCTTCAAGACCCCGGATGCAGATGCCGGTGA

AGAATAAGGCCCGCTGCTGTGTGTGGCTTCTGGATGGGACAACTGTAGAGGCAGTTCGACCAGC

CAGGGAAAGACTGGCAAGAAAAGAGTTAAGGCAAAAAAGGATGCAACAATTCTCCCGGGACTCT

GCATATTCTAGTAATAAAGACTCTACATGCTTGTTGACAGAGAGAGATACTCTGGGAACTTCTT

TGCAGTTCCCATCTCCTTTCTCTGGTACAATTTCTTTTGGTTCATTTTCAGATTCAGGCATTTT

CCCCCTTGGCTCTCAATGCTGTTTGGGTTTCCAACAATTCAGCATTAGTGGGAAAAAGTGGGCC

CTCATACACAAGCGTGTCAGGCTGTCAGTGTTTGGTGCACGCTGGGGAAGAATTTACTTTGGAA

AGTAGAAAAGCCCAGCTTTTCCTGGGACATCTTCTGTTATTGTTGATGTTTTTTTTTACCTTGT

CATTTTGGTCTAAGGTTGCCATTGCTGCTAAAGGTTACCGATTTCAAAGTCCAGATACCAAGCA

TGTGGATATGTTTAGCTACGTTTACTCACAGCCAGCGAACTGACATTAAAATAACTAACAAACA

GATTCTTTTATGTGATGCTGGAACTCTTGACAGCTATAATTATTATTCAGAAATGACTTTTTGA

AAGTAAAAGCAGCATAAAGAATTTGTCACAGGAAGGCTGTCTCAGATAAATTATGGTAAAATTT

TGTAAGGGAGCAGACTTTTAAAGACTTGCACAAATACGGATCCTGCACTGACTCTGGAAAAGGC

ATATATGTACTAGTGGCATGGAGAATGCACCATACTCATGCATGCAAATTAGACAACCAAGTAT

GAATCTATTTGTGGGTGTGCTATAGCTTTAGCCGTGTCACGGGCATCATTCTCTAATATCCACT

TGTCCATGTGAAACATGTTGCCAAAATGGTGGCCTGGCTTGTCTTCTGAACGTTTGGTTCAAAT

GTGTTTTGGTCCTGGAGGCTCAAATTTTGAGTTATTCCCACGTTTTGAAATAAAAAGAGTATAT

TCAAAAGAGCTCCTGTGCCTTCTAGTTGCCAGCCATCTGTTGTTTGCCCCTCCCCCGTGCCTTC

CTTGACCCTGGAAGGTGCCACTCCCACTGTCCTTTCCTAATAAAATGAGGAAATTGCATCGCAT

TGTCTGAGTAGGTGTCATTCTATTCTGGGGGGTGGGGTGGGGCAGGACAGCAAGGGGGAGGATT

-continued

GGGAAGACAATAGCAGGCATGCTGGGGATGCGGTGGGCTCTATGGAAGCTTGAATTCAGCTGAC

GTGCCTCGGACCGCTAGGAACCCCTAGTGATGGAGTTGGCCACTCCCTCTCTGCGCGCTCGCTC

GCTCACTGAGGCCGGGCGACCAAAGGTCGCCCGACGCCCGGGCTTTGCCCGGGCGGCCTCAGTG

AGCGAGCGAGCGCGCAGCTGCCTGCAGG

NDP Construct 4

SEQ ID NO: 12

CCTGCAGGCAGCTGCGCGCTCGCTCGCTCACTGAGGCCGCCCGGGCGTCGGGCGACCTTTGGTC

GCCCGGCCTCAGTGAGCGAGCGAGCGCGCAGAGAGGGAGTGGCCAACTCCATCACTAGGGGTTC

CTGCGGCCGCACGCGTGACATTGATTATTGACTAGTTATTAATAGTAATCAATTACGGGGTCAT

TAGTTCATAGCCCATATATGGAGTTCCGCGTTACATAACTTACGGTAAATGGCCCGCCTGGCTG

ACCGCCCAACGACCCCCGCCCATTGACGTCAATAATGACGTATGTTCCCATAGTAACGCCAATA

GGGACTTTCCATTGACGTCAATGGGTGGACTATTTACGGTAAACTGCCCACTTGGCAGTACATC

AAGTGTATCATATGCCAAGTACGCCCCCTATTGACGTCAATGACGGTAAATGGCCCGCCTGGCA

TTATGCCCAGTACATGACCTTATGGGACTTTCCTACTTGGCAGTACATCTACGTATTAGTCATC

GCTATTACCATGGGTCGAGGTGAGCCCCACGTTCTGCTTCACTCTCCCCATCTCCCCCCCCTCC

CCACCCCCAATTTTGTATTTATTTATTTTTTAATTATTTTGTGCAGCGATGGGGGCGGGGGGGG

GGGGGGCGCGCGCCAGGCGGGGCGGGGCGGGGCGAGGGGCGGGGCGGGGCGAGGCGGAGAGGTG

CGGCGGCAGCCAATCAGAGCGGCGCGCTCCGAAAGTTTCCTTTTATGGCGAGGCGGCGGCGGCG

GCGGCCCTATAAAAAGCGAAGCGCGCGGCGGGCGGGAGTCGCTGCGTTGCCTTCGCCCCGTGCC

CCGCTCCGCGCCGCCTCGCGCCGCCCGCCCCGGCTCTGACTGACCGCGTTACTCCCACAGGTGA

GCGGGCGGGACGGCCCTTCTCCTCCGGGCTGTAATTAGCGCTTGGTTTAATGACGGCTCGTTTC

TTTTCTGTGGCTGCGTGAAAGCCTTAAAGGGCTCCGGGAGGGCCCTTTGTGCGGGGGGGAGCGG

CTCGGGGGGTGCGTGCGTGTGTGTGTGCGTGGGGAGCGCCGCGTGCGGCCCGCGCTGCCCGGCG

GCTGTGAGCGCTGCGGGCGCGGCGCGGGGCTTTGTGCGCTCCGCGTGTGCGCGAGGGGAGCGCG

GCCGGGGGCGGTGCCCCGCGGTGCGGGGGGGCTGCGAGGGGAACAAAGGCTGCGTGCGGGGTGT

GTGCGTGGGGGGGTGAGCAGGGGGTGTGGGCGCGGCGGTCGGGCTGTAACCCCCCCCTGCACCC

CCCTCCCCGAGTTGCTGAGCACGGCCCGGCTTCGGGTGCGGGGCTCCGTGCGGGGCGTGGCGCG

GGGCTCGCCGTGCCGGGCGGGGGGTGGCGGCAGGTGGGGGTGCCGGGCGGGGCGGGGCCGCCTC

GGGCCGGGGAGGGCTCGGGGGAGGGGCGCGGCGGCCCCCGGAGCGCCGGCGGCTGTCGAGGCGC

GGCGAGCCGCAGCCATTGCCTTTTATGGTAATCGTGCGAGAGGGCGCAGGGACTTCCTTTGTCC

CAAATCTGTGCGGAGCCGAAATCTGGGAGGCGCCGCCGCACCCCCTCTAGCGGGCGCGGGGCGA

AGCGGTGCGGCGCCGGCAGGAAGGAAATGGGCGGGGAGGGCCTTCGTGCGTCGCCGCGCCGCCG

TCCCCTTCTCCCTCTCCAGCCTCGGGGCTGTCCGCGGGGGGACGGCTGCCTTCGGGGGGGACGG

GGCAGGGCGGGGTTCGGCTTCTGGCGTGTGACCGGCGGCTCTAGAGCCTCTGCTAACCATGTTC

ATGCCTTCTTCTTTTTCCTACAGCTCCTGGGCAACGTGCTGGTTATTGTGACCGGTGCCACCAT

GAGAAAACATGTACTAGCTGCATCCTTTTCTATGCTCTCCCTGCTGGTGATAATGGGAGATACA

GACAGTAAAACGGACAGCTCATTCATAATGGACTCGGACCCTCGACGCTGCATGAGGCACCACT

ATGTGGATTCTATCAGTCACCCATTGTACAAGTGTAGCTCAAAGATGGTGCTCCTGGCCAGGTG

CGAGGGGCACTGCAGCCAGGCGTCACGCTCCGAGCCTTTGGTGTCGTTCAGCACTGTCCTCAAG

CAACCCTTCCGTTCCTCCTGTCACTGCTGCCGGCCCCAGACTTCCAAGCTGAAGGCACTGCGGC

TGCGATGCTCAGGGGGCATGCGACTCACTGCCACCTACCGATACATCCTCTCCTGTCACTGCGA

-continued

GGAATGCAATTCCGGCTCCGGAGAGGGCAGAGGAAGTCTGCTAACATGCGGTGACGTCGAGGAG

AATCCTGGCCCAATGGTGAGCAAGGGCGAGGAGCTGTTCACCGGGGTGGTGCCCATCCTGGTCG

AGCTGGACGGCGACGTAAACGGCCACAAGTTCAGCGTGTCCGGCGAGGGCGAGGGCGATGCCAC

CTACGGCAAGCTGACCCTGAAGTTCATCTGCACCACCGGCAAGCTGCCCGTGCCCTGGCCCACC

CTCGTGACCACCCTGACCTACGGCGTGCAGTGCTTCAGCCGCTACCCCGACCACATGAAGCAGC

ACGACTTCTTCAAGTCCGCCATGCCCGAAGGCTACGTCCAGGAGCGCACCATCTTCTTCAAGGA

CGACGGCAACTACAAGACCCGCGCCGAGGTGAAGTTCGAGGGCGACACCCTGGTGAACCGCATC

GAGCTGAAGGGCATCGACTTCAAGGAGGACGGCAACATCCTGGGGCACAAGCTGGAGTACAACT

ACAACAGCCACAACGTCTATATCATGGCCGACAAGCAGAAGAACGGCATCAAGGTGAACTTCAA

GATCCGCCACAACATCGAGGACGGCAGCGTGCAGCTCGCCGACCACTACCAGCAGAACACCCCC

ATCGGCGACGGCCCCGTGCTGCTGCCCGACAACCACTACCTGAGCACCCAGTCCGCCCTGAGCA

AAGACCCCAACGAGAAGCGCGATCACATGGTCCTGCTGGAGTTCGTGACCGCCGCCGGGATCAC

TCTCGGCATGGACGAGCTGTACAAGTAATAAGGCCCGCTGCTGTGTGTGGCTTCTGGATGGGAC

AACTGTAGAGGCAGTTCGACCAGCCAGGGAAAGACTGGCAAGAAAAAGAGTTAAGGCAAAAAAGG

ATGCAACAATTCTCCCGGGACTCTGCATATTCTAGTAATAAAGACTCTACATGCTTGTTGACAG

AGAGAGATACTCTGGGAACTTCTTTGCAGTTCCCATCTCCTTTCTCTGGTACAATTTCTTTTGG

TTCATTTTCAGATTCAGGCATTTTCCCCCTTGGCTCTCAATGCTGTTTGGGTTTCCAACAATTC

AGCATTAGTGGGAAAAAGTGGGCCCTCATACACAAGCGTGTCAGGCTGTCAGTGTTTGGTGCAC

GCTGGGGAAGAATTTACTTTGGAAAGTAGAAAAGCCCAGCTTTTCCTGGGACATCTTCTGTTAT

TGTTGATGTTTTTTTTACCTTGTCATTTTGGTCTAAGGTTGCCATTGCTGCTAAAGGTTACCG

ATTTCAAAGTCCAGATACCAAGCATGTGGATATGTTTAGCTACGTTTACTCACAGCCAGCGAAC

TGACATTAAAATAACTAACAAACAGATTCTTTTATGTGATGCTGGAACTCTTGACAGCTATAAT

TATTATTCAGAAATGAGTTTTTGAAAGTAAAAGCAGCATAAAGAATTTGTCACAGGAAGGCTGT

CTCAGATAAATTATGGTAAAATTTTGTAAGGGAGCAGACTTTTAAAGACTTGCACAAATACGGA

TCCTGCACTGACTCTGGAAAAGGCATATATGTACTAGTGGCATGGAGAATGCACCATACTCATG

CATGCAAATTAGACAACCAAGTATGAATCTATTTGTGGGTGTGCTATAGCTTTAGCCGTGTCAC

GGGCATCATTCTCTAATATCCACTTGTCCATGTGAAACATGTTGCCAAAATGGTGGCCTGGCTT

GTCTTCTGAACGTTTGGTTCAAATGTGTTTTGGTCCTGGAGGCTCAAATTTTGAGTTATTCCCA

CGTTTTGAAATAAAAAGAGTATATTCAAAAGAGCTCCTGTGCCTTCTAGTTGCCAGCCATCTGT

TGTTTGCCCCTCCCCCGTGCCTTCCTTGACCCTGGAAGGTGCCACTCCCACTGTCCTTTCCTAA

TAAAATGAGGAAATTGCATCGCATTGTCTGAGTAGGTGTCATTCTATTCTGGGGGGTGGGGTGG

GGCAGGACAGCAAGGGGGAGGATTGGGAAGACAATAGCAGGCATGCTGGGGATGCGGTGGGCTC

TATGGAAGCTTGAATTCAGCTGACGTGCCTCGGACCGCTAGGAACCCCTAGTGATGGAGTTGGC

CACTCCCTCTCTGCGCGCTCGCTCGCTCACTGAGGCCGGGCGACCAAAGGTCGCCCGACGCCCG

GGCTTTGCCCGGGCGGCCTCAGTGAGCGAGCGAGCGCGCAGCTGCCTGCAGG

NDP Construct 5

SEQ ID NO: 13

CCTGCAGGCAGCTGCGCGCTCGCTCGCTCACTGAGGCCGCCCGGGCGTCGGGCGACCTTTGGTC

GCCCGGCCTCAGTGAGCGAGCGAGCGCGCAGAGAGGGAGTGGCCAACTCCATCACTAGGGGTTC

CTGCGGCCGCACGCGTGACATTGATTATTGACTAGTTATTAATAGTAATCAATTACGGGGTCAT

TAGTTCATAGCCCATATATGGAGTTCCGCGTTACATAACTTACGGTAAATGGCCCGCCTGGCTG

ACCGCCCAACGACCCCCGCCCATTGACGTCAATAATGACGTATGTTCCCATAGTAACGCCAATA

-continued

GGGACTTTCCATTGACGTCAATGGGTGGACTATTTACGGTAAACTGCCCACTTGGCAGTACATC

AAGTGTATCATATGCCAAGTACGCCCCCTATTGACGTCAATGACGGTAAATGGCCCGCCTGGCA

TTATGCCCAGTACATGACCTTATGGGACTTTCCTACTTGGCAGTACATCTACGTATTAGTCATC

GCTATTACCATGGGTCGAGGTGAGCCCCACGTTCTGCTTCACTCTCCCCATCTCCCCCCCCTCC

CCACCCCCAATTTTGTATTTATTTATTTTTTAATTATTTTGTGCAGCGATGGGGGCGGGGGGGG

GGGGGGCGCGCGCCAGGCGGGGCGGGGCGGGGCGAGGGGCGGGGCGGGGCGAGGCGGAGAGGTG

CGGCGGCAGCCAATCAGAGCGGCGCGCTCCGAAAGTTTCCTTTTATGGCGAGGCGGCGGCGGCG

GCGGCCCTATAAAAAGCGAAGCGCGCGGCGGGCGGGAGTCGCTGCGTTGCCTTCGCCCCGTGCC

CCGCTCCGCGCCGCCTCGCGCCGCCCGCCCCGGCTCTGACTGACCGCGTTACTCCCACAGGTGA

GCGGGCGGGACGGCCCTTCTCCTCCGGGCTGTAATTAGCGCTTGGTTTAATGACGGCTCGTTTC

TTTTCTGTGGCTGCGTGAAAGCCTTAAAGGGCTCCGGGAGGGCCCTTTGTGCGGGGGGGAGCGG

CTCGGGGGGTGCGTGCGTGTGTGTGTGCGTGGGGAGCGCCGCGTGCGGCCCGCGCTGCCCGGCG

GCTGTGAGCGCTGCGGGCGCGGCGCGGGGCTTTGTGCGCTCCGCGTGTGCGCGAGGGGAGCGCG

GCCGGGGGCGGTGCCCCGCGGTGCGGGGGGGCTGCGAGGGGAACAAAGGCTGCGTGCGGGGTGT

GTGCGTGGGGGGGTGAGCAGGGGGTGTGGGCGCGGCGGTCGGGCTGTAACCCCCCCCTGCACCC

CCCTCCCCGAGTTGCTGAGCACGGCCCGGCTTCGGGTGCGGGGCTCCGTGCGGGGCGTGGCGCG

GGGCTCGCCGTGCCGGGCGGGGGGTGGCGGCAGGTGGGGGTGCCGGGCGGGGCGGGGCCGCCTC

GGGCCGGGGAGGGCTCGGGGGAGGGGCGCGGCGGCCCCCGGAGCGCCGGCGGCTGTCGAGGCGC

GGCGAGCCGCAGCCATTGCCTTTTATGGTAATCGTGCGAGAGGGCGCAGGGACTTCCTTTGTCC

CAAATCTGTGCGGAGCCGAAATCTGGGAGGCGCCGCCGCACCCCCTCTAGCGGGCGCGGGGCGA

AGCGGTGCGGCGCCGGCAGGAAGGAAATGGGCGGGGAGGGCCTTCGTGCGTCGCCGCGCCGCCG

TCCCCTTCTCCCTCTCCAGCCTCGGGGCTGTCCGCGGGGGGACGGCTGCCTTCGGGGGGGACGG

GGCAGGGCGGGGTTCGGCTTCTGGCGTGTGACCGGCGGCTCTAGAGCCTCTGCTAACCATGTTC

ATGCCTTCTTCTTTTTCCTACAGCTCCTGGGCAACGTGCTGGTTATTGTGACCGGTAAGATGCT

CCGTGGAAGGGAGCCGAGCGGTGGGCAGAGGCTGAGTCCCCGATAACGAGCGCCTCACATTTCC

GTGGCATTCCCATTTGCTAGTGCGCTGCTGCGGCCGCACGCCTGATTGATATATGACTGCAATG

GCACTTTTCCATTTGACATTCTCTCTCTCTCTCTCCCTCTCTCTCTCTCCCTCTCTCTCTCCCT

CTCTCTCTCTCCCTGTGTCGCTTAAACAACAGTCCTAACTTTTGTGTGTTGCAAATATAAAAGG

CAAGCCATGTGACAGAGGGACAGAAGAACAAAAGCATTTGGAAGTAACAGGACCTCTTTCTAGC

TCTCAGAAAAGTCTGAGAAGAAAGGAGCCCTGCGTTCCCCTAAGCTGTGCAGCAGATACTGTGA

TGATGGATTGCAAGTGCAAAGAGTAAGACAAAACTCCAGCACATAAAGGACAATGACAACCAGA

AAGCTTCAGCCCGATCCTGCCCTTTCCTTGAACGGGACTGGATCCTAGGAGGTGAAGCCATTTC

CAATTTTTTGTCCTCTGCCTCCCTCTGCTGTTCTTCTAGAGAAGTTTTTCCTTACAACAGCCAC

CATGAGAAAACATGTACTAGCTGCATCCTTTTCTATGCTCTCCCTGCTGGTGATAATGGGAGAT

ACAGACAGTAAAACGGACAGCTCATTCATAATGGACTCGGACCCTCGACGCTGCATGAGGCACC

ACTATGTGGATTCTATCAGTCACCCATTGTACAAGTGTAGCTCAAAGATGGTGCTCCTGGCCAG

GTGCGAGGGGCACTGCAGCCAGGCGTCACGCTCCGAGCCTTTGGTGTCGTTCAGCACTGTCCTC

AAGCAACCCTTCCGTTCCTCCTGTCACTGCTGCCGGCCCCAGACTTCCAAGCTGAAGGCACTGC

GGCTGCGATGCTCAGGGGGCATGCGACTCACTGCCACCTACCGATACATCCTCTCCTGTCACTG

CGAGGAATGCAATTCCTAAGGCCCGCTGCTGTGTGTGGCTTCTGGATGGGACAACTGTAGAGGC

-continued

AGTTCGACCAGCCAGGGAAAGACTGGCAAGAAAAGAGTTAAGGCAAAAAAGGATGCAACAATTC

TCCCGGGACTCTGCATATTCTAGTAATAAAGACTCTAGATGCTTGTTGACAGAGAGAGATACTC

TGGGAACTTCTTTGCAGTTCCCATCTCCTTTCTCTGGTACAATTTCTTTTGGTTCATTTTCAGA

TTCAGGCATTTTCCCCCTTGGCTCTCAATGCTGTTTGGGTTTCCAACAATTCAGCATTAGTGGG

AAAAAGTGGGCCCTCATACACAAGCGTGTCAGGCTGTCAGTGTTTGGTGCACGCTGGGGAAGAA

TTTACTTTGGAAAGTAGAAAAGCCCAGCTTTTCCTGGGACATCTTCTGTTATTGTTGATGTTTT

TTTTTACCTTGTCATTTTGGTCTAAGGTTGCCATTGCTGCTAAAGGTTACCGATTTCAAAGTCC

AGATACCAAGCATGTGGATATGTTTAGCTACGTTTACTCACAGCCAGCGAACTGACATTAAAAT

AACTAACAAACAGATTCTTTTATGTGATGCTGGAACTCTTGACAGCTATAATTATTATTCAGAA

ATGACTTTTTGAAAGTAAAAGCAGCATAAAGAATTTGTCACAGGAAGGCTGTCTCAGATAAATT

ATGGTAAAATTTTGTAAGGGAGCAGACTTTTAAAGACTTGCACAAATACGGATCCTGCACTGAC

TCTGGAAAAGGCATATATGTACTAGTGGCATGGAGAATGCACCATACTCATGCATGCAAATTAG

ACAACCAAGTATGAATCTATTTGTGGGTGTGCTATAGCTTTAGCCGTGTCACGGGCATCATTCT

CTAATATCCACTTGTCCATGTGAAACATGTTGCCAAAATGGTGGCCTGGCTTGTCTTCTGAACG

TTTGGTTCAAATGTGTTTTGGTCCTGGAGGCTCAAATTTTGAGTTATTCCCACGTTTTGAAATA

AAAAGAGTATATTCAAAAGAGCTCCTGTGCCTTCTAGTTGCCAGCCATCTGTTGTTTGCCCCTC

CCCCGTGCCTTCCTTGACCCTGGAAGGTGCCACTCCCACTGTCCTTTCCTAATAAAATGAGGAA

ATTGCATCGCATTGTCTGAGTAGGTGTCATTCTATTCTGGGGGGTGGGGTGGGGCAGGACAGCA

AGGGGGAGGATTGGGAAGACAATAGCAGGCATGCTGGGGATGCGGTGGGCTCTATGGCAATTCA

GACTCCCACTAGAAGAAACAGAACTTGAAAAAAGGATAATTGTGGTGAACACCTCAACCCAGTG

GTCCAAAAACTGAAAAACTTTGACCCCGAGCACCCTCACACAGATAGACTACTGAAAGAAGGAG

AAAGGGGCACTTACTCAGTCTCCCTTATCAGATTGCCTTACGAGGAGTACTAGACTCCCTCAAG

CAAATAGATCTCACTTACCACTTGCAAAGGTATACTACTTTCACTCTATTAGACCTATATATCT

GACCAGGGTCCTATTCCAAGACAACTCTTCTACTCTTCCAGCAGACTCTTATAGAAAGAAAGAT

TCTGGGGTCCAAGAAAGCAGTACTTTCTTACAAGGAGCCAAAAAAAATAACCTTTCTTTAGCAC

TTCTAACCTTGGAGTGAACTGGTGATCAAAGAGAGGTTGGCTCCCTGGGGACAAGTGCCACAAA

TTCAGTCAACTACAAGAAAGTTGAGAACACTGTTCTCCCGAAACCAAGCTTGAATTCAGCTGAC

GTGCCTCGGACCGCTAGGAACCCCTAGTGATGGAGTTGGCCACTCCCTCTCTGCGCGCTCGCTC

GCTCACTGAGGCCGGGCGACCAAAGGTCGCCCGACGCCCGGGCTTTGCCCGGGCGGCCTCAGTG

AGCGAGCGAGCGCGCAGCTGCCTGCAGG

5' UTR

SEQ ID NO: 14

AAGATGCTCCGTGGAAGGGAGCCGAGCGGTGGGCAGAGGCTGAGTCCCCGATAACGAGCGCCTC

ACATTTCCGTGGCATTCCCATTTGCTAGTGCGCTGCTGCGGCCGCACGCCTGATTGATATATGA

CTGCAATGGCACTTTTCCATTTGACATTCTCTCTCTCTCTCTCCCTCTCTCTCTCTCCCTCTCT

CTCTCCCTCTCTCTCTCTCCCTGTGTCGCTTAAACAACAGTCCTAACTTTTGTGTGTTGCAAAT

ATAAAAGGCAAGCCATGTGACAGAGGGACAGAAGAACAAAAGCATTTGGAAGTAACAGGACCTC

TTTCTAGCTCTCAGAAAAGTCTGAGAAGAAAGGAGCCCTGCGTTCCCCTAAGCTGTGCAGCAGA

TACTGTGATGATGGATTGCAAGTGCAAAGAGTAAGACAAAACTCCAGCACATAAAGGACAATGA

CAACCAGAAAGCTTCAGCCCGATCCTGCCCTTTCCTTGAACGGGACTGGATCCTAGGAGGTGAA

GCCATTTCCAATTTTTTGTCCTCTGCCTCCCTCTGCTGTTCTTCTAGAGAAGTTTTTCCTTACA

ACA

-continued

3' UTR 1023

SEQ ID NO: 15

GGCCCGCTGCTGTGTGTGGCTTCTGGATGGGACAACTGTAGAGGCAGTTCGACCAGCCAGGGAA

AGACTGGCAAGAAAAGAGTTAAGGCAAAAAAGGATGCAACAATTCTCCCGGGACTCTGCATATT

CTAGTAATAAAGACTCTACATGCTTGTTGACAGAGAGAGATACTCTGGGAACTTCTTTGCAGTT

CCCATCTCCTTTCTCTGGTACAATTTCTTTTGGTTCATTTTCAGATTCAGGCATTTTCCCCCTT

GGCTCTCAATGCTGTTTGGGTTTCCAACAATTCAGCATTAGTGGGAAAAAGTGGGCCCTCATAC

ACAAGCGTGTCAGGCTGTCAGTGTTTGGTGCACGCTGGGGAAGAATTTACTTTGGAAAGTAGAA

AAGCCCAGCTTTTCCTGGGACATCTTCTGTTATTGTTGATGTTTTTTTTTACCTTGTCATTTTG

GTCTAAGGTTGCCATTGCTGCTAAAGGTTACCGATTTCAAAGTCCAGATACCAAGCATGTGGAT

ATGTTTAGCTACGTTTACTCACAGCCAGCGAACTGACATTAAAATAACTAACAAACAGATTCTT

TTATGTGATGCTGGAACTCTTGACAGCTATAATTATTATTCAGAAATGACTTTTTGAAAGTAAA

AGCAGCATAAAGAATTTGTCACAGGAAGGCTGTCTCAGATAAATTATGGTAAAATTTTGTAAGG

GAGCAGACTTTTAAAGACTTGCACAAATACGGATCCTGCACTGACTCTGGAAAAGGCATATATG

TACTAGTGGCATGGAGAATGCACCATACTCATGCATGCAAATTAGACAACCAAGTATGAATCTA

TTTGTGGGTGTGCTATAGCTTTAGCCGTGTCACGGGCATCATTCTCTAATATCCACTTGTCCAT

GTGAAACATGTTGCCAAAATGGTGGCCTGGCTTGTCTTCTGAACGTTTGGTTCAAATGTGTTTT

GGTCCTGGAGGCTCAAATTTTGAGTTATTCCCACGTTTTGAAATAAAAAGAGTATATTCAAAA

5'ITR cDNA sequence

SEQ ID NO: 16

CCTGCAGGCAGCTGCGCGCTCGCTCGCTCACTGAGGCCGCCCGGGCGTCGGGCGACCTTTGGTC

GCCCGGCCTCAGTGAGCGAGCGAGCGCGCAGAGAGGGAGTGGCCAACTCCATCACTAGGGGTTC

CT

CMV enhancer cDNA sequence

SEQ ID NO: 17

GACATTGATTATTGACTAGTTATTAATAGTAATCAATTACGGGGTCATTAGTTCATAGCCCATA

TATGGAGTTCCGCGTTACATAACTTACGGTAAATGGCCCGCCTGGCTGACCGCCCAACGACCCC

CGCCCATTGACGTCAATAATGACGTATGTTCCCATAGTAACGCCAATAGGGACTTTCCATTGAC

GTCAATGGGTGGACTATTTACGGTAAACTGCCCACTTGGCAGTACATCAAGTGTATCATATGCC

AAGTACGCCCCCTATTGACGTCAATGACGGTAAATGGCCCGCCTGGCATTATGCCCAGTACATG

ACCTTATGGGACTTTCCTACTTGGCAGTACATCTACGTATTAGTCATCGCTATTACCATGG

CBA promoter cDNA sequence

SEQ ID NO: 18

TCGAGGTGAGCCCCACGTTCTGCTTCACTCTCCCCATCTCCCCCCCCTCCCCACCCCCAATTTT

GTATTTATTTATTTTTTAATTATTTTGTGCAGCGATGGGGGCGGGGGGGGGGGGGGCGCGCGCC

AGGCGGGGCGGGGCGGGGCGAGGGGCGGGGCGGGGCGAGGCGGAGAGGTGCGGCGGCAGCCAAT

CAGAGCGGCGCGCTCCGAAAGTTTCCTTTTATGGCGAGGCGGCGGCGGCGGCGGCCCTATAAAA

AGCGAAGCGCGCGGCGGGCG chimeric intron cDNA sequence

SEQ ID NO: 19

GGAGTCGCTGCGTTGCCTTCGCCCCGTGCCCCGCTCCGCGCCGCCTCGCGCCGCCCGCCCCGGC

TCTGACTGACCGCGTTACTCCCACAGGTGAGCGGGCGGGACGGCCCTTCTCCTCCGGGCTGTAA

TTAGCGCTTGGTTTAATGACGGCTCGTTTCTTTTCTGTGGCTGCGTGAAAGCCTTAAAGGGCTC

CGGGAGGGCCCTTTGTGCGGGGGGGAGCGGCTCGGGGGGTGCGTGCGTGTGTGTGTGCGTGGGG

AGCGCCGCGTGCGGCCCGCGCTGCCCGGCGGCTGTGAGCGCTGCGGGCGCGGCGCGGGGCTTTG

-continued

TGCGCTCCGCGTGTGCGCGAGGGGAGCGCGGCCGGGGGCGGTGCCCCGCGGTGCGGGGGGGCTG

CGAGGGGAACAAAGGCTGCGTGCGGGGTGTGTGCGTGGGGGGGTGAGCAGGGGGTGTGGGCGCG

GCGGTCGGGCTGTAACCCCCCCCTGCACCCCCCTCCCCGAGTTGCTGAGCACGGCCCGGCTTCG

GGTGCGGGGCTCCGTGCGGGGCGTGGCGCGGGGCTCGCCGTGCCGGGCGGGGGGTGGCGGCAGG

TGGGGGTGCCGGGCGGGGCGGGGCCGCCTCGGGCCGGGGAGGGCTCGGGGGAGGGGCGCGGCGG

CCCCCGGAGCGCCGGCGGCTGTCGAGGCGCGGCGAGCCGCAGCCATTGCCTTTTATGGTAATCG

TGCGAGAGGGCGCAGGGACTTCCTTTGTCCCAAATCTGTGCGGAGCCGAAATCTGGGAGGCGCC

GCCGCACCCCCTCTAGCGGGCGCGGGGCGAAGCGGTGCGGCGCCGGCAGGAAGGAAATGGGCGG

GGAGGGCCTTCGTGCGTCGCCGCGCCGCCGTCCCCTTCTCCCTCTCCAGCCTCGGGGCTGTCCG

CGGGGGGACGGCTGCCTTCGGGGGGGACGGGGCAGGGCGGGGTTCGGCTTCTGGCGTGTGACCG

GCGGCTCTAGAGCCTCTGCTAACCATGTTCATGCCTTCTTCTTTTTCCTACAGCTCCTGGGCAA

CGTGCTGGTTATTGTG

NDP cDNA sequence

SEQ ID NO: 20

CTGAGAAAACATGTACTAGCTGCATCCTTTTCTATGCTCTCCCTGCTGGTGATAATGGGAGATA

CAGACAGTAAAACGGACAGCTCATTCATAATGGACTCGGACCCTCGACGCTGCATGAGGCACCA

CTATGTGGATTCTATCAGTCACCCATTGTACAAGTGTAGCTCAAAGATGGTGCTCCTGGCCAGG

TGCGAGGGGCACTGCAGCCAGGCGTCACGCTCCGAGCCTTTGGTGTCGTTCAGCACTGTCCTCA

AGCAACCCTTCCGTTCCTCCTGTCACTGCTGCCGGCCCCAGACTTCCAAGCTGAAGGCACTGCG

GCTGCGATGCTCAGGGGGCATGCGACTCACTGCCACCTACCGATACATCCTCTCCTGTCACTGC

GAGGAATGCAATTCCTAA

NDP cDNA sequence

SEQ ID NO: 21

CTGAGAAAACATGTACTAGCTGCATCCTTTTCTATGCTCTCCCTGCTGGTGATAATGGGAGATA

CAGACAGTAAAACGGACAGCTCATTCATAATGGACTCGGACCCTCGACGCTGCATGAGGCACCA

CTATGTGGATTCTATCAGTCACCCATTGTACAAGTGTAGCTCAAAGATGGTGCTCCTGGCCAGG

TGCGAGGGGCACTGCAGCCAGGCGTCACGCTCCGAGCCTTTGGTGTCGTTCAGCACTGTCCTCA

AGCAACCCTTCCGTTCCTCCTGTCACTGCTGCCGGCCCCAGACTTCCAAGCTGAAGGCACTGCG

GCTGCGATGCTCAGGGGGCATGCGACTCACTGCCACCTACCGATACATCCTCTCCTGTCACTGC

GAGGAATGCAATTCC

3'UTR cDNA sequence

SEQ ID NO: 22

TGCCCGCTGCTGTGTGTGGCTTCTGGATGGGACAACTGTAGAGGCAGTTCGACCAGCCAGGGAA

AGACTGGCAAGAAAAGAGTTAAGGCAAAAAAGGATGCAACAATTCTCCCGGGACTCTGCATATT

CTAGTAATAAAGACTCTACATGCTTGTTGACAGAGAGAGATACTCTGGGAACTTCTTTGCAGTT

CCCATCTCCTTTCTCTGGTACAATTTCTTTTGGTTCATTTTCAGATTCAGGCATTTTCCCCCTT

GGCTCTCAATGCTGTTTGGGTTTCCAACAATTCAGCATTAGTGGGAAAAAGTGGGCCCTCATAC

ACAAGCGTGTCAGGCTGTCAGTGTTTGGTGCACGCTGGGGAAGAATTTACTTTGGAAAGTAGAA

AAGCCCAGCTTTTCCTGGGACATCTTCTGTTATTGTTGATGTTTTTTTTTACCTTGTCATTTTG

GTCTAAGGTTGCCATTGCTGCTAAAGGTTACCGATTTCAAAGTCCAGATACCAAGCATGTGGAT

ATGTTTAGCTACGTTTACTCACAGCCAGCGAACTGACATTAAAATAACTAACAAACAGATTCTT

TTATGTGATGCTGGAACTCTTGACAGCTATAATTATTATTCAGAAATGACTTTTTGAAAGTAAA

AGCAGCATAAAGAATTTGTCACAGGAAGGCTGTCTCAGATAAATTATGGTAAAATTTTGTAAGG

GAGCAGACTTTTAAAGACTTGCACAAATACGGATCCTGCACTGACTCTGGAAAAGGCATATATG

TACTAGTGGCATGGAGAATGCACCATACTCATGCATGCAAATTAGACAACCAAGTATGAATCTA

TTTGTGGGTGTGCTATAGCTTTAGCCGTGTCACGGGCATCATTCTCTAATATCCACTTGTCCAT

GTGAAACATGTTGCCAAAATGGTGGCCTGGCTTGTCTTCTGAACGTTTGGTTCAAATGTGTTTT

GGTCCTGGAGGCTCAAATTTTGAGTTATTCCCACGTTTTGAAATAAAAAGAGTATATTCAAAA bGHpA cDNA sequence

SEQ ID NO: 23

CTGTGCCTTCTAGTTGCCAGCCATCTGTTGTTTGCCCCTCCCCCGTGCCTTCCTTGACCCTGGA

AGGTGCCACTCCCACTGTCCTTTCCTAATAAAATGAGGAAATTGCATCGCATTGTCTGAGTAGG

TGTCATTCTATTCTGGGGGGTGGGGTGGGGCAGGACAGCAAGGGGGAGGATTGGGAAGACAATA

GCAGGCATGCTGGGGATGCGGTGGGCTCTATGG stuffer cDNA sequence

SEQ ID NO: 24

TAATTCAGACTCCCACTAGAAGAAACAGAACTTGAAAAAAGGATAATTGTGGTGAACACCTCAA

CCCAGTGGTCCAAAAACTGAAAAACTTTGACCCCGAGCACCCTCACACAGATAGACTACTGAAA

GAAGGAGAAAGGGGCACTTACTCAGTCTCCCTTATCAGATTGCCTTACGAGGAGTACTAGACTC

CCTCAAGCAAATAGATCTCACTTACCACTTGCAAAGGTATACTACTTTCACTCTATTAGACCTA

TATATCTGACCAGGGTCCTATTCCAAGACAACTCTTCTACTCTTCCAGCAGACTCTTATAGAAA

GAAAGATTCTGGGGTCCAAGAAAGCAGTACTTTCTTACAAGGAGCCAAAAAAAATAACCTTTCT

TTAGCACTTCTAACCTTGGAGTGAACTGGTGATCAAAGAGAGGTTGGCTCCCTGGGGACAAGTG

CCACAAATTCAGTCAACTACAAGAAAGTTGAGAACACTGTTCTCCCGAAACC stuffer cDNA sequence

SEQ ID NO: 25

GTTGACTAAAGATTGAACCTTATTCAAAGTTAGACTCTCTTTGTTAAAGACAAACAAAACTTCC

AATAATTCAGCAACTAATAGAAAGACTCAACTTGTGAGCCACTACTTATTAATTGAGAATAGTC

ACTCAGTCTGGCAAAATATATTAGAAAGTGACACTGAGTTTAAAAAAGTGACACCTTTGATTCT

GAACAGTGAACTTTGAGACTGAAAAACTACAGCTTTGAGGCTAAATACTTGATCAAATAAAACT

ACTTACTCAAAAAACTGAGTGAAAGTCCAACAGAAAAAAGAGGGCCCACTTCCACCAGTGACAC

AAAATCCAGATTGATCGTTCTTTAAGTGACTATTCTTGCCAGAATCAGCAAGGTGGATACAAAG

GACTCTGAGAAAGAACTCTCTGAACTCTGGGCAAGGCCCCAGTCCAAAGCAATTAGTATCCTTA

GGACCAGAAAAATCTGTGGAAGGTCAGAATTTCTTGTCTGAGAAAAACAAAGCAATTCAGACTC

CCACTAGAAGAAACAGAACTTGAAAAAAGGATAATTGTGGTGAACACCTCAACCCAGTGGTCCA

AAAACTGAAAAACTTTGACCCCGAGCACCCTCACACAGATAGACTACTGAAAGAAGGAGAAAGG

GGCACTTACTCAGTCTCCCTTATCAGATTGCCTTACGAGGAGTACTAGACTCCCTCAAGCAAAT

AGATCTCACTTACCACTTGCAAAGGTATACTACTTTCACTCTATTAGACCTATATATCTGACCA

GGGTCCTATTCCAAGACAACTCTTCTACTCTTCCAGCAGACTCTTATAGAAAGAAAGATTCTGG

GGTCCAAGAAAGCAGTACTTTCTTACAAGGAGCCAAAAAAAATAACCTTTCTTTAGCACTTCTA

ACCTTGGAGTGAACTGGTGATCAAAGAGAGGTTGGCTCCCTGGGGACAAGTGCCACAAATTCAG

TCAACTACAAGAAAGTTGAGAACACTGTTCTCCCGAAACC

T2A cDNA sequence

SEQ ID NO: 26

GAGGGCAGAGGAAGTCTGCTAACATGCGGTGACGTCGAGGAGAATCCTGGCCCA tGFP cDNA sequence

SEQ ID NO: 27

ATGGAGAGCGACGAGAGCGGCCTGCCCGCCATGGAGATCGAGTGCCGCATCACCGGCACCCTGA

ACGGCGTGGAGTTCGAGCTGGTGGGCGGCGGAGAGGGCACCCCCGAGCAGGGCCGCATGACCAA

-continued

CAAGATGAAGAGCACCAAAGGCGCCCTGACCTTCAGCCCCTACCTGCTGAGCCACGTGATGGGC

TACGGCTTCTACCACTTCGGCACCTACCCCAGCGGCTACGAGAACCCCTTCCTGCACGCCATCA

ACAACGGCGGCTACACCAACACCCGCATCGAGAAGTACGAGGACGGCGGCGTGCTGCACGTGAG

CTTCAGCTACCGCTACGAGGCCGGCCGCGTGATCGGCGACTTCAAGGTGATGGGCACCGGCTTC

CCCGAGGACAGCGTGATCTTCACCGACAAGATCATCCGCAGCAACGCCACCGTGGAGCACCTGC

ACCCCATGGGCGATAACGATCTGGATGGCAGCTTCACCCGCACCTTCAGCCTGCGCGACGGCGG

CTACTACAGCTCCGTGGTGGACAGCCACATGCACTTCAAGAGCGCCATCCACCCCAGCATCCTG

CAGAACGGGGGCCCCATGTTCGCCTTCCGCCGCGTGGAGGAGGATCACAGCAACACCGAGCTGG

GCATCGTGGAGTACCAGCACGCCTTCAAGACCCCGGATGCAGATGCCGGTGAAGAATAA eGFP cDNA sequence

SEQ ID NO: 28

ATGGTGAGCAAGGGCGAGGAGCTGTTCACCGGGGTGGTGCCCATCCTGGTCGAGCTGGACGGCG

ACGTAAACGGCCACAAGTTCAGCGTGTCCGGCGAGGGCGAGGGCGATGCCACCTACGGCAAGCT

GACCCTGAAGTTCATCTGCACCACCGGCAAGCTGCCCGTGCCCTGGCCCACCCTCGTGACCACC

CTGACCTACGGCGTGCAGTGCTTCAGCCGCTACCCCGACCACATGAAGCAGCACGACTTCTTCA

AGTCCGCCATGCCCGAAGGCTACGTCCAGGAGCGCACCATCTTCTTCAAGGACGACGGCAACTA

CAAGACCCGCGCCGAGGTGAAGTTCGAGGGCGACACCCTGGTGAACCGCATCGAGCTGAAGGGC

ATCGACTTCAAGGAGGACGGCAACATCCTGGGGCACAAGCTGGAGTACAACTACAACAGCCACA

ACGTCTATATCATGGCCGACAAGCAGAAGAACGGCATCAAGGTGAACTTCAAGATCCGCCACAA

CATCGAGGACGGCAGCGTGCAGCTCGCCGACCACTACCAGCAGAACACCCCCATCGGCGACGGC

CCCGTGCTGCTGCCCGACAACCACTACCTGAGCACCCAGTCCGCCCTGAGCAAAGACCCCAACG

AGAAGCGCGATCACATGGTCCTGCTGGAGTTCGTGACCGCCGCCGGGATCACTCTCGGCATGGA

CGAGCTGTACAAG eGFP protein

SEQ ID NO: 29

MVSKGEELFTGVVPILVELDGDVNGHKFSVSGEGEGDATYGKLTLKFICTTGKLPVPWPTLVTT

LTYGVQCFSRYPDHMKQHDFFKSAMPEGYVQERTIFFKDDGNYKTRAEVKFEGDTLVNRIELKG

IDFKEDGNILGHKLEYNYNSHNVYIMADKQKNGIKVNFKIRHNIEDGSVQLADHYQQNTPIGDG

PVLLPDNHYLSTQSALSKDPNEKRDHMVLLEFVTAAGITLGMDELYK

3'ITR cDNA sequence

SEQ ID NO: 30

AGGAACCCCTAGTGATGGAGTTGGCCACTCCCTCTCTGCGCGCTCGCTCGCTCACTGAGGCCGG

GCGACCAAAGGTCGCCCGACGCCCGGGCTTTGCCCGGGCGGCCTCAGTGAGCGAGCGAGCGCGC

AGCTGCCTGCAGG

5' UTR 579

SEQ ID NO: 31

AAGATGCTCCGTGGAAGGGAGCCGAGCGGTGGGCAGAGGCTGAGTCCCCGATAACGAGCGCCTC

ACATTTCCGTGGCATTCCCATTTGCTAGTGCGCTGCTGCGGCCGCACGCCTGATTGATATATGA

CTGCAATGGCACTTTTCCATTTGACATTCTCTCTCTCTCTCCCTCTCTCTCTCTCCCTCTCT

CTCTCCCTCTCTCTCTCTCCCTGTGTCGCTTAAACAACAGTCCTAACTTTTGTGTGTTGCAAAT

ATAAAAGGCAAGCCATGTGACAGAGGGACAGAAGAACAAAAGCATTTGGAAGTAACAGGACCTC

TTTCTAGCTCTCAGAAAAGTCTGAGAAGAAAGGAGCCCTGCGTTCCCCTAAGCTGTGCAGCAGA

TAGTGTGATGATGGATTGCAAGTGCAAAGAGTAAGACAAAACTCCAGCACATAAAGGACAATGA

-continued

CAACCAGAAAGCTTCAGCCCGATCCTGCCCTTTCCTTGAACGGGACTGGATCCTAGGAGGTGAA

GCCATTTCCAATTTTTTGTCCTCTGCCTCCCTCTGCTGTTCTTCTAGAGAAGTTTTTCCTTACA

ACA

Human NDP Gene

SEQ ID NO: 32

AGAAGAACAAAAGCATTTGGAAGTAACAGGACCTCTTTCTAGCTCTCAGAAAAGTCTGAGAAGA

AAGGAGCCCTGCGTTCCCCTAAGCTGTGCAGCAGATACTGTGATGATGGATTGCAAGTGCAAAG

AGTAAGACAAAACTCCAGCACATAAAGGACAATGACAACCAGAAAGCTTCAGCCCGATCCTGCC

CTTTCCTTGAACGGGACTGGATCCTAGGAGGTGAAGCCATTTCCAATTTTTTGTCCTCTGCCTC

CCTCTGCTGTTCTTCTAGAGAAGTTTTTCCTTACAACAATGAGAAAACATGTACTAGCTGCATC

CTTTTCTATGCTCTCCCTGCTGGTGATAATGGGAGATACAGACAGTAAAACGGACAGCTCATTC

ATAATGGACTCGGACCCTCGACGCTGCATGAGGCACCACTATGTGGATTCTATCAGTCACCCAT

TGTACAAGTGTAGCTCAAAGATGGTGCTCCTGGCCAGGTGCGAGGGGCACTGCAGCCAGGCGTC

ACGCTCCGAGCCTTTGGTGTCGTTCAGCACTGTCCTCAAGCAACCCTTCCGTTCCTCCTGTCAC

TGCTGCCGGCCCCAGACTTCCAAGCTGAAGGCACTGCGGCTGCGATGCTCAGGGGGCATGCGAC

TCACTGCCACCTACCGGTACATCCTCTCCTGTCACTGCGAGGAATGCAATTCCTGAGGCCCGCT

GCTGTGTGTGGCTTCTGGATGGGACAACTGTAGAGGCAGTTCGACCAGCCAGGGAAAGACTGGC

AAGAAAAGAGTTAAGGCAAAAAAGGATGCAACAATTCTCCCGGGACTCTGCATATTCTAGTAAT

AAAGACTCTACATGCTTGTTGACAGAGAGAGATACTCTGGGAACTTCTTTGCAGTTCCCATCTC

CTTTCTCTGGTACAATTTCTTTTGGTTCATTTTCAGATTCAGGCATTTTCCCCCTTGGCTCTCA

ATGCTGTTTGGGTTTCCAACAATTCAGCATTAGTGGGAAAAAGTGGGCCCTCATACACAAGCGT

GTCAGGCTGTCAGTGTTTGGTGCACGCTGGGGAAGAATTTACTTTGGAAAGTAGAAAAGCCCAG

CTTTTCCTGGGACATCTTCTGTTATTGTTGATGTTTTTTTTTACCTTGTCATTTTGGTCTAAGG

TTGCCATTGCTGCTAAAGGTTACCGATTTCAAAGTCCAGATACCAAGCATGTGGATATGTTTAG

CTACGTTTACTCACAGCGAGCGAACTGAGATTAAAATAACTAACAAACAGATTCTTTTATGTGA

TGCTGGAACTCTTGACAGCTATAATTATTATTCAGAAATGAGTTTTTGAAAGTAAAAGCAGCAT

AAAGAATTTGTCACAGGAAGGCTGTCTCAGATAAATTATGGTAAAATTTTGTAAGGGAGCAGAC

TTTTAAAGACTTGCACAAATACGGATCCTGCACTGAGTCTGGAAAAGGCATATATGTACTAGTG

GCATGGAGAATGCACCATACTCATGCATGCAAATTAGACAACCAAGTATGAATCTATTTGTGGG

TGTGCTATAGCTTTAGCCGTGTCACGGGCATCATTCTCTAATATCCACTTGTCCATGTGAAACA

TGTTGCCAAAATGGTGGCCTGGCTTGTCTTCTGAACGTTTGGTTCAAATGTGTTTTGGTCCTGG

AGGCTCAAATTTTGAGTTATTCCCACGTTTTGAAATAAAAAGAGTATATTCAAAA

Mouse Mature NDP Protein

SEQ ID NO: 33

KTDSSFLMDSQRCMRHHYVDSISHPLYKCSSKMVLLARCEGHCSQASRSEPLVSFSTVLKQPFR

SSCHCCRPQTSKLKALRLRCSGGMRLTATYRYILSCHCEECSS

Mouse Mature NDP cDNA

SEQ ID NO: 34

AAAACAGACAGTTCATTTCTGATGGAGTCTCAACGCTGCATGAGACACCATTATGTCGATTCTA

TCAGTCACCCACTGTACAAATGTAGCTCAAAGATGGTGCTCCTGGCCAGATGTGAGGGGCACTG

CAGCCAGGCATCACGCTCTGAGCCCTTGGTGTCCTTCAGCACTGTCCTCAAGCAACCTTTCCGT

TCCTCCTGTCACTGCTGCCGACCCCAGACTTCCAAGCTGAAGGCTCTGCGTCTGCGCTGCTCAG

GGGGCATGCGACTTACTGCCACTTACCGGTACATCCTCTCCTGTCACTGTGAGGAATGCAGCTC

C

-continued

Rhesus Monkey Mature NDP Protein

SEQ ID NO: 35

MRKHVLAASFSMLSLLVIMGDTDSKTDSSFIMDSDPRRCMRHHYVDSISHPLYKCSSKMVLLAR

CEGHCSQASRSEPLVSFSTVLKQPFRSSCHCCRPQTSKLKALRLRCSGGMRLTATYRYILSCHC

EECNS

Rat Mature NDP cDNA

SEQ ID NO: 36

KTDSSFLMDSQRCMRHHYVDSISHPLYKCSSKMVLLARCEGHCSQASRSEPLVSFSTVLKQPFR

SSCHCCRPQTSKLKALRLRCSGGMRLTATYRYILSCHCEECSS

Chimpanzee Mature NDP Protein

SEQ ID NO: 37

KTDSSFVMDSDPRRCMRHHYVDSISHPLYKCSSKMVLLARCEGHCSQASRSEPLVSFSTVLKQP

FRSSCHCCRPQTSKLKALRLRCSGGMRLTATYRYILSCHCEECNS

Human Mature HSPA1A Protein

SEQ ID NO: 38

MAKAAAIGIDLGTTYSCVGVFQHGKVEIIANDQGNRTTPSYVAFTDTERLIGDAAKNQVALNPQ

NTVFDAKRLIGRKFGDPVVQSDMKHWPFQVINDGDKPKVQVSYKGETKAFYPEEISSMVLTKMK

EIAEAYLGYPVTNAVITVPAYFNDSQRQATKDAGVIAGLNVLRIINEPTAAAIAYGLDRTGKGE

RNVLIFDLGGGTFDVSILTIDDGIFEVKATAGDTHLGGEDFDNRLVNHFVEEFKRKHKKDISQN

KRAVRRLRTACERAKRTLSSSTQASLEIDSLFEGIDFYTSITRARFEELCSDLFRSTLEPVEKA

LRDAKLDKAQIHDLVLVGGSTRIPKVQKLLQDFFNGRDLNKSINPDEAVAYGAAVQAAILMGDK

SENVQDLLLLDVAPLSLGLETAGGVMTALIKRNSTIPTKQTQIFTTYSDNQPGVLIQVYEGERA

MTKDNNLLGRFELSGIPPAPRGVPQIEVTFDIDANGILNVTATDKSTGKANKITITNDKGRLSK

EEIERMVQEAEKYKAEDEVQRERVSAKNALESYAFNMKSAVEDEGLKGKISEADKKKVLDKCQE

VISWLDANTLAEKDEFEHKRKELEQVCNPIISGLYQGAGGPGPGGFGAQGPKGGSGSGPTIEEV

D

Human Mature HSPA1A cDNA

SEQ ID NO: 39

ATGGCCAAAGCCGCGGCGATCGGCATCGACCTGGGCACCACCTACTCCTGCGTGGGGGTGTTCC

AACACGGCAAGGTGGAGATCATCGCCAACGACCAGGGCAACCGCACCACCCCCAGCTACGTGGC

CTTCACGGACACCGAGCGGCTCATCGGGGATGCGGCCAAGAACCAGGTGGCGCTGAACCCGCAG

AACACCGTGTTTGACGCGAAGCGGCTGATCGGCCGCAAGTTCGGCGACCCGGTGGTGCAGTCGG

ACATGAAGCACTGGCCTTTCCAGGTGATCAACGACGGAGACAAGCCCAAGGTGCAGGTGAGCTA

CAAGGGGGAGACCAAGGCATTCTACCCCGAGGAGATCTCGTCCATGGTGCTGACCAAGATGAAG

GAGATCGCCGAGGCGTACCTGGGCTACCCGGTGACCAACGCGGTGATCACCGTGCCGGCCTACT

TCAACGACTCGCAGCGCCAGGCCACCAAGGATGCGGGTGTGATCGCGGGGCTCAACGTGCTGCG

GATCATCAACGAGCCCACGGCCGCCGCCATCGCCTACGGCCTGGACAGAACGGGCAAGGGGGAG

CGCAACGTGCTCATCTTTGACCTGGGCGGGGGCACCTTCGACGTGTCCATCCTGACGATCGACG

ACGGCATCTTCGAGGTGAAGGCCACGGCCGGGGACACCCACCTGGGTGGGGAGGACTTTGACAA

CAGGCTGGTGAACCACTTCGTGGAGGAGTTCAAGAGAAAACACAAGAAGGACATCAGCCAGAAC

AAGCGAGCCGTGAGGCGGCTGCGCACCGCCTGCGAGAGGGCCAAGAGGACCCTGTCGTCCAGCA

CCCAGGCCAGCCTGGAGATCGACTCCCTGTTTGAGGGCATCGACTTCTACACGTCCATCACCAG

GGCGAGGTTCGAGGAGCTGTGCTCCGACCTGTTCCGAAGCACCCTGGAGCCCGTGGAGAAGGCT

CTGCGCGACGCCAAGCTGGACAAGGCCCAGATTCACGACCTGGTCCTGGTCGGGGGCTCCACCC

GCATCCCCAAGGTGCAGAAGCTGCTGCAGGACTTCTTCAACGGGCGCGACCTGAACAAGAGCAT

-continued

CAACCCCGACGAGGCTGTGGCCTACGGGGCGGCGGTGCAGGCGGCCATCCTGATGGGGGACAAG

TCCGAGAACGTGCAGGACCTGCTGCTGCTGGACGTGGCTCCCCTGTCGCTGGGGCTGGAGACGG

CCGGAGGCGTGATGACTGCCCTGATCAAGCGCAACTCCACCATCCCCACCAAGCAGACGCAGAT

CTTCACCACCTACTCCGACAACCAACCCGGGGTGCTGATCCAGGTGTACGAGGGCGAGAGGGCC

ATGACGAAAGACAACAATCTGTTGGGGCGCTTCGAGCTGAGCGGCATCCCTCCGGCCCCCAGGG

GCGTGCCCCAGATCGAGGTGACCTTCGACATCGATGCCAACGGCATCCTGAACGTCACGGCCAC

GGACAAGAGCACCGGCAAGGCCAACAAGATCACCATCACCAACGACAAGGGCCGCCTGAGCAAG

GAGGAGATCGAGCGCATGGTGCAGGAGGCGGAGAAGTACAAAGCGGAGGACGAGGTGCAGCGCG

AGAGGGTGTCAGCCAAGAACGCCCTGGAGTCCTACGCCTTCAACATGAAGAGCGCCGTGGAGGA

TGAGGGGCTCAAGGGCAAGATCAGCGAGGCGGACAAGAAGAAGGTTCTGGACAAGTGTCAAGAG

GTCATCTCGTGGCTGGACGCCAACACCTTGGCCGAGAAGGACGAGTTTGAGCACAAGAGGAAGG

AGCTGGAGCAGGTGTGTAACCCCATCATCAGCGGACTGTACCAGGGTGCCGGTGGTCCCGGGCC

TGGGGGCTTCGGGGCTCAGGGTCCCAAGGGAGGGTCTGGGTCAGGCCCCACCATTGAGGAGGTG

GATTAG

Human HSPA1A Gene Sequence

SEQ ID NO: 40

AACGGCTAGCCTGAGGAGCTGCTGCGACAGTCCACTACCTTTTTCGAGAGTGACTCCCGTTGTC

CCAAGGCTTCCCAGAGCGAACCTGTGCGGCTGCAGGCACCGGCGCGTCGAGTTTCCGGCGTCCG

GAAGGACCGAGCTCTTCTCGCGGATCCAGTGTTCCGTTTCCAGCCCCCAATCTCAGAGCGGAGC

CGACAGAGAGCAGGGAACCGGCATGGCCAAAGCCGCGGCGATCGGCATCGACCTGGGCACCACC

TACTCCTGCGTGGGGGTGTTCCAACACGGCAAGGTGGAGATCATCGCCAACGACCAGGGCAACC

GCACCACCCCCAGCTACGTGGCCTTCACGGACACCGAGCGGCTCATCGGGGATGCGGCCAAGAA

CCAGGTGGCGCTGAACCCGCAGAACACCGTGTTTGACGCGAAGCGGCTGATTGGCCGCAAGTTC

GGCGACCCGGTGGTGCAGTCGGACATGAAGCACTGGCCTTTCCAGGTGATCAACGACGGAGACA

AGCCCAAGGTGCAGGTGAGCTACAAGGGGGAGACCAAGGCATTCTACCCCGAGGAGATCTCGTC

CATGGTGCTGACCAAGATGAAGGAGATCGCCGAGGCGTACCTGGGCTACCCGGTGACCAACGCG

GTGATCACCGTGCCGGCCTACTTCAACGACTCGCAGCGCCAGGCCACCAAGGATGCGGGTGTGA

TCGCGGGGCTCAACGTGCTGCGGATCATCAACGAGCCCACGGCCGCCGCCATCGCCTACGGCCT

GGACAGAACGGGCAAGGGGGAGCGCAACGTGCTCATCTTTGACCTGGGCGGGGGCACCTTCGAC

GTGTCCATCCTGACGATCGACGACGGCATCTTCGAGGTGAAGGCCACGGCCGGGGACACCCACC

TGGGTGGGGAGGACTTTGACAACAGGCTGGTGAACCACTTCGTGGAGGAGTTCAAGAGAAAACA

CAAGAAGGACATCAGCCAGAACAAGCGAGCCGTGAGGCGGCTGCGCACCGCCTGCGAGAGGGCC

AAGAGGACCCTGTCGTCCAGCACCCAGGCCAGCCTGGAGATCGACTCCCTGTTTGAGGGCATCG

ACTTCTACACGTCCATCACCAGGGCGAGGTTCGAGGAGCTGTGCTCCGACCTGTTCCGAAGCAC

CCTGGAGCCCGTGGAGAAGGCTCTGCGCGACGCCAAGCTGGACAAGGCCCAGATTCACGACCTG

GTCCTGGTCGGGGGCTCCACCCGCATCCCCAAGGTGCAGAAGCTGCTGCAGGACTTCTTCAACG

GGCGCGACCTGAACAAGAGCATCAACCCCGACGAGGCTGTGGCCTACGGGGCGGCGGTGCAGGC

GGCCATCCTGATGGGGGACAAGTCCGAGAACGTGCAGGACCTGCTGCTGCTGGACGTGGCTCCC

CTGTCGCTGGGGCTGGAGACGGCCGGAGGCGTGATGACTGCCCTGATCAAGCGCAACTCCACCA

TCCCCACCAAGCAGACGCAGATCTTCACCACCTACTCCGACAACCAACCCGGGGTGCTGATCCA

GGTGTACGAGGGCGAGAGGGCCATGACGAAAGACAACAATCTGTTGGGGCGCTTCGAGCTGAGC

GGCATCCCTCCGGCCCCCAGGGGCGTGCCCCAGATCGAGGTGACCTTCGACATCGATGCCAACG

-continued

GCATCCTGAACGTCACGGCCACGGACAAGAGCACCGGCAAGGCCAACAAGATCACCATCACCAA

CGACAAGGGCCGCCTGAGCAAGGAGGAGATCGAGCGCATGGTGCAGGAGGCGGAGAAGTACAAA

GCGGAGGACGAGGTGCAGCGCGAGAGGGTGTCAGCCAAGAACGCCCTGGAGTCCTACGCCTTCA

ACATGAAGAGCGCCGTGGAGGATGAGGGGCTCAAGGGCAAGATCAGCGAGGCGGACAAGAAGAA

GGTGCTGGACAAGTGTCAAGAGGTCATCTCGTGGCTGGACGCCAACACCTTGGCCGAGAAGGAC

GAGTTTGAGCACAAGAGGAAGGAGCTGGAGCAGGTGTGTAACCCCATCATCAGCGGACTGTACC

AGGGTGCCGGTGGTCCCGGGCCTGGGGGCTTCGGGGCTCAGGGTCCCAAGGGAGGGTCTGGGTC

AGGCCCCACCATTGAGGAGGTAGATTAGGGGCCTTTCCAAGATTGCTGTTTTTGTTTTGGAGCT

TCAAGACTTTGCATTTCCTAGTATTTCTGTTTGTCAGTTCTCAATTTCCTGTGTTTGCAATGTT

GAAATTTTTTGGTGAAGTACTGAACTTGCTTTTTTTCCGGTTTCTACATGCAGAGATGAATTTA

TACTGCCATCTTACGACTATTTCTTCTTTTTAATACACTTAACTCAGGCCATTTTTTAAGTTGG

TTACTTCAAAGTAAATAAACTTTAAAATTCAA

Mouse Mature HSPA1A Protein

SEQ ID NO: 41

MAKNTAIGIDLGTTYSCVGVFQHGKVEIIANDQGNRTTPSYVAFTDTERLIGDAAKNQVALNPQ

NTVFDAKRLIGRKFGDAVVQSDMKHWPFQVVNDGDKPKVQVNYKGESRSFFPEEISSMVLTKMK

EIAEAYLGHPVTNAVITVPAYFNDSQRQATKDAGVIAGLNVLRIINEPTAAAIAYGLDRTGKGE

RNVLIFDLGGGTFDVSILTIDDGIFEVKATAGDTHLGGEDFDNRLVSHFVEEFKRKHKKDISQN

KRAVRRLRTACERAKRTLSSSTQASLEIDSLFEGIDFYTSITRARFEELCSDLFRGTLEPVEKA

LRDAKMDKAQIHDLVLVGGSTRIPKVQKLLQDFFNGRDLNKSINPDEAVAYGAAVQAAILMGDK

SENVQDLLLLDVAPLSLGLETAGGVMTALIKRNSTIPTKQTQTFTTYSDNQPGVLIQVYEGERA

MTRDNNLLGRFELSGIPPAPRGVPQIEVTFDIDANGILNVTATDKSTGKANKITITNDKGRLSK

EEIERMVQEAERYKAEDEVQRDRVAAKNALESYAFNMKSAVEDEGLKGKLSEADKKKVLDKCQE

VISWLDSNTLADKEEFVHKREELERVCSPIISGLYQGAGAPGAGGFGAQAPKGASGSGPTIEEV

D

Mouse Mature HSPA1A cDNA

SEQ ID NO: 42

ATGGCCAAGAACACGGCGATCGGCATCGACCTGGGCACCACCTACTCGTGCGTGGGCGTGTTCC

AGCACGGCAAGGTGGAGATCATCGCCAACGACCAGGGCAACCGCACGACCCCCAGCTACGTGGC

CTTCACCGACACCGAGCGCCTCATCGGAGACGCCGCCAAGAACCAGGTGGCGCTGAACCCGCAG

AACACCGTGTTCGACGCGAAGCGGCTGATCGGCCGCAAGTTCGGCGATGCGGTGGTGCAGTCCG

ACATGAAGCACTGGCCCTTCCAGGTGGTGAACGACGGCGACAAGCCCAAGGTGCAGGTGAACTA

CAAGGGCGAGAGCCGGTCGTTCTTCCCGGAGGAGATCTCGTCCATGGTGCTGACGAAGATGAAG

GAGATCGCTGAGGCGTACCTGGGCCACCCGGTGACCAACGCGGTGATCACGGTGCCCGCCTACT

TCAACGACTCTCAGCGGCAGGCCACCAAGGACGCGGGCGTGATCGCCGGTCTAAACGTGCTGCG

GATCATCAACGAGCCCACGGCGGCCGCCATCGCCTACGGGCTGGACCGGACCGGCAAGGGCGAG

CGCAACGTGCTCATCTTCGACCTGGGGGGCGGCACGTTCGACGTGTCCATCCTGACGATCGACG

ACGGCATCTTCGAGGTGAAGGCCACGGCGGGCGACACGCACCTGGGAGGGGAGGACTTCGACAA

CCGGCTGGTGAGCCACTTCGTGGAGGAGTTCAAGAGGAAGCACAAGAAGGACATCAGCCAGAAC

AAGCGCGCGGTGCGGCGGCTGCGCACTGCGTGTGAGAGGGCCAAGAGGACGCTGTCGTCCAGCA

CCCAGGCCAGCCTGGAGATCGACTCTCTGTTCGAGGGCATCGACTTCTACACATCCATCACGCG

GGCGCGGTTCGAAGAGCTGTGCTCAGACCTGTTCCGCGGCACGCTGGAGCCCGTGGAGAAGGCC

-continued

CTGCGCGACGCCAAGATGGACAAGGCGCAGATCCACGACCTGGTGCTGGTGGGCGGCTCGACGC

GCATCCCCAAGGTGCAGAAGCTGCTGCAGGACTTCTTCAACGGGCGCGACCTGAACAAGAGCAT

CAACCCGGACGAGGCGGTGGCCTACGGGGCGGCGGTGCAGGCGGCCATCCTGATGGGGGACAAG

TCGGAGAACGTGCAGGACCTGCTGCTGCTGGACGTGGCGCCGCTGTCGCTGGGCCTGGAGACTG

CGGGCGGCGTGATGACGGCGCTCATCAAGCGCAACTCCACCATCCCCACCAAGCAGACGCAGAC

CTTCACCACCTACTCGGACAACCAGCCCGGGGTGCTGATCCAGGTGTACGAGGGCGAGAGGGCC

ATGACGCGCGACAACAACCTGCTGGGGCGCTTCGAACTGAGCGGCATCCCGCCGGCGCCCAGGG

GCGTGCCACAGATCGAGGTGACCTTCGACATCGACGCCAACGGCATCCTGAACGTCACGGCCAC

CGACAAGAGCACCGGCAAGGCCAACAAGATCACCATCACCAACGACAAGGGCCGCCTGAGCAAG

GAGGAGATCGAGCGCATGGTGCAGGAGGCCGAGCGCTACAAGGCCGAGGACGAGGTGCAGCGCG

ACAGGGTGGCCGCCAAGAACGCGCTCGAATCCTATGCCTTCAACATGAAGAGCGCCGTGGAGGA

CGAGGGTCTCAAGGGCAAGCTCAGCGAGGCTGACAAGAAGAAGGTGCTGGACAAGTGCCAGGAG

GTCATCTCCTGGCTGGACTCCAACACGCTGGCCGACAAGGAGGAGTTCGTGCACAAGCGGGAGG

AGCTGGAGCGGGTGTGCAGCCCCATCATCAGTGGGCTGTACCAGGGTGCGGGTGCTCCTGGGGC

TGGGGGCTTCGGGGCCCAGGCGCCCAAGGGAGCCTCTGGCTCAGGACCCACCATCGAGGAGGTG

GATTAGA

Rhesus Monkey Mature HSPA1A Protein

SEQ ID NO: 43

MAKAAAIGIDLGTTYSCVGVFQHGKVEIIANDQGNRTTPSYVAFTDTERLIGDAAKNQVALNPQ

NTVFDAKRLIGRKFGDPVVQSDMKHWPFQVINDGDKPKVQVSYKGETKAFYPEEISSMVLTKMK

EIAEAYLGYPVTNAVITVPAYFNDSQRQATKDAGVIAGLNVLRIINEPTAAAIAYGLDRTGKGE

RNVLIFDLGGGTFDVSILTIDDGIFEVKATAGDTHLGGEDFDNRLVNHFVEEFKRKHKKDISQN

KRAVRRLRTACERAKRTLSSSTQASLEIDSLFEGIDFYTSITRARFEELCSDLFRSTLEPVEKA

LRDAKLDKAQIHDLVLVGGSTRIPKVQKLLQDFFNGRDLNKSINPDEAVAYGAAVQAAILMGDK

SENVQDLLLLDVAPLSLGLETAGGVMTALIKRNSTIPTKQTQIFTTYSDNQPGVLIQVYEGERA

MTKDNNLLGRFELSGIPPAPRGVPQIEVTFDIDANGILNVTATDKSTGKANKITITNDKGRLSK

EEIERMVQEAEKYKAEDEVQRERVSAKNALESYAFNMKSAVEDEGLKGKISEADKKKVLDKCQE

VISWLDANTLAEKDEFEHKRKELEQVCNPIISGLYQGAGGPGPGGFGAQGPKGGSGSGPTIEEV

D

Rat Mature HSPA1A Protein

SEQ ID NO: 44

MAKKTAIGIDLGTTYSCVGVFQHGKVEIIANDQGNRTTPSYVAFTDTERLIGDAAKNQVALNPQ

NTVFDAKRLIGRKFGDPVVQSDMKHWPFQVVNDGDKPKVQVNYKGENRSFYPEEISSMVLTKMK

EIAEAYLGHPVTNAVITVPAYFNDSQRQATKDAGVIAGLNVLRIINEPTAAAIAYGLDRTGKGE

RNVLIFDLGGGTFDVSILTIDDGIFEVKATAGDTHLGGEDFDNRLVSHFVEEFKRKHKKDISQN

KRAVRRLRTACERAKRTLSSSTQASLEIDSLFEGIDFYTSITRARFEELCSDLFRGTLEPVEKA

LRDAKLDKAQIHDLVLVGGSTRIPKVQKLLQDFFNGRDLNKSINPDEAVAYGAAVQAAILMGDK

SENVQDLLLLDVAPLSLGLETAGGVMTALIKRNSTIPTKQTQTFTTYSDNQPGVLIQVYEGERA

MTRDNNLLGRFELSGIPPAPRGVPQIEVTFDIDANGILNVTATDKSTGKANKITITNDKGRLSK

EEIERMVQEAERYKAEDEVQRERVAAKNALESYAFNMKSAVEDEGLKGKISEADKKKVLDKCQE

VISWLDSNTLAEKEEFVHKREELERVCNPIISGLYQGAGAPGAGGFGAQAPKGGSGSGPTIEEV

D

-continued

Cattle HSPA1A Protein

SEQ ID NO: 45

MAKNMAIGIDLGTTYSCVGVFQHGKVEIIANDQGNRTTPSYVAFTDTERLIGDAAKNQVALNPQ

NTVFDAKRLIGRKFGDPVVQSDMKHWPFRVINDGDKPKVQVSYKGETKAFYPEEISSMVLTKMK

EIAEAYLGHPVTNAVITVPAYFNDSQRQATKDAGVIAGLNVLRIINEPTAAAIAYGLDRTGKGE

RNVLIFDLGGGTFDVSILTIDDGIFEVKATAGDTHLGGEDFDNRLVNHEVEEFKRKHKKDISQN

KRAVRRLRTACERAKRTLSSSTQASLEIDSLFEGIDFYTSITRARFEELCSDLFRSTLEPVEKA

LRDAKLDKAQIHDLVLVGGSTRIPKVQKLLQDFFNGRDLNKSINPDEAVAYGAAVQAAILMGDK

SENVQDLLLLDVAPLSLGLETAGGVMTALIKRNSTIPTKQTQIFTTYSDNQPGVLIQVYEGERA

MTRDNNLLGRFELSGIPPAPRGVPQIEVTFDIDANGILNVTATDKSTGKANKITITNDKGRLSK

EEIERMVQEAEKYKAEDEVQRERVSAKNALESYAFNMKSAVEDEGLKGKISEADKKKVLDKCQE

VISWLDANTLAEKDEFEHKRKELEQVCNPIISRLYQGAGGPGAGGFGAQGPKGGSGSGPTIEEV

D

Soluble neuropilin-1 polyadenylation signal

SEQ ID NO: 46

AAATAAAATACGAAATG

---

What is claimed is:

1. A construct comprising:

(i) a cytomegalovirus (CMV) enhancer;

(ii) a chicken β-actin (CBA) promoter;

(iii) a chimeric intron comprising the nucleic acid sequence of SEQ ID NO: 19;

(iv) a coding sequence comprising a first nucleic acid sequence encoding a Norrin Cystine Knot Growth Factor (NDP) protein; and (v) a polyadenylation sequence.

2. The construct of claim 1, wherein the first nucleic acid sequence encoding the NDP protein is an NDP gene.

3. The construct of claim 1, further comprising two adeno-associated virus (AAV) inverted terminal repeats (ITRs), wherein the two AAV ITRs flank the CMV enhancer and the polyadenylation sequence.

4. An AAV particle comprising a construct, wherein the construct comprises:

(i) a cytomegalovirus (CMV) enhancer;

(ii) a chicken β-actin (CBA) promoter;

(iii) a chimeric intron comprising the nucleic acid sequence of SEQ ID NO 19;

(iv) a coding sequence comprising a first nucleic acid sequence encoding a Norrin Cystine Knot Growth Factor (NDP) protein; and (v) a polyadenylation sequence.

5. A composition comprising a construct and a pharmaceutically acceptable carrier, diluent or excipient, wherein the construct comprises:

(i) a cytomegalovirus (CMV) enhancer;

(ii) a chicken β-actin (CBA) promoter;

(iii) a chimeric intron comprising the nucleic acid sequence of SEQ ID NO 19;

(iv) a coding sequence comprising a first nucleic acid sequence encoding a Norrin Cystine Knot Growth Factor (NDP) protein; and (v) a polyadenylation sequence.

6. A composition comprising an AAV particle and a pharmaceutically acceptable carrier, diluent or excipient, wherein the AAV particle comprises a construct, wherein the construct comprises:

(i) a cytomegalovirus (CMV) enhancer;

(ii) a chicken β-actin (CBA) promoter;

(iii) a chimeric intron comprising the nucleic acid sequence of SEQ ID NO: 19;

(iv) a coding sequence comprising a first nucleic acid sequence encoding a Norrin Cystine Knot Growth Factor (NDP) protein; and (v) a polyadenylation sequence.

7. The construct of claim 1, wherein the coding sequence further comprises a second nucleic acid sequence encoding a secretion signal protein.

8. The construct of claim 7, wherein the secretion signal protein comprises an NDP secretion signal protein.

9. The construct of claim 7, wherein the second nucleic acid sequence encoding the secretion signal protein is operably linked to the first nucleic acid sequence encoding the NDP protein.

10. The construct of claim 1, wherein the construct further comprises a 5' untranslated region (UTR).

11. The construct of claim 1, wherein the construct further comprises a 3' untranslated region (UTR).

12. The construct of claim 1, wherein the polyadenylation sequence is a bovine growth hormone polyadenylation (bGHpA) sequence.

13. The construct of claim 1, wherein the CMV enhancer comprises the nucleic acid sequence of SEQ ID NO: 17.

14. The construct of claim 1, wherein the CBA promoter comprises the nucleic acid sequence of SEQ ID NO: 18.

15. The construct of claim 10, wherein the 5' UTR comprises the nucleic acid sequence of SEQ ID NO: 14.

16. The construct of claim 8, wherein the NDP secretion signal protein comprises the amino acid sequence of SEQ ID NO: 5.

17. The construct of claim 8, wherein the NDP secretion signal protein is encoded by the nucleic acid sequence of SEQ ID NO: 6.

18. The construct of claim 1, wherein the NDP protein comprises the amino acid sequence of SEQ ID NO: 56.

19. The construct of claim 11, wherein the 3' UTR sequence comprises the nucleic acid sequence of SEQ ID NO: 15.

20. The construct of claim 12, wherein the bGHpA sequence comprises the nucleic acid sequence of SEQ ID NO: 23.

21. The AAV particle of claim 4, further comprising a capsid, wherein the capsid is or is derived from an AAV2 capsid.

22. The AAV particle of claim 4, further comprising a capsid, wherein the capsid is or is derived from an Anc80 capsid.

23. A kit comprising a composition, wherein the composition comprises (a) a construct or (b) an AAV particle comprising the construct, wherein the construct comprises:

(i) a cytomegalovirus (CMV) enhancer;

(ii) a chicken β-actin (CBA) promoter;

(iii) a chimeric intron comprising the nucleic acid sequence of SEQ ID NO: 19;

(iv) a coding sequence comprising a first nucleic acid sequence encoding a Norrin Cystine Knot Growth Factor (NDP) protein; and (v) a polyadenylation sequence.

24. The composition of claim 6, wherein the composition is a pharmaceutical composition.

25. The kit of claim 23, wherein the kit further comprises instructions for performing a method.

26. The kit of claim 25, wherein the method is a method of introducing the composition into the inner ear of a subject.

27. The kit of claim 25, wherein the method is a method of introducing the composition into the cochlea of a subject.

28. The kit of claim 25, wherein the method is a method of introducing the composition into a mammalian cell of a subject.

29. The kit of claim 28, wherein the mammalian cell is a cochlear inner hair cell or a cochlear outer hair cell.

30. The kit of claim 25, wherein the method is a method of treatment.

31. The kit of claim 25, wherein the method is a method of treating deafness or hearing loss.

32. The kit of claim 23, wherein the kit further comprises a pre-loaded syringe or a vial, wherein the pre-loaded syringe or the vial comprises the composition, wherein the composition is formulated as an aqueous composition, a solid composition, or a lyophilized composition.

33. The composition of claim 24, further comprising a pharmaceutically acceptable carrier.

* * * * *

SEQUENCE LISTING

<160> NUMBER OF SEQ ID NOS: 174

<210> SEQ ID NO 1
<211> LENGTH: 109
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 1

```
Lys Thr Asp Ser Ser Phe Ile Met Asp Ser Asp Pro Arg Arg Cys Met
1               5                   10                  15

Arg His His Tyr Val Asp Ser Ile Ser His Pro Leu Tyr Lys Cys Ser
            20                  25                  30

Ser Lys Met Val Leu Leu Ala Arg Cys Glu Gly His Cys Ser Gln Ala
        35                  40                  45

Ser Arg Ser Glu Pro Leu Val Ser Phe Ser Thr Val Leu Lys Gln Pro
    50                  55                  60

Phe Arg Ser Ser Cys His Cys Cys Arg Pro Gln Thr Ser Lys Leu Lys
65                  70                  75                  80

Ala Leu Arg Leu Arg Cys Ser Gly Gly Met Arg Leu Thr Ala Thr Tyr
                85                  90                  95

Arg Tyr Ile Leu Ser Cys His Cys Glu Glu Cys Asn Ser
            100                 105
```

<210> SEQ ID NO 2
<211> LENGTH: 330
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 2

```
aaaacggaca gctcattcat aatggactcg gaccctcgac gctgcatgag gcaccactat      60

gtggattcta tcagtcaccc attgtacaag tgtagctcaa agatggtgct cctggccagg     120
```

```
tgcgaggggc actgcagcca ggcgtcacgc tccgagcctt tggtgtcgtt cagcactgtc    180

ctcaagcaac ccttccgttc ctcctgtcac tgctgccggc cccagacttc caagctgaag    240

gcactgcggc tgcgatgctc agggggcatg cgactcactg ccacctaccg atacatcctc    300

tcctgtcact gcgaggaatg caattcctaa                                     330


<210> SEQ ID NO 3
<211> LENGTH: 641
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Met Ala Lys Ala Ala Ala Ile Gly Ile Asp Leu Gly Thr Thr Tyr Ser
1               5                   10                  15

Cys Val Gly Val Phe Gln His Gly Lys Val Glu Ile Ile Ala Asn Asp
            20                  25                  30

Gln Gly Asn Arg Thr Thr Pro Ser Tyr Val Ala Phe Thr Asp Thr Glu
        35                  40                  45

Arg Leu Ile Gly Asp Ala Ala Lys Asn Gln Val Ala Leu Asn Pro Gln
    50                  55                  60

Asn Thr Val Phe Asp Ala Lys Arg Leu Ile Gly Arg Lys Phe Gly Asp
65                  70                  75                  80

Pro Val Val Gln Ser Asp Met Lys His Trp Pro Phe Gln Val Ile Asn
                85                  90                  95

Asp Gly Asp Lys Pro Lys Val Gln Val Ser Tyr Lys Gly Glu Thr Lys
            100                 105                 110

Ala Phe Tyr Pro Glu Glu Ile Ser Ser Met Val Leu Thr Lys Met Lys
        115                 120                 125

Glu Ile Ala Glu Ala Tyr Leu Gly Tyr Pro Val Thr Asn Ala Val Ile
    130                 135                 140

Thr Val Pro Ala Tyr Phe Asn Asp Ser Gln Arg Gln Ala Thr Lys Asp
145                 150                 155                 160

Ala Gly Val Ile Ala Gly Leu Asn Val Leu Arg Ile Ile Asn Glu Pro
                165                 170                 175

Thr Ala Ala Ala Ile Ala Tyr Gly Leu Asp Arg Thr Gly Lys Gly Glu
            180                 185                 190

Arg Asn Val Leu Ile Phe Asp Leu Gly Gly Gly Thr Phe Asp Val Ser
        195                 200                 205

Ile Leu Thr Ile Asp Asp Gly Ile Phe Glu Val Lys Ala Thr Ala Gly
    210                 215                 220

Asp Thr His Leu Gly Gly Glu Asp Phe Asp Asn Arg Leu Val Asn His
225                 230                 235                 240

Phe Val Glu Glu Phe Lys Arg Lys His Lys Lys Asp Ile Ser Gln Asn
                245                 250                 255

Lys Arg Ala Val Arg Arg Leu Arg Thr Ala Cys Glu Arg Ala Lys Arg
            260                 265                 270

Thr Leu Ser Ser Ser Thr Gln Ala Ser Leu Glu Ile Asp Ser Leu Phe
        275                 280                 285

Glu Gly Ile Asp Phe Tyr Thr Ser Ile Thr Arg Ala Arg Phe Glu Glu
    290                 295                 300

Leu Cys Ser Asp Leu Phe Arg Ser Thr Leu Glu Pro Val Glu Lys Ala
305                 310                 315                 320
```

```
Leu Arg Asp Ala Lys Leu Asp Lys Ala Gln Ile His Asp Leu Val Leu
                325                 330                 335

Val Gly Gly Ser Thr Arg Ile Pro Lys Val Gln Lys Leu Leu Gln Asp
            340                 345                 350

Phe Phe Asn Gly Arg Asp Leu Asn Lys Ser Ile Asn Pro Asp Glu Ala
        355                 360                 365

Val Ala Tyr Gly Ala Ala Val Gln Ala Ala Ile Leu Met Gly Asp Lys
    370                 375                 380

Ser Glu Asn Val Gln Asp Leu Leu Leu Leu Asp Val Ala Pro Leu Ser
385                 390                 395                 400

Leu Gly Leu Glu Thr Ala Gly Gly Val Met Thr Ala Leu Ile Lys Arg
                405                 410                 415

Asn Ser Thr Ile Pro Thr Lys Gln Thr Gln Ile Phe Thr Thr Tyr Ser
            420                 425                 430

Asp Asn Gln Pro Gly Val Leu Ile Gln Val Tyr Glu Gly Glu Arg Ala
        435                 440                 445

Met Thr Lys Asp Asn Asn Leu Leu Gly Arg Phe Glu Leu Ser Gly Ile
    450                 455                 460

Pro Pro Ala Pro Arg Gly Val Pro Gln Ile Glu Val Thr Phe Asp Ile
465                 470                 475                 480

Asp Ala Asn Gly Ile Leu Asn Val Thr Ala Thr Asp Lys Ser Thr Gly
                485                 490                 495

Lys Ala Asn Lys Ile Thr Ile Thr Asn Asp Lys Gly Arg Leu Ser Lys
            500                 505                 510

Glu Glu Ile Glu Arg Met Val Gln Glu Ala Glu Lys Tyr Lys Ala Glu
        515                 520                 525

Asp Glu Val Gln Arg Glu Arg Val Ser Ala Lys Asn Ala Leu Glu Ser
    530                 535                 540

Tyr Ala Phe Asn Met Lys Ser Ala Val Glu Asp Glu Gly Leu Lys Gly
545                 550                 555                 560

Lys Ile Ser Glu Ala Asp Lys Lys Lys Val Leu Asp Lys Cys Gln Glu
                565                 570                 575

Val Ile Ser Trp Leu Asp Ala Asn Thr Leu Ala Glu Lys Asp Glu Phe
            580                 585                 590

Glu His Lys Arg Lys Glu Leu Glu Gln Val Cys Asn Pro Ile Ile Ser
        595                 600                 605

Gly Leu Tyr Gln Gly Ala Gly Gly Pro Gly Pro Gly Gly Phe Gly Ala
    610                 615                 620

Gln Gly Pro Lys Gly Gly Ser Gly Ser Gly Pro Thr Ile Glu Glu Val
625                 630                 635                 640

Asp
```

<210> SEQ ID NO 4
<211> LENGTH: 1926
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 4

```
atggccaaag ccgcggcgat cggcatcgac ctgggcacca cctactcctg cgtgggggtg     60

ttccaacacg gcaaggtgga gatcatcgcc aacgaccagg gcaaccgcac cacccccagc    120

tacgtggcct tcacggacac cgagcggctc atcggggatg cggccaagaa ccaggtggcg    180
```

```
ctgaacccgc agaacaccgt gtttgacgcg aagcggctga tcggccgcaa gttcggcgac    240

ccggtggtgc agtcggacat gaagcactgg cctttccagg tgatcaacga cggagacaag    300

cccaaggtgc aggtgagcta caagggggag accaaggcat tctaccccga ggagatctcg    360

tccatggtgc tgaccaagat gaaggagatc gccgaggcgt acctgggcta cccggtgacc    420

aacgcggtga tcaccgtgcc ggcctacttc aacgactcgc agcgccaggc caccaaggat    480

gcgggtgtga tcgcggggct caacgtgctg cggatcatca acgagcccac ggccgccgcc    540

atcgcctacg gcctggacag aacgggcaag gggagcgca acgtgctcat ctttgacctg    600

ggcgggggca ccttcgacgt gtccatcctg acgatcgacg acggcatctt cgaggtgaag    660

gccacggccg gggacaccca cctgggtggg gaggactttg acaacaggct ggtgaaccac    720

ttcgtggagg agttcaagag aaaacacaag aaggacatca gccagaacaa gcgagccgtg    780

aggcggctgc gcaccgcctg cgagagggcc aagaggaccc tgtcgtccag cacccaggcc    840

agcctggaga tcgactccct gtttgagggc atcgacttct acacgtccat caccagggcg    900

aggttcgagg agctgtgctc cgacctgttc cgaagcaccc tggagcccgt ggagaaggct    960

ctgcgcgacg ccaagctgga caaggcccag attcacgacc tggtcctggt cgggggctcc   1020

acccgcatcc ccaaggtgca gaagctgctg caggacttct tcaacgggcg cgacctgaac   1080

aagagcatca accccgacga ggctgtggcc tacggggcgg cggtgcaggc ggccatcctg   1140

atgggggaca agtccgagaa cgtgcaggac ctgctgctgc tggacgtggc tcccctgtcg   1200

ctggggctgg agacggccgg aggcgtgatg actgccctga tcaagcgcaa ctccaccatc   1260

cccaccaagc agacgcagat cttcaccacc tactccgaca accaacccgg ggtgctgatc   1320

caggtgtacg agggcgagag ggccatgacg aaagacaaca atctgttggg gcgcttcgag   1380

ctgagcggca tccctccggc ccccaggggc gtgccccaga tcgaggtgac cttcgacatc   1440

gatgccaacg gcatcctgaa cgtcacggcc acggacaaga gcaccggcaa ggccaacaag   1500

atcaccatca ccaacgacaa gggccgcctg agcaaggagg agatcgagcg catggtgcag   1560

gaggcggaga agtacaaagc ggaggacgag gtgcagcgcg agagggtgtc agccaagaac   1620

gccctggagt cctacgcctt caacatgaag agcgccgtgg aggatgaggg gctcaagggc   1680

aagatcagcg aggcggacaa gaagaaggtt ctggacaagt gtcaagaggt catctcgtgg   1740

ctggacgcca acaccttggc cgagaaggac gagtttgagc acaagaggaa ggagctggag   1800

caggtgtgta accccatcat cagcggactg taccagggtg ccggtggtcc cgggcctggg   1860

ggcttcgggg ctcagggtcc caagggaggg tctgggtcag gccccaccat tgaggaggtg   1920

gattag                                                              1926
```

<210> SEQ ID NO 5
<211> LENGTH: 24
<212> TYPE: PRT
<213> ORGANISM: Artificial Sequence
<220> FEATURE:
<223> OTHER INFORMATION: Description of Artificial Sequence: Synthetic peptide

<400> SEQUENCE: 5

```
Met Arg Lys His Val Leu Ala Ala Ser Phe Ser Met Leu Ser Leu Leu
1               5                   10                  15

Val Ile Met Gly Asp Thr Asp Ser
            20
```

<210> SEQ ID NO 6
<211> LENGTH: 69
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 6
agaaaacatg tactagctgc atccttttct atgctctccc tgctggtgat aatgggagat 60
acagacagt 69

<210> SEQ ID NO 7
<211> LENGTH: 24
<212> TYPE: PRT
<213> ORGANISM: Homo sapiens

<400> SEQUENCE: 7

Met Arg Lys His Val Leu Ala Ala Ser Phe Ser Met Leu Ser Leu Leu
1 5 10 15

Val Ile Met Gly Asp Thr Asp Ser
20

<210> SEQ ID NO 8
<211> LENGTH: 72
<212> TYPE: DNA
<213> ORGANISM: Homo sapiens

<400> SEQUENCE: 8
atgagaaaac atgtactagc tgcatccttt tctatgctct ccctgctggt gataatggga 60
gatacagaca gt 72

<210> SEQ ID NO 9
<211> LENGTH: 4185
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 9
cctgcaggca gctgcgcgct cgctcgctca ctgaggccgc ccgggcgtcg ggcgaccttt 60
ggtcgcccgg cctcagtgag cgagcgagcg cgcagagagg gagtggccaa ctccatcact 120
aggggttcct gcggccgcac gcgtgacatt gattattgac tagttattaa tagtaatcaa 180
ttacggggtc attagttcat agcccatata tggagttccg cgttacataa cttacggtaa 240
atggcccgcc tggctgaccg cccaacgacc cccgcccatt gacgtcaata atgacgtatg 300
ttcccatagt aacgccaata gggactttcc attgacgtca atgggtggac tatttacggt 360
aaactgccca cttggcagta catcaagtgt atcatatgcc aagtacgccc cctattgacg 420
tcaatgacgg taaatggccc gcctggcatt atgcccagta catgacctta tgggactttc 480
ctacttggca gtacatctac gtattagtca tcgctattac catgggtcga ggtgagcccc 540
acgttctgct tcactctccc catctccccc ccctccccac ccccaatttt gtatttattt 600 atttttaat tattttgtgc agcgatgggg gcgggggggg ggggggcgcg cgccaggcgg 660
ggcggggcgg ggcgaggggc ggggcggggc gaggcggaga ggtgcggcgg cagccaatca 720
gagcggcgcg ctccgaaagt ttccttttat ggcgaggcgg cggcggcggc ggccctataa 780
aaagcgaagc gcgcggcggg cgggagtcgc tgcgttgcct tcgccccgtg ccccgctccg 840

```
cgccgcctcg cgccgcccgc cccggctctg actgaccgcg ttactcccac aggtgagcgg    900
gcgggacggc ccttctcctc cgggctgtaa ttagcgcttg gtttaatgac ggctcgtttc    960
ttttctgtgg ctgcgtgaaa gccttaaagg gctccgggag ggccctttgt gcggggggga   1020
gcggctcggg gggtgcgtgc gtgtgtgtgt gcgtggggag cgccgcgtgc ggcccgcgct   1080
gcccggcggc tgtgagcgct gcgggcgcgg cgcggggctt tgtgcgctcc gcgtgtgcgc   1140
gaggggagcg cggccggggg cggtgccccg cggtgcgggg gggctgcgag gggaacaaag   1200
gctgcgtgcg gggtgtgtgc gtgggggggt gagcaggggg tgtgggcgcg gcggtcgggc   1260
tgtaaccccc ccctgcaccc ccctccccga gttgctgagc acggcccggc ttcgggtgcg   1320
gggctccgtg cggggcgtgg cgcggggctc gccgtgccgg gcggggggtg gcggcaggtg   1380
ggggtgccgg gcggggcggg gccgcctcgg gccggggagg gctcggggga ggggcgcggc   1440
ggcccccgga gcgccggcgg ctgtcgaggc gcggcgagcc gcagccattg ccttttatgg   1500
taatcgtgcg agagggcgca gggacttcct ttgtcccaaa tctgtgcgga gccgaaatct   1560
gggaggcgcc gccgcacccc ctctagcggg cgcggggcga agcggtgcgg cgccggcagg   1620
aaggaaatgg gcggggaggg ccttcgtgcg tcgccgcgcc gccgtcccct tctccctctc   1680
cagcctcggg gctgtccgcg gggggacggc tgccttcggg ggggacgggg cagggcgggg   1740
ttcggcttct ggcgtgtgac cggcggctct agagcctctg ctaaccatgt tcatgccttc   1800
ttctttttcc tacagctcct gggcaacgtg ctggttattg tgaccggtgc caccatgaga   1860
aaacatgtac tagctgcatc cttttctatg ctctccctgc tggtgataat gggagataca   1920
gacagtaaaa cggacagctc attcataatg gactcggacc ctcgacgctg catgaggcac   1980
cactatgtgg attctatcag tcacccattg tacaagtgta gctcaaagat ggtgctcctg   2040
gccaggtgcg aggggcactg cagccaggcg tcacgctccg agcctttggt gtcgttcagc   2100
actgtcctca agcaaccctt ccgttcctcc tgtcactgct gccggcccca gacttccaag   2160
ctgaaggcac tgcggctgcg atgctcaggg ggcatgcgac tcactgccac ctaccgatac   2220
atcctctcct gtcactgcga ggaatgcaat tcctaaggcc cgctgctgtg tgtggcttct   2280
ggatgggaca actgtagagg cagttcgacc agccagggaa agactggcaa gaaaagagtt   2340
aaggcaaaaa aggatgcaac aattctcccg ggactctgca tattctagta ataaagactc   2400
tacatgcttg ttgacagaga gagatactct gggaacttct ttgcagttcc catctccttt   2460
ctctggtaca atttcttttg gttcattttc agattcaggc attttccccc ttggctctca   2520
atgctgtttg ggtttccaac aattcagcat tagtgggaaa aagtgggccc tcatacacaa   2580
gcgtgtcagg ctgtcagtgt ttggtgcacg ctggggaaga atttactttg gaaagtagaa   2640
aagcccagct tttcctggga catcttctgt tattgttgat gttttttttt accttgtcat   2700
tttggtctaa ggttgccatt gctgctaaag gttaccgatt tcaaagtcca gataccaagc   2760
atgtggatat gtttagctac gtttactcac agccagcgaa ctgacattaa aataactaac   2820
aaacagattc ttttatgtga tgctggaact cttgacagct ataattatta ttcagaaatg   2880
actttttgaa agtaaaagca gcataaagaa tttgtcacag gaaggctgtc tcagataaat   2940
tatggtaaaa ttttgtaagg gagcagactt ttaaagactt gcacaaatac ggatcctgca   3000
ctgactctgg aaaaggcata tatgtactag tggcatggag aatgcaccat actcatgcat   3060
gcaaattaga caaccaagta tgaatctatt tgtgggtgtg ctatagcttt agccgtgtca   3120
cgggcatcat tctctaatat ccacttgtcc atgtgaaaca tgttgccaaa atggtggcct   3180
ggcttgtctt ctgaacgttt ggttcaaatg tgttttggtc ctggaggctc aaattttgag   3240
```

```
ttattcccac gttttgaaat aaaaagagta tattcaaaag agctcctgtg ccttctagtt   3300

gccagccatc tgttgtttgc ccctcccccg tgccttcctt gaccctggaa ggtgccactc   3360

ccactgtcct ttcctaataa aatgaggaaa ttgcatcgca ttgtctgagt aggtgtcatt   3420

ctattctggg gggtggggtg gggcaggaca gcaaggggga ggattgggaa gacaatagca   3480

ggcatgctgg ggatgcggtg ggctctatgg caattcagac tcccactaga agaaacagaa   3540

cttgaaaaaa ggataattgt ggtgaacacc tcaacccagt ggtccaaaaa ctgaaaaact   3600

ttgaccccga gcaccctcac acagatagac tactgaaaga aggagaaagg ggcacttact   3660

cagtctccct tatcagattg ccttacgagg agtactagac tccctcaagc aaatagatct   3720

cacttaccac ttgcaaaggt atactacttt cactctatta gacctatata tctgaccagg   3780

gtcctattcc aagacaactc ttctactctt ccagcagact cttatagaaa gaaagattct   3840

ggggtccaag aaagcagtac tttcttacaa ggagccaaaa aaaataacct ttctttagca   3900

cttctaacct tggagtgaac tggtgatcaa agagaggttg gctccctggg gacaagtgcc   3960

acaaattcag tcaactacaa gaaagttgag aacactgttc tcccgaaacc aagcttgaat   4020

tcagctgacg tgcctcggac cgctaggaac ccctagtgat ggagttggcc actccctctc   4080

tgcgcgctcg ctcgctcact gaggccgggc gaccaaaggt cgcccgacgc ccgggctttg   4140

cccgggcggc ctcagtgagc gagcgagcgc gcagctgcct gcagg                   4185
```

<210> SEQ ID NO 10
<211> LENGTH: 3662
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 10

```
cctgcaggca gctgcgcgct cgctcgctca ctgaggccgc ccgggcgtcg ggcgaccttt     60

ggtcgcccgg cctcagtgag cgagcgagcg cgcagagagg gagtggccaa ctccatcact    120

aggggttcct gcggccgcac gcgtgacatt gattattgac tagttattaa tagtaatcaa    180

ttacggggtc attagttcat agcccatata tggagttccg cgttacataa cttacggtaa    240

atggcccgcc tggctgaccg cccaacgacc cccgcccatt gacgtcaata atgacgtatg    300

ttcccatagt aacgccaata gggactttcc attgacgtca atgggtggac tatttacggt    360

aaactgccca cttggcagta catcaagtgt atcatatgcc aagtacgccc cctattgacg    420

tcaatgacgg taaatggccc gcctggcatt atgcccagta catgacctta tgggactttc    480

ctacttggca gtacatctac gtattagtca tcgctattac catgggtcga ggtgagcccc    540

acgttctgct tcactctccc catctccccc ccctccccac ccccaatttt gtatttattt    600

atttttaat tattttgtgc agcgatgggg gcgggggggg ggggggcgcg cgccaggcgg    660

ggcggggcgg ggcgaggggc ggggcggggc gaggcggaga ggtgcggcgg cagccaatca    720

gagcggcgcg ctccgaaagt ttccttttat ggcgaggcgg cggcggcggc ggccctataa    780

aaagcgaagc gcgcggcggg cgggagtcgc tgcgttgcct tcgccccgtg ccccgctccg    840

cgccgcctcg cgccgcccgc cccggctctg actgaccgcg ttactcccac aggtgagcgg    900

gcgggacggc ccttctcctc cgggctgtaa ttagcgcttg gtttaatgac ggctcgtttc    960

ttttctgtgg ctgcgtgaaa gccttaaagg gctccgggag ggccctttgt gcgggggga   1020

gcggctcggg gggtgcgtgc gtgtgtgtgt gcgtggggag cgccgcgtgc ggcccgcgct   1080
```

```
gcccggcggc tgtgagcgct gcgggcgcgg cgcggggctt tgtgcgctcc gcgtgtgcgc   1140
gaggggagcg cggccggggg cggtgccccg cggtgcgggg gggctgcgag gggaacaaag   1200
gctgcgtgcg gggtgtgtgc gtgggggggt gagcaggggg tgtgggcgcg gcggtcgggc   1260
tgtaaccccc ccctgcaccc ccctccccga gttgctgagc acggcccggc ttcgggtgcg   1320
gggctccgtg cggggcgtgg cgcggggctc gccgtgccgg gcgggggtg gcggcaggtg   1380
ggggtgccgg gcggggcggg gccgcctcgg gccggggagg gctcgggga ggggcgcggc   1440
ggcccccgga gcgccggcgg ctgtcgaggc gcggcgagcc gcagccattg ccttttatgg   1500
taatcgtgcg agagggcgca gggacttcct ttgtcccaaa tctgtgcgga gccgaaatct   1560
gggaggcgcc gccgcacccc ctctagcggg cgcggggcga agcggtgcgg cgccggcagg   1620
aaggaaatgg gcggggaggg ccttcgtgcg tcgccgcgcc gccgtcccct tctccctctc   1680
cagcctcggg gctgtccgcg gggggacggc tgccttcggg ggggacgggg cagggcgggg   1740
ttcggcttct ggcgtgtgac cggcggctct agagcctctg ctaaccatgt tcatgccttc   1800
ttcttttcc tacagctcct gggcaacgtg ctggttattg tgaccggtgc caccatgaga   1860
aaacatgtac tagctgcatc cttttctatg ctctccctgc tggtgataat gggagataca   1920
gacagtaaaa cggacagctc attcataatg gactcggacc ctcgacgctg catgaggcac   1980
cactatgtgg attctatcag tcacccattg tacaagtgta gctcaaagat ggtgctcctg   2040
gccaggtgcg aggggcactg cagccaggcg tcacgctccg agcctttggt gtcgttcagc   2100
actgtcctca agcaaccctt ccgttcctcc tgtcactgct gccggcccca gacttccaag   2160
ctgaaggcac tgcggctgcg atgctcaggg ggcatgcgac tcactgccac ctaccgatac   2220
atcctctcct gtcactgcga ggaatgcaat tcctaagagc tcctgtgcct tctagttgcc   2280
agccatctgt tgtttgcccc tcccccgtgc cttccttgac cctggaaggt gccactccca   2340
ctgtcctttc ctaataaaat gaggaaattg catcgcattg tctgagtagg tgtcattcta   2400
ttctgggggg tggggtgggg caggacagca agggggagga ttgggaagac aatagcaggc   2460
atgctgggga tgcggtgggc tctatgggtt gactaaagat tgaaccttat tcaaagttag   2520
actctctttg ttaaagacaa acaaaacttc caataattca gcaactaata gaaagactca   2580
acttgtgagc cactacttat taattgagaa tagtcactca gtctggcaaa atatattaga   2640
aagtgacact gagtttaaaa aagtgacacc tttgattctg aacagtgaac tttgagactg   2700
aaaaactaca gctttgaggc taaatacttg atcaaataaa actacttact caaaaaactg   2760
agtgaaagtc caacagaaaa aagagggccc acttccacca gtgacacaaa atccagattg   2820
atcgttcttt aagtgactat tcttgccaga atcagcaagg tggatacaaa ggactctgag   2880
aaagaactct ctgaactctg ggcaaggccc cagtccaaag caattagtat ccttaggacc   2940
agaaaaatct gtggaaggtc agaatttctt gtctgagaaa aacaaagcaa ttcagactcc   3000
cactagaaga aacagaactt gaaaaaagga taattgtggt gaacacctca acccagtggt   3060
ccaaaaactg aaaaactttg accccgagca ccctcacaca gatagactac tgaaagaagg   3120
agaaaggggc acttactcag tctcccttat cagattgcct tacgaggagt actagactcc   3180
ctcaagcaaa tagatctcac ttaccacttg caaaggtata ctactttcac tctattagac   3240
ctatatatct gaccagggtc ctattccaag acaactcttc tactcttcca gcagactctt   3300
atagaaagaa agattctggg gtccaagaaa gcagtacttt cttacaagga gccaaaaaaa   3360
ataacctttc tttagcactt ctaaccttgg agtgaactgg tgatcaaaga gaggttggct   3420
```

```
ccctggggac aagtgccaca aattcagtca actacaagaa agttgagaac actgttctcc   3480

cgaaaccaag cttgaattca gctgacgtgc ctcggaccgc taggaacccc tagtgatgga   3540

gttggccact ccctctctgc gcgctcgctc gctcactgag gccgggcgac caaaggtcgc   3600

ccgacgcccg ggctttgccc gggcggcctc agtgagcgag cgagcgcgca gctgcctgca   3660

gg                                                                   3662
```

<210> SEQ ID NO 11
<211> LENGTH: 4444
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 11

```
cctgcaggca gctgcgcgct cgctcgctca ctgaggccgc ccgggcgtcg ggcgaccttt     60

ggtcgcccgg cctcagtgag cgagcgagcg cgcagagagg gagtggccaa ctccatcact    120

aggggttcct gcggccgcac gcgtgacatt gattattgac tagttattaa tagtaatcaa    180

ttacggggtc attagttcat agcccatata tggagttccg cgttacataa cttacggtaa    240

atggcccgcc tggctgaccg cccaacgacc cccgcccatt gacgtcaata atgacgtatg    300

ttcccatagt aacgccaata gggactttcc attgacgtca atgggtggac tatttacggt    360

aaactgccca cttggcagta catcaagtgt atcatatgcc aagtacgccc cctattgacg    420

tcaatgacgg taaatggccc gcctggcatt atgcccagta catgacctta tgggactttc    480

ctacttggca gtacatctac gtattagtca tcgctattac catgggtcga ggtgagcccc    540

acgttctgct tcactctccc catctccccc ccctccccac ccccaatttt gtatttattt    600

atttttaat tattttgtgc agcgatgggg gcgggggggg gggggggcgcg cgccaggcgg    660

ggcggggcgg ggcgaggggc ggggcggggc gaggcggaga ggtgcggcgg cagccaatca    720

gagcggcgcg ctccgaaagt ttccttttat ggcgaggcgg cggcggcggc ggccctataa    780

aaagcgaagc gcgcggcggg cgggagtcgc tgcgttgcct tcgccccgtg ccccgctccg    840

cgccgcctcg cgccgcccgc cccggctctg actgaccgcg ttactcccac aggtgagcgg    900

gcgggacggc ccttctcctc cgggctgtaa ttagcgcttg gtttaatgac ggctcgtttc    960

ttttctgtgg ctgcgtgaaa gccttaaagg gctccgggag ggccctttgt gcgggggga   1020

gcggctcggg gggtgcgtgc gtgtgtgtgt gcgtggggag cgccgcgtgc ggcccgcgct   1080

gcccggcggc tgtgagcgct gcgggcgcgg cgcggggctt tgtgcgctcc gcgtgtgcgc   1140

gaggggagcg cggccggggg cggtgccccg cggtgcgggg gggctgcgag gggaacaaag   1200

gctgcgtgcg gggtgtgtgc gtggggggt gagcaggggg tgtgggcgcg gcggtcgggc   1260

tgtaaccccc ccctgcaccc ccctccccga gttgctgagc acggcccggc ttcgggtgcg   1320

gggctccgtg cggggcgtgg cgcggggctc gccgtgccgg gcggggggtg gcggcaggtg   1380

ggggtgccgg gcggggcggg gccgcctcgg gccggggagg gctcggggga ggggcgcggc   1440

ggcccccgga gcgccggcgg ctgtcgaggc gcggcgagcc gcagccattg ccttttatgg   1500

taatcgtgcg agagggcgca gggacttcct ttgtcccaaa tctgtgcgga gccgaaatct   1560

gggaggcgcc gccgcacccc ctctagcggg cgcggggcga agcggtgcgg cgccggcagg   1620

aaggaaatgg gcggggaggg ccttcgtgcg tcgccgcgcc gccgtcccct tctccctctc   1680

cagcctcggg gctgtccgcg gggggacggc tgccttcggg ggggacgggg cagggcgggg   1740
```

-continued

```
ttcggcttct ggcgtgtgac cggcggctct agagcctctg ctaaccatgt tcatgccttc   1800

ttctttttcc tacagctcct gggcaacgtg ctggttattg tgaccggtgc caccatgaga   1860

aaacatgtac tagctgcatc cttttctatg ctctccctgc tggtgataat gggagataca   1920

gacagtaaaa cggacagctc attcataatg gactcggacc ctcgacgctg catgaggcac   1980

cactatgtgg attctatcag tcacccattg tacaagtgta gctcaaagat ggtgctcctg   2040

gccaggtgcg aggggcactg cagccaggcg tcacgctccg agcctttggt gtcgttcagc   2100

actgtcctca agcaaccctt ccgttcctcc tgtcactgct gccggcccca gacttccaag   2160

ctgaaggcac tgcggctgcg atgctcaggg ggcatgcgac tcactgccac ctaccgatac   2220

atcctctcct gtcactgcga ggaatgcaat tccggctccg gagagggcag aggaagtctg   2280

ctaacatgcg gtgacgtcga ggagaatcct ggcccaatgg agagcgacga gagcggcctg   2340

cccgccatgg agatcgagtg ccgcatcacc ggcaccctga acggcgtgga gttcgagctg   2400

gtgggcggcg gagagggcac ccccgagcag ggccgcatga ccaacaagat gaagagcacc   2460

aaaggcgccc tgaccttcag cccctacctg ctgagccacg tgatgggcta cggcttctac   2520

cacttcggca cctaccccag cggctacgag aacccctcc tgcacgccat caacaacggc   2580

ggctacacca acacccgcat cgagaagtac gaggacggcg gcgtgctgca cgtgagcttc   2640

agctaccgct acgaggccgg ccgcgtgatc ggcgacttca aggtgatggg caccggcttc   2700

cccgaggaca gcgtgatctt caccgacaag atcatccgca gcaacgccac cgtggagcac   2760

ctgcacccca tgggcgataa cgatctggat ggcagcttca cccgcacctt cagcctgcgc   2820

gacggcggct actacagctc cgtggtggac agccacatgc acttcaagag cgccatccac   2880

cccagcatcc tgcagaacgg gggccccatg ttcgccttcc gccgcgtgga ggaggatcac   2940

agcaacaccg agctgggcat cgtggagtac cagcacgcct tcaagacccc ggatgcagat   3000

gccggtgaag aataaggccc gctgctgtgt gtggcttctg gatgggacaa ctgtagaggc   3060

agttcgacca gccagggaaa gactggcaag aaaagagtta aggcaaaaaa ggatgcaaca   3120

attctcccgg gactctgcat attctagtaa taaagactct acatgcttgt tgacagagag   3180

agatactctg ggaacttctt tgcagttccc atctcctttc tctggtacaa tttcttttgg   3240

ttcattttca gattcaggca ttttcccct tggctctcaa tgctgtttgg gtttccaaca   3300

attcagcatt agtgggaaaa agtgggccct catacacaag cgtgtcaggc tgtcagtgtt   3360

tggtgcacgc tggggaagaa tttactttgg aaagtagaaa agcccagctt ttcctgggac   3420

atcttctgtt attgttgatg ttttttttta ccttgtcatt ttggtctaag gttgccattg   3480

ctgctaaagg ttaccgattt caaagtccag ataccaagca tgtggatatg tttagctacg   3540

tttactcaca gccagcgaac tgacattaaa ataactaaca aacagattct tttatgtgat   3600

gctggaactc ttgacagcta taattattat tcagaaatga ctttttgaaa gtaaaagcag   3660

cataaagaat ttgtcacagg aaggctgtct cagataaatt atggtaaaat tttgtaaggg   3720

agcagacttt taaagacttg cacaaatacg gatcctgcac tgactctgga aaaggcatat   3780

atgtactagt ggcatggaga atgcaccata ctcatgcatg caaattagac aaccaagtat   3840

gaatctattt gtgggtgtgc tatagcttta gccgtgtcac gggcatcatt ctctaatatc   3900

cacttgtcca tgtgaaacat gttgccaaaa tggtggcctg gcttgtcttc tgaacgtttg   3960

gttcaaatgt gttttggtcc tggaggctca aattttgagt tattcccacg ttttgaaata   4020

aaaagagtat attcaaaaga gctcctgtgc cttctagttg ccagccatct gttgtttgcc   4080

cctcccccgt gccttccttg accctggaag gtgccactcc cactgtcctt tcctaataaa   4140
```

atgaggaaat tgcatcgcat tgtctgagta ggtgtcattc tattctgggg ggtggggtgg 4200
ggcaggacag caagggggag gattgggaag acaatagcag gcatgctggg gatgcggtgg 4260
gctctatgga agcttgaatt cagctgacgt gcctcggacc gctaggaacc cctagtgatg 4320
gagttggcca ctccctctct gcgcgctcgc tcgctcactg aggccgggcg accaaaggtc 4380
gcccgacgcc cgggctttgc ccgggcggcc tcagtgagcg agcgagcgcg cagctgcctg 4440
cagg 4444

<210> SEQ ID NO 12
<211> LENGTH: 4468
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 12
cctgcaggca gctgcgcgct cgctcgctca ctgaggccgc ccgggcgtcg ggcgaccttt 60
ggtcgcccgg cctcagtgag cgagcgagcg cgcagagagg gagtggccaa ctccatcact 120
aggggttcct gcggccgcac gcgtgacatt gattattgac tagttattaa tagtaatcaa 180
ttacggggtc attagttcat agcccatata tggagttccg cgttacataa cttacggtaa 240
atggcccgcc tggctgaccg cccaacgacc cccgcccatt gacgtcaata atgacgtatg 300
ttcccatagt aacgccaata gggactttcc attgacgtca atgggtggac tatttacggt 360
aaactgccca cttggcagta catcaagtgt atcatatgcc aagtacgccc cctattgacg 420
tcaatgacgg taaatggccc gcctggcatt atgcccagta catgacctta tgggactttc 480
ctacttggca gtacatctac gtattagtca tcgctattac catgggtcga ggtgagcccc 540
acgttctgct tcactctccc catctccccc ccctccccac ccccaatttt gtatttattt 600 atttttaat tattttgtgc agcgatgggg gcgggggggg ggggggcgcg cgccaggcgg 660
ggcggggcgg ggcgaggggc ggggcggggc gaggcggaga ggtgcggcgg cagccaatca 720
gagcggcgcg ctccgaaagt ttccttttat ggcgaggcgg cggcggcggc ggccctataa 780
aaagcgaagc gcgcggcggg cgggagtcgc tgcgttgcct tcgccccgtg ccccgctccg 840
cgccgcctcg cgccgcccgc cccggctctg actgaccgcg ttactcccac aggtgagcgg 900
gcgggacggc ccttctcctc cgggctgtaa ttagcgcttg gtttaatgac ggctcgtttc 960
ttttctgtgg ctgcgtgaaa gccttaaagg gctccgggag ggccctttgt gcgggggga 1020 gcggctcggg gggtgcgtgc gtgtgtgtgt gcgtggggag cgccgcgtgc ggcccgcgct 1080
gcccggcggc tgtgagcgct gcgggcgcgg cgcggggctt tgtgcgctcc gcgtgtgcgc 1140
gaggggagcg cggccggggg cggtgccccg cggtgcgggg gggctgcgag gggaacaaag 1200
gctgcgtgcg gggtgtgtgc gtgggggggt gagcaggggg tgtgggcgcg gcggtcgggc 1260
tgtaaccccc ccctgcaccc ccctccccga gttgctgagc acggcccggc ttcgggtgcg 1320
gggctccgtg cggggcgtgg cgcggggctc gccgtgccgg gcggggggtg gcggcaggtg 1380
ggggtgccgg gcggggcggg gccgcctcgg gccggggagg gctcggggga ggggcgcggc 1440
ggcccccgga gcgccggcgg ctgtcgaggc gcggcgagcc gcagccattg ccttttatgg 1500
taatcgtgcg agagggcgca gggacttcct ttgtcccaaa tctgtgcgga gccgaaatct 1560
gggaggcgcc gccgcacccc ctctagcggg cgcggggcga agcggtgcgg cgccggcagg 1620
aaggaaatgg gcggggaggg ccttcgtgcg tcgccgcgcc gccgtcccct tctccctctc 1680

```
cagcctcggg gctgtccgcg gggggacggc tgccttcggg ggggacgggg cagggcgggg   1740
ttcggcttct ggcgtgtgac cggcggctct agagcctctg ctaaccatgt tcatgccttc   1800
ttctttttcc tacagctcct gggcaacgtg ctggttattg tgaccggtgc caccatgaga   1860
aaacatgtac tagctgcatc cttttctatg ctctccctgc tggtgataat gggagataca   1920
gacagtaaaa cggacagctc attcataatg gactcggacc ctcgacgctg catgaggcac   1980
cactatgtgg attctatcag tcacccattg tacaagtgta gctcaaagat ggtgctcctg   2040
gccaggtgcg aggggcactg cagccaggcg tcacgctccg agcctttggt gtcgttcagc   2100
actgtcctca agcaaccctt ccgttcctcc tgtcactgct gccggcccca gacttccaag   2160
ctgaaggcac tgcggctgcg atgctcaggg ggcatgcgac tcactgccac ctaccgatac   2220
atcctctcct gtcactgcga ggaatgcaat tccggctccg gagagggcag aggaagtctg   2280
ctaacatgcg gtgacgtcga ggagaatcct ggcccaatgg tgagcaaggg cgaggagctg   2340
ttcaccgggg tggtgcccat cctggtcgag ctggacggcg acgtaaacgg ccacaagttc   2400
agcgtgtccg gcgagggcga gggcgatgcc acctacggca agctgaccct gaagttcatc   2460
tgcaccaccg gcaagctgcc cgtgccctgg cccaccctcg tgaccaccct gacctacggc   2520
gtgcagtgct tcagccgcta ccccgaccac atgaagcagc acgacttctt caagtccgcc   2580
atgcccgaag gctacgtcca ggagcgcacc atcttcttca aggacgacgg caactacaag   2640
acccgcgccg aggtgaagtt cgagggcgac accctggtga accgcatcga gctgaagggc   2700
atcgacttca aggaggacgg caacatcctg gggcacaagc tggagtacaa ctacaacagc   2760
cacaacgtct atatcatggc cgacaagcag aagaacggca tcaaggtgaa cttcaagatc   2820
cgccacaaca tcgaggacgg cagcgtgcag ctcgccgacc actaccagca gaacaccccc   2880
atcggcgacg gccccgtgct gctgcccgac aaccactacc tgagcaccca gtccgccctg   2940
agcaaagacc ccaacgagaa gcgcgatcac atggtcctgc tggagttcgt gaccgccgcc   3000
gggatcactc tcggcatgga cgagctgtac aagtaataag gcccgctgct gtgtgtggct   3060
tctggatggg acaactgtag aggcagttcg accagccagg gaaagactgg caagaaaaga   3120
gttaaggcaa aaaaggatgc aacaattctc ccgggactct gcatattcta gtaataaaga   3180
ctctacatgc ttgttgacag agagagatac tctgggaact tctttgcagt tcccatctcc   3240
tttctctggt acaatttctt ttggttcatt ttcagattca ggcattttcc cccttggctc   3300
tcaatgctgt ttgggtttcc aacaattcag cattagtggg aaaaagtggg ccctcataca   3360
caagcgtgtc aggctgtcag tgtttggtgc acgctgggga agaatttact ttggaaagta   3420
gaaaagccca gcttttcctg ggacatcttc tgttattgtt gatgtttttt tttaccttgt   3480
cattttggtc taaggttgcc attgctgcta aaggttaccg atttcaaagt ccagatacca   3540
agcatgtgga tatgtttagc tacgtttact cacagccagc gaactgacat taaaataact   3600
aacaaacaga ttcttttatg tgatgctgga actcttgaca gctataatta ttattcagaa   3660
atgacttttt gaaagtaaaa gcagcataaa gaatttgtca caggaaggct gtctcagata   3720
aattatggta aaattttgta agggagcaga cttttaaaga cttgcacaaa tacggatcct   3780
gcactgactc tggaaaaggc atatatgtac tagtggcatg gagaatgcac catactcatg   3840
catgcaaatt agacaaccaa gtatgaatct atttgtgggt gtgctatagc tttagccgtg   3900
tcacgggcat cattctctaa tatccacttg tccatgtgaa acatgttgcc aaaatggtgg   3960
cctggcttgt cttctgaacg tttggttcaa atgtgttttg gtcctggagg ctcaaatttt   4020
```

```
gagttattcc cacgttttga aataaaaaga gtatattcaa aagagctcct gtgccttcta   4080

gttgccagcc atctgttgtt tgcccctccc ccgtgccttc cttgaccctg gaaggtgcca   4140

ctcccactgt cctttcctaa taaaatgagg aaattgcatc gcattgtctg agtaggtgtc   4200

attctattct ggggggtggg gtggggcagg acagcaaggg ggaggattgg gaagacaata   4260

gcaggcatgc tggggatgcg gtgggctcta tggaagcttg aattcagctg acgtgcctcg   4320

gaccgctagg aacccctagt gatggagttg gccactccct ctctgcgcgc tcgctcgctc   4380

actgaggccg ggcgaccaaa ggtcgcccga cgcccgggct ttgcccgggc ggcctcagtg   4440

agcgagcgag cgcgcagctg cctgcagg                                      4468
```

<210> SEQ ID NO 13
<211> LENGTH: 4764
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 13

```
cctgcaggca gctgcgcgct cgctcgctca ctgaggccgc ccgggcgtcg ggcgaccttt     60

ggtcgcccgg cctcagtgag cgagcgagcg cgcagagagg gagtggccaa ctccatcact    120

aggggttcct gcggccgcac gcgtgacatt gattattgac tagttattaa tagtaatcaa    180

ttacggggtc attagttcat agcccatata tggagttccg cgttacataa cttacggtaa    240

atggcccgcc tggctgaccg cccaacgacc cccgcccatt gacgtcaata atgacgtatg    300

ttcccatagt aacgccaata gggactttcc attgacgtca atgggtggac tatttacggt    360

aaactgccca cttggcagta catcaagtgt atcatatgcc aagtacgccc cctattgacg    420

tcaatgacgg taaatggccc gcctggcatt atgcccagta catgacctta tgggactttc    480

ctacttggca gtacatctac gtattagtca tcgctattac catgggtcga ggtgagcccc    540

acgttctgct tcactctccc catctccccc ccctccccac ccccaatttt gtatttattt    600

atttttaat tattttgtgc agcgatgggg gcgggggggg ggggggcgcg cgccaggcgg    660

ggcggggcgg ggcgaggggc ggggcggggc gaggcggaga ggtgcggcgg cagccaatca    720

gagcggcgcg ctccgaaagt ttccttttat ggcgaggcgg cggcggcggc ggccctataa    780

aaagcgaagc gcgcggcggg cgggagtcgc tgcgttgcct tcgccccgtg ccccgctccg    840

cgccgcctcg cgccgcccgc cccggctctg actgaccgcg ttactcccac aggtgagcgg    900

gcgggacggc ccttctcctc cgggctgtaa ttagcgcttg gtttaatgac ggctcgtttc    960

ttttctgtgg ctgcgtgaaa gccttaaagg gctccgggag ggccctttgt gcgggggga   1020

gcggctcggg gggtgcgtgc gtgtgtgtgt gcgtggggag cgccgcgtgc ggcccgcgct   1080

gcccggcggc tgtgagcgct gcgggcgcgg cgcggggctt tgtgcgctcc gcgtgtgcgc   1140

gaggggagcg cggccggggg cggtgccccg cggtgcgggg gggctgcgag gggaacaaag   1200

gctgcgtgcg gggtgtgtgc gtgggggggt gagcaggggg tgtgggcgcg gcggtcgggc   1260

tgtaaccccc ccctgcaccc ccctccccga gttgctgagc acggcccggc ttcgggtgcg   1320

gggctccgtg cggggcgtgg cgcggggctc gccgtgccgg gcgggggtg gcggcaggtg   1380

ggggtgccgg gcggggcggg gccgcctcgg gccggggagg gctcggggga ggggcgcggc   1440

ggcccccgga gcgccggcgg ctgtcgaggc gcggcgagcc gcagccattg ccttttatgg   1500

taatcgtgcg agagggcgca gggacttcct ttgtcccaaa tctgtgcgga gccgaaatct   1560
```

-continued

```
gggaggcgcc gccgcacccc ctctagcggg cgcggggcga agcggtgcgg cgccggcagg   1620
aaggaaatgg gcggggaggg ccttcgtgcg tcgccgcgcc gccgtcccct tctccctctc   1680
cagcctcggg gctgtccgcg gggggacggc tgccttcggg ggggacgggg cagggcgggg   1740
ttcggcttct ggcgtgtgac cggcggctct agagcctctg ctaaccatgt tcatgccttc   1800
ttcttttcc tacagctcct gggcaacgtg ctggttattg tgaccggtaa gatgctccgt    1860
ggaagggagc cgagcggtgg gcagaggctg agtccccgat aacgagcgcc tcacatttcc   1920
gtggcattcc catttgctag tgcgctgctg cggccgcacg cctgattgat atatgactgc   1980
aatggcactt ttccatttga cattctctct ctctctctcc ctctctctct ctccctctct   2040
ctctccctct ctctctctcc ctgtgtcgct taaacaacag tcctaacttt tgtgtgttgc   2100
aaatataaaa ggcaagccat gtgacagagg gacagaagaa caaaagcatt tggaagtaac   2160
aggacctctt tctagctctc agaaaagtct gagaagaaag gagccctgcg ttcccctaag   2220
ctgtgcagca gatactgtga tgatggattg caagtgcaaa gagtaagaca aaactccagc   2280
acataaagga caatgacaac cagaaagctt cagcccgatc ctgccctttc cttgaacggg   2340
actggatcct aggaggtgaa gccatttcca attttttgtc ctctgcctcc ctctgctgtt   2400
cttctagaga agtttttcct tacaacagcc accatgagaa aacatgtact agctgcatcc   2460
ttttctatgc tctccctgct ggtgataatg ggagatacag acagtaaaac ggacagctca   2520
ttcataatgg actcggaccc tcgacgctgc atgaggcacc actatgtgga ttctatcagt   2580
cacccattgt acaagtgtag ctcaaagatg gtgctcctgg ccaggtgcga ggggcactgc   2640
agccaggcgt cacgctccga gcctttggtg tcgttcagca ctgtcctcaa gcaacccttc   2700
cgttcctcct gtcactgctg ccggccccag acttccaagc tgaaggcact gcggctgcga   2760
tgctcagggg gcatgcgact cactgccacc taccgataca tcctctcctg tcactgcgag   2820
gaatgcaatt cctaaggccc gctgctgtgt gtggcttctg gatgggacaa ctgtagaggc   2880
agttcgacca gccagggaaa gactggcaag aaaagagtta aggcaaaaaa ggatgcaaca   2940
attctcccgg gactctgcat attctagtaa taaagactct acatgcttgt tgacagagag   3000
agatactctg ggaacttctt tgcagttccc atctcctttc tctggtacaa tttcttttgg   3060
ttcattttca gattcaggca ttttcccccct tggctctcaa tgctgtttgg gtttccaaca  3120
attcagcatt agtgggaaaa agtgggccct catacacaag cgtgtcaggc tgtcagtgtt   3180
tggtgcacgc tggggaagaa tttactttgg aaagtagaaa agcccagctt ttcctgggac   3240
atcttctgtt attgttgatg ttttttttta ccttgtcatt ttggtctaag gttgccattg   3300
ctgctaaagg ttaccgattt caaagtccag ataccaagca tgtggatatg tttagctacg   3360
tttactcaca gccagcgaac tgacattaaa ataactaaca aacagattct tttatgtgat   3420
gctggaactc ttgacagcta taattattat tcagaaatga ctttttgaaa gtaaaagcag   3480
cataaagaat ttgtcacagg aaggctgtct cagataaatt atggtaaaat tttgtaaggg   3540
agcagacttt taaagacttg cacaaatacg gatcctgcac tgactctgga aaaggcatat   3600
atgtactagt ggcatggaga atgcaccata ctcatgcatg caaattagac aaccaagtat   3660
gaatctattt gtgggtgtgc tatagcttta gccgtgtcac gggcatcatt ctctaatatc   3720
cacttgtcca tgtgaaacat gttgccaaaa tggtggcctg gcttgtcttc tgaacgtttg   3780
gttcaaatgt gttttggtcc tggaggctca aattttgagt tattcccacg ttttgaaata   3840
aaaagagtat attcaaaaga gctcctgtgc cttctagttg ccagccatct gttgtttgcc   3900
cctcccccgt gccttccttg accctggaag gtgccactcc cactgtcctt tcctaataaa   3960
```

```
atgaggaaat tgcatcgcat tgtctgagta ggtgtcattc tattctgggg ggtggggtgg   4020

ggcaggacag caagggggag gattgggaag acaatagcag gcatgctggg gatgcggtgg   4080

gctctatggc aattcagact cccactagaa gaaacagaac ttgaaaaaag gataattgtg   4140

gtgaacacct caacccagtg gtccaaaaac tgaaaaactt tgaccccgag caccctcaca   4200

cagatagact actgaaagaa ggagaaaggg gcacttactc agtctccctt atcagattgc   4260

cttacgagga gtactagact ccctcaagca aatagatctc acttaccact tgcaaaggta   4320

tactactttc actctattag acctatatat ctgaccaggg tcctattcca agacaactct   4380

tctactcttc cagcagactc ttatagaaag aaagattctg ggtccaaga aagcagtact   4440

ttcttacaag gagccaaaaa aaataacctt tctttagcac ttctaacctt ggagtgaact   4500

ggtgatcaaa gagaggttgg ctccctgggg acaagtgcca caaattcagt caactacaag   4560

aaagttgaga acactgttct cccgaaacca agcttgaatt cagctgacgt gcctcggacc   4620

gctaggaacc cctagtgatg gagttggcca ctccctctct gcgcgctcgc tcgctcactg   4680

aggccgggcg accaaaggtc gcccgacgcc cgggctttgc ccgggcggcc tcagtgagcg   4740

agcgagcgcg cagctgcctg cagg                                          4764
```

<210> SEQ ID NO 14
<211> LENGTH: 579
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 14

```
aagatgctcc gtggaaggga gccgagcggt gggcagaggc tgagtccccg ataacgagcg     60

cctcacattt ccgtggcatt cccatttgct agtgcgctgc tgcggccgca cgcctgattg    120

atatatgact gcaatggcac ttttccattt gacattctct ctctctctct ccctctctct    180

ctctccctct ctctctccct ctctctctct ccctgtgtcg cttaaacaac agtcctaact    240

tttgtgtgtt gcaaatataa aaggcaagcc atgtgacaga gggacagaag aacaaaagca    300

tttggaagta acaggacctc tttctagctc tcagaaaagt ctgagaagaa aggagccctg    360

cgttccccta agctgtgcag cagatactgt gatgatggat tgcaagtgca aagagtaaga    420

caaaactcca gcacataaag gacaatgaca accagaaagc ttcagcccga tcctgccctt    480

tccttgaacg ggactggatc ctaggaggtg aagccatttc caattttttg tcctctgcct    540

ccctctgctg ttcttctaga gaagtttttc cttacaaca                           579
```

<210> SEQ ID NO 15
<211> LENGTH: 1023
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 15

```
ggcccgctgc tgtgtgtggc ttctggatgg gacaactgta gaggcagttc gaccagccag     60

ggaaagactg gcaagaaaag agttaaggca aaaaaggatg caacaattct cccgggactc    120

tgcatattct agtaataaag actctacatg cttgttgaca gagagagata ctctgggaac    180

ttctttgcag ttcccatctc ctttctctgg tacaatttct tttggttcat tttcagattc    240
```

aggcattttc cccettggct ctcaatgctg tttgggtttc caacaattca gcattagtgg 300
gaaaaagtgg gccctcatac acaagcgtgt caggctgtca gtgtttggtg cacgctgggg 360
aagaatttac tttggaaagt agaaaagccc agcttttcct gggacatctt ctgttattgt 420
tgatgttttt ttttaccttg tcattttggt ctaaggttgc cattgctgct aaaggttacc 480
gatttcaaag tccagatacc aagcatgtgg atatgtttag ctacgtttac tcacagccag 540
cgaactgaca ttaaaataac taacaaacag attcttttat gtgatgctgg aactcttgac 600
agctataatt attattcaga aatgactttt tgaaagtaaa agcagcataa agaatttgtc 660
acaggaaggc tgtctcagat aaattatggt aaaattttgt aagggagcag acttttaaag 720
acttgcacaa atacggatcc tgcactgact ctggaaaagg catatatgta ctagtggcat 780
ggagaatgca ccatactcat gcatgcaaat tagacaacca agtatgaatc tatttgtggg 840
tgtgctatag ctttagccgt gtcacgggca tcattctcta atatccactt gtccatgtga 900
aacatgttgc caaaatggtg gcctggcttg tcttctgaac gtttggttca aatgtgtttt 960
ggtcctggag gctcaaattt tgagttattc ccacgttttg aaataaaaag agtatattca 1020
aaa 1023

<210> SEQ ID NO 16
<211> LENGTH: 130
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 16
cctgcaggca gctgcgcgct cgctcgctca ctgaggccgc ccgggcgtcg ggcgaccttt 60
ggtcgcccgg cctcagtgag cgagcgagcg cgcagagagg gagtggccaa ctccatcact 120
aggggttcct 130

<210> SEQ ID NO 17
<211> LENGTH: 381
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 17
gacattgatt attgactagt tattaatagt aatcaattac ggggtcatta gttcatagcc 60
catatatgga gttccgcgtt acataactta cggtaaatgg cccgcctggc tgaccgccca 120
acgacccccg cccattgacg tcaataatga cgtatgttcc catagtaacg ccaataggga 180
ctttccattg acgtcaatgg gtggactatt tacggtaaac tgcccacttg gcagtacatc 240
aagtgtatca tatgccaagt acgcccccta ttgacgtcaa tgacggtaaa tggcccgcct 300
ggcattatgc ccagtacatg accttatggg actttcctac ttggcagtac atctacgtat 360
tagtcatcgc tattaccatg g 381

<210> SEQ ID NO 18
<211> LENGTH: 276
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 18

```
tcgaggtgag ccccacgttc tgcttcactc tccccatctc cccccctcc ccaccccaa     60
ttttgtattt atttattttt taattatttt gtgcagcgat gggggcgggg gggggggggg  120
cgcgcgccag gcggggcggg gcggggcgag gggcggggcg gggcgaggcg gagaggtgcg  180
gcggcagcca atcagagcgg cgcgctccga aagtttcctt ttatggcgag gcggcggcgg  240
cggcggccct ataaaaagcg aagcgcgcgg cgggcg                            276
```

<210> SEQ ID NO 19
<211> LENGTH: 1040
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 19

```
ggagtcgctg cgttgccttc gccccgtgcc ccgctccgcg ccgcctcgcg ccgcccgccc     60
cggctctgac tgaccgcgtt actcccacag gtgagcgggc gggacggccc ttctcctccg    120
ggctgtaatt agcgcttggt ttaatgacgg ctcgtttctt ttctgtggct gcgtgaaagc    180
cttaaagggc tccgggaggg ccctttgtgc ggggggggagc ggctcggggg gtgcgtgcgt   240
gtgtgtgtgc gtggggagcg ccgcgtgcgg cccgcgctgc ccggcggctg tgagcgctgc    300
gggcgcggcg cggggctttg tgcgctccgc gtgtgcgcga ggggagcgcg gccgggggcg    360
gtgccccgcg gtgcgggggg gctgcgaggg gaacaaaggc tgcgtgcggg gtgtgtgcgt    420
gggggggtga gcagggggtg tgggcgcggc ggtcgggctg taaccccccc ctgcaccccc    480
ctccccgagt tgctgagcac ggcccggctt cgggtgcggg gctccgtgcg gggcgtggcg    540
cggggctcgc cgtgccgggc ggggggtggc ggcaggtggg ggtgccgggc ggggcggggc    600
cgcctcgggc cggggagggc tcgggggagg ggcgcggcgg cccccggagc gccggcggct    660
gtcgaggcgc ggcgagccgc agccattgcc ttttatggta atcgtgcgag agggcgcagg    720
gacttccttt gtcccaaatc tgtgcggagc cgaaatctgg gaggcgccgc cgcacccct     780
ctagcgggcg cggggcgaag cggtgcggcg ccggcaggaa ggaaatgggc ggggagggcc    840
ttcgtgcgtc gccgcgccgc cgtccccttc tccctctcca gcctcggggc tgtccgcggg    900
gggacggctg ccttcggggg ggacggggca gggcggggtt cggcttctgg cgtgtgaccg    960
gcggctctag agcctctgct aaccatgttc atgccttctt ctttttccta cagctcctgg   1020
gcaacgtgct ggttattgtg                                              1040
```

<210> SEQ ID NO 20
<211> LENGTH: 402
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 20

```
ctgagaaaac atgtactagc tgcatccttt tctatgctct ccctgctggt gataatggga     60
gatacagaca gtaaaacgga cagctcattc ataatggact cggaccctcg acgctgcatg    120
aggcaccact atgtggattc tatcagtcac ccattgtaca agtgtagctc aaagatggtg    180
ctcctggcca ggtgcgaggg gcactgcagc caggcgtcac gctccgagcc tttggtgtcg    240
ttcagcactg tcctcaagca acccttccgt tcctcctgtc actgctgccg gccccagact    300
```

tccaagctga aggcactgcg gctgcgatgc tcagggggca tgcgactcac tgccacctac 360
cgatacatcc tctcctgtca ctgcgaggaa tgcaattcct aa 402

<210> SEQ ID NO 21
<211> LENGTH: 399
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 21
ctgagaaaac atgtactagc tgcatccttt tctatgctct ccctgctggt gataatggga 60
gatacagaca gtaaaacgga cagctcattc ataatggact cggaccctcg acgctgcatg 120
aggcaccact atgtggattc tatcagtcac ccattgtaca agtgtagctc aaagatggtg 180
ctcctggcca ggtgcgaggg gcactgcagc caggcgtcac gctccgagcc tttggtgtcg 240
ttcagcactg tcctcaagca acccttccgt tcctcctgtc actgctgccg gccccagact 300
tccaagctga aggcactgcg gctgcgatgc tcagggggca tgcgactcac tgccacctac 360
cgatacatcc tctcctgtca ctgcgaggaa tgcaattcc 399

<210> SEQ ID NO 22
<211> LENGTH: 1023
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 22
tgcccgctgc tgtgtgtggc ttctggatgg gacaactgta gaggcagttc gaccagccag 60
ggaaagactg gcaagaaaag agttaaggca aaaaaggatg caacaattct cccgggactc 120
tgcatattct agtaataaag actctacatg cttgttgaca gagagagata ctctgggaac 180
ttctttgcag ttcccatctc ctttctctgg tacaatttct tttggttcat tttcagattc 240
aggcattttc ccccttggct ctcaatgctg tttgggtttc caacaattca gcattagtgg 300
gaaaaagtgg gccctcatac acaagcgtgt caggctgtca gtgtttggtg cacgctgggg 360
aagaatttac tttggaaagt agaaaagccc agcttttcct gggacatctt ctgttattgt 420
tgatgttttt ttttaccttg tcattttggt ctaaggttgc cattgctgct aaaggttacc 480
gatttcaaag tccagatacc aagcatgtgg atatgtttag ctacgtttac tcacagccag 540
cgaactgaca ttaaaataac taacaaacag attcttttat gtgatgctgg aactcttgac 600
agctataatt attattcaga aatgactttt tgaaagtaaa agcagcataa agaatttgtc 660
acaggaaggc tgtctcagat aaattatggt aaaattttgt aagggagcag acttttaaag 720
acttgcacaa atacggatcc tgcactgact ctggaaaagg catatatgta ctagtggcat 780
ggagaatgca ccatactcat gcatgcaaat tagacaacca agtatgaatc tatttgtggg 840
tgtgctatag ctttagccgt gtcacgggca tcattctcta atatccactt gtccatgtga 900
aacatgttgc caaaatggtg gcctggcttg tcttctgaac gtttggttca aatgtgtttt 960
ggtcctggag gctcaaattt tgagttattc ccacgttttg aaataaaaag agtatattca 1020
aaa 1023

<210> SEQ ID NO 23

<211> LENGTH: 225
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 23

```
ctgtgccttc tagttgccag ccatctgttg tttgcccctc ccccgtgcct tccttgaccc     60

tggaaggtgc cactcccact gtcctttcct aataaaatga ggaaattgca tcgcattgtc    120

tgagtaggtg tcattctatt ctggggggtg gggtggggca ggacagcaag ggggaggatt    180

gggaagacaa tagcaggcat gctggggatg cggtgggctc tatgg                    225
```

<210> SEQ ID NO 24
<211> LENGTH: 500
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 24

```
taattcagac tcccactaga agaaacagaa cttgaaaaaa ggataattgt ggtgaacacc     60

tcaacccagt ggtccaaaaa ctgaaaaact ttgaccccga gcaccctcac acagatagac    120

tactgaaaga aggagaaagg ggcacttact cagtctccct tatcagattg ccttacgagg    180

agtactagac tccctcaagc aaatagatct cacttaccac ttgcaaaggt atactacttt    240

cactctatta gacctatata tctgaccagg gtcctattcc aagacaactc ttctactctt    300

ccagcagact cttatagaaa gaaagattct ggggtccaag aaagcagtac tttcttacaa    360

ggagccaaaa aaaataacct ttctttagca cttctaacct tggagtgaac tggtgatcaa    420

agagaggttg gctccctggg gacaagtgcc acaaattcag tcaactacaa gaaagttgag    480

aacactgttc tcccgaaacc                                                500
```

<210> SEQ ID NO 25
<211> LENGTH: 1000
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 25

```
gttgactaaa gattgaacct tattcaaagt tagactctct ttgttaaaga caaacaaaac     60

ttccaataat tcagcaacta atagaaagac tcaacttgtg agccactact tattaattga    120

gaatagtcac tcagtctggc aaaatatatt agaaagtgac actgagttta aaaaagtgac    180

acctttgatt ctgaacagtg aactttgaga ctgaaaaact acagctttga ggctaaatac    240

ttgatcaaat aaaactactt actcaaaaaa ctgagtgaaa gtccaacaga aaaaagaggg    300

cccacttcca ccagtgacac aaaatccaga ttgatcgttc tttaagtgac tattcttgcc    360

agaatcagca aggtggatac aaaggactct gagaaagaac tctctgaact ctgggcaagg    420

ccccagtcca aagcaattag tatccttagg accagaaaaa tctgtggaag gtcagaattt    480

cttgtctgag aaaaacaaag caattcagac tcccactaga agaaacagaa cttgaaaaaa    540

ggataattgt ggtgaacacc tcaacccagt ggtccaaaaa ctgaaaaact ttgaccccga    600

gcaccctcac acagatagac tactgaaaga aggagaaagg ggcacttact cagtctccct    660
```

```
tatcagattg ccttacgagg agtactagac tccctcaagc aaatagatct cacttaccac    720

ttgcaaaggt atactacttt cactctatta gacctatata tctgaccagg gtcctattcc    780

aagacaactc ttctactctt ccagcagact cttatagaaa gaaagattct ggggtccaag    840

aaagcagtac tttcttacaa ggagccaaaa aaaataacct ttctttagca cttctaacct    900

tggagtgaac tggtgatcaa agagaggttg gctccctggg gacaagtgcc acaaattcag    960

tcaactacaa gaaagttgag aacactgttc tcccgaaacc                         1000
```

<210> SEQ ID NO 26
<211> LENGTH: 54
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 26

```
gagggcagag gaagtctgct aacatgcggt gacgtcgagg agaatcctgg ccca           54
```

<210> SEQ ID NO 27
<211> LENGTH: 699
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 27

```
atggagagcg acgagagcgg cctgcccgcc atggagatcg agtgccgcat caccggcacc     60

ctgaacggcg tggagttcga gctggtgggc ggcggagagg gcacccccga gcagggccgc    120

atgaccaaca agatgaagag caccaaaggc gccctgacct tcagccccta cctgctgagc    180

cacgtgatgg gctacggctt ctaccacttc ggcacctacc ccagcggcta cgagaacccc    240

ttcctgcacg ccatcaacaa cggcggctac accaacaccc gcatcgagaa gtacgaggac    300

ggcggcgtgc tgcacgtgag cttcagctac cgctacgagg ccggccgcgt gatcggcgac    360

ttcaaggtga tgggcaccgg cttccccgag gacagcgtga tcttcaccga caagatcatc    420

cgcagcaacg ccaccgtgga gcacctgcac cccatgggcg ataacgatct ggatggcagc    480

ttcacccgca ccttcagcct gcgcgacggc ggctactaca gctccgtggt ggacagccac    540

atgcacttca agagcgccat ccaccccagc atcctgcaga acgggggccc catgttcgcc    600

ttccgccgcg tggaggagga tcacagcaac accgagctgg gcatcgtgga gtaccagcac    660

gccttcaaga ccccggatgc agatgccggt gaagaataa                           699
```

<210> SEQ ID NO 28
<211> LENGTH: 717
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 28

```
atggtgagca agggcgagga gctgttcacc ggggtggtgc ccatcctggt cgagctggac     60

ggcgacgtaa acggccacaa gttcagcgtg tccggcgagg gcgagggcga tgccacctac    120

ggcaagctga ccctgaagtt catctgcacc accggcaagc tgcccgtgcc ctggcccacc    180

ctcgtgacca ccctgaccta cggcgtgcag tgcttcagcc gctaccccga ccacatgaag    240
```

```
cagcacgact tcttcaagtc cgccatgccc gaaggctacg tccaggagcg caccatcttc    300

ttcaaggacg acggcaacta caagacccgc gccgaggtga agttcgaggg cgacaccctg    360

gtgaaccgca tcgagctgaa gggcatcgac ttcaaggagg acggcaacat cctggggcac    420

aagctggagt acaactacaa cagccacaac gtctatatca tggccgacaa gcagaagaac    480

ggcatcaagg tgaacttcaa gatccgccac aacatcgagg acggcagcgt gcagctcgcc    540

gaccactacc agcagaacac ccccatcggc gacggccccg tgctgctgcc cgacaaccac    600

tacctgagca cccagtccgc cctgagcaaa gaccccaacg agaagcgcga tcacatggtc    660

ctgctggagt tcgtgaccgc cgccgggatc actctcggca tggacgagct gtacaag       717
```

<210> SEQ ID NO 29
<211> LENGTH: 239
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 29

```
Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys
225                 230                 235
```

<210> SEQ ID NO 30
<211> LENGTH: 141
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 30

```
aggaacccct agtgatggag ttggccactc cctctctgcg cgctcgctcg ctcactgagg     60

ccgggcgacc aaaggtcgcc cgacgcccgg gctttgcccg ggcggcctca gtgagcgagc    120

gagcgcgcag ctgcctgcag g                                              141
```

<210> SEQ ID NO 31
<211> LENGTH: 579
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 31

```
aagatgctcc gtggaaggga gccgagcggt gggcagaggc tgagtccccg ataacgagcg     60

cctcacattt ccgtggcatt cccatttgct agtgcgctgc tgcggccgca cgcctgattg    120

atatatgact gcaatggcac ttttccattt gacattctct ctctctctct ccctctctct    180

ctctccctct ctctctccct ctctctctct ccctgtgtcg cttaaacaac agtcctaact    240

tttgtgtgtt gcaaatataa aaggcaagcc atgtgacaga gggacagaag aacaaaagca    300

tttggaagta acaggacctc tttctagctc tcagaaaagt ctgagaagaa aggagccctg    360

cgttccccta agctgtgcag cagatactgt gatgatggat tgcaagtgca aagagtaaga    420

caaaactcca gcacataaag gacaatgaca accagaaagc ttcagcccga tcctgccctt    480

tccttgaacg ggactggatc ctaggaggtg aagccatttc caatttttg tcctctgcct     540

ccctctgctg ttcttctaga gaagtttttc cttacaaca                           579
```

<210> SEQ ID NO 32
<211> LENGTH: 1719
<212> TYPE: DNA
<213> ORGANISM: Homo sapiens

<400> SEQUENCE: 32

```
agaagaacaa aagcatttgg aagtaacagg acctctttct agctctcaga aaagtctgag     60

aagaaaggag ccctgcgttc ccctaagctg tgcagcagat actgtgatga tggattgcaa    120

gtgcaaagag taagacaaaa ctccagcaca taaaggacaa tgacaaccag aaagcttcag    180

cccgatcctg ccctttcctt gaacgggact ggatcctagg aggtgaagcc atttccaatt    240

ttttgtcctc tgcctccctc tgctgttctt ctagagaagt tttccttac aacaatgaga     300

aaacatgtac tagctgcatc cttttctatg ctctccctgc tggtgataat gggagataca    360

gacagtaaaa cggacagctc attcataatg gactcggacc ctcgacgctg catgaggcac    420

cactatgtgg attctatcag tcacccattg tacaagtgta gctcaaagat ggtgctcctg    480

gccaggtgcg aggggcactg cagccaggcg tcacgctccg agcctttggt gtcgttcagc    540

actgtcctca agcaaccctt ccgttcctcc tgtcactgct gccggcccca gacttccaag    600

ctgaaggcac tgcggctgcg atgctcaggg ggcatgcgac tcactgccac ctaccggtac    660

atcctctcct gtcactgcga ggaatgcaat tcctgaggcc cgctgctgtg tgtggcttct    720

ggatgggaca actgtagagg cagttcgacc agccagggaa agactggcaa gaaaagagtt    780

aaggcaaaaa aggatgcaac aattctcccg ggactctgca tattctagta ataaagactc    840

tacatgcttg ttgacagaga gagatactct gggaacttct ttgcagttcc catctccttt    900
```

```
ctctggtaca atttcttttg gttcattttc agattcaggc attttccccc ttggctctca    960

atgctgtttg ggtttccaac aattcagcat tagtgggaaa aagtgggccc tcatacacaa   1020

gcgtgtcagg ctgtcagtgt ttggtgcacg ctggggaaga atttactttg gaaagtagaa   1080

aagcccagct tttcctggga catcttctgt tattgttgat gttttttttt accttgtcat   1140

tttggtctaa ggttgccatt gctgctaaag gttaccgatt tcaaagtcca gataccaagc   1200

atgtggatat gtttagctac gtttactcac agccagcgaa ctgacattaa aataactaac   1260

aaacagattc ttttatgtga tgctggaact cttgacagct ataattatta ttcagaaatg   1320

actttttgaa agtaaaagca gcataaagaa tttgtcacag gaaggctgtc tcagataaat   1380

tatggtaaaa ttttgtaagg gagcagactt ttaaagactt gcacaaatac ggatcctgca   1440

ctgactctgg aaaaggcata tatgtactag tggcatggag aatgcaccat actcatgcat   1500

gcaaattaga caaccaagta tgaatctatt tgtgggtgtg ctatagcttt agccgtgtca   1560

cgggcatcat tctctaatat ccacttgtcc atgtgaaaca tgttgccaaa atggtggcct   1620

ggcttgtctt ctgaacgttt ggttcaaatg tgttttggtc ctggaggctc aaattttgag   1680

ttattcccac gttttgaaat aaaaagagta tattcaaaa                          1719
```

```
<210> SEQ ID NO 33
<211> LENGTH: 107
<212> TYPE: PRT
<213> ORGANISM: Mus musculus

<400> SEQUENCE: 33

Lys Thr Asp Ser Ser Phe Leu Met Asp Ser Gln Arg Cys Met Arg His
1               5                   10                  15

His Tyr Val Asp Ser Ile Ser His Pro Leu Tyr Lys Cys Ser Ser Lys
            20                  25                  30

Met Val Leu Leu Ala Arg Cys Glu Gly His Cys Ser Gln Ala Ser Arg
        35                  40                  45

Ser Glu Pro Leu Val Ser Phe Ser Thr Val Leu Lys Gln Pro Phe Arg
    50                  55                  60

Ser Ser Cys His Cys Cys Arg Pro Gln Thr Ser Lys Leu Lys Ala Leu
65                  70                  75                  80

Arg Leu Arg Cys Ser Gly Gly Met Arg Leu Thr Ala Thr Tyr Arg Tyr
                85                  90                  95

Ile Leu Ser Cys His Cys Glu Glu Cys Ser Ser
            100                 105
```

```
<210> SEQ ID NO 34
<211> LENGTH: 321
<212> TYPE: DNA
<213> ORGANISM: Mus musculus

<400> SEQUENCE: 34

aaaacagaca gttcatttct gatggactct caacgctgca tgagacacca ttatgtcgat     60

tctatcagtc acccactgta caaatgtagc tcaaagatgg tgctcctggc cagatgtgag    120

gggcactgca gccaggcatc acgctctgag cccttggtgt ccttcagcac tgtcctcaag    180

caacctttcc gttcctcctg tcactgctgc cgaccccaga cttccaagct gaaggctctg    240

cgtctgcgct gctcaggggg catgcgactt actgccactt accggtacat cctctcctgt    300

cactgtgagg aatgcagctc c                                              321
```

```
<210> SEQ ID NO 35
```

```
<211> LENGTH: 133
<212> TYPE: PRT
<213> ORGANISM: Macaca mulatta

<400> SEQUENCE: 35

Met Arg Lys His Val Leu Ala Ala Ser Phe Ser Met Leu Ser Leu Leu
1               5                   10                  15

Val Ile Met Gly Asp Thr Asp Ser Lys Thr Asp Ser Ser Phe Ile Met
            20                  25                  30

Asp Ser Asp Pro Arg Arg Cys Met Arg His His Tyr Val Asp Ser Ile
        35                  40                  45

Ser His Pro Leu Tyr Lys Cys Ser Ser Lys Met Val Leu Leu Ala Arg
    50                  55                  60

Cys Glu Gly His Cys Ser Gln Ala Ser Arg Ser Glu Pro Leu Val Ser
65                  70                  75                  80

Phe Ser Thr Val Leu Lys Gln Pro Phe Arg Ser Ser Cys His Cys Cys
                85                  90                  95

Arg Pro Gln Thr Ser Lys Leu Lys Ala Leu Arg Leu Arg Cys Ser Gly
            100                 105                 110

Gly Met Arg Leu Thr Ala Thr Tyr Arg Tyr Ile Leu Ser Cys His Cys
        115                 120                 125

Glu Glu Cys Asn Ser
    130


<210> SEQ ID NO 36
<211> LENGTH: 107
<212> TYPE: PRT
<213> ORGANISM: Rattus norvegicus

<400> SEQUENCE: 36

Lys Thr Asp Ser Ser Phe Leu Met Asp Ser Gln Arg Cys Met Arg His
1               5                   10                  15

His Tyr Val Asp Ser Ile Ser His Pro Leu Tyr Lys Cys Ser Ser Lys
            20                  25                  30

Met Val Leu Leu Ala Arg Cys Glu Gly His Cys Ser Gln Ala Ser Arg
        35                  40                  45

Ser Glu Pro Leu Val Ser Phe Ser Thr Val Leu Lys Gln Pro Phe Arg
    50                  55                  60

Ser Ser Cys His Cys Cys Arg Pro Gln Thr Ser Lys Leu Lys Ala Leu
65                  70                  75                  80

Arg Leu Arg Cys Ser Gly Gly Met Arg Leu Thr Ala Thr Tyr Arg Tyr
                85                  90                  95

Ile Leu Ser Cys His Cys Glu Glu Cys Ser Ser
            100                 105


<210> SEQ ID NO 37
<211> LENGTH: 109
<212> TYPE: PRT
<213> ORGANISM: Pan troglodytes

<400> SEQUENCE: 37

Lys Thr Asp Ser Ser Phe Val Met Asp Ser Asp Pro Arg Arg Cys Met
1               5                   10                  15

Arg His His Tyr Val Asp Ser Ile Ser His Pro Leu Tyr Lys Cys Ser
            20                  25                  30

Ser Lys Met Val Leu Leu Ala Arg Cys Glu Gly His Cys Ser Gln Ala
        35                  40                  45
```

```
Ser Arg Ser Glu Pro Leu Val Ser Phe Ser Thr Val Leu Lys Gln Pro
    50                  55                  60

Phe Arg Ser Ser Cys His Cys Cys Arg Pro Gln Thr Ser Lys Leu Lys
65                  70                  75                  80

Ala Leu Arg Leu Arg Cys Ser Gly Gly Met Arg Leu Thr Ala Thr Tyr
                85                  90                  95

Arg Tyr Ile Leu Ser Cys His Cys Glu Glu Cys Asn Ser
            100                 105


<210> SEQ ID NO 38
<211> LENGTH: 641
<212> TYPE: PRT
<213> ORGANISM: Homo sapiens

<400> SEQUENCE: 38

Met Ala Lys Ala Ala Ala Ile Gly Ile Asp Leu Gly Thr Thr Tyr Ser
1               5                   10                  15

Cys Val Gly Val Phe Gln His Gly Lys Val Glu Ile Ile Ala Asn Asp
            20                  25                  30

Gln Gly Asn Arg Thr Thr Pro Ser Tyr Val Ala Phe Thr Asp Thr Glu
        35                  40                  45

Arg Leu Ile Gly Asp Ala Ala Lys Asn Gln Val Ala Leu Asn Pro Gln
    50                  55                  60

Asn Thr Val Phe Asp Ala Lys Arg Leu Ile Gly Arg Lys Phe Gly Asp
65                  70                  75                  80

Pro Val Val Gln Ser Asp Met Lys His Trp Pro Phe Gln Val Ile Asn
                85                  90                  95

Asp Gly Asp Lys Pro Lys Val Gln Val Ser Tyr Lys Gly Glu Thr Lys
            100                 105                 110

Ala Phe Tyr Pro Glu Glu Ile Ser Ser Met Val Leu Thr Lys Met Lys
        115                 120                 125

Glu Ile Ala Glu Ala Tyr Leu Gly Tyr Pro Val Thr Asn Ala Val Ile
    130                 135                 140

Thr Val Pro Ala Tyr Phe Asn Asp Ser Gln Arg Gln Ala Thr Lys Asp
145                 150                 155                 160

Ala Gly Val Ile Ala Gly Leu Asn Val Leu Arg Ile Ile Asn Glu Pro
                165                 170                 175

Thr Ala Ala Ala Ile Ala Tyr Gly Leu Asp Arg Thr Gly Lys Gly Glu
            180                 185                 190

Arg Asn Val Leu Ile Phe Asp Leu Gly Gly Gly Thr Phe Asp Val Ser
        195                 200                 205

Ile Leu Thr Ile Asp Asp Gly Ile Phe Glu Val Lys Ala Thr Ala Gly
    210                 215                 220

Asp Thr His Leu Gly Gly Glu Asp Phe Asp Asn Arg Leu Val Asn His
225                 230                 235                 240

Phe Val Glu Glu Phe Lys Arg Lys His Lys Lys Asp Ile Ser Gln Asn
                245                 250                 255

Lys Arg Ala Val Arg Arg Leu Arg Thr Ala Cys Glu Arg Ala Lys Arg
            260                 265                 270

Thr Leu Ser Ser Ser Thr Gln Ala Ser Leu Glu Ile Asp Ser Leu Phe
        275                 280                 285

Glu Gly Ile Asp Phe Tyr Thr Ser Ile Thr Arg Ala Arg Phe Glu Glu
    290                 295                 300

Leu Cys Ser Asp Leu Phe Arg Ser Thr Leu Glu Pro Val Glu Lys Ala
305                 310                 315                 320
```

```
Leu Arg Asp Ala Lys Leu Asp Lys Ala Gln Ile His Asp Leu Val Leu
                325                 330                 335

Val Gly Gly Ser Thr Arg Ile Pro Lys Val Gln Lys Leu Leu Gln Asp
            340                 345                 350

Phe Phe Asn Gly Arg Asp Leu Asn Lys Ser Ile Asn Pro Asp Glu Ala
        355                 360                 365

Val Ala Tyr Gly Ala Ala Val Gln Ala Ala Ile Leu Met Gly Asp Lys
    370                 375                 380

Ser Glu Asn Val Gln Asp Leu Leu Leu Leu Asp Val Ala Pro Leu Ser
385                 390                 395                 400

Leu Gly Leu Glu Thr Ala Gly Gly Val Met Thr Ala Leu Ile Lys Arg
                405                 410                 415

Asn Ser Thr Ile Pro Thr Lys Gln Thr Gln Ile Phe Thr Thr Tyr Ser
            420                 425                 430

Asp Asn Gln Pro Gly Val Leu Ile Gln Val Tyr Glu Gly Glu Arg Ala
        435                 440                 445

Met Thr Lys Asp Asn Asn Leu Leu Gly Arg Phe Glu Leu Ser Gly Ile
    450                 455                 460

Pro Pro Ala Pro Arg Gly Val Pro Gln Ile Glu Val Thr Phe Asp Ile
465                 470                 475                 480

Asp Ala Asn Gly Ile Leu Asn Val Thr Ala Thr Asp Lys Ser Thr Gly
                485                 490                 495

Lys Ala Asn Lys Ile Thr Ile Thr Asn Asp Lys Gly Arg Leu Ser Lys
            500                 505                 510

Glu Glu Ile Glu Arg Met Val Gln Glu Ala Glu Lys Tyr Lys Ala Glu
        515                 520                 525

Asp Glu Val Gln Arg Glu Arg Val Ser Ala Lys Asn Ala Leu Glu Ser
    530                 535                 540

Tyr Ala Phe Asn Met Lys Ser Ala Val Glu Asp Glu Gly Leu Lys Gly
545                 550                 555                 560

Lys Ile Ser Glu Ala Asp Lys Lys Lys Val Leu Asp Lys Cys Gln Glu
                565                 570                 575

Val Ile Ser Trp Leu Asp Ala Asn Thr Leu Ala Glu Lys Asp Glu Phe
            580                 585                 590

Glu His Lys Arg Lys Glu Leu Glu Gln Val Cys Asn Pro Ile Ile Ser
        595                 600                 605

Gly Leu Tyr Gln Gly Ala Gly Gly Pro Gly Pro Gly Gly Phe Gly Ala
    610                 615                 620

Gln Gly Pro Lys Gly Gly Ser Gly Ser Gly Pro Thr Ile Glu Glu Val
625                 630                 635                 640

Asp
```

<210> SEQ ID NO 39
<211> LENGTH: 1926
<212> TYPE: DNA
<213> ORGANISM: Homo sapiens

<400> SEQUENCE: 39

```
atggccaaag ccgcggcgat cggcatcgac ctgggcacca cctactcctg cgtgggggtg     60

ttccaacacg gcaaggtgga gatcatcgcc aacgaccagg gcaaccgcac cacccccagc    120

tacgtggcct tcacggacac cgagcggctc atcggggatg cggccaagaa ccaggtggcg    180

ctgaacccgc agaacaccgt gtttgacgcg aagcggctga tcggccgcaa gttcggcgac    240
```

```
ccggtggtgc agtcggacat gaagcactgg cctttccagg tgatcaacga cggagacaag     300

cccaaggtgc aggtgagcta caagggggag accaaggcat tctaccccga ggagatctcg     360

tccatggtgc tgaccaagat gaaggagatc gccgaggcgt acctgggcta cccggtgacc     420

aacgcggtga tcaccgtgcc ggcctacttc aacgactcgc agcgccaggc caccaaggat     480

gcgggtgtga tcgcggggct caacgtgctg cggatcatca acgagcccac ggccgccgcc     540

atcgcctacg gcctggacag aacgggcaag ggggagcgca acgtgctcat ctttgacctg     600

ggcgggggca ccttcgacgt gtccatcctg acgatcgacg acggcatctt cgaggtgaag     660

gccacggccg gggacaccca cctgggtggg gaggactttg acaacaggct ggtgaaccac     720

ttcgtggagg agttcaagag aaaacacaag aaggacatca gccagaacaa gcgagccgtg     780

aggcggctgc gcaccgcctg cgagagggcc aagaggaccc tgtcgtccag cacccaggcc     840

agcctggaga tcgactccct gtttgagggc atcgacttct acacgtccat caccagggcg     900

aggttcgagg agctgtgctc cgacctgttc cgaagcaccc tggagcccgt ggagaaggct     960

ctgcgcgacg ccaagctgga caaggcccag attcacgacc tggtcctggt cgggggctcc    1020

acccgcatcc ccaaggtgca gaagctgctg caggacttct tcaacgggcg cgacctgaac    1080

aagagcatca accccgacga ggctgtggcc tacggggcgg cggtgcaggc ggccatcctg    1140

atgggggaca agtccgagaa cgtgcaggac ctgctgctgc tggacgtggc tcccctgtcg    1200

ctggggctgg agacggccgg aggcgtgatg actgccctga tcaagcgcaa ctccaccatc    1260

cccaccaagc agacgcagat cttcaccacc tactccgaca accaacccgg ggtgctgatc    1320

caggtgtacg agggcgagag ggccatgacg aaagacaaca atctgttggg gcgcttcgag    1380

ctgagcggca tccctccggc ccccagggc gtgccccaga tcgaggtgac cttcgacatc    1440

gatgccaacg gcatcctgaa cgtcacggcc acggacaaga gcaccggcaa ggccaacaag    1500

atcaccatca ccaacgacaa gggccgcctg agcaaggagg agatcgagcg catggtgcag    1560

gaggcggaga agtacaaagc ggaggacgag gtgcagcgcg agagggtgtc agccaagaac    1620

gccctggagt cctacgcctt caacatgaag agcgccgtgg aggatgaggg gctcaagggc    1680

aagatcagcg aggcggacaa gaagaaggtt ctggacaagt gtcaagaggt catctcgtgg    1740

ctggacgcca acaccttggc cgagaaggac gagtttgagc acaagaggaa ggagctggag    1800

caggtgtgta accccatcat cagcggactg taccagggtg ccggtggtcc cgggcctggg    1860

ggcttcgggg ctcagggtcc caagggaggg tctgggtcag gccccaccat tgaggaggtg    1920

gattag                                                               1926
```

<210> SEQ ID NO 40
<211> LENGTH: 2400
<212> TYPE: DNA
<213> ORGANISM: Homo sapiens

<400> SEQUENCE: 40

```
aacggctagc ctgaggagct gctgcgacag tccactacct ttttcgagag tgactcccgt      60

tgtcccaagg cttcccagag cgaacctgtg cggctgcagg caccggcgcg tcgagtttcc     120

ggcgtccgga aggaccgagc tcttctcgcg gatccagtgt tccgtttcca gcccccaatc     180

tcagagcgga gccgacagag agcagggaac cggcatggcc aaagccgcgg cgatcggcat     240

cgacctgggc accacctact cctgcgtggg ggtgttccaa cacggcaagg tggagatcat     300

cgccaacgac cagggcaacc gcaccacccc cagctacgtg gccttcacgg acaccgagcg     360

gctcatcggg gatgcggcca agaaccaggt ggcgctgaac ccgcagaaca ccgtgtttga     420
```

```
cgcgaagcgg ctgattggcc gcaagttcgg cgacccggtg gtgcagtcgg acatgaagca    480
ctggcctttc caggtgatca acgacggaga caagcccaag gtgcaggtga gctacaaggg    540
ggagaccaag gcattctacc ccgaggagat ctcgtccatg gtgctgacca agatgaagga    600
gatcgccgag gcgtacctgg gctacccggt gaccaacgcg gtgatcaccg tgccggccta    660
cttcaacgac tcgcagcgcc aggccaccaa ggatgcgggt gtgatcgcgg ggctcaacgt    720
gctgcggatc atcaacgagc ccacggccgc cgccatcgcc tacggcctgg acagaacggg    780
caagggggag cgcaacgtgc tcatctttga cctgggcggg ggcaccttcg acgtgtccat    840
cctgacgatc gacgacggca tcttcgaggt gaaggccacg gccggggaca cccacctggg    900
tggggaggac tttgacaaca ggctggtgaa ccacttcgtg gaggagttca agagaaaaca    960
caagaaggac atcagccaga acaagcgagc cgtgaggcgg ctgcgcaccg cctgcgagag   1020
ggccaagagg accctgtcgt ccagcaccca ggccagcctg gagatcgact ccctgtttga   1080
gggcatcgac ttctacacgt ccatcaccag ggcgaggttc gaggagctgt gctccgacct   1140
gttccgaagc accctggagc ccgtggagaa ggctctgcgc gacgccaagc tggacaaggc   1200
ccagattcac gacctggtcc tggtcggggg ctccacccgc atccccaagg tgcagaagct   1260
gctgcaggac ttcttcaacg ggcgcgacct gaacaagagc atcaaccccg acgaggctgt   1320
ggcctacggg gcggcggtgc aggcggccat cctgatgggg gacaagtccg agaacgtgca   1380
ggacctgctg ctgctggacg tggctcccct gtcgctgggg ctggagacgg ccggaggcgt   1440
gatgactgcc ctgatcaagc gcaactccac catccccacc aagcagacgc agatcttcac   1500
cacctactcc gacaaccaac ccggggtgct gatccaggtg tacgagggcg agagggccat   1560
gacgaaagac aacaatctgt tggggcgctt cgagctgagc ggcatccctc cggcccccag   1620
gggcgtgccc cagatcgagg tgaccttcga catcgatgcc aacggcatcc tgaacgtcac   1680
ggccacggac aagagcaccg gcaaggccaa caagatcacc atcaccaacg acaagggccg   1740
cctgagcaag gaggagatcg agcgcatggt gcaggaggcg gagaagtaca aagcggagga   1800
cgaggtgcag cgcgagaggg tgtcagccaa gaacgccctg gagtcctacg ccttcaacat   1860
gaagagcgcc gtggaggatg aggggctcaa gggcaagatc agcgaggcgg acaagaagaa   1920
ggtgctggac aagtgtcaag aggtcatctc gtggctggac gccaacacct tggccgagaa   1980
ggacgagttt gagcacaaga ggaaggagct ggagcaggtg tgtaacccca tcatcagcgg   2040
actgtaccag ggtgccggtg gtcccgggcc tgggggcttc ggggctcagg gtcccaaggg   2100
agggtctggg tcaggcccca ccattgagga ggtagattag ggcctttcc aagattgctg    2160
tttttgtttt ggagcttcaa gactttgcat ttcctagtat ttctgtttgt cagttctcaa   2220
tttcctgtgt ttgcaatgtt gaaatttttt ggtgaagtac tgaacttgct ttttttccgg   2280
tttctacatg cagagatgaa tttatactgc catcttacga ctatttcttc tttttaatac   2340
acttaactca ggccattttt taagttggtt acttcaaagt aaataaactt taaaattcaa   2400
```

<210> SEQ ID NO 41
<211> LENGTH: 641
<212> TYPE: PRT
<213> ORGANISM: Mus musculus

<400> SEQUENCE: 41

```
Met Ala Lys Asn Thr Ala Ile Gly Ile Asp Leu Gly Thr Thr Tyr Ser
1               5                   10                  15

Cys Val Gly Val Phe Gln His Gly Lys Val Glu Ile Ile Ala Asn Asp
```

-continued

```
            20                  25                  30

Gln Gly Asn Arg Thr Thr Pro Ser Tyr Val Ala Phe Thr Asp Thr Glu
        35                  40                  45

Arg Leu Ile Gly Asp Ala Ala Lys Asn Gln Val Ala Leu Asn Pro Gln
    50                  55                  60

Asn Thr Val Phe Asp Ala Lys Arg Leu Ile Gly Arg Lys Phe Gly Asp
65                  70                  75                  80

Ala Val Val Gln Ser Asp Met Lys His Trp Pro Phe Gln Val Val Asn
                85                  90                  95

Asp Gly Asp Lys Pro Lys Val Gln Val Asn Tyr Lys Gly Glu Ser Arg
            100                 105                 110

Ser Phe Phe Pro Glu Glu Ile Ser Ser Met Val Leu Thr Lys Met Lys
        115                 120                 125

Glu Ile Ala Glu Ala Tyr Leu Gly His Pro Val Thr Asn Ala Val Ile
    130                 135                 140

Thr Val Pro Ala Tyr Phe Asn Asp Ser Gln Arg Gln Ala Thr Lys Asp
145                 150                 155                 160

Ala Gly Val Ile Ala Gly Leu Asn Val Leu Arg Ile Ile Asn Glu Pro
                165                 170                 175

Thr Ala Ala Ala Ile Ala Tyr Gly Leu Asp Arg Thr Gly Lys Gly Glu
            180                 185                 190

Arg Asn Val Leu Ile Phe Asp Leu Gly Gly Gly Thr Phe Asp Val Ser
        195                 200                 205

Ile Leu Thr Ile Asp Asp Gly Ile Phe Glu Val Lys Ala Thr Ala Gly
    210                 215                 220

Asp Thr His Leu Gly Gly Glu Asp Phe Asp Asn Arg Leu Val Ser His
225                 230                 235                 240

Phe Val Glu Glu Phe Lys Arg Lys His Lys Lys Asp Ile Ser Gln Asn
                245                 250                 255

Lys Arg Ala Val Arg Arg Leu Arg Thr Ala Cys Glu Arg Ala Lys Arg
            260                 265                 270

Thr Leu Ser Ser Ser Thr Gln Ala Ser Leu Glu Ile Asp Ser Leu Phe
        275                 280                 285

Glu Gly Ile Asp Phe Tyr Thr Ser Ile Thr Arg Ala Arg Phe Glu Glu
    290                 295                 300

Leu Cys Ser Asp Leu Phe Arg Gly Thr Leu Glu Pro Val Glu Lys Ala
305                 310                 315                 320

Leu Arg Asp Ala Lys Met Asp Lys Ala Gln Ile His Asp Leu Val Leu
                325                 330                 335

Val Gly Gly Ser Thr Arg Ile Pro Lys Val Gln Lys Leu Leu Gln Asp
            340                 345                 350

Phe Phe Asn Gly Arg Asp Leu Asn Lys Ser Ile Asn Pro Asp Glu Ala
        355                 360                 365

Val Ala Tyr Gly Ala Ala Val Gln Ala Ala Ile Leu Met Gly Asp Lys
    370                 375                 380

Ser Glu Asn Val Gln Asp Leu Leu Leu Leu Asp Val Ala Pro Leu Ser
385                 390                 395                 400

Leu Gly Leu Glu Thr Ala Gly Gly Val Met Thr Ala Leu Ile Lys Arg
                405                 410                 415

Asn Ser Thr Ile Pro Thr Lys Gln Thr Gln Thr Phe Thr Thr Tyr Ser
            420                 425                 430

Asp Asn Gln Pro Gly Val Leu Ile Gln Val Tyr Glu Gly Glu Arg Ala
        435                 440                 445
```

Met Thr Arg Asp Asn Asn Leu Leu Gly Arg Phe Glu Leu Ser Gly Ile
    450                 455                 460

Pro Pro Ala Pro Arg Gly Val Pro Gln Ile Glu Val Thr Phe Asp Ile
465                 470                 475                 480

Asp Ala Asn Gly Ile Leu Asn Val Thr Ala Thr Asp Lys Ser Thr Gly
                485                 490                 495

Lys Ala Asn Lys Ile Thr Ile Thr Asn Asp Lys Gly Arg Leu Ser Lys
            500                 505                 510

Glu Glu Ile Glu Arg Met Val Gln Glu Ala Glu Arg Tyr Lys Ala Glu
        515                 520                 525

Asp Glu Val Gln Arg Asp Arg Val Ala Ala Lys Asn Ala Leu Glu Ser
    530                 535                 540

Tyr Ala Phe Asn Met Lys Ser Ala Val Glu Asp Glu Gly Leu Lys Gly
545                 550                 555                 560

Lys Leu Ser Glu Ala Asp Lys Lys Lys Val Leu Asp Lys Cys Gln Glu
                565                 570                 575

Val Ile Ser Trp Leu Asp Ser Asn Thr Leu Ala Asp Lys Glu Glu Phe
            580                 585                 590

Val His Lys Arg Glu Glu Leu Glu Arg Val Cys Ser Pro Ile Ile Ser
        595                 600                 605

Gly Leu Tyr Gln Gly Ala Gly Ala Pro Gly Ala Gly Gly Phe Gly Ala
    610                 615                 620

Gln Ala Pro Lys Gly Ala Ser Gly Ser Gly Pro Thr Ile Glu Glu Val
625                 630                 635                 640

Asp

<210> SEQ ID NO 42
<211> LENGTH: 1927
<212> TYPE: DNA
<213> ORGANISM: Mus musculus

<400> SEQUENCE: 42
atggccaaga acacggcgat cggcatcgac ctgggcacca cctactcgtg cgtgggcgtg 60
ttccagcacg gcaaggtgga gatcatcgcc aacgaccagg gcaaccgcac gacccccagc 120
tacgtggcct tcaccgacac cgagcgcctc atcggagacg ccgccaagaa ccaggtggcg 180
ctgaacccgc agaacaccgt gttcgacgcg aagcggctga tcggccgcaa gttcggcgat 240
gcggtggtgc agtccgacat gaagcactgg cccttccagg tggtgaacga cggcgacaag 300
cccaaggtgc aggtgaacta caagggcgag agccggtcgt tcttcccgga ggagatctcg 360
tccatggtgc tgacgaagat gaaggagatc gctgaggcgt acctgggcca cccggtgacc 420
aacgcggtga tcacggtgcc cgcctacttc aacgactctc agcggcaggc caccaaggac 480
gcgggcgtga tcgccggtct aaacgtgctg cggatcatca acgagcccac ggcggccgcc 540
atcgcctacg ggctggaccg gaccggcaag ggcgagcgca acgtgctcat cttcgacctg 600
gggggcggca cgttcgacgt gtccatcctg acgatcgacg acggcatctt cgaggtgaag 660
gccacggcgg gcgacacgca cctgggaggg gaggacttcg acaaccggct ggtgagccac 720
ttcgtggagg agttcaagag gaagcacaag aaggacatca gccagaacaa gcgcgcggtg 780
cggcggctgc gcactgcgtg tgagagggcc aagaggacgc tgtcgtccag cacccaggcc 840
agcctggaga tcgactctct gttcgagggc atcgacttct acacatccat cacgcgggcg 900
cggttcgaag agctgtgctc agacctgttc cgcggcacgc tggagcccgt ggagaaggcc 960

```
ctgcgcgacg ccaagatgga caaggcgcag atccacgacc tggtgctggt gggcggctcg   1020

acgcgcatcc ccaaggtgca gaagctgctg caggacttct tcaacgggcg cgacctgaac   1080

aagagcatca acccggacga ggcggtggcc tacggggcgg cggtgcaggc ggccatcctg   1140

atgggggaca agtcggagaa cgtgcaggac ctgctgctgc tggacgtggc gccgctgtcg   1200

ctgggcctgg agactgcggg cggcgtgatg acggcgctca tcaagcgcaa ctccaccatc   1260

cccaccaagc agacgcagac cttcaccacc tactcggaca accagcccgg ggtgctgatc   1320

caggtgtacg agggcgagag ggccatgacg cgcgacaaca acctgctggg gcgcttcgaa   1380

ctgagcggca tcccgccggc gcccaggggc gtgcccacaga tcgaggtgac cttcgacatc   1440

gacgccaacg gcatcctgaa cgtcacggcc accgacaaga gcaccggcaa ggccaacaag   1500

atcaccatca ccaacgacaa gggccgcctg agcaaggagg agatcgagcg catggtgcag   1560

gaggccgagc gctacaaggc cgaggacgag gtgcagcgcg acagggtggc cgccaagaac   1620

gcgctcgaat cctatgcctt caacatgaag agcgccgtgg aggacgaggg tctcaagggc   1680

aagctcagcg aggctgacaa gaagaaggtg ctggacaagt gccaggaggt catctcctgg   1740

ctggactcca acacgctggc cgacaaggag gagttcgtgc acaagcggga ggagctggag   1800

cgggtgtgca gccccatcat cagtgggctg taccagggtg cgggtgctcc tggggctggg   1860

ggcttcgggg cccaggcgcc caagggagcc tctggctcag gacccaccat cgaggaggtg   1920

gattaga                                                             1927
```

<210> SEQ ID NO 43
<211> LENGTH: 641
<212> TYPE: PRT
<213> ORGANISM: Macaca mulatta

<400> SEQUENCE: 43

```
Met Ala Lys Ala Ala Ala Ile Gly Ile Asp Leu Gly Thr Thr Tyr Ser
1               5                   10                  15

Cys Val Gly Val Phe Gln His Gly Lys Val Glu Ile Ile Ala Asn Asp
            20                  25                  30

Gln Gly Asn Arg Thr Thr Pro Ser Tyr Val Ala Phe Thr Asp Thr Glu
        35                  40                  45

Arg Leu Ile Gly Asp Ala Ala Lys Asn Gln Val Ala Leu Asn Pro Gln
    50                  55                  60

Asn Thr Val Phe Asp Ala Lys Arg Leu Ile Gly Arg Lys Phe Gly Asp
65                  70                  75                  80

Pro Val Val Gln Ser Asp Met Lys His Trp Pro Phe Gln Val Ile Asn
                85                  90                  95

Asp Gly Asp Lys Pro Lys Val Gln Val Ser Tyr Lys Gly Glu Thr Lys
            100                 105                 110

Ala Phe Tyr Pro Glu Glu Ile Ser Ser Met Val Leu Thr Lys Met Lys
        115                 120                 125

Glu Ile Ala Glu Ala Tyr Leu Gly Tyr Pro Val Thr Asn Ala Val Ile
    130                 135                 140

Thr Val Pro Ala Tyr Phe Asn Asp Ser Gln Arg Gln Ala Thr Lys Asp
145                 150                 155                 160

Ala Gly Val Ile Ala Gly Leu Asn Val Leu Arg Ile Ile Asn Glu Pro
                165                 170                 175

Thr Ala Ala Ala Ile Ala Tyr Gly Leu Asp Arg Thr Gly Lys Gly Glu
            180                 185                 190

Arg Asn Val Leu Ile Phe Asp Leu Gly Gly Gly Thr Phe Asp Val Ser
```

```
        195                 200                 205

Ile Leu Thr Ile Asp Asp Gly Ile Phe Glu Val Lys Ala Thr Ala Gly
    210                 215                 220

Asp Thr His Leu Gly Gly Glu Asp Phe Asp Asn Arg Leu Val Asn His
225                 230                 235                 240

Phe Val Glu Glu Phe Lys Arg Lys His Lys Lys Asp Ile Ser Gln Asn
                245                 250                 255

Lys Arg Ala Val Arg Arg Leu Arg Thr Ala Cys Glu Arg Ala Lys Arg
            260                 265                 270

Thr Leu Ser Ser Ser Thr Gln Ala Ser Leu Glu Ile Asp Ser Leu Phe
        275                 280                 285

Glu Gly Ile Asp Phe Tyr Thr Ser Ile Thr Arg Ala Arg Phe Glu Glu
    290                 295                 300

Leu Cys Ser Asp Leu Phe Arg Ser Thr Leu Glu Pro Val Glu Lys Ala
305                 310                 315                 320

Leu Arg Asp Ala Lys Leu Asp Lys Ala Gln Ile His Asp Leu Val Leu
                325                 330                 335

Val Gly Gly Ser Thr Arg Ile Pro Lys Val Gln Lys Leu Leu Gln Asp
            340                 345                 350

Phe Phe Asn Gly Arg Asp Leu Asn Lys Ser Ile Asn Pro Asp Glu Ala
        355                 360                 365

Val Ala Tyr Gly Ala Ala Val Gln Ala Ala Ile Leu Met Gly Asp Lys
    370                 375                 380

Ser Glu Asn Val Gln Asp Leu Leu Leu Leu Asp Val Ala Pro Leu Ser
385                 390                 395                 400

Leu Gly Leu Glu Thr Ala Gly Gly Val Met Thr Ala Leu Ile Lys Arg
                405                 410                 415

Asn Ser Thr Ile Pro Thr Lys Gln Thr Gln Ile Phe Thr Thr Tyr Ser
            420                 425                 430

Asp Asn Gln Pro Gly Val Leu Ile Gln Val Tyr Glu Gly Glu Arg Ala
        435                 440                 445

Met Thr Lys Asp Asn Asn Leu Leu Gly Arg Phe Glu Leu Ser Gly Ile
    450                 455                 460

Pro Pro Ala Pro Arg Gly Val Pro Gln Ile Glu Val Thr Phe Asp Ile
465                 470                 475                 480

Asp Ala Asn Gly Ile Leu Asn Val Thr Ala Thr Asp Lys Ser Thr Gly
                485                 490                 495

Lys Ala Asn Lys Ile Thr Ile Thr Asn Asp Lys Gly Arg Leu Ser Lys
            500                 505                 510

Glu Glu Ile Glu Arg Met Val Gln Glu Ala Glu Lys Tyr Lys Ala Glu
        515                 520                 525

Asp Glu Val Gln Arg Glu Arg Val Ser Ala Lys Asn Ala Leu Glu Ser
    530                 535                 540

Tyr Ala Phe Asn Met Lys Ser Ala Val Glu Asp Glu Gly Leu Lys Gly
545                 550                 555                 560

Lys Ile Ser Glu Ala Asp Lys Lys Lys Val Leu Asp Lys Cys Gln Glu
                565                 570                 575

Val Ile Ser Trp Leu Asp Ala Asn Thr Leu Ala Glu Lys Asp Glu Phe
            580                 585                 590

Glu His Lys Arg Lys Glu Leu Glu Gln Val Cys Asn Pro Ile Ile Ser
        595                 600                 605

Gly Leu Tyr Gln Gly Ala Gly Gly Pro Gly Pro Gly Gly Phe Gly Ala
    610                 615                 620
```

```
Gln Gly Pro Lys Gly Gly Ser Gly Ser Gly Pro Thr Ile Glu Glu Val
625                 630                 635                 640

Asp


<210> SEQ ID NO 44
<211> LENGTH: 641
<212> TYPE: PRT
<213> ORGANISM: Rattus norvegicus

<400> SEQUENCE: 44

Met Ala Lys Lys Thr Ala Ile Gly Ile Asp Leu Gly Thr Thr Tyr Ser
1               5                   10                  15

Cys Val Gly Val Phe Gln His Gly Lys Val Glu Ile Ile Ala Asn Asp
            20                  25                  30

Gln Gly Asn Arg Thr Thr Pro Ser Tyr Val Ala Phe Thr Asp Thr Glu
        35                  40                  45

Arg Leu Ile Gly Asp Ala Ala Lys Asn Gln Val Ala Leu Asn Pro Gln
    50                  55                  60

Asn Thr Val Phe Asp Ala Lys Arg Leu Ile Gly Arg Lys Phe Gly Asp
65                  70                  75                  80

Pro Val Val Gln Ser Asp Met Lys His Trp Pro Phe Gln Val Val Asn
                85                  90                  95

Asp Gly Asp Lys Pro Lys Val Gln Val Asn Tyr Lys Gly Glu Asn Arg
            100                 105                 110

Ser Phe Tyr Pro Glu Glu Ile Ser Ser Met Val Leu Thr Lys Met Lys
        115                 120                 125

Glu Ile Ala Glu Ala Tyr Leu Gly His Pro Val Thr Asn Ala Val Ile
    130                 135                 140

Thr Val Pro Ala Tyr Phe Asn Asp Ser Gln Arg Gln Ala Thr Lys Asp
145                 150                 155                 160

Ala Gly Val Ile Ala Gly Leu Asn Val Leu Arg Ile Ile Asn Glu Pro
                165                 170                 175

Thr Ala Ala Ala Ile Ala Tyr Gly Leu Asp Arg Thr Gly Lys Gly Glu
            180                 185                 190

Arg Asn Val Leu Ile Phe Asp Leu Gly Gly Gly Thr Phe Asp Val Ser
        195                 200                 205

Ile Leu Thr Ile Asp Asp Gly Ile Phe Glu Val Lys Ala Thr Ala Gly
    210                 215                 220

Asp Thr His Leu Gly Gly Glu Asp Phe Asp Asn Arg Leu Val Ser His
225                 230                 235                 240

Phe Val Glu Glu Phe Lys Arg Lys His Lys Lys Asp Ile Ser Gln Asn
                245                 250                 255

Lys Arg Ala Val Arg Arg Leu Arg Thr Ala Cys Glu Arg Ala Lys Arg
            260                 265                 270

Thr Leu Ser Ser Ser Thr Gln Ala Ser Leu Glu Ile Asp Ser Leu Phe
        275                 280                 285

Glu Gly Ile Asp Phe Tyr Thr Ser Ile Thr Arg Ala Arg Phe Glu Glu
    290                 295                 300

Leu Cys Ser Asp Leu Phe Arg Gly Thr Leu Glu Pro Val Glu Lys Ala
305                 310                 315                 320

Leu Arg Asp Ala Lys Leu Asp Lys Ala Gln Ile His Asp Leu Val Leu
                325                 330                 335

Val Gly Gly Ser Thr Arg Ile Pro Lys Val Gln Lys Leu Leu Gln Asp
            340                 345                 350
```

```
Phe Phe Asn Gly Arg Asp Leu Asn Lys Ser Ile Asn Pro Asp Glu Ala
        355                 360                 365

Val Ala Tyr Gly Ala Ala Val Gln Ala Ala Ile Leu Met Gly Asp Lys
    370                 375                 380

Ser Glu Asn Val Gln Asp Leu Leu Leu Leu Asp Val Ala Pro Leu Ser
385                 390                 395                 400

Leu Gly Leu Glu Thr Ala Gly Gly Val Met Thr Ala Leu Ile Lys Arg
                405                 410                 415

Asn Ser Thr Ile Pro Thr Lys Gln Thr Gln Thr Phe Thr Thr Tyr Ser
            420                 425                 430

Asp Asn Gln Pro Gly Val Leu Ile Gln Val Tyr Glu Gly Glu Arg Ala
        435                 440                 445

Met Thr Arg Asp Asn Asn Leu Leu Gly Arg Phe Glu Leu Ser Gly Ile
    450                 455                 460

Pro Pro Ala Pro Arg Gly Val Pro Gln Ile Glu Val Thr Phe Asp Ile
465                 470                 475                 480

Asp Ala Asn Gly Ile Leu Asn Val Thr Ala Thr Asp Lys Ser Thr Gly
                485                 490                 495

Lys Ala Asn Lys Ile Thr Ile Thr Asn Asp Lys Gly Arg Leu Ser Lys
            500                 505                 510

Glu Glu Ile Glu Arg Met Val Gln Glu Ala Glu Arg Tyr Lys Ala Glu
        515                 520                 525

Asp Glu Val Gln Arg Glu Arg Val Ala Ala Lys Asn Ala Leu Glu Ser
    530                 535                 540

Tyr Ala Phe Asn Met Lys Ser Ala Val Glu Asp Glu Gly Leu Lys Gly
545                 550                 555                 560

Lys Ile Ser Glu Ala Asp Lys Lys Lys Val Leu Asp Lys Cys Gln Glu
                565                 570                 575

Val Ile Ser Trp Leu Asp Ser Asn Thr Leu Ala Glu Lys Glu Glu Phe
            580                 585                 590

Val His Lys Arg Glu Glu Leu Glu Arg Val Cys Asn Pro Ile Ile Ser
        595                 600                 605

Gly Leu Tyr Gln Gly Ala Gly Ala Pro Gly Ala Gly Gly Phe Gly Ala
    610                 615                 620

Gln Ala Pro Lys Gly Gly Ser Gly Ser Gly Pro Thr Ile Glu Glu Val
625                 630                 635                 640

Asp


<210> SEQ ID NO 45
<211> LENGTH: 641
<212> TYPE: PRT
<213> ORGANISM: Bos sp.

<400> SEQUENCE: 45

Met Ala Lys Asn Met Ala Ile Gly Ile Asp Leu Gly Thr Thr Tyr Ser
1               5                   10                  15

Cys Val Gly Val Phe Gln His Gly Lys Val Glu Ile Ile Ala Asn Asp
            20                  25                  30

Gln Gly Asn Arg Thr Thr Pro Ser Tyr Val Ala Phe Thr Asp Thr Glu
        35                  40                  45

Arg Leu Ile Gly Asp Ala Ala Lys Asn Gln Val Ala Leu Asn Pro Gln
    50                  55                  60

Asn Thr Val Phe Asp Ala Lys Arg Leu Ile Gly Arg Lys Phe Gly Asp
65                  70                  75                  80
```

```
Pro Val Val Gln Ser Asp Met Lys His Trp Pro Phe Arg Val Ile Asn
                85                  90                  95

Asp Gly Asp Lys Pro Lys Val Gln Val Ser Tyr Lys Gly Glu Thr Lys
            100                 105                 110

Ala Phe Tyr Pro Glu Glu Ile Ser Ser Met Val Leu Thr Lys Met Lys
        115                 120                 125

Glu Ile Ala Glu Ala Tyr Leu Gly His Pro Val Thr Asn Ala Val Ile
    130                 135                 140

Thr Val Pro Ala Tyr Phe Asn Asp Ser Gln Arg Gln Ala Thr Lys Asp
145                 150                 155                 160

Ala Gly Val Ile Ala Gly Leu Asn Val Leu Arg Ile Ile Asn Glu Pro
                165                 170                 175

Thr Ala Ala Ala Ile Ala Tyr Gly Leu Asp Arg Thr Gly Lys Gly Glu
            180                 185                 190

Arg Asn Val Leu Ile Phe Asp Leu Gly Gly Gly Thr Phe Asp Val Ser
        195                 200                 205

Ile Leu Thr Ile Asp Asp Gly Ile Phe Glu Val Lys Ala Thr Ala Gly
    210                 215                 220

Asp Thr His Leu Gly Gly Glu Asp Phe Asp Asn Arg Leu Val Asn His
225                 230                 235                 240

Phe Val Glu Glu Phe Lys Arg Lys His Lys Lys Asp Ile Ser Gln Asn
                245                 250                 255

Lys Arg Ala Val Arg Arg Leu Arg Thr Ala Cys Glu Arg Ala Lys Arg
            260                 265                 270

Thr Leu Ser Ser Ser Thr Gln Ala Ser Leu Glu Ile Asp Ser Leu Phe
        275                 280                 285

Glu Gly Ile Asp Phe Tyr Thr Ser Ile Thr Arg Ala Arg Phe Glu Glu
    290                 295                 300

Leu Cys Ser Asp Leu Phe Arg Ser Thr Leu Glu Pro Val Glu Lys Ala
305                 310                 315                 320

Leu Arg Asp Ala Lys Leu Asp Lys Ala Gln Ile His Asp Leu Val Leu
                325                 330                 335

Val Gly Gly Ser Thr Arg Ile Pro Lys Val Gln Lys Leu Leu Gln Asp
            340                 345                 350

Phe Phe Asn Gly Arg Asp Leu Asn Lys Ser Ile Asn Pro Asp Glu Ala
        355                 360                 365

Val Ala Tyr Gly Ala Ala Val Gln Ala Ala Ile Leu Met Gly Asp Lys
    370                 375                 380

Ser Glu Asn Val Gln Asp Leu Leu Leu Leu Asp Val Ala Pro Leu Ser
385                 390                 395                 400

Leu Gly Leu Glu Thr Ala Gly Gly Val Met Thr Ala Leu Ile Lys Arg
                405                 410                 415

Asn Ser Thr Ile Pro Thr Lys Gln Thr Gln Ile Phe Thr Thr Tyr Ser
            420                 425                 430

Asp Asn Gln Pro Gly Val Leu Ile Gln Val Tyr Glu Gly Glu Arg Ala
        435                 440                 445

Met Thr Arg Asp Asn Asn Leu Leu Gly Arg Phe Glu Leu Ser Gly Ile
    450                 455                 460

Pro Pro Ala Pro Arg Gly Val Pro Gln Ile Glu Val Thr Phe Asp Ile
465                 470                 475                 480

Asp Ala Asn Gly Ile Leu Asn Val Thr Ala Thr Asp Lys Ser Thr Gly
                485                 490                 495
```

```
Lys Ala Asn Lys Ile Thr Ile Thr Asn Asp Lys Gly Arg Leu Ser Lys
            500                 505                 510

Glu Glu Ile Glu Arg Met Val Gln Glu Ala Glu Lys Tyr Lys Ala Glu
        515                 520                 525

Asp Glu Val Gln Arg Glu Arg Val Ser Ala Lys Asn Ala Leu Glu Ser
    530                 535                 540

Tyr Ala Phe Asn Met Lys Ser Ala Val Glu Asp Glu Gly Leu Lys Gly
545                 550                 555                 560

Lys Ile Ser Glu Ala Asp Lys Lys Lys Val Leu Asp Lys Cys Gln Glu
                565                 570                 575

Val Ile Ser Trp Leu Asp Ala Asn Thr Leu Ala Glu Lys Asp Glu Phe
            580                 585                 590

Glu His Lys Arg Lys Glu Leu Glu Gln Val Cys Asn Pro Ile Ile Ser
        595                 600                 605

Arg Leu Tyr Gln Gly Ala Gly Gly Pro Gly Ala Gly Gly Phe Gly Ala
    610                 615                 620

Gln Gly Pro Lys Gly Gly Ser Gly Ser Gly Pro Thr Ile Glu Glu Val
625                 630                 635                 640

Asp


<210> SEQ ID NO 46
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 46

aaataaaata cgaaatg                                                    17


<210> SEQ ID NO 47
<211> LENGTH: 2000
<212> TYPE: DNA
<213> ORGANISM: Homo sapiens

<400> SEQUENCE: 47

taaagagttg tgagttgtgt aggtgagttg ccatggagct acaaatatga gttgatattc      60

tgaaatccta gacagccatc tccaaggtta agaaaaatcc ttatgcactc acttgcaaag     120

atatccacag catgctctta atggagaaaa acaaagcctt agatcaaata tgtaaagtaa     180

tttttagttt tttgaaaagg tatgtttggg ctatagataa atctgttcaa aaaacatgag     240

agaagataat aatggttgaa aggagacaca gtgcttgccc tcaagaagtt tttgtctagt     300

gagggagaga gaacttgtat gtaaataaaa ttgtgttact aaggtagata gtgagaagta     360

acttaagaga ggatcagata aggtattaag agaatacaga aaagggtctg gattaattct     420

gaacagcatc aaagaatgtt cttgcaagag atagtgtttt caccagatct tgaaggtatg     480

gatgagggta tacagagtga gtatattcag attctacttt aaaacaaata ctttcctctg     540

ttgtagtgga gttgagctat acatccaaca ataatgaaaa aatacacgca tatatacata     600

tatggagaga gatacatatt ttagtacatg tagcaattga ttaataaatg tacagtttaa     660

gtcgcatgca aaaccttgga gtgatagcaa acttcattgt aggatgttta gcagcatctc     720

tggtctctac tcactagatc ccaatagcat ctccctaggt gtgacaacca aaaatgtctc     780

caggcattga cctctggagg caaaaaaagc cctttattaa gaaccagtgg tatacataag     840

taaaacatac acaagagatt cctcccctct tctctgtatg tgaataaaaa ttgcaaagtt     900
```

```
catgacctgg attttccttt taggtttctt ctttagtggt tcttaacttc attgggtgaa    960

gtaagccttt gaagatctgt tgaaagctgt tgactcattc acttctcagg aaaacgcaca   1020

tgctgactac catttcagag aatttgcatc agggttctct ggggaggagt tctgagttct   1080

gtttccagga gctcgtagaa ttgtcatggt ctgcatatgc aaggcaggtg gattacggaa   1140

ggttgatgta cagaggtctg tattttggag cctcttctgt atttacttca gaacactaac   1200

aatcaggcga gaatgttctg gtttatcaaa cccttccttc tgcctttcat cttaaccatg   1260

cattagtttt aacaaagttc atcccaacag aagacaaaac actgatgagg taggatagct   1320

ccagctcctc ctccctctct tctagtcttg atttccatgt agtccagttt attccttccc   1380

tgattgtcca ggagaatgag aaaaagaaaa aacagagtct agtgggtaag aaagggccac   1440

ctggacggct tgatttggat tgtgaaataa aacacacaca catgcacacg tagaataagt   1500

ggctaaaatc tgagtaaatc gtgaactctc tgtatcctcc acccattgaa tactcctaaa   1560

agactttcta gaaattcaag gacttattaa tatagaaacc tggccattgt tcctcttctc   1620

ctccccatgt ggtatgagag cacctgtggc aggctcccag agaccacgga cctcttcctc   1680

taggcgggct ctgctcttct ttaaggagtc ccacagggcc tggcccgccc ctgacctcgc   1740

aaccccttgag attagtaacg ggatgagtga ggatccgggt ggcccctgcg tggcagccag   1800

taagagtctc agccttcccg gttcgggaaa ggggaagaat gcaggagggg taggatttct   1860

ttcctgatag gatcggttgg gaaagaccgc agcctgtgtg tgtctttccc ttcgaccaag   1920

gtgtctgttg ctccgtaaat aaaacgtccc actgccttct gagagcgcta taaaggcagc   1980

ggaagggtag tccgcggggc                                               2000
```

<210> SEQ ID NO 48
<211> LENGTH: 1400
<212> TYPE: DNA
<213> ORGANISM: Homo sapiens

<400> SEQUENCE: 48

```
ggctgctcgg aaaacaggac gaggggagag acttgctcaa taagctgaaa gttctgcccc     60

cgagagggct gcgacagctg ctggaatgtg cctgcagcgt ccgcctcttg gggacccgcg    120

gagcgcgccc tgacggttcc acgcctggcc cgggggtctg cacctctcct ccagtgcgca    180

cctggagctg cgtcccgggt caggtgcggg gagggaggga atctcagtgt ccccttccag    240

ccttgcaagc gcctttggcc cctgccccag cccctcggtt tgggggagat ttcagaacgc    300

ggacagcgcc ctggctgcgg gccatagggg actgggtgga actcgggaag cccccagagc    360

aggggcttac tcgcttcaag tttggggaac cccgggcagc gggtgcaggc cacgagaccc    420

gaaggttctc aggtgccccc ctgcaggctg gccgtgcgcg ccgtggggcg cttgtcgcga    480

gcgccgaggg ctgcaggacg cggaccagac tcgcggtgca ggggggcctg gctgcagcta    540

acaggtgatc ccgttctttc tgttcctcgc tcttcccctc cgatcgtcct cgcttaccgc    600

gtgtcctccc tcctcgctgt cctctggctc gcaggtcatg gcagcgccag gcggcaggtc    660

ggagccgccg cagctccccg agtacagctg cagctacatg gtgtcgcggc cggtctacag    720

cgagctcgct ttccagcaac agcacgagcg gcgcctgcag gagcgcaaga cgctgcggga    780

gagcctggcc aagtgctgca ggtagcggcc gcgcgggcct gcgtagagag aagcggagcg    840

gggcgtccac gccttgggga gggaagggcg tccccagcgg gcgagagtgg ggtgcgggcg    900

gcggagcccc tgggcgccag ctgcttctcc cagaggcccg actttcggtc tccggtcctc    960
```

cacgccgccc ttctggtggg agggtggctc catcagtctc gggcccgaaa tgaacttacc 1020
tgggaaactc gcctttgggg agagtgggtt ctaggagccc cgtctctctt tttcctctct 1080
gaaggaaact tggagtgcct cttggggtac agtgggtccc tgttgccttc ttgggagctt 1140
gtttaaatga aatgaatagg gaaacccagc tcttgaccag gaggagtcct tgaaacactc 1200
aagctaagta ggcgggctac cattcagtta gagaccagga tgcaagctag aacccagggg 1260
agcgcggggt gtgccaagta cttcatcagc aggctgtggg acccctgggg aaagccaccc 1320
tcagtctcta aacccaaaca tgccgtaact agatgtcaca aacataaaga aattagagtt 1380
tctaaaacct ttcattatag 1400

<210> SEQ ID NO 49
<211> LENGTH: 16
<212> TYPE: DNA
<213> ORGANISM: Artificial Sequence
<220> FEATURE:
<223> OTHER INFORMATION: Description of Artificial Sequence: Synthetic probe

<400> SEQUENCE: 49
ccagcagagt cagggc 16

<210> SEQ ID NO 50
<211> LENGTH: 900
<212> TYPE: DNA
<213> ORGANISM: Homo sapiens

<400> SEQUENCE: 50
cggaaggttg atgtacagag gtctgtattt tggagcctct tctgtattta cttcagaaca 60
ctaacaatca ggcgagaatg ttctggttta tcaaaccctt ccttctgcct ttcatcttaa 120
ccatgcatta gttttaacaa agttcatccc aacagaagac aaaacactga tgaggtagga 180
tagctccagc tcctcctccc tctcttctag tcttgatttc catgtagtcc agtttattcc 240
ttccctgatt gtccaggaga atgagaaaaa gaaaaaacag agtctagtgg gtaagaaagg 300
gccacctgga cggcttgatt tggattgtga aataaaacac acacacatgc acacgtagaa 360
taagtggcta aaatctgagt aaatcgtgaa ctctctgtat cctccaccca ttgaatactc 420
ctaaaagact ttctagaaat tcaaggactt attaatatag aaacctggcc attgttcctc 480
ttctcctccc catgtggtat gagagcacct gtggcaggct cccagagacc acggacctct 540
tcctctaggc gggctctgct cttctttaag gagtcccaca gggcctggcc cgcccctgac 600
ctcgcaaccc ttgagattag taacgggatg agtgaggatc cgggtggccc ctgcgtggca 660
gccagtaaga gtctcagcct tcccggttcg ggaaagggga agaatgcagg aggggtagga 720
tttctttcct gataggatcg gttgggaaag accgcagcct gtgtgtgtct ttcccttcga 780
ccaaggtgtc tgttgctccg taaataaaac gtcccactgc cttctgagag cgctataaag 840
gcagcggaag ggtagtccgc ggggcattcc gggcggggcg cgagcagaga caggtgagtt 900

<210> SEQ ID NO 51
<211> LENGTH: 1269
<212> TYPE: DNA
<213> ORGANISM: Homo sapiens

<400> SEQUENCE: 51
agggctattt gtacctcaac gagggcttct ctccaagaaa gccctgaatc cttttcctcc 60
tttttcctgc agattcacta taggacactt tttgaagcaa gagcatgcat tttccccctg 120
gcgctctgca gcggttctca gagcccagtg tcactcacat aggtgggact gctctcagtt 180
cagagagcgc tgggacactt aagatgaaaa gtccctggaa gttagcaaac agccatctgt 240
cactctggca tcgatttact aaaagtgact tctagggtat tctaaaccac ttttaaaaaa 300
caaatgagtc acttcgactt cctcaccccg caagagatag gaaggcagca gtggagtgct 360
cgctcaggag ctgtatttgt ttagcgatta gcctagagct ttgattttag ggcaaaagcg 420
agccagacag tgcggcagac gtaaggatca aaaaggccac ctatcattcg ccggggacgc 480
ctgcctcctt accctgataa cgtaactatt tctctgcata ggattttagt ttttgtgttt 540
ttgttttgtt ttattctgtt taatcacttc aagtatctca tccattattt gaagcgggct 600
cggaggaaac gtgccgcatc ctccagtcct tgtgcgtctg tttaggtctc tccgaagcag 660
gtccctctcg actcttagat ctgggtctcc agcacgcatg aaggggtaag ggtggggggg 720
tcccctattc cggcgcgcgg cgttgagcac tgaatcttcc aggcggaggc tcagtgggag 780
cgccgagaac tcgccagtac cgcgcgctgc ctgctgcctg ctgcctccca gcccaggact 840
tgggaaagga gggaggggac aagtggaggg aaagtggggc cgggcggggg gtgcctggga 900
agccaggctg cgctgacgtc actgggcgcg caattcgggc tggagcgctt taaaaaacga 960
gcgtgcaagc agagatgctg ctccacaccg ctcaggccgc gagcagcagc aaggcgcacc 1020
gccactgtcg ccgctgcagc cagggctgct ccgaaggccg gcgtggcggc aaccggcacc 1080
tctgtccccg ccgcgcttct cctcgccgcc cacgccgtgg ggtcaggaac gcggcgtctg 1140
gcgctgcaga cgcccgctga gttgcagaag cccacggagc ggcgcccggc gcgccacggc 1200
ccgtagcagt ccggtgctgc tctccgcccg cgtccggctc gtggcccccct acttcgggca 1260 ccgaccggt 1269

<210> SEQ ID NO 52
<211> LENGTH: 463
<212> TYPE: DNA
<213> ORGANISM: Homo sapiens

<400> SEQUENCE: 52
tgcgtatgag tgcaagtggg ttttaggacc aggatgaggc ggggtggggg tgcctacctg 60
acgaccgacc ccgacccact ggacaagcac ccaacccccca ttccccaaat tgcgcatccc 120
ctatcagaga gggggagggg aaacaggatg cggcgaggcg cgtgcgcact gccagcttca 180
gcaccgcgga cagtgccttc gcccccgcct ggcggcgcgc gccaccgccg cctcagcact 240
gaaggcgcgc tgacgtcact cgccggtccc ccgcaaactc cccttcccgg ccaccttggt 300
cgcgtccgcg ccgccgccgg cccagccgga ccgcaccacg cgaggcgcga gatagggggg 360
cacgggcgcg accatctgcg ctgcggcgcc ggcgactcag cgctgcctca gtctgcggtg 420
ggcagcggag gagtcgtgtc gtgcctgaga gcgcagtcga gaa 463

<210> SEQ ID NO 53
<211> LENGTH: 2204
<212> TYPE: DNA
<213> ORGANISM: Homo sapiens

<400> SEQUENCE: 53
cccacctccc tctctgtgct gggactcaca gagggagacc tcaggaggca gtctgtccat 60
cacatgtcca aatgcagagc ataccctggg ctgggcgcag tggcgcacaa ctgtaattcc 120
agcactttgg gaggctgatg tggaaggatc acttgagccc agaagttcta gaccagcctg 180
ggcaacatgg caagacccta tctctacaaa aaaagttaaa aaatcagcca cgtgtggtga 240

```
cacacacctg tagtcccagc tattcaggag gctgaggtga ggggatcact taaggctggg    300

aggttgaggc tgcagtgagt cgtggttgcg ccactgcact ccagcctggg caacagtgag    360

accctgtctc aaaagacaaa aaaaaaaaaa aaaaaaaaaa gaacatatcc tggtgtggag    420

taggggacgc tgctctgaca gaggctcggg ggcctgagct ggctctgtga gctggggagg    480

aggcagacag ccaggccttg tctgcaagca gacctggcag cattgggctg gccgcccccc    540

agggcctcct cttcatgccc agtgaatgac tcaccttggc acagacacaa tgttcggggt    600

gggcacagtg cctgcttccc gccgcacccc agccccccctc aaatgccttc cgagaagccc    660

attgagcagg gggcttgcat tgcaccccag cctgacagcc tggcatcttg ggataaaagc    720

agcacagccc cctaggggct gcccttgctg tgtggcgcca ccggcggtgg agaacaaggc    780

tctattcagc ctgtgcccag gaaaggggat caggggatgc ccaggcatgg acagtgggtg    840

gcaggggggg agaggagggc tgtctgcttc ccagaagtcc aaggacacaa atgggtgagg    900

ggactgggca gggttctgac cctgtgggac cagagtggag ggcgtagatg gacctgaagt    960

ctccagggac aacagggccc aggtctcagg ctcctagttg ggcccagtgg ctccagcgtt   1020

tccaaaccca tccatcccca gaggttcttc ccatctctcc aggctgatgt gtgggaactc   1080

gaggaaataa atctccagtg ggagacggag gggtggccag ggaaacgggg cgctgcagga   1140

ataaagacga gccagcacag ccagctcatg tgtaacggct ttgtggagct gtcaaggcct   1200

ggtctctggg agagaggcac agggaggcca gacaaggaag gggtgacctg gagggacaga   1260

tccaggggct aaagtcctga taaggcaaga gagtgccggc cccctcttgc cctatcagga   1320

cctccactgc cacatagagg ccatgattga cccttagaca aagggctggt gtccaatccc   1380

agcccccagc cccagaactc cagggaatga atgggcagag agcaggaatg tgggacatct   1440

gtgttcaagg gaaggactcc aggagtctgc tgggaatgag gcctagtagg aaatgaggtg   1500

gcccttgagg gtacagaaca ggttcattct tcgccaaatt cccagcacct tgcaggcact   1560

tacagctgag tgagataatg cctgggttat gaaatcaaaa agttggaaag caggtcagag   1620

gtcatctggt acagcccttc cttccctttt tttttttttt ttttgtgaga caaggtctct   1680

ctctgttgcc caggctggag tggcgcaaac acagctcact gcagcctcaa cctactgggc   1740

tcaagcaatc ctccagcctc agcctcccaa agtgctggga ttacaagcat gagccacccc   1800

actcagccct ttccttcctt tttaattgat gcataataat tgtaagtatt catcatggtc   1860

caaccaaccc tttcttgacc caccttccta gagagagggt cctcttgctt cagcggtcag   1920

ggccccagac ccatggtctg gctccaggta ccacctgcct catgcaggag ttggcgtgcc   1980

caggaagctc tgcctctggg cacagtgacc tcagtggggt gaggggagct ctccccatag   2040

ctgggctgcg gcccaacccc accccctcag gctatgccag gggtgttgc caggggcacc    2100

cgggcatcgc cagtctagcc cactccttca taaagccctc gcatcccagg agcgagcaga   2160

gccagagcag gttggagagg agacgcatca cctccgctgc tcgc                    2204
```

```
<210> SEQ ID NO 54
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54

gatacagcta gagtcctgat tgc                                            23
```

<210> SEQ ID NO 55
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 55
gatctgccaa gtacctcact atg 23

<210> SEQ ID NO 56
<211> LENGTH: 110
<212> TYPE: PRT
<213> ORGANISM: Homo sapiens

<400> SEQUENCE: 56

Met Lys Thr Asp Ser Ser Phe Ile Met Asp Ser Asp Pro Arg Arg Cys
1 5 10 15

Met Arg His His Tyr Val Asp Ser Ile Ser His Pro Leu Tyr Lys Cys
20 25 30

Ser Ser Lys Met Val Leu Leu Ala Arg Cys Glu Gly His Cys Ser Gln
35 40 45

Ala Ser Arg Ser Glu Pro Leu Val Ser Phe Ser Thr Val Leu Lys Gln
50 55 60

Pro Phe Arg Ser Ser Cys His Cys Cys Arg Pro Gln Thr Ser Lys Leu
65 70 75 80

Lys Ala Leu Arg Leu Arg Cys Ser Gly Gly Met Arg Leu Thr Ala Thr
85 90 95

Tyr Arg Tyr Ile Leu Ser Cys His Cys Glu Glu Cys Asn Ser
100 105 110

<210> SEQ ID NO 57
<211> LENGTH: 330
<212> TYPE: DNA
<213> ORGANISM: Homo sapiens

<400> SEQUENCE: 57
atgaaaacgg acagctcatt cataatggac tcggaccctc gacgctgcat gaggcaccac 60
tatgtggatt ctatcagtca cccattgtac aagtgtagct caaagatggt gctcctggcc 120
aggtgcgagg ggcactgcag ccaggcgtca cgctccgagc ctttggtgtc gttcagcact 180
gtcctcaagc aacccttccg ttcctcctgt cactgctgcc ggccccagac ttccaagctg 240
aaggcactgc ggctgcgatg ctcagggggc atgcgactca ctgccaccta ccggtacatc 300
ctctcctgtc actgcgagga atgcaattcc 330

<210> SEQ ID NO 58
<211> LENGTH: 2208
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 58
atggctgccg atggttatct tccagattgg ctcgaggaca acctctctga gggcattcgc 60
gagtggtggg acttgaaacc tggagccccg aaacccaaag ccaaccagca aaagcaggac 120
gacggccggg gtctggtgct tcctggctac aagtacctcg gacccttcaa cggactcgac 180

```
aagggggagc ccgtcaacgc ggcggacgca gcggccctcg agcacgacaa ggcctacgac    240
cagcagctca aagcgggtga caatccgtac ctgcggtata accacgccga cgccgagttt    300
caggagcgtc tgcaagaaga tacgtctttt gggggcaacc tcgggcgagc agtcttccag    360
gccaagaagc gggttctcga acctctcggt ctggttgagg aaggcgctaa gacggctcct    420
ggaaagaaga gaccggtaga gcaatcaccc caggaaccag actcctcttc gggcatcggc    480
aagaaaggcc agcagcccgc gaagaagaga ctcaactttg ggcagacagg cgactcagag    540
tcagtgcccg accctcaacc actcggagaa ccccccgcag ccccctctgg tgtgggatct    600
aatacaatgg cagcaggcgg tggcgctcca atggcagaca ataacgaagg cgccgacgga    660
gtgggtaacg cctcaggaaa ttggcattgc gattccacat ggctgggcga cagagtcatc    720
accaccagca cccgaacctg ggccctcccc acctacaaca accacctcta caagcaaatc    780
tccagccaat cgggagcaag caccaacgac aacacctact tcggctacag caccccctgg    840
gggtattttg actttaacag attccactgc cacttctcac cacgtgactg gcagcgactc    900
atcaacaaca actggggatt ccggcccaag agactcaact tcaagctctt caacatccag    960
gtcaaggagg tcacgacgaa tgatggcacc acgaccatcg ccaataacct taccagcacg   1020
gttcaggtct ttacggactc ggaataccag ctcccgtacg tcctcggctc tgcgcaccag   1080
ggctgcctgc ctccgttccc ggcggacgtc ttcatgattc ctcagtacgg gtacctgact   1140
ctgaacaatg gcagtcaggc cgtgggccgt tcctccttct actgcctgga gtactttcct   1200
tctcaaatgc tgagaacggg caacaacttt gagttcagct acacgtttga ggacgtgcct   1260
tttcacagca gctacgcgca cagccaaagc ctggaccggc tgatgaaccc cctcatcgac   1320
cagtacctgt actacctgtc tcggactcag accacgagtg gtaccgcagg aaatcggacg   1380
ttgcaatttt ctcaggccgg gcctagtagc atggcgaatc aggccaaaaa ctggctaccc   1440
gggccctgct accggcagca acgcgtctcc aagacagcga atcaaaataa caacagcaac   1500
tttgcctgga ccggtgccac caagtatcat ctgaatggca gagactctct ggtaaatccc   1560
ggtcccgcta tggcaaccca caaggacgac gaagacaaat tttttccgat gagcggagtc   1620
ttaatatttg ggaaacaggg agctggaaat agcaacgtgg accttgacaa cgttatgata   1680
accagtgagg aagaaattaa aaccaccaac ccagtggcca cagaacagta cggcacggtg   1740
gccactaacc tgcaatcgtc aaacaccgct cctgctacag ggaccgtcaa cagtcaagga   1800
gccttacctg gcatggtctg gcagaaccgg gacgtgtacc tgcagggtcc tatctgggcc   1860
aagattcctc acacggacgg acactttcat ccctcgccgc tgatgggagg ctttggactg   1920
aaacacccgc ctcctcagat cctgattaag aatacacctg ttcccgcgaa tcctccaact   1980
accttcagtc cagctaagtt tgcgtcgttc atcacgcagt acagcaccgg acaggtcagc   2040
gtggaaattg aatgggagct gcagaaagaa aacagcaaac gctggaaccc agagattcaa   2100
tacacttcca actacaacaa atctacaaat gtggactttg ctgttgacac aaatggcgtt   2160
tattctgagc ctcgccccat cggcacccgt tacctcaccc gtaatctg                2208
```

<210> SEQ ID NO 59
<211> LENGTH: 736
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 59

```
Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Gln Ser Pro Gln Glu Pro Asp Ser Ser Ser Gly Ile Gly
145                 150                 155                 160

Lys Lys Gly Gln Gln Pro Ala Lys Lys Arg Leu Asn Phe Gly Gln Thr
                165                 170                 175

Gly Asp Ser Glu Ser Val Pro Asp Pro Gln Pro Leu Gly Glu Pro Pro
            180                 185                 190

Ala Ala Pro Ser Gly Val Gly Ser Asn Thr Met Ala Ala Gly Gly Gly
        195                 200                 205

Ala Pro Met Ala Asp Asn Asn Glu Gly Ala Asp Gly Val Gly Asn Ala
    210                 215                 220

Ser Gly Asn Trp His Cys Asp Ser Thr Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Gln Ser Gly Ala Ser Thr Asn Asp Asn Thr
            260                 265                 270

Tyr Phe Gly Tyr Ser Thr Pro Trp Gly Tyr Phe Asp Phe Asn Arg Phe
        275                 280                 285

His Cys His Phe Ser Pro Arg Asp Trp Gln Arg Leu Ile Asn Asn Asn
    290                 295                 300

Trp Gly Phe Arg Pro Lys Arg Leu Asn Phe Lys Leu Phe Asn Ile Gln
305                 310                 315                 320

Val Lys Glu Val Thr Thr Asn Asp Gly Thr Thr Thr Ile Ala Asn Asn
                325                 330                 335

Leu Thr Ser Thr Val Gln Val Phe Thr Asp Ser Glu Tyr Gln Leu Pro
            340                 345                 350

Tyr Val Leu Gly Ser Ala His Gln Gly Cys Leu Pro Pro Phe Pro Ala
        355                 360                 365

Asp Val Phe Met Ile Pro Gln Tyr Gly Tyr Leu Thr Leu Asn Asn Gly
    370                 375                 380

Ser Gln Ala Val Gly Arg Ser Ser Phe Tyr Cys Leu Glu Tyr Phe Pro
385                 390                 395                 400

Ser Gln Met Leu Arg Thr Gly Asn Asn Phe Glu Phe Ser Tyr Thr Phe
                405                 410                 415
```

```
Glu Asp Val Pro Phe His Ser Ser Tyr Ala His Ser Gln Ser Leu Asp
            420                 425                 430

Arg Leu Met Asn Pro Leu Ile Asp Gln Tyr Leu Tyr Tyr Leu Ser Arg
        435                 440                 445

Thr Gln Thr Thr Ser Gly Thr Ala Gly Asn Arg Thr Leu Gln Phe Ser
    450                 455                 460

Gln Ala Gly Pro Ser Ser Met Ala Asn Gln Ala Lys Asn Trp Leu Pro
465                 470                 475                 480

Gly Pro Cys Tyr Arg Gln Gln Arg Val Ser Lys Thr Ala Asn Gln Asn
                485                 490                 495

Asn Asn Ser Asn Phe Ala Trp Thr Gly Ala Thr Lys Tyr His Leu Asn
            500                 505                 510

Gly Arg Asp Ser Leu Val Asn Pro Gly Pro Ala Met Ala Thr His Lys
        515                 520                 525

Asp Asp Glu Asp Lys Phe Phe Pro Met Ser Gly Val Leu Ile Phe Gly
    530                 535                 540

Lys Gln Gly Ala Gly Asn Ser Asn Val Asp Leu Asp Asn Val Met Ile
545                 550                 555                 560

Thr Ser Glu Glu Glu Ile Lys Thr Thr Asn Pro Val Ala Thr Glu Gln
                565                 570                 575

Tyr Gly Thr Val Ala Thr Asn Leu Gln Ser Ser Asn Thr Ala Pro Ala
            580                 585                 590

Thr Gly Thr Val Asn Ser Gln Gly Ala Leu Pro Gly Met Val Trp Gln
        595                 600                 605

Asn Arg Asp Val Tyr Leu Gln Gly Pro Ile Trp Ala Lys Ile Pro His
    610                 615                 620

Thr Asp Gly His Phe His Pro Ser Pro Leu Met Gly Gly Phe Gly Leu
625                 630                 635                 640

Lys His Pro Pro Pro Gln Ile Leu Ile Lys Asn Thr Pro Val Pro Ala
                645                 650                 655

Asn Pro Pro Thr Thr Phe Ser Pro Ala Lys Phe Ala Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Ile Gln Tyr Thr Ser Asn
    690                 695                 700

Tyr Asn Lys Ser Thr Asn Val Asp Phe Ala Val Asp Thr Asn Gly Val
705                 710                 715                 720

Tyr Ser Glu Pro Arg Pro Ile Gly Thr Arg Tyr Leu Thr Arg Asn Leu
                725                 730                 735
```

<210> SEQ ID NO 60
<211> LENGTH: 145
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 60

```
ttggccactc cctctctgcg cgctcgctcg ctcactgagg ccgcccgggc aaagcccggg     60

cgtcgggcga cctttggtcg cccggcctca gtgagcgagc gagcgcgcag agagggagtg    120

gccaactcca tcactagggg ttcct                                          145
```

<210> SEQ ID NO 61

<211> LENGTH: 145
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 61
aggaacccct agtgatggag ttggccactc cctctctgcg cgctcgctcg ctcactgagg     60
ccgggcgacc aaaggtcgcc cgacgcccgg gctttgcccg ggcggcctca gtgagcgagc    120
gagcgcgcag agagggagtg gccaa                                          145

<210> SEQ ID NO 62
<211> LENGTH: 119
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 62
ctgcgcgctc gctcgctcac tgaggccgcc cgggcgtcgg gcgacctttg gtcgcccggc     60
ctcagtgagc gagcgagcgc gcagagaggg agtggccaac tccatcacta ggggttcct     119

<210> SEQ ID NO 63
<211> LENGTH: 130
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 63
aggaacccct agtgatggag ttggccactc cctctctgcg cgctcgctcg ctcactgagg     60
ccgggcgacc aaaggtcgcc cgacgcccgg gctttgcccg ggcggcctca gtgagcgagc    120
gagcgcgcag                                                           130

<210> SEQ ID NO 64
<211> LENGTH: 279
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 64
gtcgaggtga gccccacgtt ctgcttcact ctccccatct cccccccctc cccaccccca     60
attttgtatt tatttatttt ttaattattt tgtgcagcga tgggggcggg gggggggggg    120
gggcgcgcgc caggcggggc ggggcggggc gaggggcggg gcggggcgag gcggagaggt    180
gcggcggcag ccaatcagag cggcgcgctc cgaaagtttc cttttatggc gaggcggcgg    240
cggcggcggc cctataaaaa gcgaagcgcg cggcgggcg                           279

<210> SEQ ID NO 65
<211> LENGTH: 277
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 65

```
gtcgaggtga gccccacgtt ctgcttcact ctccccatct cccccccctc cccaccccca     60

attttgtatt tatttatttt ttaattattt tgtgcagcga tgggggcggg gggggggggg    120

gcgcgcgcca ggcggggcgg ggcggggcga ggggcggggc ggggcgaggc ggagaggtgc    180

ggcggcagcc aatcagagcg gcgcgctccg aaagtttcct tttatggcga ggcggcggcg    240

gcggcggccc tataaaaagc gaagcgcgcg gcgggcg                             277


<210> SEQ ID NO 66
<211> LENGTH: 660
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 66

gacattgatt attgactagt tattaatagt aatcaattac ggggtcatta gttcatagcc     60

catatatgga gttccgcgtt acataactta cggtaaatgg cccgcctggc tgaccgccca    120

acgacccccg cccattgacg tcaataatga cgtatgttcc catagtaacg ccaataggga    180

ctttccattg acgtcaatgg gtggactatt tacggtaaac tgcccacttg gcagtacatc    240

aagtgtatca tatgccaagt acgcccccta ttgacgtcaa tgacggtaaa tggcccgcct    300

ggcattatgc ccagtacatg accttatggg actttcctac ttggcagtac atctacgtat    360

tagtcatcgc tattaccatg ggtcgaggtg agccccacgt tctgcttcac tctccccatc    420

tccccccccct ccccaccccc aattttgtat ttatttattt tttaattatt ttgtgcagcg    480

atgggggcgg gggggggggg ggggcgcgcg ccaggcgggg cggggcgggg cgaggggcgg    540

ggcggggcga ggcggagagg tgcggcggca gccaatcaga gcggcgcgct ccgaaagttt    600

ccttttatgg cgaggcggcg gcggcggcgg ccctataaaa agcgaagcgc gcggcgggcg    660


<210> SEQ ID NO 67
<211> LENGTH: 658
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 67

gacattgatt attgactagt tattaatagt aatcaattac ggggtcatta gttcatagcc     60

catatatgga gttccgcgtt acataactta cggtaaatgg cccgcctggc tgaccgccca    120

acgacccccg cccattgacg tcaataatga cgtatgttcc catagtaacg ccaataggga    180

ctttccattg acgtcaatgg gtggactatt tacggtaaac tgcccacttg gcagtacatc    240

aagtgtatca tatgccaagt acgcccccta ttgacgtcaa tgacggtaaa tggcccgcct    300

ggcattatgc ccagtacatg accttatggg actttcctac ttggcagtac atctacgtat    360

tagtcatcgc tattaccatg ggtcgaggtg agccccacgt tctgcttcac tctccccatc    420

tccccccccct ccccaccccc aattttgtat ttatttattt tttaattatt ttgtgcagcg    480

atgggggcgg gggggggggg ggcgcgcgcc aggcggggcg gggcggggcg aggggcgggg    540

cggggcgagg cggagaggtg cggcggcagc caatcagagc ggcgcgctcc gaaagtttcc    600

ttttatggcg aggcggcggc ggcggcggcc ctataaaaag cgaagcgcgc ggcgggcg      658


<210> SEQ ID NO 68
<211> LENGTH: 1725
```

<212> TYPE: DNA
<213> ORGANISM: Homo sapiens

<400> SEQUENCE: 68
ctatggagtt tgcataacaa acgtttggca gctcgctctc ttacactcca ttaacaagct 60
gtaacatata gctgcaggtt gctataatct cattaatatt ttggaaactt gaatattgag 120
tatttctgag tgctcattcc ccatatgcca gccacttctg ccatgctgac tggttccttt 180
ctctccatta ttagcaatta gcttcttacc ttccaaagtc agatccaagg tatccaagat 240
actagcaaag gaatcaacta tgtgtgcaag ttaagcatgc ttaatatcac ccaaacaaac 300
aaagaggcag catttcttaa agtaatgaag atagataaat cgggttagtc ctttgcgaca 360
ctgctggtgc tttctagagt tttatatatt ttaagcagct tgctttatat tctgtctttg 420
cctcccaccc caccagcact tttatttgtg gagggttttg gctcgccaca ctttgggaaa 480
cttatttgat ttcacggaga gctgaaggaa gatcattttt ggcaacagac aagtttaaac 540
acgatttcta tgggacattg ctaactgggg cccctaagga gaaaggggaa actgagcgga 600
gaatgggtta aatccttgga agcaggggag aggcagggga ggagagaagt cggaggagta 660
taaagaaaag gacaggaacc aagaagcgtg gggtggtttt gccgtaatgt gagtgtttct 720
taattagaga acggttgaca atagagggtc tggcagaggc tcctggccgc ggtgcggagc 780
gtctggagcg gagcacgcgc tgtcagctgg tgagcgcact ctcctttcag gcagctcccc 840
ggggagctgt gcggccacat ttaacaccat catcacccct ccccggcctc ctcaacctcg 900
gcctcctcct cgtcgacagc cttccttggc ccccaccagc agagctcaca gtagcgagcg 960
tctctcgccg tctcccgcac tcggccgggg cctctctcct cccccagctg cgcagcggga 1020
gccgccactg cccactgcac ctcccagcaa ccagcccagc acgcaaagaa gctgcgcaaa 1080
gttaaagcca agcaatgcca aggggagggg aagctggagg cgggctttga gtggcttctg 1140
ggcgcctggc gggtccagaa tcgcccagag ccgcccgcgg tcgtgcacat ctgacccgag 1200
tcagcttggg caccagccga gagccggctc cgcaccgctc ccgcacccca gccgccgggg 1260
tggtgacaca caccggagtc gaattacagc cctgcaatta acatatgaat ctgacgaatt 1320
taaaagaagg aaaaaaaaaa aaaaacctga gcaggcttgg gagtcctctg cacacaagaa 1380
cttttctcgg ggtgtaaaaa ctctttgatt ggctgctcgc acgcgcctgc ccgcgccctc 1440
cattggctga gaagacacgc gaccggcgcg aggagggggt tgggagagga gcggggggag 1500
actgagtggc gcgtgccgct ttttaaaggg gcgcagcgcc ttcagcaacc ggagaagcat 1560
agttgcacgc gacctggtgt gtgatctccg agtgggtggg ggagggtcga ggagggaaaa 1620
aaaaataaga cgttgcagaa gagacccgga aagggccttt tttttggttg agctggtgtc 1680
ccagtgctgc ctccgatcct gagcctccga gcctttgcag tgcaa 1725

<210> SEQ ID NO 69
<211> LENGTH: 381
<212> TYPE: DNA
<213> ORGANISM: Cytomegalovirus

<400> SEQUENCE: 69
gacattgatt attgactagt tattaatagt aatcaattac ggggtcatta gttcatagcc 60
catatatgga gttccgcgtt acataactta cggtaaatgg cccgcctggc tgaccgccca 120
acgacccccg cccattgacg tcaataatga cgtatgttcc catagtaacg ccaataggga 180
ctttccattg acgtcaatgg gtggactatt tacggtaaac tgcccacttg gcagtacatc 240

```
aagtgtatca tatgccaagt acgcccccta ttgacgtcaa tgacggtaaa tggcccgcct    300

ggcattatgc ccagtacatg accttatggg actttcctac ttggcagtac atctacgtat    360

tagtcatcgc tattaccatg g                                              381


<210> SEQ ID NO 70
<211> LENGTH: 1013
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 70

ggagtcgctg cgttgccttc gccccgtgcc ccgctccgcg ccgcctcgcg ccgcccgccc     60

cggctctgac tgaccgcgtt actcccacag gtgagcgggc gggacggccc ttctcctccg    120

ggctgtaatt agcgcttggt ttaatgacgg ctcgtttctt ttctgtggct gcgtgaaagc    180

cttaaagggc tccgggaggg ccctttgtgc ggggggggagc ggctcggggg gtgcgtgcgt    240

gtgtgtgtgc gtggggagcg ccgcgtgcgg cccgcgctgc ccggcggctg tgagcgctgc    300

gggcgcggcg cggggctttg tgcgctccgc gtgtgcgcga ggggagcgcg gccgggggcg    360

gtgccccgcg gtgcgggggg gctgcgaggg gaacaaaggc tgcgtgcggg gtgtgtgcgt    420

gggggggtga gcagggggtg tgggcgcggc ggtcgggctg taaccccccc ctgcaccccc    480

ctccccgagt tgctgagcac ggcccggctt cgggtgcggg gctccgtgcg gggcgtggcg    540

cggggctcgc cgtgccgggc ggggggtggc ggcaggtggg ggtgccgggc ggggcggggc    600

cgcctcgggc cggggagggc tcgggggagg ggcgcggcgg cccccggagc gccggcggct    660

gtcgaggcgc ggcgagccgc agccattgcc ttttatggta atcgtgcgag agggcgcagg    720

gacttccttt gtcccaaatc tgtgcggagc cgaaatctgg gaggcgccgc cgcacccccct   780

ctagcgggcg cggggcgaag cggtgcggcg ccggcaggaa ggaaatgggc ggggagggcc    840

ttcgtgcgtc gccgcgccgc cgtccccttc tccctctcca gcctcggggc tgtccgcggg    900

gggacggctg ccttcggggg ggacggggca gggcggggtt cggcttctgg cgtgtgaccg    960

gcggctctag agcctctgct aaccatgttc atgccttctt ctttttccta cag          1013


<210> SEQ ID NO 71
<211> LENGTH: 225
<212> TYPE: DNA
<213> ORGANISM: Bos sp.

<400> SEQUENCE: 71

ctgtgccttc tagttgccag ccatctgttg tttgcccctc ccccgtgcct tccttgaccc     60

tggaaggtgc cactcccact gtcctttcct aataaaatga ggaaattgca tcgcattgtc    120

tgagtaggtg tcattctatt ctggggggtg gggtggggca ggacagcaag ggggaggatt    180

gggaagacaa tagcaggcat gctggggatg cggtgggctc tatgg                    225


<210> SEQ ID NO 72
<211> LENGTH: 122
<212> TYPE: DNA
<213> ORGANISM: Simian virus 40

<400> SEQUENCE: 72

aacttgttta ttgcagctta taatggttac aaataaagca atagcatcac aaatttcaca     60

aataaagcat ttttttcact gcattctagt tgtggtttgt ccaaactcat caatgtatct    120
```

ta 122

<210> SEQ ID NO 73
<211> LENGTH: 22
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 73
ttgtcgacgc ggccgcacgc gt 22

<210> SEQ ID NO 74
<211> LENGTH: 44
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 74
ctcctgggca acgtgctggt tattgtgacc ggtcgctagc cacc 44

<210> SEQ ID NO 75
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 75
taagagctcg ctgatcagcc tcga 24

<210> SEQ ID NO 76
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 76
aagcttgaat tcagctgacg tgcctcggac cgtcctagg 39

<210> SEQ ID NO 77
<211> LENGTH: 14
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 77
gcggccgcac gcgt 14

<210> SEQ ID NO 78
<211> LENGTH: 82
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 78
gtaagtatca aggttacaag acaggtttaa ggagaccaat agaaactggg cttgtcgaga 60
cagagaagac tcttgcgttt ct 82

<210> SEQ ID NO 79
<211> LENGTH: 1719
<212> TYPE: DNA
<213> ORGANISM: Homo sapiens

<400> SEQUENCE: 79
agaagaacaa aagcatttgg aagtaacagg acctctttct agctctcaga aaagtctgag 60
aagaaaggag ccctgcgttc ccctaagctg tgcagcagat actgtgatga tggattgcaa 120
gtgcaaagag taagacaaaa ctccagcaca taaaggacaa tgacaaccag aaagcttcag 180
cccgatcctg ccctttcctt gaacgggact ggatcctagg aggtgaagcc atttccaatt 240
ttttgtcctc tgcctccctc tgctgttctt ctagagaagt ttttccttac aacaatgaga 300
aaacatgtac tagctgcatc cttttctatg ctctccctgc tggtgataat gggagataca 360
gacagtaaaa cggacagctc attcataatg gactcggacc ctcgacgctg catgaggcac 420
cactatgtgg attctatcag tcacccattg tacaagtgta gctcaaagat ggtgctcctg 480
gccaggtgcg aggggcactg cagccaggcg tcacgctccg agcctttggt gtcgttcagc 540
actgtcctca agcaaccctt ccgttcctcc tgtcactgct gccggcccca gacttccaag 600
ctgaaggcac tgcggctgcg atgctcaggg ggcatgcgac tcactgccac ctaccggtac 660
atcctctcct gtcactgcga ggaatgcaat tcctgaggcc cgctgctgtg tgtggcttct 720
ggatgggaca actgtagagg cagttcgacc agccagggaa agactggcaa gaaaagagtt 780
aaggcaaaaa aggatgcaac aattctcccg ggactctgca tattctagta ataaagactc 840
tacatgcttg ttgacagaga gagatactct gggaacttct ttgcagttcc catctccttt 900
ctctggtaca atttcttttg gttcattttc agattcaggc attttccccc ttggctctca 960
atgctgtttg ggtttccaac aattcagcat tagtgggaaa aagtgggccc tcatacacaa 1020
gcgtgtcagg ctgtcagtgt ttggtgcacg ctggggaaga atttactttg gaaagtagaa 1080
aagcccagct tttcctggga catcttctgt tattgttgat gttttttttt accttgtcat 1140
tttggtctaa ggttgccatt gctgctaaag gttaccgatt tcaaagtcca gataccaagc 1200
atgtggatat gtttagctac gtttactcac agccagcgaa ctgacattaa aataactaac 1260
aaacagattc ttttatgtga tgctggaact cttgacagct ataattatta ttcagaaatg 1320
actttttgaa agtaaaagca gcataaagaa tttgtcacag gaaggctgtc tcagataaat 1380
tatggtaaaa ttttgtaagg gagcagactt ttaaagactt gcacaaatac ggatcctgca 1440
ctgactctgg aaaaggcata tatgtactag tggcatggag aatgcaccat actcatgcat 1500
gcaaattaga caaccaagta tgaatctatt tgtgggtgtg ctatagcttt agccgtgtca 1560
cgggcatcat tctctaatat ccacttgtcc atgtgaaaca tgttgccaaa atggtggcct 1620
ggcttgtctt ctgaacgttt ggttcaaatg tgttttggtc ctggaggctc aaattttgag 1680
ttattcccac gttttgaaat aaaaagagta tattcaaaa 1719

<210> SEQ ID NO 80
<211> LENGTH: 107
<212> TYPE: PRT
<213> ORGANISM: Mus musculus

<400> SEQUENCE: 80

Lys Thr Asp Ser Ser Phe Leu Met Asp Ser Gln Arg Cys Met Arg His
1 5 10 15

```
His Tyr Val Asp Ser Ile Ser His Pro Leu Tyr Lys Cys Ser Ser Lys
            20                  25                  30

Met Val Leu Leu Ala Arg Cys Glu Gly His Cys Ser Gln Ala Ser Arg
        35                  40                  45

Ser Glu Pro Leu Val Ser Phe Ser Thr Val Leu Lys Gln Pro Phe Arg
    50                  55                  60

Ser Ser Cys His Cys Cys Arg Pro Gln Thr Ser Lys Leu Lys Ala Leu
65                  70                  75                  80

Arg Leu Arg Cys Ser Gly Gly Met Arg Leu Thr Ala Thr Tyr Arg Tyr
                85                  90                  95

Ile Leu Ser Cys His Cys Glu Glu Cys Ser Ser
            100                 105
```

<210> SEQ ID NO 81
<211> LENGTH: 321
<212> TYPE: DNA
<213> ORGANISM: Mus musculus

<400> SEQUENCE: 81

```
aaaacagaca gttcatttct gatggactct caacgctgca tgagacacca ttatgtcgat     60

tctatcagtc acccactgta caaatgtagc tcaaagatgg tgctcctggc cagatgtgag    120

gggcactgca gccaggcatc acgctctgag cccttggtgt ccttcagcac tgtcctcaag    180

caacctttcc gttcctcctg tcactgctgc cgaccccaga cttccaagct gaaggctctg    240

cgtctgcgct gctcaggggg catgcgactt actgccactt accggtacat cctctcctgt    300

cactgtgagg aatgcagctc c                                              321
```

<210> SEQ ID NO 82
<211> LENGTH: 133
<212> TYPE: PRT
<213> ORGANISM: Macaca mulatta

<400> SEQUENCE: 82

```
Met Arg Lys His Val Leu Ala Ala Ser Phe Ser Met Leu Ser Leu Leu
1               5                   10                  15

Val Ile Met Gly Asp Thr Asp Ser Lys Thr Asp Ser Ser Phe Ile Met
            20                  25                  30

Asp Ser Asp Pro Arg Arg Cys Met Arg His His Tyr Val Asp Ser Ile
        35                  40                  45

Ser His Pro Leu Tyr Lys Cys Ser Ser Lys Met Val Leu Leu Ala Arg
    50                  55                  60

Cys Glu Gly His Cys Ser Gln Ala Ser Arg Ser Glu Pro Leu Val Ser
65                  70                  75                  80

Phe Ser Thr Val Leu Lys Gln Pro Phe Arg Ser Ser Cys His Cys Cys
                85                  90                  95

Arg Pro Gln Thr Ser Lys Leu Lys Ala Leu Arg Leu Arg Cys Ser Gly
            100                 105                 110

Gly Met Arg Leu Thr Ala Thr Tyr Arg Tyr Ile Leu Ser Cys His Cys
        115                 120                 125

Glu Glu Cys Asn Ser
    130
```

<210> SEQ ID NO 83
<211> LENGTH: 107
<212> TYPE: PRT
<213> ORGANISM: Rattus norvegicus

<400> SEQUENCE: 83

```
Lys Thr Asp Ser Ser Phe Leu Met Asp Ser Gln Arg Cys Met Arg His
1               5                   10                  15

His Tyr Val Asp Ser Ile Ser His Pro Leu Tyr Lys Cys Ser Ser Lys
            20                  25                  30

Met Val Leu Leu Ala Arg Cys Glu Gly His Cys Ser Gln Ala Ser Arg
        35                  40                  45

Ser Glu Pro Leu Val Ser Phe Ser Thr Val Leu Lys Gln Pro Phe Arg
    50                  55                  60

Ser Ser Cys His Cys Cys Arg Pro Gln Thr Ser Lys Leu Lys Ala Leu
65                  70                  75                  80

Arg Leu Arg Cys Ser Gly Gly Met Arg Leu Thr Ala Thr Tyr Arg Tyr
                85                  90                  95

Ile Leu Ser Cys His Cys Glu Glu Cys Ser Ser
            100                 105
```

<210> SEQ ID NO 84
<211> LENGTH: 109
<212> TYPE: PRT
<213> ORGANISM: Pan troglodytes

<400> SEQUENCE: 84

```
Lys Thr Asp Ser Ser Phe Val Met Asp Ser Asp Pro Arg Arg Cys Met
1               5                   10                  15

Arg His His Tyr Val Asp Ser Ile Ser His Pro Leu Tyr Lys Cys Ser
            20                  25                  30

Ser Lys Met Val Leu Leu Ala Arg Cys Glu Gly His Cys Ser Gln Ala
        35                  40                  45

Ser Arg Ser Glu Pro Leu Val Ser Phe Ser Thr Val Leu Lys Gln Pro
    50                  55                  60

Phe Arg Ser Ser Cys His Cys Cys Arg Pro Gln Thr Ser Lys Leu Lys
65                  70                  75                  80

Ala Leu Arg Leu Arg Cys Ser Gly Gly Met Arg Leu Thr Ala Thr Tyr
                85                  90                  95

Arg Tyr Ile Leu Ser Cys His Cys Glu Glu Cys Asn Ser
            100                 105
```

<210> SEQ ID NO 85
<211> LENGTH: 641
<212> TYPE: PRT
<213> ORGANISM: Homo sapiens

<400> SEQUENCE: 85

```
Met Ala Lys Ala Ala Ala Ile Gly Ile Asp Leu Gly Thr Thr Tyr Ser
1               5                   10                  15

Cys Val Gly Val Phe Gln His Gly Lys Val Glu Ile Ile Ala Asn Asp
            20                  25                  30

Gln Gly Asn Arg Thr Thr Pro Ser Tyr Val Ala Phe Thr Asp Thr Glu
        35                  40                  45

Arg Leu Ile Gly Asp Ala Ala Lys Asn Gln Val Ala Leu Asn Pro Gln
    50                  55                  60

Asn Thr Val Phe Asp Ala Lys Arg Leu Ile Gly Arg Lys Phe Gly Asp
65                  70                  75                  80

Pro Val Val Gln Ser Asp Met Lys His Trp Pro Phe Gln Val Ile Asn
                85                  90                  95
```

```
Asp Gly Asp Lys Pro Lys Val Gln Val Ser Tyr Lys Gly Glu Thr Lys
            100                 105                 110

Ala Phe Tyr Pro Glu Glu Ile Ser Ser Met Val Leu Thr Lys Met Lys
        115                 120                 125

Glu Ile Ala Glu Ala Tyr Leu Gly Tyr Pro Val Thr Asn Ala Val Ile
    130                 135                 140

Thr Val Pro Ala Tyr Phe Asn Asp Ser Gln Arg Gln Ala Thr Lys Asp
145                 150                 155                 160

Ala Gly Val Ile Ala Gly Leu Asn Val Leu Arg Ile Ile Asn Glu Pro
                165                 170                 175

Thr Ala Ala Ala Ile Ala Tyr Gly Leu Asp Arg Thr Gly Lys Gly Glu
            180                 185                 190

Arg Asn Val Leu Ile Phe Asp Leu Gly Gly Gly Thr Phe Asp Val Ser
        195                 200                 205

Ile Leu Thr Ile Asp Asp Gly Ile Phe Glu Val Lys Ala Thr Ala Gly
    210                 215                 220

Asp Thr His Leu Gly Gly Glu Asp Phe Asp Asn Arg Leu Val Asn His
225                 230                 235                 240

Phe Val Glu Glu Phe Lys Arg Lys His Lys Lys Asp Ile Ser Gln Asn
                245                 250                 255

Lys Arg Ala Val Arg Arg Leu Arg Thr Ala Cys Glu Arg Ala Lys Arg
            260                 265                 270

Thr Leu Ser Ser Ser Thr Gln Ala Ser Leu Glu Ile Asp Ser Leu Phe
        275                 280                 285

Glu Gly Ile Asp Phe Tyr Thr Ser Ile Thr Arg Ala Arg Phe Glu Glu
    290                 295                 300

Leu Cys Ser Asp Leu Phe Arg Ser Thr Leu Glu Pro Val Glu Lys Ala
305                 310                 315                 320

Leu Arg Asp Ala Lys Leu Asp Lys Ala Gln Ile His Asp Leu Val Leu
                325                 330                 335

Val Gly Gly Ser Thr Arg Ile Pro Lys Val Gln Lys Leu Leu Gln Asp
            340                 345                 350

Phe Phe Asn Gly Arg Asp Leu Asn Lys Ser Ile Asn Pro Asp Glu Ala
        355                 360                 365

Val Ala Tyr Gly Ala Ala Val Gln Ala Ala Ile Leu Met Gly Asp Lys
    370                 375                 380

Ser Glu Asn Val Gln Asp Leu Leu Leu Leu Asp Val Ala Pro Leu Ser
385                 390                 395                 400

Leu Gly Leu Glu Thr Ala Gly Gly Val Met Thr Ala Leu Ile Lys Arg
                405                 410                 415

Asn Ser Thr Ile Pro Thr Lys Gln Thr Gln Ile Phe Thr Thr Tyr Ser
            420                 425                 430

Asp Asn Gln Pro Gly Val Leu Ile Gln Val Tyr Glu Gly Glu Arg Ala
        435                 440                 445

Met Thr Lys Asp Asn Asn Leu Leu Gly Arg Phe Glu Leu Ser Gly Ile
    450                 455                 460

Pro Pro Ala Pro Arg Gly Val Pro Gln Ile Glu Val Thr Phe Asp Ile
465                 470                 475                 480

Asp Ala Asn Gly Ile Leu Asn Val Thr Ala Thr Asp Lys Ser Thr Gly
                485                 490                 495

Lys Ala Asn Lys Ile Thr Ile Thr Asn Asp Lys Gly Arg Leu Ser Lys
            500                 505                 510

Glu Glu Ile Glu Arg Met Val Gln Glu Ala Glu Lys Tyr Lys Ala Glu
```

```
        515                 520                 525

Asp Glu Val Gln Arg Glu Arg Val Ser Ala Lys Asn Ala Leu Glu Ser
    530                 535                 540

Tyr Ala Phe Asn Met Lys Ser Ala Val Glu Asp Glu Gly Leu Lys Gly
545                 550                 555                 560

Lys Ile Ser Glu Ala Asp Lys Lys Lys Val Leu Asp Lys Cys Gln Glu
                565                 570                 575

Val Ile Ser Trp Leu Asp Ala Asn Thr Leu Ala Glu Lys Asp Glu Phe
            580                 585                 590

Glu His Lys Arg Lys Glu Leu Glu Gln Val Cys Asn Pro Ile Ile Ser
        595                 600                 605

Gly Leu Tyr Gln Gly Ala Gly Gly Pro Gly Pro Gly Gly Phe Gly Ala
    610                 615                 620

Gln Gly Pro Lys Gly Gly Ser Gly Ser Gly Pro Thr Ile Glu Glu Val
625                 630                 635                 640

Asp


<210> SEQ ID NO 86
<211> LENGTH: 1926
<212> TYPE: DNA
<213> ORGANISM: Homo sapiens

<400> SEQUENCE: 86

atggccaaag ccgcggcgat cggcatcgac ctgggcacca cctactcctg cgtgggggtg      60

ttccaacacg gcaaggtgga gatcatcgcc aacgaccagg gcaaccgcac cacccccagc     120

tacgtggcct tcacggacac cgagcggctc atcggggatg cggccaagaa ccaggtggcg     180

ctgaacccgc agaacaccgt gtttgacgcg aagcggctga tcggccgcaa gttcggcgac     240

ccggtggtgc agtcggacat gaagcactgg cctttccagg tgatcaacga cggagacaag     300

cccaaggtgc aggtgagcta caaggggggag accaaggcat tctaccccga ggagatctcg     360

tccatggtgc tgaccaagat gaaggagatc gccgaggcgt acctgggcta cccggtgacc     420

aacgcggtga tcaccgtgcc ggcctacttc aacgactcgc agcgccaggc caccaaggat     480

gcgggtgtga tcgcggggct caacgtgctg cggatcatca acgagcccac ggccgccgcc     540

atcgcctacg gcctggacag aacgggcaag ggggagcgca acgtgctcat ctttgacctg     600

ggcgggggca ccttcgacgt gtccatcctg acgatcgacg acggcatctt cgaggtgaag     660

gccacggccg gggacaccca cctgggtggg gaggactttg acaacaggct ggtgaaccac     720

ttcgtggagg agttcaagag aaaacacaag aaggacatca gccagaacaa gcgagccgtg     780

aggcggctgc gcaccgcctg cgagagggcc aagaggaccc tgtcgtccag cacccaggcc     840

agcctggaga tcgactccct gtttgagggc atcgacttct acacgtccat caccagggcg     900

aggttcgagg agctgtgctc cgacctgttc cgaagcaccc tggagcccgt ggagaaggct     960

ctgcgcgacg ccaagctgga caaggcccag attcacgacc tggtcctggt cgggggctcc    1020

acccgcatcc ccaaggtgca gaagctgctg caggacttct tcaacgggcg cgacctgaac    1080

aagagcatca accccgacga ggctgtggcc tacggggcgg cggtgcaggc ggccatcctg    1140

atgggggaca agtccgagaa cgtgcaggac ctgctgctgc tggacgtggc tcccctgtcg    1200

ctggggctgg agacggccgg aggcgtgatg actgccctga tcaagcgcaa ctccaccatc    1260

cccaccaagc agacgcagat cttcaccacc tactccgaca accaacccgg ggtgctgatc    1320

caggtgtacg agggcgagag ggccatgacg aaagacaaca atctgttggg gcgcttcgag    1380
```

```
ctgagcggca tccctccggc ccccaggggc gtgccccaga tcgaggtgac cttcgacatc   1440

gatgccaacg gcatcctgaa cgtcacggcc acggacaaga gcaccggcaa ggccaacaag   1500

atcaccatca ccaacgacaa gggccgcctg agcaaggagg agatcgagcg catggtgcag   1560

gaggcggaga agtacaaagc ggaggacgag gtgcagcgcg agagggtgtc agccaagaac   1620

gccctggagt cctacgcctt caacatgaag agcgccgtgg aggatgaggg gctcaagggc   1680

aagatcagcg aggcggacaa gaagaaggtt ctggacaagt gtcaagaggt catctcgtgg   1740

ctggacgcca acaccttggc cgagaaggac gagtttgagc acaagaggaa ggagctggag   1800

caggtgtgta accccatcat cagcggactg taccagggtg ccggtggtcc cgggcctggg   1860

ggcttcgggg ctcagggtcc caagggaggg tctgggtcag gccccaccat tgaggaggtg   1920

gattag                                                              1926
```

<210> SEQ ID NO 87
<211> LENGTH: 2400
<212> TYPE: DNA
<213> ORGANISM: Homo sapiens

<400> SEQUENCE: 87

```
aacggctagc ctgaggagct gctgcgacag tccactacct ttttcgagag tgactcccgt     60

tgtcccaagg cttcccagag cgaacctgtg cggctgcagg caccggcgcg tcgagtttcc    120

ggcgtccgga aggaccgagc tcttctcgcg gatccagtgt tccgtttcca gcccccaatc    180

tcagagcgga gccgacagag agcagggaac cggcatggcc aaagccgcgg cgatcggcat    240

cgacctgggc accacctact cctgcgtggg ggtgttccaa cacggcaagg tggagatcat    300

cgccaacgac cagggcaacc gcaccacccc cagctacgtg gccttcacgg acaccgagcg    360

gctcatcggg gatgcggcca agaaccaggt ggcgctgaac ccgcagaaca ccgtgtttga    420

cgcgaagcgg ctgattggcc gcaagttcgg cgacccggtg gtgcagtcgg acatgaagca    480

ctggcctttc caggtgatca acgacggaga caagcccaag gtgcaggtga gctacaaggg    540

ggagaccaag gcattctacc ccgaggagat ctcgtccatg gtgctgacca agatgaagga    600

gatcgccgag gcgtacctgg gctacccggt gaccaacgcg gtgatcaccg tgccggccta    660

cttcaacgac tcgcagcgcc aggccaccaa ggatgcgggt gtgatcgcgg ggctcaacgt    720

gctgcggatc atcaacgagc ccacggccgc cgccatcgcc tacggcctgg acagaacggg    780

caagggggag cgcaacgtgc tcatctttga cctgggcggg ggcaccttcg acgtgtccat    840

cctgacgatc gacgacggca tcttcgaggt gaaggccacg gccggggaca cccacctggg    900

tggggaggac tttgacaaca ggctggtgaa ccacttcgtg gaggagttca agagaaaaca    960

caagaaggac atcagccaga acaagcgagc cgtgaggcgg ctgcgcaccg cctgcgagag   1020

ggccaagagg accctgtcgt ccagcaccca ggccagcctg gagatcgact ccctgtttga   1080

gggcatcgac ttctacacgt ccatcaccag ggcgaggttc gaggagctgt gctccgacct   1140

gttccgaagc accctggagc ccgtggagaa ggctctgcgc gacgccaagc tggacaaggc   1200

ccagattcac gacctggtcc tggtcggggg ctccacccgc atccccaagg tgcagaagct   1260

gctgcaggac ttcttcaacg ggcgcgacct gaacaagagc atcaaccccg acgaggctgt   1320

ggcctacggg gcggcggtgc aggcggccat cctgatgggg gacaagtccg agaacgtgca   1380

ggacctgctg ctgctggacg tggctcccct gtcgctgggg ctggagacgg ccggaggcgt   1440

gatgactgcc ctgatcaagc gcaactccac catccccacc aagcagacgc agatcttcac   1500

cacctactcc gacaaccaac ccggggtgct gatccaggtg tacgagggcg agagggccat   1560
```

```
gacgaaagac aacaatctgt tggggcgctt cgagctgagc ggcatccctc cggcccccag   1620

gggcgtgccc cagatcgagg tgaccttcga catcgatgcc aacggcatcc tgaacgtcac   1680

ggccacggac aagagcaccg gcaaggccaa caagatcacc atcaccaacg acaagggccg   1740

cctgagcaag gaggagatcg agcgcatggt gcaggaggcg gagaagtaca aagcggagga   1800

cgaggtgcag cgcgagaggg tgtcagccaa gaacgccctg gagtcctacg ccttcaacat   1860

gaagagcgcc gtggaggatg aggggctcaa gggcaagatc agcgaggcgg acaagaagaa   1920

ggtgctggac aagtgtcaag aggtcatctc gtggctggac gccaacacct tggccgagaa   1980

ggacgagttt gagcacaaga ggaaggagct ggagcaggtg tgtaacccca tcatcagcgg   2040

actgtaccag ggtgccggtg gtcccgggcc tgggggcttc ggggctcagg gtcccaaggg   2100

agggtctggg tcaggcccca ccattgagga ggtagattag ggcctttcc aagattgctg    2160

tttttgtttt ggagcttcaa gactttgcat ttcctagtat ttctgtttgt cagttctcaa   2220

tttcctgtgt ttgcaatgtt gaaatttttt ggtgaagtac tgaacttgct ttttttccgg   2280

tttctacatg cagagatgaa tttatactgc catcttacga ctatttcttc tttttaatac   2340

acttaactca ggccattttt taagttggtt acttcaaagt aaataaactt taaaattcaa   2400
```

```
<210> SEQ ID NO 88
<211> LENGTH: 641
<212> TYPE: PRT
<213> ORGANISM: Mus musculus

<400> SEQUENCE: 88

Met Ala Lys Asn Thr Ala Ile Gly Ile Asp Leu Gly Thr Thr Tyr Ser
1               5                   10                  15

Cys Val Gly Val Phe Gln His Gly Lys Val Glu Ile Ile Ala Asn Asp
            20                  25                  30

Gln Gly Asn Arg Thr Thr Pro Ser Tyr Val Ala Phe Thr Asp Thr Glu
        35                  40                  45

Arg Leu Ile Gly Asp Ala Ala Lys Asn Gln Val Ala Leu Asn Pro Gln
    50                  55                  60

Asn Thr Val Phe Asp Ala Lys Arg Leu Ile Gly Arg Lys Phe Gly Asp
65                  70                  75                  80

Ala Val Val Gln Ser Asp Met Lys His Trp Pro Phe Gln Val Val Asn
                85                  90                  95

Asp Gly Asp Lys Pro Lys Val Gln Val Asn Tyr Lys Gly Glu Ser Arg
            100                 105                 110

Ser Phe Phe Pro Glu Glu Ile Ser Ser Met Val Leu Thr Lys Met Lys
        115                 120                 125

Glu Ile Ala Glu Ala Tyr Leu Gly His Pro Val Thr Asn Ala Val Ile
    130                 135                 140

Thr Val Pro Ala Tyr Phe Asn Asp Ser Gln Arg Gln Ala Thr Lys Asp
145                 150                 155                 160

Ala Gly Val Ile Ala Gly Leu Asn Val Leu Arg Ile Ile Asn Glu Pro
                165                 170                 175

Thr Ala Ala Ala Ile Ala Tyr Gly Leu Asp Arg Thr Gly Lys Gly Glu
            180                 185                 190

Arg Asn Val Leu Ile Phe Asp Leu Gly Gly Gly Thr Phe Asp Val Ser
        195                 200                 205

Ile Leu Thr Ile Asp Asp Gly Ile Phe Glu Val Lys Ala Thr Ala Gly
    210                 215                 220
```

```
Asp Thr His Leu Gly Gly Glu Asp Phe Asp Asn Arg Leu Val Ser His
225                 230                 235                 240

Phe Val Glu Glu Phe Lys Arg Lys His Lys Lys Asp Ile Ser Gln Asn
                245                 250                 255

Lys Arg Ala Val Arg Arg Leu Arg Thr Ala Cys Glu Arg Ala Lys Arg
            260                 265                 270

Thr Leu Ser Ser Ser Thr Gln Ala Ser Leu Glu Ile Asp Ser Leu Phe
        275                 280                 285

Glu Gly Ile Asp Phe Tyr Thr Ser Ile Thr Arg Ala Arg Phe Glu Glu
    290                 295                 300

Leu Cys Ser Asp Leu Phe Arg Gly Thr Leu Glu Pro Val Glu Lys Ala
305                 310                 315                 320

Leu Arg Asp Ala Lys Met Asp Lys Ala Gln Ile His Asp Leu Val Leu
                325                 330                 335

Val Gly Gly Ser Thr Arg Ile Pro Lys Val Gln Lys Leu Leu Gln Asp
            340                 345                 350

Phe Phe Asn Gly Arg Asp Leu Asn Lys Ser Ile Asn Pro Asp Glu Ala
        355                 360                 365

Val Ala Tyr Gly Ala Ala Val Gln Ala Ala Ile Leu Met Gly Asp Lys
    370                 375                 380

Ser Glu Asn Val Gln Asp Leu Leu Leu Leu Asp Val Ala Pro Leu Ser
385                 390                 395                 400

Leu Gly Leu Glu Thr Ala Gly Gly Val Met Thr Ala Leu Ile Lys Arg
                405                 410                 415

Asn Ser Thr Ile Pro Thr Lys Gln Thr Gln Thr Phe Thr Thr Tyr Ser
            420                 425                 430

Asp Asn Gln Pro Gly Val Leu Ile Gln Val Tyr Glu Gly Glu Arg Ala
        435                 440                 445

Met Thr Arg Asp Asn Asn Leu Leu Gly Arg Phe Glu Leu Ser Gly Ile
    450                 455                 460

Pro Pro Ala Pro Arg Gly Val Pro Gln Ile Glu Val Thr Phe Asp Ile
465                 470                 475                 480

Asp Ala Asn Gly Ile Leu Asn Val Thr Ala Thr Asp Lys Ser Thr Gly
                485                 490                 495

Lys Ala Asn Lys Ile Thr Ile Thr Asn Asp Lys Gly Arg Leu Ser Lys
            500                 505                 510

Glu Glu Ile Glu Arg Met Val Gln Glu Ala Glu Arg Tyr Lys Ala Glu
        515                 520                 525

Asp Glu Val Gln Arg Asp Arg Val Ala Ala Lys Asn Ala Leu Glu Ser
    530                 535                 540

Tyr Ala Phe Asn Met Lys Ser Ala Val Glu Asp Glu Gly Leu Lys Gly
545                 550                 555                 560

Lys Leu Ser Glu Ala Asp Lys Lys Lys Val Leu Asp Lys Cys Gln Glu
                565                 570                 575

Val Ile Ser Trp Leu Asp Ser Asn Thr Leu Ala Asp Lys Glu Glu Phe
            580                 585                 590

Val His Lys Arg Glu Glu Leu Glu Arg Val Cys Ser Pro Ile Ile Ser
        595                 600                 605

Gly Leu Tyr Gln Gly Ala Gly Ala Pro Gly Ala Gly Gly Phe Gly Ala
    610                 615                 620

Gln Ala Pro Lys Gly Ala Ser Gly Ser Gly Pro Thr Ile Glu Glu Val
625                 630                 635                 640

Asp
```

<210> SEQ ID NO 89
<211> LENGTH: 1927
<212> TYPE: DNA
<213> ORGANISM: Mus musculus

<400> SEQUENCE: 89

```
atggccaaga acacggcgat cggcatcgac ctgggcacca cctactcgtg cgtgggcgtg      60
ttccagcacg gcaaggtgga gatcatcgcc aacgaccagg gcaaccgcac gacccccagc     120
tacgtggcct tcaccgacac cgagcgcctc atcggagacg ccgccaagaa ccaggtggcg     180
ctgaacccgc agaacaccgt gttcgacgcg aagcggctga tcggccgcaa gttcggcgat     240
gcggtggtgc agtccgacat gaagcactgg cccttccagg tggtgaacga cggcgacaag     300
cccaaggtgc aggtgaacta caagggcgag agccggtcgt tcttcccgga ggagatctcg     360
tccatggtgc tgacgaagat gaaggagatc gctgaggcgt acctgggcca cccggtgacc     420
aacgcggtga tcacggtgcc cgcctacttc aacgactctc agcggcaggc caccaaggac     480
gcgggcgtga tcgccggtct aaacgtgctg cggatcatca acgagcccac ggcggccgcc     540
atcgcctacg ggctggaccg gaccggcaag ggcgagcgca acgtgctcat cttcgacctg     600
gggggcggca cgttcgacgt gtccatcctg acgatcgacg acggcatctt cgaggtgaag     660
gccacggcgg gcgacacgca cctgggaggg gaggacttcg acaaccggct ggtgagccac     720
ttcgtggagg agttcaagag gaagcacaag aaggacatca gccagaacaa gcgcgcggtg     780
cggcggctgc gcactgcgtg tgagagggcc aagaggacgc tgtcgtccag cacccaggcc     840
agcctggaga tcgactctct gttcgagggc atcgacttct acacatccat cacgcgggcg     900
cggttcgaag agctgtgctc agacctgttc cgcggcacgc tggagcccgt ggagaaggcc     960
ctgcgcgacg ccaagatgga caaggcgcag atccacgacc tggtgctggt gggcggctcg    1020
acgcgcatcc ccaaggtgca gaagctgctg caggacttct tcaacgggcg cgacctgaac    1080
aagagcatca acccggacga ggcggtggcc tacggggcgg cggtgcaggc ggccatcctg    1140
atgggggaca agtcggagaa cgtgcaggac ctgctgctgc tggacgtggc gccgctgtcg    1200
ctgggcctgg agactgcggg cggcgtgatg acggcgctca tcaagcgcaa ctccaccatc    1260
cccaccaagc agacgcagac cttcaccacc tactcggaca accagcccgg ggtgctgatc    1320
caggtgtacg agggcgagag ggccatgacg cgcgacaaca acctgctggg gcgcttcgaa    1380
ctgagcggca tcccgccggc gcccaggggc gtgccacaga tcgaggtgac cttcgacatc    1440
gacgccaacg gcatcctgaa cgtcacggcc accgacaaga gcaccggcaa ggccaacaag    1500
atcaccatca ccaacgacaa gggccgcctg agcaaggagg agatcgagcg catggtgcag    1560
gaggccgagc gctacaaggc cgaggacgag gtgcagcgcg acagggtggc cgccaagaac    1620
gcgctcgaat cctatgcctt caacatgaag agcgccgtgg aggacgaggg tctcaagggc    1680
aagctcagcg aggctgacaa gaagaaggtg ctggacaagt gccaggaggt catctcctgg    1740
ctggactcca acacgctggc cgacaaggag gagttcgtgc acaagcggga ggagctggag    1800
cgggtgtgca gccccatcat cagtgggctg taccagggtg cgggtgctcc tggggctggg    1860
ggcttcgggg cccaggcgcc caagggagcc tctggctcag gacccaccat cgaggaggtg    1920
gattaga                                                              1927
```

<210> SEQ ID NO 90
<211> LENGTH: 641
<212> TYPE: PRT

```
<213> ORGANISM: Macaca mulatta

<400> SEQUENCE: 90

Met Ala Lys Ala Ala Ala Ile Gly Ile Asp Leu Gly Thr Thr Tyr Ser
1               5                   10                  15

Cys Val Gly Val Phe Gln His Gly Lys Val Glu Ile Ile Ala Asn Asp
            20                  25                  30

Gln Gly Asn Arg Thr Thr Pro Ser Tyr Val Ala Phe Thr Asp Thr Glu
        35                  40                  45

Arg Leu Ile Gly Asp Ala Ala Lys Asn Gln Val Ala Leu Asn Pro Gln
    50                  55                  60

Asn Thr Val Phe Asp Ala Lys Arg Leu Ile Gly Arg Lys Phe Gly Asp
65                  70                  75                  80

Pro Val Val Gln Ser Asp Met Lys His Trp Pro Phe Gln Val Ile Asn
                85                  90                  95

Asp Gly Asp Lys Pro Lys Val Gln Val Ser Tyr Lys Gly Glu Thr Lys
            100                 105                 110

Ala Phe Tyr Pro Glu Glu Ile Ser Ser Met Val Leu Thr Lys Met Lys
        115                 120                 125

Glu Ile Ala Glu Ala Tyr Leu Gly Tyr Pro Val Thr Asn Ala Val Ile
    130                 135                 140

Thr Val Pro Ala Tyr Phe Asn Asp Ser Gln Arg Gln Ala Thr Lys Asp
145                 150                 155                 160

Ala Gly Val Ile Ala Gly Leu Asn Val Leu Arg Ile Ile Asn Glu Pro
                165                 170                 175

Thr Ala Ala Ala Ile Ala Tyr Gly Leu Asp Arg Thr Gly Lys Gly Glu
            180                 185                 190

Arg Asn Val Leu Ile Phe Asp Leu Gly Gly Gly Thr Phe Asp Val Ser
        195                 200                 205

Ile Leu Thr Ile Asp Asp Gly Ile Phe Glu Val Lys Ala Thr Ala Gly
    210                 215                 220

Asp Thr His Leu Gly Gly Glu Asp Phe Asp Asn Arg Leu Val Asn His
225                 230                 235                 240

Phe Val Glu Glu Phe Lys Arg Lys His Lys Lys Asp Ile Ser Gln Asn
                245                 250                 255

Lys Arg Ala Val Arg Arg Leu Arg Thr Ala Cys Glu Arg Ala Lys Arg
            260                 265                 270

Thr Leu Ser Ser Ser Thr Gln Ala Ser Leu Glu Ile Asp Ser Leu Phe
        275                 280                 285

Glu Gly Ile Asp Phe Tyr Thr Ser Ile Thr Arg Ala Arg Phe Glu Glu
    290                 295                 300

Leu Cys Ser Asp Leu Phe Arg Ser Thr Leu Glu Pro Val Glu Lys Ala
305                 310                 315                 320

Leu Arg Asp Ala Lys Leu Asp Lys Ala Gln Ile His Asp Leu Val Leu
                325                 330                 335

Val Gly Gly Ser Thr Arg Ile Pro Lys Val Gln Lys Leu Leu Gln Asp
            340                 345                 350

Phe Phe Asn Gly Arg Asp Leu Asn Lys Ser Ile Asn Pro Asp Glu Ala
        355                 360                 365

Val Ala Tyr Gly Ala Ala Val Gln Ala Ala Ile Leu Met Gly Asp Lys
    370                 375                 380

Ser Glu Asn Val Gln Asp Leu Leu Leu Leu Asp Val Ala Pro Leu Ser
385                 390                 395                 400
```

```
Leu Gly Leu Glu Thr Ala Gly Gly Val Met Thr Ala Leu Ile Lys Arg
                405                 410                 415

Asn Ser Thr Ile Pro Thr Lys Gln Thr Gln Ile Phe Thr Thr Tyr Ser
            420                 425                 430

Asp Asn Gln Pro Gly Val Leu Ile Gln Val Tyr Glu Gly Glu Arg Ala
        435                 440                 445

Met Thr Lys Asp Asn Asn Leu Leu Gly Arg Phe Glu Leu Ser Gly Ile
    450                 455                 460

Pro Pro Ala Pro Arg Gly Val Pro Gln Ile Glu Val Thr Phe Asp Ile
465                 470                 475                 480

Asp Ala Asn Gly Ile Leu Asn Val Thr Ala Thr Asp Lys Ser Thr Gly
                485                 490                 495

Lys Ala Asn Lys Ile Thr Ile Thr Asn Asp Lys Gly Arg Leu Ser Lys
            500                 505                 510

Glu Glu Ile Glu Arg Met Val Gln Glu Ala Glu Lys Tyr Lys Ala Glu
        515                 520                 525

Asp Glu Val Gln Arg Glu Arg Val Ser Ala Lys Asn Ala Leu Glu Ser
    530                 535                 540

Tyr Ala Phe Asn Met Lys Ser Ala Val Glu Asp Glu Gly Leu Lys Gly
545                 550                 555                 560

Lys Ile Ser Glu Ala Asp Lys Lys Lys Val Leu Asp Lys Cys Gln Glu
                565                 570                 575

Val Ile Ser Trp Leu Asp Ala Asn Thr Leu Ala Glu Lys Asp Glu Phe
            580                 585                 590

Glu His Lys Arg Lys Glu Leu Glu Gln Val Cys Asn Pro Ile Ile Ser
        595                 600                 605

Gly Leu Tyr Gln Gly Ala Gly Gly Pro Gly Pro Gly Gly Phe Gly Ala
    610                 615                 620

Gln Gly Pro Lys Gly Gly Ser Gly Ser Gly Pro Thr Ile Glu Glu Val
625                 630                 635                 640

Asp
```

<210> SEQ ID NO 91
<211> LENGTH: 641
<212> TYPE: PRT
<213> ORGANISM: Rattus norvegicus

<400> SEQUENCE: 91

```
Met Ala Lys Lys Thr Ala Ile Gly Ile Asp Leu Gly Thr Thr Tyr Ser
1               5                   10                  15

Cys Val Gly Val Phe Gln His Gly Lys Val Glu Ile Ile Ala Asn Asp
            20                  25                  30

Gln Gly Asn Arg Thr Thr Pro Ser Tyr Val Ala Phe Thr Asp Thr Glu
        35                  40                  45

Arg Leu Ile Gly Asp Ala Ala Lys Asn Gln Val Ala Leu Asn Pro Gln
    50                  55                  60

Asn Thr Val Phe Asp Ala Lys Arg Leu Ile Gly Arg Lys Phe Gly Asp
65                  70                  75                  80

Pro Val Val Gln Ser Asp Met Lys His Trp Pro Phe Gln Val Val Asn
                85                  90                  95

Asp Gly Asp Lys Pro Lys Val Gln Val Asn Tyr Lys Gly Glu Asn Arg
            100                 105                 110

Ser Phe Tyr Pro Glu Glu Ile Ser Ser Met Val Leu Thr Lys Met Lys
        115                 120                 125
```

```
Glu Ile Ala Glu Ala Tyr Leu Gly His Pro Val Thr Asn Ala Val Ile
    130                 135                 140

Thr Val Pro Ala Tyr Phe Asn Asp Ser Gln Arg Gln Ala Thr Lys Asp
145                 150                 155                 160

Ala Gly Val Ile Ala Gly Leu Asn Val Leu Arg Ile Ile Asn Glu Pro
                165                 170                 175

Thr Ala Ala Ala Ile Ala Tyr Gly Leu Asp Arg Thr Gly Lys Gly Glu
            180                 185                 190

Arg Asn Val Leu Ile Phe Asp Leu Gly Gly Gly Thr Phe Asp Val Ser
        195                 200                 205

Ile Leu Thr Ile Asp Asp Gly Ile Phe Glu Val Lys Ala Thr Ala Gly
    210                 215                 220

Asp Thr His Leu Gly Gly Glu Asp Phe Asp Asn Arg Leu Val Ser His
225                 230                 235                 240

Phe Val Glu Glu Phe Lys Arg Lys His Lys Lys Asp Ile Ser Gln Asn
                245                 250                 255

Lys Arg Ala Val Arg Arg Leu Arg Thr Ala Cys Glu Arg Ala Lys Arg
            260                 265                 270

Thr Leu Ser Ser Ser Thr Gln Ala Ser Leu Glu Ile Asp Ser Leu Phe
        275                 280                 285

Glu Gly Ile Asp Phe Tyr Thr Ser Ile Thr Arg Ala Arg Phe Glu Glu
    290                 295                 300

Leu Cys Ser Asp Leu Phe Arg Gly Thr Leu Glu Pro Val Glu Lys Ala
305                 310                 315                 320

Leu Arg Asp Ala Lys Leu Asp Lys Ala Gln Ile His Asp Leu Val Leu
                325                 330                 335

Val Gly Gly Ser Thr Arg Ile Pro Lys Val Gln Lys Leu Leu Gln Asp
            340                 345                 350

Phe Phe Asn Gly Arg Asp Leu Asn Lys Ser Ile Asn Pro Asp Glu Ala
        355                 360                 365

Val Ala Tyr Gly Ala Ala Val Gln Ala Ala Ile Leu Met Gly Asp Lys
    370                 375                 380

Ser Glu Asn Val Gln Asp Leu Leu Leu Leu Asp Val Ala Pro Leu Ser
385                 390                 395                 400

Leu Gly Leu Glu Thr Ala Gly Gly Val Met Thr Ala Leu Ile Lys Arg
                405                 410                 415

Asn Ser Thr Ile Pro Thr Lys Gln Thr Gln Thr Phe Thr Thr Tyr Ser
            420                 425                 430

Asp Asn Gln Pro Gly Val Leu Ile Gln Val Tyr Glu Gly Glu Arg Ala
        435                 440                 445

Met Thr Arg Asp Asn Asn Leu Leu Gly Arg Phe Glu Leu Ser Gly Ile
    450                 455                 460

Pro Pro Ala Pro Arg Gly Val Pro Gln Ile Glu Val Thr Phe Asp Ile
465                 470                 475                 480

Asp Ala Asn Gly Ile Leu Asn Val Thr Ala Thr Asp Lys Ser Thr Gly
                485                 490                 495

Lys Ala Asn Lys Ile Thr Ile Thr Asn Asp Lys Gly Arg Leu Ser Lys
            500                 505                 510

Glu Glu Ile Glu Arg Met Val Gln Glu Ala Glu Arg Tyr Lys Ala Glu
        515                 520                 525

Asp Glu Val Gln Arg Glu Arg Val Ala Ala Lys Asn Ala Leu Glu Ser
    530                 535                 540

Tyr Ala Phe Asn Met Lys Ser Ala Val Glu Asp Glu Gly Leu Lys Gly
```

```
545                 550                 555                 560

Lys Ile Ser Glu Ala Asp Lys Lys Lys Val Leu Asp Lys Cys Gln Glu
                565                 570                 575

Val Ile Ser Trp Leu Asp Ser Asn Thr Leu Ala Glu Lys Glu Glu Phe
            580                 585                 590

Val His Lys Arg Glu Glu Leu Glu Arg Val Cys Asn Pro Ile Ile Ser
        595                 600                 605

Gly Leu Tyr Gln Gly Ala Gly Ala Pro Gly Ala Gly Gly Phe Gly Ala
    610                 615                 620

Gln Ala Pro Lys Gly Gly Ser Gly Ser Gly Pro Thr Ile Glu Glu Val
625                 630                 635                 640

Asp


<210> SEQ ID NO 92
<211> LENGTH: 641
<212> TYPE: PRT
<213> ORGANISM: Bos taurus

<400> SEQUENCE: 92

Met Ala Lys Asn Met Ala Ile Gly Ile Asp Leu Gly Thr Thr Tyr Ser
1               5                   10                  15

Cys Val Gly Val Phe Gln His Gly Lys Val Glu Ile Ile Ala Asn Asp
            20                  25                  30

Gln Gly Asn Arg Thr Thr Pro Ser Tyr Val Ala Phe Thr Asp Thr Glu
        35                  40                  45

Arg Leu Ile Gly Asp Ala Ala Lys Asn Gln Val Ala Leu Asn Pro Gln
    50                  55                  60

Asn Thr Val Phe Asp Ala Lys Arg Leu Ile Gly Arg Lys Phe Gly Asp
65                  70                  75                  80

Pro Val Val Gln Ser Asp Met Lys His Trp Pro Phe Arg Val Ile Asn
                85                  90                  95

Asp Gly Asp Lys Pro Lys Val Gln Val Ser Tyr Lys Gly Glu Thr Lys
            100                 105                 110

Ala Phe Tyr Pro Glu Glu Ile Ser Ser Met Val Leu Thr Lys Met Lys
        115                 120                 125

Glu Ile Ala Glu Ala Tyr Leu Gly His Pro Val Thr Asn Ala Val Ile
    130                 135                 140

Thr Val Pro Ala Tyr Phe Asn Asp Ser Gln Arg Gln Ala Thr Lys Asp
145                 150                 155                 160

Ala Gly Val Ile Ala Gly Leu Asn Val Leu Arg Ile Ile Asn Glu Pro
                165                 170                 175

Thr Ala Ala Ala Ile Ala Tyr Gly Leu Asp Arg Thr Gly Lys Gly Glu
            180                 185                 190

Arg Asn Val Leu Ile Phe Asp Leu Gly Gly Gly Thr Phe Asp Val Ser
        195                 200                 205

Ile Leu Thr Ile Asp Asp Gly Ile Phe Glu Val Lys Ala Thr Ala Gly
    210                 215                 220

Asp Thr His Leu Gly Gly Glu Asp Phe Asp Asn Arg Leu Val Asn His
225                 230                 235                 240

Phe Val Glu Glu Phe Lys Arg Lys His Lys Lys Asp Ile Ser Gln Asn
                245                 250                 255

Lys Arg Ala Val Arg Arg Leu Arg Thr Ala Cys Glu Arg Ala Lys Arg
            260                 265                 270

Thr Leu Ser Ser Ser Thr Gln Ala Ser Leu Glu Ile Asp Ser Leu Phe
```

```
        275                 280                 285

Glu Gly Ile Asp Phe Tyr Thr Ser Ile Thr Arg Ala Arg Phe Glu Glu
    290                 295                 300

Leu Cys Ser Asp Leu Phe Arg Ser Thr Leu Glu Pro Val Glu Lys Ala
305                 310                 315                 320

Leu Arg Asp Ala Lys Leu Asp Lys Ala Gln Ile His Asp Leu Val Leu
                325                 330                 335

Val Gly Gly Ser Thr Arg Ile Pro Lys Val Gln Lys Leu Leu Gln Asp
            340                 345                 350

Phe Phe Asn Gly Arg Asp Leu Asn Lys Ser Ile Asn Pro Asp Glu Ala
        355                 360                 365

Val Ala Tyr Gly Ala Ala Val Gln Ala Ala Ile Leu Met Gly Asp Lys
    370                 375                 380

Ser Glu Asn Val Gln Asp Leu Leu Leu Leu Asp Val Ala Pro Leu Ser
385                 390                 395                 400

Leu Gly Leu Glu Thr Ala Gly Gly Val Met Thr Ala Leu Ile Lys Arg
                405                 410                 415

Asn Ser Thr Ile Pro Thr Lys Gln Thr Gln Ile Phe Thr Thr Tyr Ser
            420                 425                 430

Asp Asn Gln Pro Gly Val Leu Ile Gln Val Tyr Glu Gly Glu Arg Ala
        435                 440                 445

Met Thr Arg Asp Asn Asn Leu Leu Gly Arg Phe Glu Leu Ser Gly Ile
    450                 455                 460

Pro Pro Ala Pro Arg Gly Val Pro Gln Ile Glu Val Thr Phe Asp Ile
465                 470                 475                 480

Asp Ala Asn Gly Ile Leu Asn Val Thr Ala Thr Asp Lys Ser Thr Gly
                485                 490                 495

Lys Ala Asn Lys Ile Thr Ile Thr Asn Asp Lys Gly Arg Leu Ser Lys
            500                 505                 510

Glu Glu Ile Glu Arg Met Val Gln Glu Ala Glu Lys Tyr Lys Ala Glu
        515                 520                 525

Asp Glu Val Gln Arg Glu Arg Val Ser Ala Lys Asn Ala Leu Glu Ser
    530                 535                 540

Tyr Ala Phe Asn Met Lys Ser Ala Val Glu Asp Glu Gly Leu Lys Gly
545                 550                 555                 560

Lys Ile Ser Glu Ala Asp Lys Lys Lys Val Leu Asp Lys Cys Gln Glu
                565                 570                 575

Val Ile Ser Trp Leu Asp Ala Asn Thr Leu Ala Glu Lys Asp Glu Phe
            580                 585                 590

Glu His Lys Arg Lys Glu Leu Glu Gln Val Cys Asn Pro Ile Ile Ser
        595                 600                 605

Arg Leu Tyr Gln Gly Ala Gly Gly Pro Gly Ala Gly Gly Phe Gly Ala
    610                 615                 620

Gln Gly Pro Lys Gly Gly Ser Gly Ser Gly Pro Thr Ile Glu Glu Val
625                 630                 635                 640

Asp
```

<210> SEQ ID NO 93
<211> LENGTH: 60
<212> TYPE: DNA
<213> ORGANISM: Homo sapiens

<400> SEQUENCE: 93

```
ctctaggcgg gctctgctct tctttaagga gtcccacagg gcctggcccg cccctgacct     60
```

<210> SEQ ID NO 94
<211> LENGTH: 136
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 94

```
Met Lys Thr Asp Ser Ser Phe Ile Met Asp Ser Asp Pro Arg Arg Cys
1               5                   10                  15

Met Arg His His Tyr Val Asp Ser Ile Ser His Pro Leu Tyr Lys Cys
            20                  25                  30

Ser Ser Lys Met Val Leu Leu Ala Arg Cys Glu Gly His Cys Ser Gln
        35                  40                  45

Ala Ser Arg Ser Glu Pro Leu Val Ser Phe Ser Thr Val Leu Lys Gln
    50                  55                  60

Pro Phe Arg Ser Ser Cys His Cys Cys Arg Pro Gln Thr Ser Lys Leu
65                  70                  75                  80

Lys Ala Leu Arg Leu Arg Cys Ser Gly Gly Met Arg Leu Thr Ala Thr
                85                  90                  95

Tyr Arg Tyr Ile Leu Ser Cys His Cys Glu Glu Cys Asn Ser Gly Ser
            100                 105                 110

Arg Ala Asp Tyr Lys Asp His Asp Gly Asp Tyr Lys Asp His Asp Ile
        115                 120                 125

Asp Tyr Lys Asp Asp Asp Asp Lys
    130                 135
```

<210> SEQ ID NO 95
<211> LENGTH: 667
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 95

```
Met Ala Lys Ala Ala Ala Ile Gly Ile Asp Leu Gly Thr Thr Tyr Ser
1               5                   10                  15

Cys Val Gly Val Phe Gln His Gly Lys Val Glu Ile Ile Ala Asn Asp
            20                  25                  30

Gln Gly Asn Arg Thr Thr Pro Ser Tyr Val Ala Phe Thr Asp Thr Glu
        35                  40                  45

Arg Leu Ile Gly Asp Ala Ala Lys Asn Gln Val Ala Leu Asn Pro Gln
    50                  55                  60

Asn Thr Val Phe Asp Ala Lys Arg Leu Ile Gly Arg Lys Phe Gly Asp
65                  70                  75                  80

Pro Val Val Gln Ser Asp Met Lys His Trp Pro Phe Gln Val Ile Asn
                85                  90                  95

Asp Gly Asp Lys Pro Lys Val Gln Val Ser Tyr Lys Gly Glu Thr Lys
            100                 105                 110

Ala Phe Tyr Pro Glu Glu Ile Ser Ser Met Val Leu Thr Lys Met Lys
        115                 120                 125

Glu Ile Ala Glu Ala Tyr Leu Gly Tyr Pro Val Thr Asn Ala Val Ile
    130                 135                 140

Thr Val Pro Ala Tyr Phe Asn Asp Ser Gln Arg Gln Ala Thr Lys Asp
145                 150                 155                 160
```

```
Ala Gly Val Ile Ala Gly Leu Asn Val Leu Arg Ile Ile Asn Glu Pro
                165                 170                 175

Thr Ala Ala Ala Ile Ala Tyr Gly Leu Asp Arg Thr Gly Lys Gly Glu
            180                 185                 190

Arg Asn Val Leu Ile Phe Asp Leu Gly Gly Gly Thr Phe Asp Val Ser
        195                 200                 205

Ile Leu Thr Ile Asp Asp Gly Ile Phe Glu Val Lys Ala Thr Ala Gly
    210                 215                 220

Asp Thr His Leu Gly Gly Glu Asp Phe Asp Asn Arg Leu Val Asn His
225                 230                 235                 240

Phe Val Glu Glu Phe Lys Arg Lys His Lys Lys Asp Ile Ser Gln Asn
                245                 250                 255

Lys Arg Ala Val Arg Arg Leu Arg Thr Ala Cys Glu Arg Ala Lys Arg
            260                 265                 270

Thr Leu Ser Ser Ser Thr Gln Ala Ser Leu Glu Ile Asp Ser Leu Phe
        275                 280                 285

Glu Gly Ile Asp Phe Tyr Thr Ser Ile Thr Arg Ala Arg Phe Glu Glu
    290                 295                 300

Leu Cys Ser Asp Leu Phe Arg Ser Thr Leu Glu Pro Val Glu Lys Ala
305                 310                 315                 320

Leu Arg Asp Ala Lys Leu Asp Lys Ala Gln Ile His Asp Leu Val Leu
                325                 330                 335

Val Gly Gly Ser Thr Arg Ile Pro Lys Val Gln Lys Leu Leu Gln Asp
            340                 345                 350

Phe Phe Asn Gly Arg Asp Leu Asn Lys Ser Ile Asn Pro Asp Glu Ala
        355                 360                 365

Val Ala Tyr Gly Ala Ala Val Gln Ala Ala Ile Leu Met Gly Asp Lys
    370                 375                 380

Ser Glu Asn Val Gln Asp Leu Leu Leu Leu Asp Val Ala Pro Leu Ser
385                 390                 395                 400

Leu Gly Leu Glu Thr Ala Gly Gly Val Met Thr Ala Leu Ile Lys Arg
                405                 410                 415

Asn Ser Thr Ile Pro Thr Lys Gln Thr Gln Ile Phe Thr Thr Tyr Ser
            420                 425                 430

Asp Asn Gln Pro Gly Val Leu Ile Gln Val Tyr Glu Gly Glu Arg Ala
        435                 440                 445

Met Thr Lys Asp Asn Asn Leu Leu Gly Arg Phe Glu Leu Ser Gly Ile
    450                 455                 460

Pro Pro Ala Pro Arg Gly Val Pro Gln Ile Glu Val Thr Phe Asp Ile
465                 470                 475                 480

Asp Ala Asn Gly Ile Leu Asn Val Thr Ala Thr Asp Lys Ser Thr Gly
                485                 490                 495

Lys Ala Asn Lys Ile Thr Ile Thr Asn Asp Lys Gly Arg Leu Ser Lys
            500                 505                 510

Glu Glu Ile Glu Arg Met Val Gln Glu Ala Glu Lys Tyr Lys Ala Glu
        515                 520                 525

Asp Glu Val Gln Arg Glu Arg Val Ser Ala Lys Asn Ala Leu Glu Ser
    530                 535                 540

Tyr Ala Phe Asn Met Lys Ser Ala Val Glu Asp Glu Gly Leu Lys Gly
545                 550                 555                 560

Lys Ile Ser Glu Ala Asp Lys Lys Lys Val Leu Asp Lys Cys Gln Glu
                565                 570                 575
```

```
Val Ile Ser Trp Leu Asp Ala Asn Thr Leu Ala Glu Lys Asp Glu Phe
            580                 585                 590

Glu His Lys Arg Lys Glu Leu Glu Gln Val Cys Asn Pro Ile Ile Ser
        595                 600                 605

Gly Leu Tyr Gln Gly Ala Gly Gly Pro Gly Pro Gly Gly Phe Gly Ala
    610                 615                 620

Gln Gly Pro Lys Gly Gly Ser Gly Ser Gly Pro Thr Ile Glu Glu Val
625                 630                 635                 640

Asp Gly Ser Arg Ala Asp Tyr Lys Asp His Asp Gly Asp Tyr Lys Asp
                645                 650                 655

His Asp Ile Asp Tyr Lys Asp Asp Asp Asp Lys
            660                 665


<210> SEQ ID NO 96
<211> LENGTH: 4236
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 96

ctgcgcgctc gctcgctcac tgaggccgcc cgggcgtcgg gcgacctttg gtcgcccggc     60

ctcagtgagc gagcgagcgc gcagagaggg agtggccaac tccatcacta ggggttcctg    120

cggccgcacg cgtgacattg attattgact agttattaat agtaatcaat tacggggtca    180

ttagttcata gcccatatat ggagttccgc gttacataac ttacggtaaa tggcccgcct    240

ggctgaccgc ccaacgaccc ccgcccattg acgtcaataa tgacgtatgt tcccatagta    300

acgccaatag ggactttcca ttgacgtcaa tgggtggact atttacggta aactgcccac    360

ttggcagtac atcaagtgta tcatatgcca agtacgcccc ctattgacgt caatgacggt    420

aaatggcccg cctggcatta tgcccagtac atgaccttat gggactttcc tacttggcag    480

tacatctacg tattagtcat cgctattacc atggtcgag gtgagcccca cgttctgctt    540

cactctcccc atctcccccc cctccccacc cccaattttg tatttattta ttttttaatt    600

attttgtgca gcgatggggg cggggggggg gggggcgcgc gccaggcggg gcggggcggg    660

gcgaggggcg gggcggggcg aggcggagag gtgcggcggc agccaatcag agcggcgcgc    720

tccgaaagtt tccttttatg gcgaggcggc ggcggcggcg gccctataaa aagcgaagcg    780

cgcggcgggc gggagtcgct gcgttgcctt cgccccgtgc cccgctccgc gccgcctcgc    840

gccgcccgcc ccggctctga ctgaccgcgt tactcccaca ggtgagcggg cgggacggcc    900

cttctcctcc gggctgtaat tagcgcttgg tttaatgacg gctcgtttct tttctgtggc    960

tgcgtgaaag ccttaaaggg ctccgggagg gccctttgtg cggggggggag cggctcgggg   1020

ggtgcgtgcg tgtgtgtgtg cgtggggagc gccgcgtgcg gcccgcgctg cccggcggct   1080

gtgagcgctg cgggcgcggc gcggggcttt gtgcgctccg cgtgtgcgcg aggggagcgc   1140

ggccgggggc ggtgccccgc ggtgcggggg ggctgcgagg ggaacaaagg ctgcgtgcgg   1200

ggtgtgtgcg tgggggggtg agcagggggt gtgggcgcgg cggtcgggct gtaacccccc   1260

cctgcacccc cctccccgag ttgctgagca cggcccggct tcgggtgcgg ggctccgtgc   1320

ggggcgtggc gcggggctcg ccgtgccggg cgggggggtgg cggcaggtgg gggtgccggg   1380

cggggcgggg ccgcctcggg ccggggaggg ctcgggggag ggcgcggcg gcccccggag   1440

cgccggcggc tgtcgaggcg cggcgagccg cagccattgc cttttatggt aatcgtgcga   1500
```

```
gagggcgcag ggacttcctt tgtcccaaat ctgtgcggag ccgaaatctg ggaggcgccg   1560
ccgcaccccc tctagcgggc gcggggcgaa gcggtgcggc gccggcagga aggaaatggg   1620
cggggagggc cttcgtgcgt cgccgcgccg ccgtcccctt ctccctctcc agcctcgggg   1680
ctgtccgcgg ggggacggct gccttcgggg gggacggggc agggcggggt tcggcttctg   1740
gcgtgtgacc ggcggctcta gagcctctgc taaccatgtt catgccttct tctttttcct   1800
acagctcctg ggcaacgtgc tggttattgt gaccggtgcc accatgtacc ggatgcagct   1860
gctgagctgt atcgccctgt ctctggccct ggtcaccaat tctgccaaag ccgcggcgat   1920
cggcatcgac ctgggcacca cctactcctg cgtgggggtg ttccaacacg gcaaggtgga   1980
gatcatcgcc aacgaccagg gcaaccgcac cacccccagc tacgtggcct tcacggacac   2040
cgagcggctc atcggggatg cggccaagaa ccaggtggcg ctgaacccgc agaacaccgt   2100
gtttgacgcg aagcggctga tcggccgcaa gttcggcgac ccggtggtgc agtcggacat   2160
gaagcactgg cctttccagg tgatcaacga cggagacaag cccaaggtgc aggtgagcta   2220
caagggggag accaaggcat tctaccccga ggagatctcg tccatggtgc tgaccaagat   2280
gaaggagatc gccgaggcgt acctgggcta cccggtgacc aacgcggtga tcaccgtgcc   2340
ggcctacttc aacgactcgc agcgccaggc caccaaggat gcgggtgtga tcgcggggct   2400
caacgtgctg cggatcatca acgagcccac ggccgccgcc atcgcctacg gcctggacag   2460
aacgggcaag ggggagcgca acgtgctcat ctttgacctg ggcgggggca ccttcgacgt   2520
gtccatcctg acgatcgacg acggcatctt cgaggtgaag gccacggccg ggacacccca   2580
cctgggtggg gaggactttg acaacaggct ggtgaaccac ttcgtggagg agttcaagag   2640
aaaacacaag aaggacatca gccagaacaa gcgagccgtg aggcggctgc gcaccgcctg   2700
cgagagggcc aagaggaccc tgtcgtccag cacccaggcc agcctggaga tcgactccct   2760
gtttgagggc atcgacttct acacgtccat caccagggcg aggttcgagg agctgtgctc   2820
cgacctgttc cgaagcaccc tggagcccgt ggagaaggct ctgcgcgacg ccaagctgga   2880
caaggcccag attcacgacc tggtcctggt cgggggctcc acccgcatcc ccaaggtgca   2940
gaagctgctg caggacttct tcaacgggcg cgacctgaac aagagcatca accccgacga   3000
ggctgtggcc tacggggcgg cggtgcaggc ggccatcctg atgggggaca agtccgagaa   3060
cgtgcaggac ctgctgctgc tggacgtggc tcccctgtcg ctggggctgg agacggccgg   3120
aggcgtgatg actgccctga tcaagcgcaa ctccaccatc cccaccaagc agacgcagat   3180
cttcaccacc tactccgaca accaacccgg ggtgctgatc caggtgtacg agggcgagag   3240
ggccatgacg aaagacaaca atctgttggg gcgcttcgag ctgagcggca tccctccggc   3300
ccccaggggc gtgccccaga tcgaggtgac cttcgacatc gatgccaacg gcatcctgaa   3360
cgtcacggcc acggacaaga gcaccggcaa ggccaacaag atcaccatca ccaacgacaa   3420
gggccgcctg agcaaggagg agatcgagcg catggtgcag gaggcggaga agtacaaagc   3480
ggaggacgag gtgcagcgcg agagggtgtc agccaagaac gccctggagt cctacgcctt   3540
caacatgaag agcgccgtgg aggatgaggg gctcaagggc aagatcagcg aggcggacaa   3600
gaagaaggtt ctggacaagt gtcaagaggt catctcgtgg ctggacgcca acaccttggc   3660
cgagaaggac gagtttgagc acaagaggaa ggagctggag caggtgtgta accccatcat   3720
cagcggactg taccagggtg ccggtggtcc cgggcctggg ggcttcgggg ctcagggtcc   3780
caagggaggg tctgggtcag gccccaccat tgaggaggtg gattaagagc tcgctgatca   3840
gcctcgactg tgccttctag ttgccagcca tctgttgttt gcccctcccc cgtgccttcc   3900
```

```
ttgaccctgg aaggtgccac tcccactgtc ctttcctaat aaaatgagga aattgcatcg   3960

cattgtctga gtaggtgtca ttctattctg gggggtgggg tggggcagga cagcaagggg   4020

gaggattggg aagacaatag caggcatgct ggggatgcgg tgggctctat ggaagcttga   4080

attcagctga cgtgcctcgg accgctagga acccctagtg atggagttgg ccactccctc   4140

tctgcgcgct cgctcgctca ctgaggccgg gcgaccaaag gtcgcccgac gcccgggctt   4200

tgcccgggcg gcctcagtga gcgagcgagc gcgcag                             4236
```

<210> SEQ ID NO 97
<211> LENGTH: 4179
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 97

```
ctgcgcgctc gctcgctcac tgaggccgcc cgggcgtcgg gcgacctttg gtcgcccggc     60

ctcagtgagc gagcgagcgc gcagagaggg agtggccaac tccatcacta ggggttcctg    120

cggccgcacg cgtgacattg attattgact agttattaat agtaatcaat tacggggtca    180

ttagttcata gcccatatat ggagttccgc gttacataac ttacggtaaa tggcccgcct    240

ggctgaccgc ccaacgaccc ccgcccattg acgtcaataa tgacgtatgt tcccatagta    300

acgccaatag ggactttcca ttgacgtcaa tgggtggact atttacggta aactgcccac    360

ttggcagtac atcaagtgta tcatatgcca agtacgcccc ctattgacgt caatgacggt    420

aaatggcccg cctggcatta tgcccagtac atgaccttat gggactttcc tacttggcag    480

tacatctacg tattagtcat cgctattacc atgggtcgag gtgagcccca cgttctgctt    540

cactctcccc atctcccccc cctccccacc cccaattttg tatttattta tttttttaatt    600

attttgtgca gcgatggggg cgggggggggg ggggggcgcgc gccaggcggg gcggggcggg    660

gcgaggggcg gggcggggcg aggcggagag gtgcggcggc agccaatcag agcggcgcgc    720

tccgaaagtt tccttttatg gcgaggcggc ggcggcggcg gccctataaa aagcgaagcg    780

cgcggcgggc gggagtcgct gcgttgcctt cgccccgtgc cccgctccgc gccgcctcgc    840

gccgcccgcc ccggctctga ctgaccgcgt tactcccaca ggtgagcggg cgggacggcc    900

cttctcctcc gggctgtaat tagcgcttgg tttaatgacg gctcgtttct tttctgtggc    960

tgcgtgaaag ccttaaaggg ctccgggagg gccctttgtg cggggggggag cggctcgggg   1020

ggtgcgtgcg tgtgtgtgtg cgtggggagc gccgcgtgcg gcccgcgctg cccggcggct   1080

gtgagcgctg cgggcgcggc gcggggcttt gtgcgctccg cgtgtgcgcg aggggagcgc   1140

ggccgggggc ggtgccccgc ggtgcggggg ggctgcgagg ggaacaaagg ctgcgtgcgg   1200

ggtgtgtgcg tgggggggtg agcagggggt gtgggcgcgg cggtcgggct gtaacccccc   1260

cctgcacccc cctccccgag ttgctgagca cggcccggct tcgggtgcgg ggctccgtgc   1320

ggggcgtggc gcggggctcg ccgtgccggg cggggggtgg cggcaggtgg gggtgccggg   1380

cggggcgggg ccgcctcggg ccggggaggg ctcgggggag ggcgcggcgg gcccccggag   1440

cgccggcggc tgtcgaggcg cggcgagccg cagccattgc cttttatggt aatcgtgcga   1500

gagggcgcag ggacttcctt tgtcccaaat ctgtgcggag ccgaaatctg ggaggcgccg   1560

ccgcaccccc tctagcgggc gcggggcgaa gcggtgcggc gccggcagga aggaaatggg   1620

cggggagggc cttcgtgcgt cgccgcgccg ccgtcccctt ctccctctcc agcctcgggg   1680
```

-continued

```
ctgtccgcgg ggggacggct gccttcgggg gggacggggc agggcggggt tcggcttctg   1740

gcgtgtgacc ggcggctcta gagcctctgc taaccatgtt catgccttct tctttttcct   1800

acagctcctg ggcaacgtgc tggttattgt gaccggtgcc accatggcca aagccgcggc   1860

gatcggcatc gacctgggca ccacctactc ctgcgtgggg gtgttccaac acggcaaggt   1920

ggagatcatc gccaacgacc agggcaaccg caccaccccc agctacgtgg ccttcacgga   1980

caccgagcgg ctcatcgggg atgcggccaa gaaccaggtg gcgctgaacc cgcagaacac   2040

cgtgtttgac gcgaagcggc tgatcggccg caagttcggc gacccggtgg tgcagtcgga   2100

catgaagcac tggcctttcc aggtgatcaa cgacggagac aagcccaagg tgcaggtgag   2160

ctacaagggg gagaccaagg cattctaccc cgaggagatc tcgtccatgg tgctgaccaa   2220

gatgaaggag atcgccgagg cgtacctggg ctacccggtg accaacgcgg tgatcaccgt   2280

gccggcctac ttcaacgact cgcagcgcca ggccaccaag gatgcgggtg tgatcgcggg   2340

gctcaacgtg ctgcggatca tcaacgagcc cacggccgcc gccatcgcct acggcctgga   2400

cagaacgggc aagggggagc gcaacgtgct catctttgac ctgggcgggg gcaccttcga   2460

cgtgtccatc ctgacgatcg acgacggcat cttcgaggtg aaggccacgg ccggggacac   2520

ccacctgggt ggggaggact ttgacaacag gctggtgaac cacttcgtgg aggagttcaa   2580

gagaaaacac aagaaggaca tcagccagaa caagcgagcc gtgaggcggc tgcgcaccgc   2640

ctgcgagagg gccaagagga ccctgtcgtc cagcacccag gccagcctgg agatcgactc   2700

cctgtttgag ggcatcgact tctacacgtc catcaccagg gcgaggttcg aggagctgtg   2760

ctccgacctg ttccgaagca ccctggagcc cgtggagaag gctctgcgcg acgccaagct   2820

ggacaaggcc cagattcacg acctggtcct ggtcgggggc tccacccgca tccccaaggt   2880

gcagaagctg ctgcaggact tcttcaacgg gcgcgacctg aacaagagca tcaaccccga   2940

cgaggctgtg gcctacgggg cggcggtgca ggcggccatc ctgatggggg acaagtccga   3000

gaacgtgcag gacctgctgc tgctggacgt ggctcccctg tcgctggggc tggagacggc   3060

cggaggcgtg atgactgccc tgatcaagcg caactccacc atccccacca agcagacgca   3120

gatcttcacc acctactccg acaaccaacc cggggtgctg atccaggtgt acgagggcga   3180

gagggccatg acgaaagaca acaatctgtt ggggcgcttc gagctgagcg gcatccctcc   3240

ggcccccagg ggcgtgcccc agatcgaggt gaccttcgac atcgatgcca acggcatcct   3300

gaacgtcacg gccacggaca agagcaccgg caaggccaac aagatcacca tcaccaacga   3360

caagggccgc ctgagcaagg aggagatcga gcgcatggtg caggaggcgg agaagtacaa   3420

agcggaggac gaggtgcagc gcgagagggt gtcagccaag aacgccctgg agtcctacgc   3480

cttcaacatg aagagcgccg tggaggatga ggggctcaag ggcaagatca gcgaggcgga   3540

caagaagaag gttctggaca agtgtcaaga ggtcatctcg tggctggacg ccaacacctt   3600

ggccgagaag gacgagtttg agcacaagag gaaggagctg gagcaggtgt gtaaccccat   3660

catcagcgga ctgtaccagg gtgccggtgg tcccgggcct gggggcttcg gggctcaggg   3720

tcccaaggga gggtctgggt caggccccac cattgaggag gtggattaag agctcgctga   3780

tcagcctcga ctgtgccttc tagttgccag ccatctgttg tttgcccctc ccccgtgcct   3840

tccttgaccc tggaaggtgc cactcccact gtcctttcct aataaaatga ggaaattgca   3900

tcgcattgtc tgagtaggtg tcattctatt ctggggggtg gggtggggca ggacagcaag   3960

ggggaggatt gggaagacaa tagcaggcat gctggggatg cggtgggctc tatggaagct   4020
```

```
tgaattcagc tgacgtgcct cggaccgcta ggaacccta gtgatggagt tggccactcc   4080

ctctctgcgc gctcgctcgc tcactgaggc cgggcgacca aaggtcgccc gacgcccggg   4140

ctttgcccgg gcggcctcag tgagcgagcg agcgcgcag                          4179
```

<210> SEQ ID NO 98
<211> LENGTH: 5016
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 98

```
ctgcgcgctc gctcgctcac tgaggccgcc cgggcgtcgg gcgacctttg gtcgcccggc     60

ctcagtgagc gagcgagcgc gcagagaggg agtggccaac tccatcacta ggggttcctg    120

cggccgcacg cgtgacattg attattgact agttattaat agtaatcaat tacggggtca    180

ttagttcata gcccatatat ggagttccgc gttacataac ttacggtaaa tggcccgcct    240

ggctgaccgc ccaacgaccc ccgcccattg acgtcaataa tgacgtatgt tcccatagta    300

acgccaatag ggactttcca ttgacgtcaa tgggtggact atttacggta aactgcccac    360

ttggcagtac atcaagtgta tcatatgcca agtacgcccc ctattgacgt caatgacggt    420

aaatggcccg cctggcatta tgcccagtac atgaccttat gggactttcc tacttggcag    480

tacatctacg tattagtcat cgctattacc atgggtcgag gtgagcccca cgttctgctt    540

cactctcccc atctcccccc cctccccacc cccaattttg tatttattta tttttaatt     600

attttgtgca gcgatggggg cggggggggg gggggcgcgc gccaggcggg gcggggcggg    660

gcgaggggcg gggcggggcg aggcggagag gtgcggcggc agccaatcag agcggcgcgc    720

tccgaaagtt tccttttatg gcgaggcggc ggcggcggcg gccctataaa aagcgaagcg    780

cgcggcgggc gggagtcgct gcgttgcctt cgccccgtgc cccgctccgc gccgcctcgc    840

gccgcccgcc ccggctctga ctgaccgcgt tactcccaca ggtgagcggg cgggacggcc    900

cttctcctcc gggctgtaat tagcgcttgg tttaatgacg gctcgtttct tttctgtggc    960

tgcgtgaaag ccttaaaggg ctccgggagg gccctttgtg cggggggggag cggctcgggg   1020

ggtgcgtgcg tgtgtgtgtg cgtggggagc gccgcgtgcg gcccgcgctg cccggcggct   1080

gtgagcgctg cgggcgcggc gcggggcttt gtgcgctccg cgtgtgcgcg aggggagcgc   1140

ggccgggggc ggtgccccgc ggtgcggggg ggctgcgagg ggaacaaagg ctgcgtgcgg   1200

ggtgtgtgcg tgggggggtg agcagggggt gtgggcgcgg cggtcgggct gtaacccccc   1260

cctgcacccc cctccccgag ttgctgagca cggcccggct tcgggtgcgg ggctccgtgc   1320

ggggcgtggc gcggggctcg ccgtgccggg cggggggtgg cggcaggtgg gggtgccggg   1380

cggggcgggg ccgcctcggg ccggggaggg ctcgggggag ggcgcggcg gcccccggag    1440

cgccggcggc tgtcgaggcg cggcgagccg cagccattgc cttttatggt aatcgtgcga   1500

gagggcgcag ggacttcctt tgtcccaaat ctgtgcggag ccgaaatctg ggaggcgccg   1560

ccgcaccccc tctagcgggc gcggggcgaa gcggtgcggc gccggcagga aggaaatggg   1620

cggggagggc cttcgtgcgt cgccgcgccg ccgtcccctt ctccctctcc agcctcgggg   1680

ctgtccgcgg ggggacggct gccttcgggg gggacggggc agggcggggt tcggcttctg   1740

gcgtgtgacc ggcggctcta gagcctctgc taaccatgtt catgccttct tcttttcct    1800

acagctcctg ggcaacgtgc tggttattgt gaccggtgcc accatggcca aagccgcggc   1860
```

```
gatcggcatc gacctgggca ccacctactc ctgcgtgggg gtgttccaac acggcaaggt   1920
ggagatcatc gccaacgacc agggcaaccg caccaccccc agctacgtgg ccttcacgga   1980
caccgagcgg ctcatcgggg atgcggccaa gaaccaggtg gcgctgaacc cgcagaacac   2040
cgtgtttgac gcgaagcggc tgatcggccg caagttcggc gacccggtgg tgcagtcgga   2100
catgaagcac tggcctttcc aggtgatcaa cgacggagac aagcccaagg tgcaggtgag   2160
ctacaagggg gagaccaagg cattctaccc cgaggagatc tcgtccatgg tgctgaccaa   2220
gatgaaggag atcgccgagg cgtacctggg ctacccggtg accaacgcgg tgatcaccgt   2280
gccggcctac ttcaacgact cgcagcgcca ggccaccaag gatgcgggtg tgatcgcggg   2340
gctcaacgtg ctgcggatca tcaacgagcc cacggccgcc gccatcgcct acggcctgga   2400
cagaacgggc aagggggagc gcaacgtgct catctttgac ctgggcgggg gcaccttcga   2460
cgtgtccatc ctgacgatcg acgacggcat cttcgaggtg aaggccacgg ccggggacac   2520
ccacctgggt ggggaggact ttgacaacag gctggtgaac cacttcgtgg aggagttcaa   2580
gagaaaacac aagaaggaca tcagccagaa caagcgagcc gtgaggcggc tgcgcaccgc   2640
ctgcgagagg gccaagagga ccctgtcgtc cagcacccag gccagcctgg agatcgactc   2700
cctgtttgag ggcatcgact tctacacgtc catcaccagg gcgaggttcg aggagctgtg   2760
ctccgacctg ttccgaagca ccctggagcc cgtggagaag gctctgcgcg acgccaagct   2820
ggacaaggcc cagattcacg acctggtcct ggtcgggggc tccacccgca tccccaaggt   2880
gcagaagctg ctgcaggact tcttcaacgg gcgcgacctg aacaagagca tcaaccccga   2940
cgaggctgtg gcctacgggg cggcggtgca ggcggccatc ctgatggggg acaagtccga   3000
gaacgtgcag gacctgctgc tgctggacgt ggctcccctg tcgctggggc tggagacggc   3060
cggaggcgtg atgactgccc tgatcaagcg caactccacc atccccacca agcagacgca   3120
gatcttcacc acctactccg acaaccaacc cggggtgctg atccaggtgt acgagggcga   3180
gagggccatg acgaaagaca acaatctgtt ggggcgcttc gagctgagcg gcatccctcc   3240
ggcccccagg ggcgtgcccc agatcgaggt gaccttcgac atcgatgcca acggcatcct   3300
gaacgtcacg gccacggaca agagcaccgg caaggccaac aagatcacca tcaccaacga   3360
caagggccgc ctgagcaagg aggagatcga gcgcatggtg caggaggcgg agaagtacaa   3420
agcggaggac gaggtgcagc gcgagagggt gtcagccaag aacgccctgg agtcctacgc   3480
cttcaacatg aagagcgccg tggaggatga ggggctcaag ggcaagatca gcgaggcgga   3540
caagaagaag gttctggaca agtgtcaaga ggtcatctcg tggctggacg ccaacacctt   3600
ggccgagaag gacgagtttg agcacaagag gaaggagctg gagcaggtgt gtaaccccat   3660
catcagcgga ctgtaccagg gtgccggtgg tcccgggcct gggggcttcg ggggctcaggg   3720
tcccaaggga gggtctgggt caggccccac cattgaggag gtggatggat cccgggctga   3780
ctacaaagac catgacggtg attataaaga tcatgacatc gactacaagg atgacgatga   3840
caagggctcc ggagagggca gaggaagtct gctaacatgc ggtgacgtcg aggagaatcc   3900
tggcccaatg gagagcgacg agagcggcct gcccgccatg gagatcgagt gccgcatcac   3960
cggcaccctg aacggcgtgg agttcgagct ggtgggcggc ggagagggca cccccgagca   4020
gggccgcatg accaacaaga tgaagagcac caaaggcgcc ctgaccttca gcccctacct   4080
gctgagccac gtgatgggct acggcttcta ccacttcggc acctacccca gcggctacga   4140
gaaccccttc ctgcacgcca tcaacaacgg cggctacacc aacacccgca tcgagaagta   4200
cgaggacggc ggcgtgctgc acgtgagctt cagctaccgc tacgaggccg gccgcgtgat   4260
```

```
cggcgacttc aaggtgatgg gcaccggctt ccccgaggac agcgtgatct tcaccgacaa   4320

gatcatccgc agcaacgcca ccgtggagca cctgcacccc atgggcgata acgatctgga   4380

tggcagcttc acccgcacct tcagcctgcg cgacggcggc tactacagct ccgtggtgga   4440

cagccacatg cacttcaaga gcgccatcca ccccagcatc ctgcagaacg gggggcccat   4500

gttcgccttc cgccgcgtgg aggaggatca cagcaacacc gagctgggca tcgtggagta   4560

ccagcacgcc ttcaagaccc cggatgcaga tgccggtgaa gaataagagc tcgctgatca   4620

gcctcgactg tgccttctag ttgccagcca tctgttgttt gcccctcccc cgtgccttcc   4680

ttgaccctgg aaggtgccac tcccactgtc ctttcctaat aaaatgagga aattgcatcg   4740

cattgtctga gtaggtgtca ttctattctg gggggtgggg tggggcagga cagcaagggg   4800

gaggattggg aagacaatag caggcatgct ggggatgcgg tgggctctat ggaagcttga   4860

attcagctga cgtgcctcgg accgctagga acccctagtg atggagttgg ccactccctc   4920

tctgcgcgct cgctcgctca ctgaggccgg gcgaccaaag gtcgcccgac gcccgggctt   4980

tgcccgggcg gcctcagtga gcgagcgagc gcgcag                             5016
```

<210> SEQ ID NO 99
<211> LENGTH: 1004
<212> TYPE: DNA
<213> ORGANISM: Homo sapiens

<400> SEQUENCE: 99

```
agctgcaggt atttaaccca cacacatagt tacctttgtc acttttctac tagttgttgt     60

gtaatgggtt agctttatct attagtttct ccttcatata gctcaaggag tcaaggaata    120

cacgttctca ttgtttctaa atcagaccta aagttttatt ctaaatgatg cagatgaagg    180

ggcttattaa agtgccattg tgaatttaat catgtatatg ctgctaaaaa tcatttaatg    240

gatgaacaac ccggaaaaaa agaactctca ccacccacac acatcgtgat aaaatagggc    300

agcgttttgc acttgcttta acagcatcgc ctgagaaaaa aatttctggt tcccatcttt    360

cccctctctt acttaaaatt tcaacttcat cacagtcagc tgccgaatcg ttcaacagaa    420

tgccacactg cctttgtatt tccaaaacta tacgtctcta ttgcggacgg cacatcttta    480

tggcagccac atgcttgaaa aagaattaaa ttcagaatat tcatttggcc tcttattagt    540

tccataatac cattaaaaaa gaaagaaaga aagaaacttc ctcgcccttg ttctgctacg    600

ctgttcccat cgtaagatgc tccgtggaag ggagccgagc ggtgggcaga ggctgagtcc    660

ccgataacga gcgcctcaca tttccgtggc attcccattt gctagtgcgc tgctgcggcc    720

gcacgcctga ttgatatatg actgcaatgg cacttttcca tttgacattc tctctctctc    780

tctccctctc tctctctccc tctctctctc cctctctctc tctccctgtg tcgcttaaac    840

aacagtccta acttttgtgt gttgcaaata taaaaggcaa gccatgtgac agagggacag    900

aagaacaaaa gcatttggaa gtaacaggac ctctttctag ctctcagaaa agtctgagaa    960

gaaaggagcc ctgcgttccc ctaaggtaag caggaaaaca agcg                    1004
```

<210> SEQ ID NO 100
<211> LENGTH: 5000
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<221> NAME/KEY: misc_feature
<222> LOCATION: (1)..(5000)
<223> OTHER INFORMATION: This sequence may encompass 50, 60, 70, 100,
200, 500, 1000, 2000, 3000, 4000, or 5000 nucleotides
<220> FEATURE:
<223> OTHER INFORMATION: See specification as filed for detailed
description of substitutions and preferred embodiments

<400> SEQUENCE: 100

```
aaaaaaaaaa aaaaaaaaaa aaaaaaaaaa aaaaaaaaaa aaaaaaaaaa aaaaaaaaaa     60

aaaaaaaaaa aaaaaaaaaa aaaaaaaaaa aaaaaaaaaa aaaaaaaaaa aaaaaaaaaa    120

aaaaaaaaaa aaaaaaaaaa aaaaaaaaaa aaaaaaaaaa aaaaaaaaaa aaaaaaaaaa    180

aaaaaaaaaa aaaaaaaaaa aaaaaaaaaa aaaaaaaaaa aaaaaaaaaa aaaaaaaaaa    240

aaaaaaaaaa aaaaaaaaaa aaaaaaaaaa aaaaaaaaaa aaaaaaaaaa aaaaaaaaaa    300

aaaaaaaaaa aaaaaaaaaa aaaaaaaaaa aaaaaaaaaa aaaaaaaaaa aaaaaaaaaa    360

aaaaaaaaaa aaaaaaaaaa aaaaaaaaaa aaaaaaaaaa aaaaaaaaaa aaaaaaaaaa    420

aaaaaaaaaa aaaaaaaaaa aaaaaaaaaa aaaaaaaaaa aaaaaaaaaa aaaaaaaaaa    480

aaaaaaaaaa aaaaaaaaaa aaaaaaaaaa aaaaaaaaaa aaaaaaaaaa aaaaaaaaaa    540

aaaaaaaaaa aaaaaaaaaa aaaaaaaaaa aaaaaaaaaa aaaaaaaaaa aaaaaaaaaa    600

aaaaaaaaaa aaaaaaaaaa aaaaaaaaaa aaaaaaaaaa aaaaaaaaaa aaaaaaaaaa    660

aaaaaaaaaa aaaaaaaaaa aaaaaaaaaa aaaaaaaaaa aaaaaaaaaa aaaaaaaaaa    720

aaaaaaaaaa aaaaaaaaaa aaaaaaaaaa aaaaaaaaaa aaaaaaaaaa aaaaaaaaaa    780

aaaaaaaaaa aaaaaaaaaa aaaaaaaaaa aaaaaaaaaa aaaaaaaaaa aaaaaaaaaa    840

aaaaaaaaaa aaaaaaaaaa aaaaaaaaaa aaaaaaaaaa aaaaaaaaaa aaaaaaaaaa    900

aaaaaaaaaa aaaaaaaaaa aaaaaaaaaa aaaaaaaaaa aaaaaaaaaa aaaaaaaaaa    960

aaaaaaaaaa aaaaaaaaaa aaaaaaaaaa aaaaaaaaaa aaaaaaaaaa aaaaaaaaaa   1020

aaaaaaaaaa aaaaaaaaaa aaaaaaaaaa aaaaaaaaaa aaaaaaaaaa aaaaaaaaaa   1080

aaaaaaaaaa aaaaaaaaaa aaaaaaaaaa aaaaaaaaaa aaaaaaaaaa aaaaaaaaaa   1140

aaaaaaaaaa aaaaaaaaaa aaaaaaaaaa aaaaaaaaaa aaaaaaaaaa aaaaaaaaaa   1200

aaaaaaaaaa aaaaaaaaaa aaaaaaaaaa aaaaaaaaaa aaaaaaaaaa aaaaaaaaaa   1260

aaaaaaaaaa aaaaaaaaaa aaaaaaaaaa aaaaaaaaaa aaaaaaaaaa aaaaaaaaaa   1320

aaaaaaaaaa aaaaaaaaaa aaaaaaaaaa aaaaaaaaaa aaaaaaaaaa aaaaaaaaaa   1380

aaaaaaaaaa aaaaaaaaaa aaaaaaaaaa aaaaaaaaaa aaaaaaaaaa aaaaaaaaaa   1440

aaaaaaaaaa aaaaaaaaaa aaaaaaaaaa aaaaaaaaaa aaaaaaaaaa aaaaaaaaaa   1500

aaaaaaaaaa aaaaaaaaaa aaaaaaaaaa aaaaaaaaaa aaaaaaaaaa aaaaaaaaaa   1560

aaaaaaaaaa aaaaaaaaaa aaaaaaaaaa aaaaaaaaaa aaaaaaaaaa aaaaaaaaaa   1620

aaaaaaaaaa aaaaaaaaaa aaaaaaaaaa aaaaaaaaaa aaaaaaaaaa aaaaaaaaaa   1680

aaaaaaaaaa aaaaaaaaaa aaaaaaaaaa aaaaaaaaaa aaaaaaaaaa aaaaaaaaaa   1740

aaaaaaaaaa aaaaaaaaaa aaaaaaaaaa aaaaaaaaaa aaaaaaaaaa aaaaaaaaaa   1800

aaaaaaaaaa aaaaaaaaaa aaaaaaaaaa aaaaaaaaaa aaaaaaaaaa aaaaaaaaaa   1860

aaaaaaaaaa aaaaaaaaaa aaaaaaaaaa aaaaaaaaaa aaaaaaaaaa aaaaaaaaaa   1920

aaaaaaaaaa aaaaaaaaaa aaaaaaaaaa aaaaaaaaaa aaaaaaaaaa aaaaaaaaaa   1980

aaaaaaaaaa aaaaaaaaaa aaaaaaaaaa aaaaaaaaaa aaaaaaaaaa aaaaaaaaaa   2040

aaaaaaaaaa aaaaaaaaaa aaaaaaaaaa aaaaaaaaaa aaaaaaaaaa aaaaaaaaaa   2100
```

-continued

```
aaaaaaaaaa aaaaaaaaaa aaaaaaaaaa aaaaaaaaaa aaaaaaaaaa aaaaaaaaaa   2160
aaaaaaaaaa aaaaaaaaaa aaaaaaaaaa aaaaaaaaaa aaaaaaaaaa aaaaaaaaaa   2220
aaaaaaaaaa aaaaaaaaaa aaaaaaaaaa aaaaaaaaaa aaaaaaaaaa aaaaaaaaaa   2280
aaaaaaaaaa aaaaaaaaaa aaaaaaaaaa aaaaaaaaaa aaaaaaaaaa aaaaaaaaaa   2340
aaaaaaaaaa aaaaaaaaaa aaaaaaaaaa aaaaaaaaaa aaaaaaaaaa aaaaaaaaaa   2400
aaaaaaaaaa aaaaaaaaaa aaaaaaaaaa aaaaaaaaaa aaaaaaaaaa aaaaaaaaaa   2460
aaaaaaaaaa aaaaaaaaaa aaaaaaaaaa aaaaaaaaaa aaaaaaaaaa aaaaaaaaaa   2520
aaaaaaaaaa aaaaaaaaaa aaaaaaaaaa aaaaaaaaaa aaaaaaaaaa aaaaaaaaaa   2580
aaaaaaaaaa aaaaaaaaaa aaaaaaaaaa aaaaaaaaaa aaaaaaaaaa aaaaaaaaaa   2640
aaaaaaaaaa aaaaaaaaaa aaaaaaaaaa aaaaaaaaaa aaaaaaaaaa aaaaaaaaaa   2700
aaaaaaaaaa aaaaaaaaaa aaaaaaaaaa aaaaaaaaaa aaaaaaaaaa aaaaaaaaaa   2760
aaaaaaaaaa aaaaaaaaaa aaaaaaaaaa aaaaaaaaaa aaaaaaaaaa aaaaaaaaaa   2820
aaaaaaaaaa aaaaaaaaaa aaaaaaaaaa aaaaaaaaaa aaaaaaaaaa aaaaaaaaaa   2880
aaaaaaaaaa aaaaaaaaaa aaaaaaaaaa aaaaaaaaaa aaaaaaaaaa aaaaaaaaaa   2940
aaaaaaaaaa aaaaaaaaaa aaaaaaaaaa aaaaaaaaaa aaaaaaaaaa aaaaaaaaaa   3000
aaaaaaaaaa aaaaaaaaaa aaaaaaaaaa aaaaaaaaaa aaaaaaaaaa aaaaaaaaaa   3060
aaaaaaaaaa aaaaaaaaaa aaaaaaaaaa aaaaaaaaaa aaaaaaaaaa aaaaaaaaaa   3120
aaaaaaaaaa aaaaaaaaaa aaaaaaaaaa aaaaaaaaaa aaaaaaaaaa aaaaaaaaaa   3180
aaaaaaaaaa aaaaaaaaaa aaaaaaaaaa aaaaaaaaaa aaaaaaaaaa aaaaaaaaaa   3240
aaaaaaaaaa aaaaaaaaaa aaaaaaaaaa aaaaaaaaaa aaaaaaaaaa aaaaaaaaaa   3300
aaaaaaaaaa aaaaaaaaaa aaaaaaaaaa aaaaaaaaaa aaaaaaaaaa aaaaaaaaaa   3360
aaaaaaaaaa aaaaaaaaaa aaaaaaaaaa aaaaaaaaaa aaaaaaaaaa aaaaaaaaaa   3420
aaaaaaaaaa aaaaaaaaaa aaaaaaaaaa aaaaaaaaaa aaaaaaaaaa aaaaaaaaaa   3480
aaaaaaaaaa aaaaaaaaaa aaaaaaaaaa aaaaaaaaaa aaaaaaaaaa aaaaaaaaaa   3540
aaaaaaaaaa aaaaaaaaaa aaaaaaaaaa aaaaaaaaaa aaaaaaaaaa aaaaaaaaaa   3600
aaaaaaaaaa aaaaaaaaaa aaaaaaaaaa aaaaaaaaaa aaaaaaaaaa aaaaaaaaaa   3660
aaaaaaaaaa aaaaaaaaaa aaaaaaaaaa aaaaaaaaaa aaaaaaaaaa aaaaaaaaaa   3720
aaaaaaaaaa aaaaaaaaaa aaaaaaaaaa aaaaaaaaaa aaaaaaaaaa aaaaaaaaaa   3780
aaaaaaaaaa aaaaaaaaaa aaaaaaaaaa aaaaaaaaaa aaaaaaaaaa aaaaaaaaaa   3840
aaaaaaaaaa aaaaaaaaaa aaaaaaaaaa aaaaaaaaaa aaaaaaaaaa aaaaaaaaaa   3900
aaaaaaaaaa aaaaaaaaaa aaaaaaaaaa aaaaaaaaaa aaaaaaaaaa aaaaaaaaaa   3960
aaaaaaaaaa aaaaaaaaaa aaaaaaaaaa aaaaaaaaaa aaaaaaaaaa aaaaaaaaaa   4020
aaaaaaaaaa aaaaaaaaaa aaaaaaaaaa aaaaaaaaaa aaaaaaaaaa aaaaaaaaaa   4080
aaaaaaaaaa aaaaaaaaaa aaaaaaaaaa aaaaaaaaaa aaaaaaaaaa aaaaaaaaaa   4140
aaaaaaaaaa aaaaaaaaaa aaaaaaaaaa aaaaaaaaaa aaaaaaaaaa aaaaaaaaaa   4200
aaaaaaaaaa aaaaaaaaaa aaaaaaaaaa aaaaaaaaaa aaaaaaaaaa aaaaaaaaaa   4260
aaaaaaaaaa aaaaaaaaaa aaaaaaaaaa aaaaaaaaaa aaaaaaaaaa aaaaaaaaaa   4320
aaaaaaaaaa aaaaaaaaaa aaaaaaaaaa aaaaaaaaaa aaaaaaaaaa aaaaaaaaaa   4380
aaaaaaaaaa aaaaaaaaaa aaaaaaaaaa aaaaaaaaaa aaaaaaaaaa aaaaaaaaaa   4440
aaaaaaaaaa aaaaaaaaaa aaaaaaaaaa aaaaaaaaaa aaaaaaaaaa aaaaaaaaaa   4500
```

```
aaaaaaaaaa aaaaaaaaaa aaaaaaaaaa aaaaaaaaaa aaaaaaaaaa aaaaaaaaaa   4560

aaaaaaaaaa aaaaaaaaaa aaaaaaaaaa aaaaaaaaaa aaaaaaaaaa aaaaaaaaaa   4620

aaaaaaaaaa aaaaaaaaaa aaaaaaaaaa aaaaaaaaaa aaaaaaaaaa aaaaaaaaaa   4680

aaaaaaaaaa aaaaaaaaaa aaaaaaaaaa aaaaaaaaaa aaaaaaaaaa aaaaaaaaaa   4740

aaaaaaaaaa aaaaaaaaaa aaaaaaaaaa aaaaaaaaaa aaaaaaaaaa aaaaaaaaaa   4800

aaaaaaaaaa aaaaaaaaaa aaaaaaaaaa aaaaaaaaaa aaaaaaaaaa aaaaaaaaaa   4860

aaaaaaaaaa aaaaaaaaaa aaaaaaaaaa aaaaaaaaaa aaaaaaaaaa aaaaaaaaaa   4920

aaaaaaaaaa aaaaaaaaaa aaaaaaaaaa aaaaaaaaaa aaaaaaaaaa aaaaaaaaaa   4980

aaaaaaaaaa aaaaaaaaaa                                               5000
```

<210> SEQ ID NO 101
<211> LENGTH: 1673
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 101

```
gacattgatt attgactagt tattaatagt aatcaattac ggggtcatta gttcatagcc     60

catatatgga gttccgcgtt acataactta cggtaaatgg cccgcctggc tgaccgccca    120

acgacccccg cccattgacg tcaataatga cgtatgttcc catagtaacg ccaataggga    180

ctttccattg acgtcaatgg gtggactatt tacggtaaac tgcccacttg gcagtacatc    240

aagtgtatca tatgccaagt acgcccccta ttgacgtcaa tgacggtaaa tggcccgcct    300

ggcattatgc ccagtacatg accttatggg actttcctac ttggcagtac atctacgtat    360

tagtcatcgc tattaccatg ggtcgaggtg agccccacgt tctgcttcac tctccccatc    420

tcccccccct ccccaccccc aattttgtat ttatttattt tttaattatt ttgtgcagcg    480

atgggggcgg gggggggggg ggggcgcgcg ccaggcgggg cggggcgggg cgaggggcgg    540

ggcggggcga ggcggagagg tgcggcggca gccaatcaga gcggcgcgct ccgaaagttt    600

ccttttatgg cgaggcggcg gcggcggcgg ccctataaaa agcgaagcgc gcggcgggcg    660

ggagtcgctg cgttgccttc gccccgtgcc ccgctccgcg ccgcctcgcg ccgcccgccc    720

cggctctgac tgaccgcgtt actcccacag gtgagcgggc gggacggccc ttctcctccg    780

ggctgtaatt agcgcttggt ttaatgacgg ctcgtttctt ttctgtggct gcgtgaaagc    840

cttaaagggc tccgggaggg ccctttgtgc ggggggggagc ggctcggggg gtgcgtgcgt    900

gtgtgtgtgc gtggggagcg ccgcgtgcgg cccgcgctgc ccggcggctg tgagcgctgc    960

gggcgcggcg cggggctttg tgcgctccgc gtgtgcgcga ggggagcgcg gccgggggcg   1020

gtgccccgcg gtgcgggggg gctgcgaggg gaacaaaggc tgcgtgcggg gtgtgtgcgt   1080

gggggggtga gcagggggtg tgggcgcggc ggtcgggctg taaccccccc ctgcaccccc   1140

ctccccgagt tgctgagcac ggcccggctt cgggtgcggg gctccgtgcg gggcgtggcg   1200

cggggctcgc cgtgccgggc ggggggtggc ggcaggtggg ggtgccgggc ggggcggggc   1260

cgcctcgggc cggggagggc tcgggggagg ggcgcggcgg cccccggagc gccggcggct   1320

gtcgaggcgc ggcgagccgc agccattgcc ttttatggta atcgtgcgag agggcgcagg   1380

gacttccttt gtcccaaatc tgtgcggagc cgaaatctgg gaggcgccgc cgcacccccct   1440

ctagcgggcg cggggcgaag cggtgcggcg ccggcaggaa ggaaatgggc ggggagggcc   1500
```

```
ttcgtgcgtc gccgcgccgc cgtccccttc tccctctcca gcctcggggc tgtccgcggg   1560

gggacggctg ccttcggggg ggacggggca gggcggggtt cggcttctgg cgtgtgaccg   1620

gcggctctag agcctctgct aaccatgttc atgccttctt ctttttccta cag          1673
```

```
<210> SEQ ID NO 102
<211> LENGTH: 1671
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 102

gacattgatt attgactagt tattaatagt aatcaattac ggggtcatta gttcatagcc     60

catatatgga gttccgcgtt acataactta cggtaaatgg cccgcctggc tgaccgccca    120

acgacccccg cccattgacg tcaataatga cgtatgttcc catagtaacg ccaataggga    180

ctttccattg acgtcaatgg gtggactatt tacggtaaac tgcccacttg gcagtacatc    240

aagtgtatca tatgccaagt acgcccccta ttgacgtcaa tgacggtaaa tggcccgcct    300

ggcattatgc ccagtacatg accttatggg actttcctac ttggcagtac atctacgtat    360

tagtcatcgc tattaccatg ggtcgaggtg agccccacgt tctgcttcac tctccccatc    420

tcccccccct ccccaccccc aattttgtat ttatttattt tttaattatt ttgtgcagcg    480

atgggggcgg gggggggggg ggcgcgcgcc aggcggggcg gggcggggcg aggggcgggg    540

cggggcgagg cggagaggtg cggcggcagc caatcagagc ggcgcgctcc gaaagtttcc    600

ttttatggcg aggcggcggc ggcggcggcc ctataaaaag cgaagcgcgc ggcgggcggg    660

agtcgctgcg ttgccttcgc cccgtgcccc gctccgcgcc gcctcgcgcc gcccgccccg    720

gctctgactg accgcgttac tcccacaggt gagcgggcgg gacggccctt ctcctccggg    780

ctgtaattag cgcttggttt aatgacggct cgtttctttt ctgtggctgc gtgaaagcct    840

taaagggctc cgggagggcc ctttgtgcgg gggggagcgg ctcggggggt gcgtgcgtgt    900

gtgtgtgcgt ggggagcgcc gcgtgcggcc cgcgctgccc ggcggctgtg agcgctgcgg    960

gcgcggcgcg gggctttgtg cgctccgcgt gtgcgcgagg ggagcgcggc cgggggcggt   1020

gccccgcggt gcgggggggc tgcgagggga acaaaggctg cgtgcggggt gtgtgcgtgg   1080

gggggtgagc agggggtgtg ggcgcggcgg tcgggctgta accccccccct gcaccccccct   1140

ccccgagttg ctgagcacgg cccggcttcg ggtgcggggc tccgtgcggg gcgtggcgcg   1200

gggctcgccg tgccgggcgg ggggtggcgg caggtggggg tgccgggcgg ggcggggccg   1260

cctcgggccg gggagggctc gggggagggg cgcggcggcc cccggagcgc cggcggctgt   1320

cgaggcgcgg cgagccgcag ccattgcctt ttatggtaat cgtgcgagag ggcgcaggga   1380

cttcctttgt cccaaatctg tgcggagccg aaatctggga ggcgccgccg caccccctct   1440

agcgggcgcg gggcgaagcg gtgcggcgcc ggcaggaagg aaatgggcgg ggagggcctt   1500

cgtgcgtcgc cgcgccgccg tccccttctc cctctccagc ctcggggctg tccgcggggg   1560

gacggctgcc ttcggggggg acggggcagg gcggggttcg gcttctggcg tgtgaccggc   1620

ggctctagag cctctgctaa ccatgttcat gccttcttct ttttcctaca g            1671
```

```
<210> SEQ ID NO 103
<211> LENGTH: 60
<212> TYPE: DNA
<213> ORGANISM: Homo sapiens
```

<400> SEQUENCE: 103
ctgccttctg agagcgctat aaaggcagcg gaagggtagt ccgcggggca ttccgggcgg 60

<210> SEQ ID NO 104
<211> LENGTH: 51
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 104
gataggcacc tattggtctt actgacatcc actttgcctt tctctccaca g 51

<210> SEQ ID NO 105
<211> LENGTH: 78
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 105
ggatcccggg ctgactacaa agaccatgac ggtgattata aagatcatga catcgactac 60
aaggatgacg atgacaag 78

<210> SEQ ID NO 106
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 106
ctcctgggca acgtgctggt tattgtgacc ggtgccacc 39

<210> SEQ ID NO 107
<211> LENGTH: 34
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 107
aagcttgaat tcagctgacg tgcctcggac cgct 34

<210> SEQ ID NO 108
<211> LENGTH: 159
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 108

```
Met Ile Ser Leu Ile Ala Ala Leu Ala Val Asp Tyr Val Ile Gly Met
1               5                   10                  15

Glu Asn Ala Met Pro Trp Asn Leu Pro Ala Asp Leu Ala Trp Phe Lys
            20                  25                  30

Arg Asn Thr Leu Asn Lys Pro Val Ile Met Gly Arg His Thr Trp Glu
        35                  40                  45
```

```
Ser Ile Gly Arg Pro Leu Pro Gly Arg Lys Asn Ile Ile Leu Ser Ser
    50                  55                  60

Gln Pro Ser Thr Asp Asp Arg Val Thr Trp Val Lys Ser Val Asp Glu
65                  70                  75                  80

Ala Ile Ala Ala Cys Gly Asp Val Pro Glu Ile Met Val Ile Gly Gly
                85                  90                  95

Gly Arg Val Ile Glu Gln Phe Leu Pro Lys Ala Gln Lys Leu Tyr Leu
            100                 105                 110

Thr His Ile Asp Ala Glu Val Glu Gly Asp Thr His Phe Pro Asp Tyr
        115                 120                 125

Glu Pro Asp Asp Trp Glu Ser Val Phe Ser Glu Phe His Asp Ala Asp
    130                 135                 140

Ala Gln Asn Ser His Ser Tyr Cys Phe Glu Ile Leu Glu Arg Arg
145                 150                 155
```

<210> SEQ ID NO 109
<211> LENGTH: 483
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 109

```
ggtaccatca gtctgattgc ggcgttagcg gtagattacg ttatcggcat ggaaaacgcc     60

atgccgtgga acctgcctgc cgatctcgcc tggtttaaac gcaacacctt aaataaaccc    120

gtgattatgg gccgccatac ctgggaatca atcggtcgtc cgttgccagg acgcaaaaat    180

attatcctca gcagtcaacc gagtacggac gatcgcgtaa cgtgggtgaa gtcggtggat    240

gaagccatcg cggcgtgtgg tgacgtacca gaaatcatgg tgattggcgg cggtcgcgtt    300

attgaacagt tcttgccaaa agcgcaaaaa ctgtatctga cgcatatcga cgcagaagtg    360

gaaggcgaca cccatttccc ggattacgag ccggatgact gggaatcggt attcagcgaa    420

ttccacgatg ctgatgcgca gaactctcac agctattgct ttgagattct ggagcggcga    480

taa                                                                  483
```

<210> SEQ ID NO 110
<211> LENGTH: 474
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 110

```
atcagtctga ttgcggcgtt agcggtagat tacgttatcg gcatggaaaa cgccatgccg     60

tggaacctgc ctgccgatct cgcctggttt aaacgcaaca ccttaaataa acccgtgatt    120

atgggccgcc atacctggga atcaatcggt cgtccgttgc caggacgcaa aaatattatc    180

ctcagcagtc aaccgagtac ggacgatcgc gtaacgtggg tgaagtcggt ggatgaagcc    240

atcgcggcgt gtggtgacgt accagaaatc atggtgattg gcggcggtcg cgttattgaa    300

cagttcttgc caaaagcgca aaaactgtat ctgacgcata tcgacgcaga agtggaaggc    360

gacacccatt tcccggatta cgagccggat gactgggaat cggtattcag cgaattccac    420

gatgctgatg cgcagaactc tcacagctat tgctttgaga ttctggagcg gcga          474
```

<210> SEQ ID NO 111

```
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 111

Met Gly Val Glu Lys Gln Val Ile Arg Pro Gly Asn Gly Pro Lys Pro
1               5                   10                  15

Ala Pro Gly Gln Thr Val Thr Val His Cys Thr Gly Phe Gly Lys Asp
            20                  25                  30

Gly Asp Leu Ser Gln Lys Phe Trp Ser Thr Lys Asp Glu Gly Gln Lys
        35                  40                  45

Pro Phe Ser Phe Gln Ile Gly Lys Gly Ala Val Ile Lys Gly Trp Asp
    50                  55                  60

Glu Gly Val Ile Gly Met Gln Ile Gly Glu Val Ala Arg Leu Arg Cys
65                  70                  75                  80

Ser Ser Asp Tyr Ala Tyr Gly Ala Gly Gly Phe Pro Ala Trp Gly Ile
                85                  90                  95

Gln Pro Asn Ser Val Leu Asp Phe Glu Ile Glu Val Leu Ser Val Gln
            100                 105                 110


<210> SEQ ID NO 112
<211> LENGTH: 15834
<212> TYPE: DNA
<213> ORGANISM: Homo sapiens

<400> SEQUENCE: 112

actttattca tccttacaaa caggaataat aatagttctt atacaaggta acagaatctc      60

accagcacaa gagtaagcac ttgctaaatt gttattttga attttaataa caaattttat     120

tatttgatga tagttactta aaagtcagca ataattcagg gataattggt tgaattatta     180

atattatatt atcacctagg gcgataagca catcagaaga cttcgtttta agggaaaaag     240

agacccaagt taggagtcag aagacttggg cttcaagagt ggctgtgggt gggtataaga     300

tttctccttg gtgacaccca agggttgacg tagatgacct ctttgataac cagaaagcaa     360

gatcagcttc gctgctctgc gaaagccagc cgtggagctg cacctccctc accgcctaag     420

tctcccggga acgtcccggg cgagggaagg ggtccaaagg tcgtacacaa gaatactgat     480

agcaaagccc cttcctacgc tggtgacggc ggcgtggcgc aagatttgtg caagactccc     540

tcggattggg agcaagggtc ccgcaccttc gtggctccca tgacaaagtc tgcaactcag     600

cccgctgggg gagctgcaag gaacctgcaa gcgtcccagc ccctgcagag acccccaaga     660

aaaagtaccc ccaaaacagc ctgggttgca gatttataaa tacttcctgc gcacatgcgc     720

attggaattt acgagtggcc cggggcgcaa cgcttgccca ctgcgcctgc gccgtctggc     780

tcttccttcg gggcacagga ccagaaagtg gggtcccgtg gtcccgcaaa gaaggaaaaa     840

gaatgggtca gcagtggcca cacggcccct gtttctcgct tcttacctcg taatgcttca     900

tggctccctc ccacggcggc tactgctccg cggctgctgc tgcctaactg cgcggcacag     960

cacaggctcc ctacagcgct cgcaaccgca gcgatagact aaacgcggct ctgcgtccgc    1020

cccgcccctc caggccgcgc gcgccccgtc ggccaatcag ggcacgaggc gcccacgttc    1080

gcccctgctc cttggggccg gtccgaacca agactaggac tagcaccagg ggattgacca    1140

atcaacttgc gagaccaatc gaagggggcg gaacgcctgt aggaggggct aaagagaagg    1200

ggcttgacca tccaccaatc caaaggaggt ctctgccccg cgcgtccctt tgccacgccc    1260
```

```
cctgatggcg tcgctgtgga aaccaaggta agcgacggtt aggccagacg cgggggcggg   1320
gtaagaagtt gagtgacagg caaggcagca tccacatgac aggcggcgcc gaaggggtaa   1380
attctgaggt gggcggcccc cggggtacac cgggaacagc aggagagggc taggggctgg   1440
ggtcgcgggc tgcggagtct ggttggcgag gaggtcacta tgggaggaga ctcttgagtg   1500
ggagggaagg aaaggcgaaa cggagtcgcg aaaagctccc catttgggaa cccccaacct   1560
gcaagaacct tgagccccag ccccattctg gggtggcttc actgccgttt ttaatgaaag   1620
ccccgcccca ctttgttttt ctgttttgtt ttgtttttga aacaatctcg ttctgtcccc   1680
cagctggagt gcagtggcgc aatgacggct cacgcaacct ccgcctcccg ggttcaagcg   1740
attctcatgc ctcagcctcc caagtagatg agattacagg cacccgccac cacgcccgac   1800
taatttttgt attttttta gtagagacgg ggtttcccca tggttggcca ggctggtctt   1860
gaactcctga cctcaggtga tcctcccgcc tcagcctccc aaagtgctag gattacaggc   1920
ctgagccacc ccgcccggcc cccctccaca ctttgctccg ccctatggac aggggaacta   1980
cattggtctc tgcctgacgt ccagaatcgt gtctagtggc tccaatgggg ccactgagcc   2040
cttgaaatgg ggctggtcca ggccgggaac gatggctcac acctgtaatc ctagcacctt   2100
gggaggccga ggggggcaga tcacgaggtg aggagttcga gaccagcctg gcagatatgg   2160
tgaaacctca tcgctactaa aaatacaaaa attagccggg cgtggtggta cacacctgta   2220
gtcccagcta atcaggaggc tgaggcagaa gaattgcttg aacccgggag gcggaggttg   2280
cagtgagcca agatctcgcc actacactcc agcctgagca acagaccgtc tcaaaaaaaa   2340
aaaaagaaaa aagaaaaaga aatgggactg gtccaaattg agatgtgctg taaatgaaaa   2400
acacataaat ttctggccag gcacggtggc tcacacctgt aatcccagca cttcgggagg   2460
ccaagacagg cagatcacat gaggtcagga attcaagacc agcctggaca acgtggtgaa   2520
accctgtctc tactaaaaat acaaaaatta gccaggtgta atggtgggca cctgtaatcc   2580
cagctactag ggaggctgag aatcgcttga acccgggagg tggaggttgc agtgagccaa   2640
gatcgcacca ctgcactcca gcctgggcga cagagtgaga ttctgtctca aaaaaaaaag   2700
aaaaaaaaag aaaagacttt tgacagacaa aggaacaggc agtacctggc acacttcttc   2760
acctcctctc cttactcttg tttccagatc ctgcccctga gctttcatga gctgttgaac   2820
catctggaat tcacaggcct gtcatgagag acacgatgag aagtccttaa aggtagatca   2880
ctgattcaca ggggagcagg cggaggcaag ggtgagtcag tgcttggaac tcagtcatcc   2940
agatttggct ctggaaactt ctgaagctgt agcctttggg gatccctgac tgcgagtaca   3000
ggaagccaac gctatgtggt cttctggaaa ctcattatct ttttcactgg tgctatctgg   3060
gaaaaacaga tgaaaacctg aaggtgttct gtatgtgtgc tttcaaaagc aaggatctgg   3120
ccggacgcag tggctcaggc ctgtaatccc agcactttgg gaggccgagg caggaggatc   3180
acctgaggtc aggagtttga gaccagcttg gccaacatgg cgaaaccatc tctactaaaa   3240
gtacaaaaat tatctgggtg tggtggtggg cacctgtaat cacagctact caagtagctg   3300
aggcagaaga atcagttgaa cccaggaggc agaggttgca gtgagcagag atcacaccac   3360
tgcactccag cctgggtgac aagaatgaaa ctccgtctca aaaaaaaaaa aaaaaaaaaa   3420
aaaaaaaaaa aagcagagat atttttctgg tggcagtttg agttttgagg ccttctgtgt   3480
catgacaggc ctcactccct gcccttcttg ggtgctgggg gagagtattt gcttccaggc   3540
cacaagttaa ttttttagta gagatgggat ctcattatgt tgcccaggct gctctggaac   3600
```

```
tcctggcctc aagtgatcct ccctcctcgg cctcccaaag cgctgggatt acaggcatga   3660
gccatcccac tcggcctgag accacagtta aaatcctatc agattgagtt acctgaggta   3720
cttgattgtg aggggccatg gggatagggt tgaaacccta agacccatcc atgtgttgct   3780
ccttcaccag ttatgcaaat tttcaactta tttaatgtga tctgaagagg tgagtcttcc   3840
atctctgggt tgcagttaga tagggcatga tggtgtacaa gtaggtgtca ttttgaagag   3900
attccataca tattcccata aactcagaac gttttggaaa ttccctttttg agactgcttt   3960
tctgagcccc acacttactc aacaggcacc aaatcatcct catgcaccta ctatgctgcg   4020
tgtcaaccgg aacatacaaa taatttccac cccctcctca cccataagaa gctggcagaa   4080
aggcaagatc cagcctccaa agtagaattc ctctttgttt ttgaggggtg ttgcaggctt   4140
gaggaacccc ttgtttgccc atctggcttc cggtaaccag gctgtcagca gaaatgaaac   4200
ccacccttgg aatgaagact ggccactttg ttcaagccac tgaggacact gtactgtggc   4260
cccctgacag tgcctgtctg tagggacagc tagatcctgc tggtcccttc acagtcccag   4320
cagtggctga ttcacaatgg tgactggtag atctgttggg tcgttgttga gctgatggta   4380
actagctcct ttattaaagt aatttccaag ggagaaactg caagagacgg cctaagctgc   4440
ggcagcttcc aaggatgagc ttttctggac ctcaggtttg gggggaaccc gagaccattt   4500
gaatgccaga gatgtgatgt gtttggtaat gtcgtgtctc acaagctcct tttgtatttc   4560
ccatgggcag atcaggtcgg atcttgactt tttccagaac ctggcttggc tggtttgggt   4620
tgtgtatgaa tgagctggct cgctgggtgt gtgaggggag gtgaagctgg gactagacaa   4680
gccagggctc gttagcaagt ttctgctgtg tcaggaatcc cagagagagg tttcccaagc   4740
cctatcctgt cttgcctggg ttgtttggtt tttctccttc ttttttttt tttcattgaa   4800
gtgtaattga catgtagtaa aattcaccca ttttagtgta cagctctgaa cacatacggt   4860
catgcaacca ccactacaat caagatacag agcatttaca ccaacccaaa aaattctcca   4920
aactactcca tttgttgcag gtcccagccc ctggcaagca ttcatctgct ttctgtcctg   4980
atacttttgc cttttccaga aggttgagtg aaatggaatc atgcagcctt ttgagcctgg   5040
cttctttcac cccacataatg catatgaggt tcatctgtaa tgttgttttt ttgtatccgt   5100
agctcattcc tttttatagc tgaatagtat tccattgtgt ggatggatcc catttgttta   5160
tccattcatc cattgaagga cagttagggt ttaactgctg ttggtaataa ctaataaagc   5220
ctcagcaaac attcgctcat gagactccat ctcaaaaaaa aaaacaaaaa aagtagattt   5280
taccctgctg gtgttgctat gttgatgaaa ttgagaggag ccaggaaatg aacattataa   5340
tagtatcttt tttattttta tttttgagat ggagtctcgc tctgtcaccc aggctggagt   5400
gcagtggcgc aatctcggct cactgcaacc tccaccttct gggttcaagc gattctcctg   5460
catcagcctc ccgaatagct gggttacagg tgtgcaccac catgcccagc taatttttgt   5520
gtttttagta cagacggaat ttcaccatgt tggtcaggat ggtctccatc tcttgacctt   5580
gtgatcctcc cgcctcggcc tcccaaagtg ctgggattac aggcatgagc caccgcaccc   5640
agccatgaat ttttatatat gaacaaaggt tttcatttca catgggtatc ccactgggag   5700
tgggattgtt ggctcatatg gctatagcgc tttttgaagg tcttttttttt ttgagaacga   5760
gtctcgctct gttgtccagg ctggagtgca gtggcaccat ctcggctcat tgcaacctcc   5820
acctcctagg ttcaagtgat tctcctgcct cagcctccca aatagctggg attacaggtg   5880
cacgccacca tgcctgacta atttttgcat ttttaataga gatggggttt caccatgttg   5940
gccaggctgg tctcgaactc ctgacttcaa gggatccacc tgcctcagcc tcccaaagtg   6000
```

```
ctgagattac aggcatgagc caccgcaccc agccttgaag atcttttcca aatttatttg   6060
gatttttatt tatttttgag acagggtctc actgtctctc aggctagtgt gcagtggcac   6120
actcatagct cactgcagct tggaattcct gagctcaagt gatcctccca cctcagcctc   6180
ccaagtagct ggcacgtgcc accatgccca gcttatttct ttgtcattct ttgcagatat   6240
ggggtctcac tatgtgggcc aggctgatct ggaactcctg ggctcaagtg atcctcctgc   6300
cttggcctcc aaaagtgctg ggattacaga tgtgagccac cgcacctggc ctgaaggtct   6360
ttttttcaac aggtgaagag ctgaagacag gagtaatgca attttcttaa aattaaggct   6420
ttatgatcat ctgagtcaca ttatacacaa gctgagtgtc tactgtaagc actcagtatg   6480
ctaaacactt cagcatttta ctctctgggt gaccctgggg aagtcacatg acctctcaga   6540
atctccatct ccccacctgt aaaatgggtg taatgatagc ccaacctcat agggctgttg   6600
tgacaagtat atgagttaat attcatcgag tacttggaac aggcttggcc atgtcagtgt   6660
tagatgttat tataggccag acatggtggc ttatgcctgt aatcccaaca cttggggagg   6720
ccaaggccgg cggatcacct gagctcaggt gttcgagacc aacctgagca acatggcaaa   6780
accccatctc taccaaaacc ataatacaaa aaattagccg ggcatggtgg caggcacctg   6840
tgatcccaac tactcaggag gctggggcag gaggatcatt tgaacctggg aggtggaggt   6900
tgcagtgagc caagattgtg ccactgtgct ccagcatggg tgacagtgtg agaccccatc   6960
tcaaaaaaaa aaaaaaacaa aaacaaggcc gggtgtaggg ttcaaccctt gtaatcccag   7020
cactttggga ggccaaggtg ggtggatcat gagatcagga gttcgagatt agcctggcca   7080
acatggtgaa acccagtctc tactaaaaat acaaaaatta gccaggtgtg gtggtaggca   7140
cctataatcc cagctactca ggaggctgag gcagagaatc gcttgaaccc aggaggcgga   7200
agttgcagtg agctgagatc acaccactgc actccagcct gggtgacaga gtgagactcc   7260
atctcaaaaa taaaaataaa aatgttatta taatgttcat ttcctgttca cttcctgttc   7320
atttcctctc aatttcatcc acatagcaac accagcagcg taaaatctac tcttttcttt   7380
tcttttcttt tcgagacaga gtctggctct gttgcccagg ctggagtaca gtggcgtgat   7440
cttggctcac tgcaacctcc acctcccagg ttcaagcgat tctcctgcct cagcctcccg   7500
agtagctggg agtatgggca catgccacca tgcccagcta atttttgtgt ttttagtaga   7560
gacaccacgt tggacaggct ggtctcaaac tcctgacctc aagtgatcca cccgcctcag   7620
cttcccaaag tgctgggatt acaggcatga gccaccgcac ccggcctaat ctactcttat   7680
ctccaattta tggaggacag acctaatgct cccagagatc aagcaggctg tggaagatca   7740
cacacgtagg aaataaggaa acagttggtc caggatttga actaaagcaa ctgtcctcag   7800
actcacttgc atagttcctg tatcagtcag gattttacca aagacacaga gccagagcca   7860
gtaggagtgt gtgtgtgtgt gtgtgtgtgt gtgtgtgtgt gtgtgtgtgt gtgtctgtgt   7920
gtgtgtctgt gtttgtgtgc agagatttat ttcaaggaat tggcttacat gcttgtgggg   7980
gctggctaga caacaccaaa atctgctggg tgggctagca ggctggaaac ttaggcagga   8040
gctgatgctt tttctgccgg gaaacctcag tgtttgcttt cagtgttggc tttttttttt   8100
tttttttttt cttcgagaca gagtcttgct ctgtcaccag gctggagtgc agcggcctga   8160
tcttggctca ctgcaacctc tgcctcctgg gttcaagtaa ttctcctgcc tcagcctccc   8220
aaagtgctgg gattacaggc gtgacccacc acacccggcc tcagtgttgg ctttttaaag   8280
tctctagact gattggatga ggcccgctta catcctcaca tccttgaggg tcatgtcctg   8340
```

```
tttttaaagt caagcaactg tagacgtgct aacctaaccg catcaacata ataacttcac   8400
agcaacacct agattagtgt ttagttgaat aactaggttc tagagcttag ccacgctgac   8460
acaacaaaca actataacag cttttccaag ttaagagccc aatatctgct gaagttgacg   8520
cagaggccat tttttcagta atattctgaa gttctcagtg agtgttcagg tcacagtacc   8580
atgtccatta ggagagagtt actgggtttg tttgtttgtt taatttcctg gctcctagaa   8640
ctgattaaaa aaaaaaaaat taaaacttcc cgaactggct gggcgtggtg gctcacgcct   8700
gtaatcccag caccttggga gatcaaggcg tgttgatcac ctgaggtcag gagttcaaga   8760
ccagcctggc caacatggtg aaaccccatc tctactaaaa ctacaaaaat tagccaggca   8820
tggtcgcaag cacctgtagt cctagctact tgggaggcta aggcaggaga atcacttgaa   8880
cccaggaggc ggaggttgca gtgagctgag atcgtgccac tgcactccag cctgggctac   8940
aagagtgaaa ctccatctca aaacaaacaa acaaaacttc ctgaacatga cccaggctta   9000
ctcaaggagg ggagagttcc cagctctaac actgacccca agcacaaaga catcccttcc   9060
gcagtgtttt tagcaaaatg ttcccctcca gtgtgtcaag aaacttttat tattattatt   9120
attattatta ttattattat tttgaaactc tcactctgtc acccagtctg gagcacagtg   9180
gcacgatctt ggctcactgc aacctctgcc tctcgggttg aagcgagtct catgcctcag   9240
cctccagcgt agctgggatt acaggcacct gccaccgcac ccgactaatt tttgtatttt   9300
tagtagagac ggggtttcac cacgttggcc agactggtct cgaactcctg acctcaggtg   9360
atccacctgc ctcagcctcc caaagtgctg ggattatagg cgttgagtca ccgtgcctgg   9420
cctatggcaa gaaactttag aacaaccaga aaggcccacc cagagccatg ttaaagcctt   9480
tggaggctgc tgcacttgta attctaaatt aaatttatat tataaaatac tagtttataa   9540
agtcacaagc tctgagtttt tccccataat gctcctgata gttatttata taattttttt   9600
atggggaggt tcaggatctc actgtcatcc aggctggaga gcagtggcac aatcatagct   9660
gactgcagcc tcaaattcct gggctcaagc tatcctccta ccttggtcca ctgagtagct   9720
gggactacag gctcacatca ttgcacccgg ctaatttttt ttatttttaa tttttttgtat   9780
agatggggtc tcactatgtt gcccaggctg gaactcctgg cctcaaaaga tcctcccacc   9840
tcaccttccc agaatgctgg gatgacaggc gtgagccact gtgcccagcc tagtaacttt   9900
ttaaaaaata tcaagttctc tctccccata attgcttcag gacccctgct caagtatggt   9960
tctcgatgtc tagggaattt cagccccatc ctcccgggtt gtccagttct agtccagagt  10020
tcttgctgat gcagttacct cagagatcat tgagtgggcc aagagaacca gatctgcctg  10080
ctggatgctc ctgatagtta tttatgtaac tatccgccat gatgctcctg atagttattt  10140
atgtaacttt tttatgggga ggctgagggt ctcactgtca cccaggctgg agtgcagtgg  10200
cacaatcata gctgcctgca gcctcaaatt cctgggctca agagatcctc ccgcctcagg  10260
aggcaggagg atggtcttct tcttcaggag tccctgtctg cccaggggca gctgtcactg  10320
gaatctttta gctgccagga atgaggtgat ggctgaagag cccaccacta agaaaatggt  10380
tagtcacccc tttgacaatg cttcctttgt gccatgcctg ctctgagcac tttgcaaatg  10440
ttgactcata taaacttcaa agccctcatg atgtgggcac aactgctatc ctcattcctc  10500
attgtgcaga tgaggaagct aaggccagca aaggcctagt aactaaccca aggttaccca  10560
gccgggaaat gctggagctg ggaatgaagc ccagctgtct ggttccagag ccagtgttac  10620
atggctctga cctcccaggc agttcttcca ggaacctccc ccacttccct gggcccttcc  10680
caggtggaac ccctttctga gcctcctttt cccatcagct ctgtccttga cagaggcacc  10740
```

```
ccagactttc agagccaaac gcgatcgtgt tgcctacaat tgaggaaaca gaggccttga  10800
aaggtgtgtg acacacctat gtccccccaa attataaagg tagttgggga agaaaaagaa  10860
gcacgtgtgt aagaacgggg aatatttatg aggttctcac tgcgttccag gcactgggga  10920
cccagtgcag acaggacctg gcccctgccc aggtggcgat gtcagactgg gagggaagac  10980
acattgaaag ccaagagaca agataaattt caaatttagc ggcaagtgat cttgagaggg  11040
cagtaaaggg aagaaggcgg gactgggagg accttgggag atgcgcttcc gtccagatcc  11100
tcaccttgct ttaggaggtg agaacagagg cagtcttccg tcccaaaatc cttctcccca  11160
cggttgggag aatagcgctg gtgggttttt tgttcatttt actttatttt acttatttta  11220
tttatttatg agacggagtc tcgctctgtt gccgaggctg gagtgcaacg gccggatctc  11280
ggctcactgc aacctccgcc tccccgattc aagctattct caggcctcaa tctcctgagt  11340
agctgggatt acaggttcgt gccaccaacg cccgggtaat ttttatattt ttagcagaga  11400
tggggtttca ccatgttggc caggctggtc tcgaactcct gacctcaagt gatccgcccg  11460
cctcggcctc ccaaaatgct gggattacag gcgtgagcca ccgcgcccgg cctgtttgtt  11520
aatcttaaat agaaacggag tctccttatg ttgcctaggc tggtctccaa ctcctaggct  11580
caagagatcc tcctgtcttg gcctcaggaa gtgatgggat tacaggcatg aggctccgcg  11640
cccggcctga taggttctct tattgccatg ttgtagatag aagggggccc ctgggttagg  11700
cagacacagg ttaggtagtt cgtccggcgt caccgggcgg gagcccaccg caggccccac  11760
gagacaaggg cgagcaggtt catcgcctcc cggggaaagg actgggtagt cccaggcccc  11820
accccttcct ggaacagcaa gttcgctgtg ggtcccgacc tactgaccca ggcggagggc  11880
gggacgcagg gtagctgggg ccgcgtagag agggaaagaa ggtcgcgatt ggctcgtccc  11940
gaaaggtggg cggggcctcc tccgacctgt gcgcgcgcgc cgcggggagg tgttgccgag  12000
ggcggagcgg gagggggcgt ggccccgcgc gggcggccgt tgacggcgag gccccgcccc  12060
ggatgtcgcg tgtcgctgaa agggcggcgg cgattggccg gcgccgcggg ggcgggcggg  12120
gcggaaggtt ctggaggggg ctggcgggct ctggaagctt ccgccggacg ggtatataga  12180
gtccgggact ggtcggcggc ggagccgggg gacggcgaca gcgggtcggc gggccgcagg  12240
agggggtcat gggtaaagac tactaccaga cgttgggcct ggcccgcggc gcgtcggacg  12300
aggagatcaa gcgggcctac cgccgccagg cgctgcgcta ccacccggac aagaacaagg  12360
agcccggcgc cgaggagaag ttcaaggaga tcgctgaggc ctacgacgtg ctcagcgacc  12420
cgcgcaagcg cgagatcttc gaccgctacg gggaggaagg tgtgtgctcg cggccagggg  12480
cgcggccccg cctttgaca gacagggaaa ctgaggcacg ctggcccctc tcggcggccc  12540
cccgggaagg acgccccggg ccgtggggcc gagctgcccc gccctccggc ctcgcgggcc  12600
tccgccctcg gattggcggc cgcgcggtgg gaggaggagc cttggcccag ccgctcggcc  12660
agaagcttct agcatgtctg gggctgcccc tccccgggcg cctcctcccg cggccccgag  12720
cagccccggg gtgcggtgca tgggggtggg ggagccgggg gtgacgacgg ggacggcgcg  12780
gcggagcccg ctgcggaccc gggctcacct gggctcggcc gccggggtcc gcggggcggc  12840
gcctccggct cagctgcggg gcgaggggtt gtgaatgcag gagccgaccc cgttcgtggg  12900
cttgggggct gggttgggat aattcccggg aagtgatgac ctggccccgg cagggcacgc  12960
aggaggcagc ggccgcccag gtccggagag cggggccgcc tcggagggta aggagagcag  13020
ggctttttgt tcctgtgccc gttgatgatt caggctggct tctgggcttg atctggagct  13080
```

```
gactttttgt gcaaggatgg tggcagtgaa tgctaatgtg tgaggattta aaaactccct  13140
atttattttt gttttttttt ttcttctctt cctacgcacc attagcccta aaacgttgag  13200
agtaaacact taccgaaagc cgaccctgga ccatgtgtct ttagccatct cttggtgatg  13260
ttgccaggag gatgggtcag tccaggagtg gcagggccta ggtggcacct ggaggtgaac  13320
acctaaccgc atgagtcctt ttccactgtc aggctacgcg gaaatactgt tggtaggggg  13380
gcgtctctgc tgttggcagt gagaggtaga aacttggggt tcttccttgc tctcccctga  13440
cagacaaaaa agttcctccc ccatggcttc caagctgttt ccccctgtaa gggaagctcg  13500
agagagagtc tgctgttcag ccatctgact gcttctaaat ctgcttttca ggcctaaagg  13560
ggagtggccc cagtggcggt agcggcggtg gtgccaatgg tacctctttc agctacacat  13620
tccatggaga ccctcatgcc atgtttgctg agttcttcgg tggcagaaat ccctttgaca  13680
cctttttttgg gcagcggaac ggggaggaag gcatggacat tgatgaccca ttctctggct  13740
tccctatggg catgggtggc ttcaccaacg tgaactttgg ccgctcccgc tctgcccaag  13800
agcccgcccg aaagaagcaa gatcccccag tcacccacga ccttcgagtc tcccttgaag  13860
agatctacag cggctgtacc aagaagatga aaatctccca caagcggcta aaccccgacg  13920
gaaagagcat tcgaaacgaa gacaaaatat tgaccatcga agtgaagaag gggtggaaag  13980
aaggaaccaa aatcactttc cccaaggaag gagaccagac ctccaacaac attccagctg  14040
atatcgtctt tgttttaaag gacaagcccc acaatatctt taagagagat ggctctgatg  14100
tcatttatcc tgccaggatc agcctccggg aggtaaggtg ccaggtgggg cggtgtctgt  14160
agagggcgat ggctgctttt tgaagcagtt tagtatttgc tgaaccaatg tgttggggtg  14220
tgtggtgcgt gccaggcttg ggcacaaaca gtgaacagga ctgaccaggg cgctgttgtg  14280
gagctttcgt ggtggggacg tgtagatttg gggccaggt cttagctgca gaggcctgat  14340
gggtcttatc tatggcagac ggcctctggg caagagctga gcctcttgag ccagcttcca  14400
tctaatgctg tccttttgct tttcaaggct ctgtgtggct gcacagtgaa cgtccccact  14460
ctggacggca ggacgatacc cgtcgtattc aaagatgtta tcaggcctgg catgcggcga  14520
aaagttcctg gagaaggcct ccccctcccc aaaacacccg agaaacgtgg ggacctcatt  14580
attgagtttg aagtgatctt ccccgaaagg attccccaga catcaagaac cgtacttgag  14640
caggttcttc caatatagct atctgagctc cccaaggact gaccagggac ctttccagag  14700
ctcaaggatt tctggacctt tctaccagtt gtggaccatg agagggtggg agggcccagg  14760
gagggctttc gtactgctga atgttttcca gagcatatat tacaatcttt caaagtcgca  14820
cactagactt cagtggtttt tcgagctata gggcatcagg tggtgggaac agcaggaaaa  14880
ggcattccag tctgccccac tggtctggc agccctcccg ggatgggccc acatccacct  14940
ccagtccctg gccaggggtg agaggcagac cagcagatgg acttgatccc tctgtgtctt  15000
tttgcttctg gctggtagat aatgtcaacc tgcagtcttg attcccagac cctgtacact  15060
cctccttttc tgttgtgtga tcagtttgtg ctttattctg tatttgtctc ccatgtcttg  15120
ctcttctcct ggagaattct gtcttctctt tggccatctc aaattgagaa cctaaactat  15180
tcctgcagaa ctgcctggtt ggcgtccaca agcaatacct ctcgttccag caggaccaag  15240
ggagccagcc tccagtgagt gactccagca agtgcagcca cctctccctt gatggtctgg  15300
gagcctggcc tcagcaaggg gccttcctga cctctggctc cagtgaagct gaatgtcctc  15360
actttgtggg tcacactctt tacatttctg taaggcaatc ttggcacacg tggggcttac  15420
cagtggccca ggtaattttt tgtttcatgg actatggact ctttcaaagg gatctgatcc  15480
```

```
ttttgaattt tgcacagccc tagatacaat ccctttttgat aaaagggtct ttgcttctga  15540

ttacaggagc actgtggaac gtctgtaaat atgtttttat aattccatgt atagttggtg  15600

tacactcaaa acctgtcccc ggcagccagt gctctctgta tagggccata atggaattct  15660

gaagaaatct tggggaggga aggggagttg gaacaaatgt ctgttccctg gaggccagtc  15720

cagtgctcag acctttagac tcattgtaag ttgccactgc caacatgaga ccaaagtgtg  15780

tgactagtca atgaagtgcg acagcattaa agactgatgc taaacctcag ggga        15834
```

<210> SEQ ID NO 113
<211> LENGTH: 2242
<212> TYPE: DNA
<213> ORGANISM: Homo sapiens

<400> SEQUENCE: 113

```
ggagccgggg gacggcgaca gcgggtcggc gggccgcagg agggggtcat gggtaaagac    60

tactaccaga cgttgggcct ggcccgcggc gcgtcggacg aggagatcaa gcgggcctac   120

cgccgccagg cgctgcgcta ccacccggac aagaacaagg agcccggcgc cgaggagaag   180

ttcaaggaga tcgctgaggc ctacgacgtg ctcagcgacc cgcgcaagcg cgagatcttc   240

gaccgctacg gggaggaagg cctaaagggg agtggcccca gtggcggtag cggcggtggt   300

gccaatggta cctctttcag ctacacattc catggagacc ctcatgccat gtttgctgag   360

ttcttcggtg gcagaaatcc ctttgacacc ttttttgggc agcggaacgg ggaggaaggc   420

atggacattg atgacccatt ctctggcttc cctatgggca tgggtggctt caccaacgtg   480

aactttggcc gctcccgctc tgcccaagag cccgcccgaa agaagcaaga tcccccagtc   540

acccacgacc ttcgagtctc ccttgaagag atctacagcg gctgtaccaa gaagatgaaa   600

atctcccaca agcggctaaa ccccgacgga aagagcattc gaaacgaaga caaaatattg   660

accatcgaag tgaagaaggg gtggaaagaa ggaaccaaaa tcactttccc caaggaagga   720

gaccagacct ccaacaacat tccagctgat atcgtctttg ttttaaagga caagccccac   780

aatatcttta agagagatgg ctctgatgtc atttatcctg ccaggatcag cctccgggag   840

gctctgtgtg gctgcacagt gaacgtcccc actctggacg gcaggacgat acccgtcgta   900

ttcaaagatg ttatcaggcc tggcatgcgg cgaaaagttc ctggagaagg cctcccccctc   960

cccaaaacac ccgagaaacg tggggacctc attattgagt ttgaagtgat cttccccgaa  1020

aggattcccc agacatcaag aaccgtactt gagcaggttc ttccaatata gctatctgag  1080

ctccccaagg actgaccagg gacctttcca gagctcaagg atttctggac ctttctacca  1140

gttgtggacc atgagagggt gggagggccc agggagggct ttcgtactgc tgaatgtttt  1200

ccagagcata tattacaatc tttcaaagtc gcacactaga cttcagtggt ttttcgagct  1260

atagggcatc aggtggtggg aacagcagga aaaggcattc cagtctgccc cactgggtct  1320

ggcagccctc ccgggatggg cccacatcca cctccagtcc ctggccaggg gtgagaggca  1380

gaccagcaga tggacttgat ccctctgtgt ctttttgctt ctggctggta gataatgtca  1440

acctgcagtc ttgattccca gaccctgtac actcctcctt ttctgttgtg tgatcagttt  1500

gtgctttatt ctgtatttgt ctcccatgtc ttgctcttct cctggagaat tctgtcttct  1560

ctttggccat ctcaaattga gaacctaaac tattcctgca gaactgcctg gttggcgtcc  1620

acaagcaata cctctcgttc cagcaggacc aagggagcca gcctccagtg agtgactcca  1680

gcaagtgcag ccacctctcc cttgatggtc tgggagcctg gcctcagcaa ggggccttcc  1740
```

```
tgacctctgg ctccagtgaa gctgaatgtc ctcactttgt gggtcacact ctttacattt   1800
ctgtaaggca atcttggcac acgtggggct taccagtggc ccaggtaatt ttttgtttca   1860
tggactatgg actctttcaa agggatctga tccttttgaa ttttgcacag ccctagatac   1920
aatccctttt gataaaaggg tctttgcttc tgattacagg agcactgtgg aacgtctgta   1980
aatatgtttt tataattcca tgtatagttg gtgtacactc aaaacctgtc cccggcagcc   2040
agtgctctct gtatagggcc ataatggaat tctgaagaaa tcttggggag ggaaggggag   2100
ttggaacaaa tgtctgttcc ctggaggcca gtccagtgct cagaccttta gactcattgt   2160
aagttgccac tgccaacatg agaccaaagt gtgtgactag tcaatgaagt gcgacagcat   2220
taaagactga tgctaaacct ca                                            2242
```

<210> SEQ ID NO 114
<211> LENGTH: 1719
<212> TYPE: DNA
<213> ORGANISM: Homo sapiens

<400> SEQUENCE: 114

```
agaagaacaa aagcatttgg aagtaacagg acctctttct agctctcaga aaagtctgag     60
aagaaaggag ccctgcgttc ccctaagctg tgcagcagat actgtgatga tggattgcaa    120
gtgcaaagag taagacaaaa ctccagcaca taaaggacaa tgacaaccag aaagcttcag    180
cccgatcctg ccctttcctt gaacgggact ggatcctagg aggtgaagcc atttccaatt    240
ttttgtcctc tgcctccctc tgctgttctt ctagagaagt tttccttac aacaatgaga     300
aaacatgtac tagctgcatc cttttctatg ctctccctgc tggtgataat gggagataca    360
gacagtaaaa cggacagctc attcataatg gactcggacc ctcgacgctg catgaggcac    420
cactatgtgg attctatcag tcacccattg tacaagtgta gctcaaagat ggtgctcctg    480
gccaggtgcg aggggcactg cagccaggcg tcacgctccg agcctttggt gtcgttcagc    540
actgtcctca agcaaccctt ccgttcctcc tgtcactgct gccggcccca gacttccaag    600
ctgaaggcac tgcggctgcg atgctcaggg ggcatgcgac tcactgccac ctaccggtac    660
atcctctcct gtcactgcga ggaatgcaat tcctgaggcc cgctgctgtg tgtggcttct    720
ggatgggaca actgtagagg cagttcgacc agccagggaa agactggcaa gaaaagagtt    780
aaggcaaaaa aggatgcaac aattctcccg ggactctgca tattctagta ataaagactc    840
tacatgcttg ttgacagaga gagatactct gggaacttct ttgcagttcc catctccttt    900
ctctggtaca atttcttttg gttcattttc agattcaggc attttccccc ttggctctca    960
atgctgtttg ggtttccaac aattcagcat tagtgggaaa aagtgggccc tcatacacaa   1020
gcgtgtcagg ctgtcagtgt ttggtgcacg ctggggaaga atttactttg gaaagtagaa   1080
aagcccagct ttcctgggga catcttctgt tattgttgat gtttttttt accttgtcat    1140
tttggtctaa ggttgccatt gctgctaaag gttaccgatt tcaaagtcca gataccaagc   1200
atgtggatat gtttagctac gtttactcac agccagcgaa ctgacattaa aataactaac   1260
aaacagattc ttttatgtga tgctggaact cttgacagct ataattatta ttcagaaatg   1320
actttttgaa agtaaaagca gcataaagaa tttgtcacag gaaggctgtc tcagataaat   1380
tatggtaaaa ttttgtaagg gagcagactt ttaaagactt gcacaaatac ggatcctgca   1440
ctgactctgg aaaaggcata tatgtactag tggcatggag aatgcaccat actcatgcat   1500
gcaaattaga caaccaagta tgaatctatt tgtgggtgtg ctatagcttt agccgtgtca   1560
cgggcatcat tctctaatat ccacttgtcc atgtgaaaca tgttgccaaa atggtggcct   1620
```

ggcttgtctt ctgaacgttt ggttcaaatg tgttttggtc ctggaggctc aaattttgag 1680
ttattcccac gttttgaaat aaaaagagta tattcaaaa 1719

<210> SEQ ID NO 115
<211> LENGTH: 2400
<212> TYPE: DNA
<213> ORGANISM: Homo sapiens

<400> SEQUENCE: 115
aacggctagc ctgaggagct gctgcgacag tccactacct ttttcgagag tgactcccgt 60
tgtcccaagg cttcccagag cgaacctgtg cggctgcagg caccggcgcg tcgagtttcc 120
ggcgtccgga aggaccgagc tcttctcgcg gatccagtgt tccgtttcca gcccccaatc 180
tcagagcgga gccgacagag agcagggaac cggcatggcc aaagccgcgg cgatcggcat 240
cgacctgggc accacctact cctgcgtggg ggtgttccaa cacggcaagg tggagatcat 300
cgccaacgac cagggcaacc gcaccacccc cagctacgtg gccttcacgg acaccgagcg 360
gctcatcggg gatgcggcca agaaccaggt ggcgctgaac ccgcagaaca ccgtgtttga 420
cgcgaagcgg ctgattggcc gcaagttcgg cgacccggtg gtgcagtcgg acatgaagca 480
ctggcctttc caggtgatca acgacggaga caagcccaag gtgcaggtga gctacaaggg 540
ggagaccaag gcattctacc ccgaggagat ctcgtccatg gtgctgacca agatgaagga 600
gatcgccgag gcgtacctgg gctacccggt gaccaacgcg gtgatcaccg tgccggccta 660
cttcaacgac tcgcagcgcc aggccaccaa ggatgcgggt gtgatcgcgg ggctcaacgt 720
gctgcggatc atcaacgagc ccacggccgc cgccatcgcc tacggcctgg acagaacggg 780
caagggggag cgcaacgtgc tcatctttga cctgggcggg ggcaccttcg acgtgtccat 840
cctgacgatc gacgacggca tcttcgaggt gaaggccacg gccggggaca cccacctggg 900
tggggaggac tttgacaaca ggctggtgaa ccacttcgtg gaggagttca agagaaaaca 960
caagaaggac atcagccaga acaagcgagc cgtgaggcgg ctgcgcaccg cctgcgagag 1020
ggccaagagg accctgtcgt ccagcaccca ggccagcctg gagatcgact ccctgtttga 1080
gggcatcgac ttctacacgt ccatcaccag ggcgaggttc gaggagctgt gctccgacct 1140
gttccgaagc accctggagc ccgtggagaa ggctctgcgc gacgccaagc tggacaaggc 1200
ccagattcac gacctggtcc tggtcggggg ctccacccgc atccccaagg tgcagaagct 1260
gctgcaggac ttcttcaacg ggcgcgacct gaacaagagc atcaaccccg acgaggctgt 1320
ggcctacggg gcggcggtgc aggcggccat cctgatgggg gacaagtccg agaacgtgca 1380
ggacctgctg ctgctggacg tggctcccct gtcgctgggg ctggagacgg ccggaggcgt 1440
gatgactgcc ctgatcaagc gcaactccac catccccacc aagcagacgc agatcttcac 1500
cacctactcc gacaaccaac ccggggtgct gatccaggtg tacgagggcg agagggccat 1560
gacgaaagac aacaatctgt tggggcgctt cgagctgagc ggcatccctc cggcccccag 1620
gggcgtgccc cagatcgagg tgaccttcga catcgatgcc aacggcatcc tgaacgtcac 1680
ggccacggac aagagcaccg gcaaggccaa caagatcacc atcaccaacg acaagggccg 1740
cctgagcaag gaggagatcg agcgcatggt gcaggaggcg gagaagtaca aagcggagga 1800
cgaggtgcag cgcgagaggg tgtcagccaa gaacgccctg gagtcctacg ccttcaacat 1860
gaagagcgcc gtggaggatg aggggctcaa gggcaagatc agcgaggcgg acaagaagaa 1920
ggtgctggac aagtgtcaag aggtcatctc gtggctggac gccaacacct tggccgagaa 1980
ggacgagttt gagcacaaga ggaaggagct ggagcaggtg tgtaacccca tcatcagcgg 2040
actgtaccag ggtgccggtg gtcccgggcc tgggggcttc ggggctcagg gtcccaaggg 2100
agggtctggg tcaggcccca ccattgagga ggtagattag gggcctttcc aagattgctg 2160
tttttgtttt ggagcttcaa gactttgcat ttcctagtat ttctgtttgt cagttctcaa 2220
tttcctgtgt ttgcaatgtt gaaatttttt ggtgaagtac tgaacttgct ttttttccgg 2280
tttctacatg cagagatgaa tttatactgc catcttacga ctatttcttc tttttaatac 2340
acttaactca ggccattttt taagttggtt acttcaaagt aaataaactt taaaattcaa 2400

<210> SEQ ID NO 116
<211> LENGTH: 119
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 116
ctgcgcgctc gctcgctcac tgaggccgcc cgggcgtcgg gcgacctttg gtcgcccggc 60
ctcagtgagc gagcgagcgc gcagagaggg agtggccaac tccatcacta ggggttcct 119

<210> SEQ ID NO 117
<211> LENGTH: 14
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 117
gcggccgcac gcgt 14

<210> SEQ ID NO 118
<211> LENGTH: 381
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 118
gacattgatt attgactagt tattaatagt aatcaattac ggggtcatta gttcatagcc 60
catatatgga gttccgcgtt acataactta cggtaaatgg cccgcctggc tgaccgccca 120
acgacccccg cccattgacg tcaataatga cgtatgttcc catagtaacg ccaataggga 180
ctttccattg acgtcaatgg gtggactatt tacggtaaac tgcccacttg gcagtacatc 240
aagtgtatca tatgccaagt acgcccccta ttgacgtcaa tgacggtaaa tggcccgcct 300
ggcattatgc ccagtacatg accttatggg actttcctac ttggcagtac atctacgtat 360
tagtcatcgc tattaccatg g 381

<210> SEQ ID NO 119
<211> LENGTH: 277
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 119
gtcgaggtga gccccacgtt ctgcttcact ctccccatct cccccccctc cccaccccca 60

```
attttgtatt tatttatttt ttaattattt tgtgcagcga tgggggcggg gggggggggg    120

gcgcgcgcca ggcggggcgg ggcggggcga ggggcggggc ggggcgaggc ggagaggtgc    180

ggcggcagcc aatcagagcg gcgcgctccg aaagtttcct tttatggcga ggcggcggcg    240

gcggcggccc tataaaaagc gaagcgcgcg gcgggcg                             277


<210> SEQ ID NO 120
<211> LENGTH: 1013
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 120

ggagtcgctg cgttgccttc gccccgtgcc ccgctccgcg ccgcctcgcg ccgcccgccc     60

cggctctgac tgaccgcgtt actcccacag gtgagcgggc gggacggccc ttctcctccg    120

ggctgtaatt agcgcttggt ttaatgacgg ctcgtttctt ttctgtggct gcgtgaaagc    180

cttaaagggc tccgggaggg ccctttgtgc ggggggggagc ggctcggggg gtgcgtgcgt    240

gtgtgtgtgc gtggggagcg ccgcgtgcgg cccgcgctgc ccggcggctg tgagcgctgc    300

gggcgcggcg cggggctttg tgcgctccgc gtgtgcgcga ggggagcgcg gccgggggcg    360

gtgccccgcg gtgcgggggg gctgcgaggg gaacaaaggc tgcgtgcggg gtgtgtgcgt    420

gggggggtga gcagggggtg tgggcgcggc ggtcgggctg taaccccccc ctgcaccccc    480

ctccccgagt tgctgagcac ggcccggctt cgggtgcggg gctccgtgcg gggcgtggcg    540

cggggctcgc cgtgccgggc ggggggtggc ggcaggtggg ggtgccgggc ggggcggggc    600

cgcctcgggc cggggagggc tcgggggagg ggcgcggcgg cccccggagc gccggcggct    660

gtcgaggcgc ggcgagccgc agccattgcc ttttatggta atcgtgcgag agggcgcagg    720

gacttccttt gtcccaaatc tgtgcggagc cgaaatctgg gaggcgccgc cgcaccccct    780

ctagcgggcg cggggcgaag cggtgcggcg ccggcaggaa ggaaatgggc ggggagggcc    840

ttcgtgcgtc gccgcgccgc cgtccccttc tccctctcca gcctcggggc tgtccgcggg    900

gggacggctg ccttcggggg ggacggggca gggcggggtt cggcttctgg cgtgtgaccg    960

gcggctctag agcctctgct aaccatgttc atgccttctt ctttttccta cag           1013


<210> SEQ ID NO 121
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 121

ctcctgggca acgtgctggt tattgtgacc ggtgccacc                            39


<210> SEQ ID NO 122
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 122

atgtaccgga tgcagctgct gagctgtatc gccctgtctc tggccctggt caccaattct     60
```

<210> SEQ ID NO 123
<211> LENGTH: 1920
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 123

```
gccaaagccg cggcgatcgg catcgacctg ggcaccacct actcctgcgt gggggtgttc     60
caacacggca aggtggagat catcgccaac gaccagggca accgcaccac ccccagctac    120
gtggccttca cggacaccga gcggctcatc ggggatgcgg ccaagaacca ggtggcgctg    180
aacccgcaga acaccgtgtt tgacgcgaag cggctgatcg gccgcaagtt cggcgacccg    240
gtggtgcagt cggacatgaa gcactggcct ttccaggtga tcaacgacgg agacaagccc    300
aaggtgcagg tgagctacaa gggggagacc aaggcattct accccgagga gatctcgtcc    360
atggtgctga ccaagatgaa ggagatcgcc gaggcgtacc tgggctaccc ggtgaccaac    420
gcggtgatca ccgtgccggc ctacttcaac gactcgcagc gccaggccac caaggatgcg    480
ggtgtgatcg cggggctcaa cgtgctgcgg atcatcaacg agcccacggc cgccgccatc    540
gcctacggcc tggacagaac gggcaagggg gagcgcaacg tgctcatctt tgacctgggc    600
gggggcacct tcgacgtgtc catcctgacg atcgacgacg gcatcttcga ggtgaaggcc    660
acggccgggg acacccacct gggtggggag gactttgaca acaggctggt gaaccacttc    720
gtggaggagt tcaagagaaa acacaagaag gacatcagcc agaacaagcg agccgtgagg    780
cggctgcgca ccgcctgcga gagggccaag aggaccctgt cgtccagcac ccaggccagc    840
ctggagatcg actccctgtt tgagggcatc gacttctaca cgtccatcac cagggcgagg    900
ttcgaggagc tgtgctccga cctgttccga agcaccctgg agcccgtgga gaaggctctg    960
cgcgacgcca agctggacaa ggcccagatt cacgacctgg tcctggtcgg gggctccacc   1020
cgcatcccca aggtgcagaa gctgctgcag gacttcttca acgggcgcga cctgaacaag   1080
agcatcaacc ccgacgaggc tgtggcctac ggggcggcgg tgcaggcggc catcctgatg   1140
gggggacaagt ccgagaacgt gcaggacctg ctgctgctgg acgtggctcc cctgtcgctg   1200
gggctggaga cggccggagg cgtgatgact gccctgatca agcgcaactc caccatcccc   1260
accaagcaga cgcagatctt caccacctac tccgacaacc aacccggggt gctgatccag   1320
gtgtacgagg gcgagagggc catgacgaaa gacaacaatc tgttggggcg cttcgagctg   1380
agcggcatcc ctccggcccc caggggcgtg ccccagatcg aggtgacctt cgacatcgat   1440
gccaacggca tcctgaacgt cacggccacg gacaagagca ccggcaaggc caacaagatc   1500
accatcacca acgacaaggg ccgcctgagc aaggaggaga tcgagcgcat ggtgcaggag   1560
gcggagaagt acaaagcgga ggacgaggtg cagcgcgaga gggtgtcagc caagaacgcc   1620
ctggagtcct acgccttcaa catgaagagc gccgtggagg atgaggggct caagggcaag   1680
atcagcgagg cggacaagaa gaaggttctg gacaagtgtc aagaggtcat ctcgtggctg   1740
gacgccaaca ccttggccga gaaggacgag tttgagcaca agaggaagga gctggagcag   1800
gtgtgtaacc ccatcatcag cggactgtac cagggtgccg gtggtcccgg gcctgggggc   1860
ttcggggctc agggtcccaa gggagggtct gggtcaggcc ccaccattga ggaggtggat   1920
```

<210> SEQ ID NO 124
<211> LENGTH: 24

<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 124
taagagctcg ctgatcagcc tcga 24

<210> SEQ ID NO 125
<211> LENGTH: 225
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 125
ctgtgccttc tagttgccag ccatctgttg tttgcccctc ccccgtgcct tccttgaccc 60
tggaaggtgc cactcccact gtcctttcct aataaaatga ggaaattgca tcgcattgtc 120
tgagtaggtg tcattctatt ctggggggtg gggtggggca ggacagcaag ggggaggatt 180
gggaagacaa tagcaggcat gctggggatg cggtgggctc tatgg 225

<210> SEQ ID NO 126
<211> LENGTH: 34
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 126
aagcttgaat tcagctgacg tgcctcggac cgct 34

<210> SEQ ID NO 127
<211> LENGTH: 130
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 127
aggaacccct agtgatggag ttggccactc cctctctgcg cgctcgctcg ctcactgagg 60
ccgggcgacc aaaggtcgcc cgacgcccgg gctttgcccg ggcggcctca gtgagcgagc 120
gagcgcgcag 130

<210> SEQ ID NO 128
<211> LENGTH: 119
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 128
ctgcgcgctc gctcgctcac tgaggccgcc cgggcgtcgg gcgacctttg gtcgcccggc 60
ctcagtgagc gagcgagcgc gcagagaggg agtggccaac tccatcacta ggggttcct 119

<210> SEQ ID NO 129
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 129
gcggccgcac gcgt 14

<210> SEQ ID NO 130
<211> LENGTH: 381
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 130
gacattgatt attgactagt tattaatagt aatcaattac ggggtcatta gttcatagcc 60
catatatgga gttccgcgtt acataactta cggtaaatgg cccgcctggc tgaccgccca 120
acgacccccg cccattgacg tcaataatga cgtatgttcc catagtaacg ccaataggga 180
ctttccattg acgtcaatgg gtggactatt tacggtaaac tgcccacttg gcagtacatc 240
aagtgtatca tatgccaagt acgcccccta ttgacgtcaa tgacggtaaa tggcccgcct 300
ggcattatgc ccagtacatg accttatggg actttcctac ttggcagtac atctacgtat 360
tagtcatcgc tattaccatg g 381

<210> SEQ ID NO 131
<211> LENGTH: 277
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 131
gtcgaggtga gccccacgtt ctgcttcact ctccccatct ccccccccctc cccaccccca 60 attttgtatt tatttatttt ttaattattt tgtgcagcga tgggggcggg gggggggggg 120
gcgcgcgcca ggcggggcgg ggcggggcga ggggcggggc ggggcgaggc ggagaggtgc 180
ggcggcagcc aatcagagcg gcgcgctccg aaagtttcct tttatggcga ggcggcggcg 240
gcggcggccc tataaaaagc gaagcgcgcg gcgggcg 277

<210> SEQ ID NO 132
<211> LENGTH: 1013
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 132
ggagtcgctg cgttgccttc gccccgtgcc ccgctccgcg ccgcctcgcg ccgcccgccc 60
cggctctgac tgaccgcgtt actcccacag gtgagcgggc gggacggccc ttctcctccg 120
ggctgtaatt agcgcttggt ttaatgacgg ctcgtttctt ttctgtggct gcgtgaaagc 180
cttaaagggc tccgggaggg ccctttgtgc ggggggggagc ggctcggggg gtgcgtgcgt 240
gtgtgtgtgc gtggggagcg ccgcgtgcgg cccgcgctgc ccggcggctg tgagcgctgc 300
gggcgcggcg cggggctttg tgcgctccgc gtgtgcgcga ggggagcgcg gccgggggcg 360
gtgccccgcg gtgcgggggg gctgcgaggg gaacaaaggc tgcgtgcggg gtgtgtgcgt 420
gggggggtga gcagggggtg tgggcgcggc ggtcgggctg taaccccccc ctgcacccccc 480 ctccccgagt tgctgagcac ggcccggctt cgggtgcggg gctccgtgcg gggcgtggcg 540
cggggctcgc cgtgccgggc ggggggtggc ggcaggtggg ggtgccgggc ggggcggggc 600
cgcctcgggc cggggagggc tcgggggagg ggcgcggcgg cccccggagc gccggcggct 660
gtcgaggcgc ggcgagccgc agccattgcc ttttatggta atcgtgcgag agggcgcagg 720
gacttccttt gtcccaaatc tgtgcggagc cgaaatctgg gaggcgccgc cgcacccccct 780 ctagcgggcg cggggcgaag cggtgcggcg ccggcaggaa ggaaatgggc ggggagggcc 840
ttcgtgcgtc gccgcgccgc cgtccccttc tccctctcca gcctcggggc tgtccgcggg 900
gggacggctg ccttcggggg ggacggggca gggcggggtt cggcttctgg cgtgtgaccg 960
gcggctctag agcctctgct aaccatgttc atgccttctt ctttttccta cag 1013

<210> SEQ ID NO 133
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 133
ctcctgggca acgtgctggt tattgtgacc ggtgccacc 39

<210> SEQ ID NO 134
<211> LENGTH: 1923
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 134
atggccaaag ccgcggcgat cggcatcgac ctgggcacca cctactcctg cgtgggggtg 60
ttccaacacg gcaaggtgga gatcatcgcc aacgaccagg gcaaccgcac cacccccagc 120
tacgtggcct tcacggacac cgagcggctc atcggggatg cggccaagaa ccaggtggcg 180
ctgaacccgc agaacaccgt gtttgacgcg aagcggctga tcggccgcaa gttcggcgac 240
ccggtggtgc agtcggacat gaagcactgg cctttccagg tgatcaacga cggagacaag 300
cccaaggtgc aggtgagcta caagggggag accaaggcat tctaccccga ggagatctcg 360
tccatggtgc tgaccaagat gaaggagatc gccgaggcgt acctgggcta cccggtgacc 420
aacgcggtga tcaccgtgcc ggcctacttc aacgactcgc agcgccaggc caccaaggat 480
gcgggtgtga tcgcggggct caacgtgctg cggatcatca acgagcccac ggccgccgcc 540
atcgcctacg gcctggacag aacgggcaag ggggagcgca acgtgctcat ctttgacctg 600
ggcgggggca ccttcgacgt gtccatcctg acgatcgacg acggcatctt cgaggtgaag 660
gccacggccg gggacaccca cctgggtggg gaggactttg acaacaggct ggtgaaccac 720
ttcgtggagg agttcaagag aaaacacaag aaggacatca gccagaacaa gcgagccgtg 780
aggcggctgc gcaccgcctg cgagagggcc aagaggaccc tgtcgtccag cacccaggcc 840
agcctggaga tcgactccct gtttgagggc atcgacttct acacgtccat caccagggcg 900
aggttcgagg agctgtgctc cgacctgttc cgaagcaccc tggagcccgt ggagaaggct 960
ctgcgcgacg ccaagctgga caaggcccag attcacgacc tggtcctggt cgggggctcc 1020
acccgcatcc ccaaggtgca gaagctgctg caggacttct tcaacgggcg cgacctgaac 1080
aagagcatca accccgacga ggctgtggcc tacggggcgg cggtgcaggc ggccatcctg 1140
atgggggaca agtccgagaa cgtgcaggac ctgctgctgc tggacgtggc tcccctgtcg 1200
ctggggctgg agacggccgg aggcgtgatg actgccctga tcaagcgcaa ctccaccatc 1260
cccaccaagc agacgcagat cttcaccacc tactccgaca accaacccgg ggtgctgatc 1320
caggtgtacg agggcgagag ggccatgacg aaagacaaca atctgttggg gcgcttcgag 1380
ctgagcggca tccctccggc ccccaggggc gtgccccaga tcgaggtgac cttcgacatc 1440
gatgccaacg gcatcctgaa cgtcacggcc acggacaaga gcaccggcaa ggccaacaag 1500
atcaccatca ccaacgacaa gggccgcctg agcaaggagg agatcgagcg catggtgcag 1560
gaggcggaga agtacaaagc ggaggacgag gtgcagcgcg agagggtgtc agccaagaac 1620
gccctggagt cctacgcctt caacatgaag agcgccgtgg aggatgaggg gctcaagggc 1680
aagatcagcg aggcggacaa gaagaaggtt ctggacaagt gtcaagaggt catctcgtgg 1740
ctggacgcca acaccttggc cgagaaggac gagtttgagc acaagaggaa ggagctggag 1800
caggtgtgta accccatcat cagcggactg taccagggtg ccggtggtcc cgggcctggg 1860
ggcttcgggg ctcagggtcc caagggaggg tctgggtcag gccccaccat tgaggaggtg 1920
gat 1923

<210> SEQ ID NO 135
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 135
taagagctcg ctgatcagcc tcga 24

<210> SEQ ID NO 136
<211> LENGTH: 225
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 136
ctgtgccttc tagttgccag ccatctgttg tttgcccctc ccccgtgcct tccttgaccc 60
tggaaggtgc cactcccact gtcctttcct aataaaatga ggaaattgca tcgcattgtc 120
tgagtaggtg tcattctatt ctggggggtg gggtggggca ggacagcaag ggggaggatt 180
gggaagacaa tagcaggcat gctggggatg cggtgggctc tatgg 225

<210> SEQ ID NO 137
<211> LENGTH: 34
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 137
aagcttgaat tcagctgacg tgcctcggac cgct 34

<210> SEQ ID NO 138
<211> LENGTH: 130

<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 138
aggaacccct agtgatggag ttggccactc cctctctgcg cgctcgctcg ctcactgagg 60
ccgggcgacc aaaggtcgcc cgacgcccgg gctttgcccg ggcggcctca gtgagcgagc 120
gagcgcgcag 130

<210> SEQ ID NO 139
<211> LENGTH: 119
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 139
ctgcgcgctc gctcgctcac tgaggccgcc cgggcgtcgg gcgacctttg gtcgcccggc 60
ctcagtgagc gagcgagcgc gcagagaggg agtggccaac tccatcacta ggggttcct 119

<210> SEQ ID NO 140
<211> LENGTH: 14
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 140
gcggccgcac gcgt 14

<210> SEQ ID NO 141
<211> LENGTH: 381
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 141
gacattgatt attgactagt tattaatagt aatcaattac ggggtcatta gttcatagcc 60
catatatgga gttccgcgtt acataactta cggtaaatgg cccgcctggc tgaccgccca 120
acgacccccg cccattgacg tcaataatga cgtatgttcc catagtaacg ccaataggga 180
ctttccattg acgtcaatgg gtggactatt tacggtaaac tgcccacttg gcagtacatc 240
aagtgtatca tatgccaagt acgcccccta ttgacgtcaa tgacggtaaa tggcccgcct 300
ggcattatgc ccagtacatg accttatggg actttcctac ttggcagtac atctacgtat 360
tagtcatcgc tattaccatg g 381

<210> SEQ ID NO 142
<211> LENGTH: 277
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 142
gtcgaggtga gccccacgtt ctgcttcact ctccccatct cccccccctc cccaccccca 60
attttgtatt tatttatttt ttaattattt tgtgcagcga tgggggcggg gggggggggg 120
gcgcgcgcca ggcggggcgg ggcggggcga ggggcggggc ggggcgaggc ggagaggtgc 180
ggcggcagcc aatcagagcg gcgcgctccg aaagtttcct tttatggcga ggcggcggcg 240
gcggcggccc tataaaaagc gaagcgcgcg gcgggcg 277

<210> SEQ ID NO 143
<211> LENGTH: 1013
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 143
ggagtcgctg cgttgccttc gccccgtgcc ccgctccgcg ccgcctcgcg ccgcccgccc 60
cggctctgac tgaccgcgtt actcccacag gtgagcgggc gggacggccc ttctcctccg 120
ggctgtaatt agcgcttggt ttaatgacgg ctcgtttctt ttctgtggct gcgtgaaagc 180
cttaaagggc tccgggaggg ccctttgtgc ggggggggagc ggctcggggg gtgcgtgcgt 240
gtgtgtgtgc gtggggagcg ccgcgtgcgg cccgcgctgc ccggcggctg tgagcgctgc 300
gggcgcggcg cggggctttg tgcgctccgc gtgtgcgcga ggggagcgcg gccgggggcg 360
gtgccccgcg gtgcgggggg gctgcgaggg gaacaaaggc tgcgtgcggg gtgtgtgcgt 420
gggggggtga gcagggggtg tgggcgcggc ggtcgggctg taaccccccc ctgcaccccc 480
ctccccgagt tgctgagcac ggcccggctt cgggtgcggg gctccgtgcg gggcgtggcg 540
cggggctcgc cgtgccgggc ggggggtggc ggcaggtggg ggtgccgggc ggggcggggc 600
cgcctcgggc cggggagggc tcgggggagg ggcgcggcgg cccccggagc gccggcggct 660
gtcgaggcgc ggcgagccgc agccattgcc ttttatggta atcgtgcgag agggcgcagg 720
gacttccttt gtcccaaatc tgtgcggagc cgaaatctgg gaggcgccgc cgcacccccct 780 ctagcgggcg cggggcgaag cggtgcggcg ccggcaggaa ggaaatgggc ggggagggcc 840
ttcgtgcgtc gccgcgccgc cgtccccttc tccctctcca gcctcggggc tgtccgcggg 900
gggacggctg ccttcggggg ggacggggca gggcggggtt cggcttctgg cgtgtgaccg 960
gcggctctag agcctctgct aaccatgttc atgccttctt ctttttccta cag 1013

<210> SEQ ID NO 144
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 144
ctcctgggca acgtgctggt tattgtgacc ggtgccacc 39

<210> SEQ ID NO 145
<211> LENGTH: 1923
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 145
atggccaaag ccgcggcgat cggcatcgac ctgggcacca cctactcctg cgtgggggtg 60

```
ttccaacacg gcaaggtgga gatcatcgcc aacgaccagg gcaaccgcac cacccccagc    120

tacgtggcct tcacggacac cgagcggctc atcggggatg cggccaagaa ccaggtggcg    180

ctgaacccgc agaacaccgt gtttgacgcg aagcggctga tcggccgcaa gttcggcgac    240

ccggtggtgc agtcggacat gaagcactgg cctttccagg tgatcaacga cggagacaag    300

cccaaggtgc aggtgagcta caagggggag accaaggcat tctaccccga ggagatctcg    360

tccatggtgc tgaccaagat gaaggagatc gccgaggcgt acctgggcta cccggtgacc    420

aacgcggtga tcaccgtgcc ggcctacttc aacgactcgc agcgccaggc caccaaggat    480

gcgggtgtga tcgcggggct caacgtgctg cggatcatca acgagcccac ggccgccgcc    540

atcgcctacg gcctggacag aacgggcaag gggagcgca acgtgctcat ctttgacctg    600

ggcgggggca ccttcgacgt gtccatcctg acgatcgacg acggcatctt cgaggtgaag    660

gccacggccg gggacaccca cctgggtggg gaggactttg acaacaggct ggtgaaccac    720

ttcgtggagg agttcaagag aaaacacaag aaggacatca gccagaacaa gcgagccgtg    780

aggcggctgc gcaccgcctg cgagagggcc aagaggaccc tgtcgtccag cacccaggcc    840

agcctggaga tcgactccct gtttgagggc atcgacttct acacgtccat caccagggcg    900

aggttcgagg agctgtgctc cgacctgttc cgaagcaccc tggagcccgt ggagaaggct    960

ctgcgcgacg ccaagctgga caaggcccag attcacgacc tggtcctggt cgggggctcc   1020

acccgcatcc ccaaggtgca gaagctgctg caggacttct tcaacgggcg cgacctgaac   1080

aagagcatca accccgacga ggctgtggcc tacggggcgg cggtgcaggc ggccatcctg   1140

atgggggaca agtccgagaa cgtgcaggac ctgctgctgc tggacgtggc tcccctgtcg   1200

ctggggctgg agacggccgg aggcgtgatg actgccctga tcaagcgcaa ctccaccatc   1260

cccaccaagc agacgcagat cttcaccacc tactccgaca accaacccgg ggtgctgatc   1320

caggtgtacg agggcgagag ggccatgacg aaagacaaca atctgttggg gcgcttcgag   1380

ctgagcggca tccctccggc ccccaggggc gtgccccaga tcgaggtgac cttcgacatc   1440

gatgccaacg gcatcctgaa cgtcacggcc acggacaaga gcaccggcaa ggccaacaag   1500

atcaccatca ccaacgacaa gggccgcctg agcaaggagg agatcgagcg catggtgcag   1560

gaggcggaga agtacaaagc ggaggacgag gtgcagcgcg agagggtgtc agccaagaac   1620

gccctggagt cctacgcctt caacatgaag agcgccgtgg aggatgaggg gctcaagggc   1680

aagatcagcg aggcggacaa gaagaaggtt ctggacaagt gtcaagaggt catctcgtgg   1740

ctggacgcca acaccttggc cgagaaggac gagtttgagc acaagaggaa ggagctggag   1800

caggtgtgta accccatcat cagcggactg taccagggtg ccggtggtcc cgggcctggg   1860

ggcttcgggg ctcagggtcc caagggaggg tctgggtcag gccccaccat tgaggaggtg   1920

gat                                                                 1923
```

<210> SEQ ID NO 146
<211> LENGTH: 12
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 146

```
ggatcccggg ct                                                         12
```

<210> SEQ ID NO 147
<211> LENGTH: 66
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 147
gactacaaag accatgacgg tgattataaa gatcatgaca tcgactacaa ggatgacgat 60
gacaag 66

<210> SEQ ID NO 148
<211> LENGTH: 9
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 148 ggctccgga 9

<210> SEQ ID NO 149
<211> LENGTH: 54
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 149
gagggcagag gaagtctgct aacatgcggt gacgtcgagg agaatcctgg ccca 54

<210> SEQ ID NO 150
<211> LENGTH: 696
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 150
atggagagcg acgagagcgg cctgcccgcc atggagatcg agtgccgcat caccggcacc 60
ctgaacggcg tggagttcga gctggtgggc ggcggagagg gcacccccga gcagggccgc 120
atgaccaaca agatgaagag caccaaaggc gccctgacct tcagccccta cctgctgagc 180
cacgtgatgg gctacggctt ctaccacttc ggcacctacc ccagcggcta cgagaacccc 240
ttcctgcacg ccatcaacaa cggcggctac accaacaccc gcatcgagaa gtacgaggac 300
ggcggcgtgc tgcacgtgag cttcagctac cgctacgagg ccggccgcgt gatcggcgac 360
ttcaaggtga tgggcaccgg cttccccgag gacagcgtga tcttcaccga caagatcatc 420
cgcagcaacg ccaccgtgga gcacctgcac cccatgggcg ataacgatct ggatggcagc 480
ttcacccgca ccttcagcct gcgcgacggc ggctactaca gctccgtggt ggacagccac 540
atgcacttca agagcgccat ccaccccagc atcctgcaga acgggggccc catgttcgcc 600
ttccgccgcg tggaggagga tcacagcaac accgagctgg gcatcgtgga gtaccagcac 660
gccttcaaga ccccggatgc agatgccggt gaagaa 696

<210> SEQ ID NO 151
<211> LENGTH: 24
<212> TYPE: DNA

<213> ORGANISM: Artificial Sequence
<220> FEATURE:
<223> OTHER INFORMATION: Description of Artificial Sequence: Synthetic
      oligonucleotide

<400> SEQUENCE: 151
ggatcccggg ctgactacaa agac                                         24

<210> SEQ ID NO 152
<211> LENGTH: 225
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 152
catgacggtg attataaaga tcatgacatc gactacaagg atgacgatga caagggctcc     60
ggagagggca gaggaagtct gctaacatgc ggtgacgtcg aggagaatcc tggcccaatg    120
gagagcgacg agagcggcct gcccgccatg gagatcgagt gccgcatcac cggcaccctg    180
aacggcgtgg agttcgagct ggtgggcggc ggagagggca ccccc                    225

<210> SEQ ID NO 153
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 153
gagcagggcc gcatgaccaa caagatgaag agca                              34

<210> SEQ ID NO 154
<211> LENGTH: 130
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 154
ccaaaggcgc cctgaccttc agcccctacc tgctgagcca cgtgatgggc tacggcttct     60
accacttcgg cacctacccc agcggctacg agaacccctt cctgcacgcc atcaacaacg    120
gcggctacac                                                          130

<210> SEQ ID NO 155
<211> LENGTH: 82
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 155
gtaagtatca aggttacaag acaggtttaa ggagaccaat agaaactggg cttgtcgaga     60
cagagaagac tcttgcgttt ct                                             82

<210> SEQ ID NO 156
<211> LENGTH: 1023
<212> TYPE: DNA
<213> ORGANISM: Homo sapiens

<400> SEQUENCE: 156

```
atgggtaaag actactacca gacgttgggc ctggcccgcg gcgcgtcgga cgaggagatc     60
aagcgggcct accgccgcca ggcgctgcgc taccacccgg acaagaacaa ggagcccggc    120
gccgaggaga agttcaagga gatcgctgag gcctacgacg tgctcagcga cccgcgcaag    180
cgcgagatct tcgaccgcta cggggaggaa ggcctaaagg ggagtggccc cagtggcggt    240
agcggcggtg gtgccaatgg tacctctttc agctacacat tccatggaga ccctcatgcc    300
atgtttgctg agttcttcgg tggcagaaat ccctttgaca ccttttttgg gcagcggaac    360
ggggaggaag gcatggacat tgatgaccca ttctctggct tccctatggg catgggtggc    420
ttcaccaacg tgaactttgg ccgctcccgc tctgcccaag agcccgcccg aaagaagcaa    480
gatcccccag tcacccacga ccttcgagtc tcccttgaag agatctacag cggctgtacc    540
aagaagatga aaatctccca caagcggcta aaccccgacg gaaagagcat tcgaaacgaa    600
gacaaaatat tgaccatcga agtgaagaag gggtggaaag aaggaaccaa aatcactttc    660
cccaaggaag gagaccagac ctccaacaac attccagctg atatcgtctt tgttttaaag    720
gacaagcccc acaatatctt taagagagat ggctctgatg tcatttatcc tgccaggatc    780
agcctccggg aggctctgtg tggctgcaca gtgaacgtcc ccactctgga cggcaggacg    840
atacccgtcg tattcaaaga tgttatcagg cctggcatgc ggcgaaaagt tcctggagaa    900
ggcctccccc tccccaaaac acccgagaaa cgtggggacc tcattattga gtttgaagtg    960
atcttccccg aaaggattcc ccagacatca agaaccgtac ttgagcaggt tcttccaata   1020
tag                                                                 1023
```

<210> SEQ ID NO 157
<211> LENGTH: 2270
<212> TYPE: DNA
<213> ORGANISM: Homo sapiens

<400> SEQUENCE: 157

```
gtgcatgggg gtgggggagc cgggggtgac gacggggacg gcgcggcgga gcccgctgcg     60
gacccgggct cacctgggct cggccgccgg ggtccgcggg gcggcgcctc cggctcagct    120
gcggggcgag gggttgtgaa tgcaggagcc gaccccgttc gtgggcttgg gggctgggtt    180
gggataattc ccgggaagtg atgacctggc cccggcaggg cacgcaggag gcagcggccg    240
cccaggtccg gagagcgggg ccgcctcgga gggcctaaag gggagtggcc ccagtggcgg    300
tagcggcggt ggtgccaatg gtacctcttt cagctacaca ttccatggag accctcatgc    360
catgtttgct gagttcttcg gtggcagaaa tccctttgac accttttttg ggcagcggaa    420
cggggaggaa ggcatggaca ttgatgaccc attctctggc ttccctatgg gcatgggtgg    480
cttcaccaac gtgaactttg gccgctcccg ctctgcccaa gagcccgccc gaaagaagca    540
agatccccca gtcacccacg accttcgagt ctcccttgaa gagatctaca gcggctgtac    600
caagaagatg aaaatctccc acaagcggct aaaccccgac ggaaagagca ttcgaaacga    660
agacaaaata ttgaccatcg aagtgaagaa ggggtggaaa gaaggaacca aaatcacttt    720
ccccaaggaa ggagaccaga cctccaacaa cattccagct gatatcgtct ttgttttaaa    780
ggacaagccc cacaatatct ttaagagaga tggctctgat gtcatttatc ctgccaggat    840
cagcctccgg gaggctctgt gtggctgcac agtgaacgtc cccactctgg acggcaggac    900
gatacccgtc gtattcaaag atgttatcag gcctggcatg cggcgaaaag ttcctggaga    960
aggcctcccc ctccccaaaa cacccgagaa acgtggggac ctcattattg agtttgaagt   1020
```

gatcttcccc gaaaggattc cccagacatc aagaaccgta cttgagcagg ttcttccaat 1080
atagctatct gagctcccca aggactgacc agggaccttt ccagagctca aggatttctg 1140
gacctttcta ccagttgtgg accatgagag ggtgggaggg cccagggagg gctttcgtac 1200
tgctgaatgt tttccagagc atatattaca atctttcaaa gtcgcacact agacttcagt 1260
ggtttttcga gctatagggc atcaggtggt gggaacagca ggaaaaggca ttccagtctg 1320
ccccactggg tctggcagcc ctcccgggat gggcccacat ccacctccag tccctggcca 1380
ggggtgagag gcagaccagc agatggactt gatccctctg tgtcttttg cttctggctg 1440 gtagataatg tcaacctgca gtcttgattc ccagaccctg tacactcctc cttttctgtt 1500
gtgtgatcag tttgtgcttt attctgtatt tgtctcccat gtcttgctct tctcctggag 1560
aattctgtct tctctttggc catctcaaat tgagaaccta aactattcct gcagaactgc 1620
ctggttggcg tccacaagca atacctctcg ttccagcagg accaagggag ccagcctcca 1680
gtgagtgact ccagcaagtg cagccacctc tcccttgatg gtctgggagc ctggcctcag 1740
caaggggcct tcctgacctc tggctccagt gaagctgaat gtcctcactt tgtgggtcac 1800
actctttaca tttctgtaag gcaatcttgg cacacgtggg gcttaccagt ggcccaggta 1860
attttttgtt tcatggacta tggactcttt caaagggatc tgatcctttt gaattttgca 1920
cagccctaga tacaatccct tttgataaaa gggtctttgc ttctgattac aggagcactg 1980
tggaacgtct gtaaatatgt ttttataatt ccatgtatag ttggtgtaca ctcaaaacct 2040
gtccccggca gccagtgctc tctgtatagg gccataatgg aattctgaag aaatcttggg 2100
gagggaaggg gagttggaac aaatgtctgt tccctggagg ccagtccagt gctcagacct 2160
ttagactcat tgtaagttgc cactgccaac atgagaccaa agtgtgtgac tagtcaatga 2220
agtgcgacag cattaaagac tgatgctaaa cctcagggga aaaaaaaaaa 2270

<210> SEQ ID NO 158
<211> LENGTH: 723
<212> TYPE: DNA
<213> ORGANISM: Homo sapiens

<400> SEQUENCE: 158
atgtttgctg agttcttcgg tggcagaaat ccctttgaca ccttttttgg gcagcggaac 60
ggggaggaag gcatggacat tgatgaccca ttctctggct tccctatggg catgggtggc 120
ttcaccaacg tgaactttgg ccgctcccgc tctgcccaag agcccgcccg aaagaagcaa 180
gatcccccag tcacccacga ccttcgagtc tcccttgaag agatctacag cggctgtacc 240
aagaagatga aaatctccca caagcggcta aaccccgacg gaaagagcat tcgaaacgaa 300
gacaaaatat tgaccatcga agtgaagaag gggtggaaag aaggaaccaa aatcactttc 360
cccaaggaag gagaccagac ctccaacaac attccagctg atatcgtctt tgttttaaag 420
gacaagcccc acaatatctt taagagagat ggctctgatg tcatttatcc tgccaggatc 480
agcctccggg aggctctgtg tggctgcaca gtgaacgtcc ccactctgga cggcaggacg 540
atacccgtcg tattcaaaga tgttatcagg cctggcatgc ggcgaaaagt tcctggagaa 600
ggcctccccc tccccaaaac acccgagaaa cgtggggacc tcattattga gtttgaagtg 660
atcttccccg aaaggattcc ccagacatca agaaccgtac ttgagcaggt tcttccaata 720
tag 723

<210> SEQ ID NO 159

<211> LENGTH: 2186
<212> TYPE: DNA
<213> ORGANISM: Homo sapiens

<400> SEQUENCE: 159

```
gtggaaacca aggtaagcga cggttaggcc agacgcgggg gcggggtaag aagttgagtg     60
acaggcaagg cagcatccac atgacaggcg gcgccgaagg ggtaaattct gagatcctgc    120
ccctgagctt tcatgagctg ttgaaccatc tggaattcac aggcctgtca tgagagacac    180
gatgagaagt ccttaaaggc ctaaagggga gtggccccag tggcggtagc ggcggtggtg    240
ccaatggtac ctctttcagc tacacattcc atggagaccc tcatgccatg tttgctgagt    300
tcttcggtgg cagaaatccc tttgacacct tttttgggca gcggaacggg gaggaaggca    360
tggacattga tgacccattc tctggcttcc ctatgggcat gggtggcttc accaacgtga    420
actttggccg ctcccgctct gcccaagagc ccgcccgaaa gaagcaagat cccccagtca    480
cccacgacct tcgagtctcc cttgaagaga tctacagcgg ctgtaccaag aagatgaaaa    540
tctcccacaa gcggctaaac cccgacggaa agagcattcg aaacgaagac aaaatattga    600
ccatcgaagt gaagaagggg tggaaagaag gaaccaaaat cactttcccc aaggaaggag    660
accagacctc caacaacatt ccagctgata tcgtctttgt tttaaaggac aagccccaca    720
atatctttaa gagagatggc tctgatgtca tttatcctgc caggatcagc ctccgggagg    780
ctctgtgtgg ctgcacagtg aacgtcccca ctctggacgg caggacgata cccgtcgtat    840
tcaaagatgt tatcaggcct ggcatgcggc gaaaagttcc tggagaaggc ctccccctcc    900
ccaaaacacc cgagaaacgt ggggacctca ttattgagtt tgaagtgatc ttccccgaaa    960
ggattcccca gacatcaaga accgtacttg agcaggttct tccaatatag ctatctgagc   1020
tccccaagga ctgaccaggg acctttccag agctcaagga tttctggacc tttctaccag   1080
ttgtggacca tgagagggtg ggagggccca gggagggctt tcgtactgct gaatgttttc   1140
cagagcatat attacaatct ttcaaagtcg cacactagac ttcagtggtt tttcgagcta   1200
tagggcatca ggtggtggga acagcaggaa aaggcattcc agtctgcccc actgggtctg   1260
gcagccctcc cgggatgggc ccacatccac ctccagtccc tggccagggg tgagaggcag   1320
accagcagat ggacttgatc cctctgtgtc tttttgcttc tggctggtag ataatgtcaa   1380
cctgcagtct tgattcccag accctgtaca ctcctccttt tctgttgtgt gatcagtttg   1440
tgctttattc tgtatttgtc tcccatgtct tgctcttctc ctggagaatt ctgtcttctc   1500
tttggccatc tcaaattgag aacctaaact attcctgcag aactgcctgg ttggcgtcca   1560
caagcaatac ctctcgttcc agcaggacca agggagccag cctccagtga gtgactccag   1620
caagtgcagc cacctctccc ttgatggtct gggagcctgg cctcagcaag gggccttcct   1680
gacctctggc tccagtgaag ctgaatgtcc tcactttgtg ggtcacactc tttacatttc   1740
tgtaaggcaa tcttggcaca cgtggggctt accagtggcc caggtaattt tttgtttcat   1800
ggactatgga ctctttcaaa gggatctgat ccttttgaat tttgcacagc cctagataca   1860
atccctttg ataaaagggt ctttgcttct gattacagga gcactgtgga acgtctgtaa   1920
atatgttttt ataattccat gtatagttgg tgtacactca aaacctgtcc ccggcagcca   1980
gtgctctctg tatagggcca taatggaatt ctgaagaaat cttggggagg gaaggggagt   2040
tggaacaaat gtctgttccc tggaggccag tccagtgctc agacctttag actcattgta   2100
agttgccact gccaacatga gaccaaagtg tgtgactagt caatgaagtg cgacagcatt   2160
aaagactgat gctaaacctc agggga                                        2186
```

<210> SEQ ID NO 160
<211> LENGTH: 340
<212> TYPE: PRT
<213> ORGANISM: Homo sapiens

<400> SEQUENCE: 160

```
Met Gly Lys Asp Tyr Tyr Gln Thr Leu Gly Leu Ala Arg Gly Ala Ser
1               5                   10                  15

Asp Glu Glu Ile Lys Arg Ala Tyr Arg Arg Gln Ala Leu Arg Tyr His
            20                  25                  30

Pro Asp Lys Asn Lys Glu Pro Gly Ala Glu Glu Lys Phe Lys Glu Ile
        35                  40                  45

Ala Glu Ala Tyr Asp Val Leu Ser Asp Pro Arg Lys Arg Glu Ile Phe
    50                  55                  60

Asp Arg Tyr Gly Glu Glu Gly Leu Lys Gly Ser Gly Pro Ser Gly Gly
65                  70                  75                  80

Ser Gly Gly Gly Ala Asn Gly Thr Ser Phe Ser Tyr Thr Phe His Gly
                85                  90                  95

Asp Pro His Ala Met Phe Ala Glu Phe Phe Gly Gly Arg Asn Pro Phe
            100                 105                 110

Asp Thr Phe Phe Gly Gln Arg Asn Gly Glu Glu Gly Met Asp Ile Asp
        115                 120                 125

Asp Pro Phe Ser Gly Phe Pro Met Gly Met Gly Gly Phe Thr Asn Val
    130                 135                 140

Asn Phe Gly Arg Ser Arg Ser Ala Gln Glu Pro Ala Arg Lys Lys Gln
145                 150                 155                 160

Asp Pro Pro Val Thr His Asp Leu Arg Val Ser Leu Glu Glu Ile Tyr
                165                 170                 175

Ser Gly Cys Thr Lys Lys Met Lys Ile Ser His Lys Arg Leu Asn Pro
            180                 185                 190

Asp Gly Lys Ser Ile Arg Asn Glu Asp Lys Ile Leu Thr Ile Glu Val
        195                 200                 205

Lys Lys Gly Trp Lys Glu Gly Thr Lys Ile Thr Phe Pro Lys Glu Gly
    210                 215                 220

Asp Gln Thr Ser Asn Asn Ile Pro Ala Asp Ile Val Phe Val Leu Lys
225                 230                 235                 240

Asp Lys Pro His Asn Ile Phe Lys Arg Asp Gly Ser Asp Val Ile Tyr
                245                 250                 255

Pro Ala Arg Ile Ser Leu Arg Glu Ala Leu Cys Gly Cys Thr Val Asn
            260                 265                 270

Val Pro Thr Leu Asp Gly Arg Thr Ile Pro Val Val Phe Lys Asp Val
        275                 280                 285

Ile Arg Pro Gly Met Arg Arg Lys Val Pro Gly Glu Gly Leu Pro Leu
    290                 295                 300

Pro Lys Thr Pro Glu Lys Arg Gly Asp Leu Ile Ile Glu Phe Glu Val
305                 310                 315                 320

Ile Phe Pro Glu Arg Ile Pro Gln Thr Ser Arg Thr Val Leu Glu Gln
                325                 330                 335

Val Leu Pro Ile
            340
```

<210> SEQ ID NO 161
<211> LENGTH: 240
<212> TYPE: PRT

<213> ORGANISM: Homo sapiens

<400> SEQUENCE: 161

```
Met Phe Ala Glu Phe Phe Gly Gly Arg Asn Pro Phe Asp Thr Phe Phe
1               5                   10                  15

Gly Gln Arg Asn Gly Glu Glu Gly Met Asp Ile Asp Asp Pro Phe Ser
            20                  25                  30

Gly Phe Pro Met Gly Met Gly Gly Phe Thr Asn Val Asn Phe Gly Arg
        35                  40                  45

Ser Arg Ser Ala Gln Glu Pro Ala Arg Lys Lys Gln Asp Pro Pro Val
    50                  55                  60

Thr His Asp Leu Arg Val Ser Leu Glu Glu Ile Tyr Ser Gly Cys Thr
65                  70                  75                  80

Lys Lys Met Lys Ile Ser His Lys Arg Leu Asn Pro Asp Gly Lys Ser
                85                  90                  95

Ile Arg Asn Glu Asp Lys Ile Leu Thr Ile Glu Val Lys Lys Gly Trp
            100                 105                 110

Lys Glu Gly Thr Lys Ile Thr Phe Pro Lys Glu Gly Asp Gln Thr Ser
        115                 120                 125

Asn Asn Ile Pro Ala Asp Ile Val Phe Val Leu Lys Asp Lys Pro His
    130                 135                 140

Asn Ile Phe Lys Arg Asp Gly Ser Asp Val Ile Tyr Pro Ala Arg Ile
145                 150                 155                 160

Ser Leu Arg Glu Ala Leu Cys Gly Cys Thr Val Asn Val Pro Thr Leu
                165                 170                 175

Asp Gly Arg Thr Ile Pro Val Val Phe Lys Asp Val Ile Arg Pro Gly
            180                 185                 190

Met Arg Arg Lys Val Pro Gly Glu Gly Leu Pro Leu Pro Lys Thr Pro
        195                 200                 205

Glu Lys Arg Gly Asp Leu Ile Ile Glu Phe Glu Val Ile Phe Pro Glu
    210                 215                 220

Arg Ile Pro Gln Thr Ser Arg Thr Val Leu Glu Gln Val Leu Pro Ile
225                 230                 235                 240
```

<210> SEQ ID NO 162
<211> LENGTH: 8793
<212> TYPE: DNA
<213> ORGANISM: Homo sapiens

<400> SEQUENCE: 162

```
ctgagctgag tgacaggaag acggttcaat gggcggcgcg gaggcggagc cgtgggggcg      60

ggctcccggt cccgctatcg gcggccggcg ggcaggcgac tcctgtcccg ggtggaggcg     120

gcggagccgg agccggggga gggggcagcg gctgtctcac ggaccacggc ggcgcccgca     180

gctcctcacc ggtgagggcg ccaagccagg actcgggggt cccgggagcg gggcgtcgtg     240

aagccagggc tcctggtgtt ggggggttgg gacactgagg gcccgtaggc tctgctgcct     300

tggggatgcg gggccccggg gtctgcaggg tgctcggagt cctagaccag ggcttggctg     360

tcacaggggg cagccagcgt ctgagtcggg gaggggaggg gaggggaggg tcgagtcgga     420

ccggaccaga ttgggttctg tggggcggag gcatctgtga gcagaccagc cagccagcgc     480

gggtgacatc accgaccacc ctcccccgcc cgagcccccct cccctcctct cctcgccgcg     540

ccttttgtcc cggccgagct ccgctctgcc ccgcccatct gcgagggagg agactcccgt     600

cagtgacttc attgagtagg ttcttgggga ttggggtcgg gtcctcccca gtgagaggcg     660
```

```
acaggagctc actgcctctc gggccctcac aatcacacct gtcacaggta tacacgctgc    720
cactcacaaa cacacgcttg cactcccagc ctcactgaca cgctgccata cagccgctca    780
cagccagcca gacactgctg cacctgagag caggtggccg cgggtcttct cccttcactc    840
tccacatttg ggatcaggt ccggcacctg ctgcgccaga caggccttgc tgggcacgcg    900
cctctgagag tccaaggagg tggcttccag agctgcagca cttcaggccg gctccggtgg    960
agcgatcaga ggtgaggggc ttggctgggc atgtttaagc gcacagtgct ctcctgccca   1020
cccccagcag caccccact gcaggcccga ggagctttcc ggagcttccc acactcctgg   1080
ggagaagact tcttagccag cttgatgttt aaaattcagc tggagccctt aaaacttcga   1140
gcgtggacgc tgaatgggtt tgtaaagttt cggtaagtcc ctccggagaa gggcactcac   1200
acccataccc agtcaaaccc tccacgcggc catcccctcc attgccttcc tgcttcctcc   1260
aactcatcct catcccctct gtgacataca ggaacccccc tccggcctca cccacatatt   1320
tgaatgaatt gcaccctta tcattccttt tctcaaaccc ttcaggtatc cattttccac   1380
agacatttcc tccattattt caactctcca cattcctccc tttcaaccca tcattaaccc   1440
attttccacc tcagccattt ccatctgtca ctcatccccc tccatcagta cctcattttc   1500
tgtatcagcc atctcccctc cctgtacctc aacagtcccc ctcgccattt tctccccatt   1560
tttccttcct gcctctacct taacatcctc ctcattcttc tccatcaaag gcagtgccat   1620
gccatggggc tcctttgtca ttccaacacg tggcctgtgg gtagggggga agggaaggag   1680
ggaggaaagc agaaagagaa aaaggaggca gatcctgaaa gagcttgccc tgtgtctgcg   1740
gaggcaagag atgtatgggc ctagagcagc tagcaggtgg gtaccaggga ggaagctggc   1800
cgggtgtgga ggtaatgcag ggacaccaaa aggaggtggg tggttggtga gccgttccac   1860
tggccctctg cctggaagct gctctcgttc tctaggggca ccctcttggt gtgctagggt   1920
tctttcccag tcccagggga aagaaggtgt gggttgaggc agaaatggca gaccaccccc   1980
ccccgctccc tctcagacgg cttttgctgc catttccgaa aacggttgcc ccccccccca   2040
acgaggtgct ctttcttctc tgcctctccc aaccccaccc cccaccccat ctcccccaca   2100
gacgtgacat gctggtgggg ggcaatgggg gagtacccgc ctttgtggag ccttttcttc   2160
gtcagagaaa ggtgactccc agaaccatga gtcaacccag ccacctgcag cagggcctgt   2220
gggggcagca gtgagggcca ttgtccctgc ccacctaggg ccttgggcgc ctcccccctta  2280
cccggttaca ggcctcactc ctggaaggac accctgtaca cctccctgct gtgaagcagt   2340
cagaggcaga aaggcaggtc tcagctgtgg ctgccagcct aggacattgc tagaaagact   2400
ctggttctcc tggctttggc aggggttggc caagtctcag aagggctgag aatggcttct   2460
ggccatcccc cagagagctc tagctacagg aaagtccccc ttcccctgat atccaccaca   2520
gacacaccga tagagggaga ctggaatgga agaattcggg ttgtacgttt ctcttataac   2580
aaatgctcct gcacccacct taaaagggac tcagaggaat atgggtctga tgatgggccg   2640
gatcctaaac cacagggtgg actgggggcg tagggtgagg ctaggagagg tattaaggaa   2700
atggtggttg gttagtgccc aattgtctcc taacagctgg ggttgaaaaa gtcctgtccc   2760
caggatgctt ttgttcactc acactggtgc ttaggcggca cagccctcac agttttgtgt   2820
gtagacgctg gcaaatgagt aaagggaact gttgccctgg ttgggggaag gatagtgtcg   2880
cccccctgc taatgaggga gttggaaaca gcagtttcca aaggctgtga gtcaccctgt   2940
gatctgagtc acacgtgagg cttagcatcg tcagaggggt gggggcgggg aggcctgggg   3000
tctccgatgg cagacaggac tccagacacc cattccctga ctcagtctgg ctggccagga   3060
```

```
cagctggcgg aagacccagg cctgttcccg gtcctgggcc actgccccag ctgccctcag   3120
cctgggcacc atgcctgagg cgtggcgtag gagaccacga tgctcaggtg acctcacccg   3180
ttacactgac cttcgccagc tcctgtgtgt gggtcgctca gtccatggtg ccacctcgct   3240
cagcagggcc tctcaggggt cctcagtctg gcccaaggac cagggcctca gcctagcccc   3300
aagagtgggc cacaaccttc agcttcctgc tgggaaaacc caggaggtga ggacggaatc   3360
acagaattct agaatgtcag agccagaaga gatcatctag tccaaacctt tcattttaca   3420
gatgggggga cgcaggccca cagaacaggc atgacctgct gaaggttacc cagggagtca   3480
tttagggatt gcaagatcat caggaacagg gctggggcag aagagaaggc atcaagtctt   3540
ggccctgggt ttctttcaga aacaaggaga ccagtgctgg tccagtggct gtgatgggaa   3600
aagattatta caagattctt gggatcccat cgggggccaa cgaggatgag atcaagaaag   3660
cctaccggaa gatggccttg aagtaccacc cagacaagaa taaagaaccc aacgctgagg   3720
agaagtttaa ggagattgca gaggcctatg atgtgctaag tgaccccaag aaacggggcc   3780
tgtatgacca gtatggggag gaaggtaaga gggcagcact ccagcccaat cccggacccc   3840
tccgcttggt aggggtccca ggtgcaccag tttgtgtagc ggggaactgg aggctgtgga   3900
gggggtgagg gcagcaaggg tttccagcac tgtcacccag agaagagaga agcccaccca   3960
ctacccagct cagctcaccc tagttctccc cgcctctctc tgccccctcc ctcctcgggt   4020
tcaggcctta gagaggtctg aagcaagagc cagaggcctt ccccgccctt ctttccttcc   4080
cagccttatt agtcctgcct gaagtctccg ctgcttcatt ggctgatgag gaaggttggg   4140
gagagggagt gtgtggctct ctgaggacag agcatttaca ttcatcagca taaaagtctg   4200
gcccttaagc agcctgggaa ttaactacca gagctctgag cagaaatggt tttccccttc   4260
tctcccccgg ccctgcctgc ttctggccag cagaacagag gtggagcttt gcctcccaga   4320
ggaagtggca gggatccaag ggtggacggg gaactgctgc tggcatcttc cccccttccct   4380
ggggtagctg gtggccatgg ggtgggaggc aggaaaggcc caaataaagc ctctgagagg   4440
gaggcccctc ccagcacatc ccacggccat gatgtagctg ctaattctgg gcctgcccct   4500
cagggctgcc tgccacccgc cagccacagg cacctgtcag gctatattaa gagacattgt   4560
cacgctgagg actctccttc ctgggaagaa ctgtccttcc tccccaacag aatccacctt   4620
tctttcacat tctcctcctc ttcaccctcc cctttctatc ctcaaaacta aatgggctaa   4680
tcatatgtag ataagaaggt tattttcttc ccctcctcct ggccttgtgt tccatgcccc   4740
tctgtgaacc ctcatcctcc caactccctt ttcctattct ccatgctgcc ggttccttcc   4800
attcttcctg cctacctcct agacgtgcca actcccagat tcaccagata ccggctggaa   4860
cccccagtat tctttcagct aagacatttt tctctctggc atggagggat gggagggata   4920
ggagtggaaa agagggaagc agtgcagaca ccatgccacc atgtgacctg tcttggaatt   4980
gcacccattc ctccattcag cctcaccttt gtttagaaag aaggcaggag ctgggagagc   5040
tcccttgaga tacttcaccc cttctgccta agtgaagggg tccagacacc aggttctgat   5100
gcagaacccc atcccaggaa ggcccctgag gatgcggcat ggccttaagg ggacctccat   5160
ggcctgggga gggagaagca gcttagaaat gttggttata tttctgtcca ccctgcccaa   5220
tccccagcag ccatttatta tagagcagtt atacacacag actctgtgtg cagctccagc   5280
tagggacaag ttgctcccag cttgaaaagg gggtggtagt ggaagaatag aaatccctat   5340
agagagaatt accccttccc atcatcatca gtccagcctc cctccctctc tcactgagct   5400
```

```
ctgccaggct gcttgaactc gcttgataat cagcccctcg atagaaggaa aggagagatc   5460
ctaggtcttg ggggaggggt gaagaggcag ctgccacaag tccctgaacc gtctgccact   5520
tggcctctct agtgaaactc aaatctgccc ttgtggtccc aggaaataag aggctaattt   5580
aggctcagat ctccatgatc agttgaaatt ctagataaat ggcctcaaag agaagggtct   5640
ctttcctagc ctggacccca cccatagtct ctgtattccg gagcagttct cagtgtgaac   5700
cgtctcccca catcccccac tactgccagc accccctcct gtgcatgaag gctgcctcca   5760
ggaatctgag ccccttagac aggacctgac agagagagca gctaaggtca ccactgccat   5820
gtgccagccc attcatgcat tttggttgct caacattagg tgtggggtat ggcgtttgct   5880
gttgtataac tccagggagc tccattccca ttgtagtcta tgtctgtaca atgtgtgaat   5940
gacactccct aaagttgtgt aacaccgagc agagtgtggg aacaaagcat ttaaaaactt   6000
tttctagaaa aatagctctt catctccaag ctaatgagct ttcccacttt ttaaggcttc   6060
ctgatttccc gtttgagcag gggccaggga aagaggaaac actgctagaa gcagagtgaa   6120
agtggtcttc ctcccgggtt ggatccctag cctatttgcg actgttcact taccagcccc   6180
ctctgtggtc acatcctgtc tgatggcccc ttgtcctata tgtctttgga gataagcaaa   6240
gatttgggaa ccaagtatca cttgtaatgt gacaccaggc tagtcattca aggctttttg   6300
agacatcttt ggaccatgag tatgtggaaa agattacagg actggaagtc acatcctcta   6360
agtcctctag tcctggcttt tccacctatt gggtaagcaa gcctctttga atctcaagtt   6420
gtgcatcgtt attaaatata taattaggaa tggaagataa tcttgccaga agcctttctt   6480
actctattag cctggccctc tctgtgggat ttaaaggttg cttctttctt taagcctgtg   6540
aactgggagc tagagggcag ggggaagaca ctgggattgg ggccagaata agccacactg   6600
cccctaactt ctcctcccct ctaggcctga agaccggcgg tggcacatca ggtggctcca   6660
gtggctcctt tcactacacc tttcatgggg accccccatgc cacctttgcc tccttctttg   6720
gtggctccaa ccccttcgat atcttctttg ccagcagccg ctccactcgg cccttcagtg   6780
gctttgaccc agatgacatg gatgtggatg aagatgagga cccatttggc gctttcggcc   6840
gttttggctt caatgggctg agtaggggtc caaggcgagc cccagaacca ctgtaccctc   6900
ggcgcaaggt gcaggacccc ccagtggtgc acgagctgcg ggtgtccctg gaggagatct   6960
accatggctc caccaagcgc atgaagatca caaggcgtcg cctcaaccct gatgggcgaa   7020
ctgtgcgcac cgaggacaag atcctgcaca tagtcatcaa gcgtggctgg aaggaaggca   7080
ccaagatcac cttccccaaa gaaggcgacg ccacacctga caacatccct gctgacatcg   7140
tctttgtgct caaagacaag ccccatgcac acttccgccg agatggcacc aacgtgctct   7200
acagtgccct gatcagcctc aaggaggtgg ggcctagtca ggctgtgtgt gtgtgctggg   7260
gagatggtgg ggacattccc tctcttcccg ccagctggca cattctttcc ccacctcagt   7320
ctatttcctt ccttcccact caccttaccc cacctttcc tcactttctg cttcgtcttt   7380
cccaggcgct gtgtggctgc actgtgaaca ttcccactat cgacggccga gtgatccctt   7440
tgccctgcaa tgatgtcatc aagccaggca ccgtgaagag actccgtggg gagggccttc   7500
ccttccccaa agtgccaact cagcgaggag acctcattgt tgagttcaaa gttcgcttcc   7560
cagacagatt aacaccacag acaagacaga tccttaagca gcacctaccc tgttcctagg   7620
ctctgcccca gccagtccag agcctaccac agcaataccc ccaacactca ctccactcaa   7680
tgtgcaccca gcttgatgtc cactggacac tggcaacttt ttctaaaatg caaaaaaaag   7740
ccactggttt tcaggaaaat gttcctgtcc ctgacccctt ttagagctgg gctgcctggg   7800
```

```
gggagtggga gggaggtggg gagagctagc ccaggccagg ggtcaatgtt catgtcacta   7860

gctttcaatc cagtttccac tgcagtggct ggagagtgac ctgagtgcta cttgaagata   7920

tgtagagatt ccttatccat gcctgtacat agcatgtcct cctcccctca gctttgctaa   7980

taccagtccc ctcccttccc tttggcttcc tgctgttggg ggtggaaaag actagaaagg   8040

acattgcttt ctcagcccca cccccaggtc cacagtgtcc aaggtaatgg cacacatatt   8100

catgcacaag aagcactcac ctagagctgt ctgtgcctct ctgggagaaa ggagagagga   8160

taagaaggga aagttcacaa cctgtgaaca gggacttgag cacgagacac ttttcatctg   8220

gagcaggggg gtgagctcct cagcagcctc cgtaacagct gccctgccta cacctgcaga   8280

gctggaggtt ctgtcctccc tgctgctctc aggagtgttc aagggtggag ggcagggaat   8340

ggggcctgag gtattaaggc taagaggtgg gggacagggc ccatctacca gccttcatca   8400

ggaagggaaa gggctttggg gtcaggtggc agctattccc caccaagaga ttcagggtca   8460

caggtttttc cccacacctc tgaactcagg gcctagccac ccccaaactt ccaaatccca   8520

cttttgtgat atgtgaagct actcatttct tacccttgga ggctgtgtgg ggaatttcca   8580

gcccttttat gcctgtgtga tcccacccca cccccatagt tgtataaagg tcatagtgaa   8640

gaagctgggg gaagactgct tcagccagat cctggggtgg ggtctttagg ttttctcact   8700

ttgacaaccc ccgaatgttt ttatagtagt ttttttgtat ttttttgtaa tgacagtatt   8760

atgtaaaaaa taaagtattt taaaaatatg gca                                8793
```

```
<210> SEQ ID NO 163
<211> LENGTH: 3245
<212> TYPE: DNA
<213> ORGANISM: Homo sapiens

<400> SEQUENCE: 163

agtgagaggc gacaggagct cactgcctct cgggccctca caatcacacc tgtcacaggt     60

atacacgctg ccactcacaa acacacgctt gcactcccag cctcactgac acgctgccat    120

acagccgctc acagccagcc agacactgct gcacctgaga gcaggtggcc gcgggtcttc    180

tcccttcact ctccacattt ggggatcagg tccggcacct gctgcgccag acaggccttg    240

ctgggcacgc gcctctgaga gtccaaggag gtggcttcca gagctgcagc acttcaggcc    300

ggctccggtg gagcgatcag aggtgagggg cttggctggg catgtttaag cgcacagtgc    360

tctcctgccc acccccagca gcacccccac tgcaggcccg aggagctttc cggagcttcc    420

cacactcctg ggagaagac ttcttagcca gcttgatgtt taaaattcag ctggagccct    480

taaaacttcg agcgtggacg ctgaatgggt ttgtaaagtt tcgaaacaag gagaccagtg    540

ctggtccagt ggctgtgatg ggaaaagatt attacaagat tcttgggatc ccatcggggg    600

ccaacgagga tgagatcaag aaagcctacc ggaagatggc cttgaagtac cacccagaca    660

agaataaaga acccaacgct gaggagaagt ttaaggagat tgcagaggcc tatgatgtgc    720

taagtgaccc caagaaacgg ggcctgtatg accagtatgg ggaggaaggc ctgaagaccg    780

gcggtggcac atcaggtggc tccagtggct cctttcacta cacctttcat ggggaccccc    840

atgccacctt tgcctccttc tttggtggct ccaacccctt cgatatcttc tttgccagca    900

gccgctccac tcggcccttc agtggctttg acccagatga catggatgtg gatgaagatg    960

aggacccatt tggcgctttc ggccgttttg gcttcaatgg gctgagtagg ggtccaaggc   1020

gagccccaga accactgtac cctcggcgca aggtgcagga ccccccagtg gtgcacgagc   1080
```

-continued

```
tgcgggtgtc cctggaggag atctaccatg gctccaccaa gcgcatgaag atcacaaggc   1140
gtcgcctcaa ccctgatggg cgaactgtgc gcaccgagga caagatcctg cacatagtca   1200
tcaagcgtgg ctggaaggaa ggcaccaaga tcaccttccc caaagaaggc gacgccacac   1260
ctgacaacat ccctgctgac atcgtctttg tgctcaaaga caagccccat gcacacttcc   1320
gccgagatgg caccaacgtg ctctacagtg ccctgatcag cctcaaggag gcgctgtgtg   1380
gctgcactgt gaacattccc actatcgacg gccgagtgat ccctttgccc tgcaatgatg   1440
tcatcaagcc aggcaccgtg aagagactcc gtggggaggg ccttcccttc cccaaagtgc   1500
caactcagcg aggagacctc attgttgagt tcaaagttcg cttcccagac agattaacac   1560
cacagacaag acagatcctt aagcagcacc taccctgttc ctaggctctg ccccagccag   1620
tccagagcct accacagcaa tacccccaac actcactcca ctcaatgtgc acccagcttg   1680
atgtccactg gacactggca actttttcta aaatgcaaaa aaaagccact ggttttcagg   1740
aaaatgttcc tgtccctgac ccctttttaga gctgggctgc ctgggggggag tgggagggag   1800
gtggggagag ctagcccagg ccaggggtca atgttcatgt cactagcttt caatccagtt   1860
tccactgcag tggctggaga gtgacctgag tgctacttga agatatgtag agattcctta   1920
tccatgcctg tacatagcat gtcctcctcc cctcagcttt gctaatacca gtcccctccc   1980
ttccctttgg cttcctgctg ttgggggtgg aaaagactag aaaggacatt gctttctcag   2040
ccccaccccc aggtccacag tgtccaaggt aatggcacac atattcatgc acaagaagca   2100
ctcacctaga gctgtctgtg cctctctggg agaaaggaga gaggataaga agggaaagtt   2160
cacaacctgt gaacagggac ttgagcacga gacacttttc atctggagca gggggggtgag   2220
ctcctcagca gcctccgtaa cagctgccct gcctacacct gcagagctgg aggttctgtc   2280
ctccctgctg ctctcaggag tgttcaaggg tggagggcag ggaatggggc ctgaggtatt   2340
aaggctaaga ggtgggggac agggcccatc taccagcctt catcaggaag ggaaagggct   2400
ttggggtcag gtggcagcta ttccccacca agagattcag ggtcacaggt tttccccac   2460
acctctgaac tcagggccta gccaccccca aacttccaaa tcccactttt gtgatatgtg   2520
aagctactca tttcttaccc ttggaggctg tgtggggaat ttccagccct tttatgcctg   2580
tgtgatccca ccccaccccc atagttgtat aaaggtcata gtgaagaagc tgggggaaga   2640
ctgcttcagc cagatcctgg ggtggggtct ttaggttttc tcactttgac aacccccgaa   2700
tgtttttata gtagtttttt tgtatttttt tgtaatgaca gtattatgta aaaaataaag   2760
tattttaaaa atatggcatc tgagcaggag caacaaacct gggatggggg tggctgagga   2820
gggccactgt catcctccct cccgggctct ggtcaccttt gagaagccca agcaggccct   2880
cagtataagc tgaagctgac ctctgccttc ctcgaagcct cctgggattt ctaaaactta   2940
tacttcaaac acagcacaga cagaaagtac cactcagcta ttagaagaaa catctatttg   3000
ggaaggaaaa atatccctgc tcatgagaga cagagaccat tgtcttcaga tgtgctagca   3060
tgaaaacaga ttttctcttc ttgtctaaat ttctctgag tcagacaaat tttccttcta   3120
ggagaaaatt tttttctagg agggggtgga gaactttttt tttttttttt ttttttgac   3180
acggagtctt gctctgtcgc ccaggctgga gtgcagtgat gcgatcttgg ttcactgcag   3240
cctct                                                              3245
```

<210> SEQ ID NO 164
<211> LENGTH: 3123
<212> TYPE: DNA
<213> ORGANISM: Homo sapiens

<400> SEQUENCE: 164

```
gtcccgggtg gaggcggcgg agccggagcc gggggagggg gcagcggctg tctcacggac     60
cacggcggcg cccgcagctc ctcaccggtc cggcacctgc tgcgccagac aggccttgct    120
gggcacgcgc ctctgagagt ccaaggaggt ggcttccaga gctgcagcac ttcaggccgg    180
ctccggtgga gcgatcagag gtgaggggct tggctgggca tgtttaagcg cacagtgctc    240
tcctgcccac ccccagcagc acccccactg caggcccgag gagctttccg gagcttccca    300
cactcctggg gagaagactt cttagccagc ttgatgttta aaattcagct ggagccctta    360
aaacttcgag cgtggacgct gaatgggttt gtaaagtttc gaaacaagga gaccagtgct    420
ggtccagtgg ctgtgatggg aaaagattat tacaagattc ttgggatccc atcgggggcc    480
aacgaggatg agatcaagaa agcctaccgg aagatggcct tgaagtacca cccagacaag    540
aataaagaac ccaacgctga ggagaagttt aaggagattg cagaggccta tgatgtgcta    600
agtgacccca agaaacgggg cctgtatgac cagtatgggg aggaaggcct gaagaccggc    660
ggtggcacat caggtggctc cagtggctcc tttcactaca cctttcatgg ggacccccat    720
gccacctttg cctccttctt tggtggctcc aacccccttcg atatcttctt tgccagcagc   780
cgctccactc ggcccttcag tggctttgac ccagatgaca tggatgtgga tgaagatgag    840
gacccatttg gcgctttcgg ccgttttggc ttcaatgggc tgagtagggg tccaaggcga    900
gccccagaac cactgtaccc tcggcgcaag gtgcaggacc ccccagtggt gcacgagctg    960
cgggtgtccc tggaggagat ctaccatggc tccaccaagc gcatgaagat cacaaggcgt   1020
cgcctcaacc ctgatgggcg aactgtgcgc accgaggaca agatcctgca catagtcatc   1080
aagcgtggct ggaaggaagg caccaagatc accttcccca aagaaggcga cgccacacct   1140
gacaacatcc ctgctgacat cgtctttgtg ctcaaagaca agccccatgc acacttccgc   1200
cgagatggca ccaacgtgct ctacagtgcc ctgatcagcc tcaaggaggc gctgtgtggc   1260
tgcactgtga acattcccac tatcgacggc cgagtgatcc ctttgccctg caatgatgtc   1320
atcaagccag gcaccgtgaa gagactccgt ggggagggcc ttcccttccc caaagtgcca   1380
actcagcgag gagacctcat tgttgagttc aaagttcgct tcccagacag attaacacca   1440
cagacaagac agatccttaa gcagcaccta ccctgttcct aggctctgcc ccagccagtc   1500
cagagcctac cacagcaata cccccaacac tcactccact caatgtgcac ccagcttgat   1560
gtccactgga cactggcaac tttttctaaa atgcaaaaaa aagccactgg ttttcaggaa   1620
aatgttcctg tccctgaccc cttttagagc tgggctgcct gggggggagtg ggagggaggt  1680
ggggagagct agcccaggcc aggggtcaat gttcatgtca ctagctttca atccagtttc   1740
cactgcagtg gctggagagt gacctgagtg ctacttgaag atatgtagag attccttatc   1800
catgcctgta catagcatgt cctcctcccc tcagctttgc taataccagt cccctccctt   1860
ccctttggct tcctgctgtt gggggtggaa aagactagaa aggacattgc tttctcagcc   1920
ccacccccag gtccacagtg tccaaggtaa tggcacacat attcatgcac aagaagcact   1980
cacctagagc tgtctgtgcc tctctgggag aaaggagaga ggataagaag ggaaagttca   2040
caacctgtga acagggactt gagcacgaga cacttttcat ctggagcagg ggggtgagct   2100
cctcagcagc ctccgtaaca gctgccctgc ctacacctgc agagctggag gttctgtcct   2160
ccctgctgct ctcaggagtg ttcaagggtg gagggcaggg aatggggcct gaggtattaa   2220
ggctaagagg tgggggacag ggcccatcta ccagccttca tcaggaaggg aaagggcttt   2280
```

```
ggggtcaggt ggcagctatt ccccaccaag agattcaggg tcacaggttt ttccccacac   2340
ctctgaactc agggcctagc cacccccaaa cttccaaatc ccacttttgt gatatgtgaa   2400
gctactcatt tcttaccctt ggaggctgtg tggggaattt ccagcccttt tatgcctgtg   2460
tgatcccacc ccaccccccat agttgtataa aggtcatagt gaagaagctg gggaagact   2520
gcttcagcca gatcctgggg tggggtcttt aggttttctc actttgacaa cccccgaatg   2580
tttttatagt agtttttttg tatttttttg taatgacagt attatgtaaa aaataaagta   2640
ttttaaaaat atggcatctg agcaggagca acaaacctgg gatgggggtg gctgaggagg   2700
gccactgtca tcctccctcc cgggctctgg tcacctttga gaagcccaag caggccctca   2760
gtataagctg aagctgacct ctgccttcct cgaagcctcc tgggatttct aaaacttata   2820
cttcaaacac agcacagaca gaaagtacca ctcagctatt agaagaaaca tctatttggg   2880
aaggaaaaat atccctgctc atgagagaca gagaccattg tcttcagatg tgctagcatg   2940
aaaacagatt ttctcttctt gtctaaattt tctctgagtc agacaaattt tccttctagg   3000
agaaaatttt tttctaggag ggggtggaga actttttttt tttttttttt tttttgacac   3060
ggagtcttgc tctgtcgccc aggctggagt gcagtgatgc gatcttggtt cactgcagcc   3120
tct                                                                  3123
```

<210> SEQ ID NO 165
<211> LENGTH: 1263
<212> TYPE: DNA
<213> ORGANISM: Homo sapiens

<400> SEQUENCE: 165

```
atgtttaagc gcacagtgct ctcctgccca cccccagcag cacccccact gcaggcccga     60
ggagctttcc ggagcttccc acactcctgg ggagaagact tcttagccag cttgatgttt    120
aaaattcagc tggagccctt aaaacttcga gcgtggacgc tgaatgggtt tgtaaagttt    180
cgaaacaagg agaccagtgc tggtccagtg gctgtgatgg gaaaagatta ttacaagatt    240
cttgggatcc catcgggggc caacgaggat gagatcaaga aagcctaccg gaagatggcc    300
ttgaagtacc acccagacaa gaataaagaa cccaacgctg aggagaagtt taaggagatt    360
gcagaggcct atgatgtgct aagtgacccc aagaaacggg gcctgtatga ccagtatggg    420
gaggaaggcc tgaagaccgg cggtggcaca tcaggtggct ccagtggctc ctttcactac    480
acctttcatg ggaccccca tgccaccttt gcctccttct ttggtggctc caacccccttc    540
gatatcttct ttgccagcag ccgctccact cggcccttca gtggctttga cccagatgac    600
atggatgtgg atgaagatga ggacccattt ggcgctttcg gccgttttgg cttcaatggg    660
ctgagtaggg gtccaaggcg agccccagaa ccactgtacc ctcggcgcaa ggtgcaggac    720
cccccagtgg tgcacgagct gcgggtgtcc ctggaggaga tctaccatgg ctccaccaag    780
cgcatgaaga tcacaaggcg tcgcctcaac cctgatgggc gaactgtgcg caccgaggac    840
aagatcctgc acatagtcat caagcgtggc tggaaggaag gcaccaagat caccttcccc    900
aaagaaggcg acgccacacc tgacaacatc cctgctgaca tcgtctttgt gctcaaagac    960
aagccccatg cacacttccg ccgagatggc accaacgtgc tctacagtgc cctgatcagc   1020
ctcaaggagg cgctgtgtgg ctgcactgtg aacattccca ctatcgacgg ccgagtgatc   1080
cctttgccct gcaatgatgt catcaagcca ggcaccgtga agagactccg tggggagggc   1140
cttcccttcc ccaaagtgcc aactcagcga ggagacctca ttgttgagtt caaagttcgc   1200
ttcccagaca gattaacacc acagacaaga cagatcctta agcagcacct accctgttcc   1260
```

tag 1263

<210> SEQ ID NO 166
<211> LENGTH: 2482
<212> TYPE: DNA
<213> ORGANISM: Homo sapiens

<400> SEQUENCE: 166
gtcccgggtg gaggcggcgg agccggagcc gggggagggg gcagcggctg tctcacggac 60
cacggcggcg cccgcagctc ctcaccgcag cacccccact gcaggcccga ggagctttcc 120
ggagcttccc acactcctgg ggagaagact tcttagccag cttgatgttt aaaattcagc 180
tggagccctt aaaacttcga gcgtggacgc tgaatgggtt tgtaaagttt cgaaacaagg 240
agaccagtgc tggtccagtg gctgtgatgg gaaaagatta ttacaagatt cttgggatcc 300
catcgggggc caacgaggat gagatcaaga aagcctaccg gaagatggcc ttgaagtacc 360
acccagacaa gaataaagaa cccaacgctg aggagaagtt taaggagatt gcagaggcct 420
atgatgtgct aagtgacccc aagaaacggg gcctgtatga ccagtatggg gaggaaggcc 480
tgaagaccgg cggtggcaca tcaggtggct ccagtggctc ctttcactac acctttcatg 540
gggaccccca tgccaccttt gcctccttct ttggtggctc caacccccttc gatatcttct 600 ttgccagcag ccgctccact cggcccttca gtggctttga cccagatgac atggatgtgg 660
atgaagatga ggacccattt ggcgctttcg gccgttttgg cttcaatggg ctgagtaggg 720
gtccaaggcg agccccagaa ccactgtacc ctcggcgcaa ggtgcaggac cccccagtgg 780
tgcacgagct gcgggtgtcc ctggaggaga tctaccatgg ctccaccaag cgcatgaaga 840
tcacaaggcg tcgcctcaac cctgatgggc gaactgtgcg caccgaggac aagatcctgc 900
acatagtcat caagcgtggc tggaaggaag gcaccaagat caccttcccc aaagaaggcg 960
acgccacacc tgacaacatc cctgctgaca tcgtctttgt gctcaaagac aagccccatg 1020
cacacttccg ccgagatggc accaacgtgc tctacagtgc cctgatcagc ctcaaggagg 1080
cgctgtgtgg ctgcactgtg aacattccca ctatcgacgg ccgagtgatc cctttgccct 1140
gcaatgatgt catcaagcca ggcaccgtga agagactccg tggggagggc cttcccttcc 1200
ccaaagtgcc aactcagcga ggagacctca ttgttgagtt caaagttcgc ttcccagaca 1260
gattaacacc acagacaaga cagatcctta agcagcacct accctgttcc taggctctgc 1320
cccagccagt ccagagccta ccacagcaat acccccaaca ctcactccac tcaatgtgca 1380
cccagcttga tgtccactgg acactggcaa ctttttctaa aatgcaaaaa aaagccactg 1440
gttttcagga aaatgttcct gtccctgacc ccttttagag ctgggctgcc tggggggagt 1500
gggagggagg tggggagagc tagcccaggc caggggtcaa tgttcatgtc actagctttc 1560
aatccagttt ccactgcagt ggctggagag tgacctgagt gctacttgaa gatatgtaga 1620
gattccttat ccatgcctgt acatagcatg tcctcctccc ctcagctttg ctaataccag 1680
tcccctccct tccctttggc ttcctgctgt tgggggtgga aaagactaga aaggacattg 1740
ctttctcagc cccaccccca ggtccacagt gtccaaggta atggcacaca tattcatgca 1800
caagaagcac tcacctagag ctgtctgtgc ctctctggga gaaaggagag aggataagaa 1860
gggaaagttc acaacctgtg aacagggact tgagcacgag acacttttca tctggagcag 1920
gggggtgagc tcctcagcag cctccgtaac agctgccctg cctacacctg cagagctgga 1980
ggttctgtcc tccctgctgc tctcaggagt gttcaagggt ggagggcagg gaatggggcc 2040
tgaggtatta aggctaagag gtgggggaca gggcccatct accagccttc atcaggaagg 2100
gaaagggctt tggggtcagg tggcagctat tccccaccaa gagattcagg gtcacaggtt 2160
tttccccaca cctctgaact cagggcctag ccacccccaa acttccaaat cccacttttg 2220
tgatatgtga agctactcat ttcttaccct tggaggctgt gtggggaatt tccagccctt 2280
ttatgcctgt gtgatcccac cccaccccca tagttgtata aaggtcatag tgaagaagct 2340
gggggaagac tgcttcagcc agatcctggg gtggggtctt taggttttct cactttgaca 2400
acccccgaat gtttttatag tagttttttt gtattttttt gtaatgacag tattatgtaa 2460
aaaataaagt attttaaaaa ta 2482

<210> SEQ ID NO 167
<211> LENGTH: 2479
<212> TYPE: DNA
<213> ORGANISM: Homo sapiens

<400> SEQUENCE: 167
gtcccgggtg gaggcggcgg agccggagcc gggggagggg gcagcggctg tctcacggac 60
cacggcggcg cccgcagctc ctcaccgcac ccccactgca ggcccgagga gctttccgga 120 gcttccccaca ctcctgggga gaagacttct tagccagctt gatgtttaaa attcagctgg 180
agcccttaaa acttcgagcg tggacgctga atgggtttgt aaagtttcga aacaaggaga 240
ccagtgctgg tccagtggct gtgatgggaa aagattatta caagattctt gggatcccat 300
cgggggccaa cgaggatgag atcaagaaag cctaccggaa gatggccttg aagtaccacc 360
cagacaagaa taaagaaccc aacgctgagg agaagtttaa ggagattgca gaggcctatg 420
atgtgctaag tgaccccaag aaacggggcc tgtatgacca gtatggggag gaaggcctga 480
agaccggcgg tggcacatca ggtggctcca gtggctcctt tcactacacc tttcatgggg 540
acccccatgc cacctttgcc tccttctttg gtggctccaa ccccttcgat atcttctttg 600
ccagcagccg ctccactcgg cccttcagtg gctttgaccc agatgacatg gatgtggatg 660
aagatgagga cccatttggc gctttcggcc gttttggctt caatgggctg agtaggggtc 720
caaggcgagc ccagaaccca ctgtaccctc ggcgcaaggt gcaggacccc ccagtggtgc 780
acgagctgcg ggtgtccctg gaggagatct accatggctc caccaagcgc atgaagatca 840
caaggcgtcg cctcaaccct gatgggcgaa ctgtgcgcac cgaggacaag atcctgcaca 900
tagtcatcaa gcgtggctgg aaggaaggca ccaagatcac cttccccaaa gaaggcgacg 960
ccacacctga caacatccct gctgacatcg tctttgtgct caaagacaag ccccatgcac 1020
acttccgccg agatggcacc aacgtgctct acagtgccct gatcagcctc aaggaggcgc 1080
tgtgtggctg cactgtgaac attcccacta tcgacggccg agtgatccct ttgccctgca 1140
atgatgtcat caagccaggc accgtgaaga gactccgtgg ggagggcctt cccttcccca 1200
aagtgccaac tcagcgagga gacctcattg ttgagttcaa agttcgcttc ccagacagat 1260
taacaccaca gacaagacag atccttaagc agcacctacc ctgttcctag gctctgcccc 1320
agccagtcca gagcctacca cagcaatacc cccaacactc actccactca atgtgcaccc 1380
agcttgatgt ccactggaca ctggcaactt tttctaaaat gcaaaaaaaa gccactggtt 1440
ttcaggaaaa tgttcctgtc cctgacccct tttagagctg ggctgcctgg ggggagtggg 1500
agggaggtgg ggagagctag cccaggccag gggtcaatgt tcatgtcact agctttcaat 1560
ccagtttcca ctgcagtggc tggagagtga cctgagtgct acttgaagat atgtagagat 1620
tccttatcca tgcctgtaca tagcatgtcc tcctcccctc agctttgcta ataccagtcc 1680

```
cctcccttcc ctttggcttc ctgctgttgg gggtggaaaa gactagaaag gacattgctt   1740
tctcagcccc acccccaggt ccacagtgtc caaggtaatg gcacacatat tcatgcacaa   1800
gaagcactca cctagagctg tctgtgcctc tctgggagaa aggagagagg ataagaaggg   1860
aaagttcaca acctgtgaac agggacttga gcacgagaca cttttcatct ggagcagggg   1920
ggtgagctcc tcagcagcct ccgtaacagc tgccctgcct acacctgcag agctggaggt   1980
tctgtcctcc ctgctgctct caggagtgtt caagggtgga gggcagggaa tggggcctga   2040
ggtattaagg ctaagaggtg ggggacaggg cccatctacc agccttcatc aggaagggaa   2100
agggctttgg ggtcaggtgg cagctattcc ccaccaagag attcagggtc acaggttttt   2160
ccccacacct ctgaactcag ggcctagcca cccccaaact tccaaatccc acttttgtga   2220
tatgtgaagc tactcatttc ttacccttgg aggctgtgtg gggaatttcc agccctttta   2280
tgcctgtgtg atcccacccc acccccatag ttgtataaag gtcatagtga agaagctggg   2340
ggaagactgc ttcagccaga tcctggggtg gggtctttag gttttctcac tttgacaacc   2400
cccgaatgtt tttatagtag ttttttgta ttttttgta atgacagtat tatgtaaaaa   2460
ataaagtatt ttaaaaata                                                2479
```

<210> SEQ ID NO 168
<211> LENGTH: 1149
<212> TYPE: DNA
<213> ORGANISM: Homo sapiens

<400> SEQUENCE: 168

```
atgtttaaaa ttcagctgga gcccttaaaa cttcgagcgt ggacgctgaa tgggtttgta     60
aagtttcgaa acaaggagac cagtgctggt ccagtggctg tgatgggaaa agattattac    120
aagattcttg ggatcccatc gggggccaac gaggatgaga tcaagaaagc ctaccggaag    180
atggccttga agtaccaccc agacaagaat aaagaaccca acgctgagga gaagtttaag    240
gagattgcag aggcctatga tgtgctaagt gaccccaaga aacggggcct gtatgaccag    300
tatggggagg aaggcctgaa gaccggcggt ggcacatcag gtggctccag tggctccttt    360
cactacacct ttcatgggga cccccatgcc acctttgcct ccttctttgg tggctccaac    420
cccttcgata tcttctttgc cagcagccgc tccactcggc ccttcagtgg ctttgaccca    480
gatgacatgg atgtggatga agatgaggac cccatttggcg ctttcggccg ttttggcttc    540
aatgggctga gtaggggtcc aaggcgagcc ccagaaccac tgtaccctcg gcgcaaggtg    600
caggaccccc cagtggtgca cgagctgcgg gtgtccctgg aggagatcta ccatggctcc    660
accaagcgca tgaagatcac aaggcgtcgc ctcaaccctg atgggcgaac tgtgcgcacc    720
gaggacaaga tcctgcacat agtcatcaag cgtggctgga aggaaggcac caagatcacc    780
ttccccaaag aaggcgacgc cacacctgac aacatccctg ctgacatcgt ctttgtgctc    840
aaagacaagc cccatgcaca cttccgccga gatggcacca acgtgctcta cagtgccctg    900
atcagcctca aggaggcgct gtgtggctgc actgtgaaca ttcccactat cgacggccga    960
gtgatccctt tgccctgcaa tgatgtcatc aagccaggca ccgtgaagag actccgtggg   1020
gagggccttc ccttccccaa agtgccaact cagcgaggag acctcattgt tgagttcaaa   1080
gttcgcttcc cagacagatt aacaccacag acaagacaga tccttaagca gcacctaccc   1140
tgttcctag                                                           1149
```

<210> SEQ ID NO 169

<211> LENGTH: 2809
<212> TYPE: DNA
<213> ORGANISM: Homo sapiens

<400> SEQUENCE: 169

```
gtcccgggtg gaggcggcgg agccggagcc gggggagggg gcagcggctg tctcacggac     60
cacggcggcg cccgcagctc ctcaccgaaa caaggagacc agtgctggtc cagtggctgt    120
gatgggaaaa gattattaca agattcttgg gatcccatcg gggccaacg aggatgagat    180
caagaaagcc taccggaaga tggccttgaa gtaccaccca gacaagaata aagaacccaa    240
cgctgaggag aagtttaagg agattgcaga ggcctatgat gtgctaagtg accccaagaa    300
acggggcctg tatgaccagt atggggagga aggcctgaag accggcggtg gcacatcagg    360
tggctccagt ggctcctttc actacacctt tcatggggac ccccatgcca cctttgcctc    420
cttctttggt ggctccaacc ccttcgatat cttctttgcc agcagccgct ccactcggcc    480
cttcagtggc tttgacccag atgacatgga tgtggatgaa gatgaggacc catttggcgc    540
tttcggccgt tttggcttca atgggctgag taggggtcca aggcgagccc cagaaccact    600
gtaccctcgg cgcaaggtgc aggacccccc agtggtgcac gagctgcggg tgtccctgga    660
ggagatctac catggctcca ccaagcgcat gaagatcaca aggcgtcgcc tcaaccctga    720
tgggcgaact gtgcgcaccg aggacaagat cctgcacata gtcatcaagc gtggctggaa    780
ggaaggcacc aagatcacct tccccaaaga aggcgacgcc acacctgaca acatccctgc    840
tgacatcgtc tttgtgctca aagacaagcc ccatgcacac ttccgccgag atggcaccaa    900
cgtgctctac agtgccctga tcagcctcaa ggaggcgctg tgtggctgca ctgtgaacat    960
tcccactatc gacggccgag tgatcccttt gccctgcaat gatgtcatca agccaggcac   1020
cgtgaagaga ctccgtgggg agggccttcc cttccccaaa gtgccaactc agcgaggaga   1080
cctcattgtt gagttcaaag ttcgcttccc agacagatta acaccacaga caagacagat   1140
ccttaagcag cacctaccct gttcctaggc tctgccccag ccagtccaga gcctaccaca   1200
gcaatacccc caacactcac tccactcaat gtgcacccag cttgatgtcc actggacact   1260
ggcaactttt tctaaaatgc aaaaaaaagc cactggtttt caggaaaatg ttcctgtccc   1320
tgaccccttt tagagctggg ctgcctgggg ggagtgggag ggaggtgggg agagctagcc   1380
caggccaggg gtcaatgttc atgtcactag ctttcaatcc agtttccact gcagtggctg   1440
gagagtgacc tgagtgctac ttgaagatat gtagagattc cttatccatg cctgtacata   1500
gcatgtcctc ctcccctcag ctttgctaat accagtcccc tcccttccct ttggcttcct   1560
gctgttgggg gtggaaaaga ctagaaagga cattgctttc tcagccccac ccccaggtcc   1620
acagtgtcca aggtaatggc acacatattc atgcacaaga agcactcacc tagagctgtc   1680
tgtgcctctc tgggagaaag gagagaggat aagaagggaa agttcacaac ctgtgaacag   1740
ggacttgagc acgagacact tttcatctgg agcagggggg tgagctcctc agcagcctcc   1800
gtaacagctg ccctgcctac acctgcagag ctggaggttc tgtcctccct gctgctctca   1860
ggagtgttca agggtggagg gcagggaatg gggcctgagg tattaaggct aagaggtggg   1920
ggacagggcc catctaccag ccttcatcag gaagggaaag ggctttgggg tcaggtggca   1980
gctattcccc accaagagat tcagggtcac aggtttttcc ccacacctct gaactcaggg   2040
cctagccacc cccaaacttc caaatcccac ttttgtgata tgtgaagcta ctcatttctt   2100
acccttggag gctgtgtggg gaatttccag ccctttttatg cctgtgtgat cccaccccac   2160
ccccatagtt gtataaaggt catagtgaag aagctggggg aagactgctt cagccagatc   2220
```

ctggggtggg gtctttaggt tttctcactt tgacaacccc cgaatgtttt tatagtagtt 2280
tttttgtatt tttttgtaat gacagtatta tgtaaaaaat aaagtatttt aaaaatatgg 2340
catctgagca ggagcaacaa acctgggatg ggggtggctg aggagggcca ctgtcatcct 2400
ccctcccggg ctctggtcac ctttgagaag cccaagcagg ccctcagtat aagctgaagc 2460
tgacctctgc cttcctcgaa gcctcctggg atttctaaaa cttatacttc aaacacagca 2520
cagacagaaa gtaccactca gctattagaa gaaacatcta tttgggaagg aaaaatatcc 2580
ctgctcatga gagacagaga ccattgtctt cagatgtgct agcatgaaaa cagattttct 2640
cttcttgtct aaattttctc tgagtcagac aaattttcct tctaggagaa aatttttttc 2700
taggaggggg tggagaactt tttttttttt tttttttttt tgacacggag tcttgctctg 2760
tcgcccaggc tggagtgcag tgatgcgatc ttggttcact gcagcctct 2809

<210> SEQ ID NO 170
<211> LENGTH: 2922
<212> TYPE: DNA
<213> ORGANISM: Homo sapiens

<400> SEQUENCE: 170
gtcccgggtg gaggcggcgg agccggagcc gggggagggg gcagcggctg tctcacggac 60
cacggcggcg cccgcagctc ctcaccggtc cggcacctgc tgcgccagac aggccttgct 120
gggcacgcgc ctctgagagt ccaaggaggt ggcttccaga gctgcagcac ttcaggccgg 180
ctccggtgga gcgatcagag aaacaaggag accagtgctg gtccagtggc tgtgatggga 240
aaagattatt acaagattct tgggatccca tcgggggcca acgaggatga gatcaagaaa 300
gcctaccgga agatggcctt gaagtaccac ccagacaaga ataaagaacc caacgctgag 360
gagaagttta aggagattgc agaggcctat gatgtgctaa gtgaccccaa gaaacggggc 420
ctgtatgacc agtatgggga ggaaggcctg aagaccggcg gtggcacatc aggtggctcc 480
agtggctcct ttcactacac ctttcatggg gacccccatg ccacctttgc ctccttcttt 540
ggtggctcca accccttcga tatcttcttt gccagcagcc gctccactcg gcccttcagt 600
ggctttgacc cagatgacat ggatgtggat gaagatgagg acccatttgg cgctttcggc 660
cgttttggct tcaatgggct gagtaggggt ccaaggcgag ccccagaacc actgtaccct 720
cggcgcaagg tgcaggaccc cccagtggtg cacgagctgc gggtgtccct ggaggagatc 780
taccatggct ccaccaagcg catgaagatc acaaggcgtc gcctcaaccc tgatgggcga 840
actgtgcgca ccgaggacaa gatcctgcac atagtcatca agcgtggctg gaaggaaggc 900
accaagatca ccttccccaa agaaggcgac gccacacctg acaacatccc tgctgacatc 960
gtctttgtgc tcaaagacaa gccccatgca cacttccgcc gagatggcac caacgtgctc 1020
tacagtgccc tgatcagcct caaggaggcg ctgtgtggct gcactgtgaa cattcccact 1080
atcgacggcc gagtgatccc tttgccctgc aatgatgtca tcaagccagg caccgtgaag 1140
agactccgtg ggagagggcct tcccttcccc aaagtgccaa ctcagcgagg agacctcatt 1200
gttgagttca aagttcgctt cccagacaga ttaacaccac agacaagaca gatccttaag 1260
cagcacctac cctgttccta ggctctgccc cagccagtcc agagcctacc acagcaatac 1320
ccccaacact cactccactc aatgtgcacc cagcttgatg tccactggac actggcaact 1380
ttttctaaaa tgcaaaaaaa agccactggt tttcaggaaa atgttcctgt ccctgacccc 1440
ttttagagct gggctgcctg gggggagtgg gagggaggtg gggagagcta gcccaggcca 1500

```
ggggtcaatg ttcatgtcac tagctttcaa tccagtttcc actgcagtgg ctggagagtg   1560
acctgagtgc tacttgaaga tatgtagaga ttccttatcc atgcctgtac atagcatgtc   1620
ctcctcccct cagctttgct aataccagtc cctcccttc cctttggctt cctgctgttg   1680
ggggtggaaa agactagaaa ggacattgct ttctcagccc cacccccagg tccacagtgt   1740
ccaaggtaat ggcacacata ttcatgcaca agaagcactc acctagagct gtctgtgcct   1800
ctctgggaga aaggagagag gataagaagg gaaagttcac aacctgtgaa cagggacttg   1860
agcacgagac acttttcatc tggagcaggg gggtgagctc ctcagcagcc tccgtaacag   1920
ctgccctgcc tacacctgca gagctggagg ttctgtcctc cctgctgctc tcaggagtgt   1980
tcaagggtgg agggcaggga atggggcctg aggtattaag gctaagaggt gggggacagg   2040
gcccatctac cagccttcat caggaaggga aagggctttg ggtcaggtg gcagctattc   2100
cccaccaaga gattcagggt cacaggtttt tccccacacc tctgaactca gggcctagcc   2160
acccccaaac ttccaaatcc cacttttgtg atatgtgaag ctactcattt cttacccttg   2220
gaggctgtgt ggggaatttc cagccctttt atgcctgtgt gatcccaccc cacccccata   2280
gttgtataaa ggtcatagtg aagaagctgg gggaagactg cttcagccag atcctggggt   2340
ggggtcttta ggtttctca ctttgacaac ccccgaatgt ttttatagta gttttttgt   2400
attttttgt aatgacagta ttatgtaaaa aataaagtat tttaaaaata tggcatctga   2460
gcaggagcaa caaacctggg atgggggtgg ctgaggaggg ccactgtcat cctccctccc   2520
gggctctggt cacctttgag aagcccaagc aggccctcag tataagctga agctgacctc   2580
tgccttcctc gaagcctcct gggatttcta aaacttatac ttcaaacaca gcacagacag   2640
aaagtaccac tcagctatta gaagaaacat ctatttggga aggaaaaata tccctgctca   2700
tgagagacag agaccattgt cttcagatgt gctagcatga aaacagattt tctcttcttg   2760
tctaaatttt ctctgagtca gacaaatttt ccttctagga gaaaattttt ttctaggagg   2820
gggtggagaa cttttttttt ttttttttt ttttgacacg gagtcttgct ctgtcgccca   2880
ggctggagtg cagtgatgcg atcttggttc actgcagcct ct                     2922
```

<210> SEQ ID NO 171
<211> LENGTH: 1047
<212> TYPE: DNA
<213> ORGANISM: Homo sapiens

<400> SEQUENCE: 171

```
atgggaaaag attattacaa gattcttggg atcccatcgg gggccaacga ggatgagatc     60
aagaaagcct accggaagat ggccttgaag taccacccag acaagaataa agaacccaac    120
gctgaggaga agtttaagga gattgcagag gcctatgatg tgctaagtga ccccaagaaa    180
cggggcctgt atgaccagta tggggaggaa ggcctgaaga ccggcggtgg cacatcaggt    240
ggctccagtg gctcctttca ctacaccttt catggggacc cccatgccac ctttgcctcc    300
ttctttggtg gctccaaccc cttcgatatc ttctttgcca gcagccgctc cactcggccc    360
ttcagtggct ttgacccaga tgacatggat gtggatgaag atgaggaccc atttggcgct    420
ttcggccgtt ttggcttcaa tgggctgagt aggggtccaa ggcgagcccc agaaccactg    480
taccctcggc gcaaggtgca ggaccccca gtggtgcacg agctgcgggt gtccctggag    540
gagatctacc atggctccac caagcgcatg aagatcacaa ggcgtcgcct caaccctgat    600
gggcgaactg tgcgcaccga ggacaagatc ctgcacatag tcatcaagcg tggctggaag    660
gaaggcacca agatcacctt ccccaaagaa ggcgacgcca cacctgacaa catccctgct    720
```

```
gacatcgtct ttgtgctcaa agacaagccc catgcacact tccgccgaga tggcaccaac    780

gtgctctaca gtgccctgat cagcctcaag gaggcgctgt gtggctgcac tgtgaacatt    840

cccactatcg acggccgagt gatccctttg ccctgcaatg atgtcatcaa gccaggcacc    900

gtgaagagac tccgtgggga gggccttccc ttccccaaag tgccaactca gcgaggagac    960

ctcattgttg agttcaaagt tcgcttccca gacagattaa caccacagac aagacagatc   1020

cttaagcagc acctaccctg ttcctag                                       1047
```

```
<210> SEQ ID NO 172
<211> LENGTH: 420
<212> TYPE: PRT
<213> ORGANISM: Homo sapiens

<400> SEQUENCE: 172

Met Phe Lys Arg Thr Val Leu Ser Cys Pro Pro Pro Ala Ala Pro Pro
1               5                   10                  15

Leu Gln Ala Arg Gly Ala Phe Arg Ser Phe Pro His Ser Trp Gly Glu
            20                  25                  30

Asp Phe Leu Ala Ser Leu Met Phe Lys Ile Gln Leu Glu Pro Leu Lys
        35                  40                  45

Leu Arg Ala Trp Thr Leu Asn Gly Phe Val Lys Phe Arg Asn Lys Glu
    50                  55                  60

Thr Ser Ala Gly Pro Val Ala Val Met Gly Lys Asp Tyr Tyr Lys Ile
65                  70                  75                  80

Leu Gly Ile Pro Ser Gly Ala Asn Glu Asp Glu Ile Lys Lys Ala Tyr
                85                  90                  95

Arg Lys Met Ala Leu Lys Tyr His Pro Asp Lys Asn Lys Glu Pro Asn
            100                 105                 110

Ala Glu Glu Lys Phe Lys Glu Ile Ala Glu Ala Tyr Asp Val Leu Ser
        115                 120                 125

Asp Pro Lys Lys Arg Gly Leu Tyr Asp Gln Tyr Gly Glu Glu Gly Leu
    130                 135                 140

Lys Thr Gly Gly Gly Thr Ser Gly Gly Ser Ser Gly Ser Phe His Tyr
145                 150                 155                 160

Thr Phe His Gly Asp Pro His Ala Thr Phe Ala Ser Phe Phe Gly Gly
                165                 170                 175

Ser Asn Pro Phe Asp Ile Phe Phe Ala Ser Ser Arg Ser Thr Arg Pro
            180                 185                 190

Phe Ser Gly Phe Asp Pro Asp Asp Met Asp Val Asp Glu Asp Glu Asp
        195                 200                 205

Pro Phe Gly Ala Phe Gly Arg Phe Gly Phe Asn Gly Leu Ser Arg Gly
    210                 215                 220

Pro Arg Arg Ala Pro Glu Pro Leu Tyr Pro Arg Arg Lys Val Gln Asp
225                 230                 235                 240

Pro Pro Val Val His Glu Leu Arg Val Ser Leu Glu Glu Ile Tyr His
                245                 250                 255

Gly Ser Thr Lys Arg Met Lys Ile Thr Arg Arg Arg Leu Asn Pro Asp
            260                 265                 270

Gly Arg Thr Val Arg Thr Glu Asp Lys Ile Leu His Ile Val Ile Lys
        275                 280                 285

Arg Gly Trp Lys Glu Gly Thr Lys Ile Thr Phe Pro Lys Glu Gly Asp
    290                 295                 300

Ala Thr Pro Asp Asn Ile Pro Ala Asp Ile Val Phe Val Leu Lys Asp
```

305 310 315 320

Lys Pro His Ala His Phe Arg Arg Asp Gly Thr Asn Val Leu Tyr Ser
325 330 335

Ala Leu Ile Ser Leu Lys Glu Ala Leu Cys Gly Cys Thr Val Asn Ile
340 345 350

Pro Thr Ile Asp Gly Arg Val Ile Pro Leu Pro Cys Asn Asp Val Ile
355 360 365

Lys Pro Gly Thr Val Lys Arg Leu Arg Gly Glu Gly Leu Pro Phe Pro
370 375 380

Lys Val Pro Thr Gln Arg Gly Asp Leu Ile Val Glu Phe Lys Val Arg
385 390 395 400

Phe Pro Asp Arg Leu Thr Pro Gln Thr Arg Gln Ile Leu Lys Gln His
405 410 415

Leu Pro Cys Ser
420

<210> SEQ ID NO 173
<211> LENGTH: 382
<212> TYPE: PRT
<213> ORGANISM: Homo sapiens

<400> SEQUENCE: 173

Met Phe Lys Ile Gln Leu Glu Pro Leu Lys Leu Arg Ala Trp Thr Leu
1 5 10 15

Asn Gly Phe Val Lys Phe Arg Asn Lys Glu Thr Ser Ala Gly Pro Val
20 25 30

Ala Val Met Gly Lys Asp Tyr Tyr Lys Ile Leu Gly Ile Pro Ser Gly
35 40 45

Ala Asn Glu Asp Glu Ile Lys Lys Ala Tyr Arg Lys Met Ala Leu Lys
50 55 60

Tyr His Pro Asp Lys Asn Lys Glu Pro Asn Ala Glu Glu Lys Phe Lys
65 70 75 80

Glu Ile Ala Glu Ala Tyr Asp Val Leu Ser Asp Pro Lys Lys Arg Gly
85 90 95

Leu Tyr Asp Gln Tyr Gly Glu Glu Gly Leu Lys Thr Gly Gly Gly Thr
100 105 110

Ser Gly Gly Ser Ser Gly Ser Phe His Tyr Thr Phe His Gly Asp Pro
115 120 125

His Ala Thr Phe Ala Ser Phe Phe Gly Gly Ser Asn Pro Phe Asp Ile
130 135 140

Phe Phe Ala Ser Ser Arg Ser Thr Arg Pro Phe Ser Gly Phe Asp Pro
145 150 155 160

Asp Asp Met Asp Val Asp Glu Asp Glu Asp Pro Phe Gly Ala Phe Gly
165 170 175

Arg Phe Gly Phe Asn Gly Leu Ser Arg Gly Pro Arg Arg Ala Pro Glu
180 185 190

Pro Leu Tyr Pro Arg Arg Lys Val Gln Asp Pro Pro Val Val His Glu
195 200 205

Leu Arg Val Ser Leu Glu Glu Ile Tyr His Gly Ser Thr Lys Arg Met
210 215 220

Lys Ile Thr Arg Arg Arg Leu Asn Pro Asp Gly Arg Thr Val Arg Thr
225 230 235 240

Glu Asp Lys Ile Leu His Ile Val Ile Lys Arg Gly Trp Lys Glu Gly
245 250 255

```
Thr Lys Ile Thr Phe Pro Lys Glu Gly Asp Ala Thr Pro Asp Asn Ile
            260                 265                 270

Pro Ala Asp Ile Val Phe Val Leu Lys Asp Lys Pro His Ala His Phe
        275                 280                 285

Arg Arg Asp Gly Thr Asn Val Leu Tyr Ser Ala Leu Ile Ser Leu Lys
    290                 295                 300

Glu Ala Leu Cys Gly Cys Thr Val Asn Ile Pro Thr Ile Asp Gly Arg
305                 310                 315                 320

Val Ile Pro Leu Pro Cys Asn Asp Val Ile Lys Pro Gly Thr Val Lys
                325                 330                 335

Arg Leu Arg Gly Glu Gly Leu Pro Phe Pro Lys Val Pro Thr Gln Arg
            340                 345                 350

Gly Asp Leu Ile Val Glu Phe Lys Val Arg Phe Pro Asp Arg Leu Thr
        355                 360                 365

Pro Gln Thr Arg Gln Ile Leu Lys Gln His Leu Pro Cys Ser
    370                 375                 380


<210> SEQ ID NO 174
<211> LENGTH: 348
<212> TYPE: PRT
<213> ORGANISM: Homo sapiens

<400> SEQUENCE: 174

Met Gly Lys Asp Tyr Tyr Lys Ile Leu Gly Ile Pro Ser Gly Ala Asn
1               5                   10                  15

Glu Asp Glu Ile Lys Lys Ala Tyr Arg Lys Met Ala Leu Lys Tyr His
            20                  25                  30

Pro Asp Lys Asn Lys Glu Pro Asn Ala Glu Glu Lys Phe Lys Glu Ile
        35                  40                  45

Ala Glu Ala Tyr Asp Val Leu Ser Asp Pro Lys Lys Arg Gly Leu Tyr
    50                  55                  60

Asp Gln Tyr Gly Glu Glu Gly Leu Lys Thr Gly Gly Gly Thr Ser Gly
65                  70                  75                  80

Gly Ser Ser Gly Ser Phe His Tyr Thr Phe His Gly Asp Pro His Ala
                85                  90                  95

Thr Phe Ala Ser Phe Phe Gly Gly Ser Asn Pro Phe Asp Ile Phe Phe
            100                 105                 110

Ala Ser Ser Arg Ser Thr Arg Pro Phe Ser Gly Phe Asp Pro Asp Asp
        115                 120                 125

Met Asp Val Asp Glu Asp Glu Asp Pro Phe Gly Ala Phe Gly Arg Phe
    130                 135                 140

Gly Phe Asn Gly Leu Ser Arg Gly Pro Arg Arg Ala Pro Glu Pro Leu
145                 150                 155                 160

Tyr Pro Arg Arg Lys Val Gln Asp Pro Pro Val Val His Glu Leu Arg
                165                 170                 175

Val Ser Leu Glu Glu Ile Tyr His Gly Ser Thr Lys Arg Met Lys Ile
            180                 185                 190

Thr Arg Arg Arg Leu Asn Pro Asp Gly Arg Thr Val Arg Thr Glu Asp
        195                 200                 205

Lys Ile Leu His Ile Val Ile Lys Arg Gly Trp Lys Glu Gly Thr Lys
    210                 215                 220

Ile Thr Phe Pro Lys Glu Gly Asp Ala Thr Pro Asp Asn Ile Pro Ala
225                 230                 235                 240

Asp Ile Val Phe Val Leu Lys Asp Lys Pro His Ala His Phe Arg Arg
                245                 250                 255
```

-continued

```
Asp Gly Thr Asn Val Leu Tyr Ser Ala Leu Ile Ser Leu Lys Glu Ala
            260                 265                 270

Leu Cys Gly Cys Thr Val Asn Ile Pro Thr Ile Asp Gly Arg Val Ile
        275                 280                 285

Pro Leu Pro Cys Asn Asp Val Ile Lys Pro Gly Thr Val Lys Arg Leu
    290                 295                 300

Arg Gly Glu Gly Leu Pro Phe Pro Lys Val Pro Thr Gln Arg Gly Asp
305                 310                 315                 320

Leu Ile Val Glu Phe Lys Val Arg Phe Pro Asp Arg Leu Thr Pro Gln
                325                 330                 335

Thr Arg Gln Ile Leu Lys Gln His Leu Pro Cys Ser
            340                 345
```